United States Patent
Blake et al.

(10) Patent No.: US 8,889,704 B2
(45) Date of Patent: Nov. 18, 2014

(54) TRIAZOLOPYRIDINE COMPOUNDS AS PIM KINASE INHIBITORS

(75) Inventors: James F. Blake, Boulder, CO (US); Robert Kirk Delisle, Longmont, CO (US); Lisa A. De Meese, Phoenix, AZ (US); James M. Graham, Longmont, CO (US); Yvan Le Huerou, Boulder, CO (US); Michael Lyon, Eris, CO (US); John E. Robinson, Boulder, CO (US); Eli M. Wallace, Richardson, TX (US); Bin Wang, Dallas, TX (US); Rui Xu, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

(21) Appl. No.: 14/001,657

(22) PCT Filed: Feb. 24, 2012

(86) PCT No.: PCT/US2012/026572
§ 371 (c)(1),
(2), (4) Date: Aug. 26, 2013

(87) PCT Pub. No.: WO2012/154274
PCT Pub. Date: Nov. 15, 2012

(65) Prior Publication Data
US 2014/0005213 A1 Jan. 2, 2014

Related U.S. Application Data

(60) Provisional application No. 61/446,902, filed on Feb. 25, 2011.

(51) Int. Cl.
| C07D 471/04 | (2006.01) |
| C07D 487/04 | (2006.01) |
| C07D 487/10 | (2006.01) |
| C07D 491/048 | (2006.01) |
| C07D 401/06 | (2006.01) |
| C07D 519/00 | (2006.01) |

(52) U.S. Cl.
CPC .......... *C07D 471/04* (2013.01); *C07D 491/048* (2013.01); *C07D 487/10* (2013.01); *C07D 401/06* (2013.01); *C07D 487/04* (2013.01); *C07D 519/00* (2013.01)
USPC ............. 514/278; 514/291; 514/303; 546/15; 546/89; 546/119

(58) Field of Classification Search
None
See application file for complete search history.

(56) References Cited

U.S. PATENT DOCUMENTS

| 8,557,809 B2 | 10/2013 | Allen et al. |
| 8,575,145 B2 | 11/2013 | Allen et al. |
| 2005/0256309 A1 | 11/2005 | Altenbach et al. |
| 2007/0154919 A1 | 7/2007 | Korn et al. |
| 2007/0173508 A1 | 7/2007 | Hutchinson et al. |
| 2008/0027063 A1 | 1/2008 | Zhao et al. |
| 2008/0261988 A1 | 10/2008 | Bearss et al. |
| 2009/0042918 A1 | 2/2009 | Kearney et al. |

FOREIGN PATENT DOCUMENTS

| EP | 1277754 A1 | 1/2003 |
| WO | WO 01/34603 A2 | 5/2001 |
| WO | WO 02/012236 A1 | 9/2002 |
| WO | WO 02/072579 A1 | 9/2002 |
| WO | WO 2004/058749 A1 | 7/2004 |
| WO | WO 2004/058769 A2 | 7/2004 |
| WO | WO 2005/028624 A2 | 3/2005 |
| WO | WO 2006/018727 A2 | 2/2006 |
| WO | WO 2006/058752 A1 | 6/2006 |
| WO | WO 2007/044724 A2 | 4/2007 |
| WO | WO 2008/082839 A2 | 7/2008 |
| WO | WO 2008/121687 A2 | 10/2008 |
| WO | WO 2010/022076 A1 | 2/2010 |
| WO | WO 2010/022081 A1 | 2/2010 |

OTHER PUBLICATIONS

Bullock et al., "Structural Basis of Inhibitor Specificity of the Human Protooncogene Proviral Insertion Site in Moloney Murine Leukemia Virus (PIM-1) Kinase", *J. Med. Chem.*, 48, 7604-7614 (2005).
Chemcats Accession No. 205019468, Chembridge Screening Library, 1 page, Jun. 8, 2009.
Chen et al., "Pim-1 and Pim-2 kinases are required for efficient pre-B-cell transformation by v-Abl oncogene", *Blood*, vol. 111 (3), 1677-1685 (2008).
Patent Cooperation Treaty, International Searching Authority, Search Report and Written Opinion for PCT/US2012/026572, 10 pages, Jun. 12, 2012.
Pierce et al., "Docking Study Yields Four Novel Inhibitors of the Protooncogene Pim-1 Kinase", *J. Med. Chem.*, 51, 1972-1975 (2008).
Wilson et al., "Alkylation Studies with Aminotetrazoles", *Journal of Organic Chemistry 24*, 1046-1051 (1959).

*Primary Examiner* — Janet L Andres
*Assistant Examiner* — Timothy R Rozof
(74) *Attorney, Agent, or Firm* — Viksnins Harris & Padys PLLP; Sarah S. Mastous

(57) ABSTRACT

Compounds of Formula I: in which $R^1$, $R^2$, $R^3$, $R^4$ and $R^{10}$ have the meanings given in the specification, are receptor tyrosine inhibitors useful in the treatment of diseases mediated by PIM-1 and/or PIM-2 and/or PIM-3 kinases.

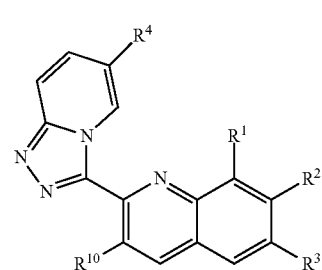

I

26 Claims, No Drawings

TRIAZOLOPYRIDINE COMPOUNDS AS PIM KINASE INHIBITORS

BACKGROUND OF THE INVENTION

The present invention relates to novel compounds, to pharmaceutical compositions comprising the compounds, to a process for making the compounds and to the use of the compounds in therapy. More particularly, it relates to certain triazolopyridine compounds useful in the treatment and prevention of diseases which can be treated with a PIM kinase inhibitor, including diseases mediated by PIM kinases. Particular compounds of this invention have been found to be inhibitors of PIM-1 and/or PIM-2 and/or PIM-3.

Protein kinases constitute a family of structurally related enzymes that are responsible for the control of a vast array of cellular processes.

The PIM kinase sub-family consists of three distinct serine/threonine protein kinase isoforms (PIM-1, -2 and -3) belonging to the calmodulin-dependent protein kinase-related (CAMK) group. PIM-2 and PIM-3 are respectively 58% and 69% identical to PIM-1 at the amino acid level.

The over-expression of PIM-1 has been reported in various human lymphomas and acute leukemias (Amson, R. et al., *Proc. Natl. Acad. Sci. U.S.A.,* 1989, 86: 8857-8861). PIM-1 has been shown to synergize with c-Myc to drive lymphomagenesis (Breuer M., et al., *Nature,* 1989, 340; 61-63), and plays an important role in cytokine signaling in T-cell development (Schmidt, T., et al., *EMBO J,* 1998, 17:5349-5359). In addition, there is evidence that PIM-1 is over-expressed in prostatic neoplasia and human prostate cancer (Valdman, A. et al., *The Prostate,* 2004, 60: 367-371; Cibull, T. L. et al., *J. Clin. Pathol.,* 2006, 59: 285-288) and may serve as a useful biomarker in identification of prostate cancer (Dhanasekaran, S. M. et al., *Nature,* 2001, 412(13): 822-826). PIM-1 has been shown to be critical for IL-6 mediated proliferation of hematopoietic cells (Hirano, T., et al., *Oncogene* 2000, 19:2548-2556), as well as STAT3 mediated cell cycle progression (Shirogane, T., et al., *Immunity* 1999, 11:709.

Recently, it has been discovered that PIM-1 is up-regulated by Flt-3 and may play an important role in Flt-3 mediated cell survival (Kim, K. T. et al *Neoplasia,* 2005, 105(4): 1759-1767). Since Flt-3 itself is implicated in leukemias like AML, additional knockdown of PIM-1 may be a useful approach to treating leukemias driven by Flt-3 or various mutations. Accordingly, PIM-1 inhibitors may be useful as therapeutic agents for a variety of cancers such as hematological cancers.

PIM-2 is a highly conserved serine/threonine kinase involved in cell proliferation and the prevention of apoptosis (Baytel et al., Biochim. Biophys. Acta Gene Struct. Expr. 1442: 274 (1998)). PIM-2 is upregulated in AML, CLL, and possibly in prostate cancer.

PIM-3 is a proto-oncogene identified in pancreatic liver and colon cancers, and is an apoptotic regulator (Popivanova, B., et al., Cancer Sci., 98(3): 321 (2007)).

Based upon the direct involvement of the PIM kinases in a wide variety of cancers downstream of STAT3/5 activation, it is expected that inhibition of the PIM kinases will result in inhibition of proliferation and survival of multiple cancer cell types. This would then be expected to provide a therapeutic benefit to cancer patients with a variety of cancers (both solid tumor and hematologic settings), as well as other conditions that are mediated by PIM kinase signaling.

In addition to the malignant cells detailed above, PIM kinases are also expressed in hematopoietically-derived cell lines and hematopoietically-derived primary cells including cells of the immune system such as B cells, T cells, monocytes, macrophages, eosinophils, basophils, and dendritic cells. Expression of PIM kinases can be induced, for example, by cytokines which utilize Jak/Stat signaling, such as IL-2, IL-3, IL-4, IL-5, IL-6, IL-7, IL-9, IL-12, IL-15, GM-CSF, IFNα, IFNγ, erythropoietin, thrombopoietin, and prolactin, and the generation, differentiation, maintenance and activation of hematopoietically-derived cells is dependent on these cytokines. Moreover, PIM proteins have been shown to be required for the efficient proliferation of peripheral T cells mediated by T-cell receptor and IL-2 signaling (Mikkers, et al., Mol. Cell. Biol., 2004, 6104). Although the exact mechanism of action of PIM kinases in an immunological setting has yet to be fully defined, they have been reported to phosphorylate a number of substrates involved in cellular proliferation, differentiation, and survival (Bullock et al., J. Biol. Chem., 2005 280:41675; Chen et al., PNAS 2002 99:2175; Dautry et al. J. Biol. Chem. 1998 263:17615).

Chronic and acute inflammatory and autoimmune diseases are associated with the overproduction of pro-inflammatory cytokines and activation of immune cells against the body's own tissues. However, many of these diseases are not adequately treated by current therapies and/or these therapies have significant side effects/risks.

A particular example of an autoimmune disease is multiple sclerosis (MS). MS is a progressive central nervous system (CNS) inflammatory autoimmune disease wherein the immune system mounts responses against CNS components. The resulting damage to axons and nerves leads to progressive neurological impairment and significant disability. MS affects over 2.5 million people worldwide (www.nationalmssociety.org); however many current therapies are only moderately effective and have questionable risk factors A need therefore remains for compounds and methods for treating autoimmune and inflammatory diseases.

International patent application, publication number WO 2004/058769 discloses, inter alia, certain 3-aryl and 3-N-arylamino-substituted [1,2,4]triazolo[4,3-b]pyridazines purported to inhibit several protein kinases, including PIM-1.

SUMMARY OF THE INVENTION

It has now been found that [1,2,4]triazolo[4,3-a]pyridine compounds bearing a quinolinyl group at the 3 position of the triazolopyridine ring are inhibitors of PIM kinases, in particular PIM-1 and/or PIM-2 and/or PIM-3 kinases, which are useful for treating diseases such as cancers and inflammatory diseases.

More specifically, one aspect of the present invention provides compounds of Formula I:

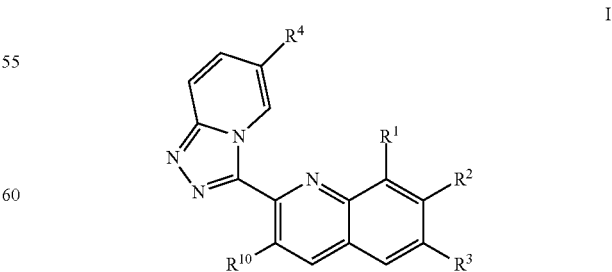

and stereoisomers, pharmaceutically acceptable salts and solvates thereof, wherein $R^1$, $R^2$, $R^3$, $R^4$ and $R^{10}$ are as defined herein.

Another aspect of the present invention provides compounds of Formula I having the Formula IA:

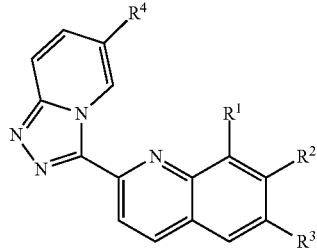

IA and stereoisomers, pharmaceutically acceptable salts and solvates thereof, wherein $R^1$, $R^2$, $R^3$, and $R^4$ are as defined herein.

Another aspect of the present invention provides methods of preventing or treating a disease or disorder modulated by PIM-1 and/or PIM-2 and/or PIM-3, comprising administering to a mammal in need of such treatment an effective amount of a compound of this invention or a stereoisomer, prodrug or pharmaceutically acceptable salt thereof. Examples of such diseases and disorders include, but are not limited to, immune cell-associated diseases and disorders, such as inflammatory and autoimmune diseases.

Another aspect of the present invention provides a pharmaceutical composition comprising a compound of the present invention or a pharmaceutically acceptable salt thereof.

Another aspect of the present invention provides the compounds of the present invention for use in therapy.

Another aspect of the present invention provides the compounds of the present invention for use in the treatment of immune cell-associated diseases. In one embodiment, the immune cell-associated disease is an inflammatory disease. In one embodiment, the immune cell-associated disease is an autoimmune disease.

Another aspect of the present invention provides the compounds of the present invention for use in the treatment of cancer.

Another aspect of the present invention provides the use of a compound of this invention in the manufacture of a medicament for the treatment of immune cell-associated diseases and disorders, such as inflammatory and autoimmune diseases.

Another aspect of the present invention provides the use of a compound of this invention in the manufacture of a medicament for the treatment of cancer.

Another aspect of the present invention provides intermediates for preparing compounds of Formula I.

Another aspect of the present invention includes methods of preparing, methods of separation, and methods of purification of the compounds of this invention.

DETAILED DESCRIPTION OF THE INVENTION

Provided herein are compounds, and pharmaceutical formulations thereof, that are potentially useful in the treatment of diseases, conditions and/or disorders modulated by PIM-1 and/or PIM-2 and/or PIM-3.

One embodiment provides compounds of Formula I having the formula:

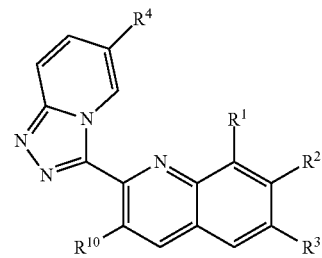

I and stereoisomers, pharmaceutically acceptable salts and solvates thereof, wherein:

$R^1$ is H, halogen, CN, OH, (1-6C)alkyl, fluoro(1-6C)alkyl, difluoro(1-6C)alkyl, trifluoro(1-6C)alkyl, hydroxy(1-6C)alkyl, cyano(1-6C)alkyl, (1-3C alkoxy)(1-6C)alkyl (optionally substituted with hydroxy), di(1-3C alkoxy)(1-6C)alkyl, (1-6C)alkoxy, fluoro(1-6C)alkoxy, difluoro(1-6C)alkoxy, trifluoro(1-6C)alkoxy, hydroxy(2-6C)alkoxy, cyano(1-6C)alkoxy, (1-3C alkoxy)(2-6C)alkoxy, di(1-3C alkoxy)(2-6C)alkoxy, (3-6C cycloalkyl)methoxy, oxetanylmethoxy (optionally substituted with methyl), (1-6C alkyl)sulfanyl, —C(=O)NR$^a$R$^b$, —CH$_2$C(=O)NR$^e$R$^d$, or (3-6C)cycloalkyl optionally substituted with —CH$_2$OH or —CH$_2$O(1-4C alkyl);

$R^a$, $R^b$, $R^e$ and $R^d$ are independently selected from H and (1-4C)alkyl;

$R^2$ is H, halogen, CN, OH, (1-6C)alkyl, fluoro(1-6C)alkyl, difluoro(1-6C)alkyl, trifluoro(1-6C)alkyl, hydroxy(1-6C)alkyl, (1-3C alkoxy)(1-6C)alkyl, (1-6C)alkoxy (optionally substituted with (1-6C alkyl)C(=O)O—, amino(1-6C alkyl)C(=O)O—, or phenyl(C=O)O—), fluoro(1-6C)alkoxy, difluoro(1-6C)alkoxy, trifluoro(1-6C)alkoxy, hydroxy(2-6C)alkoxy, (1-3C alkoxy)(2-6C)alkoxy, (3-6C cycloalkyl)methoxy, (3-6C)cycloalkoxy (optionally substituted with OH), oxetanylmethoxy (optionally substituted with methyl), tetrahydropyranyloxy, (1-6C alkyl)sulfanyl, hydroxy(2-6C alkyl)sulfanyl, (1-3C alkylsulfanyl)(2-6C)alkoxy, —COOH, hetAr$^1$, —C(=O)NR$^e$R$^f$, —NR$^e$C(=O)R$^f$, oxetanyl, or cyclopropyl optionally substituted with —CH$_2$OH or —CH$_2$O(1-6C alkyl);

or $R^1$ and $R^2$ together with the atoms to which they are attached form a 5-6 membered heterocyclic ring having 1-2 ring heteroatoms independently selected from O and N, wherein said ring is optionally substituted with (1-4C)alkyl;

hetAr$^1$ is a 5-6 membered heteroaryl ring having one or two ring nitrogen atoms and optionally substituted with one or more groups selected from (1-6C)alkyl;

$R^e$ and $R^f$ are independently H, (1-6C)alkyl or cyclopropyl optionally substituted with (1-4C)alkyl;

$R^3$ is H, halogen or (1-6C)alkyl;

$R^4$ is

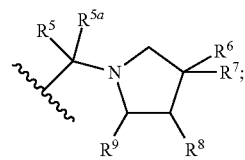

$R^5$ is CF$_3$, CH$_2$F, CHF$_2$, methyl or ethyl;
$R^{5a}$ is H or methyl;
or $R^5$ and $R^{5a}$ together with the atom to which they are attached form a cyclopropyl ring;

$R^6$ is H, $NH_2$, OH, (1-6C alkyl)NH—, fluoro(1-6C alkyl)NH—, hydroxy(1-6C alkyl)NH—, (3-6C cycloalkyl)$CH_2$NH—, (1-6C alkyl)C(=O)NH—, (1-6C alkyl)OC(=O)NH— (optionally substituted with 5-methyl-2-oxo-1,3-dioxol-4-yl), or amino(1-6C)alkyl-;

$R^7$ is H, (1-6C)alkyl, fluoro(1-6C)alkyl or hydroxy(1-6C)alkyl;

or $R^6$ and $R^7$ together with the atom to which they are attached form a 5-6 membered spirocyclic heterocycle having a ring nitrogen atom;

$R^8$ is H, halogen, OH, or (1-6C)alkoxy, or $R^6$ and $R^8$ together with the carbon atoms to which they are attached form a cyclopropyl ring optionally substituted with $NH_2$;

$R^9$ is H, or $R^6$ and $R^9$ together form a linking group having the formula —$CH_2$NH— which links the carbon atoms to which they are attached; and $R^{10}$ is H or halogen.

In one embodiment, compounds of Formula I include compounds having the Formula IA:

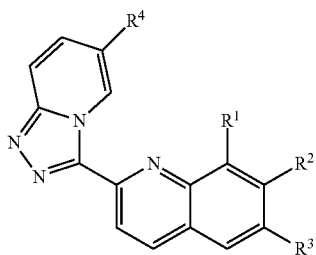

IA and stereoisomers, pharmaceutically acceptable salts and solvates thereof, wherein:

$R^1$ is H, halogen, CN, OH, (1-6C)alkyl, fluoro(1-6C)alkyl, difluoro(1-6C)alkyl, trifluoro(1-6C)alkyl, hydroxy(1-6C)alkyl, cyano(1-6C)alkyl, (1-3C alkoxy)(1-6C)alkyl (optionally substituted with hydroxy), di(1-3C alkoxy)(1-6C)alkyl, (1-6C)alkoxy, fluoro(1-6C)alkoxy, difluoro(1-6C)alkoxy, trifluoro(1-6C)alkoxy, hydroxy(2-6C)alkoxy, cyano(1-6C)alkoxy, (1-3C alkoxy)(2-6C)alkoxy, di(1-3C alkoxy)(2-6C)alkoxy, (3-6C cycloalkyl)methoxy, oxetanylmethoxy (optionally substituted with methyl), (1-6C alkyl)sulfanyl, —C(=O)$NR^aR^b$, —$CH_2$C(=O)$NR^cR^d$, or (3-6C)cycloalkyl optionally substituted with —$CH_2$OH or —$CH_2$O(1-4C alkyl);

$R^a$, $R^b$, $R^c$ and $R^d$ are independently selected from H and (1-4C)alkyl;

$R^2$ is H, halogen, CN, OH, (1-6C)alkyl, fluoro(1-6C)alkyl, difluoro(1-6C)alkyl, trifluoro(1-6C)alkyl, hydroxy(1-6C)alkyl, (1-3C alkoxy)(1-6C)alkyl, (1-6C)alkoxy (optionally substituted with (1-6C alkyl)C(=O)O— or amino(1-6C alkyl)C(=O)O—), fluoro(1-6C)alkoxy, difluoro(1-6C)alkoxy, trifluoro(1-6C)alkoxy, hydroxy(2-6C)alkoxy, (1-3C alkoxy)(2-6C)alkoxy, (3-6C cycloalkyl)methoxy, oxetanylmethoxy (optionally substituted with methyl), tetrahydropyranyloxy, (1-6C alkyl)sulfanyl, hydroxy(2-6C alkyl)sulfanyl, (1-3C alkylsulfanyl)(2-6C)alkoxy, —COOH, hetAr$^1$, —C(=O)$NR^eR^f$, —$NR^e$C(=O)$R^f$, or cyclopropyl optionally substituted with —$CH_2$OH or —$CH_2$O(1-6C alkyl);

or $R^1$ and $R^2$ together with the atoms to which they are attached form a 5-6 membered heterocyclic ring having 1-2 ring heteroatoms independently selected from O and N, wherein said ring is optionally substituted with (1-4C)alkyl;

hetAr$^1$ is a 5-6 membered heteroaryl ring having one or two ring nitrogen atoms and optionally substituted with one or more groups selected from (1-6C)alkyl;

$R^e$ and $R^f$ are independently H, (1-6C)alkyl or cyclopropyl optionally substituted with (1-4C)alkyl;

$R^3$ is H, halogen or (1-6C)alkyl;

$R^4$ is

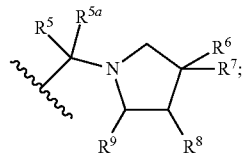

$R^5$ is $CF_3$, $CH_2$F, $CHF_2$, methyl or ethyl;

$R^{5a}$ is H or methyl;

or $R^5$ and $R^{5a}$ together with the atom to which they are attached form a cyclopropyl ring;

$R^6$ is H, $NH_2$, OH, (1-6C alkyl)NH—, fluoro(1-6C alkyl)NH—, hydroxy(1-6C alkyl)NH—, (3-6C cycloalkyl)$CH_2$NH—, (1-6C alkyl)C(=O)NH—, (1-6C alkyl)OC(=O)NH— or amino(1-6C)alkyl-;

$R^7$ is H, (1-6C)alkyl, fluoro(1-6C)alkyl or hydroxy(1-6C)alkyl;

or $R^6$ and $R^7$ together with the atom to which they are attached form a 5-6 membered spirocyclic heterocycle having a ring nitrogen atom;

$R^8$ is H, halogen, OH, or (1-6C)alkoxy, or $R^6$ and $R^8$ together with the carbon atoms to which they are attached form a cyclopropyl ring optionally substituted with $NH_2$; and $R^9$ is H, or $R^6$ and $R^9$ together form a linking group having the formula —$CH_2$NH— which links the carbon atoms to which they are attached.

The terms "(1-6C)alkyl", "(1-4C)alkyl" and "(1-3C)alkyl" as used herein refers to saturated linear or branched-chain monovalent hydrocarbon radicals of one to six carbon atoms, one to four carbon atoms, and one to three carbon atoms, respectively. Examples include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

The terms "fluoro(1-6C)alkyl," "hydroxy(1-6C)alkyl," "cyano(1-6C)alkyl," "amino(1-6C)alkyl" and "(1-3C alkoxy)(1-6C)alkyl" as used herein refer to a (1-6C)alkyl group as defined herein, wherein one of the hydrogen atoms is replaced with fluorine or a hydroxy, cyano (N≡C—), amino or (1-3C) alkoxy group, respectively.

The term "difluoro(1-6C)alkyl" as used herein refers to a (1-6C)alkyl group as defined herein, wherein two of the hydrogen atoms are each replaced with fluorine.

The term "trifluoro(1-6C)alkyl" as used herein refers to a (1-6C)alkyl group as defined herein, wherein three of the hydrogen atoms are each replaced with fluorine.

The term "di(1-3Calkoxy)(1-6C)alkyl" as used herein refers to a (1-6C)alkyl group as defined herein, wherein two of the hydrogen atoms on the alkyl portion are each replaced with a (1-3C)alkoxy group.

The terms "(1-6C)alkoxy" and "(1-4C)alkoxy" and "(2-6C)alkoxy" as used herein refers to saturated linear or branched-chain monovalent alkyl ether radicals of one to six carbon atoms, one to four carbon atoms, or two to six carbon atoms, respectively, wherein the term "alkyl" is as defined above and the radical is on the oxygen atom. Examples include methoxy, ethoxy, propoxy, isopropoxy, and butoxy.

The terms "fluoro(1-6C)alkoxy", "difluoro(1-6C)alkoxy", and trifluoro(1-6C)alkoxy" as used herein refer to (1-6C) alkoxy groups as defined herein, wherein one, two or three of the hydrogen atoms of the alkoxy group are each replaced by fluorine, respectively.

The terms "hydroxy(2-6C)alkoxy," "cyano(1-6C)alkoxy," and "(1-3C alkoxy)(2-6C)alkoxy" as used herein refer to (2-6C)alkoxy groups and (1-6C)alkoxy groups as defined herein, wherein one of the hydrogen atoms of the alkoxy group is replaced by a hydroxy, cyano (N≡C—), or a (1-3C) alkoxy group, respectively.

The term "(3-6C)cycloalkyl" as used herein refers to a cyclopropyl, cyclobutyl cyclopentyl or cyclohexyl ring.

The term "(3-6C cycloalkyl)methoxy" as used herein refers to a methoxy radical wherein one of the hydrogen atoms is replace by a (3-6C cycloalkyl) group as defined herein.

The terms "(1-6C alkyl)sulfanyl," "(1-4C alkyl)sulfanyl" and (1-3C alkyl)sulfanyl as used herein refer to a (1-6C alkyl) S—, (1-4C alkyl)S— or (1-3C alkyl)S— group, respectively, wherein the radical is on the sulfur atom and the (1-6C alkyl) portion is as defined above. Examples include methylsulfanyl (CH₃S—), ethylsulfanyl (CH₂CH₂S—) and isopropylsulfanyl ((CH₃)₂CHS—).

The terms "(1-3C alkylsulfanyl)(2-6C)alkoxy" and "(1-3C alkylsulfanyl)(2-4C)alkoxy" as used herein refer to a (2-6C) alkoxy group or a (2-4C)alkoxy group, respectively, as defined herein, wherein a carbon atom of the alkoxy group is substituted with a (1-3C alkyl)sulfanyl group as defined herein.

The term "hydroxy(2-6C alkyl)sulfanyl" as used herein refers to a (2-6C alkyl)sulfanyl group as defined herein, wherein one of the hydrogen atoms is replace by a hydroxy.

The term "oxetanylmethoxy" as used herein refers to a methoxy radical wherein one of the hydrogen atoms is replace by an oxetanyl group.

The term "halogen" as used herein means F, Cl, Br or I.

When words are used to describe a substituent, the right-most-described component of the substituent is the component that has the free valence. To illustrate, cyclopropyl-methoxy refers to a methoxy radical, wherein the radical is on the oxygen atom and the carbon atom of the methoxy radical is substituted with a cyclopropyl group as shown:

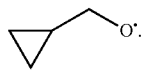

In one embodiment, $R^1$ is H.

In one embodiment, $R^1$ is halogen. In one embodiment, $R^1$ is selected from F and Cl. In one embodiment, $R^1$ is F. In one embodiment, $R^1$ is Cl.

In one embodiment, $R^1$ is CN.

In one embodiment, $R^1$ is OH.

In one embodiment, $R^1$ is (1-6C)alkyl. In one embodiment, $R^1$ is (1-4C)alkyl.

In one embodiment, $R^1$ is selected from methyl, ethyl, isopropyl, and tert-butyl.

In one embodiment, $R^1$ is fluoro(1-6C)alkyl. In one embodiment, $R^1$ is fluoro(1-4C)alkyl. In one embodiment, $R^1$ is fluoromethyl.

In one embodiment, $R^1$ is difluoro(1-6C)alkyl. In one embodiment, $R^1$ is difluoro(1-4C)alkyl. In one embodiment, $R^1$ is difluoromethyl.

In one embodiment, $R^1$ is trifluoro(1-6C)alkyl. In one embodiment, $R^1$ is trifluoro(1-4C)alkyl. In one embodiment, $R^1$ is trifluoromethyl.

In one embodiment, $R^1$ is hydroxy(1-6C)alkyl. In one embodiment, $R^1$ is 4-hydroxy-2-methylbut-2-yl, 2-hydroxyprop-2-yl and 3-hydroxy-2-methylprop-2-yl, which can be represented by the structures:

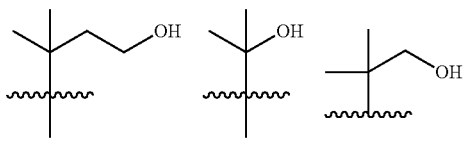

respectively.

In one embodiment, $R^1$ is cyano(1-6C)alkyl. In one embodiment, $R^1$ is cyano(1-4C)alkyl. In one embodiment, $R^1$ is 2-cyanoprop-2-yl which can be represented by the structure:

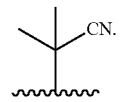

In one embodiment, $R^1$ is (1-3C alkoxy)(1-6C)alkyl optionally substituted with hydroxy. In one embodiment, $R^1$ is (1-3C alkoxy)(1-4C)alkyl. In one embodiment, $R^1$ is 2-methoxyethyl, 1-methyl-3-methoxyprop-2-yl or methoxymethyl which can be represented by the structures:

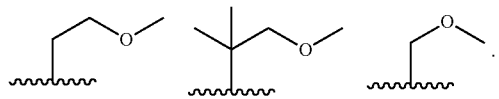

In one embodiment, $R^1$ is di(1-3C alkoxy)(1-6C)alkyl. In one embodiment, $R^1$ is di(1-3C alkoxy)(1-4C)alkyl. In one embodiment, $R^1$ is (1-4C)alkyl substituted by two methoxy groups. In one embodiment, $R^1$ is 1,3-dimethoxy-2-methylpropan-2-yl which can be represented by the structure:

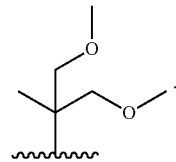 [SMILES: *C(C)(COC)COC]

In one embodiment, $R^1$ is (1-6C)alkoxy. In one embodiment, $R^1$ is (1-4C)alkoxy. In one embodiment, $R^1$ is methoxy, ethoxy or isopropoxy.

In one embodiment, $R^1$ is fluoro(1-6C)alkoxy. In one embodiment, $R^1$ is fluoro(1-4C)alkoxy. In one embodiment, $R^1$ is fluoromethoxy.

In one embodiment, $R^1$ is difluoro(1-6C)alkoxy. In one embodiment, $R^1$ is difluoro(1-4C)alkoxy. In one embodiment, $R^1$ is difluoromethoxy.

In one embodiment, $R^1$ is trifluoro(1-6C)alkoxy. In one embodiment, $R^1$ is trifluoro(1-4C)alkoxy. In one embodiment, $R^1$ is trifluoromethoxy or 2,2,2-trifluoroethoxy.

In one embodiment, $R^1$ is trifluoromethoxy.

In one embodiment, $R^1$ is hydroxy(2-6C)alkoxy. In one embodiment, $R^1$ is hydroxy(2-4C)alkoxy. In one embodiment, $R^1$ is 2-hydroxyethoxy, 2-hydroxyisopropoxy, 2-hydroxypropoxy, 2-hydroxy-2-methylpropoxy or 3-hydroxypropoxy, which can be represented by the structures:

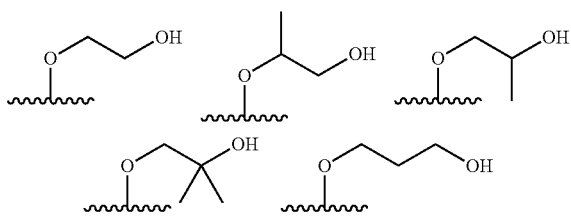

respectively.

In one embodiment, $R^1$ is cyano(1-6C)alkoxy. In one embodiment, $R^1$ is cyano(1-4C)alkoxy. In one embodiment, $R^1$ is cyanomethoxy, which can be represented by the structure:

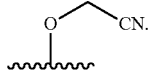

In one embodiment, $R^1$ is (1-3C alkoxy)(2-6C)alkoxy. In one embodiment, $R^1$ is (1-3C alkoxy)(2-4C)alkoxy. In one embodiment, $R^1$ is (2-4C)alkoxy substituted by methoxy. In one embodiment, $R^1$ is 2-methoxyethoxy, 3-methoxypropoxy, 2-methoxypropoxy, 3-methoxyprop-2-oxy, 2-methyl-2-methoxypropoxy or 2-methyl-3-methoxypropoxy, which can be represented by the structures:

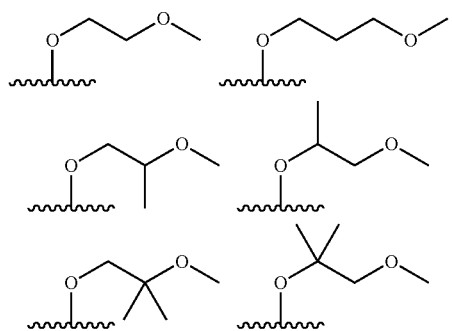

respectively.

In one embodiment, $R^1$ is di(1-3C alkoxy)(2-6C)alkoxy. In one embodiment, $R^1$ is di(1-3C alkoxy)(2-4C)alkoxy. In one embodiment, $R^1$ is 1,3-dimethoxypropan-2-yloxy which can be represented by the structure:

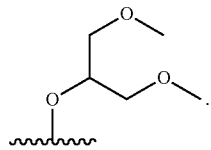 [SMILES: *OC(COC)COC]

In one embodiment, $R^1$ is (3-6C cycloalkyl)methoxy. In one embodiment, $R^1$ is cyclopropylmethoxy, which can be represented by the structure:

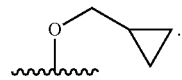

In one embodiment, $R^1$ is oxetanylmethoxy optionally substituted by methyl. In one embodiment, $R^1$ is (3-methyloxetan-3-yl)methoxy which can be represented by the structure:

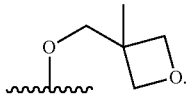 [SMILES: *OCC1(C)COC1]

In one embodiment, $R^1$ is (1-6C alkyl)sulfanyl. In one embodiment, $R^1$ is (1-4C alkyl)sulfanyl. In one embodiment, $R^1$ is ethylsulfanyl, which can be represented by the structure:

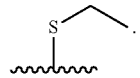

In one embodiment, $R^1$ is C(=O)$NR^aR^b$. In one embodiment, $R^a$ is hydrogen.

In one embodiment, $R^a$ is (1-6C alkyl). In one embodiment, $R^a$ is (1-4C alkyl). In one embodiment, $R^b$ is hydrogen. In one embodiment, $R^b$ is (1-6C alkyl). In one embodiment, $R^b$ is (1-4C alkyl). In one embodiment, $R^b$ is methyl or isopropyl. In one embodiment, $R^1$ is —C(=O)NHCH(CH$_3$)$_2$.

In one embodiment, $R^1$ is CH$_2$C(=O)$NR^cR^d$. In one embodiment, $R^c$ is hydrogen. In one embodiment, $R^c$ is (1-6C alkyl). In one embodiment, $R^c$ is (1-4C alkyl). In one embodiment, $R^c$ is methyl. In one embodiment, $R^d$ is hydrogen. In one embodiment, $R^d$ is (1-6C alkyl). In one embodiment, $R^d$ is (1-4C alkyl). In one embodiment, $R^d$ is methyl, ethyl or isopropyl. In one embodiment, $R^1$ is —CH$_2$(C=O)NHCH$_2$CH$_3$ or —CH$_2$(C=O)N(CH$_3$)$_2$.

In one embodiment, $R^1$ is (3-6C)cycloalkyl optionally substituted with —CH$_2$OH or —CH$_2$O(1-4C alkyl). In one embodiment, $R^1$ is (3-6C)cycloalkyl optionally substituted with —CH$_2$OH or —CH$_2$OCH$_3$. In one embodiment, $R^1$ is cyclopropyl optionally substituted with —CH$_2$OH or —CH$_2$OCH$_3$. In one embodiment, $R^1$ is cyclopropyl, hydroxymethylcyclopropyl or (methoxymethyl)cyclopropyl, which can be represented by the structures:

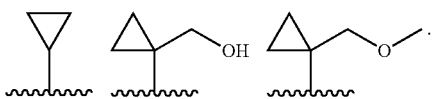

In one embodiment, $R^1$ is selected from H, F, Cl, CN, OH, methyl, ethyl, isopropyl, tert-butyl, trifluoromethyl, 4-hydroxy-2-methylbut-2-yl, 2-hydroxyprop-2-yl, 3-hydroxy-2-methylprop-2-yl, 2-cyanoprop-2-yl, 2-methoxyethyl, 1-methyl-3-methoxyprop-2-yl, methoxymethyl, 1,3-dimethoxy-2-methylpropan-2-yl, methoxy, ethoxy, isopropoxy, difluoromethoxy, trifluoromethoxy, 2-hydroxyethoxy, 2-hydroxyisopropoxy, 2-hydroxypropoxy, 2-hydroxy-2-methylpropoxy, 3-hydroxypropoxy, cyanomethoxy, 2-methoxyethoxy, 3-methoxypropoxy, 2-methoxypropoxy, 3-methoxyprop-2-oxy, 2-methyl-2-methoxypropoxy, 2-methyl-3-methoxypropoxy, 1,3-dimethoxypropan-2-yloxy, cyclopropylmethoxy, (3-methyloxetan-3-yl)methoxy, ethylsulfanyl, —C(=O)NHCH(CH$_3$)$_2$, —CH$_2$(C=O)NHCH$_2$CH$_3$, —CH$_2$(C=O)N(CH$_3$)$_2$, cyclopropyl, hydroxymethylcyclopropyl and (methoxymethyl)cyclopropyl.

In one embodiment, $R^1$ is selected from H, (1-6C)alkyl, (3-6C)cycloalkyl optionally substituted with —CH$_2$OH or —CH$_2$O(1-4C alkyl), (1-6C)alkoxy, trifluoro(1-6C)alkoxy, hydroxy(2-6C)alkoxy, (1-3C alkoxy)(2-6C)alkoxy, and (3-6C)cycloalkylmethoxy.

In one embodiment, $R^1$ is selected from H, methyl, ethyl, isopropyl, tert-butyl, cyclopropyl, methoxy, ethoxy, isopropoxy, trifluoromethoxy, 2-hydroxyethoxy, 2-hydroxypropoxy, 3-hydroxypropoxy, 2-methoxyethoxy, 3-methoxypropoxy, 2-methoxypropoxy, 3-methoxyprop-2-oxy, 2-ethoxyethoxy, 1,3-dimethoxypropan-2-yloxy and cyclopropylmethoxy.

In one embodiment, $R^1$ is selected from halogen, CN, OH, fluoro(1-6C)alkyl, difluoro(1-6C)alkyl, trifluoro(1-6C)alkyl, hydroxy(1-6C)alkyl, cyano(1-6C)alkyl, di(1-3C alkoxy)(1-6C)alkyl, fluoro(1-6C)alkoxy, difluoro(1-6C)alkoxy, trifluoro(1-6C)alkoxy, cyano(1-6C)alkoxy, di(1-3C alkoxy)(2-6C)alkoxy, oxetanylmethoxy (optionally substituted with methyl), (1-6C alkyl)sulfanyl, —C(=O)NR$^a$R$^b$, and —CH$_2$C(=O)NR$^c$R$^d$.

In one embodiment, $R^2$ is H.

In one embodiment, $R^2$ is halogen. In one embodiment, $R^2$ is selected from F, Br and Cl. In one embodiment, $R^2$ is F. In one embodiment, $R^2$ is Br. In one embodiment, $R^2$ is Cl.

In one embodiment, $R^2$ is CN.

In one embodiment, $R^2$ is OH.

In one embodiment, $R^2$ is (1-6C)alkyl. In one embodiment, $R^2$ is methyl.

In one embodiment, $R^2$ is fluoro(1-6C)alkyl. In one embodiment, $R^2$ is fluoro(1-4C)alkyl. In one embodiment, $R^2$ is fluoromethyl.

In one embodiment, $R^2$ is difluoro(1-6C)alkyl. In one embodiment, $R^2$ is difluoro(1-4C)alkyl. In one embodiment, $R^2$ is difluoromethyl.

In one embodiment, $R^2$ is trifluoro(1-6C)alkyl. In one embodiment, $R^2$ is trifluoro(1-4C)alkyl. In one embodiment, $R^2$ is trifluoromethyl.

In one embodiment, $R^2$ is hydroxy(1-6C)alkyl. In one embodiment, $R^2$ is hydroxy(1-4C)alkyl. In one embodiment, $R^2$ is 2-hydroxyethyl or 2-hydroxy-2-methylpropyl.

In one embodiment, $R^2$ is (1-3C alkoxy)(1-6C)alkyl. In one embodiment, $R^2$ is (1-3C alkoxy)(1-4C)alkyl. In one embodiment, $R^2$ is (1-4C)alkyl substituted by methoxy.

In one embodiment, $R^2$ is 2-methoxyethyl.

In one embodiment, $R^2$ is (1-6C)alkoxy optionally substituted with (1-6C alkyl)C(=O)O—, amino(1-6C alkyl)C(=O)O— or phenyl(C=O)O—. In one embodiment, $R^2$ is (1-6C)alkoxy optionally substituted with (1-6C alkyl)C(=O)O— or amino(1-6C alkyl)C(=O)O—. In one embodiment, $R^2$ is (1-4C)alkoxy optionally substituted with (1-6C alkyl)C(=O)O—, amino(1-6C alkyl)C(=O)O— or phenyl(C=O)O—. In one embodiment, $R^2$ is (1-4C)alkoxy optionally substituted with (1-6C alkyl)C(=O)O— or amino(1-6C alkyl)C(=O)O—. In one embodiment, $R^2$ is (1-4C)alkoxy optionally substituted with CH$_3$C(=O)O—, (CH$_3$)$_2$CHC(=O)O—, (CH$_3$CH$_2$)$_2$CHC(=O)O—, (CH$_3$CH$_2$)C(CH$_3$)$_2$C(=O)O—, NH$_2$CH[CH(CH$_3$)$_2$]C(=O)O— or phenyl(C=O)O—. In one embodiment, $R^2$ is (1-4C)alkoxy optionally substituted with CH$_3$C(=O)O—, (CH$_3$)$_2$CHC(=O)O—, (CH$_3$CH$_2$)$_2$CHC(=O)O—, (CH$_3$CH$_2$)C(CH$_3$)$_2$C(=O)O— or NH$_2$CH[CH(CH$_3$)$_2$]C(=O)O—. In one embodiment, $R^2$ is methoxy, ethoxy, isopropoxy, CH$_3$C(=O)OCH$_2$CH$_2$O—, (CH$_3$)$_2$CHC(=O)OCH$_2$CH$_2$O—, (CH$_3$CH$_2$)$_2$CHC(=O)OCH$_2$CH$_2$O—, (CH$_3$CH$_2$)C(CH$_3$)$_2$C(=O)OCH$_2$CH$_2$O— or NH$_2$CH[CH(CH$_3$)$_2$]C(=O)OCH$_2$CH$_2$O—.

In one embodiment, $R^2$ is fluoro(1-6C)alkoxy. In one embodiment, $R^2$ is fluoro(1-4C)alkoxy. In one embodiment, $R^2$ is fluoromethoxy.

In one embodiment, $R^2$ is difluoro(1-6C)alkoxy. In one embodiment, $R^2$ is difluoro(1-4C)alkoxy. In one embodiment, $R^2$ is difluoromethoxy.

In one embodiment, $R^2$ is trifluoro(1-6C)alkoxy. In one embodiment, $R^2$ is trifluoro(1-4C)alkoxy. In one embodiment, $R^2$ is trifluoromethoxy or 2,2,2-trifluoroethoxy.

In one embodiment, $R^2$ is hydroxy(2-6C)alkoxy. In one embodiment, $R^2$ is hydroxy(2-4C)alkoxy. In one embodiment, $R^2$ is 2-hydroxyethoxy.

In one embodiment, $R^2$ is (1-3C alkoxy)(2-6C)alkoxy. In one embodiment, $R^2$ is (1-3C alkoxy)(2-4C)alkoxy. In one embodiment, $R^2$ is (2-4C)alkoxy substituted by methoxy. In one embodiment, $R^2$ is 2-methoxyethoxy, 3-methoxyprop-2-oxy, 2-methoxypropoxy, or 2-ethyoxyethoxy, which can be represented by the structures:

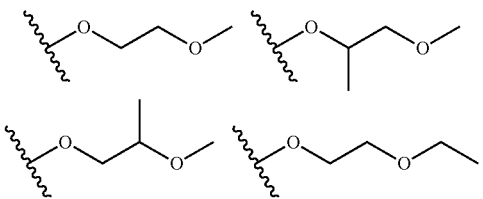

respectively.

In one embodiment, $R^2$ is (3-6C cycloalkyl)methoxy. In one embodiment, $R^2$ is cyclopropylmethoxy which can be represented by the structure:

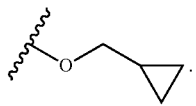

In one embodiment, $R^2$ is oxetanylmethoxy optionally substituted by methyl. In one embodiment, $R^2$ is (3-methyloxetan-3-yl)methoxy which can be represented by the structure:

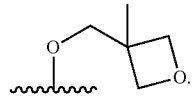

In one embodiment, R² is (3-6C)cycloalkoxy (optionally substituted with OH). In one embodiment, R² is cyclopentoxy optionally substituted with OH. In one embodiment, R² is 2-hydroxycylopentoxy.

In one embodiment, R² is tetrahydropyranyloxy, which can be represented by the structure:

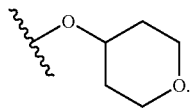

In one embodiment, R² is (1-6C alkyl)sulfanyl. In one embodiment, R² is (1-4C alkyl)sulfanyl. In one embodiment, R² is ethylsulfanyl or isopropylsulfanyl, which can be represented by the structures:

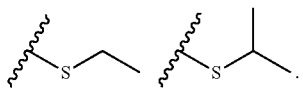

In one embodiment, R² is hydroxy(2-6C alkyl)sulfanyl. In one embodiment, R² is hydroxy(2-4C alkyl)sulfanyl. In one embodiment, R² is 2-hydroxyethylsulfanyl, which can be represented by the structure:

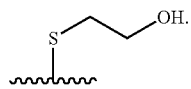 [SMILES: *SCCO]

In one embodiment, R² is (1-3C alkylsulfanyl)(2-6C)alkoxy. In one embodiment, R² is (1-3C alkylsulfanyl)(2-4C)alkoxy. In one embodiment, R² is 2-(methylsulfanyl)ethoxy, which can be represented by the structure:

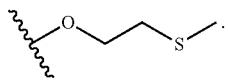 [SMILES: *OCCSC]

In one embodiment, R² is —COOH.

In one embodiment, R² is hetAr¹. In one embodiment, hetAr¹ is pyrazolyl or pyridinyl optionally substituted with one or more groups selected from (1-6C)alkyl. In one embodiment, hetAr¹ is pyrazolyl or pyridinyl optionally substituted with one or more methyl groups. Examples of R² when represented by hetAr¹ include 1,3-dimethyl-pyrazol-4-yl, 1,5-dimethyl-pyrazol-4-yl, 1-methylpyrazol-4-yl, 1,3-dimethylpyrazol-5-yl, 4-methylpyrazol-1-yl and pyrid-3-yl, which can be represented by the structures:

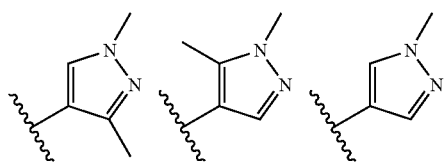

-continued

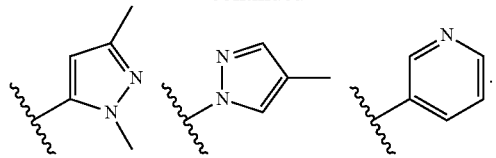

In one embodiment, R² is —C(=O)NR^eR^f. In one embodiment, R^e is hydrogen. In one embodiment, R^e is (1-6C alkyl). In one embodiment, R^e is (1-4C alkyl). In one embodiment, R^e is methyl. In one embodiment, R^f is hydrogen. In one embodiment, R^f is (1-6C alkyl). In one embodiment, R^f is (1-4C alkyl). In one embodiment, R^f is methyl, ethyl, or 2-methylbutyl. In one embodiment, R^f is cyclopropyl optionally substituted with (1-4C)alkyl. In one embodiment, R^f is cyclopropyl optionally substituted with methyl. In one embodiment, examples of R² when represented by —C(=O)NR^eR^f include methylcarbamoyl, ethylcarbamoyl, isopropylcarbamoyl, tert-butylcarbamoyl, isopentylcarbamoyl, 1-methylcyclpropylcarbamoyl and dimethylcarbamoyl, which can be represented by the structures:

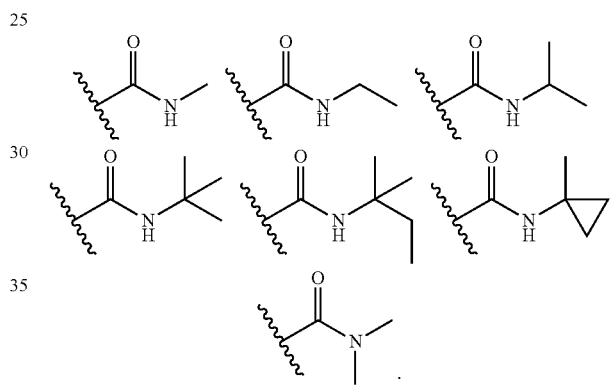

In one embodiment, R² is —NR^eC(=O)R^f. In one embodiment, R^e is hydrogen. In one embodiment, R^e is (1-6C alkyl). In one embodiment, R^e is (1-4C alkyl). In one embodiment, R^e is methyl. In one embodiment, R^f is hydrogen. In one embodiment, R^f is (1-6C alkyl). In one embodiment, R^f is (1-4C alkyl). In one embodiment, R^f is methyl, ethyl, propyl, isopropyl or tert-butyl. In one embodiment, examples of R² when represented by —NR^eC(=O)R^f include —NHC(=O)NHCH(CH₃)₂ and —NHC(=O)NHC(CH₃)₃, which can be represented by the structures:

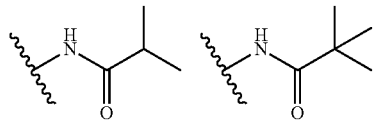

respectively.

In one embodiment, R² is oxetanyl.

In one embodiment, R² is cyclopropyl optionally substituted with CH₂OH or —CH₂O(1-6C alkyl). In one embodiment, R² is cyclopropyl optionally substituted with CH₂OH or CH₂OCH₃. In one embodiment, R² is selected from cyclopropyl, hydroxymethylcyclopropyl and methoxymethylcyclopropyl, which can be represented by the structures:

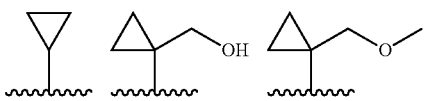

In one embodiment, $R^2$ is selected from H, F, Br, Cl, CN, OH, trifluoromethyl, 2-hydroxyethyl, 2-hydroxy-2-methylpropyl, 2-methoxyethyl, methoxy, ethoxy, isopropoxy, $CH_3C(=O)OCH_2CH_2O-$, $(CH_3)_2CHC(=O)OCH_2CH_2O-$, $(CH_3CH_2)_2CHC(=O)OCH_2CH_2O-$, $(CH_3CH_2)C(CH_3)_2C(=O)OCH_2CH_2O-$, $NH_2CH[CH(CH_3)_2]C(=O)OCH_2CH_2O-$, phenyl(C=O)O—, difluoro-methoxy, trifluoromethoxy, 2,2,2-trifluoroethoxy, 2-hydroxyethoxy, 2-methoxyethoxy, 3-methoxyprop-2-oxy, 2-methoxypropoxy, 2-ethyoxyethoxy, cyclopropylmethoxy, (3-methyloxetan-3-yl)methoxy, 2-hydroxycylopentoxy, tetrahydropyranyloxy, ethylsulfanyl, isopropylsulfanyl, 2-hydroxyethylsulfanyl, 2-(methylsulfanyl)ethoxy, —COOH, 1,3-dimethyl-pyrazol-4-yl, 1,5-dimethyl-pyrazol-4-yl, 1-methylpyrazol-4-yl, 1,3-dimethylpyrazol-5-yl, 4-methylpyrazol-1-yl pyrid-3-yl, methylcarbamoyl, ethylcarbamoyl, isopropylcarbamoyl, tert-butylcarbamoyl, isopentylcarbamoyl, 1-methylcyclopropylcarbamoyl, dimethylcarbamoyl, $—NH(C(=O)CH(CH_3)_2$, $—NHC(=O)NHC(CH_3)_3$, oxetanyl, cyclopropyl, hydroxymethylcyclopropyl and methoxymethyl-cyclopropyl.

In one embodiment, $R^2$ is selected from H, F, Br, Cl, CN, OH, trifluoromethyl, 2-hydroxyethyl, 2-hydroxy-2-methylpropyl, 2-methoxyethyl, methoxy, ethoxy, isopropoxy, $CH_3C(=O)OCH_2CH_2O-$, $(CH_3)_2CHC(=O)OCH_2CH_2O-$, $(CH_3CH_2)_2CHC(=O)OCH_2CH_2O-$, $(CH_3CH_2)C(CH_3)_2C(=O)OCH_2CH_2O-$, $NH_2CH[CH(CH_3)_2]C(=O)OCH_2CH_2O-$, difluoromethoxy, trifluoromethoxy, 2,2,2-trifluoroethoxy, 2-hydroxyethoxy, 2-methoxyethoxy, 3-methoxyprop-2-oxy, 2-methoxypropoxy, 2-ethyoxyethoxy, cyclopropylmethoxy, (3-methyloxetan-3-yl)methoxy, tetrahydropyranyloxy, ethylsulfanyl, isopropylsulfanyl, 2-hydroxyethylsulfanyl, 2-(methylsulfanyl)ethoxy, —COOH, 1,3-dimethyl-pyrazol-4-yl, 1,5-dimethyl-pyrazol-4-yl, 1-methylpyrazol-4-yl, 1,3-dimethylpyrazol-5-yl, 4-methylpyrazol-1-yl pyrid-3-yl, methylcarbamoyl, ethylcarbamoyl, isopropylcarbamoyl, tert-butylcarbamoyl, isopentylcarbamoyl, 1-methylcyclopropylcarbamoyl, dimethylcarbamoyl, $—NH(C(=O)CH(CH_3)_2$, $—NHC(=O)NHC(CH_3)_3$, cyclopropyl, hydroxymethylcyclopropyl and methoxymethyl-cyclopropyl.

In one embodiment, $R^2$ is selected from H, (1-3C alkoxy)(1-6C)alkyl, hydroxy(2-6C)alkoxy, and (1-6C)alkoxy which is optionally substituted with (1-6C alkyl)C(=O)O— or amino(1-6C alkyl)C(=O)O—.

In one embodiment, $R^2$ is selected from H, 2-methoxyethoxy, 3-methoxyprop-2-oxy, 2-methoxypropoxy, 2-ethyoxyethoxy, and 2-hydroxyethoxy.

In one embodiment, $R^2$ is selected from halogen, CN, OH, (1-6C)alkyl, fluoro(1-6C)alkyl, difluoro(1-6C)alkyl, trifluoro(1-6C)alkyl, hydroxy(1-6C)alkyl, fluoro(1-6C)alkoxy, difluoro(1-6C)alkoxy, trifluoro(1-6C)alkoxy, (1-3C alkoxy)(2-6C)alkoxy, (3-6C cycloalkyl)methoxy, oxetanylmethoxy (optionally substituted with methyl), tetrahydropyranyloxy, (1-6C alkyl)sulfanyl, hydroxy(2-6C alkyl)sulfanyl, (1-3C alkylsulfanyl)(2-6C)alkoxy, —COOH, hetAr$^1$, —C(=O)NR$^e$R$^f$, —NR$^e$C(=O)R$^f$, and cyclopropyl optionally substituted with —CH$_2$OH or —CH$_2$O(1-6C alkyl).

In one embodiment, $R^1$ and $R^2$ together with the atoms to which they are attached form a 5-6 membered heterocyclic ring having 1 to 2 ring heteroatoms independently selected from O and N, wherein said ring is optionally substituted with (1-4C)alkyl. In one embodiment, $R^1$ and $R^2$ together with the atoms to which they are attached form a 5 membered heterocyclic ring having a ring oxygen atom and optionally substituted with (1-4C)alkyl, such as methyl. A particular example of a ring formed by $R^1$ and $R^2$ together with the atoms to which they are attached includes the structure:

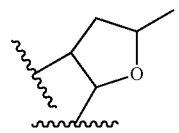

In one embodiment, $R^3$ is H.
In one embodiment, $R^3$ is halogen. In one embodiment, $R^3$ is F.
In one embodiment, $R^3$ is (1-6C)alkyl. In one embodiment, $R^3$ is (1-4C)alkyl.
In one embodiment, $R^3$ is methyl.
In one embodiment, $R^3$ is selected from H, F and methyl.
In one embodiment, $R^3$ is selected from H and F.

In one embodiment, $R^1$ is H; $R^2$ is H, F, Br, Cl, CN, OH, trifluoromethyl, 2-hydroxyethyl, 2-hydroxy-2-methylpropyl, 2-methoxyethyl, methoxy, ethoxy, isopropoxy, $CH_3C(=O)OCH_2CH_2O-$, $(CH_3)_2CHC(=O)OCH_2CH_2O-$, $(CH_3CH_2)_2CHC(=O)OCH_2CH_2O-$, $(CH_3CH_2)C(CH_3)_2C(=O)OCH_2CH_2O-$, $NH_2CH[CH(CH_3)_2]C(=O)OCH_2CH_2O-$, difluoromethoxy, trifluoromethoxy, 2,2,2-trifluoroethoxy, 2-hydroxyethoxy, 2-methoxyethoxy, 3-methoxyprop-2-oxy, 2-methoxypropoxy, 2-ethyoxyethoxy, cyclopropylmethoxy, (3-methyloxetan-3-yl)methoxy, tetrahydropyranyloxy, ethylsulfanyl, isopropylsulfanyl, 2-hydroxyethylsulfanyl, 2-(methylsulfanyl)ethoxy, —COOH, 1,3-dimethyl-pyrazol-4-yl, 1,5-dimethyl-pyrazol-4-yl, 1-methylpyrazol-4-yl, 1,3-dimethylpyrazol-5-yl, 4-methylpyrazol-1-yl pyrid-3-yl, methylcarbamoyl, ethylcarbamoyl, isopropylcarbamoyl, tert-butylcarbamoyl, isopentylcarbamoyl, 1-methylcyclopropylcarbamoyl, dimethylcarbamoyl, cyclopropyl, hydroxymethylcyclopropyl or methoxymethylcyclopropyl; and $R^3$ is H, F or methyl.

In one embodiment, $R^2$ is H; $R^1$ is H, F, Cl, CN, OH, methyl, ethyl, isopropyl, tert-butyl, trifluoromethyl, 4-hydroxy-2-methylbut-2-yl, 2-hydroxyprop-2-yl, 3-hydroxy-2-methylprop-2-yl, 2-cyanoprop-2-yl, 2-methoxyethyl, 1-methyl-3-methoxyprop-2-yl, methoxymethyl, 1,3-dimethoxy-2-methylpropan-2-yl, methoxy, ethoxy, isopropoxy, difluoromethoxy, trifluoromethoxy, 2-hydroxyethoxy, 2-hydroxyisopropoxy, 2-hydroxypropoxy, 2-hydroxy-2-methylpropoxy, 3-hydroxypropoxy, cyanomethoxy, 2-methoxyethoxy, 3-methoxypropoxy, 2-methoxypropoxy, 3-methoxyprop-2-oxy, 2-methyl-2-methoxypropoxy, 2-methyl-3-methoxypropoxy, 1,3-dimethoxypropan-2-yloxy, cyclopropylmethoxy, (3-methyloxetan-3-yl)methoxy, ethylsulfanyl, —C(=O)NHCH(CH$_3$)$_2$, —CH$_2$(C=O)NHCH$_2$CH$_3$, —CH$_2$(C=O)N(CH$_3$)$_2$, cyclopropyl, hydroxymethylcyclopropyl and (methoxymethyl)cyclopropyl; and $R^3$ is H, F or methyl.

In one embodiment, $R^3$ is H; $R^1$ is H, F, Cl, CN, OH, methyl, ethyl, isopropyl, tert-butyl, trifluoromethyl, 4-hydroxy-2-methylbut-2-yl, 2-hydroxyprop-2-yl, 3-hydroxy-2-methylprop-2-yl, 2-cyanoprop-2-yl, 2-methoxyethyl, 1-methyl-3-methoxyprop-2-yl, methoxymethyl, 1,3-dimethoxy-2-methylpropan-2-yl, methoxy, ethoxy, isopropoxy, difluoromethoxy, trifluoromethoxy, 2-hydroxyethoxy, 2-hydroxyisopropoxy, 2-hydroxypropoxy, 2-hydroxy-2-methylpropoxy, 3-hydroxypropoxy, cyanomethoxy, 2-methoxyethoxy, 3-methoxypropoxy, 2-methoxypropoxy, 3-methoxyprop-2-oxy, 2-methyl-2-methoxypropoxy, 2-methyl-3-methoxypropoxy, 1,3-dimethoxypropan-2-yloxy, cyclopropylmethoxy, (3-methyloxetan-3-yl)methoxy, ethylsulfanyl, —C(═O)NHCH(CH$_3$)$_2$, —CH$_2$(C═O)NHCH$_2$CH$_3$, —CH$_2$(C═O)N(CH$_3$)$_2$, cyclopropyl, hydroxymethylcyclopropyl and (methoxymethyl)cyclopropyl, and R$^2$ is H, F, Br, Cl, CN, OH, trifluoromethyl, 2-hydroxyethyl, 2-hydroxy-2-methylpropyl, 2-methoxyethyl, methoxy, ethoxy, isopropoxy, CH$_3$C(═O)OCH$_2$CH$_2$O—, (CH$_3$)$_2$CHC(═O)OCH$_2$CH$_2$O—, (CH$_3$CH$_2$)$_2$CHC(═O)OCH$_2$CH$_2$O—, (CH$_3$CH$_2$)C(CH$_3$)$_2$C(═O)OCH$_2$CH$_2$O—, NH$_2$CH[CH(CH$_3$)$_2$]C(═O)OCH$_2$CH$_2$O—, difluoromethoxy, trifluoromethoxy, 2,2,2-trifluoroethoxy, 2-hydroxyethoxy, 2-methoxyethoxy, 3-methoxyprop-2-oxy, 2-methoxypropoxy, 2-ethyoxyethoxy, cyclopropylmethoxy, (3-methyloxetan-3-yl)methoxy, tetrahydropyranyloxy, ethylsulfanyl, isopropylsulfanyl, 2-hydroxyethylsulfanyl, 2-(methylsulfanyl)ethoxy, —COOH, 1,3-dimethyl-pyrazol-4-yl, 1,5-dimethyl-pyrazol-4-yl, 1-methylpyrazol-4-yl, 1,3-dimethylpyrazol-5-yl, 4-methylpyrazol-1-yl pyrid-3-yl, methylcarbamoyl, ethylcarbamoyl, isopropylcarbamoyl, tert-butylcarbamoyl, isopentylcarbamoyl, 1-methylcyclpropylcarbamoyl, dimethylcarbamoyl, cyclopropyl, hydroxymethylcyclopropyl or methoxymethylcyclopropyl; and R$^2$ is H, F, Br, Cl, CN, OH, trifluoromethyl, 2-hydroxyethyl, 2-hydroxy-2-methylpropyl, 2-methoxyethyl, methoxy, ethoxy, isopropoxy, CH$_3$C(═O)OCH$_2$CH$_2$O—, (CH$_3$)$_2$CHC(═O)OCH$_2$CH$_2$O—, (CH$_3$CH$_2$)$_2$CHC(═O)OCH$_2$CH$_2$O—, (CH$_3$CH$_2$)C(CH$_3$)$_2$C(═O)OCH$_2$CH$_2$O—, NH$_2$CH[CH(CH$_3$)$_2$]C(═O)OCH$_2$CH$_2$O—, difluoromethoxy, trifluoromethoxy, 2,2,2-trifluoroethoxy, 2-hydroxyethoxy, 2-methoxyethoxy, 3-methoxyprop-2-oxy, 2-methoxypropoxy, 2-ethyoxyethoxy, cyclopropylmethoxy, (3-methyloxetan-3-yl)methoxy, tetrahydropyranyloxy, ethylsulfanyl, isopropylsulfanyl, 2-hydroxyethylsulfanyl, 2-(methylsulfanyl)ethoxy, —COOH, 1,3-dimethyl-pyrazol-4-yl, 1,5-dimethyl-pyrazol-4-yl, 1-methylpyrazol-4-yl, 1,3-dimethylpyrazol-5-yl, 4-methylpyrazol-1-yl pyrid-3-yl, methylcarbamoyl, ethylcarbamoyl, isopropylcarbamoyl, tert-butylcarbamoyl, isopentylcarbamoyl, 1-methylcyclpropylcarbamoyl, dimethylcarbamoyl, cyclopropyl, hydroxymethylcyclopropyl or methoxymethylcyclopropyl.

In one embodiment, R$^2$ and R$^3$ are H, and R$^1$ is H, F, Cl, CN, OH, methyl, ethyl, isopropyl, tert-butyl, trifluoromethyl, 4-hydroxy-2-methylbut-2-yl, 2-hydroxyprop-2-yl, 3-hydroxy-2-methylprop-2-yl, 2-cyanoprop-2-yl, 2-methoxyethyl, 1-methyl-3-methoxyprop-2-yl, methoxymethyl, 1,3-dimethoxy-2-methylpropan-2-yl, methoxy, ethoxy, isopropoxy, difluoromethoxy, trifluoromethoxy, 2-hydroxyethoxy, 2-hydroxyisopropoxy, 2-hydroxypropoxy, 2-hydroxy-2-methylpropoxy, 3-hydroxypropoxy, cyanomethoxy, 2-methoxyethoxy, 3-methoxypropoxy, 2-methoxypropoxy, 3-methoxyprop-2-oxy, 2-methyl-2-methoxypropoxy, 2-methyl-3-methoxypropoxy, 1,3-dimethoxypropan-2-yloxy, cyclopropylmethoxy, (3-methyloxetan-3-yl)methoxy, ethylsulfanyl, —C(═O)NHCH(CH$_3$)$_2$, —CH$_2$(C═O)NHCH$_2$CH$_3$, —CH$_2$(C═O)N(CH$_3$)$_2$, cyclopropyl, hydroxymethylcyclopropyl and (methoxymethyl)cyclopropyl.

In one embodiment, R$^1$ and R$^3$ are H; and R$^2$ is H, F, Br, Cl, CN, OH, trifluoromethyl, 2-hydroxyethyl, 2-hydroxy-2-methylpropyl, 2-methoxyethyl, methoxy, ethoxy, isopropoxy, CH$_3$C(═O)OCH$_2$CH$_2$O—, (CH$_3$)$_2$CHC(═O)OCH$_2$CH$_2$O—, (CH$_3$CH$_2$)$_2$CHC(═O)OCH$_2$CH$_2$O—, (CH$_3$CH$_2$)C(CH$_3$)$_2$C(═O)OCH$_2$CH$_2$O—, NH$_2$CH[CH(CH$_3$)$_2$]C(═O)OCH$_2$CH$_2$O—, difluoromethoxy, trifluoromethoxy, 2,2,2-trifluoroethoxy, 2-hydroxyethoxy, 2-methoxyethoxy, 3-methoxyprop-2-oxy, 2-methoxypropoxy, 2-ethyoxyethoxy, cyclopropylmethoxy, (3-methyloxetan-3-yl)methoxy, tetrahydropyranyloxy, ethylsulfanyl, isopropylsulfanyl, 2-hydroxyethylsulfanyl, 2-(methylsulfanyl)ethoxy, —COOH, 1,3-dimethyl-pyrazol-4-yl, 1,5-dimethyl-pyrazol-4-yl, 1-methylpyrazol-4-yl, 1,3-dimethylpyrazol-5-yl, 4-methylpyrazol-1-yl pyrid-3-yl, methylcarbamoyl, ethylcarbamoyl, isopropylcarbamoyl, tert-butylcarbamoyl, isopentylcarbamoyl, 1-methylcyclpropylcarbamoyl, dimethylcarbamoyl, cyclopropyl, hydroxymethylcyclopropyl or methoxymethylcyclopropyl.

In one embodiment, R$^1$ is selected from H, (1-6C)alkyl, (3-6C)cycloalkyl optionally substituted with —CH$_2$OH or —CH$_2$O(1-4C alkyl), (1-6C)alkoxy, trifluoro(1-6C)alkoxy, hydroxy(2-6C)alkoxy, (1-3C alkoxy)(2-6C)alkoxy, and (3-6C)cycloalkylmethoxy; R$^2$ is selected from H, (1-3C alkoxy)(1-6C)alkyl, hydroxy(2-6C)alkoxy, and (1-6C) alkoxy which is optionally substituted with (1-6C alkyl)C(═O)O— or amino(1-6C alkyl)C(═O)O—; and R$^3$ is H or F.

In one embodiment, R$^1$ is selected from H and (1-3C alkoxy)(2-6C)alkoxy; R$^2$ is H; and R$^3$ is H or F.

Referring now to R$^4$, which has the structure:

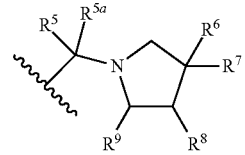

in one embodiment, R$^4$ has the absolute configuration shown in FIG. Ia,

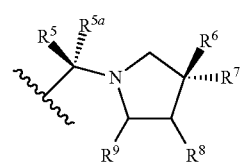

where R$^5$, R$^{5a}$, R$^6$, R$^7$, R$^8$ and R$^9$ are as defined herein.

In one embodiment, R$^4$ has the absolute configuration shown in FIG. Ib

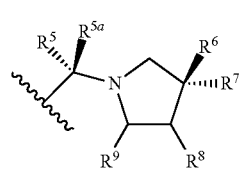

where R$^5$, R$^{5a}$, R$^6$, R$^7$, R$^8$ and R$^9$ are as defined herein.

In one embodiment, R$^4$ has the absolute configuration shown in FIG. 1c

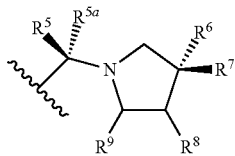

where R$^5$, R$^{5a}$, R$^6$, R$^7$, R$^8$ and R$^9$ are as defined herein.

In one embodiment, R$^4$ has the absolute configuration shown in FIG. 1d

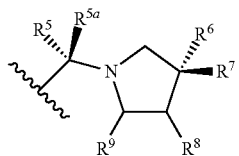

where R$^5$, R$^{5a}$, R$^6$, R$^7$, R$^8$ and R$^9$ are as defined herein.

In one embodiment, R$^5$ is CF$_3$.
In one embodiment, R$^5$ is CH$_2$F.
In one embodiment, R$^5$ is CHF$_2$.
In one embodiment, R$^5$ is methyl.
In one embodiment, R$^5$ is ethyl.
In one embodiment, R$^{5a}$ is H.
In one embodiment, R$^{5a}$ is methyl.
In one embodiment, R$^5$ is CF$_3$, CH$_2$F, CHF$_2$, methyl or ethyl and R$^{5a}$ is H.
In one embodiment, R$^5$ is CF$_3$ or methyl, and R$^{5a}$ is H.
In one embodiment, R$^5$ is CF$_3$ and R$^{5a}$ is H.
In one embodiment, R$^5$ is methyl, and R$^{5a}$ is H.
In one embodiment, R$^5$ is CF$_3$, CH$_2$F, CHF$_2$, methyl or ethyl and R$^{5a}$ is methyl.
In one embodiment, R$^5$ is CF$_3$ or methyl, and R$^{5a}$ is methyl.
In one embodiment, R$^5$ is CF$_3$ and R$^{5a}$ is methyl.
In one embodiment, R$^5$ and R$^{5a}$ are both methyl.
In one embodiment, R$^5$ and R$^{5a}$ together with the atom to which they are attached form a cyclopropyl ring.
In one embodiment, R$^6$ is H.
In one embodiment, R$^6$ is NH$_2$.
In one embodiment, R$^6$ is OH.
In one embodiment, R$^6$ is (1-6C alkyl)NH—. In one embodiment, R$^6$ is (1-4C alkyl)NH—. In one embodiment, R$^6$ is CH$_3$NH—, (CH$_3$)$_2$CHNH— or (CH$_3$)$_2$N—.
In one embodiment, R$^6$ is fluoro(1-6C alkyl)NH—. In one embodiment, R$^6$ is fluoro(1-4C alkyl)NH—. In one embodiment, R$^6$ is FCH$_2$CH$_2$NH—.
In one embodiment, R$^6$ is hydroxy(1-6C alkyl)NH—. In one embodiment, R$^6$ is hydroxy(1-4C alkyl)NH—. In one embodiment, R$^6$ is HOCH$_2$CH$_2$NH—.
In one embodiment, R$^6$ is (3-6C cycloalkyl)CH$_2$NH—. In one embodiment, R$^6$ is (cyclopropyl)CH$_2$NH—.
In one embodiment, R$^6$ is (1-6C alkyl)C(=O)NH—. In one embodiment, R$^6$ is (1-4C alkyl)C(=O)NH—. In one embodiment, R$^6$ is CH$_3$C(=O)NH—.
In one embodiment, R$^6$ is (1-6C alkyl)OC(=O)NH— optionally substituted with 5-methyl-2-oxo-1,3-dioxol-4-yl. In one embodiment, R$^6$ is (1-4C alkyl)OC(=O)NH— optionally substituted with 5-methyl-2-oxo-1,3-dioxol-4-yl. In one embodiment, R$^6$ is (CH$_3$)$_3$COC(=O)NH— or a group represented by the structure:

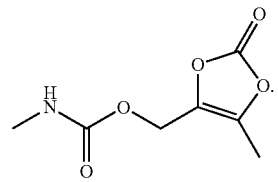

In one embodiment, R$^6$ is amino(1-6C)alkyl-. In one embodiment, R$^6$ is amino(1-4C)alkyl-. In one embodiment, R$^6$ is NH$_2$CH$_2$—.

In one embodiment, R$^6$ is selected from H, NH$_2$, OH, CH$_3$NH—, (CH$_3$)$_2$, CHNH—, FCH$_2$CH$_2$NH—, HOCH$_2$CH$_2$NH—, (cyclopropyl)CH$_2$NH—, CH$_3$C(=O)NH—, (CH$_3$)$_3$COC(=O)NH— and NH$_2$CH$_2$—.

In one embodiment, R$^7$ is H.

In one embodiment, R$^7$ is (1-6C)alkyl. In one embodiment, R$^7$ is (1-4C)alkyl.

In one embodiment, R$^7$ is methyl or ethyl.

In one embodiment, R$^7$ is fluoro(1-6C)alkyl. In one embodiment, R$^7$ is fluoro(1-4C)alkyl. In one embodiment, R$^7$ is FCH$_2$—.

In one embodiment, R$^7$ is hydroxy(1-6C)alkyl. In one embodiment, R$^7$ is hydroxy(1-4C)alkyl. In one embodiment, R$^7$ is HOCH$_2$—.

In one embodiment, R$^7$ is selected from H, methyl, ethyl, FCH$_2$— and HOCH$_2$—.

In one embodiment, R$^7$ is H and R$^6$ is H, —NH$_2$, OH, (1-6C alkyl)NH—, fluoro(1-6C alkyl)NH—, hydroxy(1-6C alkyl)NH—, (3-6C cycloalkyl)CH$_2$NH—, (1-6C alkyl)C(=O)NH—, (1-6C alkyl)OC(=O)NH— or amino(1-6C)alkyl-.

In one embodiment, R$^7$ is H and R$^6$ is H, NH$_2$, OH, CH$_3$NH—, (CH$_3$)$_2$CHNH—, FCH$_2$CH$_2$NH—, HOCH$_2$CH$_2$NH—, (cyclopropyl)CH$_2$NH—, CH$_3$C(=O)NH—, (CH$_3$)$_3$COC(=O) NH— or NH$_2$CH$_2$—.

In one embodiment, R$^7$ is H and R$^6$ is NH$_2$, CH$_3$NH—, (CH$_3$)$_2$CHNH—, FCH$_2$CH$_2$NH—, HOCH$_2$CH$_2$NH—, (cyclopropyl)CH$_2$NH—, CH$_3$C(=O)NH—, (CH$_3$)$_3$COC(=O)NH— or NH$_2$CH$_2$—.

In one embodiment, R$^7$ is H and R$^6$ is NH$_2$.

In one embodiment, R$^7$ is methyl and R$^6$ is H, —NH$_2$, OH, (1-6C alkyl)NH—, fluoro(1-6C alkyl)NH—, hydroxy(1-6C alkyl)NH—, (3-6C cycloalkyl)CH$_2$NH—, (1-6C alkyl)C(=O)NH—, (1-6C alkyl)OC(=O)NH— or amino(1-6C) alkyl-.

In one embodiment, R$^7$ is methyl and R$^6$ is H, NH$_2$, OH, CH$_3$NH—, (CH$_3$)$_2$CHNH—, FCH$_2$CH$_2$NH—, HOCH$_2$CH$_2$NH—, (cyclopropyl)CH$_2$NH—, CH$_3$C(=O)NH—, (CH$_3$)$_3$COC(=O)NH— or NH$_2$CH$_2$—.

In one embodiment, R$^7$ is methyl and R$^6$ is NH$_2$, CH$_3$NH—, (CH$_3$)$_2$CHNH—, FCH$_2$CH$_2$NH—, HOCH$_2$CH$_2$NH—, (cyclopropyl)CH$_2$NH—, CH$_3$C(=O)NH—, (CH$_3$)$_3$COC(=O) NH— or NH$_2$CH$_2$—.

In one embodiment, R$^7$ is methyl and R$^6$ is NH$_2$.

In one embodiment, R$^6$ and R$^7$ together with the atom to which they are attached form a 5-6 membered spirocyclic heterocycle having a ring nitrogen atom. An example of an R$^4$ group wherein R$^6$ and R$^7$ together with the atom to which they are attached form a 5-6 membered spirocyclic heterocycle having a ring nitrogen atom is the structure:

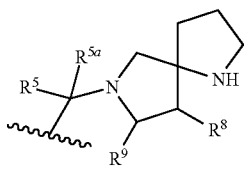

wherein $R^5$, $R^{5a}$, $R^8$ and $R^9$ are as defined herein. In one embodiment, $R^8$ is H. In one embodiment, $R^9$ is H. In one embodiment, $R^8$ and $R^9$ are both H.

In one embodiment, $R^8$ is H.

In one embodiment, $R^8$ is halogen. In one embodiment, $R^8$ is F.

In one embodiment, $R^8$ is OH.

In one embodiment, $R^8$ is (1-6C)alkoxy. In one embodiment, $R^8$ is —OMe.

In one embodiment, $R^8$ is selected from H, F, OH or —OMe.

In one embodiment, $R^8$ is selected from H, F, or OH.

In one embodiment, $R^6$ and $R^8$ together with the carbon atoms to which they are attached form a cyclopropyl ring optionally substituted with $NH_2$. An example of an $R^4$ group wherein $R^6$ and $R^8$ together with the carbon atoms to which they are attached form a cyclopropyl ring is the structure:

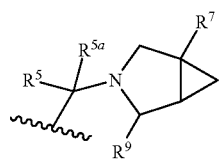

wherein $R^5$, $R^{5a}$, $R^7$ and $R^9$ are as defined herein. In one embodiment, $R^7$ is H. In one embodiment, $R^9$ is H. In one embodiment, $R^7$ and $R^9$ are both H.

In one embodiment, $R^9$ is H.

In one embodiment, $R^6$ and $R^9$ together form a linking group having the formula —$CH_2NH$— which links the carbon atoms to which they are attached, thereby forming a bicyclic ring which can be represented by the structure:

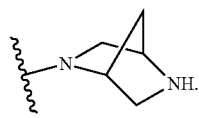 [SMILES: *N1CC2CC1CN2]

An example of an $R^4$ group wherein $R^6$ and $R^9$ together form a linking group having the formula —$CH_2NH$— which links the carbon atoms to which they are attached is the structure:

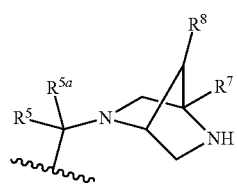

wherein $R^5$, $R^{5a}$, $R^7$ and $R^8$ are as defined herein. In one embodiment, $R^7$ is H. In one embodiment, $R^8$ is H. In one embodiment, $R^7$ and $R^8$ are both H.

In one embodiment, $R^5$ is $CF_3$; $R^{5a}$ is H; $R^8$ and $R^9$ are H; $R^6$ is selected from H, $NH_2$, OH, (1-6C alkyl)NH—, fluoro(1-6C alkyl)NH—, hydroxy(1-6C alkyl)NH—, (3-6C cycloalkyl)$CH_2NH$—, (1-6C alkyl)C(=O)NH—, (1-6C alkyl)OC(=O)NH— or amino(1-6C)alkyl-; and $R^7$ is selected from H, methyl, ethyl, $FCH_2$— and $HOCH_2$—.

In one embodiment, $R^5$ is $CF_3$; $R^{5a}$ is H; $R^8$ and $R^9$ are H; $R^6$ is selected from H, $NH_2$, OH, $CH_3NH$—, $(CH_3)_2CHNH$—, $FCH_2CH_2NH$—, $HOCH_2CH_2NH$—, (cyclopropyl)$CH_2NH$—, $CH_3C(=O)NH$—, $(CH_3)_3COC(=O)NH$—, and $NH_2CH_2$—; and $R^7$ is selected from H, methyl, ethyl, $FCH_2$— and $HOCH_2$—.

In one embodiment, $R^5$ is $CF_3$; $R^{5a}$ is H; $R^8$ and $R^9$ are H; $R^6$ is selected from H, $NH_2$, OH, $CH_3NH$—, $(CH_3)_2CHNH$—, $FCH_2CH_2NH$—, $HOCH_2CH_2NH$—, (cyclopropyl) $CH_2NH$—, $CH_3C(=O)NH$—, $(CH_3)_3COC(=O)NH$—, and $NH_2CH_2$—; and $R^7$ is H or methyl.

In one embodiment, $R^5$ is $CF_3$; $R^{5a}$ is H; $R^8$ and $R^9$ are H; $R^6$ is $NH_2$; and $R^7$ is H or methyl.

In one embodiment, $R^5$ is methyl; $R^{5a}$ is H; $R^8$ and $R^9$ are H; $R^6$ is selected from H, $NH_2$, OH, $CH_3NH$—, $(CH_3)_2CHNH$—, $FCH_2CH_2NH$—, $HOCH_2CH_2NH$—, (cyclopropyl)$CH_2NH$—, $CH_3C(=O)NH$—, $(CH_3)_3COC(=O)NH$—, and $NH_2CH_2$—; and $R^7$ is selected from H, methyl, ethyl, $FCH_2$— and $HOCH_2$—.

In one embodiment, $R^5$ is methyl; $R^{5a}$ is H; $R^8$ and $R^9$ are H; $R^6$ is selected from H, $NH_2$, OH, $CH_3NH$—, $(CH_3)_2CHNH$—, $FCH_2CH_2NH$—, $HOCH_2CH_2NH$—, (cyclopropyl)$CH_2NH$—, $CH_3C(=O)NH$—, $(CH_3)_3COC(=O)NH$—, and $NH_2CH_2$—; and $R^7$ is H or methyl.

In one embodiment, $R^5$ is methyl; $R^{5a}$ is H; $R^8$ and $R^9$ are H; $R^6$ is $NH_2$; and $R^7$ is H or methyl.

In one embodiment, $R^4$ is selected from

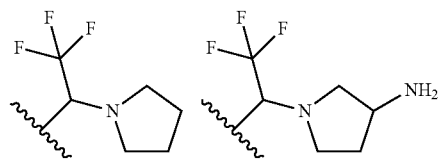

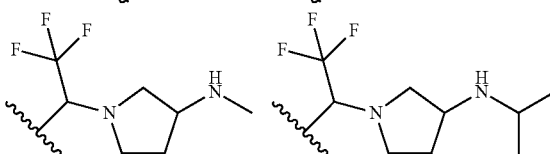

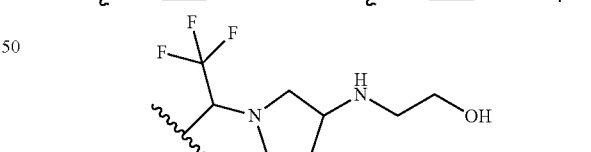

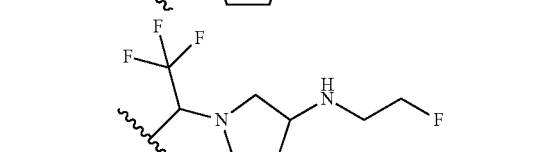

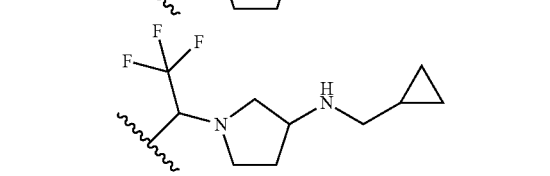

-continued

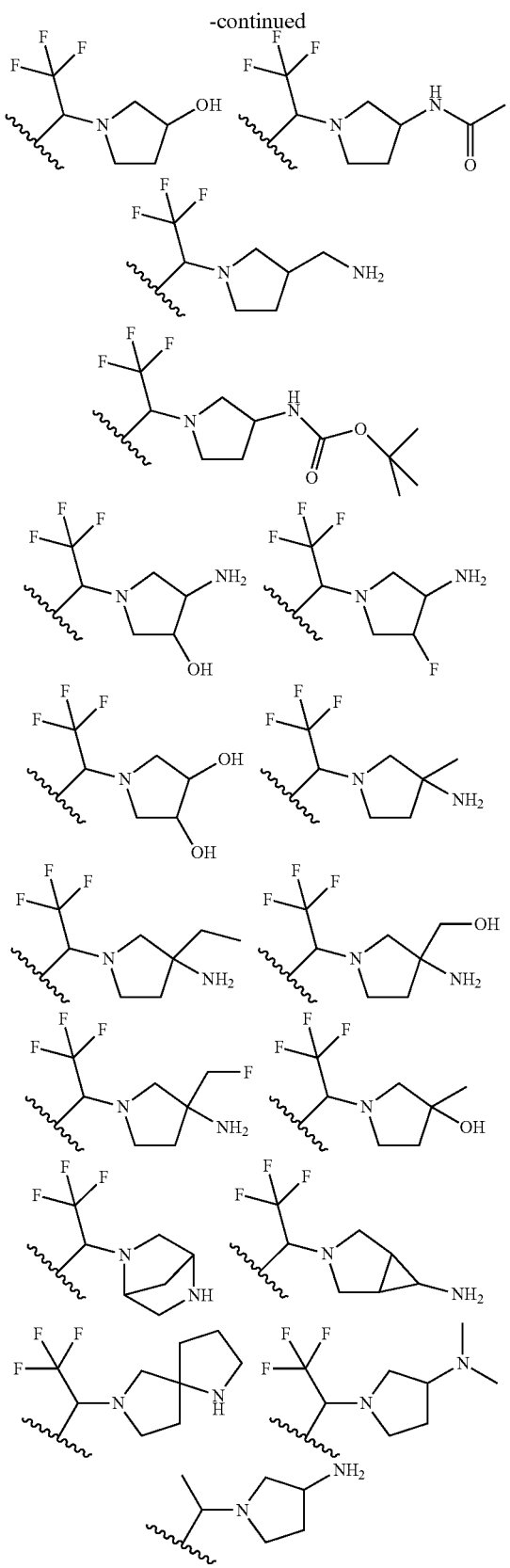

including the enantiomers and diastereomers thereof.

In one embodiment of Formula I, $R^1$ is selected from H, (1-6C)alkyl, (3-6C)cycloalkyl optionally substituted with —CH$_2$OH or —CH$_2$O(1-4C alkyl), (1-6C)alkoxy, trifluoro (1-6C)alkoxy, hydroxy(2-6C)alkoxy, (1-3C alkoxy)(2-6C)alkoxy, and (3-6C)cycloalkylmethoxy; $R^2$ is selected from H, (1-3C alkoxy)(1-6C)alkyl, hydroxy(2-6C)alkoxy, and (1-6C) alkoxy which is optionally substituted with (1-6C alkyl)C(=O)O— or amino(1-6C alkyl)C(=O)O—; $R^3$ is H or F; $R^5$ is CF$_3$; $R^{5a}$ is H; $R^6$ is selected from H, NH$_2$, OH, (1-6C alkyl)NH—, fluoro(1-6C alkyl)NH—, hydroxy(1-6C alkyl)NH—, (3-6C cycloalkyl)CH$_2$NH—, (1-6C alkyl)C(=O)NH—, (1-6C alkyl)OC(=O)NH— or amino(1-6C)alkyl-; $R^7$ is H or (1-6C)alkyl; $R^8$ is H; and $R^9$ is H.

In one embodiment of Formula I, $R^1$ is selected from H, (1-6C)alkyl, (3-6C)cycloalkyl optionally substituted with —CH$_2$OH or —CH$_2$O(1-4C alkyl), (1-6C)alkoxy, trifluoro (1-6C)alkoxy, hydroxy(2-6C)alkoxy, (1-3C alkoxy)(2-6C)alkoxy, and (3-6C)cycloalkylmethoxy; $R^2$ is selected from H, (1-3C alkoxy)(1-6C)alkyl, hydroxy(2-6C)alkoxy, and (1-6C) alkoxy which is optionally substituted with (1-6C alkyl)C(=O)O— or amino(1-6C alkyl)C(=O)O—; $R^3$ is H or F; $R^5$ is CF$_3$; $R^{5a}$ is H; $R^6$ is NH$_2$; $R^7$ is H or (1-6C)alkyl; $R^8$ is H; and $R^9$ is H.

In one embodiment, $R^{10}$ is H.

In one embodiment, $R^{10}$ is halogen. In one embodiment, $R^{10}$ is F.

In one embodiment, the compound of Formula I is selected from any one of Examples 1-328 or a pharmaceutically acceptable salt thereof. In one embodiment, the salt of a compound of Example 1-328 is a hydrochloride and dihydrochloride salt.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention. For example, compounds of Formula I can exist in unsolvated as well as solvated forms with pharmaceutically acceptable solvents such as water, ethanol, and the like.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Particular examples of salts include hydrochloride and dihydrochloride salts of compounds of Formula I.

The term "pharmaceutically acceptable" indicates that the substance or composition is compatible chemically and/or toxicologically, with the other ingredients comprising a formulation, and/or the mammal being treated therewith.

Compounds of the invention may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1$H, $^2$H, $^3$H or mixtures thereof; when carbon is mentioned, it is understood to refer to $^{11}$C, $^{12}$C, $^{13}$C, $^{14}$C or mixtures thereof; when nitrogen is mentioned, it is understood to refer to $^{13}$N, $^{14}$N, $^{15}$N or mixtures thereof; when oxygen is mentioned, it is understood to refer to $^{14}$O, $^{15}$O, $^{16}$O, $^{17}$O, $^{18}$O or mixtures thereof; and when fluoro is mentioned, it is understood to refer to $^{18}$F, $^{19}$F or mixtures thereof. The compounds according to the invention therefore also comprise compounds with one or more isotopes of one or more atom, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds of the present invention, whether radioactive or not, are intended to be encompassed within the scope of the present invention.

According to another aspect, the present invention provides a process for the preparation of a compound of Formula I or a salt thereof as defined herein which comprises:

(a) reacting a corresponding compound of formula II or a protected derivative thereof

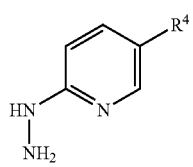

II where $R^4$ is as defined for Formula I, with a corresponding compound having the formula III or a protected derivative thereof

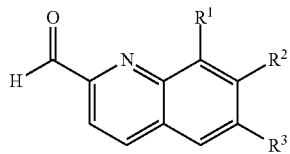

III where $R^1$, $R^2$ and $R^3$ are as defined for Formula I, in the presence of an organo hypervalent iodine reagent; or (b) for a compound of Formula I where $R^2$ is hetAr$^1$ or a cyclopropyl ring optionally substituted with —CH$_2$OH or —CH$_2$O(1-6C alkyl), reacting a corresponding compound having the formula IV or a protected derivative thereof:

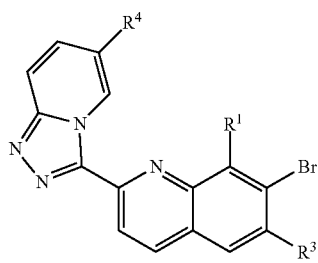

IV where $R^1$, $R^3$ and $R^4$ are as defined for Formula I, with a reagent having the formula

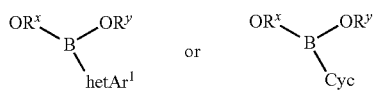

respectively, where hetAr$^1$ is as defined for Formula I, Cyc is cyclopropyl optionally substituted with —CH$_2$OH or —CH$_2$O(1-6C alkyl), and $R^x$ and $R^y$ are H or (1-6C)alkyl, or $R^x$ and $R^y$ together with the atoms to which they are connected form a 5-6 membered ring optionally substituted with 1-4 substituents selected from (1-3C alkyl), wherein said reaction takes place in the presence of a palladium catalyst and optionally in the presence of a base and a ligand; or (c) for a compound of Formula I where $R^2$ is —NR$^e$C(=O)R$^f$, reacting a corresponding compound having the formula IV or a protected derivative thereof:

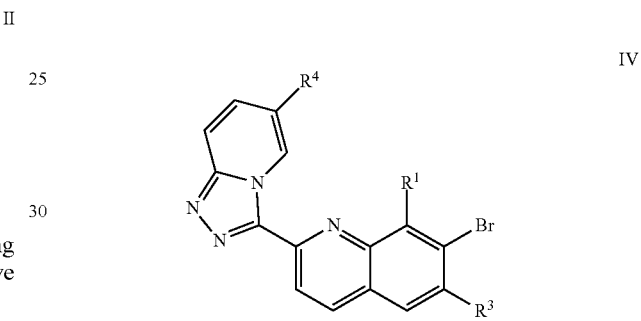

IV where $R^1$, $R^3$ and $R^4$ are as defined for Formula I, with a reagent having the formula HNR$^e$C(=O)R$^f$ in the presence of a base and a metal catalyst; or (d) for a compound of Formula I where $R^2$ is (1-6C alkyl)sulfanyl or hydroxy(2-6C alkyl)sulfanyl, reacting a corresponding compound having the formula IV or a protected derivative thereof:

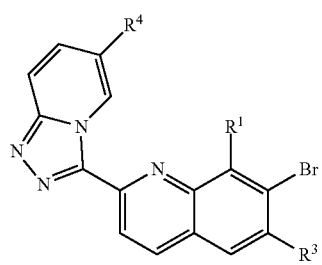

IV where $R^1$, $R^2$, $R^3$ and $R^4$ are as defined for Formula I, with a reagent having the formula HS(1-6C alkyl) or HS(1-6C alkyl)OH, respectively, in the presence of a base; or (e) for a compound of Formula I where $R^2$ is —C(=O)NR$^e$R$^f$, coupling a corresponding compound having the formula V or a protected derivative thereof:

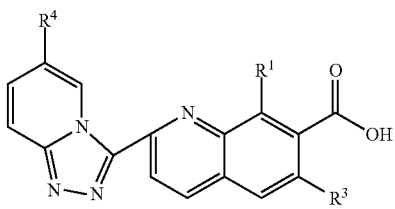

V where R¹, R³ and R⁴ are as defined for Formula I, with a reagent having the formula HNR$^e$R$^f$, where R$^e$ and R$^f$ are as defined for Formula I, in the presence of a base and a coupling reagent; or (f) for a compound of Formula I where R¹ is —CH$_2$C(=O)NR$^c$R$^d$, coupling a corresponding compound having the formula VI or a protected derivative thereof

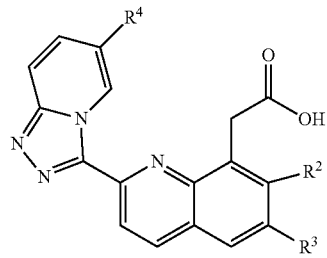

VI where R², R³ and R⁴ are as defined for Formula I, with a reagent having the formula HNR$^c$R$^d$, where R$^e$ and R$^d$ are as defined for Formula I, in the presence of a base and a coupling reagent; or (g) for a compound of Formula I where R² is (1-6C)alkoxy substituted with (1-6C alkyl)C(=O)O—, coupling a corresponding compound having the formula VII or a protected derivative thereof.

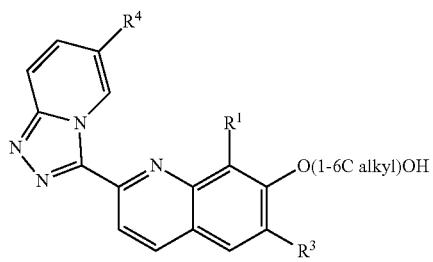

VII where R¹, R³ and R⁴ are as defined for Formula I, with a (1-6C)alkyl acid anhydride or a (1-6C)alkyl acid chloride in the presence of a base; or (h) for a compound of Formula I where R² is (1-6C)alkoxy substituted with amino(1-6C alkyl)C(=O)O—, coupling a corresponding compound having the formula VII or a protected derivative thereof

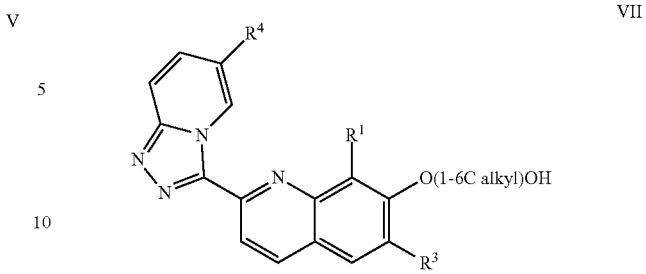

VII where R¹, R³ and R⁴ are as defined for Formula I, with a compound having the formula P¹NH(1-6C alkyl)C(=O)OH where P¹ is H or an amine protecting group, in the presence of a base and a coupling reagent; or (i) for a compound of Formula I where R⁴ is a moiety having the structure

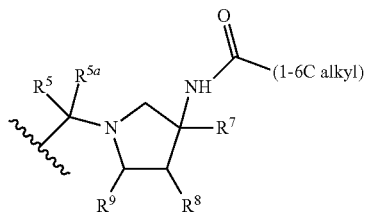

where R⁵, R$^{5a}$, and R⁷ are as defined for Formula I, R⁸ is H, halogen, OH, or (1-6C)alkoxy, and R⁹ is H, reacting a corresponding compound having the formula VIII

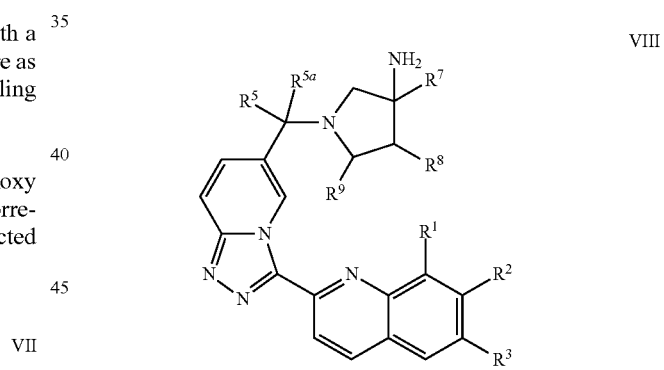

VIII where R¹, R², R³, R⁵, R$^{5a}$, and R⁷ are as defined for Formula I, R⁸ is H, halogen, OH, or (1-6C)alkoxy, and R⁹ is H, with a (1-6C)alkylcarboxylic acid anhydride or a (1-6C)alkylcarboxylic acid chloride in the presence of a base; or (j) for a compound of Formula I where R⁴ is a moiety having the structure

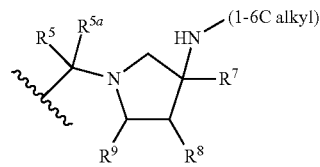

where R⁵, R$^{5a}$, and R⁷ are as defined for Formula I, R⁸ is H, halogen, OH, or (1-6C)alkoxy, and R⁹ is H, reacting a corresponding compound having the formula VIII

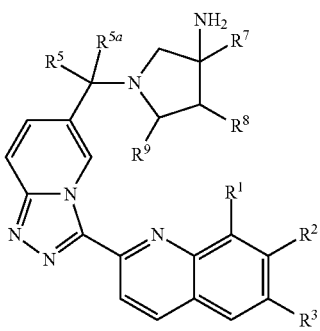

where $R^1$, $R^2$, $R^3$, $R^5$, $R^{5a}$ and $R^7$ are as defined for Formula I, $R^8$ is H, halogen, OH, or (1-6C)alkoxy, and $R^9$ is H, with a (1-6C)aldehyde or a protected (1-6C)aldehyde in the presence of a catalyst and a base followed by treatment with a reducing agent; or (k) for a compound of Formula I where $R^4$ is a moiety having the structure

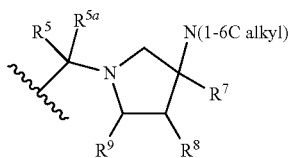

where $R^5$, $R^{5a}$, and $R^7$ are as defined for Formula I, $R^8$ is H, halogen, OH, or (1-6C)alkoxy, and $R^9$ is H, reacting a corresponding compound having the formula VIII

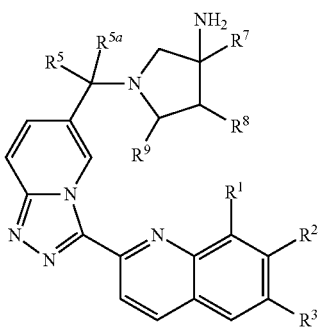

where $R^1$, $R^2$, $R^3$, $R^5$, $R^{5a}$, and $R^7$ are as defined for Formula I, $R^8$ is H, halogen, OH, or (1-6C)alkoxy, and $R^9$ is H, in the presence of a reagent having the formula HC(=O)(1-5C alkyl) and a reducing agent; or (l) for a compound of Formula I where $R^4$ is a moiety having the structure

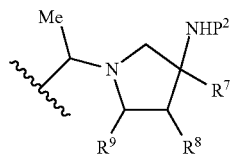

where $R^7$ is as defined for Formula I, $R^8$ is H, halogen, OH, or (1-6C)alkoxy, $R^9$ is H, and $P^2$ is H or an amine protecting group, reacting a corresponding compound having the formula IX

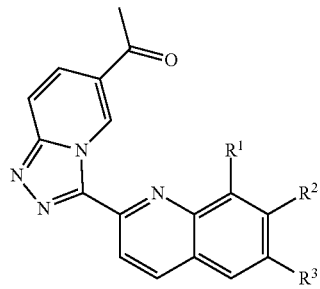

where $R^1$, $R^2$, and $R^3$ are as defined for Formula I, in the presence of a Lewis acid, followed by treatment with a reducing agent; and removing any protecting group or groups and, if desired, forming a salt.

Referring to method (a), the organo hypervalent iodine reagent refers to any hypervalent iodine reagent suitable for forming heterocyclic rings. Examples include iodobenzene diacetate and [hydroxy(tosyloxy)iodo]benzene (HTIB), which can be prepared by treating iodobenzene diacetate with p-toluenesulfonic acid monohydrate in acetonitrile. Suitable solvent systems when using iodobenzene diacetate include methanolic potassium hydroxide. Suitable solvent systems when using HTIB include neutral solvents, for example acetonitrile or dioxane. The reaction can be performed at a temperature ranging from 80 to 110° C.

Referring to method (b), suitable palladium catalysts include $PdCl_2(dppf)*dcm$, $Pd(PPh_3)_4$, $Pd_2(dba)_3$, $Pd(OAc)_2$ and $Pd(PPh_3)_2Cl_2$. Suitable ligands include $P(Cy)_3$, XPHOS, DIPHOS and rac-BINAP. The base may be, for example, an amine base such as triethylamine. Convenient solvents include IPA and toluene. The reaction can be conveniently performed at a temperature ranging from ambient temperature to 120° C., for example from 80 to 110° C.

Referring to method (c), suitable metal catalysts include copper and palladium catalysts. An example is copper (I) iodide. Suitable bases include alkali metal bases, such as alkali metal phosphates, such as potassium phosphate. Suitable solvents include aprotic solvents such as toluene. The reaction is conveniently performed at elevated temperatures, for example at 90° C.

Referring to method (d), suitable bases include amine bases, such as a tertiary amine base, such as DIEA (diisopropylethylamine) and triethylamine. Convenient solvents include aprotic solvents such as ethers (for example tetrahydrofuran or p-dioxane) or toluene. The reaction is conveniently performed at elevated temperatures, for example at 150° C.

Referring to methods (e) and (f) suitable coupling reagents include HATU, HBTU, TBTU, DCC(N,N'-dicyclohexylcarbodiimide), DIEC (1-(3-dimethylaminopropyl)-3-ethylcarboiimide), or any other amide coupling reagents well known to persons skilled in the art. Suitable bases include amine bases such as DIEA or triethylamine. Convenient solvents include aprotic solvents such as DCM, ethers (for example tetrahydrofuran or p-dioxane), toluene, DMF, or DME. The reaction is conveniently performed at ambient temperature.

Referring to method (g), the base may be, for example, a tertiary amine, such as triethylamine, dimethylaminopyridine (DMAP), or N,N-diisopropylethylamine, or an alkali metal hydride or carbonate. Suitable solvents include DCM, DCE, THF, and DMF. The reaction can be performed at ambient temperature.

Referring to method (h), suitable coupling reagents include DCC(N,N'-dicyclohexylcarbodiimide), and DIEC (1-(3-dimethylaminopropyl)-3-ethylcarboiimide). The base may be, for example, a tertiary amine, such as triethylamine, dimethylaminopyridine (DMAP) or N,N-diisopropylethylamine, or an alkali metal hydride or carbonate. Suitable solvents include DCM, DCE, THF, and DMF.

Referring to method (i), the base may be, for example, a tertiary amine, such as triethylamine, dimethylaminopyridine (DMAP), or N,N-diisopropylethylamine. Suitable solvents include DCM, DCE, THF, and DMF. The reaction can be performed at ambient temperature.

Referring to method (j), an example of a protected aldehyde is trimethyl orthoformate. The base may be, for example, a tertiary amine, such as triethylamine, dimethylaminopyridine (DMAP), or N,N-diisopropylethylamine. Suitable reducing agents include Na(OAc)$_3$BH and NaCNBH$_3$. Suitable solvents include alcohols such as methanol. The reaction is conveniently performed at temperatures between 0° C. and ambient temperature.

Referring to method (k), the base may be, for example, a tertiary amine, such as triethylamine, dimethylaminopyridine (DMAP), or N,N-diisopropylethylamine. Suitable reducing agents include Na(OAc)$_3$BH and NaCNBH$_3$. Suitable solvents include alcohols such as methanol. The reaction is conveniently performed at temperatures between 0° C. and ambient temperature.

Referring to method (l), an example of a suitable Lewis acid is tetraisopropoxytitanium. The base may be, for example, a tertiary amine, such as triethylamine, dimethylaminopyridine (DMAP), or N,N-diisopropylethylamine. Suitable reducing agents include Na(OAc)$_3$BH and NaCNBH$_3$. Suitable solvents include alcohols such as methanol. The reaction is conveniently performed at ambient temperature.

As used herein, the phrase "a protected derivative thereof" refers to a compound as described herein having one or more substituents which are protected with a suitable protecting group. Amine groups in compounds described in any of the above methods may be protected with any convenient amine protecting group, for example as described in Greene & Wuts, eds., "Protecting Groups in Organic Synthesis", 2$^{nd}$ ed. New York; John Wiley & Sons, Inc., 1991. Examples of amine protecting groups include acyl and alkoxycarbonyl groups, such as t-butoxycarbonyl (BOC), and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", 2$^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", 2$^{nd}$ ed. New York; John Wiley & Sons, Inc., 1991. Examples of alcohol protecting groups include benzyl, trityl, silyl ethers, and the like. For example, in certain embodiments of the methods described above where R$^6$ is NH, the amino moiety is protected with an alkoxycarbonyl group, such as a BOC protecting group, as follows:

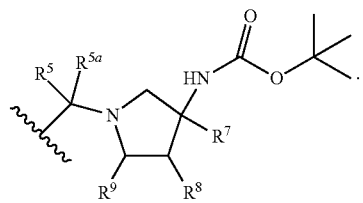

The compounds of the formulas II, IV, V, VI, VII, VIII and IX are also believed to be novel and are provided as further aspects of the invention.

In one embodiment, the compound of formula II has the structure II-A

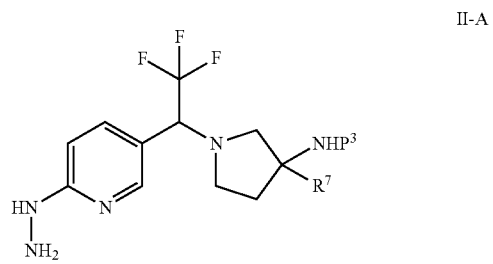

including enantiomers and diastereomers thereof, where P$^3$ is H or an amine protecting group and R$^7$ is H, (1-6C)alkyl, fluoro(1-6C)alkyl or hydroxy(1-6C)alkyl. In one embodiment, R$^7$ is H or (1-6C)alkyl. In one embodiment, R$^7$ is H or (1-C)alkyl. In one embodiment, R$^7$ is H or methyl. In one embodiment, R$^7$ is hydrogen. In one embodiment, R$^7$ is methyl.

Compounds of Formula II-A can be prepared according to Scheme 1.

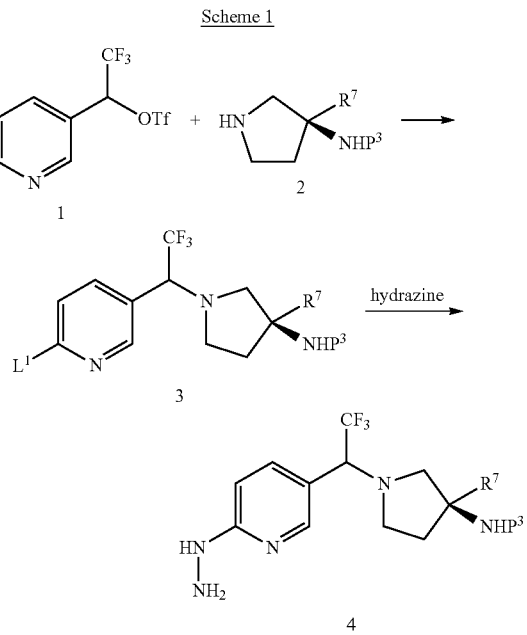

In Scheme 1, R$^7$ is as defined H or methyl, L$^1$ is a leaving group or atom, such as a halogen, for example chloro, and P$^3$ is an amino protecting group.

Compounds of Formula II-A and II-B are also believed to be novel and are provided as further aspects of the invention.

The ability of compounds to act as PIM-1, PIM-2 or PIM-3 inhibitors may be demonstrated by the enzyme assays described in Examples A, B and C, respectively.

Compounds of Formula I have been found to be inhibitors of PIM-1 and/or PIM-2 and/or PIM-3, and are useful for treating diseases and disorders which can be treated with a PIM-1 and/or PIM-2 and/or PIM-3 kinase inhibitor, including diseases mediated by PIM-1 and/or PIM-2 and/or PIM-3 kinases. Accordingly, another aspect of this invention provides a method of treating diseases or disorder mediated by a PIM-1 and/or PIM-2 and/or PIM-3 kinase in a mammal, comprising administering to said mammal one or more compounds of Formula I or a pharmaceutically acceptable salt thereof in an amount effective to treat said disease or disorder.

A subset of compounds disclosed herein were found to have an $IC_{50}$ value for PIM-1 that is at least 10 fold less than the $IC_{50}$ value for PIM-2 and further to have an $IC_{50}$ value for PIM-3 approximately equivalent to that observed for PIM-1, when tested in the enzyme assays described in Examples A, B and C. As a further example, particular compounds disclosed herein were found to have an $IC_{50}$ value for PIM-1 that is at least 100 fold less than the $IC_{50}$ value for PIM-2, and further to have an $IC_{50}$ value for PIM-3 approximately equivalent to that observed for PIM-1, when tested in the enzyme assays described in Examples A, B and C.

Accordingly, also provided herein are compounds of Formula I which are highly potent PIM-1/PIM-3 dual inhibitors and are highly selective for PIM-1 and PIM-3 relative to PIM-2, wherein a compound that is highly selective for PIM1 is defined as a compound having an $IC_{50}$ value for PIM-1 that is at least 10 fold less than the $IC_{50}$ value for PIM-2 when tested in the enzyme assays described in Examples A and B, and a compound that is highly selective for PIM3 is defined as a compound having an $IC_{50}$ value for PIM-3 that is at least 10 fold less than the $IC_{50}$ value for PIM-2 when tested in the enzyme assays described in Examples B and C.

Examples of disease and disorders which can be treated using a compound of Formula I include transplant rejection and autoimmune and inflammatory diseases and disorders. Examples of autoimmune diseases and disorders include multiple sclerosis (MS), systemic lupus erythematosis, inflammatory bowel disease (IBD), Crohn's disease, irritable bowel syndrome, pancreatitis, ulcerative colitis, diverticulosis, Grave's disease, arthritis (including rheumatoid arthritis, juvenile rheumatoid arthritis, osteoarthritis, psoriatic arthritis and ankylosing spondylitis), myasthenia gravis, vasculitis, autoimmune thyroiditis, dermatitis (including atopic dermatitis and eczematous dermatitis), psoriasis, scleroderma, asthma, allergy, systemic sclerosis, vitiligo, graft vs. host disease (GVHD), Sjogren's syndrome, glomerulonephritis, IgA nephoropathy, diabetes mellitus (type I) and asthma.

Particular examples of diseases and disorders which can be treated using a compound of Formula I include inflammatory diseases, including diseases and disorders mediated by T and B cell function. Particular examples of such diseases include multiple sclerosis, inflammatory bowel disease, lupus, psoriasis and rheumatoid arthritis.

Accordingly, a further embodiment of this invention provides a method of treating an inflammatory or autoimmune disease in a mammal in need thereof, comprising administering to a mammal in need thereof a compound of Formula I or a pharmaceutically acceptable salt thereof. In one embodiment, the disease is rheumatoid arthritis. In one embodiment, the disease is lupus. In one embodiment, the disease is multiple sclerosis. In one embodiment, the disease is inflammatory bowel disease. In one embodiment, the disease is psoriasis.

Expression of PIM kinases in immune cells can be induced by cytokines present during immune responses. Immune cells are critically dependent on cytokines for differentiation and development of effector functions during normal and pathogenic immune responses. Thus, compounds of the invention may be useful for treating diseases and disorders characterized by aberrant cytokine production and responses and/or aberrant immune cell activation.

Accordingly, another embodiment of the invention provides a method of treating diseases and disorders characterized by aberrant cytokine production and responses and/or aberrant immune cell activation in a mammal in need thereof, comprising administering to a mammal in need thereof a compound of Formula I or a pharmaceutically acceptable salt thereof.

Another embodiment provides a compound of Formula I or a pharmaceutically acceptable salt thereof for use in the treatment of diseases and disorders characterized by aberrant cytokine production and responses and/or aberrant immune cell activation in a mammal. Examples of such diseases and disorders include autoimmune and inflammatory diseases.

Example E describes a method for determining the ability of a compound of Formula I to inhibit the proliferation of T cells, as well inhibit cytokine production by T cells stimulated through T cell receptors and by cytokines in vitro. The effect of a compound on IL-4 production and IL-22 production supports the utility of compounds of Formula I in treating diseases where these cytokines have been shown to play a role. Particular examples of such diseases include asthma, MS and inflammatory bowel disease (IBD), lupus, psoriasis and rheumatoid arthritis.

As an extension of the in vitro data, Example F describes a method of determining the ability of a compound of Formula I to inhibit the generation of T cells responses to antigen in vivo as assessed by proliferation and cytokine production ex vivo. Since T cell activation or proliferation and cytokine production are often key components of autoimmune diseases, the data provided by the assay described in Example F supports the utility of compounds of Formula I in treating diseases associated with T cell proliferation and cytokine production, including autoimmune diseases such as those described herein.

B cells are also critically dependent on cytokines for production of particular types of immunoglobulins, called antibody (Ab) isotypes, in a process referred to as isotype switching. Over time, isotype switching can be observed in mice which have been immunized with proteins to produce antibodies, which can then be quantified (Shi et al, 1999 Immunity 10:197-206). Example G describes a method of determining the ability of a compound of Formula I to inhibit the production of cytokine-stimulated Ab isotypes in response to protein immunization. The ability of compounds of Formula I to affect B cells supports their use in treating autoimmune and inflammatory diseases, including diseases thought to be associated in part by pathogenic B cell and Ab responses. Examples of such diseases include lupus, multiple sclerosis and rheumatoid arthritis.

Example H describes a method of determining the effectiveness a compound of Formula I in a T cell-mediated murine model of experimental autoimmune encephalomyelitis (EAE). Furthermore, Example I describes a method of determining the effectiveness of a compound of Formula I in a second EAE model in which the disease is caused by generating an immune response to a central nervous system (CNS)

protein. EAE mimics many of the pathological features of multiple sclerosis (MS), and these models are widely used to model human disease and its treatment.

T cells also play in role in the inflammatory bowel disease (IBD), which is an autoimmune disease. Example J describes a method of determining the effectiveness of a compound of Formula I in a T cell-mediated model of this disease.

Lupus is an autoimmune disease characterized by aberrant T and B cell responses. In particular, lupus patients can exhibit elevated cytokine levels and increased amounts of anti-nuclear antibodies (Abs). In lupus, Abs can deposit in the kidneys and mediate tissue damage resulting in nephritis. Example K describes a murine model of lupus, and provides a method of determining the effectiveness of a compound of Formula I to decrease the production of anti-DNA Abs as well as decrease proteinuria, a measure of kidney damage.

Particular compounds of this invention are inhibitors of PIM-1 and therefore are useful in treating diseases and disorders mediated by PIM-1, such as cancers, for example hematological cancers and solid tumors (e.g., breast cancer, colon cancer, gliomas).

Examples of hematological cancers include, but are not limited to, leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). Certain cancers which can be treated with compounds of Formula I are cancers which of hematological origin, such as, but not limited to, cancers derived from T cells or B cells.

Accordingly, a further embodiment of this invention provides a method of treating cancer in a mammal in need thereof, comprising administering to a mammal in need thereof a compound of Formula I or a pharmaceutically acceptable salt thereof. In one embodiment, the cancer is of hematological origin. In one embodiment, the cancer derives from T cells. In one embodiment, the cancer derives from B cells.

In the field of medical oncology it is normal practice to use a combination of different forms of treatment to treat each patient with cancer. In medical oncology the other component (s) of such conjoint treatment in addition to compositions of the present invention may be, for example, surgery, radiotherapy, chemotherapy, signal transduction inhibitors and/or monoclonal antibodies. Compounds of Formula I therefore may also be useful as adjuvants to cancer treatment, that is, they can be used in combination with one or more additional drugs, for example a chemotherapeutic that works by the same or by a different mechanism of action.

Accordingly, a further aspect of this invention includes a method of treating cancer, comprising administering one or more compounds of Formula I in combination with one or more agents selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, and prenyl-protein transferase inhibitors.

Compounds of the present invention may also be used in combination with one or more additional drugs, for example an anti-inflammatory compound, an immunosuppressive compound or an immunodepleting agent that works by the same or a different mechanism of action.

Compounds of the invention may be administered together in a unitary pharmaceutical composition or separately and, when administered separately this may occur simultaneously or sequentially in any order. Such sequential administration may be close in time or remote in time.

As used herein, terms "treat" or "treatment" refer to therapeutic or palliative or measures. Beneficial or desired clinical results include, but are not limited to, alleviation, in whole or in part, of symptoms associated with a disorder or condition, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

In certain embodiments, compounds of Formula I are useful for preventing diseases and disorders as defined herein (for example autoimmune diseases, inflammatory diseases, and cancer). The term "preventing" as used herein means the prevention of the onset, recurrence or spread, in whole or in part, of the disease or condition as described herein, or a symptom thereof.

The phrase "effective amount" means an amount of compound that, when administered to a mammal in need of such treatment, is sufficient to (i) treat or prevent a particular disease, condition, or disorder mediated by a PIM-1 and/or PIM-2 and/or PIM-3 kinase, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone ("PVP") K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, for example a salt such sodium chloride, if desired. The solution is typically filtered, for example using a 0.2 micron filter, to remove impurities and contaminants.

Another formulation may be prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

Accordingly, another aspect of the present invention provides a pharmaceutical composition, which comprises a compound of Formula I or a pharmaceutically acceptable salt thereof in combination with a pharmaceutically acceptable diluent or carrier.

According to another aspect, the present invention provides a compound of Formula I or a pharmaceutically acceptable salt or solvate thereof, for use in therapy, such as the treatment of a PIM-1 and/or PIM-2 and/or PIM-3 kinase-mediated condition.

According to a further aspect, the present invention provides a compound of Formula I, or a pharmaceutically acceptable salt or solvate thereof, for use in the treatment of a PIM-1 and/or PIM-2 and/or PIM-3 kinase-mediated condition, as defined hereinabove.

Another aspect of the present invention provides a compound of this invention for use in the treatment of inflammatory and autoimmune diseases. In one embodiment, the disease is selected from multiple sclerosis, inflammatory bowel disease, lupus, psoriasis and rheumatoid arthritis.

Another aspect of the present invention provides a compound of this invention for use in the treatment of cancer. In one embodiment, the cancer is of hematological origin.

In one embodiment, the cancer derives from T cells. In one embodiment, the cancer derives from B cells.

Another aspect of the present invention provides the use of a compound of this invention in the manufacture of a medicament for the treatment of inflammatory and autoimmune diseases. In one embodiment, the disease is selected from multiple sclerosis, inflammatory bowel disease, lupus, psoriasis and rheumatoid arthritis.

Another aspect of the present invention provides the use of a compound of this invention in the manufacture of a medicament for the treatment of cancer.

Abbreviations used in herein have the following definitions:

| Abbreviation | Definition |
| --- | --- |
| ACN | acetonitrile |
| $Boc_2O$ | tert-butoxycarbonyl |
| Cbz-Cl | benzyl chloroformate |
| DAST | diethylaminosulfur trifluoride |
| DCC | dicyclohexylcarbodiimide |
| DCE | dichloroethane |
| DCM | dichloromethane |
| dcpp-$2HBF_4$ | bis(dicyclohexylphosphino)propane) tetrafluoroboric acid |
| DEA | diethylamine |
| DEAD | diethyl azodicarboxylate |
| DIAD | diisopropyl azodicarboxylate |
| DIEA | diisopropylethylamine |
| DMA | N,N-dimethylacetamide |
| DMAP | dimethylaminopyridine |
| DME | dimethoxyethane |
| DPPA | diphenylphosphoryl azide |
| e.e. | enantiomeric excess |
| $Fe(acac)_3$ | tris(acetylacetonato) iron(III) |
| HATU | (2-(7-aza-1H-benzotriazole-1-yl)-1,1,3,3-tetramethyluronium hexafluorophosphate) |
| IPA | Isopropyl alcohol |
| LAH | lithium aluminum hydride |
| NMP | N-methylpyrrolidone |
| $P(Cy)_3$ | tricyclohexylphosphine |
| $PdCl_2(dppf)*dcm$ | 1,1'-Bis(diphenylphosphino)ferrocene-palladium(II)dichloride dichloromethane complex |
| TBSOTf | tributylsilyl triflate |
| TFA | trifluoroacetic acid |
| THF | tetrahydrofuran |
| TMSCl | trimethylsilyl chloride |

EXAMPLES

The following examples illustrate the invention. In the examples described below, unless otherwise indicated all temperatures are set forth in degrees Celsius. Reagents were purchased from commercial suppliers such as Aldrich Chemical Company, Acros, Lancaster, TCI or Maybridge unless otherwise indicated, and were used without further purification unless otherwise indicated. Tetrahydrofuran (THF), dichloromethane (DCM, methylene chloride), toluene, and dioxane were purchased from Aldrich in Sure seal bottles and used as received unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was done on a Biotage system (Manufacturer: Dyax Corporation) having a silica gel column or on a silica SepPak cartridge (Waters). Chiral chromatography was done on Chiraltech® columns unless otherwise indicated.

Example A

Enzyme PIM-1 Assay

The assay for the determination of PIM-1 activity is based on the incorporation of $[^{33}P]PO_4$ from $[\gamma-^{33}P]ATP$ into PIM2tide substrate and capture of the radiolabeled peptide onto a Whatman P81 (phosphocellulose) filter plate. The amount of radiolabeled product is then measured by liquid scintillation counting. The final buffer conditions were as follows: 20 mM $K^+MOPS$, pH 7.4, 10 mM $MgCl_2$, 0.005%

Tween-20, 1 mM DTT. Assay mixtures contained 35 μM [γ-$^{33}$P]ATP (20 μCi/mL), 7.5 μM PIM2tide and 0.25 nM PIM-1 in a total volume of 50 μL. Incubations were carried out for 60 min at 22° C. and quenched with 75 μL of 200 mM H$_3$PO$_4$, filtered through a Whatman P81 plate and washed (1×200 μL and 5×100 μL) with 200 mM H$_3$PO$_4$. Fifty μL of liquid scintillation cocktail were then added per well, and the plate was counted for 30 s/well using a TopCount NXT.

IC$_{50}$ Determinations:

Compounds were prepared at 50× the final concentration in DMSO by conducting 3-fold serial dilutions from a 500-μM intermediate dilution to give a 10-point dosing curve having a high dose of 10 μM. One-μL aliquots of these were then transferred to the assay mixtures above to give a final concentration of DMSO of 2%. A standard or reference compound was typically included on each assay plate to validate that plate. For each plate, percent of control (POC) values were calculated for each well. IC$_{50}$ values were estimated from the POC values using a standard 4-parameter logistic model. The IC$_{50}$ is defined as the concentration of inhibitor at which the POC equals 50 for the fitted curve. Averaged IC$_{50}$ values of compounds tested in this assay are provided in Table 1.

Example B

PIM-2 Assay

Assay was performed as described in Example A, using 4 μM [γ-$^{33}$P]ATP (20 μCi/mL), 1.0 μM PIM2tide and 1.5 nM GST-tagged recombinant full-length human Pim-2 in place of PIM-1. Averaged IC$_{50}$ values of compounds tested in this assay are provided in Table 1.

Example C

PIM-3 Assay

Assay was performed as described in Example A, using 30 μM [γ-$^{33}$P]ATP (20 μCi/mL), 3.75 μM PIM2tide and 0.5 nM recombinant rat PIM-3 in place of PIM-1. Averaged IC$_{50}$ values of compounds tested in this assay are provided in Table 1.

TABLE 1

| Example No. | PIM-1 IC$_{50}$ (nM) | PIM-2 IC$_{50}$ (nM) | PIM-3 IC$_{50}$ (nM) |
|---|---|---|---|
| 1 | 0.43 | 161 | 1.7 |
| 2 | 0.19 | 74 | 1.0 |
| 3 | 0.13 | 53 | 0.3 |
| 4 | 0.84 | 451 | 12 |
| 5 | 0.25 | 131 | 2.6 |
| 6 | 11.1 | >1000 | >100 |
| 7 | 3.94 | >1000 | 45 |
| 8 | 1.31 | 151 | 2.5 |
| 9 | 0.68 | 403 | 4.2 |
| 10 | 1.84 | 306 | 12 |
| 11 | 0.20 | 75 | 1.1 |
| 12 | 0.40 | 51 | 1.1 |
| 13 | 0.31 | 121 | 1.0 |
| 14 | 0.15 | 76 | 0.4 |
| 15 | 0.09 | 59 | 0.3 |
| 16 | 0.28 | 140 | 6.0 |
| 17 | 0.06 | 12.4 | 1.2 |
| 18 | 0.25 | 172 | 0.5 |
| 19 | 2.38 | >1000 | 25 |
| 20 | 0.35 | 131 | 3.3 |
| 21 | 1.14 | 427 | 46 |
| 22 | 0.25 | 145 | 2.9 |
| 23 | 2.85 | 412 | 38 |
| 24 | 2.01 | 935 | 76 |
| 25 | 0.80 | 86 | 5.1 |
| 26 | 2.12 | 796 | >100 |
| 27 | 0.80 | 334 | 25 |
| 28 | 1.08 | >1000 | 8.2 |
| 29 | 5.12 | >1000 | 47 |
| 30 | 0.32 | 63 | 0.9 |
| 31 | 0.08 | 23 | 0.4 |
| 32 | 0.53 | 266 | 10 |
| 33 | 1.41 | 758.61 | 5.9 |
| 34 | 0.20 | 41 | 0.3 |
| 35 | 4.52 | >1000 | 39 |
| 36 | 0.18 | 32 | 2.0 |
| 37 | 0.11 | 22 | 0.8 |
| 38 | 0.23 | 56 | 0.5 |
| 39 | 0.08 | 18 | 1.0 |
| 40 | 0.21 | 78 | 4.7 |
| 41 | 0.11 | 16 | 2.0 |
| 42 | 0.26 | 49 | 0.5 |
| 43 | 0.13 | 65 | 1.5 |
| 44 | 0.13 | 29 | 0.2 |
| 45 | 0.21 | 29 | 0.5 |
| 46 | 0.07 | 33 | 0.3 |
| 47 | 0.09 | 51 | 3.8 |
| 48 | 1.41 | >100 | 1.9 |
| 49 | 0.22 | 68 | 0.4 |
| 50 | 4.88 | >100 | 41 |
| 51 | 0.10 | 11 | 1.1 |
| 52 | 1.39 | >100 | 2.0 |
| 53 | 0.24 | 27 | 0.3 |
| 54 | 0.41 | 67 | 0.6 |
| 55 | 0.25 | 35 | 0.3 |
| 56 | 0.14 | 16 | 2.4 |
| 57 | 0.45 | >100 | 0.9 |
| 58 | 0.60 | >100 | 0.7 |
| 59 | 0.56 | >100 | 0.8 |
| 60 | 0.19 | 77 | 4.0 |
| 61 | 0.59 | >100 | 3.7 |
| 62 | 0.71 | 2.9 | 1.4 |
| 63 | 11.7 | >100 | 25 |
| 64 | 9.33 | >100 | 14 |
| 65 | 1.45 | 18 | 2.0 |
| 66 | 0.92 | 14 | 1.7 |
| 67 | 1.63 | 63 | 3.2 |
| 68 | 4.09 | >100 | 14 |
| 69 | 0.21 | 38 | 0.5 |
| 70 | 0.18 | >100 | 0.3 |
| 71 | 0.20 | >100 | 0.3 |
| 72 | 0.19 | >100 | 2.9 |
| 73 | 0.17 | >100 | 32 |
| 74 | 0.09 | 41 | 6.7 |
| 75 | 1.84 | >100 | 18 |
| 76 | 0.40 | 52 | 3.6 |
| 77 | 0.16 | 10 | 0.3 |
| 78 | 0.24 | >100 | 10 |
| 79 | 0.16 | 58 | 3.0 |
| 80 | 6.41 | >100 | 32 |
| 81 | 0.37 | >100 | 2.8 |
| 82 | 1.12 | >100 | 30 |
| 83 | 1.13 | 28 | 1.0 |
| 84 | 0.73 | >100 | 12 |
| 85 | ND | ND | 18 |
| 86 | 0.14 | 31 | 0.3 |
| 87 | 35.5 | >100 | >100 |
| 88 | 3.26 | >100 | 18 |
| 89 | 5.38 | >100 | 14 |
| 90 | 2.26 | >100 | 23 |
| 91 | 0.25 | >100 | 2.6 |
| 92 | 0.22 | 33 | 0.8 |
| 93 | 0.20 | 83 | 0.9 |
| 94 | 0.29 | 31 | 4.6 |
| 95 | 0.19 | 79 | 3.0 |
| 96 | 0.12 | 5.4 | 0.5 |
| 97 | 0.11 | 65 | 8.1 |
| 98 | 0.38 | >100 | 1.8 |
| 99 | 0.11 | 55 | 0.6 |

TABLE 1-continued

| Example No. | PIM-1 IC$_{50}$ (nM) | PIM-2 IC$_{50}$ (nM) | PIM-3 IC$_{50}$ (nM) |
|---|---|---|---|
| 100 | 0.10 | 6.5 | 1.1 |
| 101 | 0.15 | 40 | 0.8 |
| 102 | 0.19 | 30 | 0.7 |
| 103 | 0.10 | >100 | 3.1 |
| 104 | 0.17 | >100 | 12 |
| 105 | 0.04 | 13 | 0.7 |
| 106 | 1.62 | >100 | 3.4 |
| 107 | 0.48 | >100 | 0.9 |
| 108 | 0.49 | >100 | 4.7 |
| 109 | 0.28 | >100 | 5.5 |
| 110 | 0.19 | 95 | 1.8 |
| 111 | 0.07 | 52 | 1.0 |
| 112 | 0.12 | 21 | 1.4 |
| 113 | 0.05 | >100 | 2.3 |
| 114 | 0.06 | 5.6 | 0.3 |
| 115 | 0.29 | >100 | ND |
| 116 | 0.24 | 76 | 1.8 |
| 117 | 0.21 | 210 | 0.4 |
| 118 | 0.11 | 72 | 0.8 |
| 119 | 0.21 | 23 | 0.9 |
| 120 | 0.47 | >100 | 3.0 |
| 121 | 0.13 | 8.7 | 0.2 |
| 122 | 0.20 | >100 | 0.7 |
| 123 | 0.20 | 73 | 0.4 |
| 124 | 0.21 | >100 | 0.7 |
| 125 | 0.11 | 6.2 | 0.4 |
| 126 | 0.28 | >100 | 1.9 |
| 127 | 3.28 | >100 | 11 |
| 128 | 0.58 | >100 | 0.7 |
| 129 | 1.60 | 621 | 7.7 |
| 130 | 9.03 | 756 | 28 |
| 131 | 2.18 | 787 | 17 |
| 132 | 4.42 | 538 | 16 |
| 133 | 0.16 | 77 | ND |
| 134 | 0.38 | 48 | 0.6 |
| 135 | 1.41 | 82 | 3.0 |
| 136 | 0.87 | 96 | 5.0 |
| 137 | 3.50 | >1000 | 34 |
| 138 | 2.03 | >100 | 9.5 |
| 139 | 0.58 | >100 | 4.9 |
| 140 | 0.12 | 54 | 0.5 |
| 141 | 0.20 | 90 | 0.9 |
| 142 | 0.09 | 44 | 0.5 |
| 143 | 0.09 | 38 | 0.5 |
| 144 | 0.95 | 48 | 1.0 |
| 145 | 0.25 | 30 | 0.7 |
| 146 | 0.13 | 34 | 0.3 |
| 147 | 0.11 | 36 | 0.3 |
| 148 | 0.34 | >100 | 1.2 |
| 149 | 0.17 | >100 | 0.7 |
| 150 | 0.41 | >100 | 3.5 |
| 151 | 0.49 | 85 | 1.0 |
| 152 | 0.25 | 42 | 0.3 |
| 153 | 0.19 | >100 | 1.6 |
| 154 | 0.58 | >100 | 4.2 |
| 155 | 0.34 | 45 | 1.3 |
| 156 | 0.15 | 38 | 0.4 |
| 157 | 3.44 | 239 | 12 |
| 158 | 0.16 | 41 | 1.1 |
| 159 | 0.14 | 48 | 0.5 |
| 160 | 0.16 | 46 | 0.4 |
| 161 | 0.23 | >100 | 1.9 |
| 162 | 1.24 | >100 | 35 |
| 163 | 0.30 | >100 | 10 |
| 164 | 2.63 | >100 | 7.3 |
| 165 | 3.83 | >100 | 6.6 |
| 166 | 1.33 | >100 | 8.9 |
| 167 | 2.04 | >100 | 12 |
| 168 | 1.75 | >100 | 15 |
| 169 | 6.65 | >100 | 36 |
| 170 | 0.95 | >100 | 6.2 |
| 171 | 0.29 | >100 | 0.5 |
| 172 | 2.22 | >100 | 10 |
| 173 | 0.13 | >100 | 0.4 |
| 174 | 1.10 | >100 | 0.8 |
| 175 | 0.70 | >100 | 1.4 |
| 176 | 0.17 | 92 | 2.7 |
| 177 | 0.31 | >100 | 1.7 |
| 178 | 1.81 | >100 | 19 |
| 179 | 2.44 | >100 | 4.1 |
| 180 | 3.08 | >100 | 13 |
| 181 | 0.41 | 96 | 2.7 |
| 182 | 0.75 | >100 | 4.1 |
| 183 | 0.27 | >100 | 1.2 |
| 184 | 0.41 | >100 | 1.5 |
| 185 | 0.37 | >100 | 1.0 |
| 186 | 0.16 | 67 | 0.4 |
| 187 | 0.37 | >100 | 0.9 |
| 188 | 0.30 | 111 | 1.0 |
| 189 | 0.57 | 85 | 1.5 |
| 190 | 1.03 | >100 | 1.0 |
| 191 | 0.20 | 74 | 0.2 |
| 192 | 0.17 | 80 | 0.5 |
| 193 | 13.0 | >1000 | 67 |
| 194 | >100 | >1000 | >100 |
| 195 | 21.3 | >1000 | 53 |
| 196 | 42.3 | >1000 | >100 |
| 197 | 0.30 | 150 | 0.9 |
| 198 | 0.14 | 123 | 0.2 |
| 199 | 18.7 | >1000 | 30 |
| 200 | 1.86 | 137 | 3.4 |
| 201 | 43.5 | >1000 | 42 |
| 202 | 6.62 | >1000 | 7.9 |
| 203 | 19.8 | >1000 | 37 |
| 204 | 0.48 | >1000 | 3.0 |
| 205 | 0.14 | 244 | 0.2 |
| 206 | 0.09 | 55 | 0.1 |
| 207 | 58.0 | >1000 | 40 |
| 208 | 0.41 | >1000 | 2.5 |
| 209 | 0.55 | 176 | 0.6 |
| 210 | >100 | >1000 | >100 |
| 211 | 0.52 | 645 | 4.0 |
| 212 | 0.14 | 72 | 0.3 |
| 213 | 0.64 | >1000 | 8.0 |
| 214 | 0.38 | 138 | 0.4 |
| 215 | 0.47 | >1000 | 3.1 |
| 216 | 0.38 | 56 | 0.8 |
| 217 | 0.32 | 40 | 0.4 |
| 218 | 0.26 | 33 | 0.4 |
| 219 | 0.26 | 253 | 1.2 |
| 220 | 0.28 | 72 | 0.4 |
| 221 | 0.41 | 128 | 1.0 |
| 222 | 0.22 | 77 | 0.2 |
| 223 | 0.29 | 62 | 0.3 |
| 224 | 0.36 | 94 | 0.7 |
| 225 | 0.27 | 139 | 1.1 |
| 226 | 0.27 | 235 | 0.5 |
| 227 | 0.48 | 453 | 2.5 |
| 228 | 0.79 | 916 | 3.8 |
| 229 | 0.13 | 55 | 0.3 |
| 230 | 0.64 | 211 | 3.2 |
| 231 | 0.88 | 429 | 3.5 |
| 232 | 0.20 | 206 | 0.8 |
| 233 | 0.28 | 260 | 1.1 |
| 234 | 8.22 | >1000 | 33 |
| 235 | 7.81 | >1000 | 33 |
| 236 | 1.08 | 675 | 2.4 |
| 237 | 2.91 | 211 | 1.8 |
| 238 | 0.17 | 166 | 0.6 |
| 239 | 1.66 | >1000 | 12 |
| 240 | 2.37 | >1000 | 18 |
| 241 | 2.60 | >1000 | 17 |
| 242 | 4.20 | >1000 | 21 |
| 243 | 0.54 | 728 | 2.1 |
| 244 | 1.11 | 93 | 1.0 |
| 245 | 1.04 | 125 | 0.5 |
| 246 | 1.77 | >1000 | 15 |
| 247 | 0.41 | 392 | 1.2 |
| 248 | 1.17 | >1000 | 8.1 |
| 249 | 0.51 | 83 | 0.8 |
| 250 | 2.77 | 861 | 11 |
| 251 | 0.75 | 102 | 0.8 |
| 252 | 4.05 | >1000 | 24 |
| 253 | 0.78 | 776 | 2.2 |

TABLE 1-continued

| Example No. | PIM-1 IC$_{50}$ (nM) | PIM-2 IC$_{50}$ (nM) | PIM-3 IC$_{50}$ (nM) |
|---|---|---|---|
| 254 | 0.25 | 273 | 0.9 |
| 255 | 0.24 | 284 | 0.6 |
| 256 | 0.58 | 199 | 1.0 |
| 257 | 1.45 | 724 | 9.0 |
| 258 | 2.05 | 531 | 1.9 |
| 259 | 0.12 | 54 | 0.3 |
| 260 | 0.39 | 95 | 0.5 |
| 261 | 0.60 | >1000 | 3.3 |
| 262 | 0.22 | 63 | 0.4 |
| 263 | 0.66 | 454 | 3.0 |
| 264 | 0.54 | 255 | 1.3 |
| 265 | 0.53 | >1000 | 1.3 |
| 266 | 0.50 | 690 | 1.0 |
| 267 | 0.35 | 350 | 0.7 |
| 268 | 0.89 | >1000 | 3.4 |
| 269 | 0.37 | 413 | 2.0 |
| 270 | 0.38 | 434 | 1.9 |
| 271 | 0.73 | 647 | 4.3 |
| 272 | 0.24 | 124 | 0.5 |
| 273 | 25.9 | >1000 | 43 |
| 274 | 0.40 | 961 | 1.7 |
| 275 | 0.20 | 376 | 0.7 |
| 276 | 0.20 | 44 | 0.3 |
| 277 | 0.28 | 231 | 0.7 |
| 278 | 0.23 | 180 | 0.4 |
| 279 | 0.96 | 431 | 3.1 |
| 280 | 0.62 | 418 | 2.5 |
| 281 | 0.26 | 242 | 0.7 |
| 282 | 0.28 | 166 | 0.8 |
| 283 | 0.18 | 194 | 0.7 |
| 284 | 0.28 | 50 | 0.4 |
| 285 | 0.57 | >1000 | 8.6 |
| 286 | 1.38 | >1000 | 33 |
| 287 | 0.32 | 178 | 0.7 |
| 288 | 9.42 | >1000 | 56 |
| 289 | 0.38 | 459 | 1.6 |
| 290 | 29.7 | >1000 | >100 |
| 291 | 0.19 | 82 | 0.5 |
| 292 | 0.65 | 68 | 1.1 |
| 293 | 0.40 | 468 | 1.1 |
| 294 | 0.53 | 94 | 0.7 |
| 295 | 2.55 | 522 | 12 |
| 296 | 1.51 | >1000 | 12 |
| 297 | 0.18 | 20 | 0.2 |
| 298 | 0.27 | 59 | 0.4 |
| 299 | 0.55 | 695 | 1.6 |
| 300 | 0.36 | 64 | 0.4 |
| 301 | 0.20 | 14 | 0.2 |
| 302 | 0.22 | 69 | 0.3 |
| 303 | 1.33 | 241.91 | 5.85 |
| 304 | 0.26 | 65.06 | 0.3 |
| 305 | 0.96 | 70.97 | 0.4 |
| 306 | 0.28 | 281.49 | 0.7 |
| 307 | 1.64 | 62.4 | 6.9 |
| 308 | 0.17 | 29.41 | 0.4 |
| 309 | 1.18 | 406.71 | 3 |
| 310 | 0.46 | 415.03 | 1.1 |
| 311 | 0.28 | 50.02 | 0.4 |
| 312 | 0.24 | 169.96 | 0.8 |
| 313 | 1.15 | 5698.36 | 6.1 |
| 314 | 0.22 | 18.39 | 0.4 |
| 315 | 0.19 | 25.75 | 0.4 |
| 316 | 0.48 | 763.61 | 2.8 |
| 317 | 0.34 | 194.39 | 0.4 |
| 318 | 0.94 | 218.06 | 0.8 |
| 319 | 0.11 | 111.84 | 0.3 |
| 320 | 0.14 | 111.06 | 0.3 |
| 321 | 1.68 | 1818.44 | 6.1 |
| 322 | 0.08 | 22.66 | 0.1 |
| 323 | 0.14 | 145.05 | 0.2 |
| 324 | 0.18 | 44.57 | 0.21 |
| 325 | 0.06 | 101.71 | 0.13 |
| 326 | 0.31 | 588.2 | 1.36 |
| 327 | 0.42 | 340.12 | 1.34 |
| 328 | 0.33 | 748.45 | 1.39 |

ND: Not determined

Example D

Cellular Proliferation Assay

The assay for determination of the antiproliferative activity of multiple PIM inhibitors in the JAK2-driven cell lines is conducted as follows. Cells are plated out to 96-well plates at an initial density of 10,000 cells/well in 95 pt. Compounds are prepared at 20× the final concentration in DMSO by conducting 3-fold serial dilutions to give a 10-point dosing curve having a high dose of 1000 µM. Aliquots (5 µL) of these dilutions are then transferred to the appropriate wells of the 96-well plates containing cells to yield a final DMSO concentration of 0.5%. The cells are then incubated with compound for 72 hours at 37° C., 5% $CO_2$. CelltiterBlue reagent (Promega, Catalog #: G8080) is then added (20 µL/well) and incubated at 37° C., 5% $CO_2$ for 1-8 hours depending on the cell line being analyzed. The plate is then quantified employing a fluorescence plate reader (Model: Gemini [Molecular Devices]; Settings: 560 nm (Ex)/590 nm (Em) 570 nm (cut-off) [CellTiter Blue Assay].

The values for each well are then converted to a percent of untreated control (POC). These POC values are then plotted as a function of compound concentration. A 4-parameter curve-fit analysis is performed for each compound dilution and an IC$_{50}$ value is calculated from this curve. Examples of cell lines which may be used in the assay are listed below (all are commercially available from ATCC®). Compounds described herein were shown or will be shown to be effective in this model.

| | Cell line |
|---|---|
| A | PC3 (Androgen independent prostate cancer) |
| B | K562 (Ph+ chronic myelogenous leukemia) |
| C | MV4-11 (Acute myelogenous leukemia) |
| D | BxPC3 (Pancreatic Cancer) |
| E | HepG2 (Hepatocellular Carcinoma) |
| F | BaF3 (Mouse pro-B-cell line) |
| G | BaF3 TEL-JAK2 (Mouse pro-B-cell transformed with TEL-JAK2 fusion) |
| H | BaF2 BCR-Abl (Mouse pro-B-cell transformed with BCR-Abl fusion) |

Example E

T Cell In Vitro Functional Assays

The in vitro assays which can be used to assess the effects of the compounds of the invention are described in assays A, B, C and D below. CD4+ T cells are isolated from red blood cell-depleted splenocytes of C57Bl/6J mice (Jackson Laboratories, catalog #000664) using CD4+ T cell isolation kit (Miltenyi, catalog #130-090-860).

In assay (A), purified CD4+ T cells are plated in 96 well plates at 90000 cells/well in 90 µL. A dilution series of the compounds are prepared at 100× the final concentration in DMSO and then diluted 10-fold into complete media (10× stocks). 10 µL of 10× compound stocks are added to appropriate wells of 96 well plates containing cells and incubated for 1 hour at 37° C., 5% $CO_2$. The cell/compound mixtures are then transferred to a 96 well plate coated with anti-CD3 mAb (1 µg/mL; BD Pharmingen, catalog #553057) and soluble anti-CD28 mAb (1 µg/mL; BD Pharmingen, catalog #553294) was added. Plates are cultured at 37° C., 5% $CO_2$ for 40 hours. 20 µL of the culture are removed for determination of proliferation using the CellTitre-Glo™ luminescent assay (Promega, Catalog #G7571) according to the manufacturer's protocol. The plate is quantified on a Packard TopCount instrument using luminescence protocol and data analyzed using Prism software.

In assay (B), purified CD4+ cells are treated with compound and stimulated as described for assay (A). After 40 hours, supernatants are assayed for IL-2 using R&D duo set ELISA kits (catalog #DY402). ELISA plates are quantified relative to a standard curve using Molecular Devices Versamax Reader at 450 nM and Softmax Pro software.

In assay (C), 1,000,000 cells/mL of purified CD4+ T cells are mixed with 1 µg/mL anti-CD28, 10 ng/mL IL-4 (R&D Systems cat #404-ML-010/CF) and 2 µg/mL anti-IFNγ (R&D Systems catalog #AB-485-NA) and placed into plates coated with 1 µg/mL anti-CD3. After 5 days, cells are harvested, washed and incubated overnight at 37° C., 5% $CO_2$. The following day, 50,000 cells are plated into each well of a 96 well plate. A dilution series of compounds are prepared at 200× the final concentration in DMSO, then 10× stocks are prepared by dilution in cell culture media. 10 µL of 10× stocks are added to the cells in the 96-well plate and incubated for 2 hours at 37° C., 5% $CO_2$. Cell/compound mixtures are then transferred to wells coated with 0.1 µg anti-CD3 and incubated at 37° C., 5% $CO_2$. Culture supernatants are removed 18 hours later and tested for IL-4 levels by ELISA (R&D Systems catalog #DY404). ELISA plates are quantified relative to a standard curve using Molecular Devices Versamax Reader at 450 nM and Softmax Pro software.

In assay (D), 1,000,000 cells/mL of purified CD4+ T cells are mixed with 1 µg/mL anti-CD28, 50 ng/mL IL-6 (R&D Systems cat #406-ML-025/CF), 1 ng/mL TGFβ (R&D Systems cat #303-B2-002), 2 µg/mL anti-IL-4 (R&D Systems catalog #AB-404-NA), 2 µg/mL anti-IFNγ (R&D Systems catalog #AB-485-NA) and placed into plates coated with 1 µg/mL anti-CD3. After 4 days, cells are harvested, washed and 100,000 cells are plated into 96 well plate. A dilution series of compounds are prepared at 200× the final concentration in DMSO, then 10× stocks are prepared by dilution in cell culture media. 10 µL of 10× stocks are added to the cells in the 96-well plate. After 2 hours, 50 ng IL-23 (R&D Systems catalog #1887-ML-010/CF) is added to each well and 18 hours later supernatants are removed and tested for IL-22 levels by ELISA (R&D Systems catalog #M2200). ELISA plates are quantified relative to a standard curve using Molecular Devices Versamax Reader at 450 nM and Softmax Pro software. Compounds described herein were shown or will be shown to be effective in this model.

Example F

T Cell In Vivo Functional Assay

The effect of compounds of Formula I on T cell responses can be determined by the following experiment. On Day O, C57BL/6 (Jackson Laboratories #000664, 6-8 weeks of age) are immunized at the base of the tail with 100 µg of hen egg lysozyme (HEL; Sigma #L7773) with complete Freund's adjuvant (CFA; Sigma #F5881). Starting on Day 0 and continuing until Day 7, mice are dosed twice a day by oral administration with vehicle (water) or the compound of Formula I (200 mg/kg). On Day 7, popiteal lymph nodes are removed, single cell suspensions are prepared and 500,000 cells in 200 µL are activated in 96 well plates with the indicated dose of HEL peptide. Following incubation for 72 hours at 37° C., 5% $CO_2$, supernatants are harvested for IFNγ ELISA (R&D Systems catalog #MIF00) and proliferation is assessed using the CellTitre-Glo™ luminescent assay (Promega, Catalog #G7571) with both assays performed according to the manufacturer's protocol. ELISA plates are quantified relative to a standard curve using Molecular Devices Versamax Reader at 450 nM and Softmax Pro software; proliferation can be quantitated on a Packard TopCount instrument using luminescence protocol and data analyzed using excel software. Compounds described herein were shown or will be shown to be effective in this model.

Example G

B Cell In Vivo Functional Assay

The effect of a compound of Formula I on B cell responses can be determined with the following experiment. On Day O, C57BL/6J mice (Jackson Laboratories #000664, 6-8 weeks of age) are immunized at the base of the tail with 20 µg of hen egg lysozyme (HEL; Sigma #L7773) with complete Freund's adjuvant (CFA; Sigma #F5881). Mice are re-immunized on day 7 with 20 µg HEL in alum (Pierce catalog #77161). Starting on Day 0 and continuing through Day 28, mice are dosed once a day by oral administration with vehicle (water) or the compound of Formula I (200 mg/kg). Serum is collected on days 0, 7, 14, 21, and 28 and analyzed for HEL-specific total IgG, IgG1, IgG2a, IgG2b, and IgG3 antibody production by capture ELISA (antibodies purchased from Invitrogen, catalog Nos. M30007, M32107, M32307, M32507 and M32607). ELISA plates are quantitated using Molecular Devices Versamax reader at 450 nM. The group mean titer of each antibody analyte is converted to percent of vehicle control (=100%). Compounds described herein were shown or will be shown to be effective in this model.

Example H

Adoptive Transfer Experimental Autoimmune Encephalomyelitis

The effect of a compound of Formula I on an autoimmune disease induced by T cells can be determined using an adoptive transfer EAE model, an animal model of human multiple sclerosis (Brain (2006), 129, 1953-1971). This model relies on the injection of T cells from animals with EAE into disease-free host animals. This injection of cells is known to those skilled in the art as adoptive transfer. By injecting the animals with activated, encephalogenic T cells, this model is focused on the pathogenic stage of EAE autoimmune disease. On Day −14, C57BL/6 mice (Taconic Farms; 10 weeks old) are immunized with a disease-causing protein, MOG(35-55) peptide in complete Freund's adjuvant (Hooke Laboratories, catalog #EK-0113). On Day −3, spleens are harvested, single cell suspensions are prepared and then 5,000,000 cells/mL are stimulated with 20 µg/mL MOG(33-55) peptide (Open Biosystems), 30 ng/mL IL-12 (R&D Systems catalog #419-ML-010), 10 µg/mL anti-IFNγ antibody (BD Biosciences catalog #554408) at 37° C., 5% $CO_2$. On Day 0, 1,500,000 of these cells are injected intravenously into the tail veins of C57BL/6 recipient mice. The recipient mice are divided into treatment groups for vehicle (distilled water; 10 mL/kg) or the compound of Formula I (200 mg/kg), both administered by oral gavage twice daily for 26 days. The recipient mice are scored daily days 0 through 26 using the clinical scoring system shown in Table 2. Compounds described herein were shown or will be shown to be effective in this model.

TABLE 2

| Score | Observations |
|---|---|
| 0.0 | no symptoms |
| 1.0 | limp tail |
| 2.0 | limp tail and weakness of hind legs |
| 3.0 | limp tail and complete hind limb paralysis, or partial front and hind limb paralysis, or severe head tilting combined with pushing against cage wall and spinning when picked up by tail |
| 4.0 | limp tail, complete hind limb paralysis and partial front limb paralysis |
| 5.0 | Full body paralysis, or spontaneous rolling or found dead due to paralysis |

Example I

MOG(35-55)-Induced Experimental Autoimmune Encephalomyelitis

An additional method of determining the effect of compounds of Formula I on an autoimmune disease associated with T cells and cytokines uses the MOG-induced experimental autoimmune encephalomyelitis (EAE) model. MOG-induced EAE is an animal model of human multiple sclerosis (Brain (2006), 129, 1953-1971).

On Day 0, C57BL/6J mice (Jackson Laboratories #000664, 6-8 weeks of age) are injected subcutaneously with 100 μL of complete Freund's adjuvant (CFA) prepared as a 1:1 emulsion of (a) incomplete Freund's adjuvant (Difco, catalog #263910) containing 8 mg/mL *m. tuberculosis* H37RA (Difco, catalog #231141) and (b) phosphate buffered saline (PBS) containing 1 mg/mL MOG(35-55) peptide (California Peptide Research Inc). On the day 0 and 2, mice are injected intravenously with 200 ng of pertussis toxin (List Biological Laboratories, catalog #181). On day 7, the mice are randomized into treatment groups which receive vehicle (distilled water) or the compound of Formula I (200 mg/kg) administered by oral gavage twice daily from days 7 through 27. The mice are scored daily on days 7 through 37 using the clinical scoring system shown in Table 3. Compounds described herein were shown or will be shown to be effective in this model.

TABLE 3

| Score | Observations |
|---|---|
| 0.0 | no symptoms |
| 0.5 | tail weakness |
| 1.0 | limp tail |
| 1.5 | unsteady gait, mild hind limb ataxia |
| 2.0 | partial hind limb paralysis (hind limbs carrying weight) |
| 2.5 | partial hind limb paralysis (hind limbs not carrying weight) |
| 3.0 | full hind limb paralysis |
| 3.5 | full hind limb paralysis and partial front limb paralysis |
| 4.0 | full body paralysis |

Example J

CD4+CD45RBhi Adoptive Transfer Inflammatory Bowel Disease

The following adoptive transfer model of inflammatory bowel disease (IBD) can be performed to determine the effect of compounds of Formula I on IBD, which is an autoimmune disease associated with T cells and cytokines On Day 0, CD4+ T cells are isolated from the spleens of female Balb/cAnNCrl mice (Charles River Laboratories; 12 weeks old) as described in Example E. The resulting cells are labeled with fluorescent antibodies against CD4 and CD45 markers and are sorted by flow cytometry for CD4+ CD45RBhi cells based on fluorescence. 400,000 CD4+ CD45RBhi cells are then injected intraperitoneally into C.B17/Icr-Prkdc$^{said}$/IcrIcoCrl mice (Charles River Laboratories strain code 236; 12 weeks old). This injection of cells is known to those skilled in the art as "adoptive transfer". On Day 21, mice are randomized into groups for oral gavage treatment with vehicle (1% carboxymethylcellulose sodium (CMC)/0.5% Tween 80 once daily; CMC, Sigma catalog #C9481, Tween 80 Sigma catalog #P1754) or the compound of Formula I (200 mg/kg; twice daily). Treatments continued through Day 42.

At the conclusion of the study, mice are sacrificed and the distal half of their colons are placed in 10% neutral buffered formalin (Richard Allen Scientific catalog #53120-1) and paraffin embedded, sectioned into 4 μm slices and stained with hematoxylin and eosin (H&E) for analysis by a board certified veterinary pathologist.

For each H&E stained section, submucosal edema is quantitated by measuring the distance from the muscularis mucosa to the internal border of the outer muscle layer in a non-tangential area thought to most representative the severity of this change. Mucosal thickness is also measured in a non-tangential area of the section that best represented the overall mucosal thickness. This parameter is indicative of gland elongation and mucosal hyperplasia. The extent of inflammation (macrophage, lymphocyte and polymorphonuclear leukocyte (PMN) infiltrate) is assigned severity scores according to the criteria provided in Table 4.

TABLE 4

| Severity score | Criteria |
|---|---|
| 0 | Normal |
| 1 | Minimal (generally focal affecting 1-10% of mucosa or if diffuse then minimal) |
| 2 | Mild (generally focal affecting 11-25% of mucosa or if diffuse then mild) |
| 3 | Moderate (26-50% of mucosa affected with areas of gland loss replaced by inflammatory cell infiltrate, milder in remaining areas of mucosa) |
| 4 | Marked (51-75% of mucosa affected with areas of gland loss replaced by inflammatory cell infiltrate, milder in remaining areas of mucosa) |
| 5 | Severe (76-100% of mucosa affected with areas of gland loss replaced by inflammatory cell infiltrate, milder in remaining areas of mucosa) |

The parameters reflecting epithelial cell loss/damage are scored individually using a percent area involved scoring method are provided in Table 5.

TABLE 5

| Score | Parameters |
|---|---|
| 0 | None |
| 1 | 1-10% of the mucosa affected |
| 2 | 11-25% of the mucosa affected |
| 3 | 26-50% of the mucosa affected |
| 4 | 51-75% of the mucosa affected |
| 5 | 76-100% of the mucosa affected |

Parameters that are scored using percent involvement included: colon glandular epithelial loss (this includes crypt epithelial as well as remaining gland epithelial loss), and colon erosion (this reflects loss of surface epithelium and generally is associated with mucosal hemorrhage (reflective of the bleeding seen clinically and at necropsy). The three scored parameters (inflammation, glandular epithelial loss, and erosion) are ultimately summed to arrive at a sum of histopathology scores, which indicates the overall damage and would have a maximum score of 15. Compounds described herein were shown or will be shown to be effective in this model.

Example K

MRL/lpr Lupus Model

MRL/lpr is considered to be an animal model of systemic lupus erythematosus (SLE), an autoimmune disease (Cohen and Maldonado 2003, Current Protocols in Immunology Chapter 15, Unit 15.20). MRL/lpr mice have a defect in the apoptosis of activated lymphocytes and over time develop a spontaneous and severe lymphoproliferative disorder characterized by enlarged lymphoid organs, auto-antibody production and kidney disease resulting in proteinuria. SLE patients also exhibit auto-antibodies, and some patients develop kidney disease. To determine the effect of compounds of Formula I in this model of SLE, the following experiment can be conducted.

MRL/MpJ-Fas<lpr> and age-matched MRL/MpJ control mice (Jackson Laboratories, catalog #000485 and #000486, respectively) are treated once daily with vehicle (1% CMC/0.5% Tween 80) or twice daily with the compound of Formula I (200 mg/kg) for 10 weeks. Body weights, lymphadenopathy and urine protein levels are monitored weekly. Urine protein levels are determined with Bayer Albustix dipsticks (Bayer catalog #2191) and scored according to the scale provided in Table 6.

TABLE 6

| Score | Urine protein levels |
|---|---|
| 0 | none detected |
| 0.5 | trace amounts |
| 1 | 30 mg/dL |
| 2 | 100 mg/dL |
| 3 | 300 mg/dL |
| 4 | 2000 mg/dL |

Serum levels of anti-ds-DNA antibody are measured by ELISA (Alpha Diagnostic, catalog #5120) on Day 28 and upon study termination. ELISA plates are quantitated using a Molecular Devices Versamax plate reader at 450 nM and titers calculated relative using to a standard curve using a 4-parameter curve fit with Softmax Pro software. Compounds described herein were shown or will be shown to be effective in this model.

Preparation A

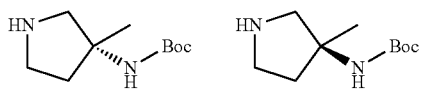

(R)-tert-butyl 3-methylpyrrolidin-3-ylcarbamate and
(S)-tert-butyl 3-methylpyrrolidin-3-ylcarbamate Step A: Preparation of benzyl 3-(tert-butoxycarbonylamino)-3-methylpyrrolidine-1-carboxylate Prepared as described in International Publication WO 2009/140320 A1, Example D, Steps A-D.

Step B: Separation of enantiomers (R)-benzyl 3-(tert-butoxycarbonylamino)-3-methylpyrrolidine-1-carboxylate and (S)-benzyl 3-(tert-butoxycarbonylamino)-3-methyl-pyrrolidine-1-carboxylate A racemic mixture of benzyl 3-(tert-butoxycarbonylamino)-3-methylpyrrolidine-1-carboxylate (14.5 g, 43.3 mmol) was separated via preparative supercritical fluid chromatography under the following conditions: Column: IC 20 mm×250 mm; flow rate: 65 mL/min; mobile phase A: 90% supercritical $CO_2$; mobile phase B: 10% isopropyl alcohol; UV detection wavelength: 214 nm. Peak one: retention time: 4.6 minutes; recovery: (R)-benzyl 3-(tert-butoxycarbonylamino)-3-methylpyrrolidine-1-carboxylate (5.97 g, 17.87 mmol). Peak two: retention time: 6.8 minutes; recovery: (S)-benzyl 3-(tert-butoxycarbonylamino)-3-methylpyrrolidine-1-carboxylate (5.98 g, 17.89 mmol).

Step C: Preparation of (R)-tert-butyl 3-methylpyrrolidin-3-ylcarbamate

Prepared as described in WO 2009/140320A1, Example D, Step E, using (R)-benzyl 3-(tert-butoxycarbonylamino)-3-methylpyrrolidine-1-carboxylate in place of racemic benzyl 3-(tert-butoxycarbonylamino)-3-methylpyrrolidine-1-carboxylate.

Step D: Preparation of (S)-tert-butyl 3-methylpyrrolidin-3-ylcarbamate

Prepared as described in International Publication WO2009/140320A1, Example D, Step E, using (S)-benzyl 3-(tert-butoxycarbonylamino)-3-methylpyrrolidine-1-carboxylate in place of racemic benzyl 3-(tert-butoxycarbonylamino)-3-methylpyrrolidine-1-carboxylate.

Preparation B

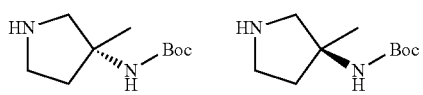

(R)-tert-butyl 3-methylpyrrolidin-3-ylcarbamate and
(S)-tert-butyl 3-methylpyrrolidin-3-ylcarbamate Step A: Preparation of 1-benzyl 3-methyl 3-methylpyrrolidine-1,3-dicarboxylate Prepared as described by Mendiola, et al., Organic Process Research & Development (2009) 13, 292-296, using methyl methacrylate in place of methyl acrylate.

Step B: Preparation of benzyl 3-(tert-butoxycarbonylamino)-3-methylpyrrolidine-1-carboxylate Prepared as described in International Publication WO 2009/140320A1, Example D, Steps C-D.

Step C: Separation of enantiomers (R)-benzyl 3-(tert-butoxycarbonylamino)-3-methylpyrrolidine-1-carboxylate and (S)-benzyl 3-(tert-butoxycarbonylamino)-3-methylpyrrolidine-1-carboxylate Separated as described in Preparation A, Step B.

Step D: Preparation of (R)-tert-butyl 3-methylpyrrolidin-3-ylcarbamate

Prepared as described in International Publication WO 2009/140320A1, Example D, Step E using (R)-benzyl 3-(tert-butoxycarbonylamino)-3-methylpyrrolidine-1-carboxylate in place of racemic benzyl 3-(tert-butoxycarbonylamino)-3-methylpyrrolidine-1-carboxylate

Step E: Preparation of (S)-tert-butyl 3-methylpyrrolidin-3-ylcarbamate

Prepared as described in International Publication WO 2009/140320A1, Example D, Step E, using (S)-benzyl 3-(tert-butoxycarbonylamino)-3-methylpyrrolidine-1-carboxylate in place of racemic benzyl 3-(tert-butoxycarbonylamino)-3-methylpyrrolidine-1-carboxylate.

Preparation C

(S)-tert-butyl 3-methylpyrrolidin-3-ylcarbamate

Step A: Preparation of (R)-3-methacryloyl-4-phenyloxazolidin-2-one

To a solution of (R)-4-phenyloxazolidin-2-one (65.00 g, 398.3 mmol) in dry THF (612.8 mL) at −78° C. was quickly added n-BuLi (167.3 mL, 418.3 mmol) dropwise, and the mixture was stirred at −78° C. for 0.5 hours. To this cold stirring solution was quickly added dropwise a solution of methacryloyl chloride (40.86 mL, 418.3 mmol) in THF (60 mL), and the mixture was allowed to warm to ambient temperature and stirred for 0.5 hours. Water (300 mL) was added and the suspension was stirred for 1 hour and then filtered to give desired product as a hard solid cake (66 g). The filtrate was concentrated under reduced pressure to a yellow solid residue, which was taken up in Et$_2$O (400 mL) and filtered to give additional pure desired product (9 g). The products were combined to give (R)-3-methacryloyl-4-phenyloxazolidin-2-one (75 g, 81% yield).

Step B: Preparation of (R)-3-((S)-1-benzyl-3-methylpyrrolidine-3-carbonyl)-4-phenyloxazolidin-2-one To a solution of (R)-3-methacryloyl-4-phenyloxazolidin-2-one (135.00 g, 583.79 mmol) and TFA (4.497 mL, 58.379 mmol) in dry toluene (50 mL) at <10° C. was quickly added dropwise N-benzyl-1-methoxy-N-((trimethylsilyl)methyl)methanamine (194.16 mL, 758.93 mmol), and the mixture was stirred at ambient temperature overnight. The reaction was filtered and the filtrate was extracted with 4N HCl (3×250 mL). The aqueous layer was washed with ethyl acetate (250 mL) then made basic with solid K$_2$CO$_3$ to pH 10. The basic aqueous layer was extracted with ethyl acetate (4×400 mL), dried (MgSO$_4$), filtered and concentrated under reduced pressure to provide (R)-3-((S)-1-benzyl-3-methylpyrrolidine-3-carbonyl)-4-phenyloxazolidin-2-one (145 g, 399 mmol, 68% yield) as a dark oil.

Step C: Preparation of (R)-benzyl 3-methyl-3-((R)-2-oxo-4-phenyloxazolidine-3-carbonyl)pyrrolidine-1-carboxylate To a suspension of (R)-3-((S)-1-benzyl-3-methylpyrrolidine-3-carbonyl)-4-phenyloxazolidin-2-one (145.50 g, 399.25 mmol) and NaHCO$_3$ (33.54 g, 399.25 mmol) in dry DCE (1000 mL) at ambient temperature was added dropwise a solution of benzylchloroformate (134.87 mL, 958.19 mmol) in DCE (100 mL) and the reaction was stirred at ambient temperature for 24 hours. The reaction was diluted with 1N HCl (500 mL) and the layers were separated. The organic layer was washed with 1M HCl (250 mL), dried (MgSO$_4$), filtered and concentrated under reduced pressure to a thick yellow residue. The residue was purified by flash chromatography (5% ethyl acetate/DCM) to give (R)-benzyl 3-methyl-3-((R)-2-oxo-4-phenyloxazolidine-3-carbonyl)pyrrolidine-1-carboxylate (85.1 g, 208.35 mmol, 52.2% yield).

Step D: Preparation of (R)-1-(benzyloxycarbonyl)-3-methylpyrrolidine-3-carboxylic acid To a solution of 2N LiOH—H$_2$O (26.43 g, 629.8 mmol) was added 30% H$_2$O$_2$ (51.94 mL, 503.9 mmol) at 0° C. To this stirring cold mixture was added a solution of (R)-benzyl 3-methyl-3-((R)-2-oxo-4-phenyloxazolidine-3-carbonyl)pyrrolidine-1-carboxylate (102.9 g, 251.9 mmol) in THF (350 mL). The reaction was stirred at 0° C. for 1 hour. To the reaction was added a solution of sodium sulfite (79.38 g, 629.8 mmol) in water (150 mL). The reaction was warmed to ambient temperature and stirred for 30 minutes. Ethyl acetate (500 mL) was added. The aqueous layer was separated, acidified with solid potassium hydrogen sulfate to pH<3, extracted with ethyl acetate (3×500 mL), washed with brine, dried (MgSO$_4$), filtered and concentrated under reduced pressure to give a solid residue (60 g). The solid was dissolved in a mixture of ethyl acetate/Hexanes (250 mL/800 mL) with heating to reflux. After complete dissolution, the mixture was allowed to cool overnight to give white granular crystals. The solids were filtered and the filtrate concentrated under reduced pressure and again subjected to crystallization conditions to give 5 g of additional solids. The combined solids were again subjected to crystallization conditions using ethyl acetate/hexanes (200 mL/600 mL) to give (R)-1-(benzyloxycarbonyl)-3-methylpyrrolidine-3-carboxylic acid (40 g, 163.7 mmol, 65% yield; >99% e.e.). Chiral HPLC method: 100 A, ISO Col 2 ADH (10.525 min (R); 12.110 min (S)).

Step E: Preparation of (S)-benzyl 3-carbamoyl-3-methylpyrrolidine-1-carboxylate To a mixture of (S)-1-(benzyloxycarbonyl)-3-methylpyrrolidine-3-carboxylic acid (32.87 g, 124.8 mmol), Boc₂O (29.97 g, 137.3 mmol) in ethyl acetate (200 mL) was added pyridine (12.62 mL, 156.1 mmol) and the reaction mixture was stirred at ambient temperature for 3 hours. A solution of 28-30% w/w NH₄OH/water (21.79 mL, 162.3 mmol) was added. The reaction was stirred at ambient temperature for 5 hours. Water (50 mL) was added. The organic layer was separated, washed with 1N HCl (50 mL) and brine, dried and concentrated under reduced pressure to give (S)-benzyl 3-carbamoyl-3-methylpyrrolidine-1-carboxylate (31.30 g, 119.3 mmol, 95.6% yield) as an oil.

Step F: Preparation of (S)-benzyl 3-(tert-butoxycarbonylamino)-3-methylpyrrolidine-1-carboxylate To (S)-Benzyl 3-carbamoyl-3-methylpyrrolidine-1-carboxylate (35.61 g, 135.8 mmol) in 1:1 MeCN/H₂O (100 mL) was added [bis(trifluoroacetoxy)iodo]benzene (58.38 g, 135.8 mmol). The reaction mixture was stirred at ambient temperature for 2 hours and then at 86° C. (bath) for 2 hours. After cooling to ambient temperature, concentrated HCl (14.85 g, 407.3 mmol) and ether (200 mL) were added. The aqueous layer was separated and basified by K₂CO₃ (46.91 g, 339.4 mmol). To the resulting solution was added THF (150 mL) and Boc₂O (37.04 g, 169.7 mmol). The reaction mixture was stirred at ambient temperature for 1 hour. Ethyl acetate (100 mL) was added. The organic layer was separated, washed with brine, dried (sodium sulfate), filtered and concentrated under reduced pressure. The residue was purified by flash chromatography (3:1 hexane/ethyl acetate) on silica gel to give (S)-benzyl 3-(tert-butoxycarbonylamino)-3-methylpyrrolidine-1-carboxylate (42.30 g, 126.5 mmol, 93.2% yield) as an oil.

Step G: Preparation of (S)-tert-butyl 3-methylpyrrolidin-3-ylcarbamate

A mixture of (S)-benzyl 3-(tert-butoxycarbonylamino)-3-methylpyrrolidine-1-carboxylate (29.35 g, 87.77 mmol) and 10% Pd/C (4.670 g, 4.388 mmol) in ethanol (50 mL) was charged with hydrogen (1 atmosphere) and stirred at ambient temperature overnight. The catalyst was removed by filtration and washed with ethanol (2×50 mL). The filtrated was concentrated under reduced pressure to give (S)-tert-butyl 3-methylpyrrolidin-3-ylcarbamate (17.13 g, 85.53 mmol, 97.45% yield) as an oil. MS APCI (+) m/z 201 (M+1) detected.

Preparation D

(R)-tert-butyl 3-methylpyrrolidin-3-ylcarbamate

Prepared as described in Preparation C using (S)-4-phenyloxazolidin-2-one in place of (R)-4-phenyloxazolidin-2-one in Step A.

Preparation E

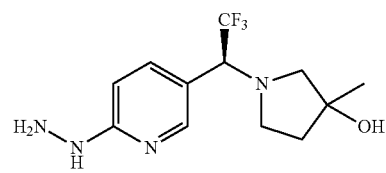 [SMILES: CC1(O)CCN([C@@H](c2ccc(NN)nc2)C(F)(F)F)C1]

Preparation of Diastereomer 1 of 3-methyl-1-((S)-2,2,2-trifluoro-1-(6-hydrazinylpyridin-3-yl)ethyl)pyrrolidin-3-ol and Diastereomer 2 of 3-methyl-1-((S)-2,2,2-trifluoro-1-(6-hydrazinylpyridin-3-yl)ethyl) pyrrolidin-3-ol

Step A: Preparation of pyrrolidin-3-one hydrochloride

To a solution of tert-butyl 3-oxopyrrolidine-1-carboxylate (12.50 g, 67.49 mmol) in DCM (90 mL) was added 4M HCl in dioxane (84.36 mL, 337.4 mmol) at ambient temperature. The reaction was stirred for 3 hours. The precipitate was filtered to give pyrrolidin-3-one hydrochloride (7.4 g, 60.9 mmol, 90.2% yield) which was used in the next step without purification.

Step B: Preparation of 1-benzylpyrrolidin-3-one

To a solution of pyrrolidin-3-one hydrochloride (7.40 g, 60.9 mmol) in DCE (122 mL) was added ethyl acetate (23.9 mL, 137 mmol) followed by benzyl chloride (8.63 g, 68.2 mmol) at ambient temperature. The reaction was heated to 70° C. for 2 hours. The reaction was cooled, diluted with DCM (100 mL), water (100 mL), the layers were separated, and the organic layer was dried (MgSO₄), filtered and concentrated under reduced pressure to give 1-benzylpyrrolidin-3-one (10.01 g, 57.2 mmol, 93.9% yield).

Step C: Preparation of (+/−) 1-benzyl-3-methylpyrrolidin-3-ol

A solution of 1-benzylpyrrolidin-3-one (9.98 g, 57.0 mmol) in THF (57.0 mL) at −20° C. was added to 1.4M MeMgBr (85.4 mL, 120 mmol). When addition was complete, the ice bath was removed and the reaction was allowed to warm to ambient temperature and then quenched with water (200 mL). The mixture was diluted with saturated NH₄Cl (200 mL) and ethyl acetate (300 mL) and stirred vigorously for 5 minutes. An inseparable emulsion formed with fine particulates. The reaction mixture was filtered under vacuum and the layers were separated. The aqueous layer was extracted with ethyl acetate (200 mL) and the organic layer was washed with brine (100 mL), dried (MgSO₄), filtered and concentrated under reduced pressure to an oil which was purified by flash chromatography (0-5% Methanol/DCM) to give (+/−)1-benzyl-3-methylpyrrolidin-3-ol (6.10 g, 31.9 mmol, 56.0% yield).

Step D: Preparation of (+/−)₃-methylpyrrolidin-3-ol

A solution of 1-benzyl-3-methylpyrrolidin-3-ol (5.80 g, 30.3 mmol) and 10% Pd/C (9.68 g, 9.10 mmol) in methanol (35 mL) was treated with ammonium formate (19.1 g, 303 mmol). The resulting black suspension was heated at a gentle reflux overnight. The reaction was allowed to cool to ambient temperature and filtered through a Celite® bed. The filtrate was evaporated in vacuo to give (+/−)3-methylpyrrolidin-3-ol as a dark oil.

Step E: Preparation of 1-((S)-1-(6-chloropyridin-3-yl)-2,2,2-trifluoroethyl)-3-methylpyrrolidin-3-ol A mixture of 3-methylpyrrolidin-3-ol (1.41 g, 13.9 mmol), (R)-1-(6-chloropyridin-3-yl)-2,2,2-trifluoroethyl trifluoromethanesulfonate (4.30 g, 12.5 mmol) and K₂CO₃ (1.93 g, 13.9 mmol) in THF (69.7 mL, 13.9 mmol) was heated in a sealed tube to 50° C. overnight. The reaction was filtered, concentrated under reduced pressure and the residue was purified by preparative HPLC (C18, 300 g, 10% MeCN/water to 95% MeCN/water over column volumes) to give 1-((S)-1-(6-chloropyridin-3-yl)-2,2,2-trifluoroethyl)-3-methylpyrrolidin-3-ol (2.01 g, 48.9% yield).

Step F: Separation of Diastereomers 1 and 2 of 1-((S)-1-(6-chloropyridin-3-yl)-2,2,2-trifluoroethyl)-3-methylpyrrolidin-3-ol A diastereomeric mixture of 1-((S)-1-(6-chloropyridin-3-yl)-2,2,2-trifluoroethyl)-3-methylpyrrolidin-3-ol (2.01 g) was subjected to preparative chiral supercritical fluid chromatographic separation under the following conditions: Column ADH 20 mm×250 mm; flow rate: 50 mL/min mobile phase A: supercritical CO₂; mobile phase B: methanol with 0.5% diethyl amine; Gradient: 10% mobile phase β isocratic; UV detection wavelength: 214 nm. Peak 1 (diastereomer 1): retention time: 8.3 min; (0.643 g). Peak 2 (diastereomer 2): retention time 9.2 min (0.696 g).

Step H: Preparation of Diastereomer 1 of 3-methyl-1-((S)-2,2,2-trifluoro-1-(6-hydrazinylpyridin-3-yl)ethyl)pyrrolidin-3-ol To a solution of Diastereomer 1 of 1-((S)-1-(6-chloropyridin-3-yl)-2,2,2-trifluoroethyl)-3-methylpyrrolidin-3-ol (0.550 g, 1.866 mmol) in sec-butanol (10 mL) was added hydrazine (0.8786 mL, 27.99 mmol) and stirred at 125° C. overnight. The reaction was concentrated from methanol (3×30 mL) to give Diastereomer 1 of 3-methyl-1-((S)-2,2,2-trifluoro-1-(6-hydrazinylpyridin-3-yl)ethyl)pyrrolidin-3-ol (0.580 g, 1.998 mmol, 107.1% yield).

Step I: Preparation of Diastereomer 2 of 3-methyl-1-((S)-2,2,2-trifluoro-1-(6-hydrazinylpyridin-3-yl)ethyl)pyrrolidin-3-ol Prepared as described in Step H using Diastereomer 2 from Step G in place of Diastereomer 1 to give Diastereomer 2 of 3-methyl-1-((S)-2,2,2-trifluoro-1-(6-hydrazinylpyridin-3-yl)ethyl)pyrrolidin-3-ol (0.628 g, 2.163 mmol, 110.9% yield).

Preparation F

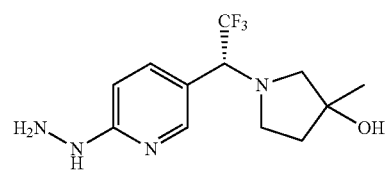 [SMILES: CC1(O)CCN([C@H](c2ccc(NN)nc2)C(F)(F)F)C1]

Preparation of Diastereomer 1 of 3-methyl-1-((R)-2,2,2-trifluoro-1-(6-hydrazinylpyridin-3-yl)ethyl)pyrrolidin-3-ol and Diastereomer 2 of 3-methyl-1-((R)-2,2,2-trifluoro-1-(6-hydrazinylpyridin-3-yl)ethyl)pyrrolidin-3-ol Prepared as described in Preparation E using (S)-1-(6-chloropyridin-3-yl)-2,2,2-trifluoroethyl trifluoromethanesulfonate in place of (R)-1-(6-chloropyridin-3-yl)-2,2,2-trifluoroethyl trifluoromethanesulfonate in Step E.

Example 1

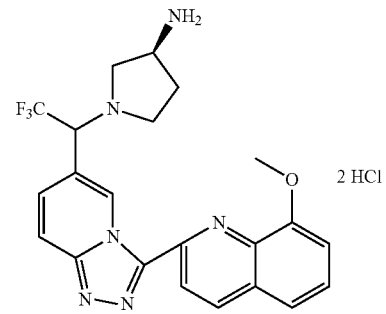 [SMILES: COc1cccc2ccc(-c3nnc4ccc(C(N5CC[C@H](N)C5)C(F)(F)F)cn34)nc12]

(3S)-1-(2,2,2-trifluoro-1-(3-(8-methoxyquinolin-2-yl)-[1,2,4]triazolo[4,3-a]pyridin-6-yl)ethyl)pyrrolidin-3-amine dihydrochloride

Step A: Preparation of 1-(6-chloropyridin-3-yl)-2,2,2-trifluoroethanol

To a solution of 6-chloronicotinaldehyde (5.93 g, 41.9 mmol) and CsF (1.27 g, 8.38 mmol) in DME (350 mL) was added trimethyl(trifluoromethyl)silane (9.82 mL, 62.8 mmol) in THF (30 mL) at 0° C. The reaction mixture was allowed to warm to ambient temperature and the reaction was stirred at ambient temperature for 18 hours. 1 N HCl (50 mL) in water was added and the reaction was stirred at ambient temperature for 1 hour. Ethyl acetate (100 mL) was added. The organic layer was separated, washed with saturated sodium bicarbonate and brine, dried (sodium sulfate), filtered and concentrated under reduced pressure. The residue was purified by flash chromatography on silica gel (4:1 hexane/ethyl acetate) to give 1-(6-chloropyridin-3-yl)-2,2,2-trifluoroethanol (8.8 g, 99.3%) as an oil.

Step B: Preparation of 1-(6-chloropyridin-3-yl)-2,2,2-trifluoroethyl trifluoromethanesulfonate To a solution of 1-(6-chloropyridin-3-yl)-2,2,2-trifluoroethanol (4.00 g, 17.96 mmol) and triethylamine (2.75 mL, 19.76 mmol) in DCM (30 mL) was added trifluoromethanesulfonic anhydride (3.17 mL, 18.86 mmol) at −40° C. and the reaction was stirred at −40° C. for 1 hour. Hexane (150 mL) and water (40 mL) were added. The organic layer was separated, washed with brine, dried (sodium sulfate), filtered and concentrated under reduced pressure to give 1-(6-chloropyridin-3-yl)-2,2,2-trifluoroethyl trifluoromethanesulfonate (6.0 g, 97.2%) as a yellow solid.

Step C: Preparation of tert-butyl (3S)-1-(1-(6-chloropyridin-3-yl)-2,2,2-trifluoroethyl)pyrrolidin-3-ylcarbamate A solution of 1-(6-chloropyridin-3-yl)-2,2,2-trifluoroethyl trifluoromethanesulfonate (0.55 g, 1.60 mmol), K₂CO₃ (0.33 g, 2.40 mmol), and (S)-tert-butyl pyrrolidin-3-ylcarbamate (0.42 g, 2.24 mmol) in THF (8 mL) was stirred at 50° C. for 20 hours. Water (20 mL) and ethyl acetate (30 mL) were added. The organic layer was separated, washed with brine, dried (sodium sulfate), filtered and concentrated under reduced pressure. The residue was purified by flash chromatography on silica gel (3:1 hexane/ethyl acetate) to give tert-butyl (3S)-1-(1-(6-chloropyridin-3-yl)-2,2,2-trifluoroethyl)pyrrolidin-3-ylcarbamate (0.45 g, 74.0%) as a white solid.

Step D: Preparation of tert-butyl (3S)-1-(2,2,2-trifluoro-1-(6-hydrazinylpyridin-3-yl)ethyl)pyrrolidin-3-ylcarbamate A solution of tert-butyl (3S)-1-(1-(6-chloropyridin-3-yl)-2,2,2-trifluoroethyl)pyrrolidin-3-ylcarbamate (5.74 g, 15.11 mmol) and anhydrous hydrazine (4.74 mL, 151.1 mmol) in i-BuOH (20 mL) in a sealed tube was stirred at 130° C. for 18 hours. After cooling to ambient temperature, water (10 mL) and ethyl acetate (30 mL) were added. The organic layer was separated, washed with saturated sodium bicarbonate and brine, dried (sodium sulfate), filtered and concentrated under reduced pressure to give tert-butyl (3S)-1-(2,2,2-trifluoro-1-(6-hydrazinylpyridin-3-yl)ethyl)pyrrolidin-3-ylcarbamate (5.34 g, 94.1%) as a white foam solid.

Step E: Preparation of tert-butyl (3S)-1-(2,2,2-trifluoro-1-(3-(8-methoxyquinolin-2-yl)-[1,2,4]triazolo[4,3-a]pyridin-6-yl)ethyl)pyrrolidin-3-ylcarbamate A solution of tert-butyl (3S)-1-(2,2,2-trifluoro-1-(6-hydrazinylpyridin-3-yl)ethyl)pyrrolidin-3-ylcarbamate (0.20 g, 0.53 mmol) and 8-methoxyquinoline-2-carbaldehyde (0.105 g, 0.53 mmol) in EtOH (10 mL) was stirred at ambient temperature for 1 hour. The solvent was removed under reduced pressure. The residue was dissolved in DCM (10 mL) and iodobenzene diacetate (0.189 g, 0.59 mmol) was added. The reaction mixture was stirred at ambient temperature for 1 hour. Ethyl acetate (20 mL) and saturated sodium bicarbonate (10 mL) were added. The organic layer was separated, washed with brine, dried (sodium sulfate), filtered and concentrated under reduced pressure. The residue was purified by flash chromatography on silica gel (eluting with ethyl acetate) to give tert-butyl (3S)-1-(2,2,2-trifluoro-1-(3-(8-methoxyquinolin-2-yl)-[1,2,4]triazolo[4,3-a]pyridin-6-yl)ethyl)pyrrolidin-3-ylcarbamate (0.27 g, 93.4%) as off white solid.

Step F: Preparation of (3S)-1-(2,2,2-trifluoro-1-(3-(8-methoxyquinolin-2-yl)-[1,2,4]triazolo[4,3-a]pyridin-6-yl)ethyl)pyrrolidin-3-amine dihydrochloride To a solution of tert-butyl (3S)-1-(2,2,2-trifluoro-1-(3-(8-methoxyquinolin-2-yl)-[1,2,4]triazolo[4,3-a]pyridin-6-yl)ethyl)pyrrolidin-3-ylcarbamate (0.050 g, 0.092 mmol) in DCM (0.5 mL) was added 5 N HCl (2.30 mL, 9.22 mmol) in IPA. The reaction mixture was stirred at ambient temperature for 30 minutes. The solvent was removed under reduced pressure. The solid obtained was suspended in ACN (3 mL) and stirred at ambient temperature for 5 minutes. The solid which formed was collected by filtration to give (3S)-1-(2,2-trifluoro-1-(3-(8-methoxyquinolin-2-yl)-[1,2,4]triazolo[4,3-a]pyridin-6-yl)ethyl)pyrrolidin-3-amine as the di-HCl salt (0.043 g, 90.5%) as light yellow solid. LCMS APCI (+) m/z 443 (M+H).

Example 2

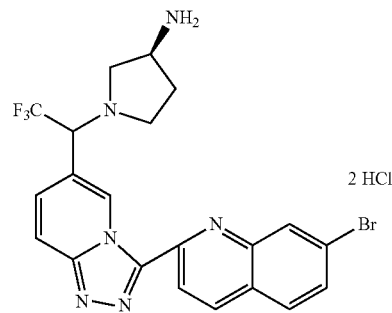 [SMILES: N[C@H]1CCN(C(c2ccc3nnc(-c4ccc5ccc(Br)cc5n4)n3c2)C(F)(F)F)C1]

(3S)-1-(1-(3-(7-bromo quinolin-2-yl)-[1,2,4]triazolo[4,3-a]pyridin-6-yl)-2,2,2-trifluoroethyl)pyrrolidin-3-amine dihydrochloride

Step A: Preparation of tert-butyl (3S)-1-(1-(3-(7-bromoquinolin-2-yl)-[1,2,4]triazolo[4,3-a]pyridin-6-yl)-2,2,2-trifluoroethyl)pyrrolidin-3-ylcarbamate Prepared as described in Example 1, Steps A-E, using 7-bromoquinoline-2-carbaldehyde in place of 8-methoxyquinoline-2-carbaldehyde in Step E.

Step B: Preparation of (3S)-1-(1-(3-(7-bromo quinolin-2-yl)-[1,2,4]triazolo[4,3-a]pyridin-6-yl)-2,2,2-trifluoroethyl)pyrrolidin-3-amine dihydrochloride Prepared as described in Example 1, Step F, using tert-butyl (3S)-1-(1-(3-(7-bromoquinolin-2-yl)-[1,2,4]triazolo[4,3-a]pyridin-6-yl)-2,2,2-trifluoroethyl)pyrrolidin-3-ylcarbamate in place of tert-butyl (3S)-1-(2,2,2-trifluoro-1-(3-(8- methoxyquinolin-2-yl)-[1,2,4]triazolo[4,3-a]pyridin-6-yl) ethyl)pyrrolidin-3-ylcarbamate. LCMS APCI (+) m/z 491 (M+H).

Example 3

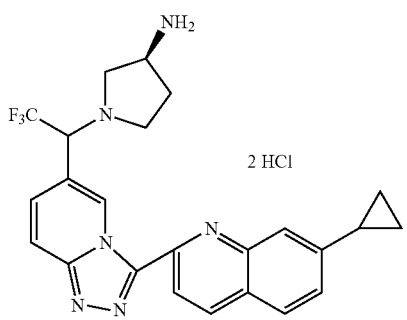 [SMILES: N[C@H]1CCN(C(c2ccc3nnc(-c4ccc5ccc(C6CC6)cc5n4)n3c2)C(F)(F)F)C1]

2 HCl (3S)-1-(1-(3-(7-cyclopropylquinolin-2-yl)-[1,2,4] triazolo[4,3-a]pyridin-6-yl)-2,2,2-trifluoroethyl)pyrrolidin-3-amine dihydrochloride Step A: Preparation tert-butyl (3S)-1-(1-(3-(7-cyclopropylquinolin-2-yl)-[1,2,4]triazolo[4,3-a]pyridin-6-yl)-2,2,2-trifluoroethyl)pyrrolidin-3-ylcarbamate A solution of tert-butyl (3S)-1-(1-(3-(7-bromo quinolin-2-yl)-[1,2,4]triazolo[4,3-a]pyridin-6-yl)-2,2,2-trifluoroethyl) pyrrolidin-3-ylcarbamate (Example 2, Step A; 0.25 g, 0.42 mmol), Pd(OAc)$_2$ (0.0048 g, 0.021 mmol), P(Cy)$_3$ (0.013 g, 0.047 mmol), and cyclopropylboronic acid (0.073 g, 0.85 mmol) in toluene (4 mL) and water (0.4 mL) was stirred at 100° C. for 6 hours. After cooling to ambient temperature, ethyl acetate (20 mL) and water (5 mL) were added. The organic layer was separated, washed with brine, dried (sodium sulfate), filtered and concentrated under reduced pressure. The residue was purified by flash chromatography on silica gel (ethyl acetate) to give tert-butyl (3S)-1-(1-(3-(7-cyclopropylquinolin-2-yl)-[1,2,4]triazolo[4,3-a]pyridin-6-yl)-2,2,2-trifluoroethyl)pyrrolidin-3-ylcarbamate (0.224 g, 95.9%) as a solid.

Step B: Preparation of (3S)-1-(1-(3-(7-cyclopropylquinolin-2-yl)-[1,2,4]triazolo[4,3-a]pyridin-6-yl)-2,2,2-trifluoroethyl)pyrrolidin-3-amine dihydrochloride Prepared as described in Example 1, Step F, using tert-butyl (3S)-1-(1-(3-(7-cyclopropylquinolin-2-yl)-[1,2,4]triazolo[4,3-a]pyridin-6-yl)-2,2,2-trifluoroethyl)pyrrolidin-3-ylcarbamate in place of tert-butyl (3S)-1-(2,2,2-trifluoro-1-

(3-(8-methoxyquinolin-2-yl)-[1,2,4]triazolo[4,3-a]pyridin-6-yl)ethyl)pyrrolidin-3-ylcarbamate. LCMS APCI (+) m/z 453 (M+H).

Example 4

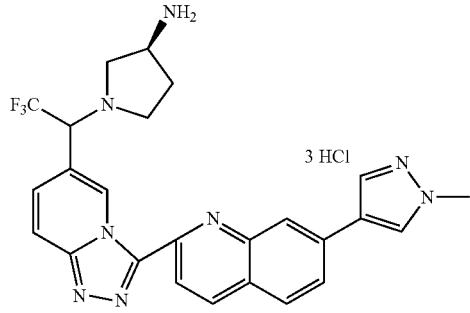 [SMILES: Cn1cc(-c2ccc3ccc(-c4nnc5ccc(C(N6CC[C@H](N)C6)C(F)(F)F)cn45)nc3c2)cn1]

3 HCl (3S)-1-(2,2,2-trifluoro-1-(3-(7-(1-methyl-1H-pyrazol-4-yl)quinolin-2-yl)-[1,2,4]triazolo[4,3-a]pyridin-6-yl)ethyl)pyrrolidin-3-amine trihydrochloride Step A: Preparation tert-butyl (3S)-1-(2,2,2-trifluoro-1-(3-(7-(1-methyl-1H-pyrazol-4-yl)quinolin-2-yl)-[1, 2,4]triazolo[4,3-a]pyridin-6-yl)ethyl)pyrrolidin-3-ylcarbamate A solution of tert-butyl (3S)-1-(1-(3-(7-bromo quinolin-2-yl)-[1,2,4]triazolo[4,3-a]pyridin-6-yl)-2,2,2-trifluoroethyl) pyrrolidin-3-ylcarbamate (Example 2, Step A; 0.18 g, 0.30 mmol), 1-methyl-4-(4,4,5,5-tetramethyl-1,3,2-dioxaborolan-2-yl)-1H-pyrazole (0.127 g, 0.61 mmol), PdCl$_2$(dppf) *dcm (0.0249 g, 0.030 mmol), and triethylamine (0.064 mL, 0.46 mmol) in IPA (3 mL) was heated at 100° C. for 3 hours. After cooling to ambient temperature, the residue was directly purified by C-18 reverse phase flash chromatography (Biotage SP4 unit, C-18 25M column, 10-90% CH$_3$CN/water gradient; 30 CV) to give tert-butyl (3S)-1-(2,2,2-trifluoro-1-(3-(7-(1-methyl-1H-pyrazol-4-yl)quinolin-2-yl)-[1,2,4]triazolo[4,3-a]pyridin-6-yl)ethyl)pyrrolidin-3-ylcarbamate (0.15 g, 83.2%) as a solid.

Step B: Preparation of (3S)-1-(2,2,2-trifluoro-1-(3-(7-(1-methyl-1H-pyrazol-4-yl)quinolin-2-yl)-[1,2,4] triazolo[4,3-a]pyridin-6-yl)ethyl)pyrrolidin-3-amine trihydrochloride Prepared as described in Example 1 using tert-butyl (3S)-1-(2,2,2-trifluoro-1-(3-(7-(1-methyl-1H-pyrazol-4-yl) quinolin-2-yl)-[1,2,4]triazolo[4,3-a]pyridin-6-yl)ethyl)pyrrolidin-3-ylcarbamate in place of tert-butyl (3S)-1-(2,2,2-trifluoro-1-(3-(8-methoxyquinolin-2-yl)-[1,2,4]triazolo[4,3- a]pyridin-6-yl)ethyl)pyrrolidin-3-ylcarbamate in Step F. LCMS APCI (+) m/z 493 (M+H).

Example 5

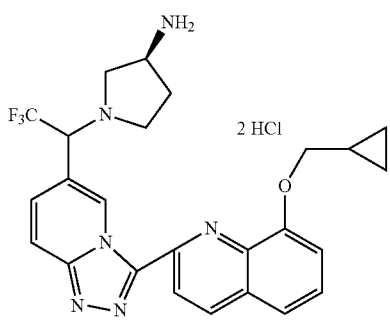 [SMILES: N[C@H]1CCN(C(c2ccc3nnc(-c4ccc5cccc(OCC6CC6)c5n4)n3c2)C(F)(F)F)C1]

(3S)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-amine dihydrochloride Step A: Preparation 8-(cyclopropylmethoxy)-2-methylquinoline A solution of 2-methylquinolin-8-ol (10.0 g, 62.82 mmol), (bromomethyl)cyclopropane (17.0 g, 125.6 mmol), and K$_2$CO$_3$ (17.80 g, 128.8 mmol) in acetone (50 mL) in a sealed flask was stirred at 88° C. for 2 days. After cooling to ambient temperature, the acetone was removed under reduced pressure. DCM (100 mL) and water (50 mL) were added. The organic layer was separated, washed with brine, dried (sodium sulfate), filtered and concentrated under reduced pressure. The residue was purified by flash chromatography on silica gel (DCM) to give 8-(cyclopropylmethoxy)-2-methylquinoline (13.2 g, 98.5%) as a solid.

Step B: Preparation of 8-(cyclopropylmethoxy)quinoline-2-carbaldehyde

To a solution of 8-(cyclopropylmethoxy)-2-methylquinoline (3.00 g, 14.1 mmol) in dioxane (100 mL) and water (1.0 mL) was added SeO$_2$ (1.87 g, 16.9 mmol). The reaction mixture was stirred at reflux for 2 hours. After cooling to ambient temperature, the solid was removed by filtration and washed with DCM. The filtrate was concentrated under reduced pressure and the residue was purified by flash chromatography on silica gel (1:4 hexane/DCM) to give 8-(cyclopropylmethoxy)quinoline-2-carbaldehyde (3.1 g, 97.0%) as a solid Step C: Preparation of (3S)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-amine dihydrochloride Prepared as described in Example 1, Step E-F, using 8-(cyclopropylmethoxy)quinoline-2-carbaldehyde in place of 8-methoxyquinoline-2-carbaldehyde. LCMS APCI (+) m/z 483 (M+H).

Example 6

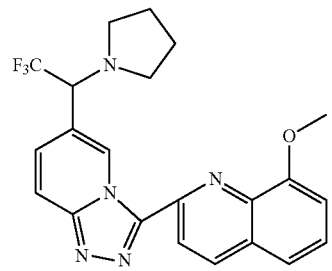 [SMILES: COc1cccc2ccc(-c3nnc4ccc(C(N5CCCC5)C(F)(F)F)cn34)nc12]

8-methoxy-2-(6-(2,2,2-trifluoro-1-(pyrrolidin-1-yl)ethyl)-[1,2,4]triazolo[4,3-a]pyridin-3-yl)quinoline Prepared as described in Example 1, Steps A-E, using pyrrolidine in place of (S)-tert-butyl pyrrolidin-3-ylcarbamate in Step C. LCMS APCI (+) m/z 428 (M+H).

Example 7

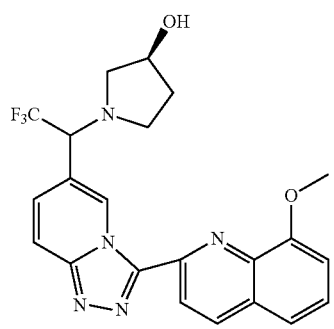 [SMILES: COc1cccc2ccc(-c3nnc4ccc(C(N5CC[C@H](O)C5)C(F)(F)F)cn34)nc12]

(3S)-1-(2,2,2-trifluoro-1-(3-(8-methoxyquinolin-2-yl)-[1,2,4]triazolo[4,3-a]pyridin-6-yl)ethyl)pyrrolidin-3-ol Prepared as described in Example 1, Steps A-E, using (S)-pyrrolidin-3-ol in place of (S)-tert-butyl pyrrolidin-3-ylcarbamate in Step C. LCMS APCI (+) m/z 444 (M+H).

Example 8

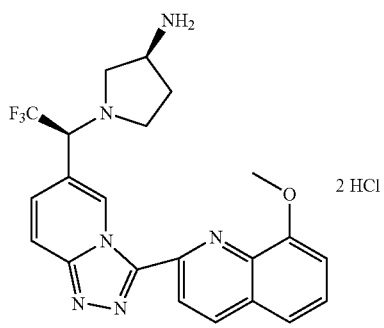 [SMILES: COc1cccc2ccc(-c3nnc4ccc([C@H](N5CC[C@H](N)C5)C(F)(F)F)cn34)nc12]

(S)-1-((S)-2,2,2-trifluoro-1-(3-(8-methoxyquinolin-2-yl)-[1,2,4]triazolo[4,3-a]pyridin-6-yl)ethyl)pyrrolidin-3-amine dihydrochloride Step A: Preparation of tert-butyl (S)-1-((S)-2,2,2-trifluoro-1-(3-(8-methoxyquinolin-2-yl)-[1,2,4]triazolo[4,3-a]pyridin-6-yl)ethyl)pyrrolidin-3-ylcarbamate The enantiomerically pure tert-butyl (S)-1-((S)-2,2,2-trifluoro-1-(3-(8-methoxyquinolin-2-yl)-[1,2,4]triazolo[4,3-a]pyridin-6-yl)ethyl)pyrrolidin-3-ylcarbamate was separated from tert-butyl (3S)-1-(2,2,2-trifluoro-1-(3-(8-methoxyquinolin-2-yl)-[1,2,4]triazolo[4,3-a]pyridin-6-yl)ethyl)pyrrolidin-3-ylcarbamate (mixture was prepared as in Example 1, Steps A-E) by chiral supercritical fluid chromatography (SFC). Conditions for analytical chromatography: Rt of the (S,S) diastereomer=6.53 min; Rt of the (R,S) diastereomer=7.02 min; OD-H, Chiral Technologies 4.6 mm×250 mm, 20% MeOH with 0.1% DEA at 3.0 mL/min. Outlet pressure: 100 bar. Conditions for preparative chromatography: OD-H, Chiral Technologies 20 mm×250 mm, 20% MeOH with 0.1% DEA at 50 mL/min. Outlet pressure: 100 bar.

Step B: Preparation of (S)-1-((S)-2,2,2-trifluoro-1-(3-(8-methoxyquinolin-2-yl)-[1,2,4]triazolo[4,3-a]pyridin-6-yl)ethyl)pyrrolidin-3-amine dihydrochloride To a solution of tert-butyl (S)-1-((S)-2,2,2-trifluoro-1-(3-(8-methoxyquinolin-2-yl)-[1,2,4]triazolo[4,3-a]pyridin-6-yl)ethyl)pyrrolidin-3-ylcarbamate (0.074 g, 0.14 mmol) in DCM (0.5 mL) was added 5 N HCl (2.73 mL, 13.6 mmol) in IPA. The reaction mixture was stirred at ambient temperature for 1 hour. The solvent was removed under reduced pressure. The solid obtained was suspended in ACN (3 mL) and stirred at ambient temperature for 5 minutes. The resulting solid was collected by filtration to give (S)-1-((S)-2,2,2-trifluoro-1-(3-(8-methoxyquinolin-2-yl)-[1,2,4]triazolo[4,3-a]pyridin-6-yl)ethyl)pyrrolidin-3-amine as the di-HCl salt (0.066 g, 93.9%) as a solid. LCMS APCI (+) m/z 443 (M+H).

Example 9A

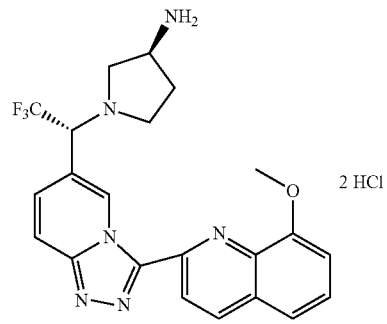 [SMILES: COc1cccc2ccc(-c3nnc4ccc([C@@H](N5CC[C@H](N)C5)C(F)(F)F)cn34)nc12]

Method A: Preparation of (S)-1-((R)-2,2,2-trifluoro-1-(3-(8-methoxyquinolin-2-yl)-[1,2,4]triazolo[4,3-a]pyridin-6-yl)ethyl)pyrrolidin-3-amine dihydrochloride Step A: Preparation of tert-butyl (S)-1-((R)-2,2,2-trifluoro-1-(3-(8-methoxyquinolin-2-yl)-[1,2,4]triazolo[4,3-a]pyridin-6-yl)ethyl)pyrrolidin-3-ylcarbamate The enantiomerically pure tert-butyl (S)-1-((R)-2,2,2-trifluoro-1-(3-(8-methoxyquinolin-2-yl)-[1,2,4]triazolo[4,3-a]pyridin-6-yl)ethyl)pyrrolidin-3-ylcarbamate was separated from tert-butyl (3S)-1-(2,2,2-trifluoro-1-(3-(8-methoxyquinolin-2-yl)-[1,2,4]triazolo[4,3-a]pyridin-6-yl)ethyl)pyrrolidin-3-ylcarbamate (prepared as in Example 1, Steps A-E) by chiral SFC (Conditions for analytical chromatography: Rt of the (S,S) diastereomer=6.53 min; Rt of the (R,S) diastereomer=7.02 min; OD-H, Chiral Technologies 4.6 mm×250 mm, 20% MeOH with 0.1% DEA at 3.0 mL/min. Outlet pressure: 100 bar. Conditions for preparative chromatography: OD-H, Chiral Technologies 20 mm×250 mm, 20% MeOH with 0.1% DEA at 50 mL/min. Outlet pressure: 100 bar).

Step B: Preparation of (S)-1-((R)-2,2,2-trifluoro-1-(3-(8-methoxyquinolin-2-yl)-[1,2,4]triazolo[4,3-a]pyridin-6-yl)ethyl)pyrrolidin-3-amine dihydrochloride To a solution of tert-butyl (S)-1-((R)-2,2,2-trifluoro-1-(3-(8-methoxyquinolin-2-yl)-[1,2,4]triazolo[4,3-a]pyridin-6-yl)ethyl)pyrrolidin-3-ylcarbamate (0.061 g, 0.11 mmol) in DCM (0.5 mL) was added 5 N HCl (2.25 ml, 11.2 mmol) in IPA. The reaction mixture was stirred at ambient temperature for 1 hour. The solvent was removed under reduced pressure. The solid obtained was suspended in ACN (3 mL) and stirred at ambient temperature for 5 minutes. The resulting solid was collected by filtration to give (S)-1-((R)-2,2,2-trifluoro-1-(3-(8-methoxyquinolin-2-yl)-[1,2,4]triazolo[4,3-a]pyridin-6- yl)ethyl)pyrrolidin-3-amine as the di-HCl salt (0.052 g, 89.7%) as a solid. LCMS APCI (+) m/z 443 (M+H).

Example 9B

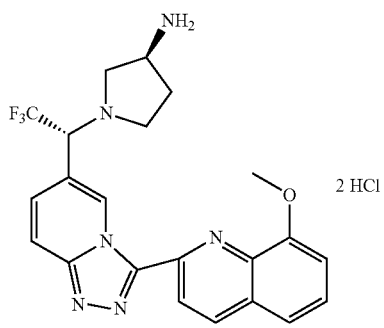 [SMILES: COc1cccc2ccc(-c3nnc4ccc([C@@H](N5CC[C@H](N)C5)C(F)(F)F)cn34)nc12]

Method B: Preparation of (S)-1-((R)-2,2,2-trifluoro-1-(3-(8-methoxyquinolin-2-yl)-[1,2,4]triazolo[4,3-a]pyridin-6-yl)ethyl)pyrrolidin-3-amine dihydrochloride Step A: Preparation of 1-(6-chloropyridin-3-yl)-2,2,2-trifluoroethanone To a solution of methyl 6-chloronicotinate (150.0 g, 874.2 mmol) and CsF (1.73 g, 11.36 mmol) in DME (480 mL) was added trimethyl(trifluoromethyl)silane (138.9 mL, 939.8 mmol) dropwise. The reaction mixture was stirred at ambient temperature for 3 hours. 4 N HCl (655.7 mL, 2623 mmol) in water was added, and the mixture was stirred at ambient temperature for 18 hours. Ethyl acetate (500 mL) was added. The organic layer was separated, washed with saturated sodium bicarbonate and brine, dried (sodium sulfate), filtered and concentrated under reduced pressure to give brown oil. The oil was dissolved in benzene (200 mL) and then dehydrated by water/benzene in a Dean-Stark apparatus. After 18 hours, mixture was distilled under reduced pressure to give 1-(6-chloropyridin-3-yl)-2,2,2-trifluoroethanone (171 g, 93.3%) as white solid.

Step B: Preparation of (S)-1-(6-chloropyridin-3-yl)-2,2,2-trifluoroethanol

To a solution of 1-(6-chloropyridin-3-yl)-2,2,2-trifluoroethanone (46.8 g, 223.3 mmol) and 1.0 M KOtBu (4.47 mL, 4.47 mmol) in t-BuOH in IPA (136 mL) and toluene (34 mL) in a autoclave was added dichloro{(S)-(−)-2,2'-bis[di(3,5-xylyl)-phosphino-1,1'-binaphthyl][(2S)-(+)-1,1-bis(4-methoxyphenyl)-3-methyl-1,2-butanediamine (0.273 g, 0.22 mmol) (Strem Chemicals). The reaction mixture was degassed by three vacuum-filling with nitrogen cycles. Hydrogen was introduced into the autoclave at a pressure of 300 psi and then reduced to 20 psi by slowly releasing the stop valve. After this procedure was repeated three times, the autoclave was pressurized to 300 psi with hydrogen. The reaction mixture was vigorously stirred at ambient temperature for 4 days (pressure was recharged to 300 psi when the internal pressure dropped below 200 psi). The pressure was released and the solvent was removed under reduced pressure. Ethyl acetate (300 mL) and 10% citric acid solution (50 mL) were added. The organic layer was separated, washed with brine, dried (sodium sulfate), filtered and concentrated under reduced pressure. The residue was purified by flash chromatography on silica gel (3:1 DCM/ethyl acetate) to give (S)-1-(6-chloropyridin-3-yl)-2,2,2-trifluoroethanol (46.76 g, 99.0%) as white solid. Enantiomeric excess was determined by chiral HPLC (Chiralcel OD-H, 90% hexanes: 10% (1:1 MeOH/EtOH) at 1.0 mL/min, 86.4% e.e. (S)-enantiomer). (S)-1-(6-chloropyridin-3-yl)-2,2,2-trifluoro ethanol (97.8 g, 462 mmol, 76% e.e.) was dissolved in 4.5% ethyl acetate/hexane (v/v) (2170 mL) with heating to reflux. After complete dissolution, it was slowly cooled to ambient temperature overnight. The resulting solid was collected by filtration, washed with hexane and dried to give (S)-1-(6-chloropyridin-3-yl)-2,2,2-trifluoroethanol (62.5 g, 63.9%) as white solid. Enantiomeric excess was determined by chiral HPLC (Chiralcel OD-H, 90% hexanes: 10% (1:1 MeOH/EtOH) at 1.0 mL/min, 98.8% e.e. (S)-enantiomer).

Step C: Preparation of (S)-1-(6-chloropyridin-3-yl)-2,2,2-trifluoroethyl trifluoromethanesulfonate To a solution of (S)-1-(6-chloropyridin-3-yl)-2,2,2-trifluoroethanol (50.0 g, 236.3 mmol) and lutidine (33.03 mL, 283.6 mmol) in DCM (500 mL) was added trifluoromethanesulfonic anhydride (43.74 ml, 260.0 mmol) slowly at −40° C. The reaction mixture was stirred at −40° C. for 3 hours. Water (200 mL) was added. The organic layer was separated, washed with brine, dried (sodium sulfate), filtered and concentrated under reduced pressure. The residue was purified by flash chromatography on silica gel (4:1 hexane/ethyl acetate) to give (S)-1-(6-chloropyridin-3-yl)-2,2,2-trifluoroethyl trifluoromethanesulfonate (79.8 g, 98.3%) as white solid.

Step D: Preparation of tert-butyl (S)-1-((R)-1-(6-chloropyridin-3-yl)-2,2,2-trifluoroethyl)pyrrolidin-3-ylcarbamate A solution of (S)-1-(6-chloropyridin-3-yl)-2,2,2-trifluoroethyl trifluoromethanesulfonate (79.8 g, 232 mmol), (S)-tert-butyl pyrrolidin-3-ylcarbamate (51.9 g, 279 mmol), and $K_2CO_3$ (44.9 g, 325 mmol) in THF (500 mL) was stirred at 56° C. for 18 hours. After cooling to ambient temperature, water (200 mL) and ethyl acetate (200 mL) were added. The organic layer was separated, washed with brine, dried (sodium sulfate), and concentrated under reduced pressure. The residue was purified by flash chromatography on silica gel (4:1 hexane/ethyl acetate) to give a thick oil. The oil was dissolved in ether (200 mL) and hexane (500 mL) was added. The solution was concentrated to about 200 mL and stirred at ambient temperature for 1 hour. Hexane (300 mL) was added, and the resulting solid was collected by filtration to give tert-butyl (S)-1-((R)-1-(6-chloropyridin-3-yl)-2,2,2-trifluoroethyl)pyrrolidin-3-ylcarbamate (68.2 g, 77.3%) as white solid. Enantiomeric excess was determined by chiral HPLC (Chiralcel OD-H, 90% hexanes/10% (1:1 MeOH/EtOH) at 1.0 mL/min, >99% d.e. (R,S)-diastereomer).

Step E: Preparation of tert-butyl (S)-1-((R)-2,2,2-trifluoro-1-(6-hydrazinylpyridin-3-yl)ethyl)pyrrolidin-3-ylcarbamate A solution of tert-butyl (S)-1-((R)-1-(6-chloropyridin-3-yl)-2,2,2-trifluoroethyl)pyrrolidin-3-ylcarbamate (68.5 g, 180.4 mmol) and anhydrous hydrazine (56.61 mL, 1804 mmol) in i-BuOH (80 mL) was stirred at 106° C. in a sealed flask for 16 hours. After cooling to ambient temperature, the solvent was removed under reduced pressure. The residue was partitioned in ethyl acetate (800 mL) and water (100 mL).

The organic layer was separated, washed with brine, dried (sodium sulfate), filtered and concentrated under reduced pressure to give tert-butyl (S)-1-((R)-2,2,2-trifluoro-1-(6-hydrazinylpyridin-3-yl)ethyl)pyrrolidin-3-ylcarbamate (68.1 g, 95.6%) as white foam solid. Enantiomeric excess was determined by chiral HPLC (Chiralcel OD-H, 90% hexane/10% (1:1 MeOH/EtOH) at 1.0 mL/min, >99% d.e. (R,S)-diastereomer).

Step F: Preparation of tert-butyl (S)-1-((R)-2,2,2-trifluoro-1-(3-(8-methoxyquinolin-2-yl)-[1,2,4]triazolo[4,3-a]pyridin-6-yl)ethyl)pyrrolidin-3-ylcarbamate A solution of tert-butyl (S)-1-((R)-2,2,2-trifluoro-1-(6-hydrazinylpyridin-3-yl)ethyl)pyrrolidin-3-ylcarbamate (0.279 g, 0.67 mmol) and 8-methoxyquinoline-2-carbaldehyde (0.125 g, 0.67 mmol) in EtOH (10 mL) was stirred at ambient temperature for 18 hours. The solvent was removed under reduced pressure. The residue was dissolved in DCM (10 mL) and iodobenzene diacetate (0.259 g, 0.80 mmol) was added. The mixture was stirred at ambient temperature for 2 hours. Ethyl acetate (20 mL) and saturated sodium bicarbonate (10 mL) were added. The organic layer was separated, washed with brine, dried (sodium sulfate), filtered and concentrated under reduced pressure. The residue obtained was purified by flash chromatography on silica gel (20:1 ethyl acetate/MeOH) to give tert-butyl (S)-1-((R)-2,2,2-trifluoro-1-(3-(8-methoxyquinolin-2-yl)-[1,2,4]triazolo[4,3-a]pyridin-6-yl)ethyl)pyrrolidin-3-ylcarbamate (0.140 g, 38.6%) as a solid.

Step G: Preparation of (S)-1-((R)-2,2,2-trifluoro-1-(3-(8-methoxyquinolin-2-yl)-[1,2,4]triazolo[4,3-a]pyridin-6-yl)ethyl)pyrrolidin-3-amine dihydrochloride To a solution of tert-butyl (S)-1-((R)-2,2,2-trifluoro-1-(3-(8-methoxyquinolin-2-yl)-[1,2,4]triazolo[4,3-a]pyridin-6-yl)ethyl)pyrrolidin-3-ylcarbamate (0.140 g, 0.26 mmol) in DCM (1.0 mL) was added 5 N HCl (5.16 ml, 25.80 mmol) in IPA. The mixture was stirred at ambient temperature for 1 hour. The solvent was removed under reduced pressure to give a solid. The solid was suspended in ACN (5 mL) and stirred for 10 minutes. The solid was collected by filtration and dried to give (S)-1-((R)-2,2,2-trifluoro-1-(3-(8-methoxyquinolin-2-yl)-[1,2,4]triazolo[4,3-a]pyridin-6-yl)ethyl)pyrrolidin-3-amine as the di-HCl salt (0.104 g, 78.2%) as a solid. Specific rotation: $[\alpha]^{24}_D = -1.01°$ (c=1.01, MeOH).

Example 10

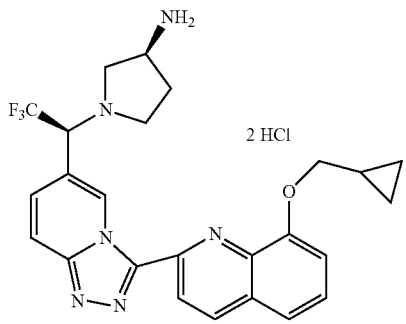 [SMILES: N[C@H]1CCN([C@@H](c2ccc3nnc(-c4ccc5cccc(OCC6CC6)c5n4)n3c2)C(F)(F)F)C1]

(S)-1-((R)-1-(3-(8-(cyclopropylmethoxy)quinolin-2-yl)-[1,2,4]triazolo[4,3-a]pyridin-6-yl)-2,2,2-trifluoroethyl)pyrrolidin-3-amine dihydrochloride Prepared as described in Example 8 using tert-butyl (3S)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-ylcarbamate (Prepared as in Example 5, Steps A-C) in place of tert-butyl (3S)-1-(2,2,2-trifluoro-1-(3-(8-methoxyquinolin-2-yl)-[1,2,4]triazolo[4,3-a]pyridin-6-yl)ethyl)pyrrolidin-3-ylcarbamate and isolating peak 1 during the chiral separation in Step A. LCMS APCI (+) m/z 483 (M+H).

Example 11

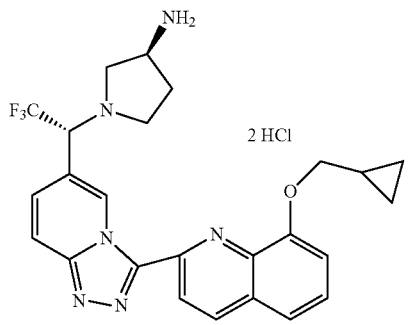 [SMILES: N[C@H]1CCN([C@H](c2ccc3nnc(-c4ccc5cccc(OCC6CC6)c5n4)n3c2)C(F)(F)F)C1]

(S)-1-((R)-1-(3-(8-(cyclopropylmethoxy)quinolin-2-yl)-[1,2,4]triazolo[4,3-a]pyridin-6-yl)-2,2,2-trifluoroethyl)pyrrolidin-3-amine dihydrochloride Prepared as described in Example 9A using tert-butyl (3S)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-ylcarbamate (Prepared as in Example 5, Steps A-C) in place of tert-butyl (3S)-1-(2,2,2-trifluoro-1-(3-(8-methoxyquinolin-2-yl)-[1,2,4]triazolo[4,3-a]pyridin-6-yl)ethyl)pyrrolidin-3-ylcarbamate and isolating peak 2 during the chiral separation in Step A. LCMS APCI (+) m/z 483 (M+H).

Example 12

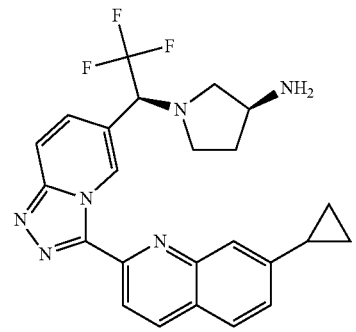 [SMILES: N[C@H]1CCN([C@@H](c2ccc3nnc(-c4ccc5ccc(C6CC6)cc5n4)n3c2)C(F)(F)F)C1]

(S)-1-((S)-1-(3-(7-cyclopropylquinolin-2-yl)-[1,2,4]triazolo[4,3-a]pyridin-6-yl)-2,2,2-trifluoroethyl)pyrrolidin-3-amine Prepared as described in Example 8, Steps A-B, substituting tert-butyl (3S)-1-(1-(3-(7-cyclopropylquinolin-2-yl)-[1, 2,4]triazolo[4,3-a]pyridin-6-yl)-2,2,2-trifluoroethyl)pyrrolidin-3-ylcarbamate (Example 3, Step A) for tert-butyl (3S)-1-(2,2,2-trifluoro-1-(3-(8-methoxyquinolin-2-yl)-[1,2,4]triazolo[4,3-a]pyridin-6-yl)ethyl)pyrrolidin-3-ylcarbamate and isolating Peak 1 during the chiral separation in Step A. LCMS APCI (+) m/z 453 (M+H).

Example 13

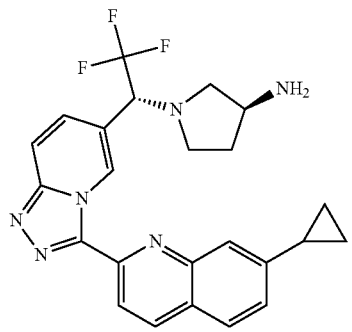 [SMILES: N[C@H]1CCN([C@H](c2ccc3nnc(-c4ccc5ccc(C6CC6)cc5n4)n3c2)C(F)(F)F)C1]

(S)-1-((R)-1-(3-(7-cyclopropylquinolin-2-yl)-[1,2,4]triazolo[4,3-a]pyridin-6-yl)-2,2,2-trifluoroethyl)pyrrolidin-3-amine Prepared as described in Example 8, Steps A-B, substituting tert-butyl (3S)-1-(1-(3-(7-cyclopropylquinolin-2-yl)-[1,2,4]triazolo[4,3-a]pyridin-6-yl)-2,2,2-trifluoroethyl)pyrrolidin-3-ylcarbamate (Example 3, Step A) for tert-butyl (3S)-1-(2,2,2-trifluoro-1-(3-(8-methoxyquinolin-2-yl)-[1,2,4]triazolo[4,3-a]pyridin-6-yl)ethyl)pyrrolidin-3-ylcarbamate, isolating Peak 2 during the chiral separation in Step A. LCMS APCI (+) m/z 453 (M+H).

Example 14

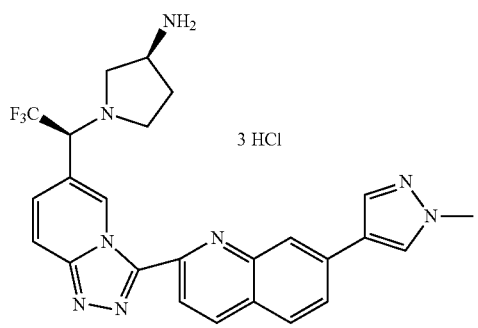 [SMILES: Cn1cc(-c2ccc3ccc(-c4nnc5ccc([C@H](N6CC[C@H](N)C6)C(F)(F)F)cn45)nc3c2)cn1]

(S)-1-((S)-2,2,2-trifluoro-1-(3-(7-(1-methyl-1H-pyrazol-4-yl)quinolin-2-yl)-[1,2,4]triazolo[4,3-a]pyridin-6-yl)ethyl)pyrrolidin-3-amine tri-hydrochloride Prepared as described in Example 8, Steps A-B, using tert-butyl (3S)-1-(2,2,2-trifluoro-1-(3-(7-(1-methyl-1H-pyrazol-4-yl)quinolin-2-yl)-[1,2,4]triazolo[4,3-a]pyridin-6-yl)ethyl)pyrrolidin-3-ylcarbamate (Example 4, Step A) in place of tert-butyl (3S)-1-(2,2,2-trifluoro-1-(3-(8-methoxyquinolin-2-yl)-[1,2,4]triazolo[4,3-a]pyridin-6-yl)ethyl)pyrrolidin-3-ylcarbamate and isolating peak 1 during the chiral separation in Step A. LCMS APCI (+) m/z 493 (M+H).

Example 15

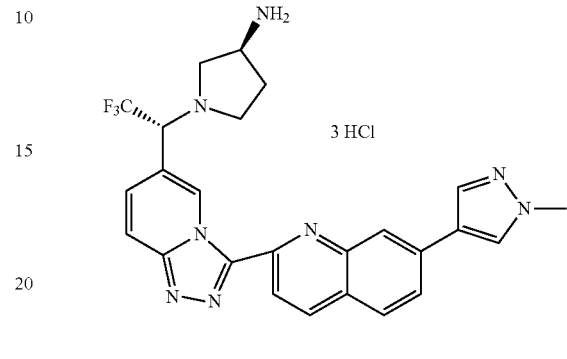

(S)-1-((R)-2,2,2-trifluoro-1-(3-(7-(1-methyl-1H-pyrazol-4-yl)quinolin-2-yl)-[1,2,4]triazolo[4,3-a]pyridin-6-yl)ethyl)pyrrolidin-3-amine tri-hydrochloride Prepared as described in Example 9A, Steps A-B, using tert-butyl (3S)-1-(2,2,2-trifluoro-1-(3-(7-(1-methyl-1H-pyrazol-4-yl)quinolin-2-yl)-[1,2,4]triazolo[4,3-a]pyridin-6-yl)ethyl)pyrrolidin-3-ylcarbamate (Example 4, Step A) in place of tert-butyl (3S)-1-(2,2,2-trifluoro-1-(3-(8-methoxyquinolin-2-yl)-[1,2,4]triazolo[4,3-a]pyridin-6-yl)ethyl)pyrrolidin-3-ylcarbamate and isolating peak 2 during the chiral separation in Step A. LCMS APCI (+) m/z 493 (M+H).

Example 16

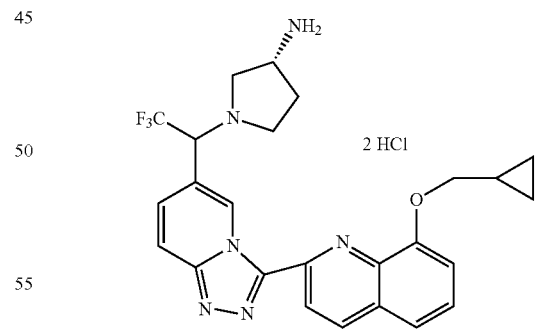

(3R)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-amine dihydrochloride Prepared as described in Example 1, Steps A-F, using (R)-tert-butyl pyrrolidin-3-ylcarbamate in place of (S)-tert-butyl pyrrolidin-3-ylcarbamate in Step C, and substituting 8-(cyclopropylmethoxy)quinoline-2-carbaldehyde for 8-methoxyquinoline-2-carbaldehyde in Step E. LCMS APCI (+) m/z 483 (M+H).

Example 17

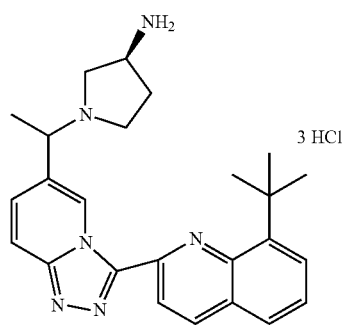 [SMILES: CC(c1ccc2nnc(-c3ccc4cccc(C(C)(C)C)c4n3)n2c1)N1CC[C@H](N)C1]

(3S)-1-(1-(3-(8-tert-butylquinolin-2-yl)-[1,2,4]triazolo[4,3-a]pyridin-6-yl)ethyl)pyrrolidin-3-amine trihydrochloride Step A: Preparation of methyl 6-hydrazinylnicotinate A solution of methyl 6-fluoronicotinate (13.9 g, 89.60 mmol) and hydrazine (5.625 ml, 179.2 mmol) in THF (200 mL) were heated at 56° C. for 2 hours. After cooling to ambient temperature, the solvent was removed under reduced pressure and water (200 mL) was added. The suspension was stirred at ambient temperature for 1 hour. The solid was collected by filtration, washed with water and dried to give methyl 6-hydrazinylnicotinate (13.4 g, 89.5%) as a solid.

Step B: Preparation of (E)-methyl 6-(2-((8-tert-butylquinolin-2-yl)methylene)hydrazinyl)nicotinate A solution of methyl 6-hydrazinylnicotinate (1.00 g, 5.98 mmol) and 8-tert-butylquinoline-2-carbaldehyde (1.28 g, 5.98 mmol) in absolute ethanol (20 mL) was stirred at ambient temperature for 4 hours. The solid that formed was collected by filtration, washed with ethanol (10 mL), ether (100 mL) and dried to give (E)-methyl 6-(2-((8-tert-butylquinolin-2-yl)methylene)hydrazinyl)nicotinate (1.78 g, 82.1%) as a solid.

Step C: Preparation of 3-(8-tert-butylquinolin-2-yl)-[1,2,4]triazolo[4,3-a]pyridine-6-carboxylic acid To a suspension of (E)-methyl 6-(2-((8-tert-butylquinolin-2-yl)methylene)hydrazinyl)nicotinate (1.78 g, 4.91 mmol) in DCM (40 mL) was added iodobenzene diacetate (1.90 g, 5.89 mmol). The reaction mixture was stirred at ambient temperature for 4 hours. The solvent was removed, and the resulting residue was suspended in 1:1 hexane/ether (50 mL) and stirred at ambient temperature for 10 minutes. The solid that formed was collected by filtration. The solid was then suspended in 1:1 THF/H$_2$O (50 mL) and LiOH—H$_2$O (0.82 g, 19.6 mmol) was added. The reaction mixture was stirred at ambient temperature for 2 hours. THF was removed under reduced pressure. The resulting aqueous solution was acidified with saturated potassium hydrogen sulfate to pH~3-4. The solid that formed was collected by filtration, washed with water, 1:1 hexane/ether (50 mL) and dried to give 3-(8-tert-butylquinolin-2-yl)-[1,2,4]triazolo[4,3-a]pyridine-6-carboxylic acid (1.55 g, 91.1%) as solid.

Step D: Preparation of 3-(8-tert-butylquinolin-2-yl)-N-methoxy-[1,2,4]triazolo[4,3-a]pyridine-6-carboxamide A solution of 3-(8-tert-butylquinolin-2-yl)-[1,2,4]triazolo[4,3-a]pyridine-6-carboxylic acid (0.60 g, 1.73 mmol) and N,O-dimethylhydroxylamine hydrochloride (0.25 g, 2.60 mmol) and DIEA (0.91 mL, 5.20 mmol) in DMF (1 mL) was added HATU (1.15 g, 3.03 mmol) and the reaction mixture was stirred at ambient temperature for 1 hour. Water (10 mL) and ethyl acetate (30 mL) were added. The organic layer was separated, washed with brine, dried (sodium sulfate), filtered and concentrated under reduced pressure. The residue was purified by flash chromatography on silica gel (1:3 hexane/ethyl acetate) to give 3-(8-tert-butylquinolin-2-yl)-N-methoxy-N-methyl-[1,2,4]triazolo[4,3-a]pyridine-6-carboxamide (0.54 g, 80.6%) as solid.

Step E: Preparation of 1-(3-(8-tert-butylquinolin-2-yl)-[1,2,4]triazolo[4,3-a]pyridin-6-yl)ethanone To a solution of 3-(8-tert-butylquinolin-2-yl)-N-methoxy-N-methyl-[1,2,4]triazolo[4,3-a]pyridine-6-carboxamide (0.54 g, 1.40 mmol) in THF (10 mL) was added 1 N MeMgBr (2.00 mL, 2.79 mmol) in THF at −78° C. After addition, the reaction mixture was allowed to warm to ambient temperature and stirred at ambient for 20 hours. Water (10 mL) and ethyl acetate (30 mL) were added. The organic layer was separated, washed with brine, dried (sodium sulfate), filtered and concentrated under reduced pressure. The residue was purified by flash chromatography on silica gel (1:1 DCM/ethyl acetate) to give 14348-tert-butylquinolin-2-yl)-[1,2,4]triazolo[4,3-a]pyridin-6-yl)ethanone (0.385 g, 80.0%) as solid.

Step F: Preparation of tert-butyl (3S)-1-(1-(3-(8-tert-butylquinolin-2-yl)-[1,2,4]triazolo[4,3-a]pyridin-6-yl)ethyl)pyrrolidin-3-ylcarbamate To a solution of (S)-tert-butyl pyrrolidin-3-ylcarbamate (0.502 g, 2.69 mmol), 1-(3-(8-tert-butylquinolin-2-yl)-[1,2,4]triazolo[4,3-a]pyridin-6-yl)ethanone (0.464 g, 1.35 mmol) in THF (20 mL) was added tetraisopropoxytitanium (0.79 mL, 2.69 mmol) and the reaction mixture was stirred at ambient temperature for 18 hours. Ethanol (2 mL) and NaBH$_4$ (0.204 g, 5.39 mmol) were added and the mixture was stirred at ambient temperature for 2 hours. Water (10 mL), concentrated ammonium hydroxide (2 mL) and ethyl acetate (20 mL) were added. The organic layer was separated, washed with brine, dried (sodium sulfate), filtered and concentrated under reduced pressure. The residue was purified by C-18 reverse phase flash chromatography (Biotage SP4 unit, C-18 25M column, 0-90% CH$_3$CN/water gradient; 25 CV) to give tert-butyl (3S)-1-(1-(3-(8-tert-butylquinolin-2-yl)-[1,2,4]triazolo[4,3-a]pyridin-6-yl)ethyl)pyrrolidin-3-ylcarbamate (0.485 g, 69.9%) as solid.

Step G: Preparation of (3S)-1-(1-(3-(8-tert-butylquinolin-2-yl)-[1,2,4]triazolo[4,3-a]pyridin-6-yl)ethyl)pyrrolidin-3-amine trihydrochloride To a solution of tert-butyl (3S)-1-(1-(3-(8-tert-butylquinolin-2-yl)-[1,2,4]triazolo[4,3-a]pyridin-6-yl)ethyl)pyrrolidin-3-ylcarbamate (0.028 g, 0.0544 mmol) in DCM (2 mL) was added 5 N HCl (0.33 ml, 1.63 mmol) in IPA. The mixture was stirred at ambient temperature for 1 hour. The solvent was removed under reduced pressure to give (3S)-1-(1-(3-(8-tert-butylquinolin-2-yl)-[1,2,4]triazolo[4,3-a]pyridin-6-yl)ethyl)pyrrolidin-3-amine tri-HCl salt (0.027 g, 94.7%) as solid. LCMS APCI (+) m/z 415 (M+H).

Example 18

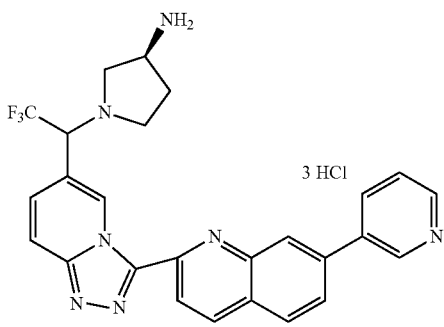 [SMILES: N[C@H]1CCN(C(c2ccc3nnc(-c4ccc5ccc(-c6cccnc6)cc5n4)n3c2)C(F)(F)F)C1]

(3S)-1-(2,2,2-trifluoro-1-(3-(7-(pyridin-3-yl)quinolin-2-yl)-[1,2,4]triazolo[4,3-a]pyridin-6-yl)ethyl)pyrrolidin-3-amine tri-hydrochloride Prepared as described in Example 4, Steps A-B, using 3-(4,4,5,5-tetramethyl-1,3,2-dioxaborolan-2-yl)pyridine in place of 1-methyl-4-(4,4,5,5-tetramethyl-1,3,2-dioxaborolan-2-yl)-1H-pyrazole in Step A. LCMS APCI (+) m/z 490 (M+H).

Example 19

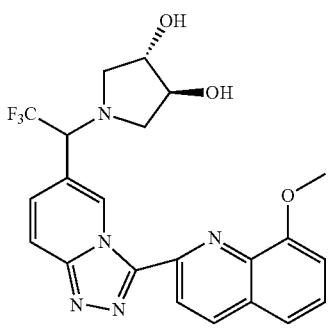 [SMILES: COc1cccc2ccc(-c3nnc4ccc(C(N5C[C@H](O)[C@@H](O)C5)C(F)(F)F)cn34)nc12]

(3S,4S)-1-(2,2,2-trifluoro-1-(3-(8-methoxyquinolin-2-yl)-[1,2,4]triazolo[4,3-a]pyridin-6-yl)ethyl)pyrrolidine-3,4-diol Prepared as described in Example 1, Steps A-E, using (3S,4S)-pyrrolidine-3,4-diol in place of (S)-tert-butyl pyrrolidin-3-ylcarbamate in Step C. LCMS APCI (+) m/z 460 (M+H).

Example 20

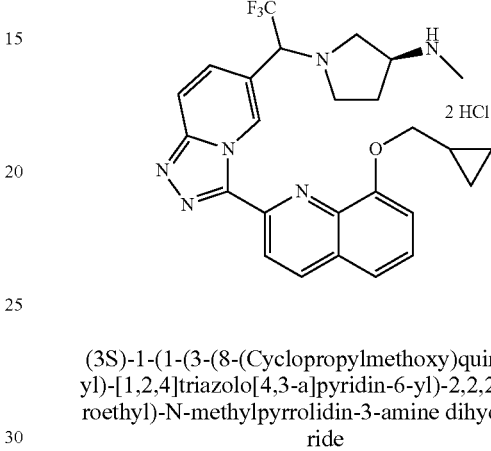

(3S)-1-(1-(3-(8-(Cyclopropylmethoxy)quinolin-2-yl)-[1,2,4]triazolo[4,3-a]pyridin-6-yl)-2,2,2-trifluoroethyl)-N-methylpyrrolidin-3-amine dihydrochloride Step A: Preparation of (S)-benzyl 3-(tert-butoxycarbonylamino)pyrrolidine-1-carboxylate To a solution of (S)-tert-butyl pyrrolidin-3-ylcarbamate (6.0 g, 32.2 mmol) and DIEA (12.5 g, 16.8 mL, 96.6 mmol) in dichloromethane (60 mL) cooled to 0° C. on an ice-bath was added benzyl chloroformate (8.7 g, 7.2 mL, 48.3 mmol), and the resulting mixture stirred at 0° C. for 2 hours. The mixture was diluted with dichloromethane (30 mL) and washed successively with cold aqueous 10% HCl, water, saturated sodium bicarbonate solution and brine. The organic phase was dried (MgSO$_4$), filtered and concentrated under reduced pressure. The residue was purified by flash chromatography silica gel (Biotage, 65M; 20% ethyl acetate/hexanes) to afford (S)-benzyl 3-(tert-butoxycarbonylamino)pyrrolidine-1-carboxylate (10 g, 97%).

Step B: Preparation of (S)-benzyl 3-(tert-butoxycarbonyl(methyl)amino)pyrrolidine-1-carboxylate To a suspension of 60% dispersion of sodium hydride in mineral oil (1.5 g, 37.5 mmol) in anhydrous DMF (20 mL) cooled on an ice-bath to 0° C. was added dropwise a solution of (S)-benzyl 3-(tert-butoxycarbonylamino)pyrrolidine-1-carboxylate (10 g, 31.2 mmol) in anhydrous DMF (100 mL). The resulting mixture was stirred at 0° C. for 1 hour then at ambient temperature for 2 hours. The mixture was subsequently cooled to 0° C. and treated dropwise with iodomethane (2.1 mL, 34.3 mmol), and the mixture stirred at 0° C. for 1 hour then warmed to ambient temperature and stirred for 18 hours. The reaction mixture was diluted with water (300 mL) and the mixture extracted with ethyl acetate. The combined organic layers were washed with water and brine, dried (MgSO$_4$), filtered and concentrated under reduced pressure. The residual oil was purified by column chromatography (Biotage, 65M; 10-20% ethyl acetate:hexanes) to afford (S)-benzyl 3-(tert-butoxycarbonyl(methyl)amino)pyrrolidine-1-carboxylate (7.2 g, 69%).

Step C: Preparation of (S)-tert-butyl methyl(pyrrolidin-3-yl)carbamate

To a suspension of 5% Pd/C (4.60 g, 2.16 mmol) in ethanol (40 mL) was added slowly a solution of (S)-benzyl 3-(tert-butoxycarbonyl(methyl)amino)pyrrolidine-1-carboxylate (7.2 g, 21.6 mmol) in methanol (20 mL). The mixture was evacuated and backfilled with nitrogen and then evacuated and backfilled with hydrogen then stirred under a hydrogen atmosphere for 2 hours. The suspension was filtered through a pad of Celite and washed with methanol (60 mL). The filtrate was concentrated under reduced pressure to afford (S)-tert-butyl methyl(pyrrolidin-3-yl)carbamate (4.3 g, 99%).

Step D: Preparation of tert-butyl (3S)-1-(1-(6-chloropyridin-3-yl)-2,2,2-trifluoroethyl)pyrrolidin-3-yl (methyl)carbamate Prepared as described in Example 1, Step C, using 1-(6-chloropyridin-3-yl)-2,2,2-trifluoroethyl trifluoromethanesulfonate (1.50 g, 4.37 mmol) and (S)-tert-butyl methyl(pyrrolidin-3-yl)carbamate (1.2 g, 6.11 mmol) to afford tert-butyl (3S)-1-(1-(6-chloropyridin-3-yl)-2,2,2-trifluoroethyl)pyrrolidin-3-yl(methyl)carbamate (1.15 g, 67%).

Step E: Preparation of tert-butyl methyl((3S)-1-(2,2,2-trifluoro-1-(6-hydrazinylpyridin-3-yl)ethyl)pyrrolidin-3-yl)carbamate Prepared as described in Example 1, Step D, using tert-butyl (3S)-1-(1-(6-chloropyridin-3-yl)-2,2,2-trifluoroethyl)pyrrolidin-3-yl(methyl)carbamate (1.15 g, 2.92 mmol) to afford tert-butyl methyl((3S)-1-(2,2,2-trifluoro-1-(6-hydrazinylpyridin-3-yl)ethyl)pyrrolidin-3-yl)carbamate (1.0 g, 88%).

Step F: Preparation of (3S)-1-(1-(3-(8-(cyclopropylmethoxy)quinolin-2-yl)-[1,2,4]triazolo[4,3-a]pyridin-6-yl)-2,2,2-trifluoroethyl)-N-methylpyrrolidin-3-amine dihydrochloride A solution of 8-(cyclopropylmethoxy)quinoline-2-carbaldehyde (0.14 g, 0.62 mmol) and tert-butyl methyl((3S)-1-(2,2,2-trifluoro-1-(6-hydrazinylpyridin-3-yl)ethyl)pyrrolidin-3-yl)carbamate (0.20 g, 0.51 mmol) in ethanol (10 mL) was stirred at ambient temperature for 16 hours. The solvent was removed under reduced pressure. The residue was dissolved in dichloromethane (10 mL) and treated with iodobenzene diacetate (0.20 g, 0.62 mmol) and stirred at ambient temperature for 4 hours. The mixture was partitioned between ethyl acetate (20 mL) and saturated sodium bicarbonate solution (10 mL). The organic layer was separated, washed with brine, dried (MgSO$_4$, filtered and concentrated under reduced pressure. The residue was purified by reverse phase chromatography (Biotage SP4, C-18 25M; 10-90% CH$_3$CN/water gradient). The residue was dissolved in dichloromethane (1 mL), treated with TFA (4 mL) and stirred at ambient temperature for 1 hour. The solution was concentrated under reduced pressure and the residue was purified by reverse phase chromatography (Biotage SP4, C-18 25M; 10-70% CH3CN/water gradient). The TFA salt was dissolved in methanol (0.50 mL) and treated with 2N HCl in diethyl ether (4 mL) and stirred for 10 minutes. The solvent was removed under reduced pressure and the solid obtained suspended in MeCN (5 mL) and stirred for 10 minutes. The solid was collected by filtration to afford (3S)-1-(1-(3-(8-(cyclopropylmethoxy)quinolin-2-yl)-[1,2,4]triazolo[4,3-a]pyridin-6-yl)-2,2,2-trifluoroethyl)-N-methylpyrrolidin-3-amine (0.129 g, 44%). LCMS APCI (+) m/z 497 (M+H).

Example 21

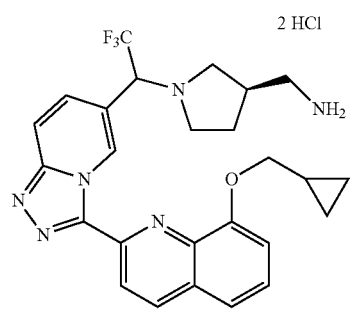 [SMILES: NC[C@H]1CCN(C(c2ccc3nnc(-c4ccc5cccc(OCC6CC6)c5n4)n3c2)C(F)(F)F)C1]

((3R)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-yl)methanamine dihydrochloride Prepared as described in Example 1, Steps A-F, using (S)-tert-butyl pyrrolidin-3-ylmethylcarbamate in place of (S)-tert-butyl pyrrolidin-3-ylcarbamate in Step C, and substituting 8-(cyclopropylmethoxy)quinoline-2-carbaldehyde for 8-methoxyquinoline-2-carbaldehyde in Step E. MS APCI (+) m/z 497 (M+1) detected.

Example 22

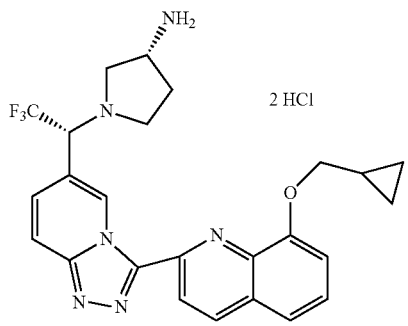 [SMILES: N[C@@H]1CCN([C@H](c2ccc3nnc(-c4ccc5cccc(OCC6CC6)c5n4)n3c2)C(F)(F)F)C1]

(R)-1-((R)-1-(3-(8-(cyclopropylmethoxy)quinolin-2-yl)-[1,2,4]triazolo[4,3-a]pyridin-6-yl)-2,2,2-trifluoroethyl)pyrrolidin-3-amine Prepared as described in Example 9A, Steps A-B, using tert-butyl (3R)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-ylcarbamate in place of tert-butyl (3S)-1-(2,2,2-trifluoro-1-(3-(8-methoxyquinolin-2-yl)-[1,2,4]triazolo[4,3- a]pyridin-6-yl)ethyl)pyrrolidin-3-ylcarbamate and isolating peak 2 during the chiral separation in Step A. LCMS APCI (+) m/z 483 (M+H).

Example 23

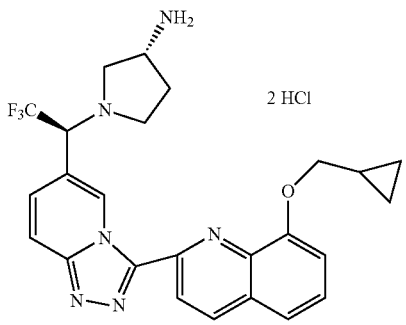 [SMILES: N[C@@H]1CCN([C@@H](c2ccc3nnc(-c4ccc5cccc(OCC6CC6)c5n4)n3c2)C(F)(F)F)C1]

(R)-1-((S)-1-(3-(8-(cyclopropylmethoxy)quinolin-2-yl)-[1,2,4]triazolo[4,3-a]pyridin-6-yl)-2,2,2-trifluoroethyl)pyrrolidin-3-amine Prepared as described in Example 8, Steps A-B, using tert-butyl (3R)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-ylcarbamate in place of tert-butyl (3S)-1-(2,2,2-trifluoro-1-(3-(8-methoxyquinolin-2-yl)-[1,2,4]triazolo[4,3-a]pyridin-6-yl)ethyl)pyrrolidin-3-ylcarbamate and isolating peak 1 during the chiral separation in Step A. LCMS APCI (+) m/z 483 (M+H).

Example 24

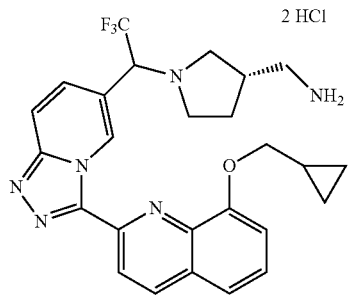 [SMILES: NC[C@@H]1CCN(C(c2ccc3nnc(-c4ccc5cccc(OCC6CC6)c5n4)n3c2)C(F)(F)F)C1]

((3S)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-yl)methanamine dihydrochloride Prepared as described in Example 1, Steps A-F, using (R)-tert-butyl pyrrolidin-3-ylmethylcarbamate in place of (S)-tert-butyl pyrrolidin-3-ylmethylcarbamate in Step C, and using 8-(cyclopropylmethoxy)quinoline-2-carbaldehyde in place of 8-methoxyquinoline-2-carbaldehyde in Step E. MS APCI (+) m/z 497 (M+1) detected.

Example 25

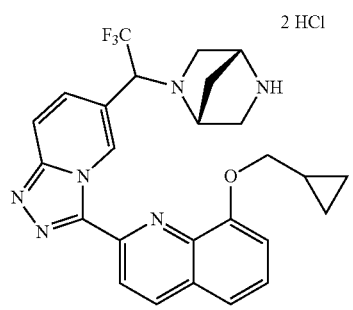 [SMILES: FC(F)(F)C(c1ccc2nnc(-c3ccc4cccc(OCC5CC5)c4n3)n2c1)N1C[C@H]2C[C@@H]1CN2]

2-(6-(1-((1R,4R)-2,5-diazabicyclo[2.2.1]heptan-2-yl)-2,2,2-trifluoroethyl)-[1,2,4]triazolo[4,3-a]pyridin-3-yl)-8-(cyclopropylmethoxy)quinoline dihydrochloride Prepared as described in Example 1, Steps A-F, using (1R,4R)-tert-butyl 2,5-diazabicyclo[2.2.1]heptane-2-carboxylate in place of (S)-tert-butyl pyrrolidin-3-ylmethylcarbamate in Step C, and using 8-(cyclopropylmethoxy)quinoline-2-carbaldehyde in place of 8-methoxyquinoline-2-carbaldehyde in Step E. MS APCI (+) m/z 495 (M+1) detected.

Example 26

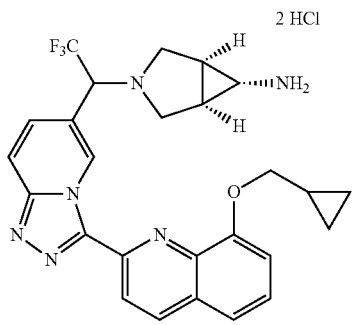 [SMILES: N[C@@H]1[C@H]2CN(C(c3ccc4nnc(-c5ccc6cccc(OCC7CC7)c6n5)n4c3)C(F)(F)F)C[C@@H]12]

(1R,5S,6S)-3-(1-(3-(8-(cyclopropylmethoxy)quinolin-2-yl)-[1,2,4]triazolo[4,3-a]pyridin-6-yl)-2,2,2-trifluoroethyl)-3-azabicyclo[3.1.0]hexanesan-6-amine dihydrochloride Prepared as described in Example 1, Steps A-F, using tert-butyl (1R,5S,6S)-3-azabicyclo[3.1.0]hexanesan-6-ylcarbamate in place of (S)-tert-butyl pyrrolidin-3-ylmethylcarbamate in Step C, and using 8-(cyclopropylmethoxy)

quinoline-2-carbaldehyde in place of 8-methoxyquinoline-2-carbaldehyde in Step E. MS APCI (+) m/z 495 (M+1) detected.

Example 27

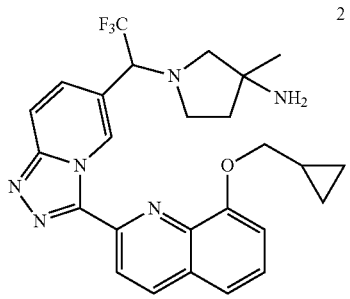

1-(1-(3-(8-(cyclopropylmethoxy)quinolin-2-yl)-[1,2,4]triazolo[4,3-a]pyridin-6-yl)-2,2,2-trifluoroethyl)-3-methylpyrrolidin-3-amine dihydrochloride Prepared as described in Example 1, Steps A-F, using (+/−) tert-butyl 3-methylpyrrolidin-3-ylcarbamate in place of (S)-tert-butyl pyrrolidin-3-ylmethylcarbamate in Step C, and using 8-(cyclopropylmethoxy)quinoline-2-carbaldehyde in place of 8-methoxyquinoline-2-carbaldehyde in Step E to provide a mixture of products. The products were separated by semi-preparative HPLC to give the title product. MS APCI (+) m/z 497 (M+1) detected.

Example 28

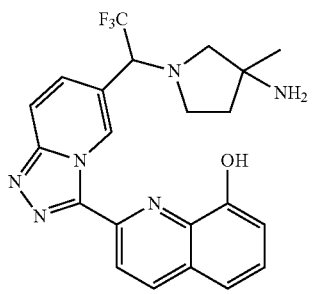

2-(6-(1-(3-amino-3-methylpyrrolidin-1-yl)-2,2,2-trifluoroethyl)-[1,2,4]triazolo[4,3-a]pyridin-3-yl)quinolin-8-ol dihydrochloride Prepared as described in Example 1, Steps A-F, using (+/−) tert-butyl 3-methylpyrrolidin-3-ylcarbamate in place of (S)-tert-butyl pyrrolidin-3-ylmethylcarbamate in Step C, and using 8-(cyclopropylmethoxy)quinoline-2-carbaldehyde in place of 8-methoxyquinoline-2-carbaldehyde in Step E to provide a mixture of products. The products were separated by semi-preparative HPLC to give the named product. MS APCI (+) m/z 443 (M+1) detected.

Example 29

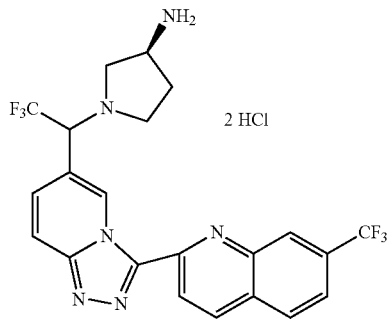 [SMILES: N[C@H]1CCN(C(c2ccc3nnc(-c4ccc5ccc(C(F)(F)F)cc5n4)n3c2)C(F)(F)F)C1]

(3S)-1-(2,2,2-trifluoro-1-(3-(7-(trifluoromethyl)quinolin-2-yl)-[1,2,4]triazolo[4,3-a]pyridin-6-yl)ethyl)pyrrolidin-3-amine dihydrochloride Step A: Preparation 2-methyl-7-(trifluoromethyl)quinoline To a solution of 3-(trifluoromethyl)aniline (12.43 mL, 99.92 mmol) in 6 N HCl (50 mL) in water was added (E)-but-2-enal (18.77 mL, 229.8 mmol) dropwise at reflux. The reaction was stirred at reflux for 3 hours. After cooling to ambient temperature, ethyl acetate (200 mL) was added. The aqueous layer was separated, basified with ammonium hydroxide to about pH 9, and extracted with DCM (2×200 mL). The combined organic layers were dried (sodium sulfate), filtered and concentrated under reduced pressure. The residue was purified by flash chromatography on silica gel (5:1 hexane/ethyl acetate) to give 2-methyl-7-(trifluoromethyl)quinoline (6.1 g, 28.9%) as a solid.

Step B: Preparation of ((3S)-1-(2,2,2-trifluoro-1-(3-(7-(trifluoromethyl)quinolin-2-yl)-[1,2,4]triazolo[4,3-a]pyridin-6-yl)ethyl)pyrrolidin-3-amine dihydrochloride Prepared as described in Example 5, Steps A-C, using 2-methyl-7-(trifluoromethyl)quinoline in place of 8-(cyclopropylmethoxy)-2-methylquinoline in Step B. LCMS APCI (+) m/z 481 (M+H).

Example 30

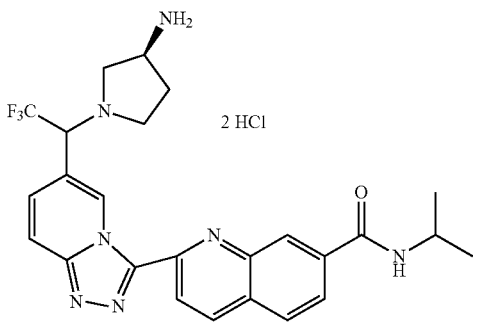 [SMILES: CC(C)NC(=O)c1ccc2ccc(-c3nnc4ccc(C(N5CC[C@H](N)C5)C(F)(F)F)cn34)nc2c1]

2-(6-(1-((S)-3-aminopyrrolidin-1-yl)-2,2,2-trifluoro-ethyl)-[1,2,4]triazolo[4,3-a]pyridin-3-yl)-N-isopropylquinoline-7-carboxamide dihydrochloride Step A: Preparation 2-methylquinoline-7-carboxylic acid A mixture of 2-methyl-7-(trifluoromethyl)quinoline (5.2 g, 24.6 mmol) and 80% $H_2SO_4$ (18.1 g, 148 mmol) was heated at 230° C. for 20 minutes. After cooling to ambient temperature, the mixture was basified by 6 N NaOH to about pH 12. The resulting solid was removed by filtration. The filtrate was acidified by 2 N HCl to about pH 3, extracted with 3:1 DCM/IPA (2×50 mL), dried (sodium sulfate), filtered and concentrated under reduced pressure to give 2-methylquinoline-7-carboxylic acid (3.3 g, 71.6%) as a solid.

Step B: Preparation methyl 2-methylquinoline-7-carboxylate

To a solution of 2-methylquinoline-7-carboxylic acid (1.00 g, 5.34 mmol) and $K_2CO_3$ (2.36 g, 17.1 mmol) in DMA (10 mL) was added MeI (0.35 mL, 5.61 mmol) dropwise at ambient temperature. The reaction was stirred at ambient temperature for 18 hours. Water (30 mL) and ethyl acetate (50 mL) were added. The organic layer was separated, washed with water and brine, dried (sodium sulfate), filtered and concentrated under reduced pressure. The residue was purified by flash chromatography on silica gel (1:5 hexane/ethyl acetate) to give methyl 2-methylquinoline-7-carboxylate (0.99 g, 92.1%) as a solid.

Step C: Preparation methyl 2-formylquinoline-7-carboxylate

To a solution of methyl 2-methylquinoline-7-carboxylate (0.99 g, 4.92 mmol) in dioxane (60 mL) and water (0.6 mL) was added $SeO_2$ (0.66 g, 5.90 mmol) and the mixture was stirred at reflux for 2 hours. After cooling to ambient temperature, the solid was removed by filtration and washed with DCM. The filtrate was concentrated under reduced pressure. The residue was purified by flash chromatography on silica gel (1:4 hexane/ethyl acetate) to give methyl 2-formylquinoline-7-carboxylate (0.75 g, 70.8%) as a solid.

Step D: Preparation of 2-(6-(1-((S)-3-(tert-butoxycarbonylamino)pyrrolidin-1-yl)-2,2,2-trifluoroethyl)-[1,2,4]triazolo[4,3-a]pyridin-3-yl)quinoline-7-carboxylic acid A solution of tert-butyl (3S)-1-(2,2,2-trifluoro-1-(6-hydrazinylpyridin-3-yl)ethyl)pyrrolidin-3-ylcarbamate (Example 1, Step D; 0.46 g, 1.03 mmol) and methyl 2-formylquinoline-7-carboxylate (0.22 g, 1.03 mmol) in EtOH (10 mL) was stirred at ambient temperature for 1 hour. The solvent was removed under reduced pressure. The residue was dissolved in DCM (10 mL) and iodo benzene diacetate (0.40 g, 1.24 mmol) was added. The mixture was stirred at ambient temperature for 1 hour. Ethyl acetate (20 mL) and saturated sodium bicarbonate (10 mL) were added. The organic layer was separated, washed with brine, dried (sodium sulfate), filtered and concentrated under reduced pressure. The residue obtained was dissolved in THF (5 mL) and 2 N LiOH (5.15 mL, 10.30 mmol) was added. The mixture was stirred at ambient temperature for 6 hours. Ether (20 mL) was added. The aqueous layer was separated and acidified with saturated potassium hydrogen sulfate to about pH 3. The resulting solid was collected by filtration to give 2-(6-(1-((S)-3-(tert-butoxycarbonylamino)pyrrolidin-1-yl)-2,2,2-trifluoroethyl)-[1,2,4]triazolo[4,3-a]pyridin-3-yl)quinoline-7-carboxylic acid (0.45 g, 78.5%) as a solid.

Step E: Preparation of tert-butyl (3S)-1-(2,2,2-trifluoro-1-(3-(7-(isopropylcarbamoyl)quinolin-2-yl)-[1,2,4]triazolo[4,3-a]pyridin-6-yl)ethyl)pyrrolidin-3-ylcarbamate To a solution of 2-(6-(1-((S)-3-(tert-butoxycarbonylamino)pyrrolidin-1-yl)-2,2,2-trifluoroethyl)-[1,2,4]triazolo[4,3-a]pyridin-3-yl)quinoline-7-carboxylic acid (0.075 g, 0.135 mmol), HATU (0.062 g, 0.16 mmol) and propan-2-amine (0.057 ml, 0.67 mmol) in DMF (1 mL) was added DIEA (0.047 mL, 0.27 mmol) and the reaction mixture was stirred at ambient temperature for 4 hours. The reaction mixture was purified directly by C-18 reverse phase flash chromatography (Biotage SP4 unit, C-18 25M column, 0-90% $CH_3CN$/water gradient; 30 CV)) to give tert-butyl (3S)-1-(2,2,2-trifluoro-1-(3-(7-(isopropylcarbamoyl)quinolin-2-yl)-[1,2,4]triazolo[4,3-a]pyridin-6-yl)ethyl)pyrrolidin-3-ylcarbamate (0.023 g, 28.6%) as a solid.

Step F: Preparation of 2-(6-(1-((S)-3-aminopyrrolidin-1-yl)-2,2,2-trifluoroethyl)-[1,2,4]triazolo[4,3-a]pyridin-3-yl)-N-isopropylquinoline-7-carboxamide dihydrochloride To a solution of tert-butyl (3S)-1-(2,2,2-trifluoro-1-(3-(7-(isopropylcarbamoyl)quinolin-2-yl)-[1,2,4]triazolo[4,3-a]pyridin-6-yl)ethyl)pyrrolidin-3-ylcarbamate (0.023 g, 0.039 mmol) in DCM (0.5 mL) was added 5 N HCl (0.39 mL, 1.92 mmol) in IPA. The mixture was stirred at ambient temperature for 1 hour. The solvent was removed under reduced pressure to give 2-(6-(1-((S)-3-aminopyrrolidin-1-yl)-2,2,2-trifluoroethyl)-[1,2,4]triazolo[4,3-a]pyridin-3-yl)-N-isopropylquinoline-7-carboxamide dihydrochloride (0.023 g, 95.7%) as a solid. LCMS APCI (+) m/z 498 (M+H).

Example 31

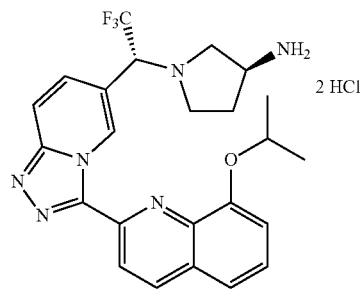 [SMILES: CC(C)Oc1cccc2ccc(-c3nnc4ccc([C@@H](N5CC[C@H](N)C5)C(F)(F)F)cn34)nc12]

(S)-1-((R)-2,2,2-trifluoro-1-(3-(8-isopropoxyquinolin-2-yl)-[1,2,4]triazolo[4,3-a]pyridin-6-yl)ethyl)pyrrolidin-3-amine dihydrochloride Step A: Preparation of 8-isopropoxyquinoline-2-carbaldehyde Prepared as described in Example 5, Steps A-B, using 2-iodopropane in place of (bromomethyl)cyclopropane in Step A.

Step B: Preparation of (S)-1-((R)-2,2,2-trifluoro-1-(3-(8-isopropoxyquinolin-2-yl)-[1,2,4]triazolo[4,3-a]pyridin-6-yl)ethyl)pyrrolidin-3-amine dihydrochloride Prepared as described in Example 9B, Steps A-G, using 8-isopropoxyquinoline-2-carbaldehyde in place of 8-methoxyquinoline-2-carbaldehyde in Step F. LCMS APCI (+) m/z 471 (M+H). Specific rotation: [α]$^{20}_D$=+2.83° (c=1.07, MeOH).

Example 32

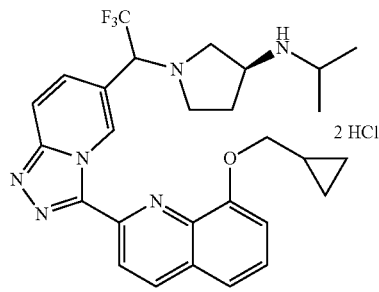 [SMILES: CC(C)N[C@H]1CCN(C(c2ccc3nnc(-c4ccc5cccc(OCC6CC6)c5n4)n3c2)C(F)(F)F)C1]

(3S)-1-(1-(3-(8-(cyclopropylmethoxy)quinolin-2-yl)-[1,2,4]triazolo[4,3-a]pyridin-6-yl)-2,2,2-trifluoroethyl)-N-isopropylpyrrolidin-3-amine dihydrochloride To a solution of (3S)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-amine (Example 5; 0.15 g, 0.27 mmol), DIEA (0.14 mL, 0.81 mmol) and trimethyl orthoformate (0.59 mL, 5.40 mmol) in methanol (6 mL) was added acetone (0.30 mL, 0.41 mmol) and the mixture stirred at ambient temperature for 18 hours. The solution was cooled to 0° C. on an ice-bath and sodium borohydride (0.02 g, 0.54 mmol) was added and the mixture stirred at ambient temperature for 1 hour, then poured in a saturated sodium bicarbonate solution (10 mL) and extracted with ethyl acetate (20 mL). The organic layer was washed with brine, dried (MgSO$_4$) filtered and concentrated under reduced pressure. The residue was purified by reverse phase chromatography (Biotage SP4, C-18 25M; 10-70% CH$_3$CN/water gradient). The residue was stirred in methanol (0.20 mL) and treated with 2N HCl in diethyl ether (2 mL) and stirred for 30 minutes and the solvents removed under reduced pressure. The residue was dissolved in methanol (0.50 mL) and treated with dichloromethane (0.50 mL) and hexanes (0.50 mL) and concentrated under reduced pressure to afford (3S)-1-(1-(3-(8-(cyclopropylmethoxy)quinolin-2-yl)-[1,2,4]triazolo[4,3-a]pyridin-6-yl)-2,2,2-trifluoroethyl)-N-isopropylpyrrolidin-3-amine (0.49 g, 30%). LCMS APCI (+) m/z 525 (M+H).

Example 33

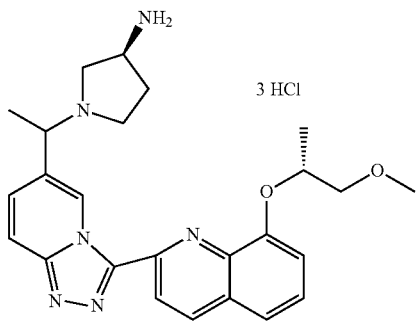 [SMILES: COC[C@@H](C)Oc1cccc2ccc(-c3nnc4ccc(C(C)N5CC[C@H](N)C5)cn34)nc12]

(3S)-1-(1-(3-(8-((R)-1-methoxypropan-2-yloxy)quinolin-2-yl)-[1,2,4]triazolo[4,3-a]pyridin-6-yl)ethyl)pyrrolidin-3-amine trihydrochloride Prepared as described in Example 1, Steps D-F, using tert-butyl (3S)-1-(1-(6-fluoropyridin-3-yl)ethyl)pyrrolidin-3-ylcarbamate in place of tert-butyl (3S)-1-(1-(6-chloropyridin-3-yl)-2,2,2-trifluoroethyl)pyrrolidin-3-ylcarbamate in Step D and substituting (R)-8-(1-methoxypropan-2-yloxy)quinoline-2-carbaldehyde for 8-methoxyquinoline-2-carbaldehyde in Step E. LCMS APCI (+) m/z 447 (M+H).

Example 34

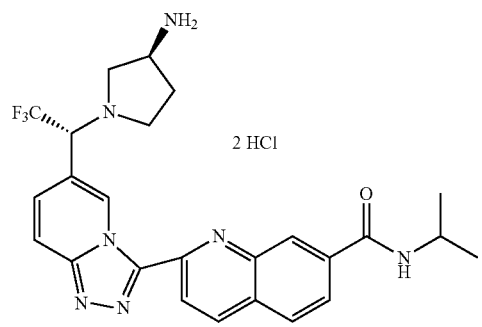 [SMILES: CC(C)NC(=O)c1ccc2ccc(-c3nnc4ccc([C@@H](N5CC[C@H](N)C5)C(F)(F)F)cn34)nc2c1]

2-(6-((R)-1-((S)-3-aminopyrrolidin-1-yl)-2,2,2-trifluoroethyl)-[1,2,4]triazolo[4,3-a]pyridin-3-yl)-N-isopropylquinoline-7-carboxamide dihydrochloride Prepared as described in Example 30, Steps A-F, using tert-butyl (S)-1-((R)-2,2,2-trifluoro-1-(6-hydrazinylpyridin-3-yl)ethyl)pyrrolidin-3-ylcarbamate (Example 9B, Steps A-E) in place of tert-butyl (3S)-1-(2,2,2-trifluoro-1-(6-hydrazinylpyridin-3-yl)ethyl)pyrrolidin-3-ylcarbamate in Step D. LCMS APCI (+) m/z 498 (M+H).

Example 35

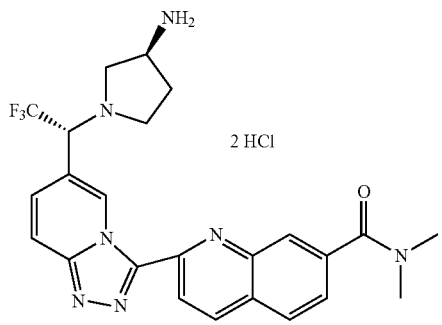 [SMILES: CN(C)C(=O)c1ccc2ccc(-c3nnc4ccc([C@@H](N5CC[C@H](N)C5)C(F)(F)F)cn34)nc2c1]

2-(6-((R)-1-((S)-3-aminopyrrolidin-1-yl)-2,2,2-trifluoroethyl)-[1,2,4]triazolo[4,3-a]pyridin-3-yl)-N,N-dimethylquinoline-7-carboxamide dihydrochloride Prepared as described in Example 30, Steps A-F, using tert-butyl (S)-1-((R)-2,2,2-trifluoro-1-(6-hydrazinylpyridin-3-yl)ethyl)pyrrolidin-3-ylcarbamate (Example 9B, Steps A-E) in place of tert-butyl (3S)-1-(2,2,2-trifluoro-1-(6-hydrazinylpyridin-3-yl)ethyl)pyrrolidin-3-ylcarbamate in Step D, and using dimethyl amine in place of propan-2-amine in Step E. LCMS APCI (+) m/z 484 (M+H).

Example 36

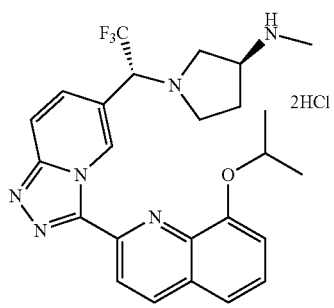 [SMILES: CN[C@H]1CCN([C@H](c2ccc3nnc(-c4ccc5cccc(OC(C)C)c5n4)n3c2)C(F)(F)F)C1]

(S)—N-methyl-1-((R)-2,2,2-trifluoro-1-(3-(8-isopropoxyquinolin-2-yl)-[1,2,4]triazolo[4,3-a]pyridin-6-yl)ethyl)pyrrolidin-3-amine dihydrochloride Step A: Preparation of tert-butyl methyl((S)-1-((R)-2,2,2-trifluoro-1-(6-hydrazinylpyridin-3-yl)ethyl)pyrrolidin-3-yl)carbamate Prepared as describe in Example 20 using (S)-1-(6-chloropyridin-3-yl)-2,2,2-trifluoroethyl trifluoromethanesulfonate in place of 1-(6-chloropyridin-3-yl)-2,2,2-trifluoroethyl trifluoromethanesulfonate.

Step B: Preparation of (S)—N-methyl-1-((R)-2,2,2-trifluoro-1-(3-(8-isopropoxyquinolin-2-yl)-[1,2,4]triazolo[4,3-a]pyridin-6-yl)ethyl)pyrrolidin-3-amine dihydrochloride Prepared as described in Example 9B, Steps A-G, using tert-butyl methyl((S)-1-((R)-2,2,2-trifluoro-1-(6-hydrazinylpyridin-3-yl)ethyl)pyrrolidin-3-yl)carbamate in place of tert-butyl (S)-1-((R)-2,2,2-trifluoro-1-(6-hydrazinylpyridin-3-yl)ethyl)pyrrolidin-3-yl)carbamate and using 8-isopropoxyquinoline-2-carbaldehyde in place of 8-methoxyquinoline-2-carbaldehyde in Step F. LCMS APCI (+) m/z 485 (M+H).

Example 37

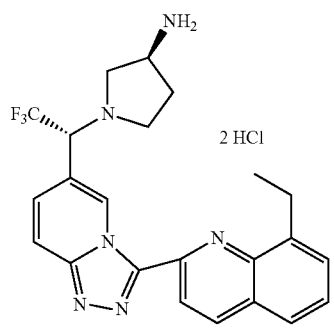 [SMILES: CCc1cccc2ccc(-c3nnc4ccc([C@@H](N5CC[C@H](N)C5)C(F)(F)F)cn34)nc12]

(S)-1-((R)-1-(3-(8-ethylquinolin-2-yl)-[1,2,4]triazolo[4,3-a]pyridin-6-yl)-2,2,2-trifluoroethyl)pyrrolidin-3-amine dihydrochloride Step A: Preparation of 8-ethyl-2-methylquinoline A solution of 2-ethylaniline (4.00 g, 33.0 mmol) in 6 N HCl (40 mL) was added (E)-but-2-enal (6.20 ml, 75.9 mmol) dropwise at reflux. The reaction was heated at reflux for 3 hours. After cooling to ambient temperature, ethyl acetate (40 mL) was added. The aqueous layer was separated, basified with ammonium hydroxide to about pH 9, and extracted with DCM (2×50 mL). The combined organic layer was dried (sodium sulfate) and concentrated under reduced pressure. The residue was purified by flash chromatography on silica gel (3:1 hexane/DCM) to give 8-ethyl-2-methylquinoline (3.34 g, 59.1%) as a solid.

Step B: Preparation of 8-ethylquinoline-2-carbaldehyde

A solution of 8-ethyl-2-methylquinoline (3.34 g, 19.5 mmol) in dioxane (150 mL) and water (1.5 mL) was added SeO$_2$ (2.60 g, 23.4 mmol) and the mixture was stirred at reflux for 2 hours. After cooling to ambient temperature, the solid was removed by filtration and washed with DCM. The filtrate was concentrated under reduced pressure and the residue was purified by flash chromatography on silica gel (1:1 hexane/DCM) to give 8-ethylquinoline-2-carbaldehyde (3.1 g, 85.8%) as a solid.

Step C: Preparation of (S)-1-((R)-1-(3-(8-ethylquinolin-2-yl)-[1,2,4]triazolo[4,3-a]pyridin-6-yl)-2,2,2-trifluoroethyl)pyrrolidin-3-amine dihydrochloride Prepared as described in Example 9B, Steps A-G, using 8-ethylquinoline-2-carbaldehyde in place of 8-methoxyquinoline-2-carbaldehyde in Step F. LCMS APCI (+) m/z 441 (M+H).

Example 38

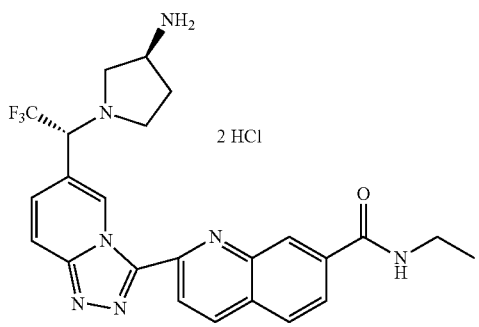 [SMILES: CCNC(=O)c1ccc2ccc(-c3nnc4ccc([C@@H](N5CC[C@H](N)C5)C(F)(F)F)cn34)nc2c1]

2-(6-((R)-1-((S)-3-aminopyrrolidin-1-yl)-2,2,2-trifluoroethyl)-[1,2,4]triazolo[4,3-a]pyridin-3-yl)-N-ethylquinoline-7-carboxamide dihydrochloride Prepared as described in Example 30, Steps A-F, using tert-butyl (S)-1-((R)-2,2,2-trifluoro-1-(6-hydrazinylpyridin-3-yl)ethyl)pyrrolidin-3-ylcarbamate in place of tert-butyl (3S)-1-(2,2,2-trifluoro-1-(6-hydrazinylpyridin-3-yl)ethyl)pyrrolidin-3-ylcarbamate in Step D, and using ethyl amine in place of propan-2-amine in Step E. LCMS APCI (+) m/z 484 (M+H).

Example 39

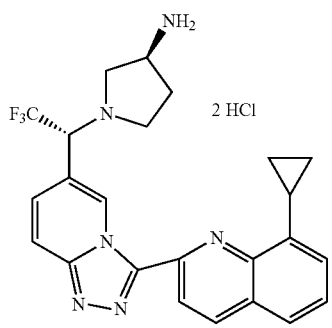 [SMILES: N[C@H]1CCN([C@H](c2ccc3nnc(-c4ccc5cccc(C6CC6)c5n4)n3c2)C(F)(F)F)C1]

(S)-1-((R)-1-(3-(8-cyclopropylquinolin-2-yl)-[1,2,4]triazolo[4,3-a]pyridin-6-yl)-2,2,2-trifluoroethyl)pyrrolidin-3-amine dihydrochloride Prepared as described in Example 37, Steps A-C, using 2-cyclopropylaniline in place of 2-ethylaniline in Step A. LCMS APCI (+) m/z 453 (M+H).

Example 40

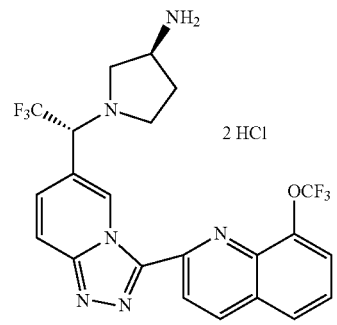 [SMILES: N[C@H]1CCN([C@H](c2ccc3nnc(-c4ccc5cccc(OC(F)(F)F)c5n4)n3c2)C(F)(F)F)C1]

(S)-1-((R)-2,2,2-trifluoro-1-(3-(8-(trifluoromethoxy)quinolin-2-yl)-[1,2,4]triazolo[4,3-a]pyridin-6-yl)ethyl)pyrrolidin-3-amine dihydrochloride Prepared as described in Example 37 using 2-(trifluoromethoxy)aniline in place of 2-ethylaniline in Step A. LCMS APCI (+) m/z 497 (M+H).

Example 41

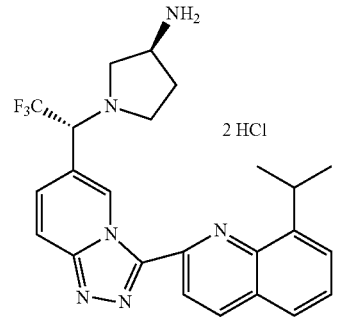 [SMILES: CC(C)c1cccc2ccc(-c3nnc4ccc([C@@H](N5CC[C@H](N)C5)C(F)(F)F)cn34)nc12]

(S)-1-((R)-2,2,2-trifluoro-1-(3-(8-isopropylquinolin-2-yl)-[1,2,4]triazolo[4,3-a]pyridin-6-yl)ethyl)pyrrolidin-3-amine dihydrochloride Prepared as described in Example 37, Steps A-C, using 2-isopropylaniline in place of 2-ethylaniline in Step A. LCMS APCI (+) m/z 455 (M+H).

Example 42

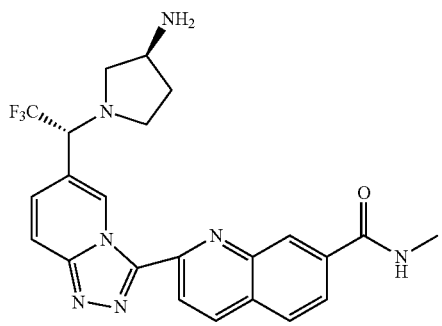 [SMILES: CNC(=O)c1ccc2ccc(-c3nnc4ccc([C@@H](N5CC[C@H](N)C5)C(F)(F)F)cn34)nc2c1]

2-(6-((R)-1-((S)-3-aminopyrrolidin-1-yl)-2,2,2-trifluoroethyl)-[1,2,4]triazolo[4,3-a]pyridin-3-yl)-N-methylquinoline-7-carboxamide dihydrochloride Prepared as described in Example 30, Steps A-F, using tert-butyl (S)-1-((R)-2,2,2-trifluoro-1-(6-hydrazinylpyridin-3-yl)ethyl)pyrrolidin-3-ylcarbamate in place of tert-butyl (3S)-1-(2,2,2-trifluoro-1-(6-hydrazinylpyridin-3-yl)ethyl)pyrrolidin-3-ylcarbamate in Step D, and using methylamine in place of propan-2-amine in Step E. LCMS APCI (+) m/z 470 (M+H).

Example 43

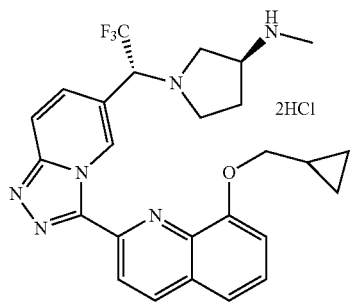 [SMILES: CN[C@H]1CCN([C@H](c2ccc3nnc(-c4ccc5cccc(OCC6CC6)c5n4)n3c2)C(F)(F)F)C1]

(S)-1-((R)-1-(3-(8-(cyclopropylmethoxy)quinolin-2-yl)-[1,2,4]triazolo[4,3-a]pyridin-6-yl)-2,2,2-trifluoroethyl)-N-methylpyrrolidin-3-amine dihydrochloride Prepared as described in Example 9B, Steps A-G, using tert-butyl methyl((S)-1-((R)-2,2,2-trifluoro-1-(6-hydrazinylpyridin-3-yl)ethyl)pyrrolidin-3-yl)carbamate in place of tert-butyl (S)-1-((R)-2,2,2-trifluoro-1-(6-hydrazinylpyridin-3-yl)ethyl)pyrrolidin-3-yl)carbamate and using 8-(cyclopropylmethoxy)quinoline-2-carbaldehyde in Step F. LCMS APCI (+) m/z 497 (M+H).

Example 44

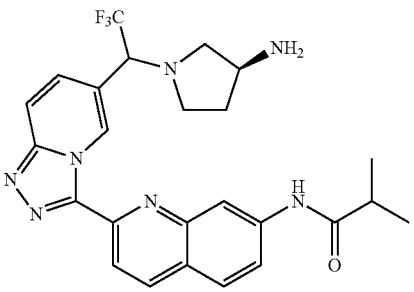 [SMILES: CC(C)C(=O)Nc1ccc2ccc(-c3nnc4ccc(C(N5CC[C@H](N)C5)C(F)(F)F)cn34)nc2c1]

N-(2-(6-(1-((S)-3-aminopyrrolidin-1-yl)-2,2,2-trifluoroethyl)-[1,2,4]triazolo[4,3-a]pyridin-3-yl)quinolin-7-yl)isobutyramide Step A: Preparation of tert-Butyl (3S)-1-(1-(3-(7-bromoquinolin-2-yl)-[1,2,4]triazolo[4,3-a]pyridin-6-yl)-2,2,2-trifluoroethyl)pyrrolidin-3-ylcarbamate Prepared as described in Example 1, Steps A-E, using 7-bromoquinoline-2-carbaldehyde in place of 8-methoxyquinoline-2-carbaldehyde in Step E.

Step B: Preparation of tert-butyl (3S)-1-(2,2,2-trifluoro-1-(3-(7-isobutyramidoquinolin-2-yl)-[1,2,4]triazolo[4,3-a]pyridin-6-yl)ethyl)pyrrolidin-3-ylcarbamate tert-Butyl (3S)-1-(1-(3-(7-bromo quinolin-2-yl)-[1,2,4]triazolo[4,3-a]pyridin-6-yl)-2,2,2-trifluoroethyl)pyrrolidin-3-ylcarbamate (50 mg, 0.085 mmol), isobutyramide (18.4 mg, 0.211 mmol), K$_3$PO$_4$ (53.8 mg, 0.254 mmol), and Cu(I)I (1.61 mg, 0.0085 mmol) were weighed into a 40 mL Teflon® capped vial. The vial was purged with N$_2$, followed by addition of toluene (20 mL) and N1,N2-dimethylethane-1,2-diamine (4.55 µL, 0.042 mmol). The reaction was sealed and heated to 90° C. overnight, after which the reaction complete by TLC. The crude reaction was concentrated, then purified by flash column chromatography (eluting with 10% MeOH/DCM), affording the desired product (55 mg, 97% yield).

Step C: Preparation of N-(2-(6-(1-((S)-3-aminopyrrolidin-1-yl)-2,2,2-trifluoroethyl)-[1,2,4]triazolo[4,3-a]pyridin-3-yl)quinolin-7-yl)isobutyramide tert-Butyl (3S)-1-(2,2,2-trifluoro-1-(3-(7-isobutyramido quinolin-2-yl)-[1,2,4]triazolo[4,3-a]pyridin-6-yl)ethyl)pyrrolidin-3-ylcarbamate (56 mg, 0.094 mmol) was weighed into a 100 mL 1 neck round bottom flask, and dissolve in 5 mL of chloroform, followed by addition of HCl (937 µL, 3.7 mmol). The reaction was then allowed to stir at ambient temperature for 1 hour, at which time the deprotection was complete and light yellow precipitate formed. The reaction was concentrated under vacuum, affording N-(2-(6-(1-((S)-3-aminopyrrolidin-1-yl)-2,2,2-trifluoroethyl)-[1,2,4]triazolo

[4,3-a]pyridin-3-yl)quinolin-7-yl)isobutyramide (32 mg, 69% yield) as a light yellow semi-solid. LCMS APCI (+) m/z 498.2 (M+H).

Example 45

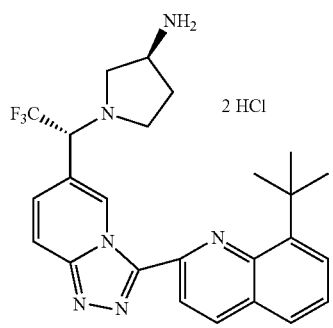 [SMILES: CC(C)(C)c1cccc2ccc(-c3nnc4ccc([C@@H](N5CC[C@H](N)C5)C(F)(F)F)cn34)nc12]

(S)-1-((R)-1-(3-(8-tert-butylquinolin-2-yl)-[1,2,4] triazolo[4,3-a]pyridin-6-yl)-2,2,2-trifluoroethyl)pyrrolidin-3-amine dihydrochloride Prepared as described in Example 37, Steps A-C, using 2-tert-butylaniline in place of 2-ethylaniline in Step A. LCMS APCI (+) m/z 469 (M+H).

Example 46

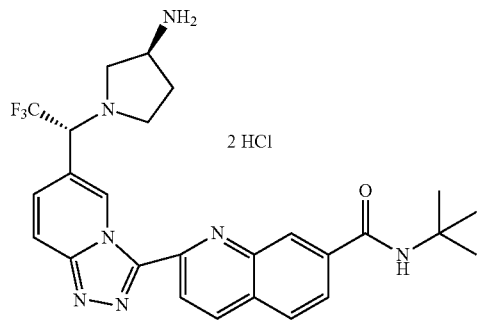 [SMILES: CC(C)(C)NC(=O)c1ccc2ccc(-c3nnc4ccc([C@@H](N5CC[C@H](N)C5)C(F)(F)F)cn34)nc2c1]

2-(6-((R)-1-((S)-3-aminopyrrolidin-1-yl)-2,2,2-trifluoroethyl)-[1,2,4]triazolo[4,3-a]pyridin-3-yl)-N-tert-butylquinoline-7-carboxamide dihydrochloride Prepared as described in Example 30, Steps A-F, using tert-butyl (S)-1-((R)-2,2,2-trifluoro-1-(6-hydrazinylpyridin-3-yl)ethyl)pyrrolidin-3-ylcarbamate in place of tert-butyl (3S)-1-(2,2,2-trifluoro-1-(6-hydrazinylpyridin-3-yl)ethyl) pyrrolidin-3-ylcarbamate in Step D, and using tert-butylamine in place of propan-2-amine in Step E. LCMS APCI (+) m/z 512 (M+H).

Example 47

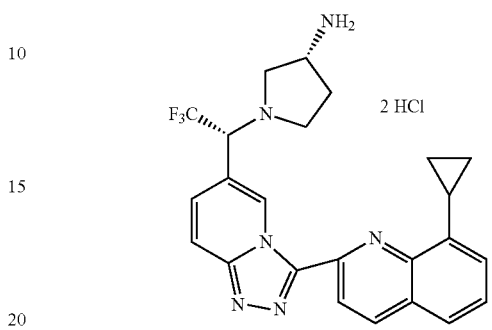

(R)-1-((R)-1-(3-(8-cyclopropylquinolin-2-yl)-[1,2,4] triazolo[4,3-a]pyridin-6-yl)-2,2,2-trifluoroethyl)pyrrolidin-3-amine dihydrochloride Prepared as described in Example 9B, Steps A-G, using (R)-tert-butyl pyrrolidin-3-ylcarbamate in place of (S)-tert-butyl pyrrolidin-3-ylcarbamate in Step D, and using 8-cyclopropylquinoline-2-carbaldehyde in place of 8-methoxyquinoline-2-carbaldehyde in Step F. LCMS APCI (+) m/z 453 (M+H).

Example 48

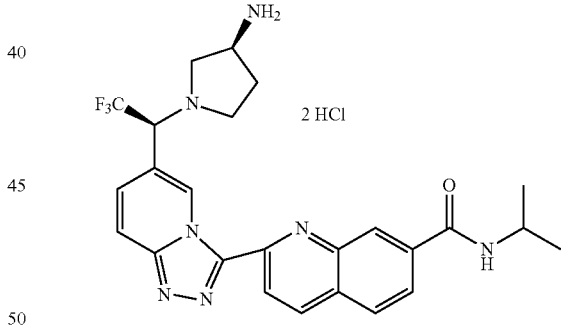

2-(6-((S)-1-((S)-3-aminopyrrolidin-1-yl)-2,2,2-trifluoroethyl)-[1,2,4]triazolo[4,3-a]pyridin-3-yl)-N-isopropylquinoline-7-carboxamide dihydrochloride Step A: Preparation of (R)-1-(6-chloropyridin-3-yl)-2,2,2-trifluoroethanol To a solution of 1-(6-chloropyridin-3-yl)-2,2,2-trifluoroethanone (Example 9B, Step A; 85.0 g, 406 mmol) and 1.0 M KOtBu (8.11 mL, 8.11 mmol) in t-BuOH in IPA (200 mL) and toluene (50 mL) in a autoclave was added dichloro{(R)-(+)-2,2'-bis[di(3,5-xylyl)-phosphino-1,1'-binaphthyl][(2R)-(−)-1,1-bis(4-methoxyphenyl)-3-methyl-1,2-butanediamine (0.991 g, 0.81 mmol) (Strem Chemicals). The reaction mixture was degassed by three vacuum-filling with nitrogen cycles. Hydrogen was introduced into the autoclave at a pressure of 300 psi and then reduced to 20 psi by slowly releasing the stop valve. After this procedure was repeated three times, the autoclave was pressurized to 520 psi with hydrogen. The reaction mixture was vigorously stirred at ambient temperature for 2 days (pressure was recharged to 520 psi when the internal pressure dropped below 200 psi). The pressure was released and the solvent was removed under reduced pressure. Ethyl acetate (300 mL) and 10% citric acid solution (50 mL) were added. The organic layer was separated, washed with brine, dried (sodium sulfate), filtered and concentrated under reduced pressure. The residue was purified by flash chromatography on silica gel (3:1 DCM/ethyl acetate) to give (S)-1-(6-chloropyridin-3-yl)-2,2,2-trifluoroethanol (83.5 g, 97.3%) as white solid. Enantiomeric excess was determined by chiral HPLC (Chiralcel OD-H, 90% hexanes: 10% (1:1 MeOH/EtOH) at 1.0 mL/min, 77.2% e.e. (R)-enantiomer). (R)-1-(6-chloropyridin-3-yl)-2,2,2-trifluoro ethanol (171 g, 808 mmol, 77.2% e.e.) was dissolved in 4.5% ethyl acetate/hexane (v/v) (3410 mL) with heating to reflux. After complete dissolution, it was slowly cooled to ambient temperature overnight. The resulting solid was collected by filtration, washed with hexane and dried to give (R)-1-(6-chloropyridin-3-yl)-2,2,2-trifluoroethanol (97.1 g, 56.8%) as white solid. Enantiomeric excess was determined by chiral HPLC (Chiralcel OD-H, 90% hexanes: 10% (1:1 MeOH/EtOH) at 1.0 mL/min, 98.9% e.e. (R)-enantiomer).

Step B: Preparation of tert-butyl (S)-1-((S)-2,2,2-trifluoro-1-(6-hydrazinylpyridin-3-yl)ethyl)pyrrolidin-3-ylcarbamate Prepared as described in Example 9B, Steps C-E, using (R)-1-(6-chloropyridin-3-yl)-2,2,2-trifluoroethanol in place of (S)-1-(6-chloropyridin-3-yl)-2,2,2-trifluoroethanol in Step C.

Step C: Preparation of 2-(6-((S)-1-((S)-3-aminopyrrolidin-1-yl)-2,2,2-trifluoroethyl)-[1,2,4]triazolo[4,3-a]pyridin-3-yl)-N-isopropylquinoline-7-carboxamide dihydrochloride Prepared as described in Example 30, Steps A-F, using tert-butyl (S)-1-((S)-2,2,2-trifluoro-1-(6-hydrazinylpyridin-3-yl)ethyl)pyrrolidin-3-ylcarbamate in place of tert-butyl (3S)-1-(2,2,2-trifluoro-1-(6-hydrazinylpyridin-3-yl)ethyl)pyrrolidin-3-ylcarbamate in Step D. LCMS APCI (+) m/z 498 (M+H).

Example 49

2-(6-((R)-1-((R)-3-aminopyrrolidin-1-yl)-2,2,2-trifluoroethyl)-[1,2,4]triazolo[4,3-a]pyridin-3-yl)-N-isopropylquinoline-7-carboxamide dihydrochloride Prepared as described in Example 30, Steps A-F, using tert-butyl (R)-1-((R)-2,2,2-trifluoro-1-(6-hydrazinylpyridin-3-yl)ethyl)pyrrolidin-3-ylcarbamate (prepared following the procedure of Example 1, Steps A-D) in place of tert-butyl (3S)-1-(2,2,2-trifluoro-1-(6-hydrazinylpyridin-3-yl)ethyl) pyrrolidin-3-ylcarbamate in Step D. LCMS APCI (+) m/z 498 (M+H).

Example 50

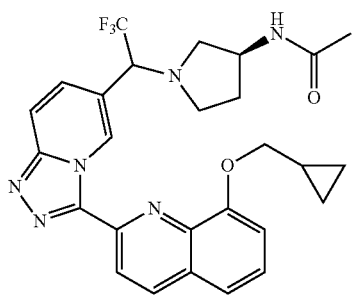

N-((3S)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-yl)acetamide A solution of (3S)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-amine (Example 5; 0.15 g, 0.27 mmol), DIEA (0.14 mL, 0.81 mmol) and acetic anhydride (0.038 mL, 0.41 mmol) in dichloromethane (4 mL) was stirred at ambient temperature for 18 hours. The mixture was partitioned between ethyl acetate (15 mL) and water (5 mL). The organic layer was separated and washed with aqueous 1N HCl (5 mL), water and brine, then dried (MgSO$_4$), filtered and concentrated under reduced pressure to afford N-((3S)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-yl)acetamide (0.076 g, 54%). LCMS APCI (+) m/z 525 (M+H).

Example 51

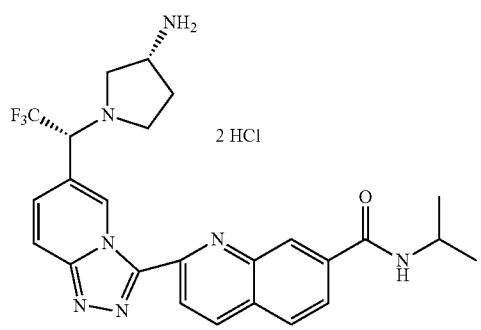 [SMILES: CC(C)NC(=O)c1ccc2ccc(-c3nnc4ccc([C@@H](N5CC[C@@H](N)C5)C(F)(F)F)cn34)nc2c1]

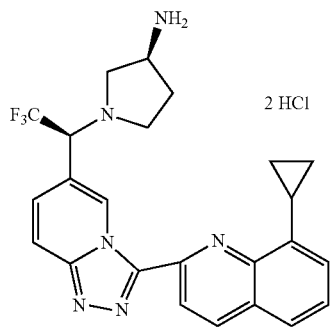 [SMILES: N[C@H]1CCN([C@@H](c2ccc3nnc(-c4ccc5cccc(C6CC6)c5n4)n3c2)C(F)(F)F)C1]

(S)-1-((S)-1-(3-(8-cyclopropylquinolin-2-yl)-[1,2,4]triazolo[4,3-a]pyridin-6-yl)-2,2,2-trifluoroethyl)pyrrolidin-3-amine dihydrochloride Prepared as described in Example 9B, Steps C-G, using (R)-1-(6-chloropyridin-3-yl-2,2,2-trifluoroethanol in place of (S)-1-(6-chloropyridin-3-yl-2,2,2-trifluoroethanol in Step C, and using 8-cyclopropylquinoline-2-carbaldehyde in place of 8-methoxyquinoline-2-carbaldehyde in Step F. LCMS APCI (+) m/z 453 (M+H).

Example 52

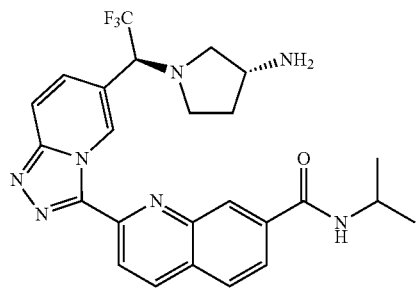 [SMILES: CC(C)NC(=O)c1ccc2ccc(-c3nnc4ccc([C@H](N5CC[C@@H](N)C5)C(F)(F)F)cn34)nc2c1]

2-(6-((S)-1-((R)-3-aminopyrrolidin-1-yl)-2,2,2-trifluoroethyl)-[1,2,4]triazolo[4,3-a]pyridin-3-yl)-N-isopropylquinoline-7-carboxamide Prepared as described in Example 30, Steps A-E, using tert-butyl (R)-1-((S)-2,2,2-trifluoro-1-(6-hydrazinylpyridin-3-yl)ethyl)pyrrolidin-3-ylcarbamate in place of tert-butyl (3S)-1-(2,2,2-trifluoro-1-(6-hydrazinylpyridin-3-yl)ethyl)pyrrolidin-3-ylcarbamate in Step D. LCMS APCI (+) m/z 498 (M+H).

Example 53

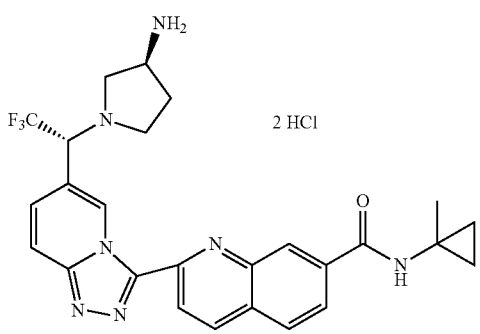 [SMILES: CC1(NC(=O)c2ccc3ccc(-c4nnc5ccc([C@@H](N6CC[C@H](N)C6)C(F)(F)F)cn45)nc3c2)CC1]

2-(6-((R)-1-((S)-3-aminopyrrolidin-1-yl)-2,2,2-trifluoroethyl)-[1,2,4]triazolo[4,3-a]pyridin-3-yl)-N-(1-methylcyclopropyl)quinoline-7-carboxamide dihydrochloride Prepared as described in Example 30, Steps A-F, using tert-butyl (S)-1-((R)-2,2,2-trifluoro-1-(6-hydrazinylpyridin-3-yl)ethyl)pyrrolidin-3-ylcarbamate in place of tert-butyl (3S)-1-(2,2,2-trifluoro-1-(6-hydrazinylpyridin-3-yl)ethyl)pyrrolidin-3-ylcarbamate in Step D, and using 1-methylcyclopropanamine in place of propan-2-amine in Step E. LCMS APCI (+) m/z 510 (M+H).

Example 54

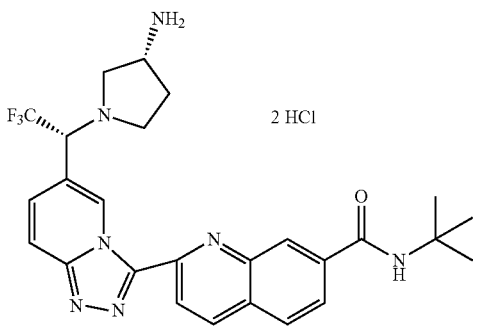 [SMILES: CC(C)(C)NC(=O)c1ccc2ccc(-c3nnc4ccc([C@@H](N5CC[C@@H](N)C5)C(F)(F)F)cn34)nc2c1]

2-(6-((R)-1-((R)-3-aminopyrrolidin-1-yl)-2,2,2-trifluoroethyl)-[1,2,4]triazolo[4,3-a]pyridin-3-yl)-N-tert-butylquinoline-7-carboxamide dihydrochloride Prepared as described in Example 30, Steps A-F, using tert-butyl (R)-1-((R)-2,2,2-trifluoro-1-(6-hydrazinylpyridin-3-yl)ethyl)pyrrolidin-3-ylcarbamate in place of tert-butyl (3S)-1-(2,2,2-trifluoro-1-(6-hydrazinylpyridin-3-yl)ethyl)pyrrolidin-3-ylcarbamate in Step D, and using tert-butylamine in place of propan-2-amine in Step E. LCMS APCI (+) m/z 512 (M+H).

Example 55

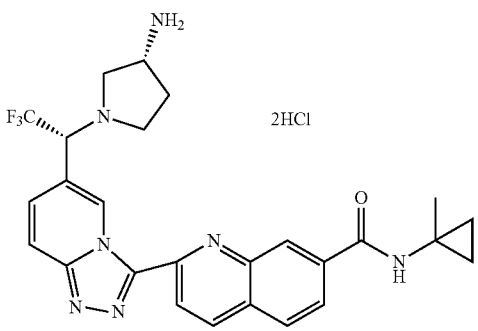 [SMILES: CC1(NC(=O)c2ccc3ccc(-c4nnc5ccc([C@@H](N6CC[C@@H](N)C6)C(F)(F)F)cn45)nc3c2)CC1]

2-(6-((R)-1-((R)-3-aminopyrrolidin-1-yl)-2,2,2-trifluoroethyl)-[1,2,4]triazolo[4,3-a]pyridin-3-yl)-N-(1-methylcyclopropyl)quinoline-7-carboxamide dihydrochloride Prepared as described in Example 30, Steps A-F, using tert-butyl (R)-1-((R)-2,2,2-trifluoro-1-(6-hydrazinylpyridin-3-yl)ethyl)pyrrolidin-3-ylcarbamate in place of tert-butyl (3S)-1-(2,2,2-trifluoro-1-(6-hydrazinylpyridin-3-yl)ethyl)

pyrrolidin-3-ylcarbamate in Step D, and using 1-methylcyclopropanamine in place of propan-2-amine in Step E. LCMS APCI (+) m/z 510 (M+H).

Example 56

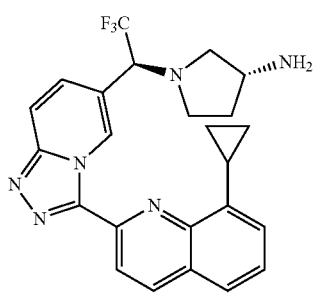 [SMILES: N[C@@H]1CCN([C@@H](c2ccc3nnc(-c4ccc5cccc(C6CC6)c5n4)n3c2)C(F)(F)F)C1]

(R)-1-((S)-1-(3-(8-cyclopropylquinolin-2-yl)-[1,2,4]triazolo[4,3-a]pyridin-6-yl)-2,2,2-trifluoroethyl)pyrrolidin-3-amine Step A: Preparation of 8-cyclopropylquiniline-2-carbaldehyde Prepared according to Example 37, Steps A-B, using 2-cyclopropylaniline in place of 2-ethylaniline in Step A.

Step B: Preparation of (R)-1-((S)-1-(3-(8-cyclopropylquinolin-2-yl)-[1,2,4]triazolo[4,3-a]pyridin-6-yl)-2,2,2-trifluoroethyl)pyrrolidin-3-amine Prepared as described in Example 9B, Steps A-F, using 8-cyclopropylquiniline-2-carbaldehyde in place of 8-methoxyquinoline-2-carbaldehyde in Step F and using tert-butyl (R)-1-((S)-2,2,2-trifluoro-1-(6-hydrazinylpyridin-3-yl)ethyl)pyrrolidin-3-ylcarbamate in place of tert-butyl (S)-1-((R)-2,2,2-trifluoro-1-(6-hydrazinylpyridin-3-yl)ethyl)pyrrolidin-3-ylcarbamate in Step F. LCMS APCI (+) m/z 453.2 (M+H).

Example 57

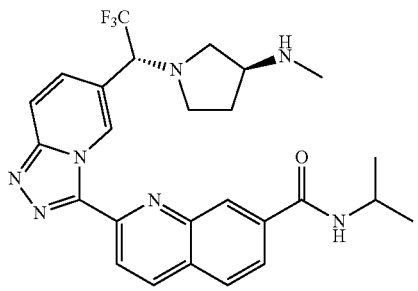 [SMILES: CN[C@H]1CCN([C@H](c2ccc3nnc(-c4ccc5ccc(C(=O)NC(C)C)cc5n4)n3c2)C(F)(F)F)C1]

N-isopropyl-2-(6-((R)-2,2,2-trifluoro-1-((S)-3-(methylamino)pyrrolidin-1-yl)ethyl)-[1,2,4]triazolo[4,3-a]pyridin-3-yl)quinoline-7-carboxamide Prepared as described in Example 30, Steps A-E, using tert-butyl methyl((S)-1-((R)-2,2,2-trifluoro-1-(6-hydrazinylpyridin-3-yl)ethyl)pyrrolidin-3-yl)carbamate in place of tert-butyl (3S)-1-(2,2,2-trifluoro-1-(3-(7-(isopropylcarbamoyl)quinolin-2-yl)-[1,2,4]triazolo[4,3-a]pyridin-6-yl)ethyl)pyrrolidin-3-ylcarbamate. LCMS APCI (+) m/z 512 (M+H).

Example 58

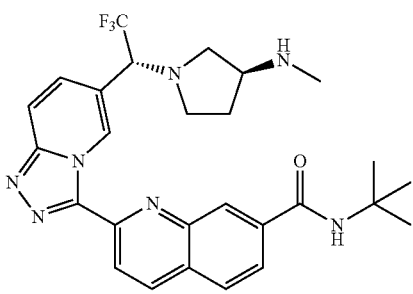 [SMILES: CN[C@H]1CCN([C@H](c2ccc3nnc(-c4ccc5ccc(C(=O)NC(C)(C)C)cc5n4)n3c2)C(F)(F)F)C1]

N,N-tert-butyl-2-(6-((R)-2,2,2-trifluoro-1-((S)-3-(methylamino)pyrrolidin-1-yl)ethyl)-[1,2,4]triazolo[4,3-a]pyridin-3-yl)quinoline-7-carboxamide Prepared as described in Example 30, Steps A-E substituting tert-butyl methyl((S)-1-((R)-2,2,2-trifluoro-1-(6-hydrazinylpyridin-3-yl)ethyl)pyrrolidin-3-yl)carbamate for tert-butyl (3S)-1-(2,2,2-trifluoro-1-(3-(7-(isopropylcarbamoyl)quinolin-2-yl)-[1,2,4]triazolo[4,3-a]pyridin-6-yl)ethyl)pyrrolidin-3-ylcarbamate in Step D, and using tert-butylamine in place of propan-2-amine in Step E. LCMS APCI (+) m/z 526.3 (M+H).

Example 59

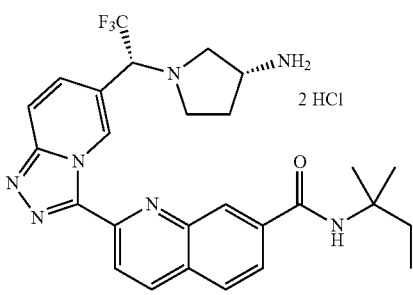 [SMILES: CCC(C)(C)NC(=O)c1ccc2ccc(-c3nnc4ccc([C@@H](N5CC[C@@H](N)C5)C(F)(F)F)cn34)nc2c1]

2-(6-((R)-1-((R)-3-aminopyrrolidin-1-yl)-2,2,2-trifluoroethyl)-[1,2,4]triazolo[4,3-a]pyridin-3-yl)-N-tert-pentylquinoline-7-carboxamide dihydrochloride Prepared as described in Example 30 using tert-butyl (R)-1-((R)-2,2,2-trifluoro-1-(6-hydrazinylpyridin-3-yl)ethyl)pyrrolidin-3-ylcarbamate in place of tert-butyl (3S)-1-(2,2,2-trifluoro-1-(6-hydrazinylpyridin-3-yl)ethyl)pyrrolidin-3-ylcarbamate in Step D, and using 2-methylbutan-2-amine in place of propan-2-amine in Step E. LCMS APCI (+) m/z 526 (M+H).

Example 60

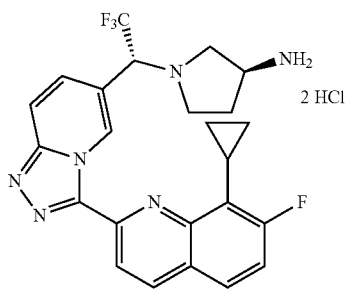 [SMILES: N[C@H]1CCN([C@H](c2ccc3nnc(-c4ccc5ccc(F)c(C6CC6)c5n4)n3c2)C(F)(F)F)C1]

(S)-1-((R)-1-(3-(8-cyclopropyl-7-fluoro quinolin-2-yl)-[1,2,4]triazolo[4,3-a]pyridin-6-yl)-2,2,2-trifluoroethyl)pyrrolidin-3-amine dihydrochloride

Step A: Preparation of 8-bromo-7-fluoro-2-methylquinoline

Prepared as described in Example 37, Step A, using 2-bromo-3-fluoroaniline in place of 2-ethylaniline.

Step B: Preparation of 8-cyclopropyl-7-fluoro-2-methylquinoline

A solution of 8-bromo-7-fluoro-2-methylquinoline (1.00 g, 4.17 mmol), Pd(OAc)$_2$ (0.047 g, 0.21 mmol), P(Cy)$_3$ (0.13 g, 0.46 mmol), K$_3$PO$_4$ (3.09 g, 14.6 mmol) and cyclopropylboronic acid (0.72 g, 8.33 mmol) in toluene (20 mL) and water (2 mL) was stirred at 100° C. for 8 hours. After cooling to ambient temperature, ethyl acetate (20 mL) and water (5 mL) were added. The organic layer was separated, washed with brine, dried (sodium sulfate), filtered and concentrated under reduced pressure. The residue was purified by flash chromatography (3:1 hexane/DCM) to give 8-cyclopropyl-7-fluoro-2-methylquinoline (0.78 g, 92.7%) as an oil.

Step C: Preparation of (S)-1-((R)-1-(3-(8-cyclopropyl-7-fluoroquinolin-2-yl)-[1,2,4]triazolo[4,3-a]pyridin-6-yl)-2,2,2-trifluoroethyl)pyrrolidin-3-amine dihydrochloride Prepared as described in Example 37 using 8-cyclopropyl-7-fluoro-2-methylquinoline in place of 8-ethyl-2-methylquinoline in Step B. LCMS APCI (+) m/z 471 (M+H).

Example 61

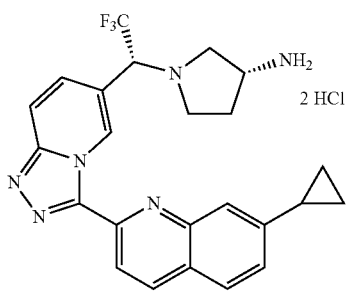 [SMILES: N[C@@H]1CCN([C@H](c2ccc3nnc(-c4ccc5ccc(C6CC6)cc5n4)n3c2)C(F)(F)F)C1]

(R)-1-((R)-1-(3-(7-cyclopropylquinolin-2-yl)-[1,2,4]triazolo[4,3-a]pyridin-6-yl)-2,2,2-trifluoroethyl)pyrrolidin-3-amine dihydrochloride

Step A: Preparation of tert-butyl (R)-1-((R)-1-(3-(7-bromoquinolin-2-yl)-[1,2,4]triazolo[4,3-a]pyridin-6-yl)-2,2,2-trifluoroethyl)pyrrolidin-3-ylcarbamate Prepared as described in Example 9B, Steps A-F, using 7-bromoquinoline-2-carbaldehyde in place of 8-methoxyquinoline-2-carbaldehyde in Step F.

Step B: Preparation of (R)-1-((R)-1-(3-(7-cyclopropylquinolin-2-yl)-[1,2,4]triazolo[4,3-a]pyridin-6-yl)-2,2,2-trifluoroethyl)pyrrolidin-3-amine dihydrochloride Prepared as described in Example 3, Steps A-B, using tert-butyl (R)-1-((R)-1-(3-(7-bromo quinolin-2-yl)-[1,2,4]triazolo[4,3-a]pyridin-6-yl)-2,2,2-trifluoroethyl)pyrrolidin-3-ylcarbamate in place of tert-butyl (3S)-1-(1-(3-(7-bromo quinolin-2-yl)-[1,2,4]triazolo[4,3-a]pyridin-6-yl)-2,2,2-trifluoroethyl)pyrrolidin-3-ylcarbamate in Step A. LCMS APCI (+) m/z 453 (M+H).

Example 62

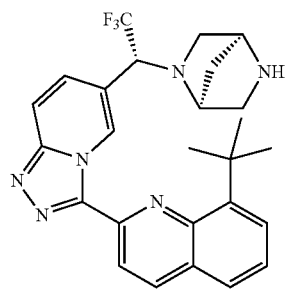

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)-8-tert-butylquinoline Prepared as described in Example 1, Steps A-F, using (1S,4S)-tert-butyl 2,5-diazabicyclo[2.2.1]heptane-2-carboxylate in place of (S)-tert-butyl pyrrolidin-3-ylmethylcarbamate in Step C, and using 8-tert-butylquinoline-2-carbaldehyde in place of 8-methoxyquinoline-2-carbaldehyde in Step E. MS APCI (+) m/z 481 (M+1) detected.

Example 63

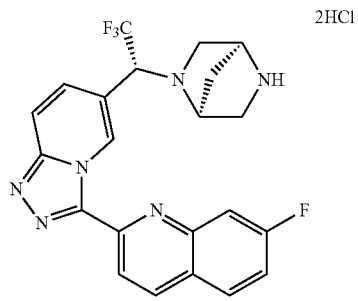 [SMILES: Fc1ccc2ccc(-c3nnc4ccc([C@@H](N5C[C@@H]6C[C@H]5CN6)C(F)(F)F)cn34)nc2c1]

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)-7-fluoro quinoline dihydrochloride Step B Prepared as described in Example 1, Steps A-F, using (1S, 4S)-tert-butyl 2,5-diazabicyclo[2.2.1]heptane-2-carboxylate in place of (S)-tert-butyl pyrrolidin-3-ylmethylcarbamate in Step C, and using 7-fluoroquinoline-2-carbaldehyde (prepared as described in Example 1, Steps A-E, using 3-fluoroaniline) in place of 8-methoxyquinoline-2-carbaldehyde in Step E. MS APCI (+) m/z 443 (M+1) detected.

Example 64

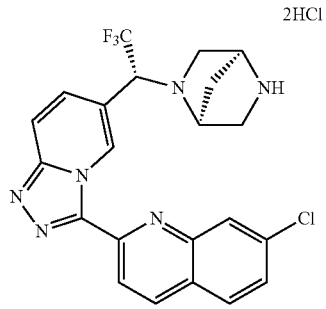 [SMILES: FC(F)(F)[C@@H](c1ccc2nnc(-c3ccc4ccc(Cl)cc4n3)n2c1)N1C[C@@H]2C[C@H]1CN2]

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)-7-chloro quinoline dihydrochloride Prepared as described in Example 1, Steps A-F, using (1S, 4S)-tert-butyl 2,5-diazabicyclo[2.2.1]heptane-2-carboxylate in place of (S)-tert-butyl pyrrolidin-3-ylmethylcarbamate in Step C, and using 7-chloroquinoline-2-carbaldehyde (prepared as described in Example 1, Steps A-E, using 3-chloroaniline)) in place of 8-methoxyquinoline-2-carbaldehyde in Step E. MS APCI (+) m/z 459 (M+1) detected.

Example 65

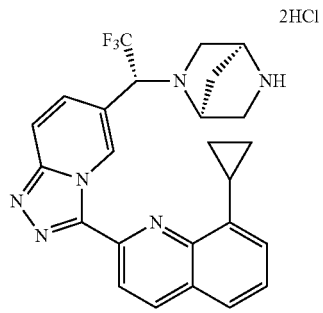 [SMILES: FC(F)(F)[C@@H](c1ccc2nnc(-c3ccc4cccc(C5CC5)c4n3)n2c1)N1C[C@@H]2C[C@H]1CN2]

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)-8-cyclopropylquinoline dihydrochloride Prepared as described in Example 1, Steps A-F, using (1S, 4S)-tert-butyl 2,5-diazabicyclo[2.2.1]heptane-2-carboxylate in place of (S)-tert-butyl pyrrolidin-3-ylmethylcarbamate in Step C, and using 8-cyclopropylquinoline-2-carbaldehyde in place of 8-methoxyquinoline-2-carbaldehyde in Step E. MS APCI (+) m/z 465 (M+1) detected.

Example 66

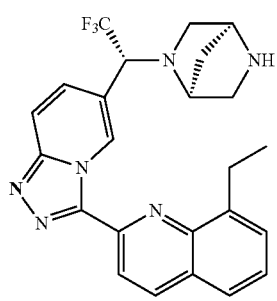

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)-8-ethylquinoline dihydrochloride Prepared as described in Example 1, Steps A-F, using (1S, 4S)-tert-butyl 2,5-diazabicyclo[2.2.1]heptane-2-carboxylate in place of (S)-tert-butyl pyrrolidin-3-ylmethylcarbamate in Step C, and using 8-ethylquinoline-2-carbaldehyde in place of 8-methoxyquinoline-2-carbaldehyde in Step E. MS APCI (+) m/z 453 (M+1) detected.

Example 67

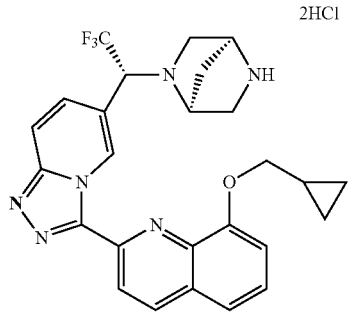 [SMILES: "2HCl" ; FC(F)(F)[C@@H](c1ccc2nnc(-c3ccc4cccc(OCC5CC5)c4n3)n2c1)N1C[C@@H]2C[C@H]1CN2]

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)-8-(cyclopropylmethoxy)quinoline dihydrochloride Prepared as described in Example 1, Steps A-F, using (1S, 4S)-tert-butyl 2,5-diazabicyclo[2.2.1]heptane-2-carboxylate in place of (S)-tert-butyl pyrrolidin-3-ylmethylcarbamate in Step C, and using 8-(cyclopropylmethoxy)quinoline-2-carbaldehyde in place of 8-methoxyquinoline-2-carbaldehyde in Step E. MS APCI (+) m/z 495 (M+1) detected.

Example 68

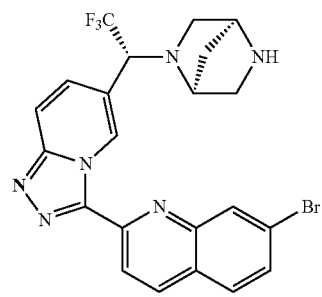

2-(6-((R)-1-(1S,4S)-2,5-diazabicyclo[2.2.1]heptan-2-yl)-2,2,2-trifluoroethyl)-[1,2,4]triazolo[4,3-a]pyridin-3-yl)-7-bromo quinoline dihydrochloride Prepared as described in Example 1, Steps A-F, using (1S, 4S)-tert-butyl 2,5-diazabicyclo[2.2.1]heptane-2-carboxylate in place of (S)-tert-butyl pyrrolidin-3-ylmethylcarbamate in Step C, and using 7-bromoquinoline-2-carbaldehyde (prepared as described in Example 1, Steps A-E, using 3-bromoaniline) in place of 8-methoxyquinoline-2-carbaldehyde in Step E. MS APCI (+) m/z 504 (M+1) detected.

Example 69

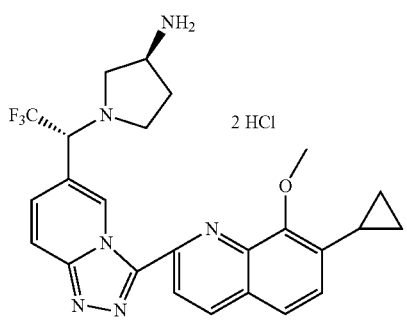 [SMILES: COc1c(C2CC2)ccc2ccc(-c3nnc4ccc([C@@H](N5CC[C@H](N)C5)C(F)(F)F)cn34)nc12 ; "2 HCl"]

(S)-1-((R)-1-(3-(7-cyclopropyl-8-methoxyquinolin-2-yl)-[1,2,4]triazolo[4,3-a]pyridin-6-yl)-2,2,2-trifluoroethyl)pyrrolidin-3-amine dihydrochloride

Step A: Preparation of 7-bromo-8-methoxy-2-methylquinoline

To a solution of 7-bromo-2-methylquinolin-8-ol (4.10 g, 14.64 mmol) and Cs$_2$CO$_3$ (11.92 g, 36.59 mmol) in NMP (20 mL) was added iodomethane (1.01 mL, 16.10 mmol) at 0° C. The reaction was warmed to ambient temperature and stirred at ambient temperature for 40 minutes. Water (30 mL) was and added and extracted with DCM (30 mL), dried (sodium sulfate), filtered and concentrated under reduced pressure. The residue was purified by flash chromatography on silica gel (DCM) to give 7-bromo-8-methoxy-2-methylquinoline (3.62 g, 91.23%) as an oil.

Step B: Preparation of 7-cyclopropyl-8-methoxy-2-methylquinoline

A solution of 7-bromo-8-methoxy-2-methylquinoline (1.00 g, 3.97 mmol), Pd(OAc)$_2$ (0.045 g, 0.198 mmol), P(Cy)$_3$ (0.122 g, 0.44 mmol) and cyclopropylboronic acid (0.68 g, 7.93 mmol) in toluene (4 mL) and water (0.4 mL) was stirred at 100° C. for 6 hours. After cooling to ambient temperature, ethyl acetate (20 mL) and water (5 mL) were added. The organic layer was separated, washed with brine, dried (sodium sulfate), filtered and concentrated under reduced pressure to give 7-cyclopropyl-8-methoxy-2-methylquinoline (0.84 g, 99%) as an oil.

Step C: Preparation of (S)-1-((R)-1-(3-(7-cyclopropyl-8-methoxyquinolin-2-yl)-[1,2,4]triazolo[4,3-a]pyridin-6-yl)-2,2,2-trifluoroethyl)pyrrolidin-3-amine dihydrochloride Prepared as described in Example 37, Steps A-C, using 7-cyclopropyl-8-methoxy-2-methylquinoline in place of 8-ethyl-2-methylquinoline in Step B. LCMS APCI (+) m/z 483 (M+H).

Example 70

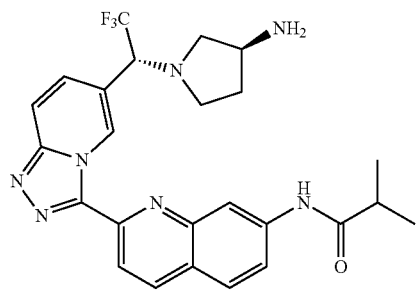 [SMILES: CC(C)C(=O)Nc1ccc2ccc(-c3nnc4ccc([C@@H](N5CC[C@H](N)C5)C(F)(F)F)cn34)nc2c1]

N-(2-(6-((R)-1-((S)-3-aminopyrrolidin-1-yl)-2,2,2-trifluoroethyl)-[1,2,4]triazolo[4,3-a]pyridin-3-yl)quinolin-7-yl)isobutyramide Prepared as described in Example 44, Steps B-C, substituting tert-butyl (S)-1-((R)-2,2,2-trifluoro-1-(6-hydrazinylpyridin-3-yl)ethyl)pyrrolidin-3-ylcarbamate (Example 9B, Steps A-E) for tert-butyl (3S)-1-(2,2,2-trifluoro-1-(6-hydrazinylpyridin-3-yl)ethyl)pyrrolidin-3-ylcarbamate in Step B. LCMS APCI (+) m/z 498.2 (M+H).

Example 71

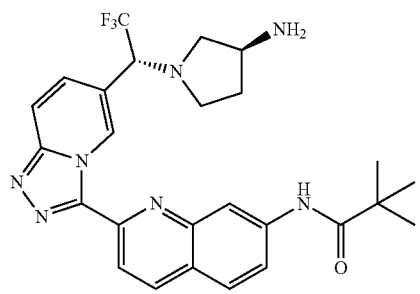 [SMILES: CC(C)(C)C(=O)Nc1ccc2ccc(-c3nnc4ccc([C@@H](N5CC[C@H](N)C5)C(F)(F)F)cn34)nc2c1]

N-(2-(6-((R)-1-((S)-3-aminopyrrolidin-1-yl)-2,2,2-trifluoroethyl)-[1,2,4]triazolo[4,3-a]pyridin-3-yl)quinolin-7-yl)pivalamide Prepared as described in Example 44, Steps B-C, substituting tert-butylamide for isopropylamide and tert-butyl (S)-1-((R)-2,2,2-trifluoro-1-(6-hydrazinylpyridin-3-yl)ethyl)pyrrolidin-3-ylcarbamate for (3S)-1-(2,2,2-trifluoro-1-(6-hydrazinylpyridin-3-yl)ethyl)pyrrolidin-3-ylcarbamate in Step B. LCMS APCI (+) m/z 512.2 (M+H).

Example 72

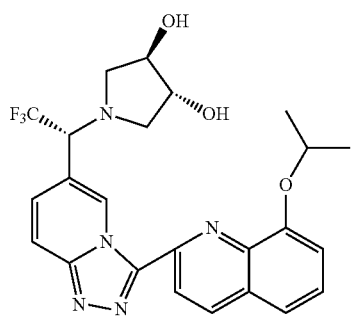 [SMILES: CC(C)Oc1cccc2ccc(-c3nnc4ccc([C@@H](N5C[C@@H](O)[C@H](O)C5)C(F)(F)F)cn34)nc12]

(3R,4R)-1-((R)-2,2,2-trifluoro-1-(3-(8-isopropoxyquinolin-2-yl)-[1,2,4]triazolo[4,3-a]pyridin-6-yl)ethyl)pyrrolidine-3,4-diol Prepared as described in Example 9B, Steps A-F, using (3R,4R)-pyrrolidine-3,4-diol in place of (S)-tert-butyl pyrrolidin-3-ylcarbamate in Step D, and using 8-isopropoxyquinoline-2-carbaldehyde in place of 8-methoxyquinoline-2-carbaldehyde in Step F. LCMS APCI (+) m/z 488 (M+H).

Example 73

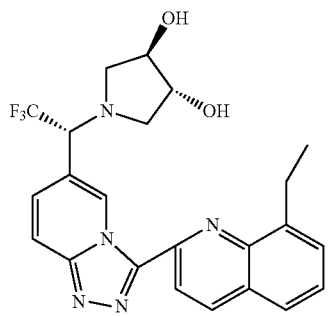 [SMILES: CCc1cccc2ccc(-c3nnc4ccc([C@@H](N5C[C@@H](O)[C@H](O)C5)C(F)(F)F)cn34)nc12]

(3R,4R)-1-((R)-1-(3-(8-ethylquinolin-2-yl)-[1,2,4]triazolo[4,3-a]pyridin-6-yl)-2,2,2-trifluoroethyl)pyrrolidine-3,4-diol Prepared as described in Example 9B, Steps A-F, using (3R,4R)-pyrrolidine-3,4-diol in place of (S)-tert-butyl pyrrolidin-3-ylcarbamate in Step D, and using 8-ethylquinoline-2- carbaldehyde in place of 8-methoxyquinoline-2-carbaldehyde in Step F. LCMS APCI (+) m/z 458 (M+H).

Example 74

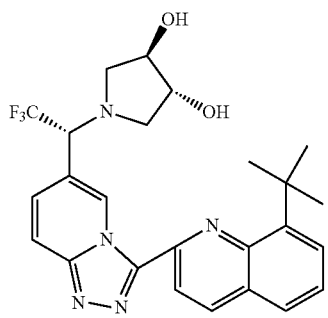 [SMILES: CC(C)(C)c1cccc2ccc(-c3nnc4ccc([C@@H](N5C[C@@H](O)[C@H](O)C5)C(F)(F)F)cn34)nc12]

(3R,4R)-1-((R)-1-(3-(8-tert-butylquinolin-2-yl)-[1,2,4]triazolo[4,3-a]pyridin-6-yl)-2,2,2-trifluoroethyl)pyrrolidine-3,4-diol Prepared as described in Example 9B, Steps A-F, using (3R,4R)-pyrrolidine-3,4-diol in place of (S)-tert-butyl pyrrolidin-3-ylcarbamate in Step D, and using 8-tert-butylquinoline-2-carbaldehydeldehyde in place of 8-methoxyquinoline-2-carbaldehyde in Step F. LCMS APCI (+) m/z 486 (M+H).

Example 75

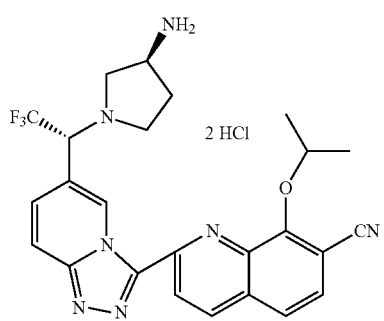 [SMILES: CC(C)Oc1c(C#N)ccc2ccc(-c3nnc4ccc([C@@H](N5CC[C@H](N)C5)C(F)(F)F)cn34)nc12 ; "2 HCl"]

2-(6-((R)-1-((S)-3-aminopyrrolidin-1-yl)-2,2,2-trifluoroethyl)-[1,2,4]triazolo[4,3-a]pyridin-3-yl)-8-isopropoxyquinoline-7-carbonitrile dihydrochloride

Step A: Preparation of 7-bromo-8-isopropoxy-2-methylquinoline

A solution of 7-bromo-2-methylquinolin-8-ol (1.00 g, 4.20 mmol), K$_2$CO$_3$ (1.74 g, 12.6 mmol), and 2-iodopropane (0.84 ml, 8.40 mmol) in acetone (20 mL) was stirred at 88° C. in a seal tube for 24 hours. After cooling to ambient temperature, ethyl acetate (50 mL) and water (30 mL) was added. The organic layer was separated, washed with brine, dried (sodium sulfate), filtered and concentrated under reduced pressure. The residue was purified by flash chromatography on silica gel (5:1 hexane/ethyl acetate) to give 7-bromo-8-isopropoxy-2-methylquinoline (1.13 g, 96.0%) as an oil.

Step B: Preparation of 8-isopropoxy-2-methylquinoline-7-carbonitrile

A solution of 7-bromo-8-isopropoxy-2-methylquinoline (1.13 g, 4.03 mmol), PdCl$_2$(dppf) dichloromethane adduct (0.165 g, 0.202 mmol), zinc (0.063 g, 0.97 mmol) and dicyanozinc (0.31 g, 2.62 mmol) in DMA (5 mL) was stirred at 100° C. for 18 hours. After cooling to ambient temperature, water (10 mL) and ethyl acetate (20 mL) were added. The organic layer was separated, washed with brine, dried (sodium sulfate), filtered and concentrated under reduced pressure. The residue was purified by flash chromatography on silica gel (DCM) to give 8-isopropoxy-2-methylquinoline-7-carbonitrile (0.83 g, 91.1%) as a solid.

Step C: Preparation of 2-(6-((R)-1-((S)-3-aminopyrrolidin-1-yl)-2,2,2-trifluoroethyl)-[1,2,4]triazolo[4,3-a]pyridin-3-yl)-8-isopropoxyquinoline-7-carbonitrile dihydrochloride Prepared as described in Example 37 using 8-isopropoxy-2-methylquinoline-7-carbonitrile in place of 8-ethyl-2-methylquinoline in Step B. LCMS APCI (+) m/z 496 (M+H).

Example 76

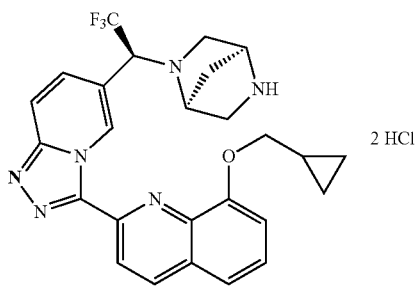 [SMILES: FC(F)(F)[C@H](c1ccc2nnc(-c3ccc4cccc(OCC5CC5)c4n3)n2c1)N1C[C@@H]2C[C@H]1CN2 ; "2 HCl"]

2-(6-((S)-1-((1S,4S)-2,5-diazabicyclo[2.2.1]heptan-2-yl)-2,2,2-trifluoroethyl)-[1,2,4]triazolo[4,3-a]pyridin-3-yl)-8-(cyclopropylmethoxy)quinoline dihydrochloride Prepared as described in Example 67, using (1S,4S)-tert-butyl 5-((S)-2,2,2-trifluoro-1-(6-hydrazinylpyridin-3-yl)ethyl)-2,5-diazabicyclo[2.2.1]heptane-2-carboxylate in place of (1S,4S)-tert-butyl 5-((R)-2,2,2-trifluoro-1-(6-hydrazinylpyridin-3-yl)ethyl)-2,5-diazabicyclo[2.2.1]heptane-2-carboxylate. LCMS APCI (+) m/z 495 (M+H).

Example 77

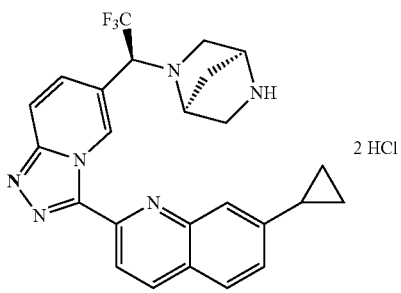 [SMILES: FC(F)(F)[C@H](c1ccc2nnc(-c3ccc4ccc(C5CC5)cc4n3)n2c1)N1C[C@@H]2C[C@H]1CN2 ; "2 HCl"]

2-(6-((S)-1-((1S,4S)-2,5-diazabicyclo[2.2.1]heptan-2-yl)-2,2,2-trifluoroethyl)-[1,2,4]triazolo[4,3-a]pyridin-3-yl)-7-cyclopropylquinoline dihydrochloride Step A: Preparation of (1S,4S)-tert-butyl 5-((S)-1-(3-(7-bromoquinolin-2-yl)-[1,2,4]triazolo[4,3-a]pyridin-6-yl)-2,2,2-trifluoroethyl)-2,5-diazabicyclo[2.2.1]heptane-2-carboxylate Prepared according to the method of Example 68 substituting (1S,4S)-tert-butyl-5-((S)-2,2,2-trifluoro-1-(6-hydrazinylpyridin-3-yl)ethyl)-2,5-diazabicyclo[2.2.1]heptane-2-carboxylate for (1S,4S)-tert-butyl-5-((R)-2,2,2-trifluoro-1-(6-hydrazinylpyridin-3-yl)ethyl)-2,5-diazabicyclo[2.2.1]heptane-2-carboxylate.

Step B: Preparation of 2-(6-((S)-1-((1S,4S)-2,5-diazabicyclo[2.2.1]heptan-2-yl)-2,2,2-trifluoroethyl)-[1,2,4]triazolo[4,3-a]pyridin-3-yl)-7-cyclopropylquinoline dihydrochloride Prepared according to the method of Example 3 substituting (1S,4S)-tert-butyl 5-((S)-1-(3-(7-bromo quinolin-2-yl)-[1,2,4]triazolo[4,3-a]pyridin-6-yl)-2,2,2-trifluoroethyl)-2,5-diazabicyclo[2.2.1]heptane-2-carboxylate for tert-butyl (3S)-1-(1-(3-(7-bromoquinolin-2-yl)-[1,2,4]triazolo[4,3-a]pyridin-6-yl)-2,2,2-trifluoroethyl)pyrrolidin-3-ylcarbamate. LCMS APCI (+) m/z 465 (M+H).

Example 78

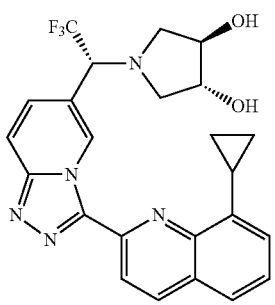 [SMILES: O[C@@H]1CN([C@H](c2ccc3nnc(-c4ccc5cccc(C6CC6)c5n4)n3c2)C(F)(F)F)C[C@H]1O]

(3R,4R)-1-((R)-1-(3-(8-cyclopropylquinolin-2-yl)-[1,2,4]triazolo[4,3-a]pyridin-6-yl)-2,2,2-trifluoroethyl)pyrrolidine-3,4-diol Prepared as described in Example 9B, Steps A-F, using (3R,4R)-pyrrolidine-3,4-diol in place of (S)-tert-butyl pyrrolidin-3-ylcarbamate in Step D, and substituting 8-cyclopropylquinoline-2-carbaldehyde in place of 8-methoxyquinoline-2-carbaldehyde in Step F. LCMS APCI (+) m/z 470 (M+H).

Example 79

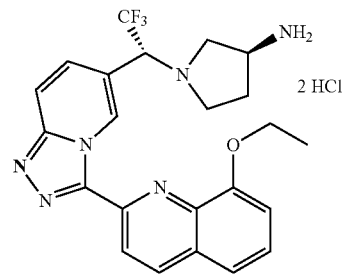 [SMILES: CCOc1cccc2ccc(-c3nnc4ccc([C@@H](N5CC[C@H](N)C5)C(F)(F)F)cn34)nc12 ; "2 HCl"]

(S)-1-((R)-1-(3-(8-ethoxyquinolin-2-yl)-[1,2,4]triazolo[4,3-a]pyridin-6-yl)-2,2,2-trifluoroethyl)pyrrolidin-3-amine Prepared as described in Example 31 using iodoethane in place of 2-iodopropane in Step A. LCMS APCI (+) m/z 457 (M+H).

Example 80

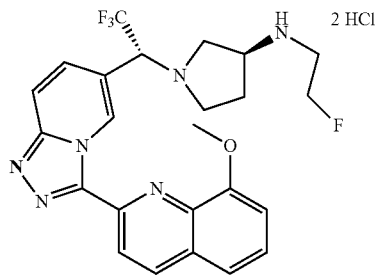 [SMILES: COc1cccc2ccc(-c3nnc4ccc([C@@H](N5CC[C@H](NCCF)C5)C(F)(F)F)cn34)nc12 ; "2 HCl"]

(S)—N-(2-fluoroethyl)-1-((R)-2,2,2-trifluoro-1-(3-(8-methoxyquinolin-2-yl)-[1,2,4]triazolo[4,3-a]pyridin-6-yl)ethyl)pyrrolidin-3-amine dihydrochloride Step A: Preparation of (S)-benzyl 3-(tert-butoxycarbonyl(2-fluoroethylamino)pyrrolidine-1-carboxylate To a solution of (S)-benzyl 3-(tert-butoxycarbonylamino)pyrrolidine-1-carboxylate (2.3 g, 7.1 mmol) and 1-fluoro-2-bromoethane in anhydrous DMF (15 mL) was added a 60% dispersion of sodium hydride in mineral oil (0.43 g, 10.7 mmol). The mixture was stirred at 50° C. for 18 hours under nitrogen atmosphere. The reaction mixture was partitioned between water (50 mL) and ethyl acetate (100 mL). The organic layer was separated and washed with brine, dried (MgSO₄), filtered and concentrated under reduced pressure. The residue was purified by column chromatography (Biotage, 40M; 10-20% ethyl acetate/hexane gradient) to afford (S)-benzyl 3-(tert-butoxycarbonyl(2-fluoroethylamino)pyrrolidine-1-carboxylate (1.77 g, 35%).

Step B: Preparation of tert-butyl (S)-1-((R)-1-(6-chloropyridin-3-yl)-2,2,2-trifluoroethyl)pyrrolidin-3-yl(2-fluoroethyl)carbamate To a suspension of 5% Pd/C (1.4 g, 2.2 mmol) in ethanol (12 mL) was added slowly a solution of (S)-benzyl 3-(tert-butoxycarbonyl(2-fluoroethyl)amino)pyrrolidine-1-carboxylate (2.44 g, 21.6 mmol) in methanol (5 mL). The mixture was evacuated and backfilled with nitrogen and then evacuated and backfilled with hydrogen, then stirred under a hydrogen atmosphere for 2 hours. The suspension was filtered through a pad of Celite and washed with a methanol (50 ml). The filtrate was concentrated under reduced pressure to afford (S)-tert-butyl 2-fluoroethyl(pyrrolidin-3-yl)carbamate. To a solution of (S)-1-(6-chloropyridin-3-yl)-2,2,2-trifluoroethyl trifluoromethanesulfonate (0.97 g, 2.82 mmol) in anhydrous THF (5 mL) was added (S)-tert-butyl 2-fluoroethyl(pyrrolidin-3-yl)carbamate (0.92 g, 3.95 mmol) and K₂CO₃ (0.59 g, 4.23 mmol). The resulting mixture was heated with stirring at 50° C. for 18 hours. After cooling to ambient temperature the mixture was partitioned between water (12 mL) and ethyl acetate (30 mL). The organic layer was separated, washed with brine, dried (MgSO₄), filtered and concentrated under reduced pressure and the residue obtained purified by column chromatography (Biotage 25M; 10% ethyl acetate:hexanes) to afford tert-butyl (S)-1-((R)-1-(6-chloropyridin-3-yl)-2,2,2-trifluoroethyl)pyrrolidin-3-yl(2-fluoroethyl)carbamate (0.58 g, 48%).

Step C: Preparation of tert-butyl 2-fluoroethyl((S)-1-((R)-2,2,2-trifluoro-1-(6-hydrazinylpyridin-3-yl)ethyl)pyrrolidin-3-yl)carbamate Prepared as described in Example 9B, Step E, substituting tert-butyl (S)-1-((R)-1-(6-chloropyridin-3-yl)-2,2,2-trifluoroethyl)pyrrolidin-3-yl(2-fluoroethyl)carbamate (0.58 g, 1.36 mmol) to afford tert-butyl 2-fluoroethyl((S)-1-((R)-2,2,2-trifluoro-1-(6-hydrazinylpyridin-3-yl)ethyl)pyrrolidin-3-yl)carbamate (0.523 g, 92%).

Step D: Preparation of tert-butyl 2-fluoroethyl((S)-1-((R)-2,2,2-trifluoro-1-(3-(8-methoxyquinolin-2-yl)-[1,2,4]triazolo[4,3-a]pyridin-6-yl)ethyl)pyrrolidin-3-yl)carbamate Prepared as described in Example 9B, Step F, using tert-butyl 2-fluoroethyl((S)-1-((R)-2,2,2-trifluoro-1-(6-hydrazinylpyridin-3-yl)ethyl)pyrrolidin-3-yl)carbamate (0.10 g, 0.237 mmol) in place of tert-butyl (S)-1-((R)-2,2,2-trifluoro-1-(6-hydrazinylpyridin-3-yl)ethyl)pyrrolidin-3-yl)carbamate and 8-methoxyquinoline-2-carbaldehyde (0.044 g, 0.237 mmol). LCMS APCI (+) m/z 589 (M+H).

Step E: Preparation of (S)—N-(2-fluoroethyl)-1-((R)-2,2,2-trifluoro-1-(3-(8-methoxyquinolin-2-yl)-[1,2,4]triazolo[4,3-a]pyridin-6-yl)ethyl)pyrrolidin-3-amine dihydrochloride Prepared as described in Example 9B, Step G, substituting tert-butyl 2-fluoroethyl((S)-1-((R)-2,2,2-trifluoro-1-(3-(8-methoxyquinolin-2-yl)-[1,2,4]triazolo[4,3-c]pyridin-6-yl)ethyl)pyrrolidin-3-yl)carbamate. LCMS APCI (+) m/z 489 (M+H).

Example 81

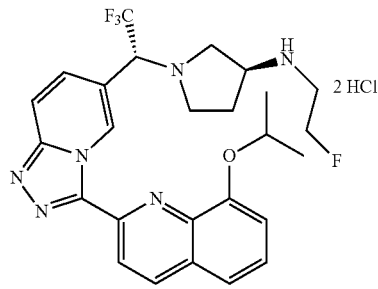 [SMILES: CC(C)Oc1cccc2ccc(-c3nnc4ccc([C@@H](N5CC[C@H](NCCF)C5)C(F)(F)F)cn34)nc12]

(S)—N-(2-fluoroethyl)-1-((R)-2,2,2-trifluoro-1-(3-(8-isopropoxyquinolin-2-yl)-[1,2,4]triazolo[4,3-a]pyridin-6-yl)ethyl)pyrrolidin-3-amine dihydrochloride Step A: Preparation of tert-butyl 2-fluoroethyl((S)-1-((R)-2,2,2-trifluoro-1-(3-(8-isopropoxyquinolin-2-yl)-[1,2,4]triazolo[4,3-a]pyridin-6-yl)ethyl)pyrrolidin-3-yl)carbamate Prepared as described in Example 9B, Step F, using tert-butyl 2-fluoroethyl((S)-1-((R)-2,2,2-trifluoro-1-(6-hydrazinylpyridin-3-yl)ethyl)pyrrolidin-3-yl)carbamate (0.10 g, 0.237 mmol) in place of tert-butyl (S)-1-((R)-2,2,2-trifluoro-1-(6-hydrazinylpyridin-3-yl)ethyl)pyrrolidin-3-yl)carbamate and using 8-isopropoxyquinoline-2-carbaldehyde (0.051 g, 0.237 mmol) in place of 8-methoxyquinoline-2-carbaldehyde. LCMS APCI (+) m/z 617 (M+H).

Step B: Preparation of (S)—N-(2-fluoroethyl)-1-((R)-2,2,2-trifluoro-1-(3-(8-isopropoxyquinolin-2-yl)-[1,2,4]triazolo[4,3-a]pyridin-6-yl)ethyl)pyrrolidin-3-amine dihydrochloride Prepared as described in Example 9B, Step G, substituting tert-butyl 2-fluoroethyl((S)-1-((R)-2,2,2-trifluoro-1-(3-(8-isopropoxyquinolin-2-yl)-[1,2,4]triazolo[4,3-c]pyridin-6-yl)ethyl)pyrrolidin-3-yl)carbamate in Step G. LCMS APCI (+) m/z 517 (M+H).

Example 82

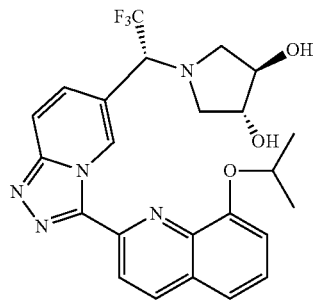 [SMILES: CC(C)Oc1cccc2ccc(-c3nnc4ccc([C@@H](N5C[C@@H](O)[C@H](O)C5)C(F)(F)F)cn34)nc12]

(3R,4R)-1-((S)-2,2,2-trifluoro-1-(3-(8-isopropoxyquinolin-2-yl)-[1,2,4]triazolo[4,3-a]pyridin-6-yl)ethyl)pyrrolidine-3,4-diol Prepared as described in Example 9B, Steps A-F, using (3R,4R)-pyrrolidine-3,4-diol in place of (S)-tert-butylpyrrolidin-3-ylcarbamate in Step D and using 8-isopropoxyquinoline-2-carbaldehyde in place of 8-methoxyquinoline-2-carbaldehyde in Step F. LCMS APCI (+) m/z 488 (M+H).

Example 83

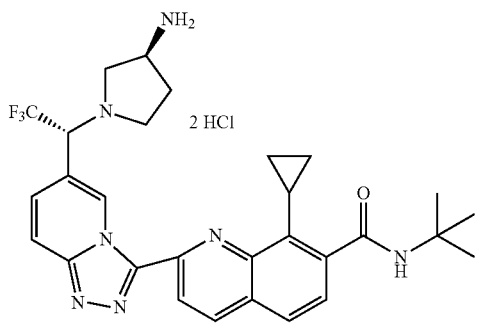 [SMILES: CC(C)(C)NC(=O)c1ccc2ccc(-c3nnc4ccc([C@@H](N5CC[C@H](N)C5)C(F)(F)F)cn34)nc2c1C1CC1]

2-(6-((R)-1-((S)-3-aminopyrrolidin-1-yl)-2,2,2-trifluoroethyl)-[1,2,4]triazolo[4,3-a]pyridin-3-yl)-N-tert-butyl-8-cyclopropylquinoline-7-carboxamide dihydrochloride

Step A: Preparation of 2-cyclopropyl-3-nitrobenzoic acid

A solution of 2-bromo-3-nitrobenzoic acid (1.17 g, 4.28 mmol), Pd(OAc)$_2$ (0.048 g, 0.21 mmol), P(Cy)$_3$ (0.132 g, 0.471 mmol), K$_3$PO$_4$ (3.18 g, 15.0 mmol) and cyclopropylboronic acid (0.735 g, 8.56 mmol) in toluene (4 mL) and water (1 mL) was stirred at 100° C. for 6 hours. After cooling to ambient temperature, ethyl acetate (20 mL) and water (5 mL) were added. The aqueous layer was separated and acidified with saturated potassium hydrogen sulfate to about pH 3-4. The resulting solid was collected by filtration to give 2-cyclopropyl-3-nitrobenzoic acid (0.63 g, 71.0%) as a solid.

Step B: Preparation of 3-amino-2-cyclopropylbenzoic acid

A solution of 2-cyclopropyl-3-nitrobenzoic acid (0.63 g, 3.04 mmol) and 5% Pt/C (0.59 g, 0.152 mmol) in methanol (10 mL) was charged with 40 psi of hydrogen and shaken for 3 hours. The catalyst was removed by filtration and washed with methanol (10 mL). The filtrate was concentrated under reduced pressure to give 3-amino-2-cyclopropylbenzoic acid (0.51 g, 94.1%) as a solid.

Step C: Preparation of 8-cyclopropyl-2-methylquinoline-7-carboxylic acid

A solution of 3-amino-2-cyclopropylbenzoic acid (0.507 g, 2.86 mmol) in 6 N HCl (8 mL) was added (E)-but-2-enal (0.47 mL, 5.72 mmol) dropwise at reflux. The reaction mixture was stirred at reflux for 2 hours. After cooling to ambient temperature, the reaction mixture was basified with sodium hydroxide to about pH 12 and DCM (20 mL) was added. The aqueous layer was separated and acidified with saturated potassium hydrogen sulfate to about pH 3-4. The aqueous layer was then extracted with 3:1 CHCl$_3$/IPA (2×30 mL), dried (sodium sulfate), filtered and concentrated under reduced pressure to give 8-cyclopropyl-2-methylquinoline-7-carboxylic acid (0.18 g, 27.7%) as a solid.

Step D: Preparation of N-tert-butyl-8-cyclopropyl-2-methylquinoline-7-carboxamide To a solution of 8-cyclopropyl-2-methylquinoline-7-carboxylic acid (0.050 g, 0.220 mmol) and 2-methylpropan-2-amine (0.116 mL, 1.10 mmol) in DMF (1 mL) was added HATU (0.125 g, 0.33 mmol) at ambient temperature and the reaction mixture was stirred at ambient temperature for 1 hour. The reaction mixture was purified directly by C-18 reverse phase flash chromatography (Biotage SP4 unit, C-18 25M column, 0-90% CH$_3$CN/water gradient; 25 column volumes) to give N-tert-butyl-8-cyclopropyl-2-methylquinoline-7-carboxamide (0.033 g, 53.1%) as a solid.

Step E: Preparation of 2-(6-((R)-1-((S)-3-aminopyrrolidin-1-yl)-2,2,2-trifluoroethyl)-[1,2,4]triazolo[4,3-a]pyridin-3-yl)-N-tert-butyl-8-cyclopropylquinoline-7-carboxamide dihydrochloride Prepared as described in Example 37 using N-tert-butyl-8-cyclopropyl-2-methylquinoline-7-carboxamide in place of 8-ethyl-2-methylquinoline in Step B. LCMS APCI (+) m/z 552 (M+H).

Example 84

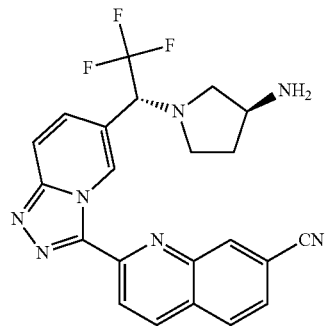 [SMILES: N#Cc1ccc2ccc(-c3nnc4ccc([C@@H](N5CC[C@H](N)C5)C(F)(F)F)cn34)nc2c1]

2-(6-((R)-1-((S)-3-aminopyrrolidin-1-yl)-2,2,2-trifluoroethyl)-[1,2,4]triazolo[4,3-a]pyridin-3-yl)quinoline-7-carbonitrile Prepared as described in Example 31, Steps A-B, substituting 7-cyanoquinoline-2-carbaldehyde for 8-methoxy-2-carbaldehyde in Step B. LCMS APCI (−) m/z 436 (M1−H).

Example 85

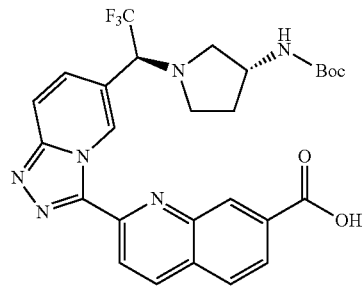 [SMILES: CC(C)(C)OC(=O)N[C@@H]1CCN([C@@H](c2ccc3nnc(-c4ccc5ccc(C(=O)O)cc5n4)n3c2)C(F)(F)F)C1]

2-(6-((S)-1-((R)-3-(tert-butoxycarbonylamino)pyrrolidin-1-yl)-2,2,2-trifluoroethyl)-[1,2,4]triazolo[4,3-a]pyridin-3-yl)quinoline-7-carboxylic acid Prepared as described in Example 30, substituting tert-butyl (R)-1-((S)-2,2,2-trifluoro-1-(6-hydrazinylpyridin-3-yl)ethyl)pyrrolidin-3-ylcarbamate for tert-butyl (3S)-1-(2,2,2-trifluoro-1-(6-hydrazinylpyridin-3-yl)ethyl)pyrrolidin-3-ylcarbamate. LC MS APCI (−) m/z 555 (M1−H).

Example 86

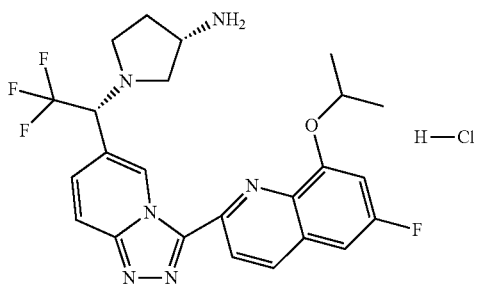

(S)-1-((R)-2,2,2-trifluoro-1-(3-(6-fluoro-8-isopropoxyquinolin-2-yl)-[1,2,4]triazolo[4,3-a]pyridin-6-yl)ethyl)pyrrolidin-3-amine hydrochloride Step A: Preparation of
6-fluoro-2-methylquinolin-8-ol To 2-amino-5-fluorophenol (5.0 g, 39 mmol) in refluxing 6N HCl (50 mL) was added dropwise over 10 minutes (E)-but-2-enal (5.5 g, 79 mmol). The reaction was heated to reflux for 3 hours then cooled down and neutralized (pH=7-8) by addition of NH₄OH. The aqueous phase was extracted with DCM. The combined organic phases were dried over MgSO₄, filtered and concentrated to yield 6-fluoro-2-methylquinolin-8-ol (5.7 g, 82% yield) as a dark oil which solidified upon standing.

Step B: Preparation of
6-fluoro-8-isopropoxy-2-methylquinoline

To 6-fluoro-2-methylquinolin-8-ol (1.0 g, 5.6 mmol) in acetone (20 mL) were added 2-iodopropane (1.9 g, 11 mmol) and K₂CO₃ (2.3 g, 17 mmol). The reaction was heated to 70° C. for 20 hours in a sealed tube and then cooled. Water was added and the aqueous phase was extracted with DCM. The combined organic phases were washed with brine, dried with MgSO₄, filtered and concentrated under reduced pressure to yield 6-fluoro-8-isopropoxy-2-methylquinoline (1.1 g, 89% yield) as a dark oil.

Step C: Preparation of
6-fluoro-8-isopropoxyquinoline-2-carbaldehyde

To 6-fluoro-8-isopropoxy-2-methylquinoline (1.1 g, 5.02 mmol) in dioxane/water (3.5 ml/0.3 mL) at ambient temperature was added selenium dioxide (0.668 g, 6.02 mmol) and the reaction was heated to reflux for 2-3 hours. After cooling, the reaction was filtered and the solids were washed with DCM. The filtrate was dried over MgSO₄, filtered and concentrated under reduced pressure. The crude material was purified by reverse phase chromatography (SP4, 25M, eluting with a gradient of water/ACN 100:0 to 0:100, 20 column volumes) to yield 6-fluoro-8-isopropoxyquinoline-2-carbaldehyde (410 mg, 35.0% yield) as a tan solid.

Step D: Preparation of tert-butyl (S)-1-((R)-2,2,2-trifluoro-1-(6-((E)-2-((6-fluoro-8-isopropoxyquinolin-2-yl)methylene)hydrazinyl)pyridin-3-yl)ethyl)pyrrolidin-3-ylcarbamate tert-Butyl (S)-1-((R)-2,2,2-trifluoro-1-(6-hydrazinylpyridin-3-yl)ethyl)pyrrolidin-3-ylcarbamate (100 mg, 0.266 mmol) and 6-fluoro-8-isopropoxyquinoline-2-carbaldehyde (62.1 mg, 0.266 mmol) were stirred in ethanol (5 mL) for 72 hours at ambient temperature. The reaction was concentrated under reduced pressure to yield tert-butyl (S)-1-((R)-2,2,2-trifluoro-1-(6-((E)-2-((6-fluoro-8-isopropoxyquinolin-2-yl)methylene)hydrazinyl)pyridin-3-yl)ethyl)pyrrolidin-3-ylcarbamate (157 mg, 99.8% yield) as a yellow paste.

Step E: Preparation of tert-butyl (S)-1-((R)-2,2,2-trifluoro-1-(3-(6-fluoro-8-isopropoxyquinolin-2-yl)-[1,2,4]triazolo[4,3-a]pyridin-6-yl)ethyl)pyrrolidin-3-ylcarbamate To tert-butyl (S)-1-((R)-2,2,2-trifluoro-1-(6-((E)-2-((6-fluoro-8-isopropoxyquinolin-2-yl)methylene)hydrazinyl)pyridin-3-yl)ethyl)pyrrolidin-3-ylcarbamate (157 mg, 0.266 mmol) in DCM (10 mL) was added iodosobenzene diacetate (94.2 mg, 0.292 mmol) and the reaction was stirred at ambient temperature for 2 hours. The reaction was concentrated to dryness and the residue purified by reverse phase chromatography (SP4, 12M, eluting with a gradient of water/ACN 100:0 to 0:100, 20 column volumes) to yield tert-butyl (S)-1-((R)-2,2,2-trifluoro-1-(3-(6-fluoro-8-isopropoxyquinolin-2-yl)-[1,2,4]triazolo[4,3-a]pyridin-6-yl)ethyl)pyrrolidin-3-ylcarbamate (124 mg, 79.3% yield) as a beige solid.

Step F: (S)-1-((R)-2,2,2-trifluoro-1-(3-(6-fluoro-8-isopropoxyquinolin-2-yl)-[1,2,4]triazolo[4,3-a]pyridin-6-yl)ethyl)pyrrolidin-3-amine hydrochloride To tert-butyl (S)-1-((R)-2,2,2-trifluoro-1-(3-(6-fluoro-8-isopropoxyquinolin-2-yl)-[1,2,4]triazolo[4,3-a]pyridin-6-yl)ethyl)pyrrolidin-3-ylcarbamate (120 mg, 0.204 mmol) was added TFA (2 mL) and the reaction was stirred for 30 minutes. After concentrating to dryness, the residue was dissolved in methanol and added to 2N HCl in ether. The resulting solid was filtered and dried under high vacuum to yield (S)-1-((R)-2,2,2-trifluoro-1-(3-(6-fluoro-8-isopropoxyquinolin-2-yl)-[1,2,4]triazolo[4,3-a]pyridin-6-yl)ethyl)pyrrolidin-3-amine (105 mg, 105% yield) hydrochloride as a beige solid. LCMS APCI (+) m/z 489 (M+H). Specific rotation: $[\alpha]^{26}_D = +1.43°$ (c=0.93, MeOH).

Example 87

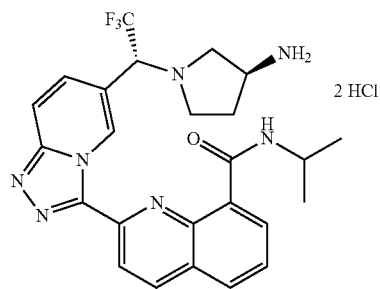 [SMILES: CC(C)NC(=O)c1cccc2ccc(-c3nnc4ccc([C@@H](N5CC[C@H](N)C5)C(F)(F)F)cn34)nc12]

2-(6-((R)-1-((S)-3-aminopyrrolidin-1-yl)-2,2,2-trifluoroethyl)-[1,2,4]triazolo[4,3-a]pyridin-3-yl)-N-isopropylquinoline-8-carboxamide dihydrochloride Prepared as described in Example 83, Steps C-E, using 2-aminobenzoic acid in place of 3-amino-2-cyclopropylbenzoic acid in Step C, and substituting propan-2-amine for 2-methylpropan-2-amine in Step D. LCMS APCI (+) m/z 498 (M+H).

Example 88

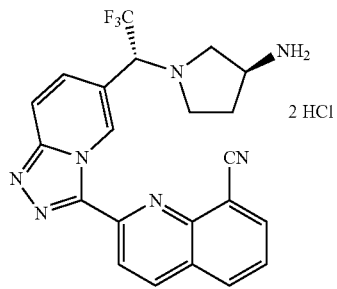 [SMILES: N#Cc1cccc2ccc(-c3nnc4ccc([C@@H](N5CC[C@H](N)C5)C(F)(F)F)cn34)nc12]

2-(6-((R)-1-((S)-3-aminopyrrolidin-1-yl)-2,2,2-trifluoroethyl)-[1,2,4]triazolo[4,3-a]pyridin-3-yl)quinoline-8-carbonitrile dihydrochloride

Step A: Preparation of 2-methylquinolin-8-yl trifluoromethanesulfonate

A solution of 2-methylquinolin-8-ol (10.0 g, 62.8 mmol) and 2,6-lutidine (10.2 mL, 88 mmol) in anhydrous dichloromethane (200 mL) was cooled to −20° C. and treated with trifluoromethanesulfonic anhydride (12.7 mL, 75.4 mmol). The resulting mixture was stirred at −20° C. for 1 hour then quenched by addition of water (50 mL). The organic layers were separated and washed with brine, dried (MgSO$_4$), filtered and concentrated under reduced pressure. The residue was purified by column chromatography (Biotage, 40 M; 5% ethyl acetate/hexane) to afford 2-methylquinolin-8-yl trifluoromethanesulfonate (18 g, 98%).

Step B: Preparation of 2-methylquinoline-8-carbonitrile

To a solution of 2-methylquinolin-8-yl trifluoromethanesulfonate (3.0 g, 10.3 mmol) in acetonitrile (26 mL) was added sodium cyanide (1.0 g, 20.6 mmol). The solution was degassed under nitrogen for 10 minutes, followed by addition of copper (I) iodide (0.20 g, 1.03 mmol) and Pd(PPh$_3$)$_4$ (0.60 g, 0.52 mmol) under nitrogen. The mixture was heated at reflux for 2 hours. After cooling the mixture was diluted with ethyl acetate (50 mL) and filtered through Celite and washed with ethyl acetate (50 mL). The filtrate was washed with water and brine, dried (MgSO$_4$), filtered and concentrated under reduced pressure. The residue was purified by column chromatography (Biotage, 40 M; 20% ethyl acetate:hexanes) to afford 2-methylquinoline-8-carbonitrile (1.70 g, 98%).

Step C: Preparation of 2-formylquinoline-8-carbonitrile

To a solution of 2-methylquinoline-8-carbonitrile (1.70 g, 10.1 mmol) in 1,4-dioxane (50 mL) and water (1 mL), was added selenium dioxide (2.80 g, 25.3 mmol) and the resulting mixture heated at reflux for 7 hours. After cooling to ambient temperature, the solids formed were removed by filtration through a pad of Celite® and washed with 1:1 mixture of ethyl acetate/dichloromethane (50 mL). The filtrate was concentrated under reduced pressure and the residue obtained purified by column chromatography (Biotage, 40M; 1% MeOH: dichloromethane) to give 2-formylquinoline-8-carbonitrile (1.51 g, 82%).

Step D: Preparation of 2-(6-((R)-1-((S)-3-aminopyrrolidin-1-yl)-2,2,2-trifluoroethyl)-[1,2,4]triazolo[4,3-a]pyridin-3-yl)quinoline-8-carbonitrile dihydrochloride Prepared as described in Example 9B, Steps F and G, using tert-butyl (S)-1-((R)-2,2,2-trifluoro-1-(6-hydrazinylpyridin- 3-yl)ethyl)pyrrolidin-3-ylcarbamate and 2-formylquinoline-8-carbonitrile in Step F. LCMS APCI (+) m/z 438 (M+H).

Example 89

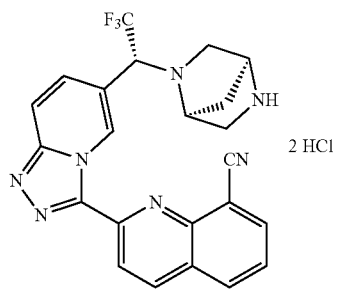 [SMILES: N#Cc1cccc2ccc(-c3nnc4ccc([C@@H](N5C[C@@H]6C[C@H]5CN6)C(F)(F)F)cn34)nc12]

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)quinoline-8-carbonitrile dihydrochloride Prepared as described in Example 9B, Steps A-G, using (1S,4S)-tert-butyl 5-((R)-2,2,2-trifluoro-1-(6-hydrazinylpyridin-3-yl)ethyl)-2,5-di azabicyclo[2.2.1]heptane-2-carboxylate in place of tert-butyl (S)-1-((R)-2,2,2-trifluoro-1-(6-hydrazinylpyridin-3-yl)ethyl)pyrrolidine-3-ylcarbamate and using 2-formylquinoline-8-carbonitrile in place of 8-methoxyquiniline-2-carbaldehyde in Step F. LCMS APCI (+) m/z 450 (M+H).

Example 90

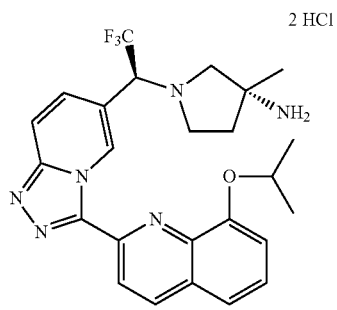 [SMILES: CC(C)Oc1cccc2ccc(-c3nnc4ccc([C@H](N5CC[C@@](C)(N)C5)C(F)(F)F)cn34)nc12]

(R)-3-methyl-1-((S)-2,2,2-trifluoro-1-(3-(8-isopropoxyquinolin-2-yl)-[1,2,4]triazolo[4,3-a]pyridin-6-yl)ethyl)pyrrolidin-3-amine dihydrochloride Prepared as described in Example 8 using (R)-tert-butyl 3-methylpyrrolidin-3-ylcarbamate (Preparation A) in place of (S)-tert-butyl pyrrolidin-3-ylmethylcarbamate, and substituting 8-isopropoxyquinoline-2-carbaldehyde for 8-methoxyquinoline-2-carbaldehyde. MS APCI (+) m/z 485 (M+1) detected.

Example 91

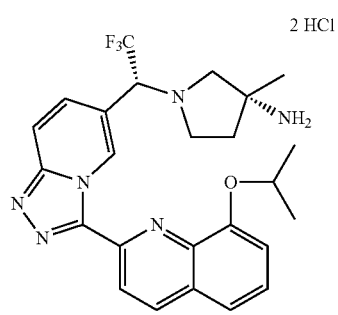 [SMILES: CC(C)Oc1cccc2ccc(-c3nnc4ccc([C@@H](N5CC[C@@](C)(N)C5)C(F)(F)F)cn34)nc12]

(R)-3-methyl-1-((R)-2,2,2-trifluoro-1-(3-(8-isopropoxyquinolin-2-yl)-[1,2,4]triazolo[4,3-a]pyridin-6-yl)ethyl)pyrrolidin-3-amine dihydrochloride Prepared as described in Example 1 using (R)-tert-butyl 3-methylpyrrolidin-3-ylcarbamate (Preparation A) in place of (S)-tert-butyl pyrrolidin-3-ylmethylcarbamate, and substituting 8-isopropoxyquinoline-2-carbaldehyde for 8-methoxyquinoline-2-carbaldehyde. MS APCI (+) m/z 485 (M+1) detected.

Example 92

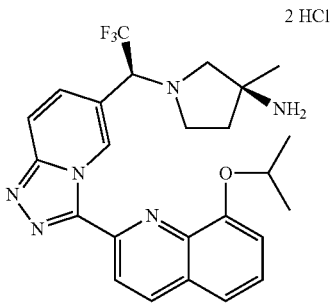 [SMILES: CC(C)Oc1cccc2ccc(-c3nnc4ccc([C@H](N5CC[C@](C)(N)C5)C(F)(F)F)cn34)nc12]

(S)-3-methyl-1-((S)-2,2,2-trifluoro-1-(3-(8-isopropoxyquinolin-2-yl)-[1,2,4]triazolo[4,3-a]pyridin-6-yl)ethyl)pyrrolidin-3-amine dihydrochloride Step A: Preparation of tert-butyl (S)-1-((S)-1-(6-chloropyridin-3-yl)-2,2,2-trifluoroethyl)-3-methylpyrrolidin-3-ylcarbamate Prepared as described in Example 1, Step C using (S)-tert-butyl 3-methylpyrrolidin-3-ylcarbamate (Preparation A) in place of (S)-tert-butyl pyrrolidin-3-ylcarbamate.

Step B: Preparation of tert-butyl (S)-3-methyl-1-(S)-2,2,2-trifluoro-1-(6-hydrazinylpyridin-3-yl)ethyl)pyrrolidin-3-ylcarbamate Prepared as described in Example 1, Step D using tert-butyl (S)-1-((S)-1-(6-chloropyridin-3-yl)-2,2,2-trifluoroethyl)-3-methylpyrrolidin-3-ylcarbamate in place of tert-butyl (3S)-1-(1-(6-chloropyridin-3-yl)-2,2,2-trifluoroethyl)pyrrolidin-3-ylcarbamate

Step C: Preparation of tert-butyl (S)-3-methyl-1-(S)-2,2,2-trifluoro-1-(6-((E)-2-((8-isopropoxyquinolin-2-yl)methylene)hydrazinyl)pyridin-3-yl)ethyl)pyrrolidin-3-ylcarbamate To a solution of tert-butyl (S)-3-methyl-1-((S)-2,2,2-trifluoro-1-(6-hydrazinylpyridin-3-yl)ethyl)pyrrolidin-3-ylcarbamate (1.30 g, 3.34 mmol) in Ethanol (25 mL) was added 8-isopropoxyquinoline-2-carbaldehyde (0.719 g, 3.34 mmol) and stirred at ambient temperature overnight. The reaction was concentrated and the residue purified by chromatography (C18, 300 g, 10% MeCN/water to 95% MeCN/water over 25 column volumes) to give tert-butyl (S)-3-methyl-1-((S)-2,2,2-trifluoro-1-(6-((E)-2-((8-isopropoxyquinolin-2-yl)methylene)hydrazinyl)pyridin-3-yl)ethyl)pyrrolidin-3-ylcarbamate (1.33 g, 2.27 mmol, 67.9% yield).

Step D: Preparation of tert-butyl (S)-3-methyl-1-((S)-2,2,2-trifluoro-1-(3-(8-isopropoxyquinolin-2-yl)-[1,2,4]triazolo[4,3-a]pyridin-6-yl)ethyl)pyrrolidin-3-ylcarbamate To a stirred solution of tert-butyl (S)-3-methyl-1-((S)-2,2,2-trifluoro-1-(6-((E)-2-((8-isopropoxyquinolin-2-yl)methylene)hydrazinyl)pyridin-3-yl)ethyl)pyrrolidin-3-ylcarbamate (1.33 g, 2.27 mmol) in DCM (20 mL) was added iodo benzene diacetate (0.949 g, 2.95 mmol). The reaction mixture was stirred at ambient temperature for 2 hours and then partitioned between ethyl acetate and saturated aqueous NaHCO$_3$. The aqueous layer was extracted with ethyl acetate. The combined organic layers were washed with brine, dried and concentrated. The residue was purified by chromatography (1:3 hexane/ethyl acetate) to give tert-butyl (S)-3-methyl-1-((S)-2,2,2-trifluoro-1-(3-(8-isopropoxyquinolin-2-yl)-[1,2,4]triazolo[4,3-a]pyridin-6-yl)ethyl)pyrrolidin-3-ylcarbamate (1.30 g, 98%).

Step E: Preparation of (S)-3-methyl-1-((S)-2,2,2-trifluoro-1-(3-(8-isopropoxyquinolin-2-yl)-[1,2,4]triazolo[4,3-a]pyridin-6-yl)ethyl)pyrrolidin-3-amine dihydrochloride To a stirred solution of tert-butyl (S)-3-methyl-1-((S)-2,2,2-trifluoro-1-(3-(8-isopropoxyquinolin-2-yl)-[1,2,4]triazolo[4,3-a]pyridin-6-yl)ethyl)pyrrolidin-3-ylcarbamate (1.30 g, 2.22 mmol) in DCM (20 mL) was added 4N HCl in dioxane (5.56 mL, 22.2 mmol). The reaction mixture was stirred at ambient temperature for 3 hours. Diethyl ether (100 mL) was added to the reaction mixture. The suspension was stirred for 10 min. The solid was collected by filtration to give (S)-3-methyl-1-((S)-2,2,2-trifluoro-1-(3-(8-isopropoxyquinolin-2-yl)-[1,2,4]triazolo[4,3-a]pyridin-6-yl)ethyl)pyrrolidin-3-amine dihydrochloride (1.20 g, 97%). MS APCI (+) m/z 485 (M+1) detected. Specific rotation: $[\alpha]^{20}_D = -2.14°$ (c=0.97, MeOH).

Example 93

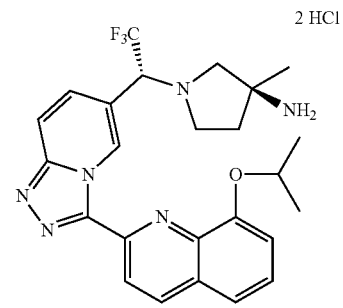 [SMILES: CC(C)Oc1cccc2ccc(-c3nnc4ccc([C@@H](N5CC[C@](C)(N)C5)C(F)(F)F)cn34)nc12]

(S)-3-methyl-1-((R)-2,2,2-trifluoro-1-(3-(8-isopropoxyquinolin-2-yl)-[1,2,4]triazolo[4,3-a]pyridin-6-yl)ethyl)pyrrolidin-3-amine dihydrochloride Prepared as described in Example 1 using (S)-tert-butyl 3-methylpyrrolidin-3-ylcarbamate (Preparation A) in place of (S)-tert-butyl pyrrolidin-3-ylmethylcarbamate, and substituting 8-isopropoxyquinoline-2-carbaldehyde for 8-methoxyquinoline-2-carbaldehyde. MS APCI (+) m/z 485 (M+1) detected.

Example 94

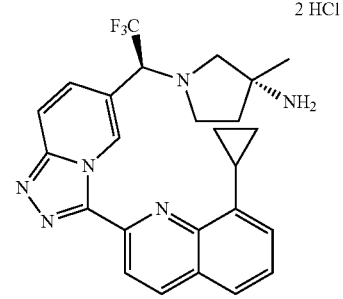 [SMILES: C[C@@]1(N)CCN([C@@H](c2ccc3nnc(-c4ccc5cccc(C6CC6)c5n4)n3c2)C(F)(F)F)C1]

(R)-1-((S)-1-(3-(8-cyclopropylquinolin-2-yl)-[1,2,4]triazolo[4,3-a]pyridin-6-yl)-2,2,2-trifluoroethyl)-3-methylpyrrolidin-3-amine dihydrochloride Prepared as described in Example 1, Steps A-E using (R)-tert-butyl 3-methylpyrrolidin-3-ylcarbamate (Preparation A) in place of (S)-tert-butyl pyrrolidin-3-ylmethylcarbamate, and substituting 8-cyclopropylquinoline-2-carbaldehyde for 8-methoxyquinoline-2-carbaldehyde, and separating the enantiomers according to the chiral chromatography conditions described in Example 8, Step A, followed by preparation of the HCl salt according to Example 8, Step B. MS APCI (+) m/z 467 (M+1) detected.

Example 95

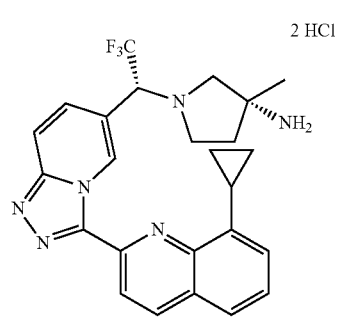 [SMILES: C[C@@]1(N)CCN([C@H](c2ccc3nnc(-c4ccc5cccc(C6CC6)c5n4)n3c2)C(F)(F)F)C1]

(R)-1-((R)-1-(3-(8-cyclopropylquinolin-2-yl)-[1,2,4]triazolo[4,3-a]pyridin-6-yl)-2,2,2-trifluoroethyl)-3-methylpyrrolidin-3-amine dihydrochloride Prepared as described in Example 1 using (R)-tert-butyl 3-methylpyrrolidin-3-ylcarbamate (Preparation A) in place of (S)-tert-butyl pyrrolidin-3-ylmethylcarbamate, and substituting 8-cyclopropylquinoline-2-carbaldehyde for 8-methoxyquinoline-2-carbaldehyde. MS APCI (+) m/z 467 (M+1) detected.

Example 96

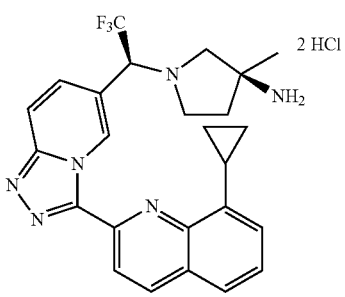 [SMILES: C[C@]1(N)CCN([C@@H](c2ccc3nnc(-c4ccc5cccc(C6CC6)c5n4)n3c2)C(F)(F)F)C1]

(S)-1-((S)-1-(3-(8-cyclopropylquinolin-2-yl)-[1,2,4]triazolo[4,3-a]pyridin-6-yl)-2,2,2-trifluoroethyl)-3-methylpyrrolidin-3-amine dihydrochloride Prepared as described in Example 1, Steps A-E using (S)-tert-butyl 3-methylpyrrolidin-3-ylcarbamate (Preparation A) in place of (S)-tert-butyl pyrrolidin-3-ylmethylcarbamate, and substituting 8-cyclopropylquinoline-2-carbaldehyde for 8-methoxyquinoline-2-carbaldehyde, and separating the enantiomers according to the chiral chromatography conditions described in Example 8, Step A, followed by preparation of the HCl salt according to Example 8, Step B. MS APCI (+) m/z 467 (M+1) detected.

Example 97

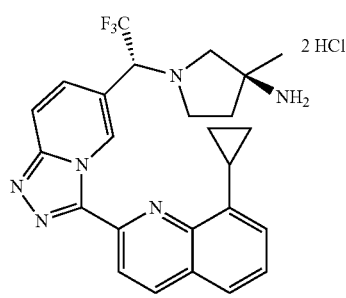 [SMILES: C[C@]1(N)CCN([C@H](c2ccc3nnc(-c4ccc5cccc(C6CC6)c5n4)n3c2)C(F)(F)F)C1]

(S)-1-((R)-1-(3-(8-cyclopropylquinolin-2-yl)-[1,2,4]triazolo[4,3-a]pyridin-6-yl)-2,2,2-trifluoroethyl)-3-methylpyrrolidin-3-amine dihydrochloride Prepared as described in Example 1 using (S)-tert-butyl 3-methylpyrrolidin-3-ylcarbamate (Preparation A) in place of (S)-tert-butyl pyrrolidin-3-ylmethylcarbamate, and substituting 8-cyclopropylquinoline-2-carbaldehyde for 8-methoxyquinoline-2-carbaldehyde. MS APCI (+) m/z 467 (M+1) detected.

Example 98

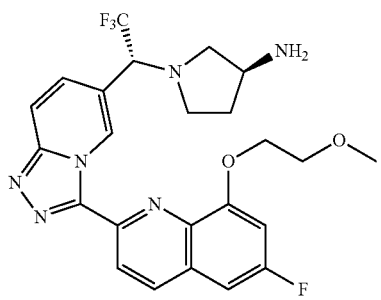 [SMILES: COCCOc1cc(F)cc2ccc(-c3nnc4ccc([C@@H](N5CC[C@H](N)C5)C(F)(F)F)cn34)nc12]

(S)-1-((R)-2,2,2-trifluoro-1-(3-(6-fluoro-8-(2-methoxyethoxy)quinolin-2-yl)-[1,2,4]triazolo[4,3-a]pyridin-6-yl)ethyl)pyrrolidin-3-amine hydrochloride Prepared as described in Example 86, substituting 2-iodopropane in Step B with 1-bromo-2-methoxyethane (32 mg, 64% yield). LCMS APCI (+) m/z 505 (M+H).

Example 99

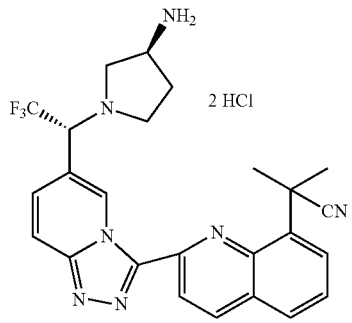 [SMILES: CC(C)(C#N)c1cccc2ccc(-c3nnc4ccc([C@@H](N5CC[C@H](N)C5)C(F)(F)F)cn34)nc12]

2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)-2-methylpropanenitrile dihydrochloride Step A: Preparation of 8-(bromomethyl)-2-methylquinoline To a solution of 2,8-dimethylquinoline (3.00 g, 19.1 mmol) in carbon tetrachloride (50 mL) were added benzoyl peroxide (0.0139 g, 0.057 mmol) and N-bromosuccinimide (3.57 g, 20.0 mmol). The reaction mixture was heated at reflux for 18 hours. The solid was removed by filtration and the filtrate was concentrated under reduced pressure. The residue was dissolved in DCM (100 mL), washed with saturated sodium bicarbonate and brine, dried (sodium sulfate), filtered and concentrated under reduced pressure to give 8-(bromomethyl)-2-methylquinoline (1.50 g, 33.3%) as a solid.

Step B: Preparation of 2-(2-methylquinolin-8-yl)acetonitrile

To a solution of 8-(bromomethyl)-2-methylquinoline (1.50 g, 6.35 mmol) in DMSO (20 mL) was added NaCN (0.62 g, 12.7 mmol). The mixture was stirred at ambient temperature for 10 minutes. Water (100 mL) and ether (100 mL) were added. The organic layer was separated, washed with brine, dried (sodium sulfate), and concentrated under reduced pressure. The residue was purified by flash chromatography on silica gel (1:1 hexane/ethyl acetate) to give 2-(2-methylquinolin-8-yl)acetonitrile (0.75 g, 58.3%) as a solid.

Step C: Preparation of 2-methyl-2-(2-methylquinolin-8-yl)propanenitrile

To a mixture of 60% NaH (0.33 g, 8.15 mmol) in DMSO (15 mL) at 20-35° C. was slowly added a solution of 2-(2-methylquinolin-8-yl)acetonitrile (0.75 g, 3.70 mmol) and iodomethane (0.58 mL, 9.26 mmol) in THF (5 mL). The reaction mixture was stirred at ambient temperature for 20 hours. Brine (40 mL) and ether (50 mL) were added. The organic layer was separated, washed with brine, dried (sodium sulfate), filtered and concentrated under reduced pressure. The residue was purified by flash chromatography on silica gel (30:1 hexane/ethyl acetate) to give 2-methyl-2-(2-methylquinolin-8-yl)propanenitrile (0.17 g, 22.1%) as a solid.

Step D: Preparation of 2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)-2-methylpropanenitrile dihydrochloride Prepared as described in Example 37, Steps B-C, using 2-methyl-2-(2-methylquinolin-8-yl)propanenitrile in place of 8-ethyl-2-methylquinoline in Step B. LCMS APCI (+) m/z 480 (M+H).

Example 100

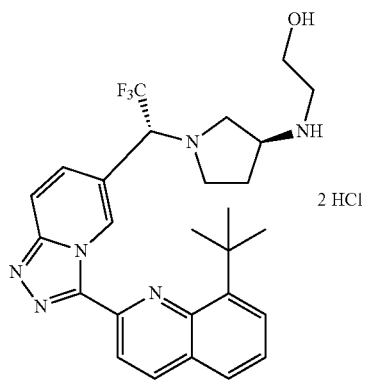 [SMILES: CC(C)(C)c1cccc2ccc(-c3nnc4ccc([C@@H](N5CC[C@H](NCCO)C5)C(F)(F)F)cn34)nc12]

2-((S)-1-((R)-1-(3-(8-tert-butylquinolin-2-yl)-[1,2,4]triazolo[4,3-a]pyridin-6-yl)-2,2,2-trifluoroethyl)pyrrolidin-3-ylamino)ethanol dihydrochloride Step A: Preparation of (S)-benzyl 3-(tert-butoxycarbonyl(2-tert-butoxyethyl)amino)pyrrolidine-1-carboxylate To a solution of (S)-benzyl 3-(tert-butoxycarbonylamino)pyrrolidine-1-carboxylate (2.50 g, 7.80 mmol) in anhydrous DMF (20 mL) cooled to 0° C. in an ice bath was added a 60% dispersion of sodium hydride in mineral oil (0.47 g, 11.7 mmol). The mixture was allowed to warm to ambient temperature and stirred for 1 hour. 2-tert-Butoxyethyl methanesulfonate (2.3 g, 11.7 mmol) was added and the mixture was stirred at 0° C. in an ice bath, then allowed to slowly warm to ambient temperature and stirred for 18 hours. The mixture was partitioned between water (50 mL) and ethyl acetate (100 mL). The layers were separated and washed with aqueous 1N HCl, water and brine, dried (MgSO₄), filtered and concentrated under reduced pressure. The residue was purified by column chromatography (Biotage, 40M; 20% ethyl acetate/hexane) to afford (S)-benzyl 3-(tert-butoxycarbonyl(2-tert-butoxyethyl)amino)pyrrolidine-1-carboxylate (2.87 g, 88%).

Step B: Preparation of (S)-tert-butyl 2-tert-butoxyethyl(pyrrolidin-3-yl)carbamate Prepared as described in Example 20 using (S)-benzyl 3-(tert-butoxycarbonyl(2-tert-butoxyethyl)amino)pyrrolidine-1-carboxylate (2.87 g, 6.82 mmol) in place of (S)-benzyl 3-(tert-butoxycarbonyl(methyl)amino)pyrrolidine-1-carboxylate in Step C to provide the desired product in quantitative yield.

Step C: Preparation of tert-butyl 2-tert-butoxyethyl ((S)-1-((R)-1-(6-chloropyridin-3-yl)-2,2,2-trifluoroethyl)pyrrolidin-3-yl)carbamate Prepared as described in Example 9B, Step D, using (S)-1-(6-chloropyridin-3-yl)-2,2,2-trifluoroethyl trifluoromethanesulfonate (1.50 g, 4.37 mmol) and (S)-tert-butyl 2-tert-butoxyethyl(pyrrolidin-3-yl)carbamate (2.0 g, 6.98 mmol) in place of (S)-tert-butyl pyrrolidin-3-ylcarbamate (1.69 g, 81%)

Step D: Preparation of tert-butyl 2-tert-butoxyethyl (S)-1-((R)-2,2,2-trifluoro-1-(6-hydrazinylpyridin-3-yl)ethyl)pyrrolidin-3-yl)carbamate Prepared as described in Example 9B, Step E, using tert-butyl 2-tert-butoxyethyl((S)-1-((R)-1-(6-chloropyridin-3-yl)-2,2,2-trifluoroethyl)pyrrolidin-3-yl)carbamate (1.69 g, 3.52 mmol) in place of tert-butyl (S)-1-((R)-1-(6-chloropyridin-3-yl)-2,2,2-trifluoroethyl)pyrrolidin-3-ylcarbamate (1.55 g, 93%)

Step E Preparation of 2-((S)-1-((R)-1-(3-(8-tert-butylquinolin-2-yl)-[1,2,4]triazolo[4,3-a]pyridin-6-yl)-2,2,2-trifluoroethyl)pyrrolidin-3-ylamino)ethanol dihydrochloride Prepared as described in Example 9B, Step F, using tert-butyl 2-tert-butoxyethyl((S)-1-((R)-2,2,2-trifluoro-1-(6-hydrazinylpyridin-3-yl)ethyl)pyrrolidin-3-yl)carbamate in place of tert-butyl (S)-1-((R)-2,2,2-trifluoro-1-(6-hydrazinylpyridin-3-yl)ethyl)pyrrolidine-3-ylcarbamate and substituting 8-tert-butylquinoline-2-carbaldehyde. LCMS APCI (+) m/z 513 (M+H).

Example 101

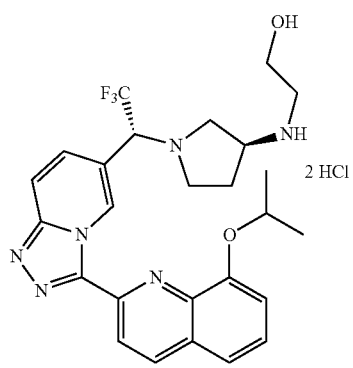 [SMILES: CC(C)Oc1cccc2ccc(-c3nnc4ccc([C@@H](N5CC[C@H](NCCO)C5)C(F)(F)F)cn34)nc12]

2-((S)-1-((R)-2,2,2-trifluoro-1-(3-(8-isopropoxyquinolin-2-yl)-[1,2,4]triazolo[4,3-a]pyridin-6-yl)ethyl)pyrrolidin-3-ylamino)ethanol dihydrochloride Prepared as described in Example 9B, Step F, using tert-butyl 2-tert-butoxyethyl((S)-1-((R)-2,2,2-trifluoro-1-(6-hydrazinylpyridin-3-yl)ethyl)pyrrolidin-3-yl)carbamate in place of tert-butyl (S)-1-((R)-2,2,2-trifluoro-1-(6-hydrazinylpyridin-3-yl)ethyl)pyrrolidine-3-ylcarbamate and using 8-isopropoxyquinoline-2-carbaldehyde in place of 8-methoxyquiniline-2-carbaldehyde. LCMS APCI (+) m/z 515 (M+H).

Example 102

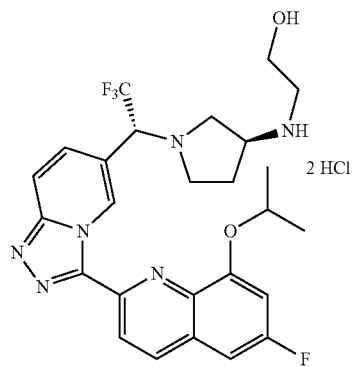 [SMILES: CC(C)Oc1cc(F)cc2ccc(-c3nnc4ccc([C@@H](N5CC[C@H](NCCO)C5)C(F)(F)F)cn34)nc12]

2-((S)-1-((R)-2,2,2-trifluoro-1-(3-(6-fluoro-8-isopropoxyquinolin-2-yl)-[1,2,4]triazolo[4,3-a]pyridin-6-yl)ethyl)pyrrolidin-3-ylamino)ethanol dihydrochloride Prepared as described in Example 9B, Step F, using tert-butyl 2-tert-butoxyethyl((S)-1-((R)-2,2,2-trifluoro-1-(6-hydrazinylpyridin-3-yl)ethyl)pyrrolidin-3-yl)carbamate in place of tert-butyl (S)-1-((R)-2,2,2-trifluoro-1-(6-hydrazinylpyridin-3-yl)ethyl)pyrrolidine-3-ylcarbamate substituting 6-fluoro-8-isopropoxyquinoline-2-carbaldehyde in place of 8-methoxyquiniline-2-carbaldehyde. LCMS APCI (+) m/z 533 (M+H).

Example 103

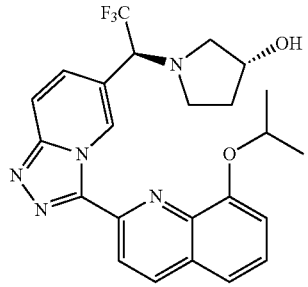 [SMILES: CC(C)Oc1cccc2ccc(-c3nnc4ccc([C@H](N5CC[C@@H](O)C5)C(F)(F)F)cn34)nc12]

(R)-1-((S)-2,2,2-trifluoro-1-(3-(8-isopropoxyquinolin-2-yl)-[1,2,4]triazolo[4,3-a]pyridin-6-yl)ethyl)pyrrolidin-3-ol Step A: Preparation of 8-isopropoxyquinoline-2-carbaldehyde Prepared as described in Example 5, Steps A-B, using 2-iodopropane in place of (bromomethyl)cyclopropane in Step A.

Step B: Preparation of (R)-1-((S)-2,2,2-trifluoro-1-(3-(8-isopropoxyquinolin-2-yl)-[1,2,4]triazolo[4,3-a]pyridin-6-yl)ethyl)pyrrolidin-3-ol Prepared as described in Example 9B, Steps A-F, using (R)-1-((S)-2,2,2-trifluoro-1-(6-hydrazinylpyridin-3-yl)ethyl)pyrrolidin-3-ol in place of tert-butyl (S)-1-((R)-2,2,2-trifluoro-1-(6-hydrazinylpyridin-3-yl)ethyl)pyrrolidin-3-yl-carbamate and using 8-isopropoxyquinoline-2-carbaldehyde in place of 8-methoxyquinoline-2-carbaldehyde in Step F. LCMS APCI (+) m/z 472.1 (M+H).

Example 104

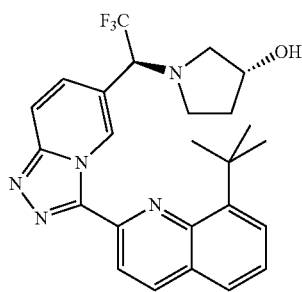 [SMILES: CC(C)(C)c1cccc2ccc(-c3nnc4ccc([C@H](N5CC[C@@H](O)C5)C(F)(F)F)cn34)nc12]

(R)-1-((S)-2,2,2-trifluoro-1-(3-(8-isopropoxyquinolin-2-yl)-[1,2,4]triazolo[4,3-a]pyridin-6-yl)ethyl)pyrrolidin-3-ol Prepared as described in Example 103, substituting 8-tert-butylquinoline-2-carbaldehyde for 8-isopropoxyquinoline-2-carbaldehyde. LCMS APCI (+) m/z 470.1 (M+H).

Example 105

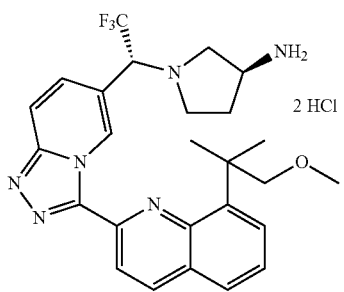 [SMILES: COCC(C)(C)c1cccc2ccc(-c3nnc4ccc([C@@H](N5CC[C@H](N)C5)C(F)(F)F)cn34)nc12]

(S)-1-((R)-2,2,2-trifluoro-1-(3-(8-(1-methoxy-2-methylpropan-2-yl)quinolin-2-yl)-[1,2,4]triazolo[4,3-a]pyridin-6-yl)ethyl)pyrrolidin-3-amine dihydrochloride

Step A: Preparation of diethyl 2-(2-methylquinolin-8-yl)malonate

A solution of 8-bromo-2-methylquinoline (2.00 g, 9.01 mmol), Pd(PtBu$_3$)$_2$ (0.23 g, 0.45 mmol), Cs$_2$CO$_3$ (11.74 g, 36.02 mmol) and diethyl malonate (2.73 mL, 18.01 mmol) in dioxane (25 mL) was heated at 118° C. in a sealed tube for 1 hour. After cooling to ambient temperature, ethyl acetate (30 mL) and water (15 mL) were added. The organic layer was separated, washed with brine, dried (sodium sulfate), filtered and concentrated under reduced pressure. The residue was purified by flash chromatography on silica gel (7:1 hexane/ethyl acetate) to give diethyl 2-(2-methylquinolin-8-yl)malonate (2.24 g, 82.54%) as an oil.

Step B: Preparation of 2-(2-methylquinolin-8-yl)acetic acid

A solution of diethyl 2-(2-methylquinolin-8-yl)malonate (2.34 g, 7.77 mmol), 6 N HCl (7.77 mL, 46.6 mmol) in water, and acetic acid (7.77 mL) was heated at 106° C. for 18 hours. After cooling to ambient temperature, the solvent was removed under reduced pressure to give 2-(2-methylquinolin-8-yl)acetic acid (1.56 g, 99.8%) as a solid.

Step C: Preparation of methyl 2-(2-methylquinolin-8-yl)acetate

To a solution of 2-(2-methylquinolin-8-yl)acetic acid (1.45 g, 7.21 mmol) in dry MeOH (100 mL) was added chlorotrimethylsilane (1.82 mL, 14.4 mmol) dropwise at 0° C. After addition, the reaction mixture was stirred at reflux for 2 hours. After cooling to ambient temperature, the solvent was removed under reduced pressure. The residue was partitioned between ethyl acetate (50 mL) and saturated sodium bicarbonate (20 mL). The organic layer was separated, washed with brine, dried (sodium sulfate), filtered and concentrated under reduced pressure. The residue was purified by flash chromatography on silica gel (5:1 hexane/ethyl acetate) to give methyl 2-(2-methylquinolin-8-yl)acetate (1.35 g, 87.0%) as an oil.

Step D: Preparation of methyl 2-methyl-2-(2-methylquinolin-8-yl)propanoate

To a mixture of NaH (0.58 g, 14.43 mmol) in DMSO (15 mL) at 20-35° C. was slowly added a solution of methyl 2-(2-methylquinolin-8-yl)acetate (1.35 g, 6.272 mmol) and iodomethane (1.08 ml, 17.25 mmol) in THF (5 mL). The reaction mixture was stirred at ambient temperature for 20 hours. Brine (20 mL) and ether (50 mL) were added. The organic layer was separated, washed with brine, dried (sodium sulfate), filtered and concentrated under reduced pressure to give methyl 2-(2-methylquinolin-8-yl)propanoate (1.44 g, 100%) as an oil. The methyl 2-(2-methylquinolin-8-yl)propanoate (1.44 g, 6.28 mmol) was taken up in THF (10 mL) and 1 N lithium bis(trimethylsilyl)amide (12.56 mL, 12.56 mmol) in THF was added at 0° C. After addition, the reaction mixture was stirred at ambient temperature for 40 minutes. Iodomethane (0.78 mL, 12.56 mmol) was added dropwise and the reaction mixture was stirred at ambient temperature for 18 hours. Water (10 mL) and ether (50 mL) were added. The organic layer was separated, washed with brine, dried (sodium sulfate), filtered and concentrated under reduced pressure. The residue was purified by flash chromatography on silica gel (8:1 hexane/ethyl acetate) to give methyl 2-methyl-2-(2-methylquinolin-8-yl)propanoate (0.67 g, 43.9%) as an oil.

Step E: Preparation of 2-methyl-2-(2-methylquinolin-8-yl)propan-1-ol

To a solution of methyl 2-methyl-2-(2-methylquinolin-8-yl)propanoate (0.57 g, 2.3 mmol) in THF (10 mL) was added 1 N LAH (5.9 mL, 5.9 mmol) in THF at 0° C. and stirred at 0°

C. for 6 hours. Sodium sulfate decahydrate (2.0 g) was added and the reaction mixture was stirred at ambient temperature for 30 minutes. The solid was removed by filtration and washed with ethyl acetate (30 mL). The filtrate was concentrated under reduced pressure and the residue was purified by flash chromatography on silica gel (1:1 hexane/ethyl acetate) to give 2-methyl-2-(2-methylquinolin-8-yl)propan-1-ol (0.43 g, 85%) as an oil.

Step F: Preparation of 8-(1-methoxy-2-methylpropan-2-yl)-2-methylquinoline

To a solution of 2-methyl-2-(2-methylquinolin-8-yl)propan-1-ol (0.43 g, 2.00 mmol) and iodomethane (0.37 mL, 5.99 mmol) in DMSO (10 mL) was added NaH (0.16 g, 3.99 mmol) at ambient temperature and stirred at ambient temperature for 30 minutes. Water (10 mL) and ether (40 mL) were added. The organic layer was separated, washed with brine, dried (sodium sulfate), filtered and concentrated under reduced pressure. The residue was purified by flash chromatography on silica gel (5:1 hexane/ethyl acetate) to give 8-(1-methoxy-2-methylpropan-2-yl)-2-methylquinoline (0.43 g, 93.0%) as an oil.

Step G: Preparation of (S)-1-((R)-2,2,2-trifluoro-1-(3-(8-(1-methoxy-2-methylpropan-2-yl)quinolin-2-yl)-[1,2,4]triazolo[4,3-a]pyridin-6-yl)ethyl)pyrrolidin-3-amine dihydrochloride Prepared as described in Example 37, Steps B-C, using 8-(1-methoxy-2-methylpropan-2-yl)-2-methylquinoline in place of 8-ethyl-2-methylquinoline in Step B. LCMS APCI (+) m/z 499 (M+H).

Example 106

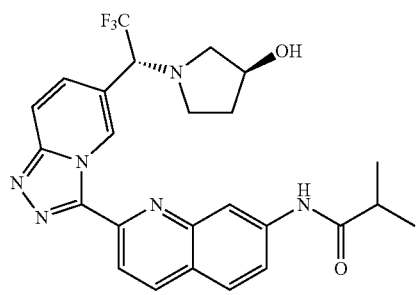 [SMILES: CC(C)C(=O)Nc1ccc2ccc(-c3nnc4ccc([C@@H](N5CC[C@H](O)C5)C(F)(F)F)cn34)nc2c1]

N-(2-(6-((R)-2,2,2-trifluoro-1-((S)-3-hydroxypyrrolidin-1-yl)ethyl)-[1,2,4]triazolo[4,3-a]pyridin-3-yl)quinolin-7-yl)isobutyramide Step A: Preparation of (S)-1-((R)-1-(3-(7-bromoquinolin-2-yl)-[1,2,4]triazolo[4,3-a]pyridin-6-yl)-2,2,2-trifluoroethyl)pyrrolidin-3-ol Prepared as described in Example 30, Steps A-F, using (S)-pyrrolidin-3-ol in place of tert-butyl (3S)-1-(2,2,2-trifluoro-1-(6-hydrazinylpyridin-3-yl)ethyl)pyrrolidin-3-ylcarbamate in Step D.

Step B: Preparation of N-(2-(6-((R)-2,2,2-trifluoro-1-((S)-3-hydroxypyrrolidin-1-yl)ethyl)-[1,2,4]triazolo[4,3-a]pyridin-3-yl)quinolin-7-yl)isobutyramide Prepared as described in Example 44, Steps B-C, substituting (S)-1-((R)-1-(3-(7-bromoquinolin-2-yl)-[1,2,4]triazolo[4,3-a]pyridin-6-yl)-2,2,2-trifluoroethyl)pyrrolidin-3-ol for tert-Butyl (3S)-1-(1-(3-(7-bromo quinolin-2-yl)-[1,2,4]triazolo[4,3-a]pyridin-6-yl)-2,2,2-trifluoroethyl)pyrrolidin-3-ylcarbamate. LCMS APCI (+) m/z 499.1 (M+H).

Example 107

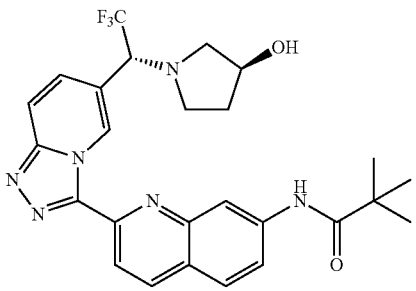 [SMILES: CC(C)(C)C(=O)Nc1ccc2ccc(-c3nnc4ccc([C@@H](N5CC[C@H](O)C5)C(F)(F)F)cn34)nc2c1]

N-(2-(6-((R)-2,2,2-trifluoro-1-((S)-3-hydroxypyrrolidin-1-yl)ethyl)-[1,2,4]triazolo[4,3-a]pyridin-3-yl)quinolin-7-yl)pivalamide Prepared as described in Example 44, Steps B-C, substituting (S)-1-((R)-1-(3-(7-bromo quinolin-2-yl)-[1,2,4]triazolo[4,3-a]pyridin-6-yl)-2,2,2-trifluoroethyl)pyrrolidin-3-ol for tert-Butyl (3S)-1-(1-(3-(7-bromo quinolin-2-yl)-[1,2,4]triazolo[4,3-a]pyridin-6-yl)-2,2,2-trifluoroethyl)pyrrolidin-3-ylcarbamate and tert-butylamide for isopropylamide. LCMS APCI (+) m/z 513.3 (M+H).

Example 108

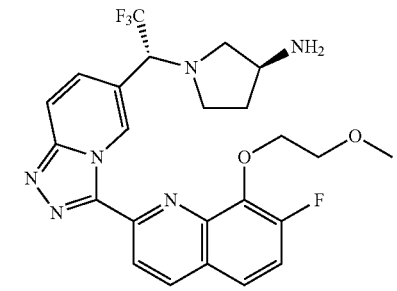 [SMILES: COCCOc1c(F)ccc2ccc(-c3nnc4ccc([C@@H](N5CC[C@H](N)C5)C(F)(F)F)cn34)nc12]

(S)-1-((R)-2,2,2-trifluoro-1-(3-(7-fluoro-8-(2-methoxyethoxy)quinolin-2-yl)-[1,2,4]triazolo[4,3-a]pyridin-6-yl)ethyl)pyrrolidin-3-amine hydrochloride Prepared as described in Example 86, using 2-amino-6-fluorophenol in place of 2-amino-5-fluorophenol in Step A and using 1-bromo-2-methoxyethane in place of 2-iodopropane in Step B. LCMS APCI (+) m/z 505 (M+H).

Example 109

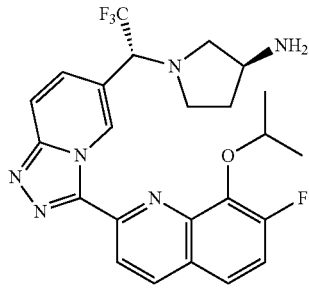 [SMILES: CC(C)Oc1c(F)ccc2ccc(-c3nnc4ccc([C@@H](N5CC[C@H](N)C5)C(F)(F)F)cn34)nc12]

(S)-1-((R)-2,2,2-trifluoro-1-(3-(7-fluoro-8-isopropoxyquinolin-2-yl)-[1,2,4]triazolo[4,3-a]pyridin-6-yl)ethyl)pyrrolidin-3-amine hydrochloride Prepared as described in Example 86, using 2-amino-6-fluorophenol in place of 2-amino-5-fluorophenol in Step A. LCMS APCI (+) m/z 489 (M+H).

Example 110

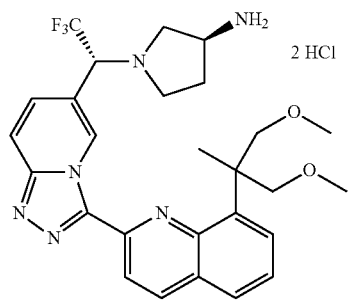 [SMILES: COCC(C)(COC)c1cccc2ccc(-c3nnc4ccc([C@@H](N5CC[C@H](N)C5)C(F)(F)F)cn34)nc12]

(S)-1-((R)-1-(3-(8-(1,3-dimethoxy-2-methylpropan-2-yl)quinolin-2-yl)-[1,2,4]triazolo[4,3-a]pyridin-6-yl)-2,2,2-trifluoroethyl)pyrrolidin-3-amine dihydrochloride Prepared as described in Example 105 using diethyl 2-(2-methylquinolin-8-yl)malonate in place of methyl 2-(2-methylquinolin-8-yl)acetate in Step D. LCMS APCI (+) m/z 529 (M+H).

Example 111

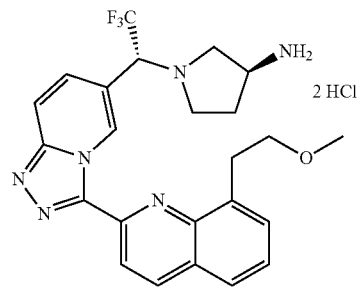 [SMILES: COCCc1cccc2ccc(-c3nnc4ccc([C@@H](N5CC[C@H](N)C5)C(F)(F)F)cn34)nc12 ; "2 HCl"]

(S)-1-((R)-2,2,2-trifluoro-1-(3-(8-(2-methoxyethyl)quinolin-2-yl)-[1,2,4]triazolo[4,3-a]pyridin-6-yl)ethyl)pyrrolidin-3-amine dihydrochloride Prepared as described in Example 105 using methyl 2-(2-methylquinolin-8-yl)acetate in place of methyl 2-(2-methylquinolin-8-yl)acetate in Step D. LCMS APCI (+) m/z 471 (M+H).

Example 112

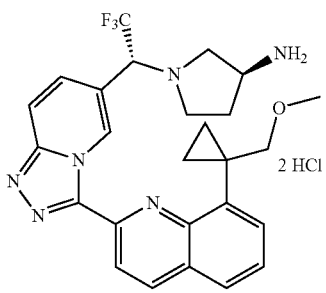 [SMILES: COCC1(c2cccc3ccc(-c4nnc5ccc([C@@H](N6CC[C@H](N)C6)C(F)(F)F)cn45)nc23)CC1]

(S)-1-((R)-2,2,2-trifluoro-1-(3-(8-(1-(methoxymethyl)cyclopropyl)quinolin-2-yl)-[1,2,4]triazolo[4,3-a]pyridin-6-yl)ethyl)pyrrolidin-3-amine dihydrochloride Step A: Preparation of methyl 1-(2-methylquinolin-8-yl)cyclopropanecarboxylate To a solution of methyl 2-(2-methylquinolin-8-yl)acetate (0.78 g, 3.62 mmol) in DMSO (10 mL) and THF (5 mL) was added 60% NaH (0.72 g, 18.12 mmol) and the reaction mixture was stirred at ambient temperature for 30 minutes. 1-Bromo-2-chloroethane (0.90 mL, 10.87 mmol) was added slowly, and the reaction mixture was stirred at ambient temperature for 40 hours. Water (10 mL) and ether (50 mL) were added. The organic layer was separated, washed with brine, dried (sodium sulfate), filtered and concentrated under reduced pressure. The residue was purified by flash chromatography on silica gel (7:1 hexane/ethyl acetate) to give methyl 1-(2-methylquinolin-8-yl)cyclopropanecarboxylate (0.416 g, 47.6%) as an oil.

Step B: Preparation of (S)-1-((R)-2,2,2-trifluoro-1-(3-(8-(1-(methoxymethyl)cyclopropyl)quinolin-2-yl)-[1,2,4]triazolo[4,3-a]pyridin-6-yl)ethyl)pyrrolidin-3-amine dihydrochloride Prepared as described in Example 105 using methyl 1-(2-methylquinolin-8-yl)cyclopropanecarboxylate in place of methyl 2-methyl-2-(2-methylquinolin-8-yl)propanoate in Step E. LCMS APCI (+) m/z 497 (M+H).

Example 113

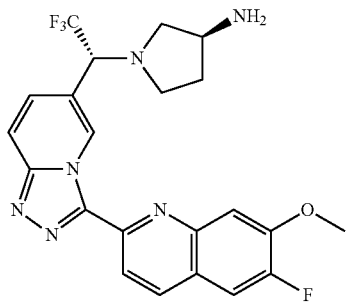 [SMILES: COc1cc2nc(-c3nnc4ccc([C@@H](N5CC[C@H](N)C5)C(F)(F)F)cn34)ccc2cc1F]

(S)-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-amine hydrochloride Step A: Preparation of 6-fluoro-7-methoxy-2-methylquinoline To 4-fluoro-3-methoxyaniline (1.0 g, 7.1 mmol) in refluxing 6N HCl (20 mL) was added dropwise (E)-but-2-enal (0.99 g, 14 mmol) and the reaction was heated to reflux for 2 hours. After cooling, the reaction was neutralized with ammonium hydroxide and extracted with DCM. The combined organic phases were dried over MgSO₄, filtered and concentrated under reduced pressure to yield 6-fluoro-7-methoxy-2-methylquinoline as a brown solid.

Step B: Preparation of 6-fluoro-7-methoxyquinoline-2-carbaldehyde

To 6-fluoro-7-methoxy-2-methylquinoline (1.4 g, 7.3 mmol) in dioxane/water (10 ml/1 mL) at ambient temperature was added selenium dioxide (0.97 g, 8.8 mmol) and the reaction was heated to reflux for 2-3 hours. After cooling, the reaction was filtered and the solids were washed with DCM. The filtrate was dried over MgSO₄, filtered, and concentrated under reduced pressure. The crude material was purified by reverse phase chromatography (SP4, 25M, eluting with a gradient of water/ACN 100:0 to 0:100, 20 column volumes) to yield 6-fluoro-7-methoxyquinoline-2-carbaldehyde (1.1 g, 73% yield) as a tan solid.

Step C: Preparation of tert-butyl (S)-1-((R)-2,2,2-trifluoro-1-(6-((E)-2-((6-fluoro-7-methoxyquinolin-2-yl)methylene)hydrazinyl)pyridin-3-yl)ethyl)pyrrolidin-3-ylcarbamate To 6-fluoro-7-methoxyquinoline-2-carbaldehyde (54.7 mg, 0.266 mmol) in ethanol (5 mL) was added tert-butyl (S)-1-((R)-2,2,2-trifluoro-1-(6-hydrazinylpyridin-3-yl)ethyl)pyrrolidin-3-ylcarbamate (100 mg, 0.266 mmol) and the reaction was stirred for 24 hours at ambient temperature. The reaction was concentrated to dryness and used as is in the next step.

Step D: Preparation of tert-butyl (S)-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-ylcarbamate To tert-butyl (S)-1-((R)-2,2,2-trifluoro-1-(6-((E)-2-((6-fluoro-7-methoxyquinolin-2-yl)methylene)hydrazinyl)pyridin-3-yl)ethyl)pyrrolidin-3-ylcarbamate (150 mg, 0.267 mmol) in DCM (5 mL) was added iodosobenzene acetate (112 mg, 0.347 mmol), and the reaction was stirred at ambient temperature for 2 hours. After concentration, the residue was purified by reverse phase chromatography (SP4, 12M, eluting with a gradient of water/ACN 100:0 to 0:100, 20 column volumes) to yield tert-butyl (S)-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-ylcarbamate (109 mg, 72.9% yield) as beige solid.

Step E: Preparation of (S)-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-amine hydrochloride tert-Butyl (S)-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-ylcarbamate (109 mg, 0.194 mmol) was stirred in TFA (3 mL) for 1 hour and then concentrated. The residue was dissolved in minimum methanol and added dropwise to a 4N HCl in ether solution. The resulting solid was filtered and dried to yield (S)-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-amine (67 mg, 74.8% yield) hydrochloride as an off-white solid. LCMS APCI (+) m/z 461 (M+H). Specific rotation: $[\alpha]^{20}_D = +1.07°$ (c=0.96, MeOH).

Example 114

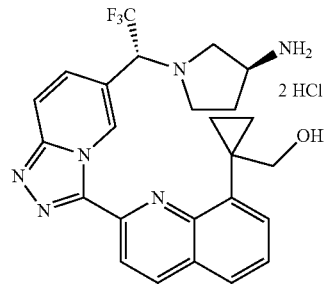 [SMILES: N[C@H]1CCN([C@H](c2ccc3nnc(-c4ccc5cccc(C6(CO)CC6)c5n4)n3c2)C(F)(F)F)C1]

(1-(2-(6-((R)-1-((S)-3-aminopyrrolidin-1-yl)-2,2,2-trifluoroethyl)-[1,2,4]triazolo[4,3-a]pyridin-3-yl)quinolin-8-yl)cyclopropyl)methanol dihydrochloride Step A: Preparation of 8-(1-((tert-butyldimethylsilyloxy)methyl)cyclopropyl)-2-methylquinoline To a solution of (1-(2-methylquinolin-8-yl)cyclopropyl)methanol (0.050 g, 0.234 mmol) and triethylamine (0.065 mL, 0.47 mmol) in DCM (5 mL) was added TBSOTf (0.065 mL, 0.28 mmol) at ambient temperature and the reaction was stirred at ambient temperature for 1 hour. Saturated sodium bicarbonate (10 mL) and DCM (20 mL) were added. The organic layer was separated, washed with brine, dried (sodium sulfate), filtered and concentrated under reduced pressure. The residue was purified by flash chromatography on silica gel (10:1 hexane/ethyl acetate) to give 8-(1-((tert-butyldimethylsilyloxy)methyl)cyclopropyl)-2-methylquinoline (0.071 g, 92.5%) as an oil.

Step B: Preparation of ((1-(2-(6-((R)-1-((S)-3-aminopyrrolidin-1-yl)-2,2,2-trifluoroethyl)-[1,2,4]triazolo[4,3-a]pyridin-3-yl)quinolin-8-yl)cyclopropyl)methanol dihydrochloride Prepared as described in Example 37, Steps B-C, using 8-(1-((tert-butyldimethylsilyloxy)methyl)cyclopropyl)-2-methylquinoline in place of 8-ethyl-2-methylquinoline in Step B. LCMS APCI (+) m/z 483 (M+H).

Example 115

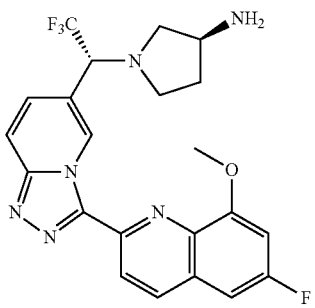 [SMILES: COc1cc(F)cc2ccc(-c3nnc4ccc([C@@H](N5CC[C@H](N)C5)C(F)(F)F)cn34)nc12]

(S)-1-((R)-2,2,2-trifluoro-1-(3-(6-fluoro-8-methoxyquinolin-2-yl)-[1,2,4]triazolo[4,3-a]pyridin-6-yl)ethyl)pyrrolidin-3-amine hydrochloride Step A: Preparation of 6-fluoro-8-methoxy-2-methylquinoline To 4-fluoro-2-methoxyaniline (370 mg, 2.62 mmol) in refluxing 6N HCl (5 mL) was added dropwise (E)-but-2-enal (367 mg, 5.24 mmol). The reaction was heated to reflux for 2 hours then cooled and neutralized with NH₄OH. The aqueous phase was extracted with DCM, and the combined organic phases dried over MgSO₄ and concentrated to yield 6-fluoro-8-methoxy-2-methylquinoline (500 mg, 99.8% yield) as a brown solid.

Step B: Preparation of 6-fluoro-8-methoxyquinoline-2-carbaldehyde

To 6-fluoro-8-methoxy-2-methylquinoline (500 mg, 2.62 mmol) in dioxane/water (5 mL/0.5 mL) at ambient temperature was added selenium dioxide (348 mg, 3.14 mmol) and the reaction was heated to reflux for 2-3 hours. After cooling, the reaction was filtered and the solids were washed with DCM. The filtrate was dried over MgSO₄, filtered and concentrated under reduced pressure. The residue was purified by reverse phase chromatography (SP4, 25M, eluting with a gradient of water/ACN 100:0 to 0:100, 20 column volumes) to yield 6-fluoro-8-methoxyquinoline-2-carbaldehyde (423 mg, 78.8% yield) as a tan solid.

Step C: Preparation of tert-butyl (S)-1-((R)-2,2,2-trifluoro-1-(6-((E)-2-((6-fluoro-8-methoxyquinolin-2-yl)methylene)hydrazinyl)pyridin-3-yl)ethyl)pyrrolidin-3-ylcarbamate tert-Butyl (S)-1-((R)-2,2,2-trifluoro-1-(6-hydrazinylpyridin-3-yl)ethyl)pyrrolidin-3-ylcarbamate (200 mg, 0.533 mmol) and 6-fluoro-8-methoxyquinoline-2-carbaldehyde (109 mg, 0.533 mmol) were stirred in ethanol at ambient temperature for 24 hours. The reaction was concentrated and used as is in the next step.

Step D: Preparation of tert-butyl (S)-1-((R)-2,2,2-trifluoro-1-(3-(6-fluoro-8-methoxyquinolin-2-yl)-[1,2,4]triazolo[4,3-a]pyridin-6-yl)ethyl)pyrrolidin-3-ylcarbamate To tert-butyl (S)-1-((R)-2,2,2-trifluoro-1-(6-((E)-2-((6-fluoro-8-methoxyquinolin-2-yl)methylene)hydrazinyl)pyridin-3-yl)ethyl)pyrrolidin-3-ylcarbamate (300 mg, 0.533 mmol) in DCM (5 mL) was added iodosobenzene diacetate (206 mg, 0.640 mmol) and the reaction was stirred at ambient temperature for 2 hours. After concentration, the residue was purified by reverse phase chromatography (SP4, 12M, eluting with a gradient of water/ACN 100:0 to 0:100, 20 column volumes) to yield tert-butyl (S)-1-((R)-2,2,2-trifluoro-1-(3-(6-fluoro-8-methoxyquinolin-2-yl)-[1,2,4]triazolo[4,3-a]pyridin-6-yl)ethyl)pyrrolidin-3-ylcarbamate (189 mg, 63.2% yield) as a beige solid Step E: Preparation of (S)-1-((R)-2,2,2-trifluoro-1-(3-(6-fluoro-8-methoxyquinolin-2-yl)-[1,2,4]triazolo[4,3-a]pyridin-6-yl)ethyl)pyrrolidin-3-amine hydrochloride tert-butyl (S)-1-((R)-2,2,2-trifluoro-1-(3-(6-fluoro-8-methoxyquinolin-2-yl)-[1,2,4]triazolo[4,3-a]pyridin-6-yl)ethyl)pyrrolidin-3-ylcarbamate (189 mg, 0.337 mmol) was stirred in TFA (3 mL) for 1 hour then concentrated. The residue was dissolved in minimum methanol and added dropwise to a 4N HCl in ether solution. The resulting solid was filtered and dried to yield (S)-1-((R)-2,2,2-trifluoro-1-(3-(6-fluoro-8-methoxyquinolin-2-yl)-[1,2,4]triazolo[4,3-a]pyridin-6-yl)ethyl)pyrrolidin-3-amine hydrochloride (77 mg, 49.6% yield) as an off-white solid. LCMS APCI (+) m/z 461 (M+H). Specific rotation: $[\alpha]^{20}_D$=–0.15° (c=0.97, MeOH).

Example 116

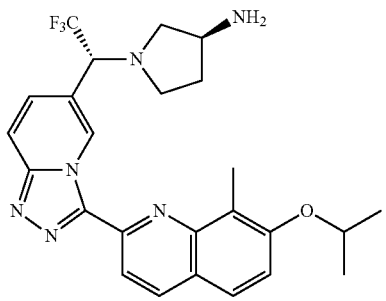 [SMILES: Cc1c(OC(C)C)ccc2ccc(-c3nnc4ccc([C@@H](N5CC[C@H](N)C5)C(F)(F)F)cn34)nc12]

(S)-1-((R)-2,2,2-trifluoro-1-(3-(7-isopropoxy-8-methylquinolin-2-yl)-[1,2,4]triazolo[4,3-a]pyridin-6-yl)ethyl)pyrrolidin-3-amine hydrochloride Step A: Preparation of 2,8-dimethylquinolin-7-ol To 3-amino-2-methylphenol (5.0 g, 41 mmol) in refluxing 6N HCl (100 mL) was added dropwise (E)-but-2-enal (5.7 g, 81 mmol) and the reaction was heated to reflux for 2 hours. After cooling, the reaction was neutralized with ammonium hydroxide and extracted with DCM. The combined organic phases were dried over MgSO$_4$, filtered and concentrated under reduced pressure to yield 2,8-dimethylquinolin-7-ol (9.0 g, 51% yield) as a brown solid.

Step B: Preparation of 7-isopropoxy-2,8-dimethylquinoline 2,8-Dimethylquinolin-7-ol (1.0 g, 2.31 mmol), 2-iodopropane (0.785 g, 4.62 mmol) and potassium carbonate (0.957 g, 6.93 mmol) in acetone (15 mL) were heated to 70° C. in a sealed tube for 18 hours. After cooling, water (20 mL) was added and the aqueous phase was extracted with DCM. The combined organic phases were dried over MgSO$_4$, filtered and concentrated under reduced pressure. The residue was purified by reverse phase chromatography (SP4, 25M, eluting with a gradient of water/ACN 100:0 to 0:100, 20 column volumes) to yield 7-isopropoxy-2,8-dimethylquinoline (120 mg, 24.1% yield) as an oil Step C: Preparation of 7-isopropoxy-8-methylquinoline-2-carbaldehyde To 7-isopropoxy-2,8-dimethylquinoline (120 mg, 0.557 mmol) in dioxane/water (5 mL/0.5 mL) at ambient temperature was added selenium dioxide (74.2 mg, 0.669 mmol) and the reaction was heated to reflux for 2 hours. After cooling, the reaction was filtered and the solids were washed with DCM. The filtrate was dried over MgSO$_4$, filtered and concentrated under reduced pressure. The residue was purified by reverse phase chromatography (SP4, 12M, eluting with a gradient of water/ACN 100:0 to 0:100, 20 column volumes) to yield 7-isopropoxy-8-methylquinoline-2-carbaldehyde (45 mg, 35.2% yield) as a tan solid.

Step D: Preparation of (S)-1-((R)-2,2,2-trifluoro-1-(3-(7-isopropoxy-8-methylquinolin-2-yl)-[1,2,4]triazolo[4,3-a]pyridin-6-yl)ethyl)pyrrolidin-3-amine hydrochloride Prepared as in Example 86 Steps D, E, and F, replacing 6-fluoro-8-isopropoxyquinoline-2-carbaldehyde in Step D with 7-isopropoxy-8-methylquinoline-2-carbaldehyde. LCMS APCI (+) m/z 485 (M+H).

Example 117

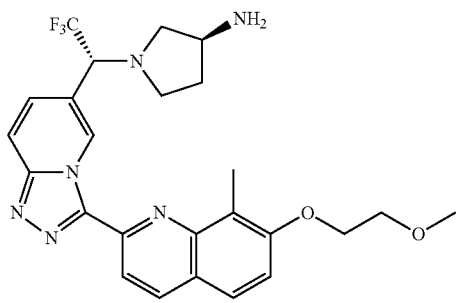 [SMILES: COCCOc1ccc2ccc(-c3nnc4ccc([C@@H](N5CC[C@H](N)C5)C(F)(F)F)cn34)nc2c1C]

(S)-1-((R)-2,2,2-trifluoro-1-(3-(7-(2-methoxyethoxy)-8-methylquinolin-2-yl)-[1,2,4]triazolo[4,3-a]pyridin-6-yl)ethyl)pyrrolidin-3-amine hydrochloride Step A: Preparation of 7-(2-methoxyethoxy)-2,8-dimethylquinoline 1-Bromo-2-methoxyethane (0.64 g, 4.6 mmol), 2,8-dimethylquinolin-7-ol (1.0 g, 2.3 mmol) and potassium carbonate (0.96 g, 6.9 mmol) in acetone (15 mL) were heated to 70° C. in a sealed tube for 18 hours. After cooling, water (20 mL) was added and the aqueous phase was extracted with DCM. The combined organic phases were dried over MgSO$_4$, filtered and concentrated under reduced pressure. The residue was purified by reverse phase chromatography (SP4, 25M, eluting with a gradient of water/ACN 100:0 to 0:100, 20 column volumes) to yield 7-(2-methoxyethoxy)-2,8-dimethylquinoline (90 mg, 17% yield) as an oil Step B: Preparation of 7-(2-methoxyethoxy)-8-methylquinoline-2-carbaldehyde To 7-(2-methoxyethoxy)-2,8-dimethylquinoline (90 mg, 0.39 mmol) in dioxane/water (5 mL/0.5 mL) at ambient temperature was added selenium dioxide (52 mg, 0.47 mmol) and the reaction was heated to reflux for 1 hour. After cooling, the reaction was filtered and the solids washed with DCM. The filtrate was dried over MgSO$_4$, filtered and concentrated under reduced pressure. The residue was purified by reverse phase chromatography (SP4, 12M, eluting with a gradient of water/ACN 100:0 to 0:100, 20 column volumes) to yield 7-(2-methoxyethoxy)-8-methylquinoline-2-carbaldehyde (67 mg, 70% yield) as a tan solid.

Step C: Preparation of tert-butyl (S)-1-((R)-2,2,2-trifluoro-1-(6-((E)-2-((7-(2-methoxyethoxy)-8-methylquinolin-2-yl)methylene)hydrazinyl)pyridin-3-yl)ethyl)pyrrolidin-3-ylcarbamate tert-Butyl (S)-1-((R)-2,2,2-trifluoro-1-(6-hydrazinylpyridin-3-yl)ethyl)pyrrolidin-3-ylcarbamate (98.0 mg, 0.261 mmol) and 7-(2-methoxyethoxy)-8-methylquinoline-2-carbaldehyde (64 mg, 0.261 mmol) were stirred in ethanol at ambient temperature for 24 hours. The reaction was concentrated and used as is in the next step.

Step D: Preparation of tert-butyl (S)-1-((R)-2,2,2-trifluoro-1-(3-(7-(2-methoxyethoxy)-8-methylquinolin-2-yl)-[1,2,4]triazolo[4,3-a]pyridin-6-yl)ethyl)pyrrolidin-3-ylcarbamate To tert-butyl (S)-1-((R)-2,2,2-trifluoro-1-(6-((E)-2-((7-(2-methoxyethoxy)-8-methylquinolin-2-yl)methylene)hydrazinyl)pyridin-3-yl)ethyl)pyrrolidin-3-ylcarbamate (157 mg, 0.261 mmol) in DCM (5 mL) was added iodosobenzene diacetate (101 mg, 0.313 mmol) and the reaction was stirred at ambient temperature for 2 hours. After concentration, the residue was purified by reverse phase chromatography (SP4, 12M, eluting with a gradient of water/ACN 100:0 to 0:100, 20 column volumes) to yield tert-butyl (S)-1-((R)-2,2,2-trifluoro-1-(3-(7-(2-methoxyethoxy)-8-methylquinolin-2-yl)-[1,2,4]triazolo[4,3-a]pyridin-6-yl)ethyl)pyrrolidin-3-ylcarbamate (93 mg, 59.4% yield) as a beige solid Step E: Preparation of (S)-1-((R)-2,2,2-trifluoro-1-(3-(7-(2-methoxyethoxy)-8-methylquinolin-2-yl)-[1,2,4]triazolo[4,3-a]pyridin-6-yl)ethyl)pyrrolidin-3-amine hydrochloride tert-butyl (S)-1-((R)-2,2,2-trifluoro-1-(3-(7-(2-methoxyethoxy)-8-methylquinolin-2-yl)-[1,2,4]triazolo[4,3-a]pyridin-6-yl)ethyl)pyrrolidin-3-ylcarbamate (93 mg, 0.15 mmol) was stirred in TFA (3 mL) for 1 hour and then concentrated. The residue was dissolved in minimum methanol and added dropwise to a 4N HCl in ether solution. The resulting solid was filtered and dried to yield (S)-1-((R)-2,2,2-trifluoro-1-(3-(7-(2-methoxyethoxy)-8-methylquinolin-2-yl)-[1,2,4]triazolo[4,3-a]pyridin-6-yl)ethyl)pyrrolidin-3-amine hydrochloride (87 mg, 112% yield) as an off-white solid. LCMS APCI (+) m/z 501 (M+H).

Example 118

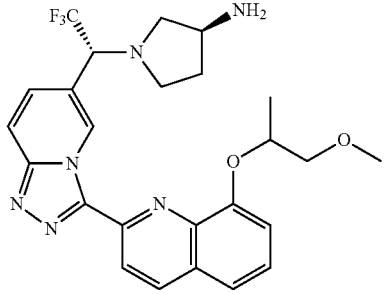 [SMILES: COCC(C)Oc1cccc2ccc(-c3nnc4ccc([C@@H](N5CC[C@H](N)C5)C(F)(F)F)cn34)nc12]

(3S)-1-((1R)-2,2,2-trifluoro-1-(3-(8-(1-methoxypropan-2-yloxy)quinolin-2-yl)-[1,2,4]triazolo[4,3-a]pyridin-6-yl)ethyl)pyrrolidin-3-amine hydrochloride Step A: Preparation of 8-(1-methoxypropan-2-yloxy)-2-methylquinoline To 2-methylquinolin-8-ol (1.0 g, 6.28 mmol) in THF (5 mL) was added PPh$_3$ (6.92 g, 26.4 mmol), DEAD (1.58 ml, 10.1 mmol) and 1-methoxypropan-2-ol (0.736 g, 8.17 mmol). The reaction was stirred for 24 hours at ambient temperature and then water was added. The aqueous phase was extracted with DCM and the combined organic phases dried over MgSO$_4$, filtered and purified by reverse chromatography (SP4, 40M, eluting with a gradient of water/ACN 100:0 to 0:100, 20 column volumes) to yield 8-(1-methoxypropan-2-yloxy)-2-methylquinoline (1.0 g, 68.8% yield) as a clear liquid Step B: Preparation of 8-(1-methoxypropan-2-yloxy)quinoline-2-carbaldehyde To 8-(1-methoxypropan-2-yloxy)-2-methylquinoline (1.0 g, 4.32 mmol) in dioxane/water (10/1 mL) was added selenium dioxide (0.576 g, 5.19 mmol) and the reaction was heated to reflux for 2 hours. The reaction was concentrated to dryness and the residue purified by reverse phase chromatography (SP4, 25M, eluting with a gradient of water/ACN 100:0 to 0:100, 20 column volumes) to yield 8-(1-methoxypropan-2-yloxy)quinoline-2-carbaldehyde (874 mg, 82.4% yield) as a solid Step C: Preparation of (3S)-1-((1R)-2,2,2-trifluoro-1-(3-(8-(1-methoxypropan-2-yloxy)quinolin-2-yl)-[1,2,4]triazolo[4,3-a]pyridin-6-yl)ethyl)pyrrolidin-3-amine hydrochloride Prepared as in Example 86 Steps D, E, and F, replacing 6-fluoro-8-isopropoxyquinoline-2-carbaldehyde in Step D with 8-(1-methoxypropan-2-yloxy)quinoline-2-carbaldehyde. LCMS APCI (+) m/z 501 (M+H).

Example 119

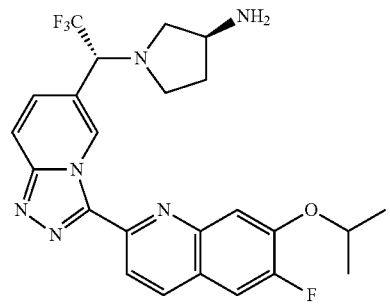 [SMILES: CC(C)Oc1cc2nc(-c3nnc4ccc([C@@H](N5CC[C@H](N)C5)C(F)(F)F)cn34)ccc2cc1F]

(S)-1-((R)-2,2,2-trifluoro-1-(3-(6-fluoro-7-isopropoxyquinolin-2-yl)-[1,2,4]triazolo[4,3-a]pyridin-6-yl)ethyl)pyrrolidin-3-amine hydrochloride Step A: Preparation of 6-fluoro-7-methoxy-2-methylquinoline To 4-fluoro-3-methoxyaniline (4.0 g, 28 mmol) refluxing in 6N HCl (50 mL) was added dropwise (E)-but-2-enal (4.0 g, 57 mmol). The reaction was heated to reflux for 2 hours then cooled and neutralized with NH$_4$OH. The organic phase was extracted with DCM. The combined organic phases dried over MgSO$_4$, filtered and concentrated under reduced pressure to provide 6-fluoro-7-methoxy-2-methylquinoline (5.2 g, 96% yield) as a dark brown paste.

Step B: Preparation of 6-fluoro-2-methylquinolin-7-ol

6-Fluoro-7-methoxy-2-methylquinoline (5.2 g, 19 mmol) was heated to reflux in 48% aqueous HBr for 48 hours. After cooling, the reaction was basified (pH 8) by addition of NH₄OH. The resulting solid was filtered, washed with water and dried to yield 6-fluoro-2-methylquinolin-7-ol (4.5 g, 93% yield) as a black solid.

Step C: Preparation of 6-fluoro-7-isopropoxy-2-methylquinoline

To 6-fluoro-2-methylquinolin-7-ol (800 mg, 3.16 mmol) in acetone (5 mL) were added 2-iodopropane (1075 mg, 6.32 mmol) and potassium carbonate (1310 mg, 9.48 mmol). The reaction was stirred at 70° C. in a sealed tube for 18 hours then cooled and diluted with water. The aqueous phase was extracted with DCM, dried over MgSO₄, filtered and concentrated under reduced pressure to yield 6-fluoro-7-isopropoxy-2-methylquinoline (270 mg, 39.0% yield) as an oil.

Step D: Preparation of 6-fluoro-7-isopropoxyquinoline-2-carbaldehyde

To 6-fluoro-7-isopropoxy-2-methylquinoline (270 mg, 1.23 mmol) in dioxane/water (5 mL/0.05 mL) was added selenium dioxide (164 mg, 1.48 mmol) and the reaction was heated to reflux for 2 hours. After cooling and concentrating, the residue was purified by chromatography (SP4, 25M, eluting with a gradient of water/ACN 100:0 to 0:100, 20 column volumes) to yield 6-fluoro-7-isopropoxyquinoline-2-carbaldehyde as a solid.

Step E: Preparation of tert-butyl (S)-1-((R)-2,2,2-trifluoro-1-(6-((E)-2-((6-fluoro-7-isopropoxyquinolin-2-yl)methylene)hydrazinyl)pyridin-3-yl)ethyl)pyrrolidin-3-ylcarbamate tert-Butyl (S)-1-((R)-2,2,2-trifluoro-1-(6-hydrazinylpyridin-3-yl)ethyl)pyrrolidin-3-ylcarbamate (451 mg, 1.20 mmol) and 6-fluoro-7-isopropoxyquinoline-2-carbaldehyde (280 mg, 1.20 mmol) in ethanol (5 mL) were stirred at ambient temperature for 24 hours. After concentration, the residue was used in the next step without purification.

Step F: Preparation of tert-butyl (S)-1-((R)-2,2,2-trifluoro-1-(3-(6-fluoro-7-isopropoxyquinolin-2-yl)-[1,2,4]triazolo[4,3-a]pyridin-6-yl)ethyl)pyrrolidin-3-ylcarbamate To tert-butyl (S)-1-((R)-2,2,2-trifluoro-1-(6-((E)-2-((6-fluoro-7-isopropoxyquinolin-2-yl)methylene)hydrazinyl)pyridin-3-yl)ethyl)pyrrolidin-3-ylcarbamate (700 mg, 1.19 mmol) in DCM was added iodosobenzene acetate (496 mg, 1.54 mmol) and the reaction was stirred at ambient temperature for 2 hours. After concentration, the residue was purified by reverse phase chromatography (SP4, 25M, eluting with a gradient of water/ACN 100:0 to 0:100, 25 column volumes) to yield tert-butyl (S)-1-((R)-2,2,2-trifluoro-1-(3-(6-fluoro-7-isopropoxyquinolin-2-yl)-[1,2,4]triazolo[4,3-a]pyridin-6-yl)ethyl)pyrrolidin-3-ylcarbamate (280 mg, 40.1% yield) as a beige solid.

Step G: Preparation of (S)-1-((R)-2,2,2-trifluoro-1-(3-(6-fluoro-7-isopropoxyquinolin-2-yl)-[1,2,4]triazolo[4,3-a]pyridin-6-yl)ethyl)pyrrolidin-3-amine tert-Butyl (S)-1-((R)-2,2,2-trifluoro-1-(3-(6-fluoro-7-isopropoxyquinolin-2-yl)-[1,2,4]triazolo[4,3-a]pyridin-6-yl)ethyl)pyrrolidin-3-ylcarbamate (280 mg, 0.476 mmol) was stirred in TFA (3 mL) for 1 hour then concentrated. The residue was dissolved in minimum methanol and added dropwise to a 4N HCl in ether solution. The resulting solid was filtered and dried to yield (S)-1-((R)-2,2,2-trifluoro-1-(3-(6-fluoro-7-isopropoxyquinolin-2-yl)-[1,2,4]triazolo[4,3-a]pyridin-6-yl)ethyl)pyrrolidin-3-amine (150 mg, 64.6% yield) hydrochloride as an off-white solid. LCMS APCI (+) m/z 489 (M+H).

Example 120

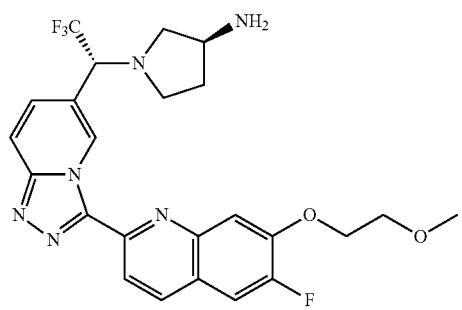 [SMILES: COCCOc1cc2nc(-c3nnc4ccc([C@@H](N5CC[C@H](N)C5)C(F)(F)F)cn34)ccc2cc1F]

(S)-1-((R)-2,2,2-trifluoro-1-(3-(6-fluoro-7-(2-methoxyethoxy)quinolin-2-yl)-[1,2,4]triazolo[4,3-a]pyridin-6-yl)ethyl)pyrrolidin-3-amine hydrochloride Prepared as in Example 119 substituting 2-iodopropane in Step C with 1-bromo-2-methoxyethane. LCMS APCI (+) m/z 505 (M+H).

Example 121

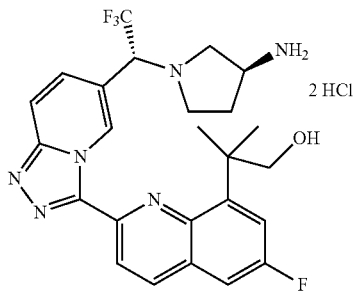 [SMILES: CC(C)(CO)c1cc(F)cc2ccc(-c3nnc4ccc([C@@H](N5CC[C@H](N)C5)C(F)(F)F)cn34)nc12 ; "2 HCl"]

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-yl)-2-methylpropan-1-ol dihydrochloride

Step A: Preparation of 2-(6-fluoro-2-methylquinolin-8-yl)-2-methylpropan-1-ol Prepared as described in Example 105 using 8-bromo-6-fluoro-2-methylquinoline in place of 8-bromo-2-methylquinoline in Step A.

Step B: Preparation of 2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-yl)-2-methylpropan-1-ol dihydrochloride Prepared as described in Example 114 using 2-(6-fluoro-2-methylquinolin-8-yl)-2-methylpropan-1-ol in place of (1-(2-methylquinolin-8-yl)cyclopropyl)methanol in Step A. LCMS APCI (+) m/z 503 (M+H).

Example 122

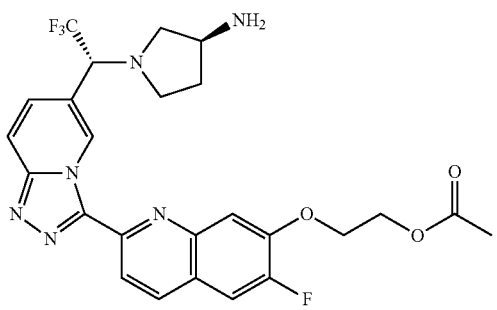 [SMILES: CC(=O)OCCOc1cc2nc(-c3nnc4ccc([C@@H](N5CC[C@H](N)C5)C(F)(F)F)cn34)ccc2cc1F]

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)ethyl acetate hydrochloride

Step A: Preparation of 2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)-6-fluoroquinolin-7-yloxy)ethyl acetate Prepared as in Example 119 (Steps A-F) substituting 2-iodopropane in Step C with 2-bromoethyl acetate.

Step B: Preparation of 2-(2-(6-((R)-1-((S)-3-aminopyrrolidin-1-yl)-2,2,2-trifluoroethyl)-[1,2,4]triazolo[4,3-a]pyridin-3-yl)-6-fluoro quinolin-7-yloxy) ethyl acetate 2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)-6-fluoroquinolin-7-yloxy)ethyl acetate (40 mg, 0.063 mmol) was stirred in TFA (3 mL) for 1 hour and then concentrated. The residue was dissolved in minimum methanol and added dropwise to a 4N HCl in ether solution. The resulting solid was filtered and dried to yield 2-(2-(6-((R)-1-((S)-3-aminopyrrolidin-1-yl)-2,2,2-trifluoroethyl)-[1,2,4]triazolo[4,3-a]pyridin-3-yl)-6-fluoro quinolin-7-yloxy)ethyl acetate (27 mg, 80% yield) hydrochloride as an off-white solid. LCMS APCI (+) m/z 505 (M+H).

Example 123

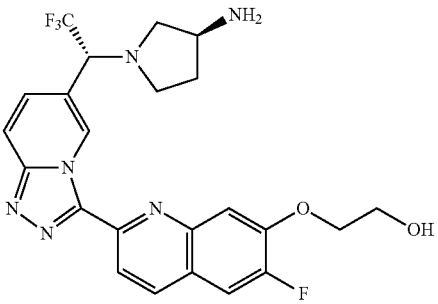 [SMILES: N[C@H]1CCN([C@H](c2ccc3nnc(-c4ccc5cc(F)c(OCCO)cc5n4)n3c2)C(F)(F)F)C1]

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)ethanol hydrochloride

Step A: Preparation of tert-butyl (S)-1-((R)-2,2,2-trifluoro-1-(3-(6-fluoro-7-(2-hydroxyethoxy)quinolin-2-yl)-[1,2,4]triazolo[4,3-a]pyridin-6-yl)ethyl)pyrrolidin-3-ylcarbamate To 2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)-6-fluoro quinolin-7-yloxy)ethyl acetate (250 mg, 0.395 mmol) (Example 122, Step A) in MeOH (5 mL) was added 2N LiOH (1 mL) and the reaction was stirred at ambient temperature for 1 hour. The reaction was concentrated and the residue purified by reverse phase chromatography (SP4, 12M, eluting with a gradient of water/ACN 100:0 to 0:100, 25 column volumes) to yield tert-butyl (S)-1-((R)-2,2,2-trifluoro-1-(3-(6-fluoro-7-(2-hydroxyethoxy)quinolin-2-yl)-[1,2,4]triazolo[4,3-a]pyridin-6-yl)ethyl)pyrrolidin-3-ylcarbamate (210 mg, 90.0% yield) as a white solid.

Step B: Preparation of 2-(2-(6-((R)-1-((S)-3-aminopyrrolidin-1-yl)-2,2,2-trifluoroethyl)-[1,2,4]triazolo[4,3-a]pyridin-3-yl)-6-fluoro quinolin-7-yloxy) ethanol hydrochloride tert-butyl (S)-1-((R)-2,2,2-trifluoro-1-(3-(6-fluoro-7-(2-hydroxyethoxy)quinolin-2-yl)-[1,2,4]triazolo[4,3-a]pyridin-6-yl)ethyl)pyrrolidin-3-ylcarbamate (200 mg, 0.339 mmol) was stirred in TFA (3 mL) for 1 hour and then concentrated. The residue was dissolved in minimum methanol and added dropwise to a 4N HCl in ether solution. The resulting solid was filtered and dried to yield 2-(2-(6-((R)-1-((S)-3-aminopyrrolidin-1-yl)-2,2,2-trifluoroethyl)-[1,2,4]triazolo[4,3- a]pyridin-3-yl)-6-fluoro quinolin-7-yloxy)ethanol (128 mg, 77.1% yield) hydrochloride as an off-white solid. LCMS APCI (+) m/z 491 (M+H).

Example 124

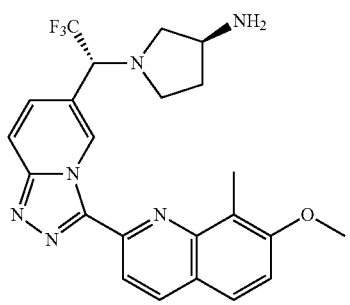

(S)-1-((R)-2,2,2-trifluoro-1-(3-(7-methoxy-8-methylquinolin-2-yl)-[1,2,4]triazolo[4,3-a]pyridin-6-yl) ethyl)pyrrolidin-3-amine hydrochloride Prepared as in Example 117, substituting 1-bromo-2-methoxyethane in Step A with iodomethane. LCMS APCI (+) m/z 457 (M+H).

Example 125

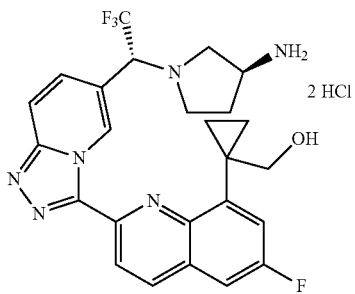 [SMILES: N[C@H]1CCN([C@H](c2ccc3nnc(-c4ccc5cc(F)cc(C6(CO)CC6)c5n4)n3c2)C(F)(F)F)C1 ; "2 HCl"]

(1-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-yl)cyclopropyl)methanol dihydrochloride Prepared as described in Example 114 using 2-(6-fluoro-2-methylquinolin-8-yl)-2-methylpropan-1-ol in place of (1-(2-methylquinolin-8-yl)cyclopropyl)methanol in Step A. LCMS APCI (+) m/z 501 (M+H).

Example 126

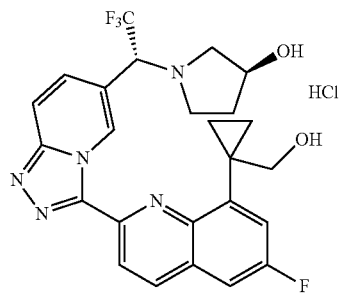 [SMILES: OCC1(c2cc(F)cc3ccc(-c4nnc5ccc([C@@H](N6CC[C@H](O)C6)C(F)(F)F)cn45)nc23)CC1 ; Cl]

(S)-1-((R)-2,2,2-trifluoro-1-(3-(6-fluoro-8-(1-(hydroxymethyl)cyclopropyl)quinolin-2-yl)-[1,2,4]triazolo[4,3-a]pyridin-6-yl)ethyl)pyrrolidin-3-ol hydrochloride Step A: Preparation of (S)-1-((R)-1-(3-(7-bromoquinolin-2-yl)-[1,2,4]triazolo[4,3-a]pyridin-6-yl)-2,2,2-trifluoroethyl)pyrrolidin-3-ol Prepared as in Example 1, Steps A-E, using (S)-pyrrolidin-3-ol in place of (S)-tert-butyl pyrrolidin-3-ylcarbamate in Step C.

Step B: Preparation of 8-(1-(((tert-butyldimethylsilyl)oxy)methyl)cyclopropyl)-6-fluoro-2-methylquinoline Prepared according to Example 114, Step A, using 2-(6-fluoro-2-methylquinolin-8-yl)-2-methylpropan-1-ol in place of (1-(2-methylquinolin-8-yl)cyclopropyl)methanol.

Step C: Preparation of (S)-1-((R)-2,2,2-trifluoro-1-(3-(6-fluoro-8-(1-(hydroxymethyl)cyclopropyl) quinolin-2-yl)-[1,2,4]triazolo[4,3-a]pyridin-6-yl) ethyl)pyrrolidin-3-ol hydrochloride Prepared as described in Example 114, Step B, using (S)-1-((R)-1-(3-(7-bromo quinolin-2-yl)-[1,2,4]triazolo[4,3-a] pyridin-6-yl)-2,2,2-trifluoroethyl)pyrrolidin-3-ol and 8-(1-(((tert-butyldimethylsilyl)oxy)methyl)cyclopropyl)-6-fluoro-2-methylquinoline. LCMS APCI (+) m/z 502 (M+H).

Example 127

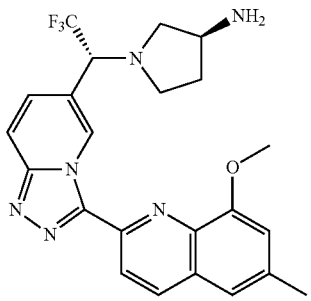 [SMILES: COc1cc(C)cc2ccc(-c3nnc4ccc([C@@H](N5CC[C@H](N)C5)C(F)(F)F)cn34)nc12]

(S)-1-((R)-2,2,2-trifluoro-1-(3-(8-methoxy-6-methylquinolin-2-yl)-[1,2,4]triazolo[4,3-a]pyridin-6-yl)ethyl)pyrrolidin-3-amine hydrochloride Prepared as in Example 86, substituting 4-fluoro-2-methoxyaniline in Step A with 2-amino-5-methylphenol and 2-iodopropane in Step B with iodomethane. LCMS APCI (+) m/z 457 (M+H).

Example 128

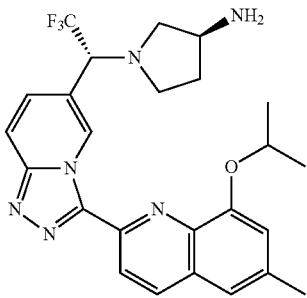 [SMILES: Cc1cc(OC(C)C)c2nc(-c3nnc4ccc([C@@H](N5CC[C@H](N)C5)C(F)(F)F)cn34)ccc2c1]

(S)-1-((R)-2,2,2-trifluoro-1-(3-(8-isopropoxy-6-methylquinolin-2-yl)-[1,2,4]triazolo[4,3-a]pyridin-6-yl)ethyl)pyrrolidin-3-amine hydrochloride Prepared as in Example 86, substituting 4-fluoro-2-methoxyaniline in Step A with 2-amino-5-methylphenol. LCMS APCI (+) m/z 485 (M+H).

Example 129

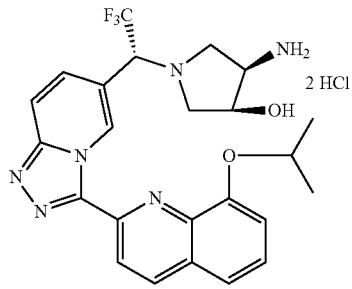 [SMILES: CC(C)Oc1cccc2ccc(-c3nnc4ccc([C@@H](N5C[C@@H](N)[C@@H](O)C5)C(F)(F)F)cn34)nc12]

(3S,4R)-4-amino-1-((R)-2,2,2-trifluoro-1-(3-(8-isopropoxyquinolin-2-yl)-[1,2,4]triazolo[4,3-a]pyridin-6-yl)ethyl)pyrrolidin-3-ol dihydrochloride Step A: Preparation of (3S,4S)-tert-butyl 3,4-dihydroxypyrrolidine-1-carboxylate To a stirred solution of (3S,4S)-pyrrolidine-3,4-diol (2.49 g, 24.1 mmol) (Example 19) in methanol (70 mL) at ambient temperature was added triethylamine (6.7 mL, 48.3 mmol), followed by DMAP (0.12 g, 0.97 mmol) and Boc$_2$O (7.90 g, 36.2 mmol). The mixture was stirred at ambient temperature for 18 hours. The mixture was concentrated under reduced pressure. The residue was purified by column chromatography (Biotage 40M; 5% MeOH/dichloromethane) to afford (3S,4S)-tert-butyl 3,4-dihydroxypyrrolidine-1-carboxylate (2.79 g, 57%).

Step B: Preparation of (3S,4S)-tert-butyl 3-(bis(4-methoxyphenyl)(phenyl)methoxy)-4-hydroxypyrrolidine-1-carboxylate To a solution of (3S,4S)-tert-butyl 3,4-dihydroxypyrrolidine-1-carboxylate (2.79 g, 13.7 mmol) in anhydrous pyridine (144 mL) was added 4,4'-(chloro(phenyl)methylene)bis(methoxybenzene) (5.43 g 15.2 mmol) and the resulting mixture stirred at ambient temperature for 4 days. The reaction was quenched with methanol (10 mL) and concentrated under reduced pressure. The residue was stirred in diethyl ether (150 mL) and the solid which precipitated was collected by filtration. The filtrate was concentrated under reduced pressure and purified by column chromatography (Biotage, 40M; 1% methanol:dichloromethane) to afford (3S,4S)-tert-butyl 3-(bis(4-methoxyphenyl)(phenyl)methoxy)-4-hydroxypyrrolidine-1-carboxylate (4.48 g, 65%).

Step C: Preparation of (3S,4S)-tert-butyl 3-(bis(4-methoxyphenyl)(phenyl)methoxy)-4-(methylsulfonyloxy)pyrrolidine-1-carboxylate To a solution of (3S,4S)-tert-butyl 3-(bis(4-methoxyphenyl)(phenyl)methoxy)-4-hydroxypyrrolidine-1-carboxylate (3.50 g, 6.92 mmol) and DMAP (4.23 g, 34.61 mmol) in dichloromethane (60 mL) at 0° C. in an ice bath was added methanesulfonyl chloride (2.69 mL, 34.61 mmol) dropwise. The resulting mixture was stirred at ambient temperature for 1 hour, cooled to 0° C. in an ice bath and quenched with water (15 mL). The layers were separated and the organic layer was washed with saturated sodium bicarbonate solution (60 mL), dried (MgSO$_4$), filtered and concentrated under reduced pressure to give (3S,4S)-tert-butyl 3-(bis(4-methoxyphenyl)(phenyl)methoxy)-4-(methylsulfonyloxy)pyrrolidine-1-carboxylate (4.01 g, 99%).

Step D: Preparation of (3R,4S)-tert-butyl 3-azido-4-(bis(4-methoxyphenyl)(phenyl)methoxy)pyrrolidine-1-carboxylate To a solution of (3S,4S)-tert-butyl 3-(bis(4-methoxyphenyl)(phenyl)methoxy)-4-(methylsulfonyloxy)pyrrolidine-1-carboxylate (4.0 g, 6.85 mmol) in anhydrous DMSO (70 mL) was added sodium azide (1.78 g, 27.4 mmol). The resulting mixture was heated at 100° C. for 18 hours. The solution was cooled to ambient temperature, poured into water (150 mL) and the solid which separated was collected by filtration and washed with water and dried to afford (3R,4S)-tert-butyl 3-azido-4-(bis(4-methoxyphenyl)(phenyl)methoxy)pyrrolidine-1-carboxylate (3.37 g, 93%).

Step E: Preparation of (3R,4S)-tert-butyl 3-(benzyloxycarbonylamino)-4-(bis(4-methoxyphenyl)(phenyl)methoxy)pyrrolidine-1-carboxylate To a solution of (3R,4S)-tert-butyl 3-azido-4-(bis(4-methoxyphenyl)(phenyl)methoxy)pyrrolidine-1-carboxylate (3.0 g, 5.65 mmol) in anhydrous THF (70 mL) was added triphenylphosphine (2.97 g, 11.3 mmol). The resulting mixture was stirred at ambient temperature for 18 hours. The mixture was concentrated under reduced pressure and to the residue were added methanol (35 mL) and a 0.5 N sodium hydroxide solution (35 mL). The mixture was stirred at ambient temperature 18 hours, and then partitioned between water (35 mL) and ethyl acetate (150 mL). The layers were separated and the aqueous layer was back extracted with ethyl acetate. The combined organic extracts washed with water and brine, dried (MgSO₄), filtered and concentrated under reduce pressure. The residue was purified by column chromatography (Biotage 40M; 2.5% MeOH:dichloromethane). To a solution of (3R,4S)-tert-butyl 3-amino-4-(bis(4-methoxyphenyl)(phenyl)methoxy)pyrrolidine-1-carboxylate (2.85 g, 5.65 mmol) in a 50% mixture of 1,4-dioxane/water (20 mL) was added sodium carbonate (0.72 g, 6.78 mmol) and the mixture cooled to 0° C. in an ice bath. Benzyl chloroformate (1 mL, 6.78 mmol) was added dropwise and the mixture was stirred at 0° C. for 30 minutes and then at ambient temperature for 18 hours. The mixture was partitioned between water (20 mL) and diethyl ether (100 mL), and the layers were separated. The organic layer was washed sequentially with water, saturated sodium bicarbonate and brine, then dried (MgSO₄), filtered and concentrated under reduced pressure. The residue was purified by column chromatography (Biotage 40M 25% ethyl acetate/hexanes) to afford (3R,4S)-tert-butyl 3-(benzyloxycarbonylamino)-4-(bis(4-methoxyphenyl)(phenyl)methoxy)pyrrolidine-1-carboxylate (2.18 g, 60%).

Step F: Preparation of Benzyl (3R,4S)-4-hydroxypyrrolidin-3-ylcarbamate

A solution of (3R,4S)-tert-butyl 3-(benzyloxycarbonylamino)-4-(bis(4-methoxyphenyl)(phenyl)methoxy)pyrrolidine-1-carboxylate (2.18 g, 3.14 mmol) was stirred in a 10% TFA/dichloromethane solution (30 mL) for 30 minutes. The solution was concentrated under reduced pressure and the residue dissolved in ethyl acetate (15 mL) and treated with 2N HCl-diethyl ether (30 mL) for 1 hour. The resulting precipitate was collected by filtration and washed with ethyl acetate and dried to an off-white solid. The solid was dissolved in a 50% MeOH:dichloromethane solution (30 mL) and stirred with solid sodium carbonate (5 g) for 2.5 hours. The solids were collected by filtration and washed with 50% MeOH/dichloromethane solution and the filtrate concentrated under reduced pressure to give benzyl (3R,4S)-4-hydroxypyrrolidin-3-ylcarbamate (0.80 g, 99%).

Step G: Preparation of benzyl (3R,4S)-1-((R)-1-(6-chloropyridin-3-yl)-2,2,2-trifluoroethyl)-4-hydroxy-pyrrolidin-3-ylcarbamate Prepared as described in Example 9B using (S)-1-(6-chloropyridin-3-yl)-2,2,2-trifluoroethyl trifluoromethanesulfonate (1.06 g, 3.08 mmol) and benzyl (3R,4S)-4-hydroxypyrrolidin-3-ylcarbamate (0.802 g, 3.39 mmol) in place of (S)-tert-butyl pyrrolidin-3-ylcarbamate in Step D (1.16 g, 88%).

Step H: Preparation of tert-butyl (3R,4S)-4-hydroxy-1-((R)-2,2,2-trifluoro-1-(6-hydrazinylpyridin-3-yl)ethyl)pyrrolidin-3-ylcarbamate To a solution of benzyl (3R,4S)-1-((R)-1-(6-chloropyridin-3-yl)-2,2,2-trifluoroethyl)-4-hydroxypyrrolidin-3-ylcarbamate (1.16 g, 2.7 mmol) in acetonitrile (2 mL) cooled to 0° C. in an ice bath was added iodotrimethylsilane (1.22 mL, 8.10 mmol) and the mixture allowed to warm to ambient temperature for 1 hour. The reaction mixture was poured into aqueous 1N HCl (15 mL) and stirred for 10 minutes and extracted with diethyl ether. The aqueous layer was pH adjusted to 10 with a 5N sodium hydroxide solution and extracted with ethyl acetate. The organic extract was dried (MgSO₄), filtered and concentrated under reduced pressure. The residue (0.512 g, 1.29 mmol) was combined with anhydrous hydrazine (0.81 mL, 25.87 mmol) in i-BuOH (3 mL) in a sealed tube and heated with stirring at 100° C. for 18 hours. After cooling, the mixture was partitioned between water (15 mL) and ethyl acetate (50 mL). The layers were separated and the organic layer was washed with saturated sodium bicarbonate and brine, dried (MgSO₄), filtered and concentrated under reduced pressure to afford tert-butyl (3R,4S)-4-hydroxy-1-((R)-2,2,2-trifluoro-1-(6-hydrazinylpyridin-3-yl)ethyl)pyrrolidin-3-ylcarbamate (0.44 g, 86%).

Step I: Preparation of (3S,4R)-4-amino-1-((R)-2,2,2-trifluoro-1-(3-(8-isopropoxyquinolin-2-yl)-[1,2,4]triazolo[4,3-a]pyridin-6-yl)ethyl)pyrrolidin-3-ol dihydrochloride Prepared as described in Example 9B using tert-butyl (3R,4S)-4-hydroxy-1-((R)-2,2,2-trifluoro-1-(6-hydrazinylpyridin-3-yl)ethyl)pyrrolidin-3-ylcarbamate in place of tert-butyl (S)-1-((R)-2,2,2-trifluoro-1-(6-hydrazinylpyridin-3-yl)ethyl)pyrrolidine-3-ylcarbamate and substituting 8-isoproxyquinoline-2-carbaldehyde in Step F. LCMS APCI (+) m/z 487 (M+H).

Example 130

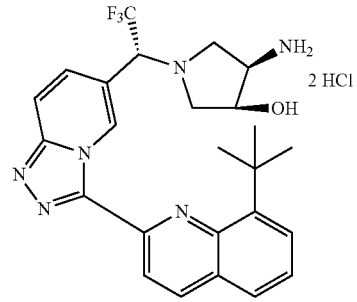 [SMILES: CC(C)(C)c1cccc2ccc(-c3nnc4ccc([C@@H](N5C[C@@H](N)[C@@H](O)C5)C(F)(F)F)cn34)nc12]

(3S,4R)-4-amino-1-((R)-1-(3-(8-tert-butylquinolin-2-yl)-[1,2,4]triazolo[4,3-a]pyridin-6-yl)-2,2,2-trifluoroethyl)pyrrolidin-3-ol dihydrochloride Prepared as described in Example 9B using tert-butyl (3R,4S)-4-hydroxy-1-((R)-2,2,2-trifluoro-1-(6-hydrazinylpyridin-3-yl)ethyl)pyrrolidin-3-ylcarbamate in place of tert-butyl (S)-1-((R)-2,2,2-trifluoro-1-(6-hydrazinylpyridin-3-yl)ethyl)pyrrolidine-3-ylcarbamate and substituting 8-tert-butylquinoline-2-carbaldehyde for 8-methoxyquinoline-2-carbaldehyde in Step F. LCMS APCI (+) m/z 485 (M+H).

Example 131

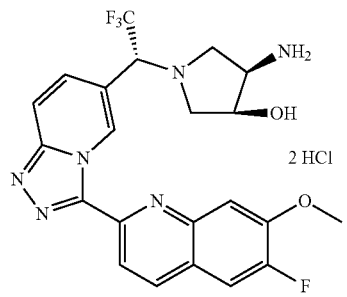 [SMILES: COc1cc2nc(-c3nnc4ccc([C@@H](N5C[C@@H](N)[C@@H](O)C5)C(F)(F)F)cn34)ccc2cc1F]

(3S,4R)-4-amino-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-ol dihydrochloride Prepared as described in Example 9B using tert-butyl (3R,4S)-4-hydroxy-1-((R)-2,2,2-trifluoro-1-(6-hydrazinylpyridin-3-yl)ethyl)pyrrolidin-3-ylcarbamate in place of tert-butyl (S)-1-((R)-2,2,2-trifluoro-1-(6-hydrazinylpyridin-3-yl)ethyl)pyrrolidine-3-ylcarbamate and substituting 6-fluoro-7-methoxyquinoline-2-carbaldehyde for 8-methoxyquinoline-2-carbaldehyde in Step F. LCMS APCI (+) m/z 477 (M+H).

Example 132

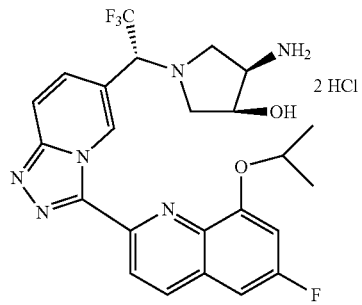 [SMILES: CC(C)Oc1cc(F)cc2ccc(-c3nnc4ccc([C@@H](N5C[C@@H](N)[C@@H](O)C5)C(F)(F)F)cn34)nc12]

(3S,4R)-4-amino-1-((R)-2,2,2-trifluoro-1-(3-(6-fluoro-8-isopropoxyquinolin-2-yl)-[1,2,4]triazolo[4,3-a]pyridin-6-yl)ethyl)pyrrolidin-3-ol dihydrochloride Prepared as described in Example 9B using tert-butyl (3R,4S)-4-hydroxy-1-((R)-2,2,2-trifluoro-1-(6-hydrazinylpyridin-3-yl)ethyl)pyrrolidin-3-ylcarbamate in place of tert-butyl (S)-1-((R)-2,2,2-trifluoro-1-(6-hydrazinylpyridin-3-yl)ethyl)pyrrolidine-3-ylcarbamate and substituting 6-fluoro-8-isopropoxyquinoline-2-carbaldehyde for 8-methoxyquinoline-2-carbaldehyde in Step F. LCMS APCI (+) m/z 505 (M+H).

Example 133

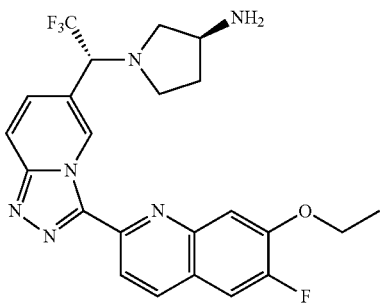 [SMILES: CCOc1cc2nc(-c3nnc4ccc([C@@H](N5CC[C@H](N)C5)C(F)(F)F)cn34)ccc2cc1F]

(S)-1-((R)-1-(3-(7-ethoxy-6-fluoroquinolin-2-yl)-[1,2,4]triazolo[4,3-a]pyridin-6-yl)-2,2,2-trifluoroethyl)pyrrolidin-3-amine hydrochloride Step A: Preparation of
7-ethoxy-6-fluoro-2-methylquinoline 6-fluoro-2-methylquinolin-7-ol (500 mg, 1.41 mmol) (Example 119, Step B), potassium carbonate (585 mg, 4.23 mmol) and bromoethane (308 mg, 2.82 mmol) in acetone (10 mL) were stirred at 70° C. in a sealed tube for 20 hours. After dilution with water (50 mL) the reaction was extracted with DCM. The organic phases were concentrated and the residue purified by reverse phase chromatography (SP4, 25M, eluting with a gradient of water/ACN 100:0 to 0:100, 20 column volumes) to yield 7-ethoxy-6-fluoro-2-methylquinoline (190 mg, 65.6% yield) as a solid.

Step B: Preparation of
7-ethoxy-6-fluoroquinoline-2-carbaldehyde

To 7-ethoxy-6-fluoro-2-methylquinoline (180 mg, 0.877 mmol) in dioxane/water (5 mL/0.05 mL) was added selenium dioxide (136 mg, 1.23 mmol) and the reaction was heated to reflux for 2 hours. After cooling, DCM was added followed by MgSO$_4$. After concentration, the residue was used in the next step without purification.

Step C: Preparation of tert-butyl (S)-1-((R)-1-(6-((E)-2-((7-ethoxy-6-fluoroquinolin-2-yl)methylene)hydrazinyl)pyridin-3-yl)-2,2,2-trifluoroethyl)pyrrolidin-3-ylcarbamate tert-butyl (S)-1-((R)-2,2,2-trifluoro-1-(6-hydrazinylpyridin-3-yl)ethyl)pyrrolidin-3-ylcarbamate (240 mg, 0.639 mmol) and 7-ethoxy-6-fluoroquinoline-2-carbaldehyde (140 mg, 0.639 mmol) in ethanol (5 mL) were stirred at ambient temperature for 24 hours. After concentration, the residue was used in the next step without purification.

Step D: tert-butyl (S)-1-((R)-1-(3-(7-ethoxy-6-fluoroquinolin-2-yl)-[1,2,4]triazolo[4,3-a]pyridin-6-yl)-2,2,2-trifluoroethyl)pyrrolidin-3-ylcarbamate To tert-butyl (S)-1-((R)-1-(6-((E)-2-((7-ethoxy-6-fluoroquinolin-2-yl)methylene)hydrazinyl)pyridin-3-yl)-2,2,2-trifluoroethyl)pyrrolidin-3-ylcarbamate (368 mg, 0.638 mmol) in DCM was added iodosobenzene acetate (267 mg, 0.830 mmol) and the reaction was stirred at ambient temperature for 2 hours. After concentration, the residue was purified by reverse phase chromatography (SP4, 25M, eluting with a gradient of water/ACN 100:0 to 0:100, 20 column volumes) to yield tert-butyl (S)-1-((R)-1-(3-(7-ethoxy-6-fluoroquinolin-2-yl)-[1,2,4]triazolo[4,3-a]pyridin-6-yl)-2,2,2-trifluoroethyl)pyrrolidin-3-ylcarbamate (265 mg, 72.3% yield) as a beige solid Step E: (S)-1-((R)-1-(3-(7-ethoxy-6-fluoro quinolin-2-yl)-[1,2,4]triazolo[4,3-a]pyridin-6-yl)-2,2,2-trifluoroethyl)pyrrolidin-3-amine tert-butyl (S)-1-((R)-1-(3-(7-ethoxy-6-fluoro quinolin-2-yl)-[1,2,4]triazolo[4,3-a]pyridin-6-yl)-2,2,2-trifluoroethyl)pyrrolidin-3-ylcarbamate (265 mg, 0.461 mmol) was stirred in TFA (3 mL) for 1 hour and then concentrated. The residue was dissolved in minimum methanol and added dropwise to a 4N HCl in ether solution. The resulting solid was filtered and dried to yield (S)-1-((R)-1-(3-(7-ethoxy-6-fluoro quinolin-2-yl)-[1,2,4]triazolo[4,3-a]pyridin-6-yl)-2,2,2-trifluoroethyl)pyrrolidin-3-amine (186 mg, 85.0% yield) hydrochloride as an off-white solid. LCMS APCI (+) m/z 475 (M+H). Specific rotation: $[\alpha]^{24}_D = 1.84°$ (c=1.03, MeOH).

Example 134

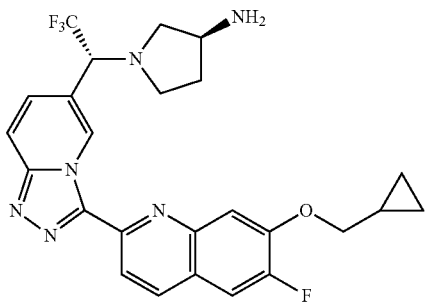 [SMILES: N[C@H]1CCN([C@H](c2ccc3nnc(-c4ccc5cc(F)c(OCC6CC6)cc5n4)n3c2)C(F)(F)F)C1]

(S)-1-((R)-1-(3-(7-(cyclopropylmethoxy)-6-fluoro-quinolin-2-yl)-[1,2,4]triazolo[4,3-a]pyridin-6-yl)-2,2,2-trifluoroethyl)pyrrolidin-3-amine hydrochloride Prepared as in Example 133, substituting bromoethane in Step A with (bromomethyl)cyclopropane. LCMS APCI (+) m/z 501 (M+H).

Example 135

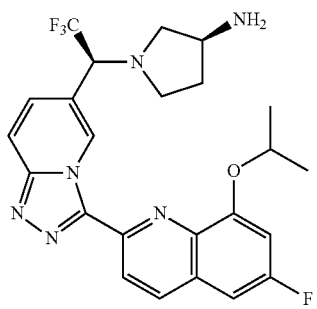 [SMILES: CC(C)Oc1cc(F)cc2ccc(-c3nnc4ccc([C@H](N5CC[C@H](N)C5)C(F)(F)F)cn34)nc12]

(S)-1-((S)-2,2,2-trifluoro-1-(3-(6-fluoro-8-isopropoxyquinolin-2-yl)-[1,2,4]triazolo[4,3-a]pyridin-6-yl)ethyl)pyrrolidin-3-amine hydrochloride Prepared as in Example 86, substituting tert-butyl (S)-1-((R)-2,2,2-trifluoro-1-(6-hydrazinylpyridin-3-yl)ethyl)pyrrolidin-3-ylcarbamate in Step D with tert-butyl (S)-1-((S)-2,2,2-trifluoro-1-(6-hydrazinylpyridin-3-yl)ethyl)pyrrolidin-3-ylcarbamate. LCMS APCI (+) m/z 489 (M+H).

Example 136

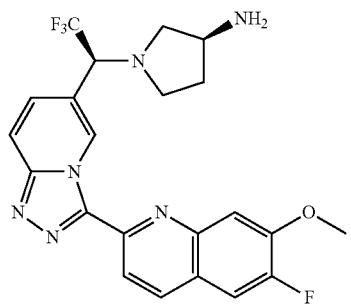 [SMILES: COc1cc2nc(-c3nnc4ccc([C@H](N5CC[C@H](N)C5)C(F)(F)F)cn34)ccc2cc1F]

(S)-1-((S)-2,2,2-trifluoro-1-(3-(6-fluoro-7-methoxyquinolin-2-yl)-[1,2,4]triazolo[4,3-a]pyridin-6-yl)ethyl)pyrrolidin-3-amine hydrochloride Prepared as in Example 113, substituting tert-butyl (S)-1-((R)-2,2,2-trifluoro-1-(6-hydrazinylpyridin-3-yl)ethyl)pyrrolidin-3-ylcarbamate in Step C with tert-butyl (S)-1-((S)-2,2,2-trifluoro-1-(6-hydrazinylpyridin-3-yl)ethyl)pyrrolidin-3-ylcarbamate. LCMS APCI (+) m/z 461 (M+H).

Example 137

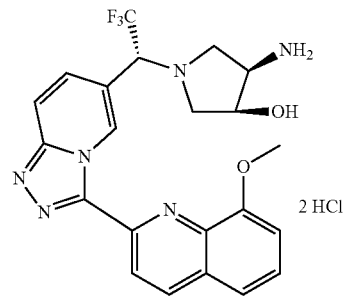 [SMILES: COc1cccc2ccc(-c3nnc4ccc([C@@H](N5C[C@@H](N)[C@@H](O)C5)C(F)(F)F)cn34)nc12]

(3S,4R)-4-amino-1-((R)-2,2,2-trifluoro-1-(3-(8-methoxyquinolin-2-yl)-[1,2,4]triazolo[4,3-a]pyridin-6-yl)ethyl)pyrrolidin-3-ol dihydrochloride Prepared as described in Example 9B, using tert-butyl (3R,4S)-4-hydroxy-1-((R)-2,2,2-trifluoro-1-(6-hydrazinylpyridin-3-yl)ethyl)pyrrolidin-3-ylcarbamate in place of tert-butyl (S)-1-((R)-2,2,2-trifluoro-1-(6-hydrazinylpyridin-3-yl)ethyl)pyrrolidine-3-ylcarbamate in Step F. LCMS APCI (+) m/z 459 (M+H).

Example 138

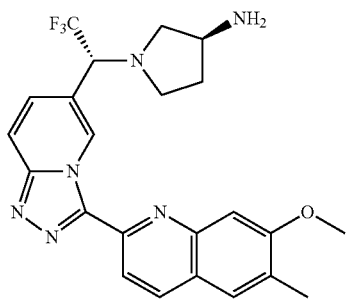 [SMILES: COc1cc2nc(-c3nnc4ccc([C@@H](N5CC[C@H](N)C5)C(F)(F)F)cn34)ccc2cc1C]

(S)-1-((R)-2,2,2-trifluoro-1-(3-(7-methoxy-6-methylquinolin-2-yl)-[1,2,4]triazolo[4,3-a]pyridin-6-yl)ethyl)pyrrolidin-3-amine hydrochloride

Step A: Preparation of 7-methoxy-2,6-dimethylquinoline

To 3-methoxy-4-methylaniline (1.0 g, 7.29 mmol) in refluxing in 6N HCl (50 mL) was added dropwise (E)-but-2-enal (1.02 g, 14.6 mmol). The reaction was heated to reflux for 2 hours then cooled down and neutralized with $NH_4OH$. The organic phase was extracted with DCM and the combined organic phases dried over $MgSO_4$, filtered and concentrated under reduced pressure to leave a dark residue. The residue was purified by reverse phase chromatography (SP4, 25M, eluting with a gradient of water/ACN 100:0 to 0:100, 20 column volumes) to yield 7-methoxy-2,6-dimethylquinoline (580 mg, 29.7% yield) as a beige solid.

Step B: Preparation of 7-methoxy-6-methylquinoline-2-carbaldehyde

To 7-methoxy-2,6-dimethylquinoline (580 mg, 3.10 mmol) in dioxane/water (15/0.015 mL) was added selenium dioxide (447 mg, 4.03 mmol) and the reaction was heated to reflux for 5 hours. After cooling, DCM was added followed by $MgSO_4$. After concentration, the residue was used in the next step without purification.

Step C: Preparation of tert-butyl (S)-1-((R)-2,2,2-trifluoro-1-(6-((E)-2-((7-methoxy-6-methylquinolin-2-yl)methylene)hydrazinyl)pyridin-3-yl)ethyl)pyrrolidin-3-ylcarbamate tert-butyl (S)-1-((R)-2,2,2-trifluoro-1-(6-hydrazinylpyridin-3-yl)ethyl)pyrrolidin-3-ylcarbamate (187 mg, 0.497 mmol) and 7-methoxy-6-methylquinoline-2-carbaldehyde (100 mg, 0.497 mmol) in ethanol (5 mL) were stirred at ambient temperature for 24 hours. After concentration, the residue was used in the next step without purification.

Step D: Preparation of tert-butyl (S)-1-((R)-2,2,2-trifluoro-1-(3-(7-methoxy-6-methylquinolin-2-yl)-[1,2,4]triazolo[4,3-a]pyridin-6-yl)ethyl)pyrrolidin-3-ylcarbamate To tert-butyl (S)-1-((R)-2,2,2-trifluoro-1-(6-((E)-2-((7-methoxy-6-methylquinolin-2-yl)methylene)hydrazinyl)pyridin-3-yl)ethyl)pyrrolidin-3-ylcarbamate (278 mg, 0.498 mmol) in DCM was added iodosobenzene diacetate (208 mg, 0.647 mmol) and the reaction was stirred at ambient temperature for 2 hours. After concentration, the residue was purified by reverse phase chromatography (SP4, 25M, eluting with a gradient of water/ACN 100:0 to 0:100, 25 column volumes) to yield tert-butyl (S)-1-((R)-2,2,2-trifluoro-1-(3-(7-methoxy-6-methylquinolin-2-yl)-[1,2,4]triazolo[4,3-a]pyridin-6-yl)ethyl)pyrrolidin-3-ylcarbamate (130 mg, 46.9% yield) as a beige solid

Step E: Preparation of (S)-1-((R)-2,2,2-trifluoro-1-(3-(7-methoxy-6-methylquinolin-2-yl)-[1,2,4]triazolo[4,3-a]pyridin-6-yl)ethyl)pyrrolidin-3-amine hydrochloride tert-Butyl (S)-1-((R)-2,2,2-trifluoro-1-(3-(7-methoxy-6-methylquinolin-2-yl)-[1,2,4]triazolo[4,3-a]pyridin-6-yl)ethyl)pyrrolidin-3-ylcarbamate (154 mg, 0.277 mmol) was stirred in TFA (3 mL) for 1 hour then concentrated. The residue was dissolved in minimum methanol and added dropwise to a 4N HCl in ether solution. The resulting solid was filtered and dried to yield (S)-1-((R)-2,2,2-trifluoro-1-(3-(7-methoxy-6-methylquinolin-2-yl)-[1,2,4]triazolo[4,3-a]pyridin-6-yl)ethyl)pyrrolidin-3-amine (109 mg, 86.3% yield) hydrochloride as a solid. LCMS APCI (+) m/z 457 (M+H).

Example 139

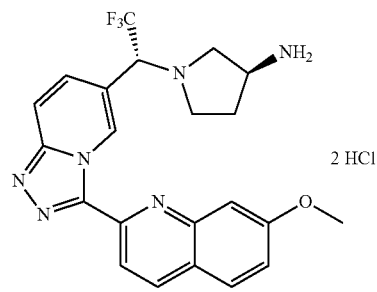 [SMILES: COc1ccc2ccc(-c3nnc4ccc([C@@H](N5CC[C@H](N)C5)C(F)(F)F)cn34)nc2c1 ; "2 HCl"]

(S)-1-((R)-2,2,2-trifluoro-1-(3-(7-methoxyquinolin-2-yl)-[1,2,4]triazolo[4,3-a]pyridin-6-yl)ethyl)pyrrolidin-3-amine dihydrochloride Prepared according to the method of Example 113 substituting 3-methoxyaniline for 4-fluoro-3-methoxyaniline. LCMS APCI (+) m/z 443 (M+H).

Example 140

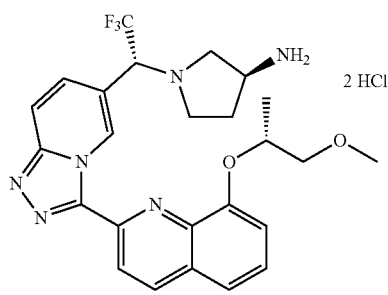 [SMILES: COC[C@@H](C)Oc1cccc2ccc(-c3nnc4ccc([C@@H](N5CC[C@H](N)C5)C(F)(F)F)cn34)nc12 ; "2 HCl"]

(S)-1-((R)-2,2,2-trifluoro-1-(3-(8-((R)-1-methoxypropan-2-yloxy)quinolin-2-yl)-[1,2,4]triazolo[4,3-a]pyridin-6-yl)ethyl)pyrrolidin-3-amine dihydrochloride Step A: Preparation of (R)-8-(1-methoxypropan-2-yloxy)-2-methylquinoline To a solution of 2-methylquinolin-8-ol (1.0 g, 6.3 mmol) in tetrahydrofuran (5.2 mL, 6.3 mmol) was added triphenylphosphine (6.9 g, 26 mmol), diethyl azodicarboxylate (1.6 mL, 10 mmol), and (S)-1-methoxypropan-2-ol (0.80 mL, 8.2 mmol) and the resultant mixture allowed to stir at ambient temperature for 24 hours. The reaction mixture was diluted with water (10 mL) and extracted with dichloromethane (2×20 mL). The combined organic extracts dried over sodium sulfate, filtered and concentrated under reduced pressure. Purification of the residue by reverse phase chromatography on C18 (0-80% acetonitrile/water) afforded the title compound (0.46 g, 28%).

Step B: Preparation of (R)-8-(1-methoxypropan-2-yloxy)quinoline-2-carbaldehyde

To a solution of (R)-8-(1-methoxypropan-2-yloxy)-2-methylquinoline (0.45 g, 1.9 mmol) in dioxane (35 mL) and water (0.35 mL) was added selenium dioxide (0.26 g, 2.3 mmol) and the resultant mixture heated at reflux for 2 hours. The cooled reaction mixture was filtered through a plug of Celite® to remove solids, rinsing with dichloromethane. The filtrate was concentrated under reduced pressure and purified by normal phase chromatography on silica gel (10-20% ethyl acetate/hexanes) to afford the title compound (0.42 g, 88%).

Step C: Preparation of tert-butyl (S)-1-((R)-2,2,2-trifluoro-1-(3-(8-((R)-1-methoxypropan-2-yloxy)quinolin-2-yl)-[1,2,4]triazolo[4,3-a]pyridin-6-yl)ethyl)pyrrolidin-3-ylcarbamate A solution of tert-butyl (S)-1-((R)-2,2,2-trifluoro-1-(6-hydrazinylpyridin-3-yl)ethyl)pyrrolidin-3-ylcarbamate (0.33 g, 0.87 mmol) and (R)-8-(1-methoxypropan-2-yloxy)quinoline-2-carbaldehyde (0.21 g, 0.87 mmol) in ethanol (4.3 mL, 0.87 mmol) was allowed to stir at ambient temperature for 12 hours. The solvent was removed under reduced pressure. The residue was dissolved in dichloromethane (4.3 mL) and iodosobenzene diacetate (0.31 g, 0.95 mmol) was added. The reaction mixture was stirred at ambient temperature for 1 hour. Ethyl acetate (20 mL) and saturated sodium bicarbonate (10 mL) were added. The organic layer was separated, washed with brine, dried over sodium sulfate, filtered and concentrated under reduced pressure. The residue was purified by reverse phase chromatography on C18 (25-100% acetonitrile/water) to give the title compound (0.38 g, 73%).

Step D: Preparation of (S)-1-((R)-2,2,2-trifluoro-1-(3-(8-((R)-1-methoxypropan-2-yloxy)quinolin-2-yl)-[1,2,4]triazolo[4,3-a]pyridin-6-yl)ethyl)pyrrolidin-3-amine dihydrochloride To a solution of tert-butyl (S)-1-((R)-2,2,2-trifluoro-1-(3-(8-((R)-1-methoxypropan-2-yloxy)quinolin-2-yl)-[1,2,4]triazolo[4,3-a]pyridin-6-yl)ethyl)pyrrolidin-3-ylcarbamate (0.37 g, 0.61 mmol) in dichloromethane (1 mL) was added hydrochloric acid (5-6M in 2-propanol; 8.7 mL, 0.61 mmol). The reaction mixture was stirred at ambient temperature for 30 minutes. The solvent was removed under reduced pressure, and the resulting solid was suspended in acetonitrile (3 mL) and stirred at ambient temperature for 5 minutes. The solid was collected by vacuum filtration to give the title compound (0.31 g, 87%). LCMS APCI (+) m/z 501 (M+H). Specific rotation: $[\alpha]^{25}_D = 0.48°$ (c=1.03, MeOH).

Example 141

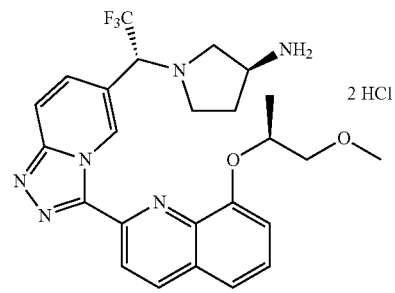 [SMILES: COC[C@H](C)Oc1cccc2ccc(-c3nnc4ccc([C@@H](N5CC[C@H](N)C5)C(F)(F)F)cn34)nc12]

(S)-1-((R)-2,2,2-trifluoro-1-(3-(8-((S)-1-methoxypropan-2-yloxy)quinolin-2-yl)-[1,2,4]triazolo[4,3-a]pyridin-6-yl)ethyl)pyrrolidin-3-amine dihydrochloride Prepared according to the method of Example 140 substituting (R)-1-methoxypropan-2-ol for (S)-1-methoxypropan-2-ol. LCMS APCI (+) m/z 501 (M+H).

Example 142

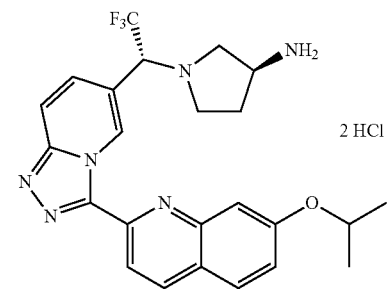 [SMILES: CC(C)Oc1ccc2ccc(-c3nnc4ccc([C@@H](N5CC[C@H](N)C5)C(F)(F)F)cn34)nc2c1]

(S)-1-((R)-2,2,2-trifluoro-1-(3-(7-isopropoxyquinolin-2-yl)-[1,2,4]triazolo[4,3-a]pyridin-6-yl)ethyl)pyrrolidin-3-amine dihydrochloride Prepared according to the method of Example 119 substituting 3-methoxyaniline for 4-fluoro-3-methoxyaniline in Step A. LCMS APCI (+) m/z 471 (M+H).

Example 143

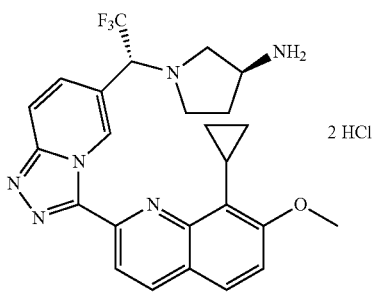 [SMILES: COc1ccc2ccc(-c3nnc4ccc([C@@H](N5CC[C@H](N)C5)C(F)(F)F)cn34)nc2c1C1CC1]

(S)-1-((R)-1-(3-(8-cyclopropyl-7-methoxyquinolin-2-yl)-[1,2,4]triazolo[4,3-a]pyridin-6-yl)-2,2,2-trifluoroethyl)pyrrolidin-3-amine dihydrochloride Step A: Preparation of 8-cyclopropyl-7-methoxy-2-methylquinoline Prepared according to Example 37, Step A, substituting 2-bromo-3-methoxyaniline for 2-ethylaniline.

Step B: Preparation of 8-cyclopropyl-7-methoxyquinoline-2-carbaldehyde

Prepared according to Example 60, Step B, replacing 8-bromo-7-fluoro-2-methylquinoline with 8-cyclopropyl-7-methoxy-2-methylquinoline.

Step C: (S)-1-((R)-1-(3-(8-cyclopropyl-7-methoxyquinolin-2-yl)-[1,2,4]triazolo[4,3-a]pyridin-6-yl)-2,2,2-trifluoroethyl)pyrrolidin-3-amine dihydrochloride Prepared as described in Example 9B, using 8-cyclopropyl-7-methoxyquinoline-2-carbaldehyde in place of 8-ethyl-2-methylquinoline in Step F. LCMS APCI (+) m/z 483 (M+H).

Example 144

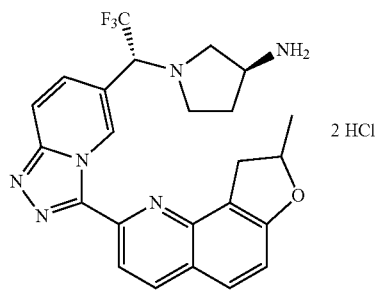 [SMILES: CC1Cc2c(ccc3ccc(-c4nnc5ccc([C@@H](N6CC[C@H](N)C6)C(F)(F)F)cn45)nc23)O1]

(3S)-1-((1R)-2,2,2-trifluoro-1-(3-(8-methyl-8,9-dihydrofuro[2,3-h]quinolin-2-yl)-[1,2,4]triazolo[4,3-a]pyridin-6-yl)ethyl)pyrrolidin-3-amine dihydrochloride Step A: Preparation of 8-cyclopropyl-7-methoxy-2-methylquinoline Prepared according to the method of Example 60 substituting 2-bromo-3-methoxyaniline for 2-bromo-3-fluoroaniline.

Step B: Preparation of 2,8-dimethyl-8,9-dihydrofuro[2,3-h]quinoline

A solution of 8-cyclopropyl-7-methoxy-2-methylquinoline (0.53 g, 2.5 mmol) in hydrobromic acid (48%; 9.9 mL, 2.5 mmol) was heated at reflux for 3 days. After cooling, the reaction mixture was neutralized to pH 8 by addition of ammonium hydroxide and extracted with dichloromethane (3×20 mL). The combined organic extracts were washed with water, dried over magnesium sulfate, filtered and concentrated under reduced pressure. Purification by reverse phase chromatography on C18 (0-100% acetonitrile/water) afforded the title compound (0.39 g, 79%).

Step C: Preparation of (3S)-1-((1R)-2,2,2-trifluoro-1-(3-(8-methyl-8,9-dihydrofuro[2,3-h]quinolin-2-yl)-[1,2,4]triazolo[4,3-a]pyridin-6-yl)ethyl)pyrrolidin-3-amine dihydrochloride Prepared according to the method of Example 37, Steps B and C, substituting 2,8-dimethyl-8,9-dihydrofuro[2,3-h]quinoline for 8-ethyl-2-methylquinoline in Step B. LCMS APCI (+) m/z 469 (M+H).

Example 145

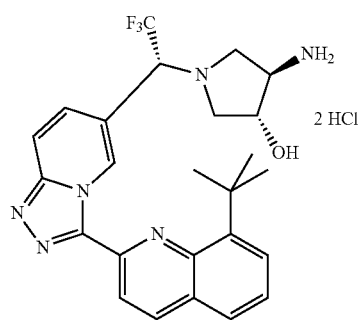 [SMILES: CC(C)(C)c1cccc2ccc(-c3nnc4ccc([C@@H](N5C[C@@H](N)[C@H](O)C5)C(F)(F)F)cn34)nc12]

(3R,4R)-4-amino-1-((R)-1-(3-(8-tert-butylquinolin-2-yl)-[1,2,4]triazolo[4,3-a]pyridin-6-yl)-2,2,2-trifluoroethyl)pyrrolidin-3-ol dihydrochloride Step A: Preparation of (3R,4R)-tert-butyl 3-(benzyloxycarbonylamino)-4-hydroxypyrrolidine-1-carboxylate To a solution of (3R,4R)-tert-butyl 3-amino-4-hydroxypyrrolidine-1-carboxylate (4.40 g, 21.76 mmol) and Na₂CO₃ (2.77 g, 26.11 mmol) in dioxane (50 mL) and water (50 mL) was added Cbz-Cl (3.87 mL, 26.11 mmol) at 0° C. The reaction mixture was warmed to ambient temperature and stirred at ambient temperature for 3 hours. Ethyl acetate (50 mL) was added. The organic layer was separated, washed with brine, dried (sodium sulfate), filtered and concentrated under reduced pressure. The residue was purified by flash chromatography on silica gel (5:1 hexane/ethyl acetate) to give (3R,4R)-tert-butyl 3-(benzyloxycarbonylamino)-4-hydroxypyrrolidine-1-carboxylate (4.91 g, 67.1%) as an oil.

Step B: Preparation of benzyl (3R,4R)-4-hydroxypyrrolidin-3-ylcarbamate

To a solution of (3R,4R)-tert-butyl 3-(benzyloxycarbonylamino)-4-hydroxypyrrolidine-1-carboxylate (4.91 g, 14.60 mmol) in DCM (20 mL) was added TFA (11.25 mL, 146.0 mmol) and the mixture was stirred at ambient temperature for 1 hour. The solvent was removed under reduced pressure. 6 N HCl in water (10 mL) was added. The mixture was stirred at ambient temperature for 30 minutes and neutralized with saturated sodium bicarbonate to about pH 8. It was extracted with DCM:IPA=4:1 (50 mL). The organic layer was separated, dried (sodium sulfate), filtered and concentrated under reduced pressure to give benzyl (3R,4R)-4-hydroxypyrrolidin-3-ylcarbamate (2.45 g, 71.0%) as a solid.

Step C: Preparation of benzyl (3R,4R)-1-((R)-1-(6-chloropyridin-3-yl)-2,2,2-trifluoroethyl)-4-hydroxypyrrolidin-3-ylcarbamate A solution of (S)-1-(6-chloropyridin-3-yl)-2,2,2-trifluoroethyl trifluoromethanesulfonate (2.50 g, 7.28 mmol), benzyl (3R,4R)-4-hydroxypyrrolidin-3-ylcarbamate (2.41 g, 10.2 mmol) and K₂CO₃ (1.51 g, 10.9 mmol) in THF (40 mL) was stirred at 56° C. for 12 hours. Water (20 mL) and ethyl acetate (40 mL) were added. The organic layer was separated, washed with brine, dried (sodium sulfate), filtered and concentrated under reduced pressure. The residue was purified by flash chromatography on silica gel (20:1 ethyl acetate/MeOH) to give benzyl (3R,4R)-1-((R)-1-(6-chloropyridin-3-yl)-2,2,2-trifluoroethyl)-4-hydroxypyrrolidin-3-ylcarbamate (1.85 g, 59.2%) as a solid.

Step D: Preparation of benzyl tert-butyl (3R,4R)-1-((R)-1-(6-chloropyridin-3-yl)-2,2,2-trifluoroethyl)-4-hydroxypyrrolidin-3-ylcarbamate To a solution of benzyl (3R,4R)-1-((R)-1-(6-chloropyridin-3-yl)-2,2,2-trifluoroethyl)-4-hydroxypyrrolidin-3-ylcarbamate (1.85 g, 4.30 mmol) in ACN (20 mL) was added iodotrimethylsilane (1.85 mL, 12.9 mmol) at 0° C. After addition, the reaction mixture was warmed to ambient temperature and stirred at ambient temperature for 1 hour. ACN was removed under reduced pressure. 1 N HCl (10 mL) and ether (20 mL) were added. The aqueous layer was separated and basified with solid NaOH to about pH 12. THF (15 mL) and Boc₂O (1.88 g, 8.61 mmol) were added. The mixture was stirred at ambient temperature for 20 hours. Ethyl acetate (20 mL) was added. The organic layer was separated, washed with brine, dried (sodium sulfate), filtered and concentrated under reduced pressure. The residue was purified by flash chromatography on silica gel (1:2 hexane/ethyl acetate) to give tert-butyl (3R,4R)-1-((R)-1-(6-chloropyridin-3-yl)-2,2,2-trifluoroethyl)-4-hydroxypyrrolidin-3-ylcarbamate (0.67 g, 39.3%) as a solid.

Step E: Preparation of (3R,4R)-4-amino-1-((R)-1-(3-(8-tert-butylquinolin-2-yl)-[1,2,4]triazolo[4,3-a]pyridin-6-yl)-2,2,2-trifluoroethyl)pyrrolidin-3-ol dihydrochloride Prepared as described in Example 9B using tert-butyl (3R,4R)-1-((R)-1-(6-chloropyridin-3-yl)-2,2,2-trifluoroethyl)-4-hydroxypyrrolidin-3-ylcarbamate in place of tert-butyl (S)-1-((R)-1-(6-chloropyridin-3-yl)-2,2,2-trifluoroethyl)pyrrolidin-3-ylcarbamate in Step E, and substituting 8-tert-butylquinoline-2-carbaldehyde for 8-methoxyquinoline-2-carbaldehyde in Step F. LCMS APCI (+) m/z 485 (M+H).

Example 146

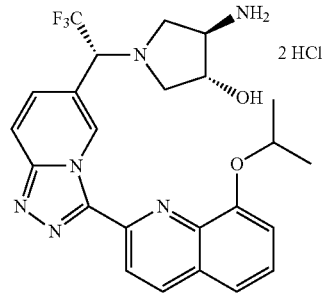 [SMILES: CC(C)Oc1cccc2ccc(-c3nnc4ccc([C@@H](N5C[C@@H](N)[C@H](O)C5)C(F)(F)F)cn34)nc12]

(3R,4R)-4-amino-1-((R)-2,2,2-trifluoro-1-(3-(8-isopropoxyquinolin-2-yl)-[1,2,4]triazolo[4,3-a]pyridin-6-yl)ethyl)pyrrolidin-3-ol dihydrochloride Prepared as described in Example 9B using tert-butyl (3R,4R)-1-((R)-1-(6-chloropyridin-3-yl)-2,2,2-trifluoroethyl)-4-hydroxypyrrolidin-3-ylcarbamate in place of tert-butyl (S)-1-((R)-1-(6-chloropyridin-3-yl)-2,2,2-trifluoroethyl)pyrrolidin-3-ylcarbamate in Step E, and substituting 8-isopropoxyquinoline-2-carbaldehyde for 8-methoxyquinoline-2-carbaldehyde in Step F. LCMS APCI (+) m/z 487 (M+H).

Example 147

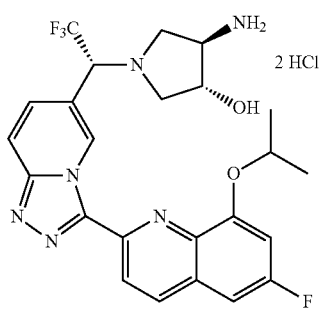 [SMILES: CC(C)Oc1cc(F)cc2ccc(-c3nnc4ccc([C@@H](N5C[C@@H](N)[C@H](O)C5)C(F)(F)F)cn34)nc12]

(3R,4R)-4-amino-1-((R)-2,2,2-trifluoro-1-(3-(6-fluoro-8-isopropoxyquinolin-2-yl)-[1,2,4]triazolo[4,3-a]pyridin-6-yl)ethyl)pyrrolidin-3-ol dihydrochloride Prepared as described in Example 9B using tert-butyl (3R, 4R)-1-((R)-1-(6-chloropyridin-3-yl)-2,2,2-trifluoroethyl)-4-hydroxypyrrolidin-3-ylcarbamate in place of tert-butyl (S)-1-((R)-1-(6-chloropyridin-3-yl)-2,2,2-trifluoroethyl)pyrrolidin-3-ylcarbamate in Step E, and substituting 6-fluoro-8-isopropoxyquinoline-2-carbaldehyde for 8-methoxyquinoline-2-carbaldehyde in Step F. LCMS APCI (+) m/z 505 (M+H).

Example 148

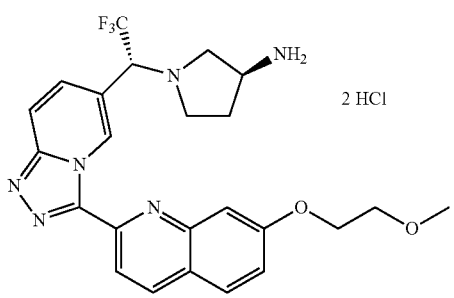 [SMILES: COCCOc1ccc2ccc(-c3nnc4ccc([C@@H](N5CC[C@H](N)C5)C(F)(F)F)cn34)nc2c1]

(S)-1-((R)-2,2,2-trifluoro-1-(3-(7-(2-methoxyethoxy)quinolin-2-yl)-[1,2,4]triazolo[4,3-a]pyridin-6-yl)ethyl)pyrrolidin-3-amine dihydrochloride Step A: Preparation of 7-(2-methoxyethoxy)-2-methylquinoline A mixture of 2-methylquinolin-7-ol (0.20 g, 1.3 mmol), 1-bromo-2-methoxyethane (0.24 mL, 2.5 mmol) and potassium carbonate (0.52 g, 3.8 mmol) in acetone (5.0 mL, 1.3 mmol) was heated at 70° C. for 12 hours. The cooled reaction mixture was diluted with water (10 mL) extracted with dichloromethane (3×20 mL). The combined organic extracts were dried over magnesium sulfate, filtered and concentrated under reduced pressure. The residue was purified by normal phase chromatography on silica gel (10-50% ethyl acetate/hexanes) to provide title compound (0.16 g, 60%).

Step B: Preparation of 7-(2-methoxyethoxy)quinoline-2-carbaldehyde

To a solution of 7-(2-methoxyethoxy)-2-methylquinoline (0.16 g, 0.76 mmol) in dioxane (15 mL) and water (0.15 mL) was added selenium dioxide (0.10 g, 0.91 mmol) and the resultant mixture heated at reflux for 2 hours. The cooled reaction mixture was filtered through a plug of Celite® to remove solids, rinsing with dichloromethane. The filtrate was concentrated under reduced pressure and purified by normal phase chromatography on silica gel (10-20% ethyl acetate/hexanes) to afford the title compound (0.12 g, 70%).

Step C: Preparation of tert-butyl (S)-1-((R)-2,2,2-trifluoro-1-(3-(7-(2-methoxyethoxy)quinolin-2-yl)-[1,2,4]triazolo[4,3-a]pyridin-6-yl)ethyl)pyrrolidin-3-ylcarbamate A solution of tert-butyl (S)-1-((R)-2,2,2-trifluoro-1-(6-hydrazinylpyridin-3-yl)ethyl)pyrrolidin-3-ylcarbamate (0.20 g, 0.53 mmol) and 7-(2-methoxyethoxy)quinoline-2-carbaldehyde (0.12 g, 0.53 mmol) in ethanol (2.7 mL, 0.53 mmol) was allowed to stir at ambient temperature for 12 hours. The solvent was removed under reduced pressure. The residue was dissolved in dichloromethane (2.7 mL) and iodosobenzene diacetate (0.19 g, 0.59 mmol) was added. The reaction mixture was stirred at ambient temperature for 1 hour. Ethyl acetate (20 mL) and saturated sodium bicarbonate (10 mL) were added. The organic layer was separated, washed with brine, dried over sodium sulfate, filtered and concentrated under reduced pressure. The residue was purified by reverse phase chromatography on C18 (0-100% acetonitrile/water) to give the title compound (0.20 g, 63%).

Step D: Preparation of (S)-1-((R)-2,2,2-trifluoro-1-(3-(7-(2-methoxyethoxy)quinolin-2-yl)-[1,2,4]triazolo[4,3-a]pyridin-6-yl)ethyl)pyrrolidin-3-amine dihydrochloride To a solution of tert-butyl (S)-1-((R)-2,2,2-trifluoro-1-(3-(7-(2-methoxyethoxy)quinolin-2-yl)-[1,2,4]triazolo[4,3-a]pyridin-6-yl)ethyl)pyrrolidin-3-ylcarbamate (0.20 g, 0.33 mmol) in dichloromethane (1 mL) was added hydrochloric acid (5-6M in 2-propanol; 8.3 mL, 0.61 mmol). The reaction mixture was stirred at ambient temperature for 30 minutes. The solvent was removed under reduced pressure, and the solid obtained was suspended in acetonitrile (3 mL) and stirred at ambient temperature for 5 minutes. The solid formed was collected by vacuum filtration to give the title compound (0.17 g, 91%). LCMS APCI (+) m/z 487 (M+H).

Example 149

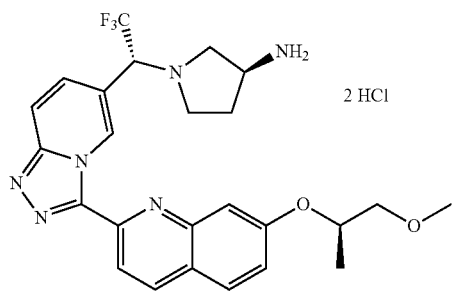 [SMILES: COC[C@@H](C)Oc1ccc2ccc(-c3nnc4ccc([C@@H](N5CC[C@H](N)C5)C(F)(F)F)cn34)nc2c1]

(S)-1-((R)-2,2,2-trifluoro-1-(3-(7-((R)-1-methoxypropan-2-yloxy)quinolin-2-yl)-[1,2,4]triazolo[4,3-a]pyridin-6-yl)ethyl)pyrrolidin-3-amine dihydrochloride Step A: Preparation of (R)-7-(1-methoxypropan-2-yloxy)-2-methylquinoline To a solution of 2-methylquinolin-7-ol (0.20 g, 1.3 mmol) in tetrahydrofuran (1.1 mL, 1.3 mmol) was added triphenylphosphine (0.82 g, 3.1 mmol), diethyl azodicarboxylate (0.32 mL, 2.0 mmol), and (S)-1-methoxypropan-2-ol (0.16 mL, 1.6 mmol) and the resultant mixture allowed to stir at ambient temperature for 24 hours. The reaction mixture was diluted with water (10 mL) and extracted with dichloromethane (2×20 mL). The combined organic extracts dried over sodium sulfate, filtered and concentrated under reduced pressure. Purification by reverse phase chromatography on C18 (0-80% acetonitrile/water) afforded the title compound (0.22 g, 66%).

Step B: Preparation of (R)-7-(1-methoxypropan-2-yloxy)quinoline-2-carbaldehyde

To a solution of (R)-7-(1-methoxypropan-2-yloxy)-2-methylquinoline (0.22 g, 0.96 mmol) in dioxane (7 mL) and water (0.07 mL) was added selenium dioxide (0.13 g, 1.2 mmol) and the resultant mixture heated at reflux for 2 hours. The cooled reaction mixture was filtered through a plug of Celite® to remove solids, rinsing with dichloromethane. The filtrate was concentrated under reduced pressure and purified by normal phase chromatography on silica gel (10-20% ethyl acetate/hexanes) to afford the title compound (0.11 g, 46%).

Step C: Preparation of tert-butyl (S)-1-((R)-2,2,2-trifluoro-1-(3-(7-((R)-1-methoxypropan-2-yloxy)quinolin-2-yl)-[1,2,4]triazolo[4,3-a]pyridin-6-yl)ethyl)pyrrolidin-3-ylcarbamate A solution of tert-butyl (S)-1-((R)-2,2,2-trifluoro-1-(6-hydrazinylpyridin-3-yl)ethyl)pyrrolidin-3-ylcarbamate (0.17 g, 0.44 mmol) and (R)-7-(1-methoxypropan-2-yloxy)quinoline-2-carbaldehyde (0.11 g, 0.44 mmol) in ethanol (2.2 mL, 0.44 mmol) was allowed to stir at ambient temperature for 12 hours. The solvent was removed under reduced pressure. The residue was dissolved in dichloromethane (2.2 mL) and iodosobenzene diacetate (0.16 g, 0.49 mmol) was added. The reaction mixture was stirred at ambient temperature for 1 hour. Ethyl acetate (20 mL) and saturated sodium bicarbonate (10 mL) were added. The organic layer was separated, washed with brine, dried over sodium sulfate, filtered and concentrated under reduced pressure. The residue was purified by reverse phase chromatography on C18 (0-100% acetonitrile/water) to give the title compound (0.11 g, 42%).

Step D: Preparation of (S)-1-((R)-2,2,2-trifluoro-1-(3-(7-((R)-1-methoxypropan-2-yloxy)quinolin-2-yl)-[1,2,4]triazolo[4,3-a]pyridin-6-yl)ethyl)pyrrolidin-3-amine dihydrochloride To a solution of tert-butyl (S)-1-((R)-2,2,2-trifluoro-1-(3-(7-((R)-1-methoxypropan-2-yloxy)quinolin-2-yl)-[1,2,4]triazolo[4,3-a]pyridin-6-yl)ethyl)pyrrolidin-3-ylcarbamate (0.11 g, 0.18 mmol) in dichloromethane (1 mL) was added hydrochloric acid (5-6M in 2-propanol; 9.2 mL, 0.18 mmol). The reaction mixture was stirred at ambient temperature for 30 minutes. The solvent was removed under reduced pressure, and the resulting solid was suspended in acetonitrile (3 mL) and stirred at ambient temperature for 5 minutes. The solid formed was collected by vacuum filtration to give the title compound (0.084 g, 77%). LCMS APCI (+) m/z 501 (M+H).

Example 150

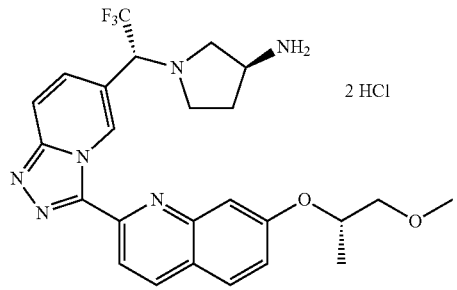 [SMILES: COC[C@H](C)Oc1ccc2ccc(-c3nnc4ccc([C@@H](N5CC[C@H](N)C5)C(F)(F)F)cn34)nc2c1]

(S)-1-((R)-2,2,2-trifluoro-1-(3-(7-((S)-1-methoxypropan-2-yloxy)quinolin-2-yl)-[1,2,4]triazolo[4,3-a]pyridin-6-yl)ethyl)pyrrolidin-3-amine dihydrochloride Prepared according to the method of Example 149 substituting (R)-1-methoxypropan-2-ol for (S)-1-methoxypropan-2-ol. LCMS APCI (+) m/z 501 (M+H).

Example 151

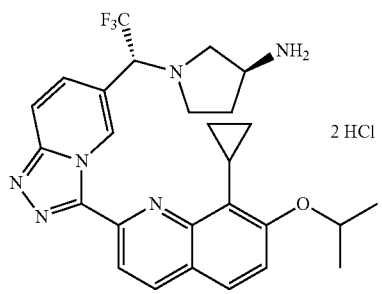 [SMILES: CC(C)Oc1ccc2ccc(-c3nnc4ccc([C@@H](N5CC[C@H](N)C5)C(F)(F)F)cn34)nc2c1C1CC1]

(S)-1-((R)-1-(3-(8-cyclopropyl-7-isopropoxyquino-lin-2-yl)-[1,2,4]triazolo[4,3-a]pyridin-6-yl)-2,2,2-trifluoroethyl)pyrrolidin-3-amine dihydrochloride

Step A: Preparation of 8-bromo-2-methylquinolin-7-ol

Prepared according to the method of Example 144, Step B, substituting 8-bromo-7-methoxy-2-methylquinoline for 8-cyclopropyl-7-methoxy-2-methylquinoline.

Step B: Preparation of 8-bromo-7-isopropoxy-2-methylquinoline

A mixture of 8-bromo-2-methylquinolin-7-ol (0.093 g, 0.39 mmol), 2-iodopropane (0.078 mL, 0.78 mmol) and potassium carbonate (0.16 g, 1.2 mmol) in acetone (1.6 mL, 0.39 mmol) was heated at 70° C. for 12 hours. After cooling, the reaction mixture was diluted with water (10 mL) and extracted with dichloromethane (3×20 mL). The combined organic extracts were dried over magnesium sulfate, filtered and concentrated under reduced pressure. Purification by normal phase chromatography on silica (10% ethyl acetate/hexanes) provided the title compound.

Step C: Preparation of (S)-1-((R)-1-(3-(8-cyclopropyl-7-isopropoxyquinolin-2-yl)-[1,2,4]triazolo[4,3-a]pyridin-6-yl)-2,2,2-trifluoroethyl)pyrrolidin-3-amine dihydrochloride Prepared according to the method of Example 143, Steps B and C, substituting 8-bromo-7-isopropoxy-2-methylquinoline for 8-cyclopropyl-7-methoxy-2-methylquinoline. LCMS APCI (+) m/z 511 (M+H).

Example 152

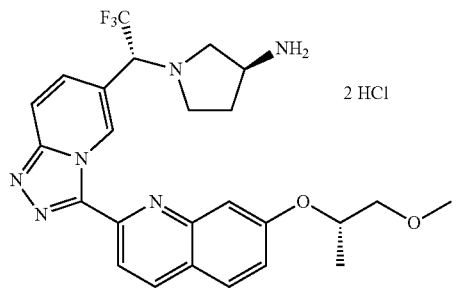 [SMILES: COC[C@H](C)Oc1ccc2ccc(-c3nnc4ccc([C@@H](N5CC[C@H](N)C5)C(F)(F)F)cn34)nc2c1]

(S)-1-((R)-1-(3-(8-cyclopropyl-7-(2-methoxyethoxy)quinolin-2-yl)-[1,2,4]triazolo[4,3-a]pyridin-6-yl)-2,2,2-trifluoroethyl)pyrrolidin-3-amine dihydrochloride Prepared according to the method of Example 151 substituting 1-bromo-2-methoxyethane for 2-iodopropane in Step B. LCMS APCI (+) m/z 527 (M+H).

Example 153

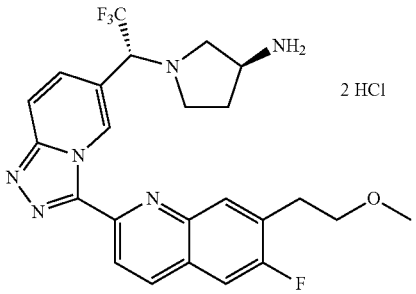 [SMILES: COCCc1cc2nc(-c3nnc4ccc([C@@H](N5CC[C@H](N)C5)C(F)(F)F)cn34)ccc2cc1F]

(S)-1-((R)-2,2,2-trifluoro-1-(3-(6-fluoro-7-(2-methoxyethyl)quinolin-2-yl)-[1,2,4]triazolo[4,3-a]pyridin-6-yl)ethyl)pyrrolidin-3-amine dihydrochloride

Step A: Preparation of 7-bromo-6-fluoro-2-methylquinoline

To a solution of 3-bromo-4-fluoroaniline (10.00 g, 52.63 mmol) in 6N HCl (150 mL) was added (E)-but-2-enal (7.524 mL, 92.10 mmol) dropwise over 10 minutes at 106° C. The reaction was stirred at 106° C. for 2 hours. After cooling to ambient temperature, the reaction mixture was basified with ammonium hydroxide to about pH 12, extracted with DCM (2×100 mL), dried (sodium sulfate), filtered and concentrated under reduced pressure. The residue was purified by flash chromatography on silica gel (hexane/ethyl acetate 5:1) to give 7-bromo-6-fluoro-2-methylquinoline (3.26 g, 25.8%) as a solid.

Step B: Preparation of (S)-1-((R)-2,2,2-trifluoro-1-(3-(6-fluoro-7-(2-methoxyethyl)quinolin-2-yl)-[1,2,4]triazolo[4,3-a]pyridin-6-yl)ethyl)pyrrolidin-3-amine dihydrochloride Prepared as described in Example 105 using 7-bromo-6-fluoro-2-methylquinoline in place of 8-bromo-2-methylquinoline in Step A. LCMS APCI (+) m/z 489 (M+H). Specific rotation: $[\alpha]^{26}_D$=0.73° (c=1.10, MeOH).

Example 154

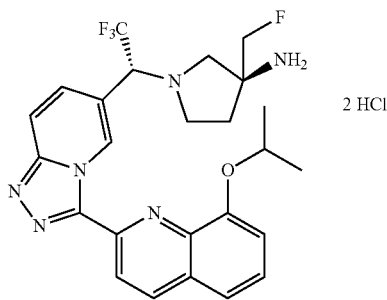 [SMILES: CC(C)Oc1cccc2ccc(-c3nnc4ccc([C@@H](N5CC[C@@](N)(CF)C5)C(F)(F)F)cn34)nc12]

(S)-3-(fluoromethyl)-1-((R)-2,2,2-trifluoro-1-(3-(8-isopropoxyquinolin-2-yl)-[1,2,4]triazolo[4,3-a]pyridine-6-yl)ethyl)pyrrolidine-3-amine dihydrochloride Step A: Preparation of ethyl 2-(fluoromethyl)acrylate To a solution of ethyl 2-(hydroxymethyl)acrylate (3.0 g, 23.1 mmol) in dichloromethane (40 mL) cooled to −78° C., was added DAST (3.32 mL, 25.4 mmol). The reaction mixture was stirred at −78° C. for 30 minutes and then at ambient temperature for 1 hour. The reaction was quenched with water (40 mL) and the layers were separated. The organic layer was washed with brine, dried (MgSO$_4$), filtered and concentrated under reduced pressure to afford ethyl 2-(fluoromethyl)acrylate (2.54 g, 83%).

Step B: Preparation of ethyl 1-benzyl-3-(fluoromethyl)pyrrolidine-3-carboxylate

To a solution of ethyl 2-(fluoromethyl)acrylate (2.54 g, 19.2 mmol) and N-benzyl-N-(methoxymethyl)trimethylsilylmethylamine (5.1 mL, 19.2 mmol) in dichloromethane (15 mL) cooled to 0° C. in an ice bath, was added 1M solution of TFA in dichloromathane (1.8 mL), and the resulting mixture stirred at 0-2° C. for 75 minutes. The reaction was diluted with dichloromethane (20 mL) and washed with saturated sodium bicarbonate solution, brine and dried (MgSO$_4$), filtered and concentrated under reduced pressure. The residue was purified by column chromatography (Biotage 40M; 10% ethyl acetate/hexanes) to afford ethyl 1-benzyl-3-(fluoromethyl)pyrrolidine-3-carboxylate (2.98 g, 58%).

Step C: Preparation of ethyl 3-(fluoromethyl)pyrrolidine-3-carboxylate

A solution of ethyl 1-benzyl-3-(fluoromethyl)pyrrolidine-3-carboxylate (2.98 g, 11.2 mmol) and ammonium formate (3.54 g, 56.2 mmol) in ethanol (100 mL) was flushed with nitrogen for 15 minutes. 10% Pd/C (1.2 g, 1.12 mmol) was added and the mixture heated at reflux for 30 minutes. The reaction mixture was cooled to ambient temperature, filtered through a pad of Celite, washing with ethanol (50 mL). The filtrate was concentrated under reduced pressure to afford ethyl 3-(fluoromethyl)pyrrolidine-3-carboxylate (1.86 g, 95%).

Step D: Preparation of 1-benzyl 3-ethyl 3-(fluoromethyl)pyrrolidine-1,3-dicarboxylate To a solution of ethyl 3-(fluoromethyl)pyrrolidine-3-carboxylate (1.86 g, 10.62 mmol) in a 1:1 mixture of 1,4-dioxane/water (18 mL) was added sodium carbonate (1.35 g, 12.74 mmol) and the mixture cooled to 0° C. in an ice bath. Benzyl chloroformate (1.79 mL, 12.74 mmol) was added dropwise and the resulting mixture was stirred at 0° C. for 30 minutes, then at ambient temperature for 18 hours. The mixture was partitioned between water and ether, and the layers separated. The organic layer was washed sequentially with water, saturated sodium bicarbonate solution and brine, then dried (MgSO$_4$), filtered and concentrated under reduced pressure. The residue was purified by chromatography (Biotage 25M; 15% ethyl acetate/hexanes) to afford 1-benzyl 3-ethyl 3-(fluoromethyl)pyrrolidine-1,3-dicarboxylate (3.3 g, 100%).

Step E: Preparation of 1-(benzyloxycarbonyl)-3-(fluoromethyl)pyrrolidine-3-carboxylic acid To a solution of 1-benzyl-3-ethyl 3-(fluoromethyl)pyrrolidine-1,3-dicarboxylate (3.3 g, 10.7 mmol) in anhydrous THF (30 mL) cooled to 0° C. in an ice bath, was added LiOH—H$_2$O (1.79 g, 42.7 mmol) followed by water (6 mL). The mixture was stirred at ambient temperature for 3 hours, diluted with water and washed with ethyl acetate, then acidified with aqueous 1M HCl. The solution was extracted with ethyl acetate and the combined organic extracts were washed brine, then dried (MgSO$_4$), filtered and concentrated under reduced pressure to give 1-(benzyloxycarbonyl)-3-(fluoromethyl)pyrrolidine-3-carboxylic acid (2.77 g, 92%).

Step F: Preparation of benzyl 3-(tert-butoxycarbonylamino)-3-(fluoromethyl)pyrrolidine-1-carboxylate To a solution of 1-(benzyloxycarbonyl)-3-(fluoromethyl)pyrrolidine-3-carboxylic acid (2.77 g, 9.85 mmol) in anhydrous t-BuOH (30 mL) was added triethylamine (6.86 mL, 49.24 mmol) and diphenyl phosphoryl azide (3.29 mL, 14.77 mmol). The mixture was heated at reflux for 16 hours under a nitrogen atmosphere. The mixture was cooled to ambient temperature, and partitioned between diethyl ether and water. The organic layer was separated and washed with saturated sodium bicarbonate solution and brine, dried (MgSO$_4$), filtered and concentrated under reduced pressure. The residue was purified by column chromatography (Biotage 40M, 20% ethyl acetate/hexanes) to afford benzyl 3-(tert-butoxycarbonylamino)-3-(fluoromethyl)pyrrolidine-1-carboxylate (2.27 g, 65%).

Step G: Preparation of tert-butyl 3-(fluoromethyl)pyrrolidin-3-ylcarbamate

A solution of ethyl benzyl-3-(tert-butoxycarbonylamino)-3-(fluoromethyl)pyrrolidine-1-carboxylate (2.27 g, 6.44 mmol) and ammonium formate (3.03 g, 32.2 mmol) in ethanol (60 mL) was flushed with nitrogen for 15 minutes. 10% Pd/C (0.69 g, 0.644 mmol) was added and the mixture heated at reflux for 30 minutes. The reaction mixture was cooled to ambient temperature, filtered through a pad of Celite and washed with ethanol (30 mL) and concentrated under reduced pressure to afford tert-butyl 3-(fluoromethyl)pyrrolidin-3-ylcarbamate (1.4 g, 100%).

Step H: Preparation of tert-butyl 1-((R)-1-(6-chloro-pyridin-3-yl)-2,2,2-trifluoroethyl)-3-(fluoromethyl)pyrrolidin-3-ylcarbamate Prepared as described in Example 9B using (S)-1-(6-chloropyridin-3-yl)-2,2,2-trifluoroethyl trifluoromethanesulfonate (1.10 g, 3.20 mmol) and tert-butyl 3-(fluoromethyl)pyrrolidin-3-ylcarbamate (0.70 g, 3.21 mmol) in place of (S)-tert-butyl pyrrolidin-3-ylcarbamate in Step D (1.03 g, 78%).

Step I: Preparation of tert-butyl 3-(fluoromethyl)-1-((R)-2,2,2-trifluoro-1-(6-hydrazinylpyridin-3-yl)ethyl)pyrrolidin-3-ylcarbamate Prepared as described in Example 9B substituting tert-butyl 1-((R)-1-(6-chloropyridin-3-yl)-2,2,2-trifluoroethyl)-3-(fluoromethyl)pyrrolidin-3-ylcarbamate (1.0 g, 2.43 mmol) in Step E (0.980 g, 99%).

Step J: Preparation of tert-butyl 3-(fluoromethyl)-1-((R)-2,2,2-trifluoro-1-(3-(8-isopropoxyquinolin-2-yl)-[1,2,4]triazolo[4,3-a]pyridin-6-yl)ethyl)pyrrolidin-3-ylcarbamate Prepared as described in Example 9B using tert-butyl 3-(fluoromethyl)-1-((R)-2,2,2-trifluoro-1-(6-hydrazinylpyridin-3-yl)ethyl)pyrrolidin-3-ylcarbamate in place of tert-butyl (S)-1-((R)-2,2,2-trifluoro-1-(6-hydrazinylpyridin-3-yl)ethyl)pyrrolidine-3-ylcarbamate and substituting 8-isopropoxyquinoline-2-carbaldehyde in Step F. LCMS APCI (+) m/z 603 (M+H).

Step K: Stereoisomer (S) of tert-butyl 3-(fluoromethyl)-1-((R)-2,2,2-trifluoro-1-(3-(8-isopropoxyquinolin-2-yl)-[1,2,4]triazolo[4,3-a]pyridin-6-yl)ethyl)pyrrolidin-3-ylcarbamate The racemic material from Step J was purified by Chiral HPLC (OD-H, Chiral Technologies) 10% EtOH: 90% hexanes, to provide the first eluting peak as a single stereoisomer (99% ee), designated (S) stereoisomer by proton NMR analysis of the Mosher amide.

Step L: Preparation of (S)-3-(fluoromethyl)-1-((R)-2,2,2-trifluoro-1-(3-(8-isopropoxyquinolin-2-yl)-[1,2,4]triazolo[4,3-a]pyridine-6-yl)ethyl)pyrrolidine-3-amine dihydrochloride Prepared as described in Example 9B, Step G, substituting tert-butyl 3-(fluoromethyl)-1-((R)-2,2,2-trifluoro-1-(3-(8-isopropoxyquinolin-2-yl)-[1,2,4]triazolo[4,3-c]pyridin-6-yl)ethyl)pyrrolidin-3-ylcarbamate. LCMS APCI (+) m/z 503 (M+H).

Example 155

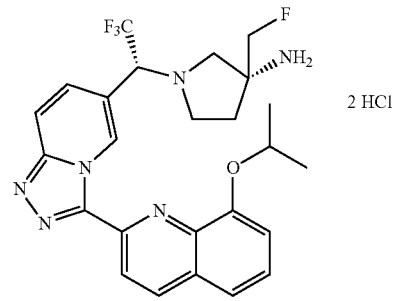 [SMILES: CC(C)Oc1cccc2ccc(-c3nnc4ccc([C@@H](N5CC[C@](N)(CF)C5)C(F)(F)F)cn34)nc12]

(R)-3-(fluoromethyl)-1-((R)-2,2,2-trifluoro-1-(3-(8-isopropoxyquinolin-2-yl)-[1,2,4]triazolo[4,3-a]pyridine-6-yl)ethyl)pyrrolidine-3-amine dihydrochloride

Step A: Preparation of Stereoisomer (R) of tert-butyl 3-(fluoromethyl)-1-((R)-2,2,2-trifluoro-1-(3-(8-isopropoxyquinolin-2-yl)-[1,2,4]triazolo[4,3-a]pyridin-6-yl)ethyl)pyrrolidin-3-ylcarbamate The racemic material from Example 154, Step J, was purified by Chiral HPLC (OD-H, Chiral Technologies) eluting with 10% EtOH/90% hexanes, to provide the second eluting peak as a single stereoisomer (99% ee), designated (R) by $^1$H NMR analysis of the Mosher amide.

Step B: Preparation of (R)-3-(fluoromethyl)-1-((R)-2,2,2-trifluoro-1-(3-(8-isopropoxyquinolin-2-yl)-[1,2,4]triazolo[4,3-a]pyridine-6-yl)ethyl)pyrrolidine-3-amine dihydrochloride Prepared as described in Example 9B, Step G, substituting (R)-tert-butyl 3-(fluoromethyl)-1-((R)-2,2,2-trifluoro-1-(3-(8-isopropoxyquinolin-2-yl)-[1,2,4]triazolo[4,3-c]pyridin-6-yl)ethyl)pyrrolidin-3-ylcarbamate. LCMS APCI (+) m/z 503 (M+H).

Example 156

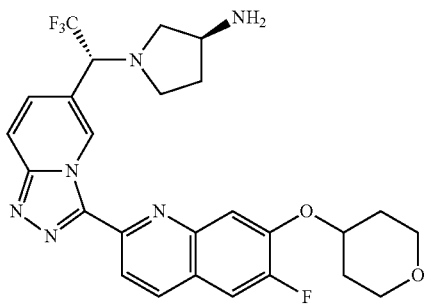 [SMILES: N[C@H]1CCN([C@H](c2ccc3nnc(-c4ccc5cc(F)c(OC6CCOCC6)cc5n4)n3c2)C(F)(F)F)C1]

(S)-1-((R)-2,2,2-trifluoro-1-(3-(6-fluoro-7-(tetrahydro-2H-pyran-4-yloxy)quinolin-2-yl)-[1,2,4]triazolo[4,3-a]pyridin-6-yl)ethyl)pyrrolidin-3-amine hydrochloride Prepared as in Example 133, substituting iodoethane in Step A with 4-bromotetrahydro-2H-pyran. LCMS APCI (+) m/z 531 (M+H).

Example 157

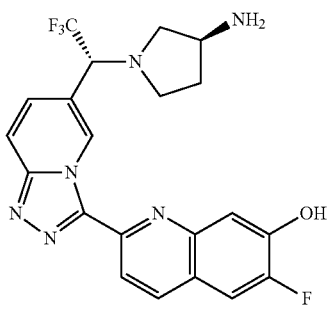 [SMILES: N[C@H]1CCN([C@H](c2ccc3nnc(-c4ccc5cc(F)c(O)cc5n4)n3c2)C(F)(F)F)C1]

2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-ol hydrochloride (S)-1-((R)-1-(3-(7-(cyclopropylmethoxy)-6-fluoroquinolin-2-yl)-[1,2,4]triazolo[4,3-a]pyridin-6-yl)-2,2,2-trifluoroethyl)pyrrolidin-3-amine hydrochloride (Example 134; 50 mg, 0.1 mmol) was heated to 60° C. in 6N HCl in IPA for 3 days. After concentration, the residue was dissolve in 1 mL of MeOH then added to 2N HCl in ether. The resulting solid was dried under high vacuum to yield 2-(6-((R)-1-((S)-3-aminopyrrolidin-1-yl)-2,2,2-trifluoroethyl)-[1,2,4]triazolo[4,3-a]pyridin-3-yl)-6-fluoro quinolin-7-ol hydrochloride (39 mg, 87% yield) as a solid. LCMS APCI (+) m/z 447 (M+H).

Example 158

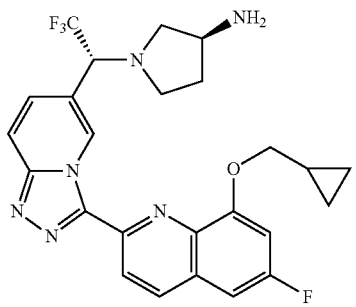 [SMILES: N[C@H]1CCN([C@H](c2ccc3nnc(-c4ccc5cc(F)cc(OCC6CC6)c5n4)n3c2)C(F)(F)F)C1]

(S)-1-((R)-1-(3-(8-(cyclopropylmethoxy)-6-fluoroquinolin-2-yl)-[1,2,4]triazolo[4,3-a]pyridin-6-yl)-2,2,2-trifluoroethyl)pyrrolidin-3-amine hydrochloride Prepared as in Example 86, substituting 2-iodo-propane in Step B with (bromomethyl)cyclopropane. LCMS APCI (+) m/z 501 (M+H).

Example 159

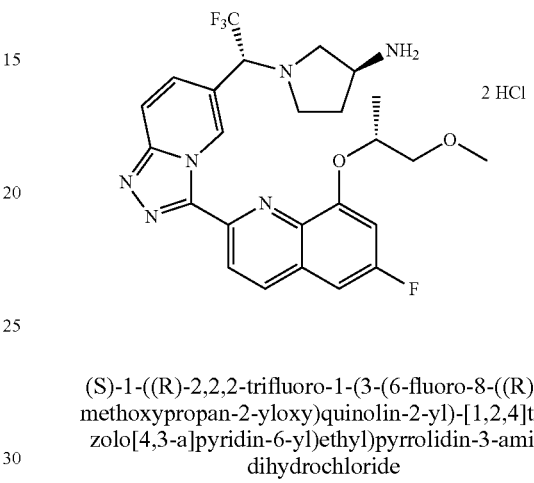

(S)-1-((R)-2,2,2-trifluoro-1-(3-(6-fluoro-8-((R)-1-methoxypropan-2-yloxy)quinolin-2-yl)-[1,2,4]triazolo[4,3-a]pyridin-6-yl)ethyl)pyrrolidin-3-amine dihydrochloride Step A: Preparation of (R)-6-fluoro-8-(1-methoxypropan-2-yloxy)-2-methylquinoline To a solution of 6-fluoro-2-methylquinolin-8-ol (0.50 g, 2.8 mmol) in tetrahydrofuran (2.4 mL, 2.8 mmol) was added triphenylphosphine (2.6 g, 9.9 mmol), diisopropyl azodicarboxylate (0.91 mg, 4.5 mmol), and (S)-1-methoxypropan-2-ol (0.33 mg, 3.7 mmol) and the resultant mixture allowed to stir at ambient temperature for 24 hours. The reaction mixture was diluted with water (10 mL) and extracted with dichloromethane (2×20 mL). The combined organic extracts dried over sodium sulfate, filtered and concentrated under reduced pressure. Purification by normal phase chromatography on silica gel (0-2% methanol/dichloromethane) afforded the title compound which was taken on to the subsequent step without further purification, assuming theoretical yield (0.70 g, 100%) was obtained, despite being contaminated with residual triphenylphosphine oxide.

Step B: Preparation of (R)-6-fluoro-8-(1-methoxypropan-2-yloxy)quinoline-2-carbaldehyde To a solution of (R)-6-fluoro-8-(1-methoxypropan-2-yloxy)-2-methylquinoline (0.70 g, 2.8 mmol) in dioxane (55 mL) and water (0.55 mL) was added selenium dioxide (0.38 g, 3.4 mmol) and the resultant mixture heated at reflux for 2 hours. The cooled reaction mixture was filtered through a plug of Celite® to remove solids, rinsing with dichloromethane. The filtrate was concentrated under reduced pressure and purified by normal phase chromatography on silica gel (10-30% ethyl acetate/hexanes) to afford the title compound (0.66 g, 89%).

Step C: Preparation of tert-butyl (S)-1-((R)-2,2,2-trifluoro-1-(3-(6-fluoro-8-((R)-1-methoxypropan-2-yloxy)quinolin-2-yl)-[1,2,4]triazolo[4,3-a]pyridin-6-yl)ethyl)pyrrolidin-3-ylcarbamate A solution of tert-butyl (S)-1-((R)-2,2,2-trifluoro-1-(6-hydrazinylpyridin-3-yl)ethyl)pyrrolidin-3-ylcarbamate (0.16 g, 0.43 mmol) and (R)-6-fluoro-8-(1-methoxypropan-2-yloxy)quinoline-2-carbaldehyde (0.11 g, 0.43 mmol) in ethanol (2.2 mL, 0.43 mmol) was allowed to stir at ambient temperature for 12 hours. The solvent was removed under reduced pressure. The residue was dissolved in dichloromethane (2.2 mL) and iodosobenzene diacetate (0.15 g, 0.47 mmol) was added. The reaction mixture was stirred at ambient temperature for 1 hour. Ethyl acetate (20 mL) and saturated sodium bicarbonate (10 mL) were added. The organic layer was separated, washed with brine, dried over sodium sulfate, filtered and concentrated under reduced pressure. The residue was purified by reverse phase chromatography on C18 (0-100% acetonitrile/water) to give the title compound (0.12 g, 44%).

Step D: Preparation of (S)-1-((R)-2,2,2-trifluoro-1-(3-(6-fluoro-8-((R)-1-methoxypropan-2-yloxy)quinolin-2-yl)-[1,2,4]triazolo[4,3-a]pyridin-6-yl)ethyl)pyrrolidin-3-amine dihydrochloride To a solution of tert-butyl (S)-1-((R)-2,2,2-trifluoro-1-(3-(6-fluoro-8-((R)-1-methoxypropan-2-yloxy)quinolin-2-yl)-[1,2,4]triazolo[4,3-a]pyridin-6-yl)ethyl)pyrrolidin-3-ylcarbamate (0.12 g, 0.19 mmol) in dichloromethane (0.5 mL) was added hydrochloric acid (5-6M in 2-propanol; 9.5 mL, 0.61 mmol). The reaction mixture was stirred at ambient temperature for 30 minutes. The solvent was removed under reduced pressure, and the solid obtained was suspended in acetonitrile (3 mL) and stirred at ambient temperature for 5 minutes. The solid formed was collected by vacuum filtration to give the title compound (0.89 g, 79%). LCMS APCI (+) m/z 519 (M+H). Specific rotation: $[\alpha]^{24}_D = 2.44°$ (c=0.97, MeOH).

Example 160

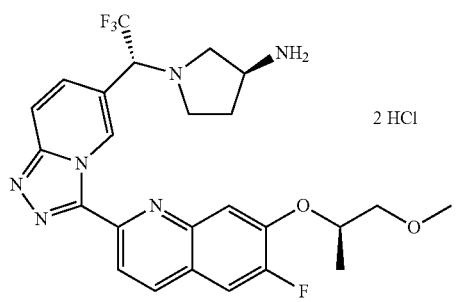 [SMILES: COC[C@@H](C)Oc1cc2nc(-c3nnc4ccc([C@@H](N5CC[C@H](N)C5)C(F)(F)F)cn34)ccc2cc1F]

(S)-1-((R)-2,2,2-trifluoro-1-(3-(6-fluoro-7-((R)-1-methoxypropan-2-yloxy)quinolin-2-yl)-[1,2,4]triazolo[4,3-a]pyridin-6-yl)ethyl)pyrrolidin-3-amine dihydrochloride Prepared according to the method of Example 149, substituting 6-fluoro-2-methylquinolin-7-ol for 2-methylquinolin-7-ol in Step A. LCMS APCI (+) m/z 519 (M+H).

Example 161

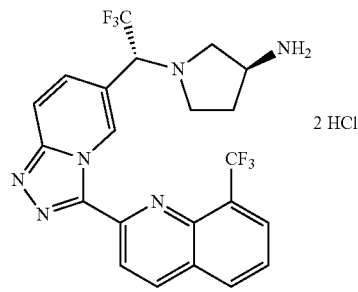 [SMILES: N[C@H]1CCN([C@H](c2ccc3nnc(-c4ccc5cccc(C(F)(F)F)c5n4)n3c2)C(F)(F)F)C1]

(S)-1-((R)-2,2,2-trifluoro-1-(3-(8-(trifluoromethyl)quinolin-2-yl)-[1,2,4]triazolo[4,3-a]pyridin-6-yl)ethyl)pyrrolidin-3-amine dihydrochloride Prepared according to the method of Example 140, Steps B-D, substituting 8-(trifluoromethyl)quinoline-2-carbaldehyde for (R)-8-(1-methoxypropan-2-yloxy)quinoline-2-carbaldehyde in Step B. LCMS APCI (+) m/z 481 (M+H).

Example 162

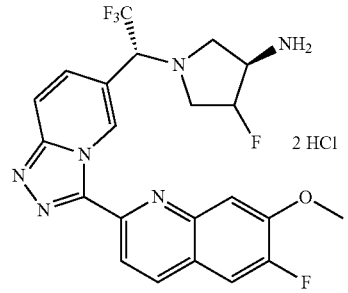 [SMILES: COc1cc2nc(-c3nnc4ccc([C@@H](N5CC(F)[C@H](N)C5)C(F)(F)F)cn34)ccc2cc1F]

(3R)-4-fluoro-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-amine dihydrochloride

Step A: Preparation of (3R,4R)-tert-butyl 3-azido-4-hydroxypyrrolidine-1-carboxylate A 500 mL round-bottomed flask was charged with tert-butyl 6-oxa-3-azabicyclo[3.1.0]hexane-3-carboxylate (15.42 g, 83.25 mmol), (1S,2S)-(−)-[1,2-cyclohexanediamino-N,N'-bis(3,5-di-t-butylsalicylidene)]chromium (III) chloride (1.18 g, 1.67 mmol) and azidotrimethylsilane (12.8 mL, 91.58 mmol) and the resulting mixture was stirred at ambient temperature under a nitrogen atmosphere for 48 hours. The dark red-brown mixture was diluted with chloroform (250 mL)

and washed sequentially with water and brine, dried (MgSO₄), filtered and concentrated under reduced pressure. The residue was dissolved in methanol (830 mL) and treated with potassium carbonate (11.51 g, 83.25 mmol) and the mixture was stirred at ambient temperature for 5 hours. The methanolic solution was filtered through a pad of Celite washed with methanol and concentrated under reduced pressure. The residue was partitioned between water and ethyl acetate. The layers were separated and the aqueous back extracted with EtOAc. The combined organic extracts were washed with saturated sodium bicarbonate solution, water and brine, dried (MgSO₄), filtered and concentrated. The residue was purified by column chromatography (Biotage 40M; 20% ethyl acetate/hexanes) to give (3R,4R)-tert-butyl 3-azido-4-hydroxypyrrolidine-1-carboxylate (18 g, 95%). Enantiomeric excess was determined by Chiral HPLC (AD-H, Chiralcel, 10% EtOH: 90% hexanes at 0.80 mL/min, 94.5% e.e.

Step B: Preparation of (3R,4R)-4-azidopyrrolidin-3-ol (3R,4R)-tert-butyl 3-azido-4-hydroxypyrrolidine-1-carboxylate (3.6 g, 16.0 mmol) was stirred in 10% TFA in dichloromethane (100 mL) for 2 hours. The mixture was concentrated under reduced pressure and the residue obtained dissolved in a 10% MeOH/dichloromethane solution (50 mL) and treated with potassium carbonate (20 g) and the suspension stirred at ambient temperature for 2 hours, then filtered through a pad of Celite and washed with 10% MeOH: dichloromethane. The filtrate was concentrated to afford (3R,4R)-4-azidopyrrolidin-3-ol in quantitative yield.

Step C: Preparation of (3R,4R)-4-azido-1-((R)-1-(6-chloropyridin-3-yl)-2,2,2-trifluoroethyl)pyrrolidin-3-ol Prepared as described in Example 9B using (S)-1-(6-chloropyridin-3-yl)-2,2,2-trifluoroethyl trifluoromethanesulfonate (5.06 g, 14.7 mmol) and (3R,4R)-4-azidopyrrolidin-3-ol (2.08 g, 16.2 mmol) in place of (S)-tert-butyl pyrrolidin-3-ylcarbamate in Step D (2.44 g, 52%).

Step D: Preparation of 5-((1R)-1-((3R)-3-azido-4-fluoropyrrolidin-1-yl)-2,2,2-trifluoroethyl)-2-chloropyridine To a solution of (3S,4R)-4-azido-1-((R)-1-(6-chloropyridin-3-yl)-2,2,2-trifluoroethyl)pyrrolidin-3-ol (2.4 g, 7.5 mmol) in dichloromethane (30 mL) at −78° C., was added diethylaminosulfur trifluoride (1.17 mL, 8.95 mmol). The resulting solution was allowed to warm to ambient temperature and stirred overnight. The mixture was concentrated under reduced pressure and the residue was dissolved in ethyl acetate and washed with water and brine, then dried (MgSO₄), filtered and concentrated. The crude residue was purified by column chromatography (Biotage, 40M; 10-25% ethyl acetate/hexanes gradient) to afford 5-((1R)-1-((3R)-3-azido-4-fluoropyrrolidin-1-yl)-2,2,2-trifluoroethyl)-2-chloropyridine (1.02 g, 42%).

Step E: Preparation of tert-butyl (3R)-1-((R)-1-(6-chloropyridin-3-yl)-2,2,2-trifluoroethyl)-4-fluoropyrrolidin-3-ylcarbamate To a solution of 5-((1R)-1-((3R)-3-azido-4-fluoropyrrolidin-1-yl)-2,2,2-trifluoroethyl)-2-chloropyridine (1.0 g, 3.15 mmol) in anhydrous THF (40 mL) was added triphenylphosphine (1.65 g, 6.30 mmol). The resulting mixture was stirred at ambient temperature overnight then concentrated under reduced pressure. The residue was dissolved in methanol (20 mL) and 0.5 M sodium hydroxide solution (20 mL). The mixture was stirred at ambient temperature overnight and then concentrated. The residue was adjusted to pH 3 with aqueous 6N HCl and washed with dichloromethane. The aqueous layer was basified with 5N NaOH and the solution extracted with ethyl acetate. The combined organic extracts were washed with brine, dried (MgSO₄), filtered and concentrated. The crude amine was dissolved in ethyl acetate (10 mL) and DIEA (1.10 mL, 6.30 mmol) was added. The mixture cooled to 0° C. in an ice bath and Boc₂O (0.83 g, 3.78 mmol) was added The mixture was allowed to warm to ambient temperature and stirred overnight, then partitioned between water and ethyl acetate. The layers were separated and the organic layer was washed sequentially with aqueous 1N HCl, saturated sodium bicarbonate solution and brine, then dried (MgSO₄), filtered and concentrated under reduced pressure. The residue was purified by column chromatography (Biotage 25M; 10-20% ethyl acetate/hexanes gradient) to afford tert-butyl (3R)-1-((R)-1-(6-chloropyridin-3-yl)-2,2,2-trifluoroethyl)-4-fluoropyrrolidin-3-ylcarbamate (0.584 g, 47%).

Step F: Preparation of tert-butyl (3R)-4-fluoro-1-((R)-2,2,2-trifluoro-1-(6-hydrazinylpyridin-3-yl)ethyl)pyrrolidin-3-ylcarbamate Prepared as described in Example 9B, Step E, substituting tert-butyl (3R)-1-((R)-1-(6-chloropyridin-3-yl)-2,2,2-trifluoroethyl)-4-fluoropyrrolidin-3-ylcarbamate (0.565 g, 98%).

Step G: Preparation of (3R)-4-fluoro-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-amine dihydrochloride Prepared as described in Example 9B, Step F, using tert-butyl (3R)-4-fluoro-1-((R)-2,2,2-trifluoro-1-(6-hydrazinylpyridin-3-yl)ethyl)pyrrolidin-3-ylcarbamate in place of tert-butyl (S)-1-((R)-2,2,2-trifluoro-1-(6-hydrazinylpyridin-3-yl)ethyl)pyrrolidin-3-yl)carbamate and substituting 6-fluoro-7-methoxyquinoline-2-carbaldehyde for 8-methoxyquinoline-2-carbaldehyde. LCMS APCI (+) m/z 479 (M+H).

Example 163

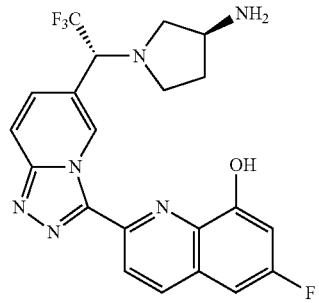 [SMILES: N[C@H]1CCN([C@H](c2ccc3nnc(-c4ccc5cc(F)cc(O)c5n4)n3c2)C(F)(F)F)C1]

2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-ol hydrochloride (S)-1-((R)-1-(3-(8-(cyclopropylmethoxy)-6-fluoroquinolin-2-yl)-[1,2,4]triazolo[4,3-a]pyridin-6-yl)-2,2,2-trifluoroethyl)pyrrolidin-3-amine hydrochloride (Example 158; 200 mg, 0.400 mmol) was stirred in 5-6N HCl (2 mL) in IPA in a sealed tube at 60° C. for 14 hours. The reaction mixture was concentrated under reduced pressure to provide 2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-ol hydrochloride (128 mg, 71.8% yield) as a solid. LCMS APCI (+) m/z 447 (M+H).

Example 164

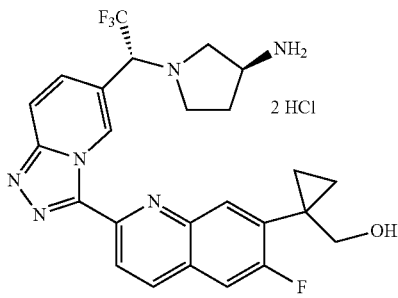 [SMILES: N[C@H]1CCN([C@H](c2ccc3nnc(-c4ccc5cc(F)c(C6(CO)CC6)cc5n4)n3c2)C(F)(F)F)C1]

(1-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yl)cyclopropyl)methanol dihydrochloride Prepared as described in Example 114 using (1-(6-fluoro-2-methylquinolin-7-yl)cyclopropyl)methanol in place of (1-(2-methylquinolin-8-yl)cyclopropyl)methanol in Step A. LCMS APCI (+) m/z 501 (M+H).

Example 165

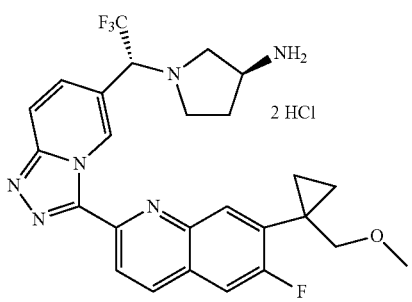 [SMILES: COCC1(c2cc3nc(-c4nnc5ccc([C@@H](N6CC[C@H](N)C6)C(F)(F)F)cn45)ccc3cc2F)CC1]

(S)-1-((R)-2,2,2-trifluoro-1-(3-(6-fluoro-7-(1-(methoxymethyl)cyclopropyl)quinolin-2-yl)-[1,2,4]triazolo[4,3-a]pyridin-6-yl)ethyl)pyrrolidin-3-amine dihydrochloride Prepared as described in Example 112 using methyl 2-(6-fluoro-2-methylquinolin-7-yl)acetate in place of methyl 2-(2-methylquinolin-8-yl)acetate in Step A. LCMS APCI (+) m/z 515 (M+H).

Example 166

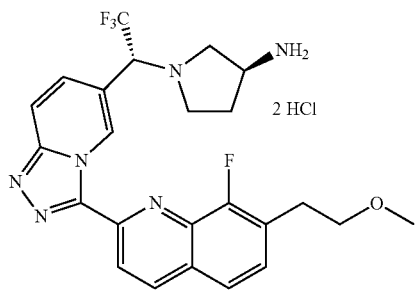 [SMILES: COCCc1ccc2ccc(-c3nnc4ccc([C@@H](N5CC[C@H](N)C5)C(F)(F)F)cn34)nc2c1F]

(S)-1-((R)-2,2,2-trifluoro-1-(3-(8-fluoro-7-(2-methoxyethyl)quinolin-2-yl)-[1,2,4]triazolo[4,3-a]pyridin-6-yl)ethyl)pyrrolidin-3-amine dihydrochloride Step A: Preparation of tert-butyl 3-bromo-2-fluorophenylcarbamate A solution of 3-bromo-2-fluorobenzoic acid (6.86 g, 31.32 mm 1), triethylamine (5.24 mL, 37.59 mmol) and DPPA (7.45 mL, 34.46 mmol) in t-BuOH (30 mL) was stirred at reflux for 20 hours. After cooling to ambient temperature, the solvent was removed under reduced pressure. The residue was dissolved in ethyl acetate (100 mL), washed with brine, dried (sodium sulfate), filtered and concentrated under reduced pressure. The residue was purified by flash chromatography on silica gel (4:1 hexane/ethyl acetate) to give tert-butyl 3-bromo-2-fluorophenylcarbamate (6.0 g, 66.0%) as an oil.

Step B: Preparation of 7-bromo-8-fluoro-2-methylquinoline

A solution of tert-butyl 3-bromo-2-fluorophenylcarbamate (6.0 g, 20.7 mmol) in 4N HCl (30 mL) in dioxane was stirred at ambient temperature for 2 hours. The solvent was removed under reduced pressure. The residue was dissolved in 6 N HCl (100 mL) and (E)-but-2-enal (2.96 ml, 36.2 mmol) was added dropwise at 106° C. The reaction was stirred at 106° C. for 2 hours. After cooling to ambient temperature, the reaction mixture was basified with ammonium hydroxide to about pH 12, extracted with DCM (2×100 mL), dried (sodium sulfate), filtered and concentrated under reduced pressure. The residue was purified by flash chromatography on silica gel (5:1 hexane/ethyl acetate) to give 7-bromo-8-fluoro-2-methylquinoline (2.99 g, 60.2%) as a solid.

Step C: Preparation of (S)-1-((R)-2,2,2-trifluoro-1-(3-(8-fluoro-7-(2-methoxyethyl)quinolin-2-yl)-[1,2,4]triazolo[4,3-a]pyridin-6-yl)ethyl)pyrrolidin-3-amine dihydrochloride Prepared as described in Example 105 using 7-bromo-8-fluoro-2-methylquinoline in place of 8-bromo-2-methylquinoline in Step A. LCMS APCI (+) m/z 489 (M+H).

Example 167

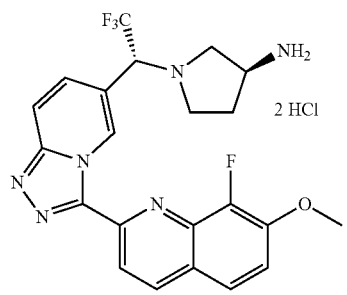 [SMILES: COc1ccc2ccc(-c3nnc4ccc([C@@H](N5CC[C@H](N)C5)C(F)(F)F)cn34)nc2c1F]

(S)-1-((R)-2,2,2-trifluoro-1-(3-(8-fluoro-7-methoxyquinolin-2-yl)-[1,2,4]triazolo[4,3-a]pyridin-6-yl)ethyl)pyrrolidin-3-amine dihydrochloride Step A: Preparation of 2-fluoro-3-methoxybenzoic acid A suspension of 2-fluoro-3-hydroxybenzoic acid (12.0 g, 76.9 mmol) and potassium carbonate (23.4 g, 169 mmol) in acetone (154 mL) was stirred at ambient temperature for 1 hour. To the mixture was added dimethyl sulfate (21.8 mL, 231 mmol) and the mixture stirred at ambient temperature for 30 minutes then heated at reflux for 4 hours. The mixture was cooled to ambient temperature, filtered and concentrated under reduced pressure. The residue was dissolved in anhydrous THF (154 mL) and the solution cooled to 0° C. in an ice bath. To this solution was added LiOH—H$_2$O (12.9 g, 307 mmol) followed by water (30 mL) and the resulting mixture stirred at ambient temperature for 3 hours. The mixture was concentrated under reduced pressure and the residue partitioned between water and ethyl acetate and the layers separated. The aqueous layer was acidified with 1N HCl solution and extracted with ethyl acetate. The combined organic extracts were washed with brine and dried (MgSO$_4$), filtered and concentrated under reduced pressure to afford 2-fluoro-3-methoxybenzoic acid (12.31 g, 94%).

Step B: Preparation of tert-butyl 2-fluoro-3-methoxyphenylcarbamate

A solution of 2-fluoro-3-methoxybenzoic acid (2.50 g, 14.69 mmol) and DIEA (3.07 mL, 17.63 mmol) in a mixture of toluene (12 mL) and t-BuOH (12 mL) was stirred over 4 Å molecular sieves (3 g) for 1 hour at ambient temperature, followed by addition of diphenyl phosphoryl azide (3.9 mL, 17.63 mmol) and the mixture heated at reflux for 18 hours. The cooled reaction mixture was filtered and the filtrate concentrated under reduced pressure. The residue was dissolved in ethyl acetate (50 mL) and washed with 1N HCl solution, saturated sodium bicarbonate solution, water and brine, then dried (MgSO$_4$), filtered and concentrated under reduced pressure. The residue was purified by column chromatography (Biotage 40M; 2.5% ethyl acetate/hexanes) to afford tert-butyl 2-fluoro-3-methoxyphenylcarbamate (2.27 g, 64% Yield).

Step C: Preparation of 8-fluoro-7-methoxy-2-methylquinoline

A solution of tert-butyl 2-fluoro-3-methoxyphenylcarbamate (2.27 g, 9.41 mmol) in methanol (5 mL) was treated with 4N HCl in 1,4-dioxane (30 mL) for 2 hours. The solvent was removed under reduced pressure and the residue stirred in aqueous 6N HCl (20 mL) at 106° C. A solution of crotonaldehyde (1.56 mL, 18.8 mmol) in n-BuOH (2 mL) was added dropwise from an addition funnel over 20 minutes and the resulting mixture was heated at reflux for an additional 2 hours. The reaction was cooled to ambient temperature and the mixture carefully pH adjusted to 9 with ammonium hydroxide. The mixture was extracted with dichloromethane and the combined dichloromethane extracts were dried (MgSO$_4$), filtered and concentrated under reduced pressure. The residue was purified by column chromatography (Biotage 40M; 10% ethyl acetate/hexanes) to afford 8-fluoro-7-methoxy-2-methylquinoline (1.20 g, 6.28 mmol, 67%).

Step D: Preparation of 8-fluoro-7-methoxyquinoline-2-carbaldehyde

Prepared as described in Example 37, Step B, using 8-fluoro-7-methoxy-2-methylquinoline (0.60 g, 3.14 mmol) in place of 8-ethyl-2-methylquinoline (0.43 g, 79%).

Step E: Preparation of (S)-1-((R)-2,2,2-trifluoro-1-(3-(8-fluoro-7-methoxyquinolin-2-yl)-[1,2,4]triazolo[4,3-a]pyridin-6-yl)ethyl)pyrrolidin-3-amine dihydrochloride Prepared as described in Example 9B using tert-butyl (S)-1-((R)-2,2,2-trifluoro-1-(6-hydrazinylpyridin-3-yl)ethyl)pyrrolidin-3-ylcarbamate and substituting 8-fluoro-7-methoxyquinoline-2-carbaldehyde in Step F. LCMS APCI (+) m/z 461 (M+H).

Example 168

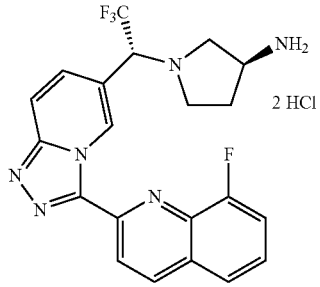 [SMILES: N[C@H]1CCN([C@H](c2ccc3nnc(-c4ccc5cccc(F)c5n4)n3c2)C(F)(F)F)C1]

(S)-1-((R)-2,2,2-trifluoro-1-(3-(8-fluoroquinolin-2-yl)-[1,2,4]triazolo[4,3-a]pyridin-6-yl)ethyl)pyrrolidin-3-amine dihydrochloride Prepared as described in Example 9B using 8-fluoroquinoline-2-carbaldehyde in place of 8-methoxyquinoline-2-carbaldehyde in Step F. LCMS APCI (+) m/z 431 (M+H).

Example 169

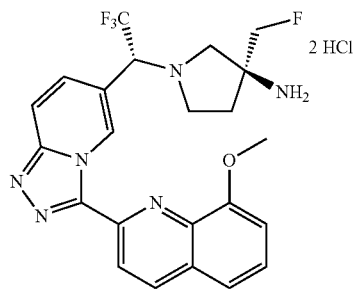 [SMILES: COc1cccc2ccc(-c3nnc4ccc([C@@H](N5CC[C@@](N)(CF)C5)C(F)(F)F)cn34)nc12]

(S)-3-(fluoromethyl)-1-((R)-2,2,2-trifluoro-1-(3-(8-methoxyquinolin-2-yl)-[1,2,4]triazolo[4,3-a]pyridin-6-yl)ethyl)pyrrolidin-3-amine Step A: Preparation of tert-butyl 3-(fluoromethyl)-1-((R)-2,2,2-trifluoro-1-(3-(8-methoxyquinolin-2-yl)-[1,2,4]triazolo[4,3-a]pyridin-6-yl)ethyl)pyrrolidin-3-ylcarbamate Prepared as described in Example 9B using tert-butyl 3-(fluoromethyl)-1-((R)-2,2,2-trifluoro-1-(6-hydrazinylpyridin-3-yl)ethyl)pyrrolidin-3-ylcarbamate (Example 154; 0.20 g, 0.491 mmol) in place of tert-butyl (S)-1-((R)-2,2,2-trifluoro-1-(6-hydrazinylpyridin-3-yl)ethyl)pyrrolidine-3-ylcarbamate and 8-methoxyquinoline-2-carbaldehyde (0.092 g, 0.491 mmol) in Step E (0.229 g, 81%). LCMS APCI (+) m/z 575 (M+H).

Step B: Isolation of Stereoisomer (S) of tert-butyl 3-(fluoromethyl)-1-((R)-2,2,2-trifluoro-1-(3-(8-methoxyquinolin-2-yl)-[1,2,4]triazolo[4,3-a]pyridin-6-yl)ethyl pyrrolidin-3-ylcarbamate The racemic material from Step A was purified by Chiral HPLC (IC, Chiral Technologies) 20% EtOH: 80% hexanes, to provide the first eluting peak as a single stereoisomer (99% e.e.), designated (S) by Proton NMR analysis of the Mosher amide.

Step C: Preparation of (S)-3-(fluoromethyl)-1-((R)-2,2,2-trifluoro-1-(3-(8-methoxyquinolin-2-yl)-[1,2,4]triazolo[4,3-a]pyridin-6-yl)ethyl)pyrrolidin-3-amine Prepared as described in Example 9B, Steps F and G, using (S)-tert-butyl 3-(fluoromethyl)-1-((R)-2,2,2-trifluoro-1-(3-(8-methoxyquinolin-2-yl)-[1,2,4]triazolo[4,3-a]pyridin-6-yl)ethyl)pyrrolidin-3-ylcarbamate in Step F. LCMS APCI (+) m/z 475 (M+H).

Example 170

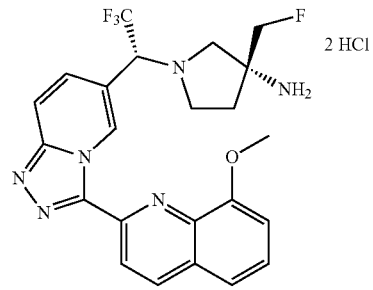 [SMILES: COc1cccc2ccc(-c3nnc4ccc([C@@H](N5CC[C@](N)(CF)C5)C(F)(F)F)cn34)nc12]

(R)3-(fluoromethyl)-1-((R)-2,2,2-trifluoro-1-(3-(8-methoxyquinolin-2-yl)-[1,2,4]triazolo[4,3-a]pyridin-6-yl)ethyl)pyrrolidin-3-amine Step A: Isolation of Stereoisomer (R) of tert-butyl 3-(fluoromethyl)-1-((R)-2,2,2-trifluoro-1-(3-(8-methoxyquinolin-2-yl)-[1,2,4]triazolo[4,3-a]pyridin-6-yl)ethyl)pyrrolidin-3-ylcarbamate The racemic material from Example 169 was purified by Chiral HPLC (Chiral Technologies) IC 20% EtOH: 80% hexanes, to provide the second eluting peak as a single stereoisomer (99% ee), designated (R) by Proton NMR analysis of the Mosher amide.

Step B: Preparation of (R)-3-(fluoromethyl)-1-((R)-2,2,2-trifluoro-1-(3-(8-methoxyquinolin-2-yl)-[1,2,4]triazolo[4,3-a]pyridin-6-yl)ethyl)pyrrolidin-3-amine Prepared as described in Example 9B, Steps F and G, substituting (R)-tert-butyl 3-(fluoromethyl)-1-((R)-2,2,2-trifluoro-1-(3-(8-methoxyquinolin-2-yl)-[1,2,4]triazolo[4,3-a]pyridin-6-yl)ethyl)pyrrolidin-3-ylcarbamate. LCMS APCI (+) m/z 475 (M+H).

Example 171

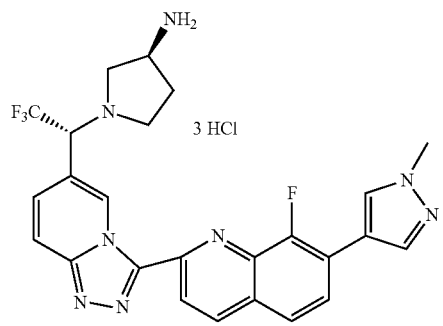 [SMILES: Cn1cc(-c2ccc3ccc(-c4nnc5ccc([C@@H](N6CC[C@H](N)C6)C(F)(F)F)cn45)nc3c2F)cn1]

(S)-1-((R)-2,2,2-trifluoro-1-(3-(8-fluoro-7-(1-methyl-1H-pyrazol-4-yl)quinolin-2-yl)-[1,2,4]triazolo[4,3-a]pyridin-6-yl)ethyl)pyrrolidin-3-amine tri-hydrochloride Step A: Preparation of 8-fluoro-2-methyl-7-(1-methyl-1H-pyrazol-4-yl)quinoline A solution of 7-bromo-8-fluoro-2-methylquinoline (0.15 g, 0.63 mmol), 1-methyl-4-(4,4,5,5-tetramethyl-1,3,2-dioxaborolan-2-yl)-1H-pyrazole (0.26 g, 1.25 mmol), $PdCl_2$(dppf)*dcm (0.051 g, 0.063 mmol), CsF (0.247 g, 1.62 mmol) and triethylamine (0.13 mL, 0.94 mmol) in IPA (3 mL) was heated at 100° C. in a sealed tube for 6 hours. After cooling to ambient temperature, water (10 mL) and ethyl acetate (20 mL) were added. The organic layer was separated, washed with brine, dried (sodium sulfate), filtered and concentrated under reduced pressure. The residue was purified by flash chromatography on silica gel (ethyl acetate) to give 8-fluoro-2-methyl-7-(1-methyl-1H-pyrazol-4-yl)quinoline (0.132 g, 87.6%) as a solid.

Step B: Preparation of (S)-1-((R)-2,2,2-trifluoro-1-(3-(8-fluoro-7-(1-methyl-1H-pyrazol-4-yl)quinolin-2-yl)-[1,2,4]triazolo[4,3-a]pyridin-6-yl)ethyl)pyrrolidin-3-amine tri-hydrochloride Prepared as described in Example 37, Steps B-C, using 8-fluoro-2-methyl-7-(1-methyl-1H-pyrazol-4-yl)quinoline in place of 8-ethyl-2-methylquinoline in Step B. LCMS APCI (+) m/z 511 (M+H).

Example 172

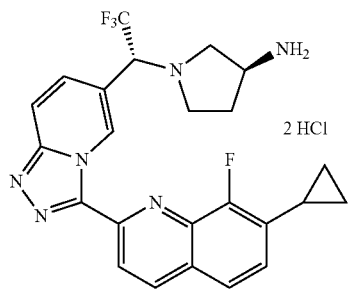 [SMILES: N[C@H]1CCN([C@H](c2ccc3nnc(-c4ccc5ccc(C6CC6)c(F)c5n4)n3c2)C(F)(F)F)C1]

(S)-1-((R)-1-(3-(7-cyclopropyl-8-fluoroquinolin-2-yl)-[1,2,4]triazolo[4,3-a]pyridin-6-yl)-2,2,2-trifluoroethyl)pyrrolidin-3-amine dihydrochloride Step A: Preparation of 7-cyclopropyl-8-fluoro-2-methylquinoline A solution of 7-bromo-8-fluoro-2-methylquinoline (0.15 g, 0.63 mmol), $Pd(PPh_3)_4$ (0.072 g, 0.063 mmol) and 0.5 M cyclopropylzinc(II) bromide (2.50 ml, 1.25 mmol) in THF was stirred at reflux for 12 hours. After cooling to ambient temperature, ethyl acetate (20 mL) and water (5 mL) were added. The organic layer was separated, washed with brine, dried (sodium sulfate), filtered and concentrated under reduced pressure. The residue was purified by flash chromatography on silica gel (hexane/ethyl acetate 2:1) to give 7-cyclopropyl-8-fluoro-2-methylquinoline (0.10 g, 80.3%) as a solid.

Step B: Preparation of (S)-1-((R)-1-(3-(7-cyclopropyl-8-fluoroquinolin-2-yl)-[1,2,4]triazolo[4,3-a]pyridin-6-yl)-2,2,2-trifluoroethyl)pyrrolidin-3-amine dihydrochloride Prepared as described in Example 37, Steps B-C, using 7-cyclopropyl-8-fluoro-2-methylquinoline in place of 8-ethyl-2-methylquinoline in Step B. LCMS APCI (+) m/z 471 (M+H).

Example 173

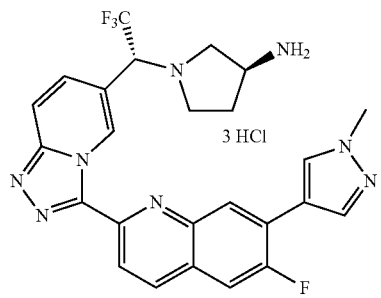 [SMILES: Cn1cc(-c2cc3nc(-c4nnc5ccc([C@@H](N6CC[C@H](N)C6)C(F)(F)F)cn45)ccc3cc2F)cn1]

(S)-1-((R)-2,2,2-trifluoro-1-(3-(6-fluoro-7-(1-methyl-1H-pyrazol-4-yl)quinolin-2-yl)-[1,2,4]triazolo[4,3-a]pyridin-6-yl)ethyl)pyrrolidin-3-amine tri-hydrochloride Prepared as described in Example 171, using 7-bromo-6-fluoro-2-methylquinoline in place of 7-bromo-8-fluoro-2-methylquinoline in Step A. LCMS APCI (+) m/z 511 (M+H).

Example 174

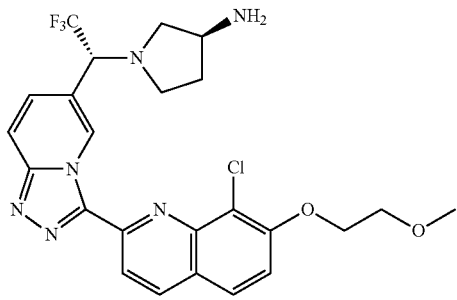

(S)-1-((R)-1-(3-(8-chloro-7-(2-methoxyethoxy) quinolin-2-yl)-[1,2,4]triazolo[4,3-a]pyridin-6-yl)-2, 2,2-trifluoroethyl)pyrrolidin-3-amine hydrochloride Step A: Preparation of
8-chloro-2-methylquinolin-7-ol 2-Methylquinolin-7-ol (200 mg, 1.26 mmol) was added to a solution of 1-chloropyrrolidine-2,5-dione (168 mg, 1.26 mmol) and zirconium(IV) chloride (14.6 mg, 0.0628 mmol) in DCM (10 mL) and the reaction was stirred at ambient temperature for 24 hours. The reaction was diluted with chloroform (30 mL) and washed with an aqueous sodium carbonate solution followed by brine. After drying (MgSO₄), the solution was filtered and concentrated under reduced pressure and the residue was purified by reverse phase chromatography (SP4, 25 M, eluting with a gradient of water/ACN 90:10 to 0:100, 30 column volumes) to yield 8-chloro-2-methylquinolin-7-ol (134 mg, 55.1% yield) as a thick oil.

Step B: Preparation of
8-chloro-7-(2-methoxyethoxy)-2-methylquinoline 8-chloro-2-methylquinolin-7-ol (80 mg, 0.41 mmol), potassium carbonate (171 mg, 1.2 mmol) and 1-bromo-2-methoxyethane (115 mg, 0.83 mmol) in acetone (10 mL) were stirred at 70° C. in a sealed tube for 20 hours. After dilution with water (50 mL) the reaction was extracted with DCM. The DCM phases were concentrated under reduced pressure and the residue purified by reverse phase chromatography (SP4, 25M, eluting with a gradient of water/ACN 100:0 to 0:100, 20 column volumes) to yield 8-chloro-7-(2-methoxyethoxy)-2-methylquinoline as a solid.

Step C: Preparation of (S)-1-((R)-1-(3-(8-chloro-7-(2-methoxyethoxy)quinolin-2-yl)-[1,2,4]triazolo[4,3-a]pyridin-6-yl)-2,2,2-trifluoroethyl)pyrrolidin-3-amine hydrochloride Prepared following Steps B-E of Example 117, substituting 2,8-dimethylquinolin-7-ol with 8-chloro-7-(2-methoxyethoxy)-2-methylquinoline in Step B. LCMS APCI (+) m/z 521 (M+H).

Example 175

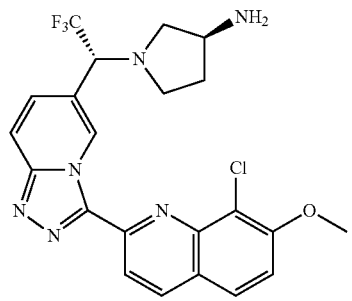 [SMILES: COc1ccc2ccc(-c3nnc4ccc([C@@H](N5CC[C@H](N)C5)C(F)(F)F)cn34)nc2c1Cl]

(S)-1-((R)-1-(3-(8-chloro-7-methoxyquinolin-2-yl)-[1,2,4]triazolo[4,3-a]pyridin-6-yl)-2,2,2-trifluoroethyl)pyrrolidin-3-amine hydrochloride Prepared as in Example 174, substituting 1-bromo-2-methoxyethane in Step B with iodomethane. LCMS APCI (+) m/z 477 (M+H).

Example 176

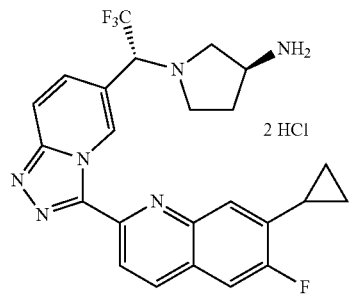 [SMILES: N[C@H]1CCN([C@H](c2ccc3nnc(-c4ccc5cc(F)c(C6CC6)cc5n4)n3c2)C(F)(F)F)C1]

(S)-1-((R)-1-(3-(7-cyclopropyl-6-fluoroquinolin-2-yl)-[1,2,4]triazolo[4,3-a]pyridin-6-yl)-2,2,2-trifluoroethyl)pyrrolidin-3-amine dihydrochloride Prepared as described in Example 172, using 7-bromo-6-fluoro-2-methylquinoline in place of 7-bromo-8-fluoro-2-methylquinoline in Step A. LCMS APCI (+) m/z 471 (M+H).

Example 177

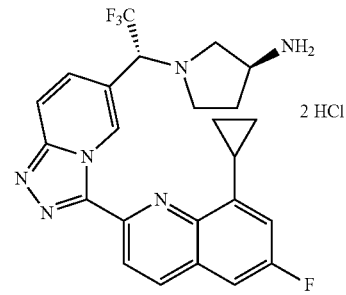 [SMILES: N[C@H]1CCN([C@H](c2ccc3nnc(-c4ccc5cc(F)cc(C6CC6)c5n4)n3c2)C(F)(F)F)C1]

(S)-1-((R)-1-(3-(8-cyclopropyl-6-fluoroquinolin-2-yl)-[1,2,4]triazolo[4,3-a]pyridin-6-yl)-2,2,2-trifluoroethyl)pyrrolidin-3-amine dihydrochloride Prepared as described in Example 172, using 8-bromo-6-fluoro-2-methylquinoline in place of 7-bromo-8-fluoro-2-methylquinoline in Step A. LCMS APCI (+) m/z 471 (M+H).

Example 178

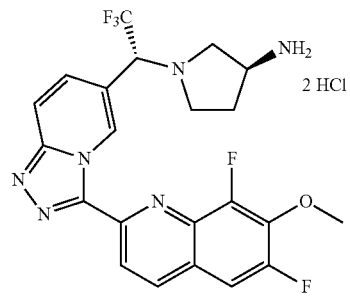 [SMILES: COc1c(F)cc2ccc(-c3nnc4ccc([C@@H](N5CC[C@H](N)C5)C(F)(F)F)cn34)nc2c1F]

(S)-1-((R)-1-(3-(6,8-difluoro-7-methoxyquinolin-2-yl)-[1,2,4]triazolo[4,3-a]pyridin-6-yl)-2,2,2-trifluoroethyl)pyrrolidin-3-amine dihydrochloride Step A: Preparation of 6,8-difluoro-7-methoxyquinoline-2-carbaldehyde Prepared as described in Example 167, Steps A-D, using 2,4-difluoro-3-methoxybenzoic acid (5.0 g, 26.58 mmol) in place of 2-fluoro-3-methoxybenzoic acid in Step B (0.942 g, 65%).

Preparation of (S)-1-((R)-1-(3-(6,8-difluoro-7-methoxyquinolin-2-yl)-[1,2,4]triazolo[4,3-a]pyridin-6-yl)-2,2,2-trifluoroethyl)pyrrolidin-3-amine dihydrochloride Prepared as described in Example 9B, Steps F and G, using tert-butyl (S)-1-((R)-2,2,2-trifluoro-1-(6-hydrazinylpyridin-3-yl)ethyl)pyrrolidin-3-ylcarbamate and 6,8-difluoro-7-methoxyquinoline-2-carbaldehyde in place of 8-methoxyquinoline-2-carbaldehyde in Step F. LCMS APCI (+) m/z 479 (M+H).

Example 179

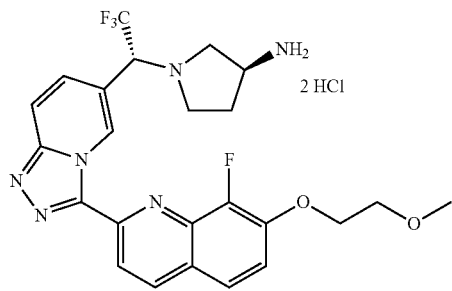 [SMILES: COCCOc1ccc2ccc(-c3nnc4ccc([C@@H](N5CC[C@H](N)C5)C(F)(F)F)cn34)nc2c1F]

(S)-1-((R)-2,2,2-trifluoro-1-(3-(8-fluoro-7-(2-methoxyethoxy)quinolin-2-yl)-[1,2,4]triazolo[4,3-a]pyridin-6-yl)ethyl)pyrrolidin-3-amine dihydrochloride Step A: Preparation of 8-fluoro-7-methoxy-2-methylquinoline Prepared as described in Example 167, Steps A-C (1.20 g, 67%).

Step B: Preparation of 8-fluoro-2-methylquinolin-7-ol

A solution of 8-fluoro-7-methoxy-2-methylquinoline (0.57 g, 2.96 mmol) was stirred in dichloromethane (5 mL) and treated with a 1M solution of BBr$_3$ in dichloromethane (15 mL). The resulting mixture was heated at reflux for 16 hours, then poured into crushed ice and basified with a 6N NaOH solution to pH 14. The organic layer was separated and the aqueous layer was further extracted with dichloromethane. The organic layer was pH adjusted to 6 with aqueous 6N HCl and extracted with ethyl acetate. The combined organic extracts were dried (MgSO$_4$), filtered and concentrated under reduced pressure to afford 8-fluoro-2-methylquinolin-7-ol in quantitative yield.

Step C: Preparation of 8-fluoro-7-(2-methoxyethoxy)-2-methylquinoline

To a mixture of 8-fluoro-2-methylquinolin-7-ol (0.30 g, 1.69 mmol) and potassium carbonate (0.70 mg, 5.08 mmol) in acetone (7 mL) was added 1-bromo-2-methoxyethane (0.47 g, 3.39 mmol) and the mixture heated at 70° C. for 18 hours. Additional bromo-2-methoxyethane (0.150 mL) and potassium carbonate (0.35 g) were added and heating was continued for 16 hours. The mixture was partitioned between water and ethyl acetate and the layers were separated. The organic layer was dried (MgSO$_4$), filtered and concentrated under reduced pressure. The residue was purified by column chromatography (Biotage, 25M; 25% ethyl acetate:hexanes) to afford 8-fluoro-7-(2-methoxyethoxy)-2-methylquinoline (0.217 g, 54%).

Step D: Preparation of 8-fluoro-7-(2-methoxyethoxy)quinoline-2-carbaldehyde

Prepared as described in Example 37, substituting 8-fluoro-7-(2-methoxyethoxy)-2-methylquinoline (0.216 g, 0.918 mmol) in Step B (0.20 g, 87%).

Step E: Preparation of (S)-1-((R)-2,2,2-trifluoro-1-(3-(8-fluoro-7-(2-methoxyethoxy)quinolin-2-yl)-[1,2,4]triazolo[4,3-a]pyridin-6-yl)ethyl)pyrrolidin-3-amine dihydrochloride Prepared as described in Example 9B, Steps F and G, using tert-butyl (S)-1-((R)-2,2,2-trifluoro-1-(6-hydrazinylpyridin-3-yl)ethyl)pyrrolidin-3-ylcarbamate and 8-fluoro-7-(2-methoxyethoxy)quinoline-2-carbaldehyde in place of 8-methoxyquinoline-2-carbaldehyde in Step F. LCMS APCI (+) m/z 505 (M+H).

Example 180

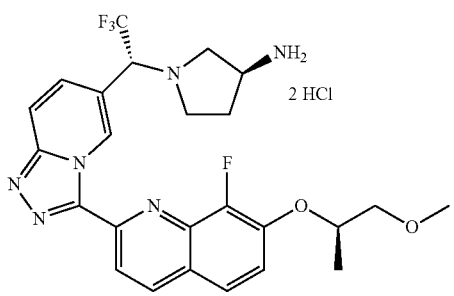 [SMILES: COC[C@@H](C)Oc1ccc2ccc(-c3nnc4ccc([C@@H](N5CC[C@H](N)C5)C(F)(F)F)cn34)nc2c1F]

(S)-1-((R)-2,2,2-trifluoro-1-(3-(8-fluoro-7-((R)-1-methoxypropan-2-yloxy)quinolin-2-yl)-[1,2,4]triazolo[4,3-a]pyridin-6-yl)ethyl)pyrrolidin-3-amine dihydrochloride Step A: Preparation of (R)-8-fluoro-7-(1-methoxypropan-2-yloxy)-2-methylquinoline Prepared as described in Example 140, Step A, using 8-fluoro-2-methylquinolin-7-ol (0.30 g, 1.69 mmol) in place of 2-methylquinolin-8-ol and using (S)-1-methoxypropan-2-ol (0.196 g, 46%).

Step B: Preparation of (R)-8-fluoro-7-(1-methoxypropan-2-yloxy)quinoline-2-carbaldehyde Prepared as described in Example 37, Step B, using (R)-8-fluoro-7-(1-methoxypropan-2-yloxy)-2-methylquinoline (0.195 g, 0.782 mmol) to provide 0.141 g (69%) of the desired product.

Step C: Preparation of (S)-1-((R)-2,2,2-trifluoro-1-(3-(8-fluoro-7-((R)-1-methoxypropan-2-yloxy)quinolin-2-yl)-[1,2,4]triazolo[4,3-a]pyridin-6-yl)ethyl)pyrrolidin-3-amine dihydrochloride Prepared as described in Example 9B, Steps F and G, using tert-butyl (S)-1-((R)-2,2,2-trifluoro-1-(6-hydrazinylpyridin-3-yl)ethyl)pyrrolidin-3-ylcarbamate and (R)-8-fluoro-7-(1-methoxypropan-2-yloxy)quinoline-2-carbaldehyde in Step F. LCMS (APCI) (+) m/z 519 (M+H).

Example 181

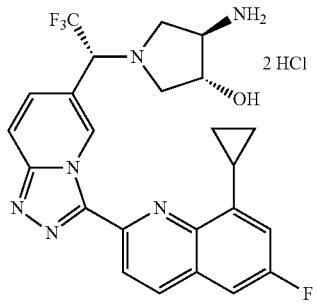 [SMILES: N[C@@H]1CN([C@H](c2ccc3nnc(-c4ccc5cc(F)cc(C6CC6)c5n4)n3c2)C(F)(F)F)C[C@H]1O]

(3R,4R)-4-amino-1-((R)-1-(3-(8-cyclopropyl-6-fluoroquinolin-2-yl)-[1,2,4]triazolo[4,3-a]pyridin-6-yl)-2,2,2-trifluoroethyl)pyrrolidin-3-ol dihydrochloride Prepared as described in Example 9B, Steps E-G, using tert-butyl (3R,4R)-1-((R)-1-(6-chloropyridin-3-yl)-2,2,2-trifluoroethyl)-4-hydroxypyrrolidin-3-ylcarbamate in place of tert-butyl (S)-1-((R)-1-(6-chloropyridin-3-yl)-2,2,2-trifluoroethyl)pyrrolidin-3-ylcarbamate in Step E, and substituting 6-fluoro-8-cyclopropylquinoline-2-carbaldehyde for 8-methoxyquinoline-2-carbaldehyde in Step F. LCMS APCI (+) m/z 487 (M+H).

Example 182

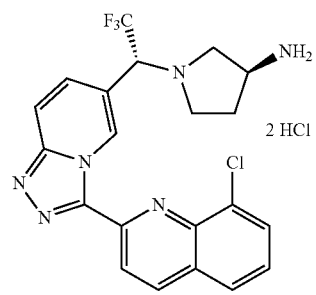 [SMILES: N[C@H]1CCN([C@H](c2ccc3nnc(-c4ccc5cccc(Cl)c5n4)n3c2)C(F)(F)F)C1]

(S)-1-((R)-2,2,2-trifluoro-1-(3-(8-chloroquinolin-2-yl)-[1,2,4]triazolo[4,3-a]pyridin-6-yl)ethyl)pyrrolidin-3-amine dihydrochloride Prepared as described in Example 9B, Steps F and G, using 8-chloroquinoline-2-carbaldehyde in place of 8-methoxyquinoline-2-carbaldehyde in Step F. LCMS APCI (+) m/z 447 (M+H).

Example 183

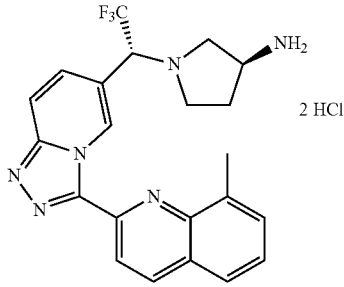 [SMILES: Cc1cccc2ccc(-c3nnc4ccc([C@@H](N5CC[C@H](N)C5)C(F)(F)F)cn34)nc12]

(S)-1-((R)-2,2,2-trifluoro-1-(3-(8-methylquinolin-2-yl)-[1,2,4]triazolo[4,3-a]pyridin-6-yl)ethyl)pyrrolidin-3-amine dihydrochloride Step A: Preparation of 2,8-dimethylquinoline Prepared as described in Example 37, Step A, using o-toluidine (8.0 g, 74.7 mmol) in place of 2-ethylaniline (5.72 g, 49%).

Step B: Preparation of 8-methylquinoline-2-carbaldehyde

Prepared as described in Example 37, Step B, using 2,8-dimethylquinoline (5.72 g, 36.4 mmol) in place of 8-ethyl-2-methylquinolinepyrrolidin-3-ylcarbamate in Step B (5.47 g, 88%).

Step C: Preparation of (S)-1-((R)-2,2,2-trifluoro-1-(3-(8-methylquinolin-2-yl)-[1,2,4]triazolo[4,3-a]pyridin-6-yl)ethyl)pyrrolidin-3-amine dihydrochloride Prepared as described in Example 9B, Steps F and G, using 8-methylquinoline-2-carbaldehyde and tert-butyl (S)-1-((R)-2,2,2-trifluoro-1-(6-hydrazinylpyridin-3-yl)ethyl)pyrrolidine-3-ylcarbamate. APCI (+) m/z 427 (M+H).

Example 184

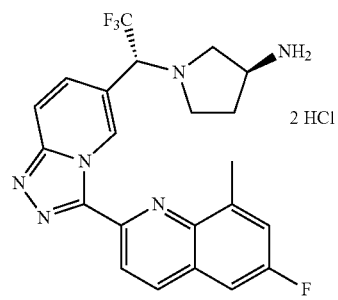 [SMILES: Cc1cc(F)cc2ccc(-c3nnc4ccc([C@@H](N5CC[C@H](N)C5)C(F)(F)F)cn34)nc12]

(S)-1-((R)-2,2,2-trifluoro-1-(3-(6-fluoro-8-methylquinolin-2-yl)-[1,2,4]triazolo[4,3-a]pyridin-6-yl)ethyl)pyrrolidin-3-amine dihydrochloride Step A: Preparation of 6-fluoro-2,8-dimethylquinoline Prepared as described in Example 37, Step A, using 4-fluoro-2, methylaniline in place of 2-ethylaniline, to afford 6-fluoro-2,8-dimethylquinoline (21 g, 98%).

Step B: Preparation of 6-fluoro-8-methylquinoline-2-carbaldehyde

Prepared as described in Example 37, Step B, using 6-fluoro-2,8-dimethylquinoline (5.62 g, 32.1 mmol) in place of 8-ethyl-2-methylquinoline (3.08 g, 51%).

Step C: Preparation of (S)-1-((R)-2,2,2-trifluoro-1-(3-(6-fluoro-8-methylquinolin-2-yl)-[1,2,4]triazolo[4,3-a]pyridin-6-yl)ethyl)pyrrolidin-3-amine dihydrochloride Prepared as described in Example 9B, Steps F and G, using tert-butyl (S)-1-((R)-2,2,2-trifluoro-1-(6-hydrazinylpyridin-3-yl)ethyl)pyrrolidin-3-ylcarbamate and using 6-fluoro-8-methylquinoline-2-carbaldehyde in Step F. LCMS APCI (+) m/z 445 (M+H).

Example 185

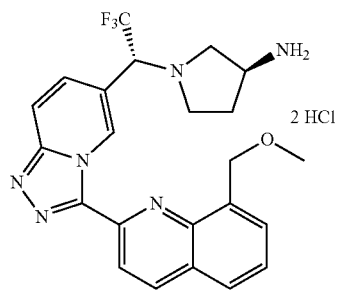 [SMILES: COCc1cccc2ccc(-c3nnc4ccc([C@@H](N5CC[C@H](N)C5)C(F)(F)F)cn34)nc12]

(S)-1-((R)-2,2,2-trifluoro-1-(3-(8-(methoxymethyl)quinolin-2-yl)-[1,2,4]triazolo[4,3-a]pyridin-6-yl)ethyl)pyrrolidin-3-amine dihydrochloride Step A: Preparation of 1-(methoxymethyl)-2-nitrobenzene To a solution of (2-nitrophenyl)methanol (5.13 g, 33.50 mmol) in DCM (75 mL) was added 3.35 N NaOH (75 mL, 251.2 mmol) in water at ambient temperature and stirred at ambient temperature for 10 minutes. $Me_2SO_4$ (6.38 ml, 67.0 mmol) and tetrabutylammonium hydrogen sulfate (0.57 g, 1.68 mmol) were added and the mixture stirred vigorously for 20 hours at ambient temperature. The reaction mixture was diluted with DCM (100 mL) and organic layer was separated, washed with brine, dried (sodium sulfate), filtered and concentrated under reduced pressure. The residue was purified by flash chromatography on silica gel (5:1 hexane/ethyl acetate) to give 1-(methoxymethyl)-2-nitrobenzene (5.12 g, 91.4%) as an oil.

Step B: Preparation of 2-(methoxymethyl)aniline

A solution of 1-(methoxymethyl)-2-nitrobenzene (4.30 g, 25.7 mmol) and $PtO_2$ (0.29 g, 1.29 mmol) in MeOH (30 mL) was charged with 1 atmosphere hydrogen and stirred at ambient temperature for 1 hour. Charcoal (5 g) was added and the reaction mixture was stirred for 10 minutes. The solid was removed by filtration and washed with methanol. The filtrate was concentrated under reduced pressure to give 2-(methoxymethyl)aniline (3.42 g, 96.9%) as a solid.

Step C: Preparation of 8-(methoxymethyl)-2-methylquinoline

Prepared as described in Example 37, Step A, using 2-(methoxymethyl)aniline in place of 2-ethylaniline.

Step C: Preparation of (S)-1-((R)-2,2,2-trifluoro-1-(3-(8-(methoxymethyl)quinolin-2-yl)-[1,2,4]triazolo[4,3-a]pyridin-6-yl)ethyl)pyrrolidin-3-amine dihydrochloride Prepared as described in Example 37, Steps B-C, using 8-(methoxymethyl)-2-methylquinoline in place of 8-ethyl-2-methylquinoline in Step B. LCMS APCI (+) m/z 457 (M+H).

Example 186

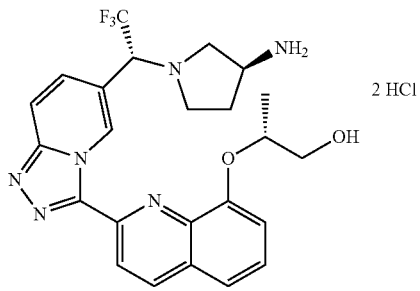 [SMILES: C[C@H](CO)Oc1cccc2ccc(-c3nnc4ccc([C@@H](N5CC[C@H](N)C5)C(F)(F)F)cn34)nc12]

(R)-2-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)propan-1-ol dihydrochloride

Step A: Preparation of (S)-1-(tert-butyldimethylsilyloxy)propan-2-ol

A solution of (S)-propane-1,2-diol (1.9 mL, 26 mmol), tert-butyldimethylsilyl chloride (4.87 g, 32 mmol), and imidazole (4.5 g, 66 mmol) in anhydrous dimethylformamide (6.6 mL, 26 mmol) was allowed to stir at ambient temperature for 12 hours. The reaction mixture was poured into ethyl acetate (50 mL) and washed sequentially with saturated aqueous sodium bicarbonate (30 mL) and water (30 mL). The organic extract was dried over sodium sulfate, filtered and concentrated under reduced pressure to give the title compound (5.2 g, 104%) which was used without further purification.

Step B: Preparation of (R)-8-(1-(tert-butyldimethylsilyloxy)propan-2-yloxy)-2-methylquinoline To a solution of 2-methylquinolin-8-ol (0.40 g, 2.5 mmol) in tetrahydrofuran (2.1 mL, 2.5 mmol) was added triphenylphosphine (1.6 g, 6.3 mmol), diethyl azodicarboxylate (0.63 mL, 4.0 mmol), and (S)-1-(tert-butyldimethylsilyloxy)propan-2-ol (0.62 g, 3.3 mmol). The resultant mixture was allowed to stir at ambient temperature for 24 hours. The reaction mixture was diluted with water (10 mL) and extracted with dichloromethane (2×20 mL). The combined organic extracts were dried over magnesium sulfate and concentrated under reduced pressure. The residue was purified by normal phase chromatography on silica gel (10-30% ethyl acetate/hexanes) to provide the title compound (0.33 g, 40%).

Step C: Preparation of (R)-8-(1-(tert-butyldimethylsilyloxy)propan-2-yloxy)quinoline-2-carbaldehyde To a solution of (R)-8-(1-(tert-butyldimethylsilyloxy)propan-2-yloxy)-2-methylquinoline (0.33 g, 1.0 mmol) in dioxane (40 mL) and water (0.4 mL) was added selenium dioxide (0.13 g, 1.2 mmol) and the resultant mixture heated at reflux for 1 hour. The cooled reaction mixture was filtered through a plug of Celite® to remove solids, rinsing with dichloromethane and the filtrate was concentrated under reduced pressure. The residue was purified by normal phase chromatography on silica gel (10% ethyl acetate/hexanes) providing the title compound (0.29 g, 84%).

Step D: Preparation of tert-butyl (S)-1-((R)-1-(3-(8-((R)-1-(tert-butyldimethylsilyloxy)propan-2-yloxy)quinolin-2-yl)-[1,2,4]triazolo[4,3-a]pyridin-6-yl)-2,2,2-trifluoroethyl)pyrrolidin-3-ylcarbamate A solution of tert-butyl (S)-1-((R)-2,2,2-trifluoro-1-(6-hydrazinylpyridin-3-yl)ethyl)pyrrolidin-3-ylcarbamate (Example 9B, Steps A-E; 0.32 g, 0.84 mmol) and (R)-8-(1-(tert-butyldimethylsilyloxy)propan-2-yloxy)quinoline-2-carbaldehyde (0.29 g, 0.84 mmol) in ethanol (4.2 mL, 0.84 mmol) was allowed to stir at ambient temperature for 12 hours. The solvent was removed under reduced pressure. The residue was dissolved in dichloromethane (4.2 mL) and iodosobenzene diacetate (0.30 g, 0.92 mmol) was added. The reaction mixture was stirred at ambient temperature for 1 hour. Ethyl acetate (20 mL) and saturated sodium bicarbonate (10 mL) were added. The organic layer was separated, washed with brine, dried over sodium sulfate, filtered and concentrated under reduced pressure. The residue was purified by reverse phase chromatography on C18 (0-100% acetonitrile/water) to give the title compound (0.29 g, 49%).

Step E: Preparation of (R)-2-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)propan-1-ol dihydrochloride To a solution of tert-butyl (S)-1-((R)-1-(3-(8-((R)-1-(tert-butyldimethylsilyloxy)propan-2-yloxy)quinolin-2-yl)-[1,2,4]triazolo[4,3-a]pyridin-6-yl)-2,2,2-trifluoroethyl)pyrrolidin-3-ylcarbamate (0.29 g, 0.41 mmol) in dichloromethane (1 mL) was added trifluoroacetic acid (2 mL) was stirred at ambient temperature for 30 minutes. The reaction mixture was concentrated under reduced pressure. The residue was purified by reverse phase chromatography on C18 (0-80% acetonitrile/water). The material isolated after purification was dissolved in methanol (0.5 mL) and added dropwise to hydrochloric acid (2M in diethyl ether; 5 mL). The resulting salt was collected by vacuum filtration to provide the title compound (0.17 g, 73%). LCMS APCI (+) m/z 487 (M+H).

Example 187

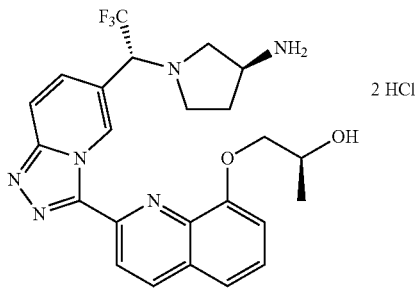 [SMILES: C[C@H](O)COc1cccc2ccc(-c3nnc4ccc([C@@H](N5CC[C@H](N)C5)C(F)(F)F)cn34)nc12]

(S)-1-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)propan-2-ol dihydrochloride Step A: Preparation of (S)-1-(2-methylquinolin-8-yloxy)propan-2-ol A mixture of 2-methylquinolin-8-ol (0.50 g, 3.1 mmol), cesium carbonate (3.1 g, 9.4 mmol), and S-(−)-propylene oxide (0.66 mL, 9.4 mmol) in dimethylformamide (3.7 mL, 3.1 mmol) was vigorously stirred at 80° C. for 12 hours. The cooled reaction mixture was diluted with water (30 mL) and stirred at ambient temperature for 30 minutes. The solids which formed were collected by vacuum filtration providing the title compound (0.36 g, 53%) which was used without further purification.

Step B: Preparation of (S)-8-(2-hydroxypropoxy)quinoline-2-carbaldehyde

To a solution of (S)-1-(2-methylquinolin-8-yloxy)propan-2-ol (0.15 g, 0.69 mmol) in dioxane (10 mL) and water (0.1 mL) was added selenium dioxide (0.092 g, 0.83 mmol) and the resultant mixture heated at reflux for 2.5 hours. The cooled reaction mixture was filtered through a plug of Celite® to remove solids, rinsing with dichloromethane, and the filtrate was concentrated under reduced pressure. The residue was purified by normal phase chromatography on silica gel (20-40% ethyl acetate/hexanes) providing the title compound (0.091 g, 57%).

Step C: Preparation of tert-butyl (S)-1-((R)-2,2,2-trifluoro-1-(3-(8-((S)-2-hydroxypropoxy)quinolin-2-yl)-[1,2,4]triazolo[4,3-a]pyridin-6-yl)ethyl)pyrrolidin-3-ylcarbamate A solution of tert-butyl (S)-1-((R)-2,2,2-trifluoro-1-(6-hydrazinylpyridin-3-yl)ethyl)pyrrolidin-3-ylcarbamate (0.16 g, 0.39 mmol) and (S)-8-(2-hydroxypropoxy)quinoline-2-carbaldehyde (0.91 g, 0.39 mmol) in ethanol (2.0 mL, 0.39 mmol) was allowed to stir at ambient temperature for 12 hours. The solvent was removed under reduced pressure. The residue was dissolved in dichloromethane (2.0 mL) and iodosobenzene diacetate (0.14 g, 0.43 mmol) was added. The reaction mixture was stirred at ambient temperature for 1 hour. Ethyl acetate (20 mL) and saturated sodium bicarbonate (10 mL) were added. The organic layer was separated, washed with brine, dried over sodium sulfate, filtered and concentrated under reduced pressure. The residue was purified by reverse phase chromatography on C18 (0-100% acetonitrile/water) to give the title compound (0.11 g, 49%).

Step D: Preparation of (S)-1-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)propan-2-ol dihydrochloride A solution of tert-butyl (S)-1-((R)-2,2,2-trifluoro-1-(3-(8-((S)-2-hydroxypropoxy)quinolin-2-yl)-[1,2,4]triazolo[4,3-a]pyridin-6-yl)ethyl)pyrrolidin-3-ylcarbamate (0.11 g, 0.19 mmol) in dichloromethane (1 mL) and trifluoroacetic acid (2 mL) was stirred at ambient temperature for 30 minutes. The reaction mixture was concentrated under reduced pressure. The residue was by reverse phase chromatography on C18 (0-80% acetonitrile/water). The material isolated after purification was dissolved in methanol (0.5 mL) and added dropwise to hydrochloric acid (2M in diethyl ether; 5 mL). The resulting salt was collected by vacuum filtration to provide the title compound (0.026 g, 25%). LCMS APCI (+) m/z 487 (M+H).

Example 188

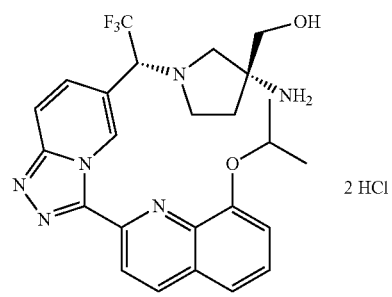 [SMILES: CC(C)Oc1cccc2ccc(-c3nnc4ccc([C@@H](N5CC[C@](N)(CO)C5)C(F)(F)F)cn34)nc12]

((R)-3-amino-1-((R)-2,2,2-trifluoro-1-(3-(8-isopropoxyquinolin-2-yl)-[1,2,4]triazolo[4,3-a]pyridin-6-yl)ethyl)pyrrolidin-3-yl)methanol dihydrochloride Step A: Preparation of (S)-methyl 3-(benzyloxycarbonyloxy)-2-(tert-butoxycarbonylamino)propanoate A solution of N-(tert-butoxycarbonyl)-L-serine methyl ester (25.0 g, 114 mmol) in DCM (570 mL) was cooled to −50° C. Pyridine (23.0 mL, 285 mmol) was added. CBZ-Cl (18.9 mL, 125 mmol) was added dropwise over 1 hour. The reaction mixture was warmed to ambient temperature and stirred overnight. The reaction mixture was then diluted with DCM, washed with 10% citric acid and brine, dried and concentrated under reduced pressure. The residue was purified by flash chromatography on silica gel (5:1 hexanes/EtOAc) to give (S)-methyl 3-(benzyloxycarbonyloxy)-2-(tert-butoxycarbonylamino)propanoate (36.0 g, 89%).

Step B: Preparation of methyl 2-(tert-butoxycarbonylamino)acrylate

A mixture of (S)-methyl 3-(benzyloxycarbonyloxy)-2-(tert-butoxycarbonylamino)propanoate (36.0 g, 102 mmol), $K_2CO_3$ (28.2 g, 204 mmol) and DMF (204 mL) was heated at 65° C. for 1 hour. After cooling, the reaction mixture was partitioned between ether and water. The aqueous layer was extracted with ether. The combined organic layers were washed with water and brine, dried and concentrated under reduced pressure. The residue was purified by flash chromatography on silica gel (10:1 hexanes/EtOAc) to give methyl 2-(tert-butoxycarbonylamino)acrylate (16.5 g, 81%) as a colorless oil, which was used directly in the next step.

Step C: Preparation of methyl 1-benzyl-3-(tert-butoxycarbonylamino)pyrrolidine-3-carboxylate To a solution of methyl 2-(tert-butoxycarbonylamino)acrylate (16.5 g, 82.0 mmol) and N-(Methoxymethyl)-N-(trimethylsilylmethyl)benzylamine (19.5 g, 82.0 mmol) in DCM (400 mL) was added dropwise TFA (0.32 mL) at 0° C. under nitrogen. The reaction mixture was allowed to warm to ambient temperature and stirred overnight. The reaction mixture was diluted with DCM, washed with saturated aqueous $NaHCO_3$ and brine, dried and concentrated under reduced pressure. The residue was purified by flash chromatography on silica gel (3% MeOH in DCM) to give methyl 1-benzyl-3-(tert-butoxycarbonylamino)pyrrolidine-3-carboxylate (21.7 g, 79%).

Step D: Preparation of tert-butyl 1-benzyl-3-(hydroxymethyl)pyrrolidin-3-ylcarbamate To a solution of methyl 1-benzyl-3-(tert-butoxycarbonylamino)pyrrolidine-3-carboxylate (21.7 g, 64.9 mmol) in THF (320 mL) was added dropwise a solution of LiAlH$_4$ in THF (1.0 M, 55.2 mL, 55.2 mmol) at −78° C. under nitrogen. The reaction mixture was warmed to 0° C. for 5 minutes and then quenched by dropwise addition of water (2.1 mL) followed by 15% NaOH (2.1 mL) and water (6.3 mL). The reaction mixture was stirred at ambient temperature for 15 minutes and then filtered through Celite®. The filtrate was concentrated under reduced pressure and purified by flash chromatography on silica gel (4% MeOH in DCM) to give tert-butyl 1-benzyl-3-(hydroxymethyl)pyrrolidin-3-ylcarbamate (11.2 g, 56%) as a colorless oil.

Step E: Isolation of (R)-tert-butyl 1-benzyl-3-(hydroxymethyl)pyrrolidin-3-ylcarbamate The enantiomerically pure (R)-tert-butyl 1-benzyl-3-(hydroxymethyl)pyrrolidin-3-ylcarbamate (3.95 g) was separated from racemic tert-butyl 1-benzyl-3-(hydroxymethyl)pyrrolidin-3-ylcarbamate (11.0 g, 35.9 mmol) by chiral SFC (for analysis: Rt of the (R) enantiomer=4.22 min; Rt of the (S) enantiomer=6.45 min; Chiralpak AD-H 4.6 mm×150 mm, 85/15 heptane/EtOH (with 0.2% DEA) at 1.5 mL/min. For preparative SFC: AD-H 21 mm×250 mm, 8% EtOH with 0.1% DEA at 65 mL/min).

Step F: Preparation of (R)-tert-butyl 3-(hydroxymethyl)pyrrolidin-3-ylcarbamate

A mixture of (R)-tert-butyl 1-benzyl-3-(hydroxymethyl) pyrrolidin-3-ylcarbamate (387 mg, 1.26 mmol), 10% Pd/C (134 mg, 0.126 mmol), ammonium formate (398 mg, 6.32 mmol) and MeOH (10 mL) was heated at reflux under nitrogen for 3 hours. After cooling, the reaction mixture was filtered through Celite®. The filtrate was concentrated under reduced pressure. The residue was taken up in DCM and filtered through Celite again. Removal of the solvent gave (R)-tert-butyl 3-(hydroxymethyl)pyrrolidin-3-ylcarbamate (260 mg, 95%), which was used in the next Step without further purification.

Step G: Preparation of ((R)-3-amino-1-((R)-2,2,2-trifluoro-1-(3-(8-isopropoxyquinolin-2-yl)-[1,2,4] triazolo[4,3-a]pyridin-6-yl)ethyl)pyrrolidin-3-yl) methanol dihydrochloride Prepared as described in Example 9B, Steps D-G, using (R)-tert-butyl 3-(hydroxymethyl)pyrrolidin-3-ylcarbamate in place of (S)-tert-butyl pyrrolidin-3-ylcarbamate in Step D, and substituting 8-isopropoxyquinoline-2-carbaldehyde for 8-methoxyquinoline-2-carbaldehyde in Step F. LCMS APCI (+) m/z 501 (M+H).

Example 189

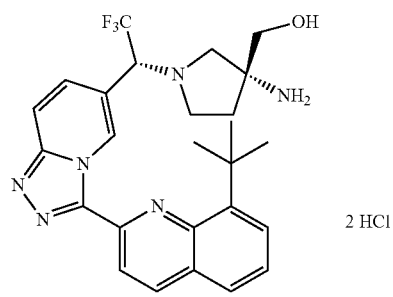 [SMILES: CC(C)(C)c1cccc2ccc(-c3nnc4ccc([C@@H](N5CC[C@](N)(CO)C5)C(F)(F)F)cn34)nc12]

((R)-3-amino-1-((R)-1-(3-(8-tert-butylquinolin-2-yl)-[1,2,4]triazolo[4,3-a]pyridin-6-yl)-2,2,2-trifluoroethyl)pyrrolidin-3-yl)methanol dihydrochloride Prepared as described in Example 9B, Steps D-G, using (R)-tert-butyl 3-(hydroxymethyl)pyrrolidin-3-ylcarbamate in place of (S)-tert-butyl pyrrolidin-3-ylcarbamate in Step D, and substituting 8-tert-butylquinoline-2-carbaldehyde for 8-methoxyquinoline-2-carbaldehyde in Step F. LCMS APCI (+) m/z 499 (M+H).

Example 190

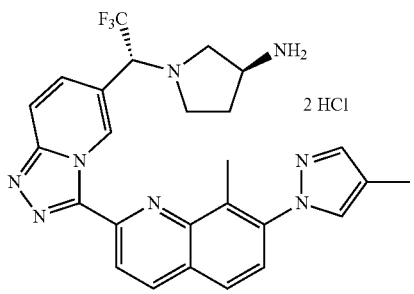 [SMILES: Cc1cnn(-c2ccc3ccc(-c4nnc5ccc([C@@H](N6CC[C@H](N)C6)C(F)(F)F)cn45)nc3c2C)c1]

(S)-1-((R)-2,2,2-trifluoro-1-(3-(8-methyl-7-(4-methyl-1H-pyrazol-1-yl)quinolin-2-yl)-[1,2,4]triazolo [4,3-a]pyridin-6-yl)ethyl)pyrrolidin-3-amine dihydrochloride Step A: Preparation of 7-bromo-2,8-dimethylquinoline Prepared as described in Example 37, Step A, using 3-Bromo-2-methylaniline (8.49 g, 45.6 mmol) in place of 2-ethylaniline (5.94 g, 55%).

Step B: Preparation of 2,8-dimethyl-7-(4-methyl-1H-pyrazol-1-yl)quinoline

A mixture of 7-Bromo-2,8-methylaniline (2.00 g, 8.47 mmol), 4-methyl-1H-pyrazole (1.04 g, 1.02 mL, 12.71 mmol), Cs$_2$CO$_3$ (5.52 g, 16.94 mmol) and CuO (0.067 g, 0.847 mmol) and Fe(acac)$_3$ (0.90 g, 2.54 mmol) in anhydrous DMF (10 mL) was stirred at 116° C. in an oil bath for 24 hours. The mixture was cooled to ambient temperature and partitioned between water (50 mL) and EtOAc (150 mL). The solids were removed by filtration and the layers were separated. The organic layer was washed with brine and dried (MgSO$_4$), filtered and concentrated under reduced pressure. The residue was purified by column chromatography (Biotage 40M; 7% ethyl acetate/hexanes) to afford 2,8-dimethyl-7-(4-methyl-1H-pyrazol-1-yl)quinoline (1.96 g, 97%).

Step C: Preparation of 8-methyl-7-(4-methyl-1H-pyrazol-1-yl)quinoline-2-carbaldehyde Prepared as described in Example 37, Step B, using 2,8-dimethyl-7-(4-methyl-1H-pyrazol-1-yl)quinoline (1.96 g, 8.26 mmol) in place of 8-ethyl-2-methylquinoline (1.79 g, 86%).

Step D: Preparation of (S)-1-((R)-2,2,2-trifluoro-1-(3-(8-methyl-7-(4-methyl-1H-pyrazol-1-yl)quinolin-2-yl)-[1,2,4]triazolo[4,3-a]pyridin-6-yl)ethyl)pyrrolidin-3-amine Prepared as described in Example 9B, Step F, using tert-butyl (S)-1-((R)-2,2,2-trifluoro-1-(6-hydrazinylpyridin-3-yl)ethyl)pyrrolidin-3-ylcarbamate and substituting 8-methyl-7-(4-methyl-1H-pyrazol-1-yl)quinoline-2-carb aldehyde for 8-methoxyquinoline-2-carb aldehyde. LCMS APCI (+) m/z 507 (M+H).

Example 191

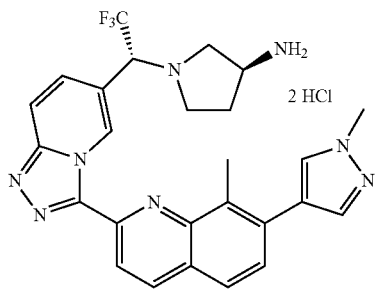 [SMILES: Cc1c(-c2cnn(C)c2)ccc2ccc(-c3nnc4ccc([C@@H](N5CC[C@H](N)C5)C(F)(F)F)cn34)nc12]

(S)-1-((R)-2,2,2-trifluoro-1-(3-(8-methyl-7-(1-methyl-1H-pyrazol-4-yl)quinolin-2-yl)-[1,2,4]triazolo[4,3-a]pyridin-6-yl)ethyl)pyrrolidin-3-amine dihydrochloride Step A: Preparation of 2,8-dimethyl-7-(4-methyl-1H-pyrazol-1-yl)quinoline In a sealed tube a mixture of 7-bromo-2,8-dimethylquinoline (0.60 g, 2.54 mmol), 1-methyl-4-(4,4,5,5-tetramethyl-1,3,2-dioxaborolan-2-yl)-1H-pyrazole (1.06 g, 5.08 mmol), PdCl$_2$(dppf)*dcm (0.208 g, 0.254 mmol), CsF (1.00 g, 6.61 mmol) and triethylamine (0.531 mL, 3.81 mmol) in isopropyl alcohol (17 mL) was heated at 100° C. on an oil bath for 6 hours. The mixture was cooled to ambient temperature and partitioned between water (25 mL) and ethyl acetate (50 mL). The solids were removed by filtration through a pad of Celite and washed with additional ethyl acetate. The layers were separated and the organic layer washed with brine and dried (MgSO$_4$), filtered and concentrated under reduced pressure. The residue was purified by column chromatography (Biotage 25M; 25% ethyl acetate/hexane) to afford 2,8-dimethyl-7-(4-methyl-1H-pyrazol-1-yl)quinoline (0.60 g, 91%).

Step B: Preparation of 8-methyl-7-(4-methyl-1H-pyrazol-1-yl)quinoline-2-carbaldehyde Prepared as described in Example 37, using 2,8-dimethyl-7-(1-methyl-1H-pyrazol-4-yl)quinoline (0.60 g, 2.53 mmol) in place of 8-ethyl-2-methylquinoline in Step B (0.507 g, 80%).

Step C: Preparation of (S)-1-((R)-2,2,2-trifluoro-1-(3-(8-methyl-7-(1-methyl-1H-pyrazol-4-yl)quinolin-2-yl)-[1,2,4]triazolo[4,3-a]pyridin-6-yl)ethyl)pyrrolidin-3-amine Prepared as described in Example 9B, Step F, using tert-butyl (S)-1-((R)-2,2,2-trifluoro-1-(6-hydrazinylpyridin-3-yl)ethyl)pyrrolidin-3-ylcarbamate and 8-methyl-7-(1-methyl-1H-pyrazol-4-yl)quinoline-2-carbaldehyde. LCMS APCI (+) m/z 507 (M+H).

Example 192

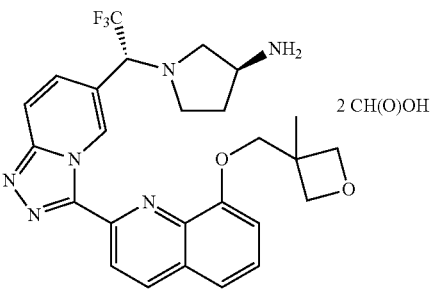 [SMILES: CC1(COc2cccc3ccc(-c4nnc5ccc([C@@H](N6CC[C@H](N)C6)C(F)(F)F)cn45)nc23)COC1]

(S)-1-((R)-2,2,2-trifluoro-1-(3-(8-(3-methyloxetan-3-yl)methoxy)quinolin-2-yl)-[1,2,4]triazolo[4,3-a]pyridin-6-yl)ethyl)pyrrolidin-3-amine diformate Step A: Preparation of tert-butyl (S)-1-((R)-2,2,2-trifluoro-1-(3-(8-((3-methyloxetan-3-yl)methoxy)quinolin-2-yl)-[1,2,4]triazolo[4,3-a]pyridin-6-yl)ethyl)pyrrolidin-3-ylcarbamate Prepared according to the method of Example 140, Steps A-C, substituting (3-methyloxetan-3-yl)methanol for (S)-1-methoxypropan-2-ol in Step A.

Step B: Preparation of (S)-1-((R)-2,2,2-trifluoro-1-(3-(8-(3-methyloxetan-3-yl)methoxy)quinolin-2-yl)-[1,2,4]triazolo[4,3-a]pyridin-6-yl)ethyl)pyrrolidin-3-amine diformate tert-Butyl (S)-1-((R)-2,2,2-trifluoro-1-(3-(8-((3-methyloxetan-3-yl)methoxy)quinolin-2-yl)-[1,2,4]triazolo[4,3-a]pyridin-6-yl)ethyl)pyrrolidin-3-ylcarbamate (0.032 g, 0.053 mmol) was dissolved in formic acid (0.53 mL, 0.053 mmol) and stirred at ambient temperature for 12 hours. The reaction mixture was concentrated under reduced pressure and purified by reverse phase chromatography on a C18 column (0-100% acetonitrile/water) to give the title compound (0.025 g, 75%). LCMS APCI (+) m/z 513 (M+H).

Example 193

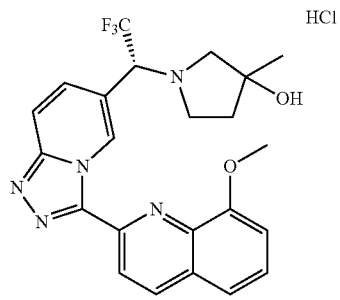 [SMILES: Cl ; COc1cccc2ccc(-c3nnc4ccc([C@@H](N5CCC(C)(O)C5)C(F)(F)F)cn34)nc12]

Diastereomer 1 of 3-methyl-1-((R)-2,2,2-trifluoro-1-(3-(8-methoxyquinolin-2-yl)-[1,2,4]triazolo[4,3-a]pyridin-6-yl)ethyl)pyrrolidin-3-ol hydrochloride Prepared as described in Example 9B, Steps F-G, using 3-methyl-1-((R)-2,2,2-trifluoro-1-(6-hydrazinylpyridin-3-yl)ethyl)pyrrolidin-3-ol Diastereomer 1 (Preparation F) in place of tert-butyl (S)-1-((R)-2,2,2-trifluoro-1-(6-hydrazinylpyridin-3-yl)ethyl)pyrrolidin-3-ylcarbamate in Step F. MS APCI (+) m/z 458 (M+1) detected.

Example 194

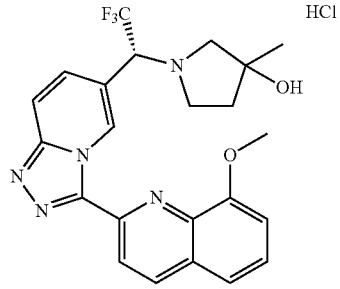 [SMILES: Cl ; COc1cccc2ccc(-c3nnc4ccc([C@@H](N5CCC(C)(O)C5)C(F)(F)F)cn34)nc12]

Diastereomer 2 of 3-methyl-1-((R)-2,2,2-trifluoro-1-(3-(8-methoxyquinolin-2-yl)-[1,2,4]triazolo[4,3-a]pyridin-6-yl)ethyl)pyrrolidin-3-ol hydrochloride Prepared as described in Example 9B, Steps F-G, using 3-methyl-1-((R)-2,2,2-trifluoro-1-(6-hydrazinylpyridin-3-yl)ethyl)pyrrolidin-3-ol Diastereomer 2 (Preparation F) in place of tert-butyl (S)-1-((R)-2,2,2-trifluoro-1-(6-hydrazinylpyridin-3-yl)ethyl)pyrrolidin-3-ylcarbamate in Step F. MS APCI (+) m/z 458 (M+1) detected Example 195

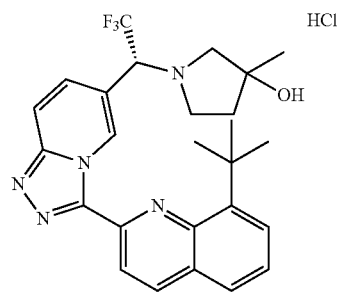 [SMILES: Cl ; CC1(O)CCN([C@H](c2ccc3nnc(-c4ccc5cccc(C(C)(C)C)c5n4)n3c2)C(F)(F)F)C1]

Diastereomer 1 of 1-((R)-1-(3-(8-tert-butylquinolin-2-yl)-[1,2,4]triazolo[4,3-a]pyridin-6-yl)-2,2,2-trifluoroethyl)-3-methylpyrrolidin-3-ol hydrochloride Prepared as described in Example 9B, Steps F-G, using 3-methyl-1-((R)-2,2,2-trifluoro-1-(6-hydrazinylpyridin-3-yl)ethyl)pyrrolidin-3-ol Diastereomer 1 (Preparation F) in place of tert-butyl (S)-1-((R)-2,2,2-trifluoro-1-(6-hydrazinylpyridin-3-yl)ethyl)pyrrolidin-3-ylcarbamate and substituting 8-tert-butylquinoline-2-carbaldehyde for 8-methoxyquinoline-2-carbaldehyde in Step F. MS APCI (+) m/z 484 (M+1) detected.

Example 196

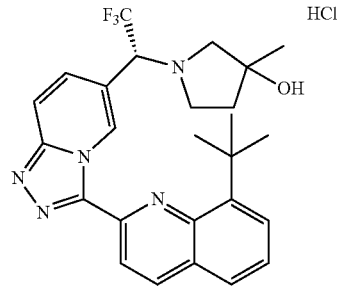 [SMILES: Cl ; CC1(O)CCN([C@H](c2ccc3nnc(-c4ccc5cccc(C(C)(C)C)c5n4)n3c2)C(F)(F)F)C1]

Diastereomer 2 of 1-((R)-1-(3-(8-tert-butylquinolin-2-yl)-[1,2,4]triazolo[4,3-a]pyridin-6-yl)-2,2,2-trifluoroethyl)-3-methylpyrrolidin-3-ol hydrochloride Prepared as described in Example 9B, Steps F-G, using 3-methyl-1-((R)-2,2,2-trifluoro-1-(6-hydrazinylpyridin-3-yl)ethyl)pyrrolidin-3-ol Diastereomer 2 (Preparation F) in place of tert-butyl (S)-1-((R)-2,2,2-trifluoro-1-(6-hydrazinylpyridin-3-yl)ethyl)pyrrolidin-3-ylcarbamate and substituting 8-tert-butylquinoline-2-carbaldehyde for 8-methoxyquinoline-2-carbaldehyde in Step F. MS APCI (+) m/z 484 (M+1) detected.

Example 197

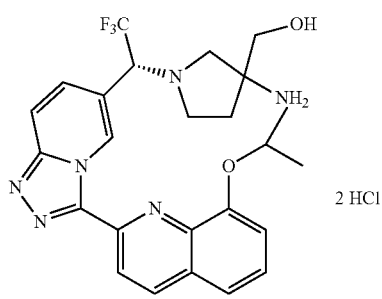 [SMILES: CC(C)Oc1cccc2ccc(-c3nnc4ccc([C@@H](N5CCC(N)(CO)C5)C(F)(F)F)cn34)nc12 ; "2 HCl"]

(3-amino-1-((R)-2,2,2-trifluoro-1-(3-(8-isopropoxyquinolin-2-yl)-[1,2,4]triazolo[4,3-a]pyridin-6-yl)ethyl)pyrrolidin-3-yl)methanol dihydrochloride Prepared as described in Example 9B, Steps D-G, using tert-butyl 3-(hydroxymethyl)pyrrolidin-3-ylcarbamate in place of (S)-tert-butyl pyrrolidin-3-ylcarbamate in Step D, and substituting 8-isopropoxyquinoline-2-carbaldehyde for 8-methoxyquinoline-2-carbaldehyde in Step F. LCMS APCI (+) m/z 501 (M+H).

Example 198

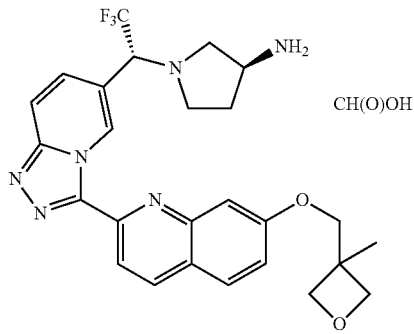

(S)-1-((R)-2,2,2-trifluoro-1-(3-(7-((3-methyloxetan-3-yl)methoxy)quinolin-2-yl)-[1,2,4]triazolo[4,3-a]pyridin-6-yl)ethyl)pyrrolidin-3-amine diformate Prepared according to the method of Example 192, substituting 2-methylquinolin-7-ol for 2-methylquinolin-8-ol. LCMS APCI (+) m/z 513 (M+H).

Example 199

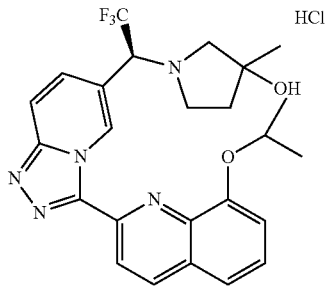 [SMILES: CC(C)Oc1cccc2ccc(-c3nnc4ccc([C@H](N5CCC(C)(O)C5)C(F)(F)F)cn34)nc12 ; Cl]

3-methyl-1-((S)-2,2,2-trifluoro-1-(3-(8-isopropoxyquinolin-2-yl)-[1,2,4]triazolo[4,3-a]pyridin-6-yl)ethyl)pyrrolidin-3-ol hydrochloride Diastereomer 1

Prepared as described in Example 9B, Steps F-G, using Diastereomer 1 of 3-methyl-1-((S)-2,2,2-trifluoro-1-(6-hydrazinylpyridin-3-yl)ethyl)pyrrolidin-3-ol (Preparation E, Step H) in place of tert-butyl (S)-1-((R)-2,2,2-trifluoro-1-(6-hydrazinylpyridin-3-yl)ethyl)pyrrolidin-3-ylcarbamate, and substituting 8-isopropoxyquinoline-2-carbaldehyde for 8-methoxyquinoline-2-carbaldehyde. MS APCI (+) m/z 486 (M+1) detected.

Example 200

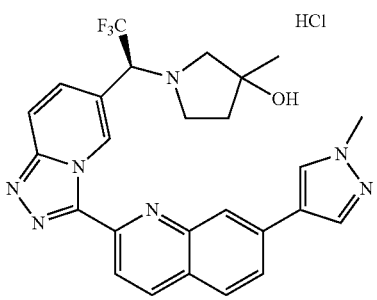 [SMILES: Cl ; Cn1cc(-c2ccc3ccc(-c4nnc5ccc([C@H](N6CCC(C)(O)C6)C(F)(F)F)cn45)nc3c2)cn1]

3-methyl-1-((S)-2,2,2-trifluoro-1-(3-(7-(1-methyl-1H-pyrazol-4-yl)quinolin-2-yl)-[1,2,4]triazolo[4,3-a]pyridin-6-yl)ethyl)pyrrolidin-3-ol hydrochloride Diastereomer 1

Prepared as described in Example 9B, Steps F and G, using Diastereomer 1 of 3-methyl-1-((S)-2,2,2-trifluoro-1-(6-hydrazinylpyridin-3-yl)ethyl)pyrrolidin-3-ol (Preparation E, Step H) in place of tert-butyl (S)-1-((R)-2,2,2-trifluoro-1-(6-hydrazinylpyridin-3-yl)ethyl)pyrrolidin-3-ylcarbamate, and substituting 7-(1-methyl-1H-pyrazol-4-yl)quinoline-2-carbaldehyde for 8-methoxyquinoline-2-carbaldehyde. MS APCI (+) m/z 508 (M+1) detected.

Example 201

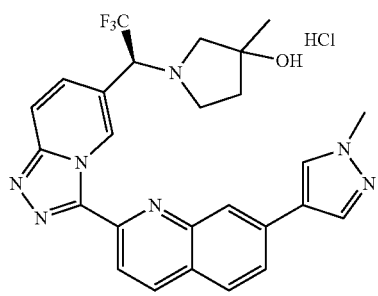 [SMILES: Cn1cc(-c2ccc3ccc(-c4nnc5ccc([C@H](N6CCC(C)(O)C6)C(F)(F)F)cn45)nc3c2)cn1 ; Cl]

Diastereomer 2 of 3-methyl-1-((S)-2,2,2-trifluoro-1-(3-(7-(1-methyl-1H-pyrazol-4-yl)quinolin-2-yl)-[1,2,4]triazolo[4,3-a]pyridin-6-yl)ethyl)pyrrolidin-3-ol hydrochloride Prepared as described in Example 9B, Steps F-G, using Diastereomer 2 of 3-methyl-1-((S)-2,2,2-trifluoro-1-(6-hydrazinylpyridin-3-yl)ethyl)pyrrolidin-3-ol (Preparation E, Step I) in place of tert-butyl (S)-1-((R)-2,2,2-trifluoro-1-(6-hydrazinylpyridin-3-yl)ethyl)pyrrolidin-3-ylcarbamate, and substituting 7-(1-methyl-1H-pyrazol-4-yl)quinoline-2-carbaldehyde for 8-methoxyquinoline-2-carbaldehyde. MS APCI (+) m/z 508 (M+1) detected.

Example 202

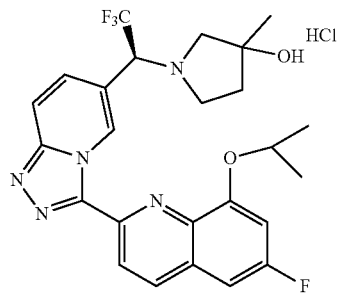 [SMILES: CC(C)Oc1cc(F)cc2ccc(-c3nnc4ccc([C@H](N5CCC(C)(O)C5)C(F)(F)F)cn34)nc12 ; Cl]

Diastereomer 1 of 3-methyl-1-((S)-2,2,2-trifluoro-1-(3-(6-fluoro-8-isopropoxyquinolin-2-yl)-[1,2,4]triazolo[4,3-a]pyridin-6-yl)ethyl)pyrrolidin-3-ol hydrochloride Prepared as described in Example 9B, Steps F-G, using Diastereomer 1 of 3-methyl-1-((S)-2,2,2-trifluoro-1-(6-hydrazinylpyridin-3-yl)ethyl)pyrrolidin-3-ol (Preparation E, Step H) in place of tert-butyl (S)-1-((R)-2,2,2-trifluoro-1-(6-hydrazinylpyridin-3-yl)ethyl)pyrrolidin-3-ylcarbamate, and substituting 6-fluoro-8-isopropoxyquinoline-2-carbaldehyde for 8-methoxyquinoline-2-carbaldehyde. MS APCI (+) m/z 504 (M+1) detected.

Example 203

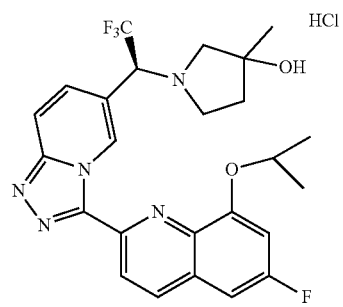 [SMILES: Cl ; CC(C)Oc1cc(F)cc2ccc(-c3nnc4ccc([C@H](N5CCC(C)(O)C5)C(F)(F)F)cn34)nc12]

Diastereomer 2 of 3-methyl-1-((S)-2,2,2-trifluoro-1-(3-(6-fluoro-8-isopropoxyquinolin-2-yl)-[1,2,4]triazolo[4,3-a]pyridin-6-yl)ethyl)pyrrolidin-3-ol hydrochloride Prepared as described in Example 9B, Steps F-G, using Diastereomer 2 of 3-methyl-1-((S)-2,2,2-trifluoro-1-(6-hydrazinylpyridin-3-yl)ethyl)pyrrolidin-3-ol (Preparation E, Step I) in place of tert-butyl (S)-1-((R)-2,2,2-trifluoro-1-(6-hydrazinylpyridin-3-yl)ethyl)pyrrolidin-3-ylcarbamate, and substituting 6-fluoro-8-isopropoxyquinoline-2-carbaldehyde for 8-methoxyquinoline-2-carbaldehyde. MS APCI (+) m/z 504 (M+1) detected.

Example 204

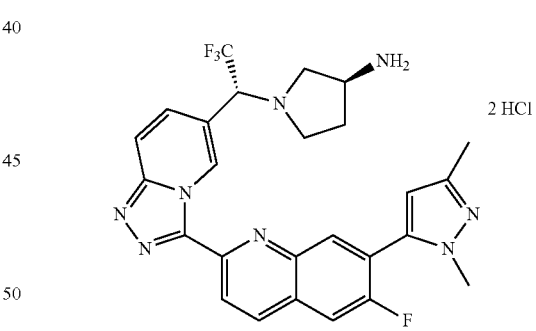

(3S)-1-((1R)-1-(3-(7-(1,3-dimethyl-1H-pyrazol-5-yl)-6-fluoro quinolin-2-yl)-[1,2,4]triazolo[4,3-a]pyridin-6-yl)-2,2,2-trifluoroethyl)pyrrolidin-3-amine dihydrochloride Step A: Preparation of tert-butyl (S)-1-((R)-1-(3-(7-bromo-6-fluoroquinolin-2-yl)-[1,2,4]triazolo[4,3-a]pyridin-6-yl)-2,2,2-trifluoroethyl)pyrrolidin-3-ylcarbamate Prepared according to the method of Example 113, Steps A-C, substituting 3-bromo-4-fluoroaniline for 4-fluoro-3-methoxyaniline in Step A.

Step B: Preparation of tert-butyl (3S)-1-((1R)-1-(3-(7-(1,3-dimethyl-1H-pyrazol-5-yl)-6-fluoroquinolin-2-yl)-[1,2,4]triazolo[4,3-a]pyridin-6-yl)-2,2,2-trifluoroethyl)pyrrolidin-3-ylcarbamate A mixture of tert-butyl (S)-1-((R)-1-(3-(7-bromo-6-fluoro quinolin-2-yl)-[1,2,4]triazolo[4,3-a]pyridin-6-yl)-2,2,2-trifluoroethyl)pyrrolidin-3-ylcarbamate (0.10 g, 0.16 mmol), 1,3-dimethyl-5-(4,4,5,5-tetramethyl-1,3,2-dioxaborolan-2-yl)-1H-pyrazole (0.073 g, 0.33 mmol) and cesium fluoride (0.065 g, 0.43 mmol) in 2-propanol (3.3 mL, 0.16 mmol) was degassed with nitrogen. Maintaining a nitrogen atmosphere, triethylamine (0.034 mL, 0.25 mmol) and dichloro[1,1'-bis(diphenylphosphino)ferrocene]palladium(II) dichloromethane adduct (0.013 g, 0.016 mmol) were added, and the vessel sealed and heated at 100° C. for 17 hours. After cooling, the reaction mixture was diluted with ethyl acetate (10 mL), filtered through a plug of Celite®, and concentrated under reduced pressure. Purification of the residue by reverse phase chromatography on a C18 column (0-100% acetonitrile/water) provided the title compound (0.074 g, 72%).

Step C: Preparation of (3S)-1-((1R)-1-(3-(7-(1,3-dimethyl-1H-pyrazol-5-yl)-6-fluoro quinolin-2-yl)-[1,2,4]triazolo[4,3-a]pyridin-6-yl)-2,2,2-trifluoroethyl)pyrrolidin-3-amine dihydrochloride Prepared according to the method of Example 1, Step F, substituting tert-butyl (3S)-1-((1R)-1-(3-(7-(1,3-dimethyl-1H-pyrazol-5-yl)-6-fluoro quinolin-2-yl)-[1,2,4]triazolo[4,3-a]pyridin-6-yl)-2,2,2-trifluoroethyl)pyrrolidin-3-ylcarbamate for tert-butyl (3S)-1-(2,2,2-trifluoro-1-(3-(8-methoxyquinolin-2-yl)-[1,2,4]triazolo[4,3-a]pyridin-6-yl)ethyl)pyrrolidin-3-ylcarbamate. LCMS APCI (+) m/z 525 (M+H).

Example 205

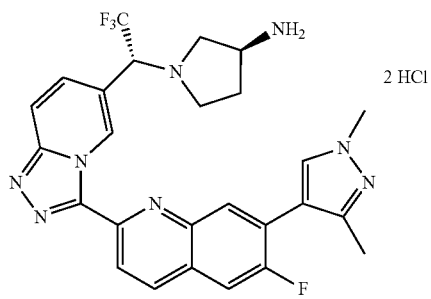 [SMILES: Cc1nn(C)cc1-c1cc2nc(-c3nnc4ccc([C@@H](N5CC[C@H](N)C5)C(F)(F)F)cn34)ccc2cc1F]

(3 S)-1-((1R)-1-(3-(7-(1,3-dimethyl-1H-pyrazol-4-yl)-6-fluoro quinolin-2-yl)-[1,2,4]triazolo[4,3-a]pyridin-6-yl)-2,2,2-trifluoroethyl)pyrrolidin-3-amine dihydrochloride Prepared according to the method of Example 204, substituting 1,3-dimethyl-4-(4,4,5,5-tetramethyl-1,3,2-dioxaborolan-2-yl)-1H-pyrazole for 1,3-dimethyl-5-(4,4,5,5-tetramethyl-1,3,2-dioxaborolan-2-yl)-1H-pyrazole in Step B. LCMS APCI (+) m/z 525 (M+H).

Example 206

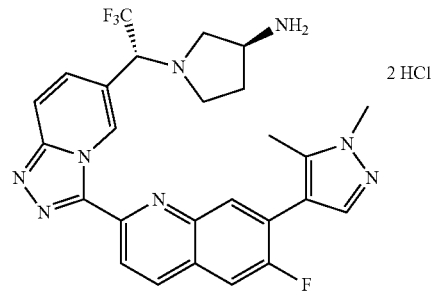 [SMILES: Cc1c(-c2cc3nc(-c4nnc5ccc([C@@H](N6CC[C@H](N)C6)C(F)(F)F)cn45)ccc3cc2F)cnn1C]

(3 S)-1-((1R)-1-(3-(7-(1,5-dimethyl-1H-pyrazol-4-yl)-6-fluoro quinolin-2-yl)-[1,2,4]triazolo[4,3-a]pyridin-6-yl)-2,2,2-trifluoroethyl)pyrrolidin-3-amine dihydrochloride Prepared according to the method of Example 204, substituting 1,5-dimethyl-4-(4,4,5,5-tetramethyl-1,3,2-dioxaborolan-2-yl)-1H-pyrazole for 1,3-dimethyl-5-(4,4,5,5-tetramethyl-1,3,2-dioxaborolan-2-yl)-1H-pyrazole in Step B. LCMS APCI (+) m/z 525 (M+H).

Example 207

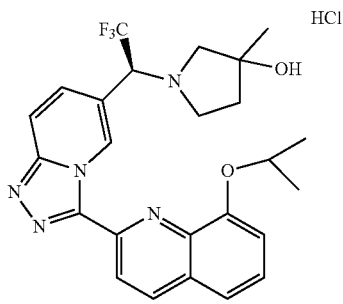 [SMILES: Cl ; CC(C)Oc1cccc2ccc(-c3nnc4ccc([C@H](N5CCC(C)(O)C5)C(F)(F)F)cn34)nc12]

3-methyl-1-((S)-2,2,2-trifluoro-1-(3-(8-isopropoxyquinolin-2-yl)-[1,2,4]triazolo[4,3-a]pyridin-6-yl)ethyl)pyrrolidin-3-ol hydrochloride Diastereomer 2

Prepared as described in Example 8, using Diastereomer 2 of 3-methyl-1-((S)-2,2,2-trifluoro-1-(6-hydrazinylpyridin-3-yl)ethyl)pyrrolidin-3-ol (Preparation E, Step I) in place of tert-butyl (S)-1-((R)-2,2,2-trifluoro-1-(6-hydrazinylpyridin-3-yl)ethyl)pyrrolidin-3-ylcarbamate, and substituting 8-isopropoxyquinoline-2-carbaldehyde for 8-methoxyquinoline-2-carbaldehyde. MS APCI (+) m/z 486 (M+1) detected.

Example 208

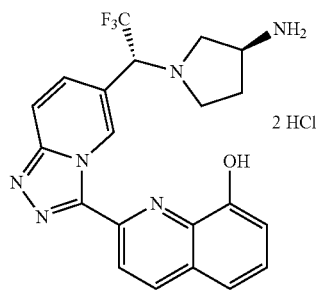 [SMILES: N[C@H]1CCN([C@H](c2ccc3nnc(-c4ccc5cccc(O)c5n4)n3c2)C(F)(F)F)C1]

2-(6-((R)-1-((S)-3-aminopyrrolidin-1-yl)-2,2,2-trifluoroethyl)-[1,2,4]triazolo[4,3-a]pyridin-3-yl)quinolin-8-ol dihydrochloride (S)-1-((R)-1-(3-(8-(cyclopropylmethoxy)quinolin-2-yl)-[1,2,4]triazolo[4,3-a]pyridin-6-yl)-2,2,2-trifluoroethyl)pyrrolidin-3-amine dihydrochloride (Example 11; 0.040 g, 0.074 mmol) in 5 N HCl (0.294 mL, 1.47 mmol) in IPA was stirred at 56° C. for 20 hours. The solvent was removed and ACN (5 mL) was added. The resulting solid was collected by filtration to give 2-(6-((R)-1-((S)-3-aminopyrrolidin-1-yl)-2,2,2-trifluoroethyl)-[1,2,4]triazolo[4,3-a]pyridin-3-yl)quinolin-8-ol as the di-HCl salt (0.032 g, 86.7%) as a solid.

Example 209

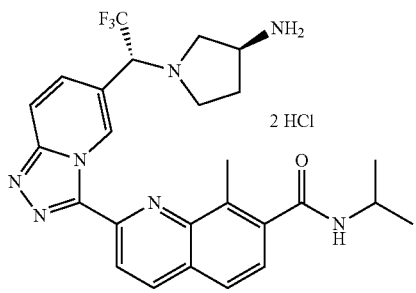 [SMILES: Cc1c(C(=O)NC(C)C)ccc2ccc(-c3nnc4ccc([C@@H](N5CC[C@H](N)C5)C(F)(F)F)cn34)nc12]

2-(6-((R)-1-((S)-3-aminopyrrolidin-1-yl)-2,2,2-trifluoroethyl)-[1,2,4]triazolo[4,3-a]pyridin-3-yl)-N-isopropyl-8-methylquinoline-7-carboxamide Step A: Preparation of 2,8-dimethylquinoline-7-carboxylic acid A 250 mL round-bottomed flask was charged with 7-bromo-2,8-dimethylquinoline (2.0 g, 8.47 mmol), potassium 2-ethoxy-2-oxoacetate (1.98 g, 12.7 mmol) and dcpp-2HBF$_4$ (0.311 g, 0.508 mmol) in anhydrous NMP (28 mL) and nitrogen was bubbled into the mixture for 10 minutes, followed by the addition of Pd(TFA)$_2$ (0.085 g, 0.254 mmol). The mixture was heated at 150° C. in an oil bath under a nitrogen atmosphere for 18 hours. The reaction mixture was cooled to ambient temperature and treated with a 2N NaOH solution (20 mL), and the mixture stirred at ambient temperature for 18 hours. The mixture was diluted with water (100 mL) and washed with ethyl acetate (180 mL). The aqueous layer was adjusted to pH 3 with 6N HCl and extracted with a 10% IPA-ethyl acetate solution. The combined organic extracts were washed with brine, dried (MgSO$_4$), filtered and concentrated under reduced pressure. The residue was purified by reverse phase chromatography (Biotage SP4, 40M, C-18; 0-40% MeCN—H$_2$O) to afford 2,8-dimethylquinoline-7-carboxylic acid (0.921 g, 54% yield).

Step B: Preparation of N-isopropyl-2,8-dimethylquinoline-7-carboxamide

A mixture of 2,8-dimethylquinoline-7-carboxylic acid (0.20 g, 0.994 mmol), isopropylamine (0.102 mL, 1.19 mmol) and HATU (0.491 g, 1.29 mmol) in anhydrous MeCN (5 mL) under a nitrogen atmosphere was cooled to 0° C. in an ice bath. To the cooled mixture was added dropwise DIEA (0.69 mL, 3.98 mmol) and the resulting mixture stirred at ambient temperature for 18 hours. The mixture was diluted with water, neutralized with aqueous 1N HCl and extracted with ethyl acetate. The combined organic extracts were washed with water and brine, dried (MgSO$_4$), filtered and concentrated under reduced pressure. The residue was purified by reverse phase chromatography (Biotage SP4, 25M C-18, 5-60% MeCN—H$_2$O) to afford N-isopropyl-2,8-dimethylquinoline-7-carboxamide (0.223 g, 93%).

Step C: Preparation of 2-formyl-N-isopropyl-8-methylquinoline-7-carboxamide

Prepared as described in Example 37, Step B, using N-isopropyl-2,8-dimethylquinoline-7-carboxamide (0.219 g, 0.904 mmol) in place of 8-ethyl-2-methylquinoline in Step B (0.21 g, 90%).

Step D: Preparation of 2-(6-((R)-1-((S)-3-aminopyrrolidin-1-yl)-2,2,2-trifluoroethyl)-[1,2,4]triazolo[4,3-a]pyridin-3-yl)-N-isopropyl-8-methylquinoline-7-carboxamide dihydrochloride Prepared as described in Example 9B, Steps F and G, using tert-butyl (S)-1-((R)-2,2,2-trifluoro-1-(6-hydrazinylpyridin-3-yl)ethyl)pyrrolidin-3-ylcarbamate and substituting 2-formyl-N-isopropyl-8-methylquinoline-7-carboxamide in Step F. LCMS APCI (+) m/z 512 (M+H).

Example 210

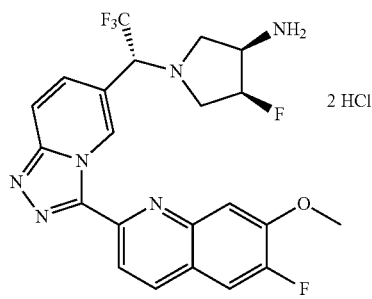 [SMILES: COc1cc2nc(-c3nnc4ccc([C@@H](N5C[C@@H](N)[C@@H](F)C5)C(F)(F)F)cn34)ccc2cc1F]

(3R,4S)-4-fluoro-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-amine dihydrochloride Step A: Isolation of the (S) stereoisomer of tert-butyl (3R)-4-fluoro-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-ylcarbamate The racemic material from Example 162 was purified by Chiral SFC (For analysis: OD-H, Chiral Technologies 4.6 mm×150 mm, 10-90% EtOH: hexanes, 0.80 mL/min. For preparative OD-H: Chiral Technologies, 20 mm×250 mm, 30% EtOH, 50 mL/min). Isolation of the first eluting peak provided as a single stereoisomer (99% e.e.), designated as the (S) enantiomer by Proton NMR analysis.

Step B: Preparation of (3R,4S)-4-fluoro-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-amine dihydrochloride Prepared as described in Example 9B, Step G, from tert-butyl (3R,4S)-4-fluoro-1-((R)-2,2,2-trifluoro-1-(3-(6-fluoro-7-methoxyquinolin-2-yl)-[1,2,4]triazolo[4,3-c]pyridin-6-yl)ethyl)pyrrolidin-3-ylcarbamate. LCMS APCI (+) m/z 479 (M+H).

Example 211

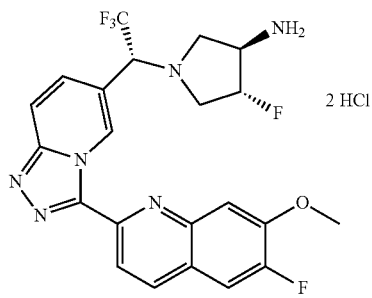 [SMILES: COc1cc2nc(-c3nnc4ccc([C@@H](N5C[C@@H](N)[C@H](F)C5)C(F)(F)F)cn34)ccc2cc1F]

(3R,4R)-4-fluoro-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-amine dihydrochloride Step A: Isolation of the (R) stereoisomer of tert-butyl (3R)-4-fluoro-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-ylcarbamate The racemic material from Example 162, was purified by Chiral SFC (For analysis: OD-H, Chiral Technologies 4.6 mm×150 mm, 10-90% EtOH: hexanes, 0.80 mL/min. For preparative OD-H, Chiral Technologies, 20 mm×250 mm, 30% EtOH, 50 mL/min), to provide the second eluting peak as a single stereoisomer (99% ee), designated as the (R) enantiomer by Proton NMR analysis.

Step B: Preparation of (3R,4R)-4-fluoro-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-amine dihydrochloride Prepared as described in Example 9B, Step G, from tert-butyl (3R,4R)-4-fluoro-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-ylcarbamate. LCMS APCI (+) m/z 479 (M+H).

Example 212

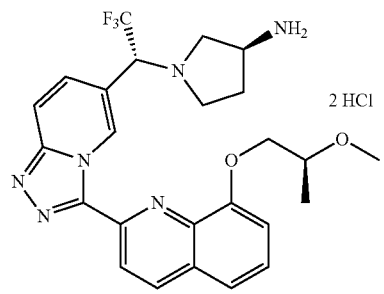 [SMILES: CO[C@@H](C)COc1cccc2ccc(-c3nnc4ccc([C@@H](N5CC[C@H](N)C5)C(F)(F)F)cn34)nc12]

(S)-1-((R)-2,2,2-trifluoro-1-(3-(8-((S)-2-methoxypropoxy)quinolin-2-yl)-[1,2,4]triazolo[4,3-a]pyridin-6-yl)ethyl)pyrrolidin-3-amine dihydrochloride Prepared according to the method of Example 140, substituting (S)-2-methoxypropan-1-ol for (S)-1-methoxypropan-2-ol. LCMS APCI (+) m/z 501 (M+H).

Example 213

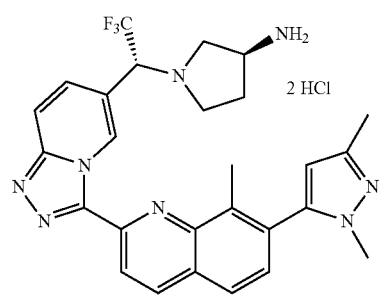 [SMILES: Cc1cc(-c2ccc3ccc(-c4nnc5ccc([C@@H](N6CC[C@H](N)C6)C(F)(F)F)cn45)nc3c2C)n(C)n1]

(3S)-1-((1R)-1-(3-(7-(1,3-dimethyl-1H-pyrazol-5-yl)-8-methylquinolin-2-yl)-[1,2,4]triazolo[4,3-a]pyridin-6-yl)-2,2,2-trifluoroethyl)pyrrolidin-3-amine Step A: Preparation of tert-butyl (S)-1-((R)-1-(3-(7-bromo-8-methylquinolin-2-yl)-[1,2,4]triazolo[4,3-a]pyridin-6-yl)-2,2,2-trifluoroethyl)pyrrolidin-3-ylcarbamate Prepared as described in Example 9B, Step F, using tert-butyl (S)-1-((R)-2,2,2-trifluoro-1-(6-hydrazinylpyridin-3-yl)ethyl)pyrrolidin-3-ylcarbamate (0.80 g, 2.13 mmol) and 7-bromo-8-methylquinoline-2-carbaldehyde (0.533 g, 2.13 mmol) in place of 8-methoxyquinoline-2-carbaldehyde to provide tert-butyl (S)-1-((R)-1-(3-(7-bromo-8-methylquinolin-2-yl)-[1,2,4]triazolo[4,3-a]pyridin-6-yl)-2,2,2-trifluoroethyl)pyrrolidin-3-ylcarbamate (1.01 g, 79%).

Step B: Preparation of tert-butyl (S)-1-((R)-1-(3-(7-(1,3-dimethyl-1H-pyrazol-5-yl)-8-methylquinolin-2-yl)-[1,2,4]triazolo[4,3-a]pyridin-6-yl)-2,2,2-trifluoroethyl)pyrrolidin-3-ylcarbamate Prepared as described in Example 191, using tert-butyl (S)-1-((R)-1-(3-(7-bromo-8-methylquinolin-2-yl)-[1,2,4]

triazolo[4,3-a]pyridin-6-yl)-2,2,2-trifluoroethyl)pyrrolidin-3-ylcarbamate in place of 7-bromo-2,8-dimethylquinoline and substituting 1,3-dimethyl-5-(4,4,5,5-tetramethyl-1,3,2-dioxaborolan-2-yl)-1H-pyrazole in Step A. LCMS APCI (+) m/z 621 (M+H).

Step C: Preparation of (3S)-1-((1R)-1-(3-(7-(1,3-dimethyl-1H-pyrazol-5-yl)-8-methylquinolin-2-yl)-[1,2,4]triazolo[4,3-a]pyridin-6-yl)-2,2,2-trifluoroethyl)pyrrolidin-3-amine dihydrochloride Prepared as described in Example 9B, Step G substituting tert-butyl (S)-1-((R)-1-(3-(7-(1,3-dimethyl-1H-pyrazol-5-yl)-8-methylquinolin-2-yl)-[1,2,4]triazolo[4,3-a]pyridin-6-yl)-2,2,2-trifluoroethyl)pyrrolidin-3-ylcarbamate. LCMS APCI (+) m/z 521 (M+H).

Example 214

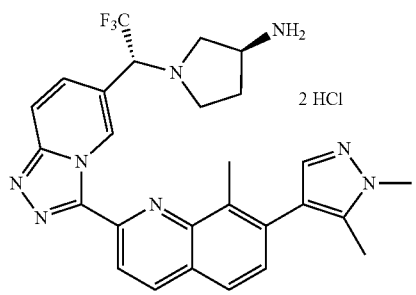 [SMILES: Cc1c(-c2cnn(C)c2C)ccc2ccc(-c3nnc4ccc([C@@H](N5CC[C@H](N)C5)C(F)(F)F)cn34)nc12]

(3S)-1-((1R)-1-(3-(7-(1,5-dimethyl-1H-pyrazol-4-yl)-8-methylquinolin-2-yl)-[1,2,4]triazolo[4,3-a]pyridin-6-yl)-2,2,2-trifluoroethyl)pyrrolidin-3-amine dihydrochloride Step A: Preparation of tert-butyl (S)-1-((R)-1-(3-(7-(1,5-dimethyl-1H-pyrazol-5-yl)-8-methylquinolin-2-yl)-[1,2,4]triazolo[4,3-a]pyridin-6-yl)-2,2,2-trifluoroethyl)pyrrolidin-3-ylcarbamate Prepared as described in Example 191, using tert-butyl (S)-1-((R)-1-(3-(7-bromo-8-methylquinolin-2-yl)-[1,2,4]triazolo[4,3-a]pyridin-6-yl)-2,2,2-trifluoroethyl)pyrrolidin-3-ylcarbamate in place of 7-bromo-2,8-dimethylquinoline and using 1,5-dimethyl-5-(4,4,5,5-tetramethyl-1,3,2-dioxaborolan-2-yl)-1H-pyrazole in Step A. LCMS APCI (+) m/z 621 (M+H).

Step C: Preparation of (3S)-1-((1R)-1-(3-(7-(1,5-dimethyl-1H-pyrazol-5-yl)-8-methylquinolin-2-yl)-[1,2,4]triazolo[4,3-a]pyridin-6-yl)-2,2,2-trifluoroethyl)pyrrolidin-3-amine dihydrochloride Prepared as described in Example 9B, Step G, using tert-butyl (S)-1-((R)-1-(3-(7-(1,5-dimethyl-1H-pyrazol-5-yl)-8-methylquinolin-2-yl)-[1,2,4]triazolo[4,3-a]pyridin-6-yl)-2,2,2-trifluoroethyl)pyrrolidin-3-ylcarbamate. LCMS APCI (+) m/z 521 (M+H).

Example 215

(S)-1-((R)-1-(3-(7-(difluoromethoxy)-6-fluoroquinolin-2-yl)-[1,2,4]triazolo[4,3-a]pyridin-6-yl)-2,2,2-trifluoroethyl)pyrrolidin-3-amine dihydrochloride Step A: Preparation of 7-(difluoromethoxy)-6-fluoro-2-methylquinoline A heterogeneous solution of 6-fluoro-2-methylquinolin-7-ol (0.30 g, 1.7 mmol) in dichloromethane (2.3 mL, 1.7 mmol) was added to a solution of potassium hydroxide (0.48 g, 8.5 mmol) in water (1.4 mL, 1.7 mmol) at 0° C. followed by addition of tetrabutylammonium bromide (0.055 g, 0.17 mmol). While at 0° C., chlorodifluoromethane gas was bubbled through the mixture for 10 minutes, followed by 45 minutes of stirring at 0° C. This process was repeated three times. The reaction mixture was diluted with water (10 mL) and dichloromethane (20 mL) and the aqueous layer further extracted with dichloromethane (2×20 mL). The combined organic extracts were washed with 1M sodium hydroxide (10 mL), dried over magnesium sulfate, filtered, and concentrated under reduced pressure. The residue was purified by reverse phase chromatography on a C18 column (0-100% acetonitrile/water) yielding the title compound (0.12 g, 30%).

Step B: Preparation of (S)-1-((R)-1-(3-(7-(difluoromethoxy)-6-fluoro quinolin-2-yl)-[1,2,4]triazolo[4,3-a]pyridin-6-yl)-2,2,2-trifluoroethyl)pyrrolidin-3-amine dihydrochloride Prepared according to the method of Example 140, substituting 7-(difluoromethoxy)-6-fluoro-2-methylquinoline for (R)-8-(1-methoxypropan-2-yloxy)-2-methylquinoline. LCMS APCI (+) m/z 497 (M+H).

Example 216

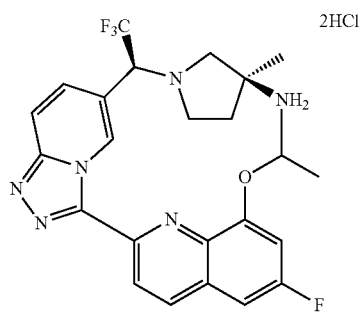 [SMILES: CC1N[C@@]2(C)CCN(C2)[C@H](C(F)(F)F)c2ccc3nnc(n3c2)-c2ccc3cc(F)cc(c3n2)O1]

(S)-3-methyl-1-((S)-2,2,2-trifluoro-1-(3-(6-fluoro-8-isopropoxyquinolin-2-yl)-[1,2,4]triazolo[4,3-a]pyridin-6-yl)ethyl)pyrrolidin-3-amine dihydrochloride Prepared as described in Example 8 using (S)-tert-butyl 3-methylpyrrolidin-3-ylcarbamate (from Preparation A) in place of (S)-tert-butyl pyrrolidin-3-ylcarbamate, and substituting 6-fluoro-8-isopropoxyquinoline-2-carbaldehyde for 8-methoxyquinoline-2-carbaldehyde. MS APCI (+) m/z 503 (M+1) detected.

Example 217

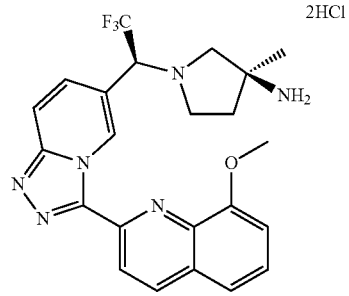 [SMILES: COc1cccc2ccc(-c3nnc4ccc([C@H](N5CC[C@](C)(N)C5)C(F)(F)F)cn34)nc12]

(S)-3-methyl-1-((S)-2,2,2-trifluoro-1-(3-(8-methoxyquinolin-2-yl)-[1,2,4]triazolo[4,3-a]pyridin-6-yl)ethyl)pyrrolidin-3-amine dihydrochloride Prepared as described in Example 8, using (S)-tert-butyl 3-methylpyrrolidin-3-ylcarbamate (Preparation A) in place of (S)-tert-butyl pyrrolidin-3-ylcarbamate. MS APCI (+) m/z 457 (M+1) detected.

Example 218

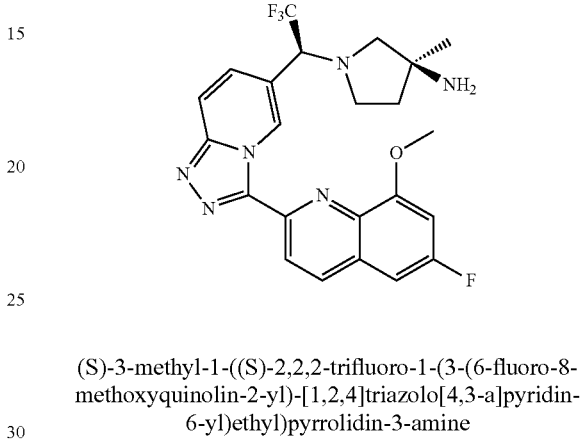

(S)-3-methyl-1-((S)-2,2,2-trifluoro-1-(3-(6-fluoro-8-methoxyquinolin-2-yl)-[1,2,4]triazolo[4,3-a]pyridin-6-yl)ethyl)pyrrolidin-3-amine Step A: Preparation of tert-butyl (S)-1-((S)-1-(6-chloropyridin-3-yl)-2,2,2-trifluoroethyl)-3-methylpyrrolidin-3-ylcarbamate Prepared as described in Example 1, Step C, using (S)-tert-butyl 3-methylpyrrolidin-3-ylcarbamate (Preparation C) in place of (S)-tert-butyl pyrrolidin-3-ylcarbamate.

Step B: Preparation of tert-butyl (S)-3-methyl-1-((S)-2,2,2-trifluoro-1-(6-hydrazinylpyridin-3-yl)ethyl)pyrrolidin-3-ylcarbamate Prepared as described in Example 1, Step D, using tert-butyl (S)-1-((S)-1-(6-chloropyridin-3-yl)-2,2,2-trifluoroethyl)-3-methylpyrrolidin-3-ylcarbamate in place of tert-butyl (3S)-1-(1-(6-chloropyridin-3-yl)-2,2,2-trifluoroethyl)pyrrolidin-3-ylcarbamate.

Step C: Preparation of tert-butyl (S)-3-methyl-1-((S)-2,2,2-trifluoro-1-(6-((E)-2-((6-fluoro-8-methoxyquinolin-2-yl)methylene)hydrazinyl)pyridin-3-yl)ethyl)pyrrolidin-3-ylcarbamate To a solution of tert-butyl (S)-3-methyl-1-((S)-2,2,2-trifluoro-1-(6-hydrazinylpyridin-3-yl)ethyl)pyrrolidin-3-ylcarbamate (1.00 g, 2.57 mmol) in DCM (15 mL) was added 6-fluoro-8-methoxyquinoline-2-carbaldehyde (0.5269 g, 2.568 mmol) and the reaction mixture was stirred at ambient temperature overnight. The reaction was concentrated under reduced pressure and the residue purified by chromatography (C18, 300 g, 10% MeCN/water to 95% MeCN/water over 25 column volumes) to give tert-butyl (S)-3-methyl-1-((S)-2,2,2-trifluoro-1-(6-((E)-2-((6-fluoro-8-methoxyquinolin-2-yl)methylene)hydrazinyl)pyridin-3-yl)ethyl)pyrrolidin-3-ylcarbamate (1.132 g, 1.963 mmol, 76.45% yield).

Step D: Preparation of tert-butyl (S)-3-methyl-1-((S)-2,2,2-trifluoro-1-(3-(6-fluoro-8-methoxyquinolin-2-yl)-[1,2,4]triazolo[4,3-a]pyridin-6-yl)ethyl)pyrrolidin-3-ylcarbamate To a solution of tert-butyl (S)-3-methyl-1-((S)-2,2,2-trifluoro-1-(6-((E)-2-((6-fluoro-8-methoxyquinolin-2-yl)methylene)hydrazinyl)pyridin-3-yl)ethyl)pyrrolidin-3-ylcarbamate (1.130 g, 1.960 mmol) in DCM (10 mL) was added iodobenzene diacetate (0.6312 g, 1.960 mmol) and stirred overnight at ambient temperature The reaction was concentrated under reduced pressure and the residue was purified by chromatography (C18, 300 g, 10% MeCN/water to 95% MeCN/water over 25 column volumes) to give tert-butyl (S)-3-methyl-1-((S)-2,2,2-trifluoro-1-(3-(6-fluoro-8-methoxyquinolin-2-yl)-[1,2,4]triazolo[4,3-a]pyridin-6-yl)ethyl)pyrrolidin-3-ylcarbamate (0.906 g, 1.577 mmol, 80.46% yield)

Step E: Preparation of (S)-3-methyl-1-((S)-2,2,2-trifluoro-1-(3-(6-fluoro-8-methoxyquinolin-2-yl)-[1,2,4]triazolo[4,3-a]pyridin-6-yl)ethyl)pyrrolidin-3-amine To a solution of tert-butyl (S)-3-methyl-1-((S)-2,2,2-trifluoro-1-(3-(6-fluoro-8-methoxyquinolin-2-yl)-[1,2,4]triazolo[4,3-a]pyridin-6-yl)ethyl)pyrrolidin-3-ylcarbamate (0.900 g, 1.57 mmol) in DCM (8 mL) was added 4M HCl in dioxane (2 mL) and the reaction stirred for 2.5 hours. The reaction was diluted DCM (100 mL) and washed with saturated Na$_2$CO$_3$ (25 mL), dried (MgSO$_4$), filtered and concentrated under reduced pressure. The residue was purified by normal phase chromatography (5% [10% NH$_4$OH]/DCM) to give (S)-3-methyl-1-((S)-2,2,2-trifluoro-1-(3-(6-fluoro-8-methoxyquinolin-2-yl)-[1,2,4]triazolo[4,3-a]pyridin-6-yl)ethyl)pyrrolidin-3-amine (0.690 g, 1.45 mmol, 92.8% yield) MS APCI (+) m/z 475 (M+1) detected.

Example 219

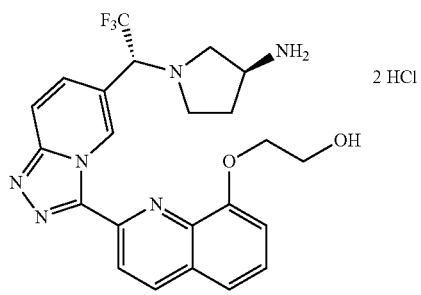 [SMILES: N[C@H]1CCN([C@H](c2ccc3nnc(-c4ccc5cccc(OCCO)c5n4)n3c2)C(F)(F)F)C1]

2-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)ethanol dihydrochloride

Step A: Preparation of 2-(2-methylquinolin-8-yloxy)ethyl acetate

A mixture of 2-methylquinolin-8-ol (0.30 g, 1.9 mmol), 2-bromoethyl acetate (0.8.2 mL, 7.6 mmol) and potassium carbonate (1.6 g, 12 mmol) in acetone (7.5 mL, 1.9 mmol) was heated at 70° C. for 12 hours. The cooled reaction mixture was diluted with water (10 mL) and extracted with dichloromethane (3×20 mL). The combined organic extracts were dried over magnesium sulfate, filtered and concentrated under reduced pressure. The residue was purified by reverse phase chromatography on a C18 column (0-100% acetonitrile/water) to provide the title compound (0.29 g, 63%).

Step B: Preparation of 2-(2-formylquinolin-8-yloxy)ethyl acetate

To a solution of 2-(2-methylquinolin-8-yloxy)ethyl acetate (0.29 g, 1.2 mmol) in dioxane (20 mL) and water (0.20 mL) was added selenium dioxide (0.16 g, 1.4 mmol) and the resultant mixture heated at reflux for 2 hours. The cooled reaction mixture was filtered through a plug of Celite® to remove solids, rinsing with dichloromethane. The filtrate was concentrated under reduced pressure and purified by normal phase chromatography on silica gel (10-20% ethyl acetate/hexanes) to afford the title compound (0.30 g, 99%).

Step C: Preparation of 2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)quinolin-8-yloxy)ethyl acetate A solution of tert-butyl (S)-1-((R)-2,2,2-trifluoro-1-(6-hydrazinylpyridin-3-yl)ethyl)pyrrolidin-3-ylcarbamate (0.48 g, 1.2 mmol) and 2-(2-methylquinolin-8-yloxy)ethyl acetate (0.30 g, 1.2 mmol) in ethanol (5.8 mL, 1.2 mmol) was allowed to stir at ambient temperature for 12 hours. The solvent was removed under reduced pressure. The residue was dissolved in dichloromethane (5.8 mL) and iodosobenzene diacetate (0.41 g, 1.3 mmol) was added. The reaction mixture was stirred at ambient temperature for 1 hour. Ethyl acetate (20 mL) and saturated sodium bicarbonate (10 mL) were added. The organic layer was separated, washed with brine, dried over sodium sulfate, filtered and concentrated under reduced pressure. The residue was purified by reverse phase chromatography on a C18 column (0-100% acetonitrile/water) to give the title compound (0.47 g, 66%).

Step D: Preparation of tert-butyl (S)-1-((R)-2,2,2-trifluoro-1-(3-(8-(2-hydroxyethoxy)quinolin-2-yl)-[1,2,4]triazolo[4,3-a]pyridin-6-yl)ethyl)pyrrolidin-3-ylcarbamate To a solution of 2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)quinolin-8-yloxy)ethyl acetate (0.47 g, 0.76 mmol) in methanol (5 mL) was added lithium hydroxide (2M; 1.9 mL, 0.76 mmol) and the mixture allowed to stir at ambient temperature for 1 hour. The reaction mixture was extracted with dichloromethane (2×30 mL). The combined organic extracts were dried over magnesium sulfate, filtered and concentrated under reduced pressure. The residue was purified by reverse phase chromatography on C18 (0-100% acetonitrile/water) to provide the title compound (0.40 g, 92%).

Step E: Preparation of 2-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)ethanol dihydrochloride To a solution of tert-butyl (S)-1-((R)-2,2,2-trifluoro-1-(3-(8-(2-hydroxyethoxy)quinolin-2-yl)-[1,2,4]pyridin-6-yl)ethyl)pyrrolidin-3-ylcarbamate (0.40 g, 0.70 mmol) in dichloromethane (1 mL) was added hydrochloric acid (5-6M in 2-propanol; 7.0 mL, 0.61 mmol). The reaction mixture was stirred at ambient temperature for 30 minutes. The solvent was removed under reduced pressure, and the resulting solid was suspended in acetonitrile (3 mL) and stirred at ambient temperature for 5 minutes. The resulting solid was collected by vacuum filtration to give the title compound (0.38 g, 99%). LCMS APCI (+) m/z 473 (M+H).

Example 220

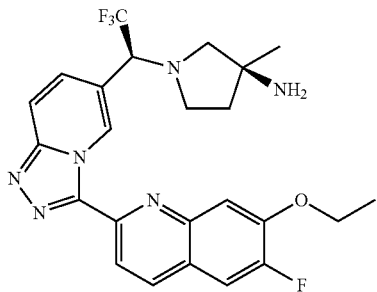 [SMILES: CCOc1cc2nc(-c3nnc4ccc([C@H](N5CC[C@](C)(N)C5)C(F)(F)F)cn34)ccc2cc1F]

(S)-1-((S)-1-(3-(7-ethoxy-6-fluoroquinolin-2-yl)-[1,2,4]triazolo[4,3-a]pyridin-6-yl)-2,2,2-trifluoroethyl)-3-methylpyrrolidin-3-amine Step A: Preparation of tert-butyl (S)-1-((S)-1-(6-chloropyridin-3-yl)-2,2,2-trifluoroethyl)-3-methylpyrrolidin-3-ylcarbamate Prepared as described in Example 1, Step C, using (S)-tert-butyl 3-methylpyrrolidin-3-ylcarbamate (Preparation C) in place of (S)-tert-butyl pyrrolidin-3-ylcarbamate.

Step B: Preparation of tert-butyl (S)-3-methyl-1-((S)-2,2,2-trifluoro-1-(6-hydrazinylpyridin-3-yl)ethyl)pyrrolidin-3-ylcarbamate Prepared as described in Example 1, Step D, using tert-butyl (S)-1-((S)-1-(6-chloropyridin-3-yl)-2,2,2-trifluoroethyl)-3-methylpyrrolidin-3-ylcarbamate in place of tert-butyl (3S)-1-(1-(6-chloropyridin-3-yl)-2,2,2-trifluoroethyl)pyrrolidin-3-ylcarbamate.

Step C: Preparation of tert-butyl (S)-1-((S)-1-(6-((E)-2-((7-ethoxy-6-fluoroquinolin-2-yl)methylene)hydrazinyl)pyridin-3-yl)-2,2,2-trifluoroethyl)-3-methylpyrrolidin-3-ylcarbamate To a solution of tert-butyl (S)-3-methyl-1-((S)-2,2,2-trifluoro-1-(6-hydrazinylpyridin-3-yl)ethyl)pyrrolidin-3-ylcarbamate (Example 122, Steps A and B; 5.113 g, 13.13 mmol) in ethanol (25 mL) was added 7-ethoxy-6-fluoroquinoline-2-carbaldehyde (2.878 g, 13.13 mmol) and stirred overnight at ambient temperature. The precipitate was filtered to give desired product as a pale yellow solid (5.276 g). The filtrate was subjected to chromatography (C18, 300 g, 75 mL/min, 10% MeCN/H$_2$O to 95% MeCN over 25 column volumes) and combined with the filtered product to give tert-butyl (S)-1-((S)-1-(6-((E)-2-((7-ethoxy-6-fluoro quinolin-2-yl)methylene)hydrazinyl)pyridin-3-yl)-2,2,2-trifluoroethyl)-3-methylpyrrolidin-3-ylcarbamate (6.322 g, 10.70 mmol, 81.53% yield).

Step D: Preparation of tert-butyl (S)-1-((S)-1-(3-(7-ethoxy-6-fluoro quinolin-2-yl)-[1,2,4]triazolo[4,3-a]pyridin-6-yl)-2,2,2-trifluoroethyl)-3-methylpyrrolidin-3-ylcarbamate A solution of tert-butyl (S)-1-((S)-1-(6-((E)-2-((7-ethoxy-6-fluoroquinolin-2-yl)methylene)hydrazinyl)pyridin-3-yl)-2,2,2-trifluoroethyl)-3-methylpyrrolidin-3-ylcarbamate (6.320 g, 10.70 mmol) and iodobenzene diacetate (3.447 g, 10.70 mmol) in DCM (50 mL) was stirred overnight at ambient temperature. The reaction was concentrated under reduced pressure and the residue subjected to chromatography (10% ethyl acetate/hexanes to 50% ethyl acetate/hexanes over 4 column volumes) to give tert-butyl (S)-1-((S)-1-(3-(7-ethoxy-6-fluoro quinolin-2-yl)-[1,2,4]triazolo[4,3-a]pyridin-6-yl)-2,2,2-trifluoroethyl)-3-methylpyrrolidin-3-ylcarbamate (5.406 g, 9.18 mmol, 85.83% yield).

Step E: Preparation of (S)-1-((S)-1-(3-(7-ethoxy-6-fluoro quinolin-2-yl)-[1,2,4]triazolo[4,3-a]pyridin-6-yl)-2,2,2-trifluoroethyl)-3-methylpyrrolidin-3-amine A solution of tert-butyl (S)-1-((S)-1-(3-(7-ethoxy-6-fluoro quinolin-2-yl)-[1,2,4]triazolo[4,3-a]pyridin-6-yl)-2,2,2-trifluoroethyl)-3-methylpyrrolidin-3-ylcarbamate (5.406 g, 9.185 mmol) in DCM (40 mL) was added 4M HCl in dioxane (22.96 mL, 91.85 mmol) and stirred at ambient temperature for 1.5 h. The filtered precipitate was dissolved in water and basified (1N NaOH), extracted with ethyl acetate (3×200 mL), washed with brine (200 mL), dried (MgSO$_4$), filtered concentrated under reduced pressure and the residue purified by flash chromatography (1 column volume DCM, increasing to 10% methanol/DCM over 2 column volumes, holding for 3 column volumes, then switching to 10% [10% NH$_4$OH/Methanol]/DCM for 7 column volumes) to give (S)-1-((S)-1-(3-(7-ethoxy-6-fluoroquinolin-2-yl)-[1,2,4]triazolo[4,3-a]pyridin-6-yl)-2,2,2-trifluoroethyl)-3-methylpyrrolidin-3-amine (4.13 g, 8.45 mmol, 92.05% yield). MS APCI (+) m/z 489 (M+1) detected. Specific rotation: $[\alpha]^{20}_D = -0.87°$ (c=1.02, MeOH).

Example 221

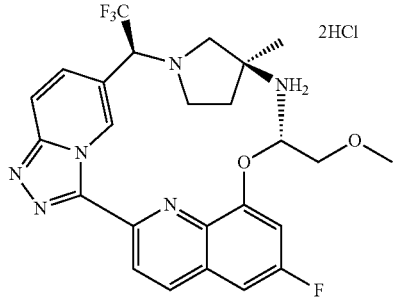 [SMILES: COC[C@H]1N[C@@]2(C)CCN(C2)[C@H](C(F)(F)F)c2ccc3nnc(n3c2)-c2ccc3cc(F)cc(c3n2)O1]

(S)-3-methyl-1-((S)-2,2,2-trifluoro-1-(3-(6-fluoro-8-((R)-1-methoxypropan-2-yloxy)quinolin-2-yl)-[1,2,4]triazolo[4,3-a]pyridin-6-yl)ethyl)pyrrolidin-3-amine dihydrochloride Prepared as described in Example 9B, Steps D-G, using (S)-tert-butyl 3-methylpyrrolidin-3-ylcarbamate (Preparation B) in place of (S)-tert-butyl pyrrolidin-3-ylcarbamate in Step D and using (R)-6-fluoro-8-(1-methoxypropan-2-yloxy)quinoline-2-carbaldehyde in place of 8-methoxyquinoline-2-carbaldehyde in Step F. MS APCI (+) m/z 533 (M+1) detected.

Example 222

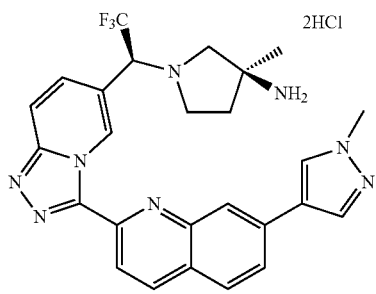 [SMILES: Cn1cc(-c2ccc3ccc(-c4nnc5ccc([C@H](N6CC[C@](C)(N)C6)C(F)(F)F)cn45)nc3c2)cn1]

(S)-3-methyl-1-((S)-2,2,2-trifluoro-1-(3-(7-(1-methyl-1H-pyrazol-4-yl)quinolin-2-yl)-[1,2,4]triazolo[4,3-a]pyridin-6-yl)ethyl)pyrrolidin-3-amine dihydrochloride Prepared as described in Example 9B, Steps D-G, using (S)-tert-butyl 3-methylpyrrolidin-3-ylcarbamate (Preparation A) in place of (S)-tert-butyl pyrrolidin-3-ylcarbamate in Step D and using 7-(1-methyl-1H-pyrazol-4-yl)quinoline-2-carbaldehyde in place of 8-methoxyquinoline-2-carbaldehyde in Step F. MS APCI (+) m/z 507 (M+1) detected.

Example 223

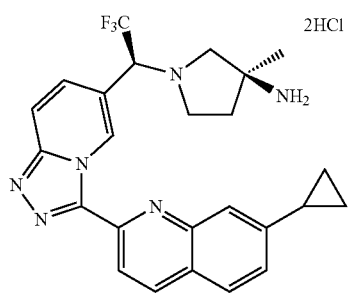 [SMILES: C[C@]1(N)CCN([C@@H](c2ccc3nnc(-c4ccc5ccc(C6CC6)cc5n4)n3c2)C(F)(F)F)C1]

(S)-1-((S)-1-(3-(7-cyclopropylquinolin-2-yl)-[1,2,4]triazolo[4,3-a]pyridin-6-yl)-2,2,2-trifluoroethyl)-3-methylpyrrolidin-3-amine dihydrochloride Prepared as described in Example 9B, Steps D-G, using (S)-tert-butyl 3-methylpyrrolidin-3-ylcarbamate (Preparation A) in place of (S)-tert-butyl pyrrolidin-3-ylcarbamate in Step D and using 7-cyclopropylquinoline-2-carbaldehyde in place of 8-methoxyquinoline-2-carbaldehyde in Step F. MS APCI (+) m/z 467 (M+1) detected.

Example 224

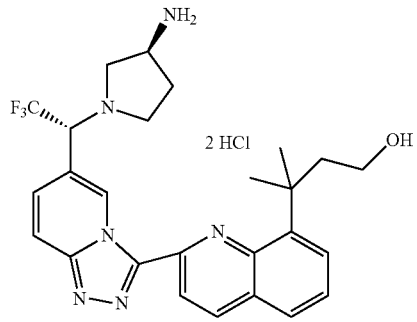 [SMILES: CC(C)(CCO)c1cccc2ccc(-c3nnc4ccc([C@@H](N5CC[C@H](N)C5)C(F)(F)F)cn34)nc12]

3-(2-(6-((R)-1-((S)-3-aminopyrrolidin-1-yl)-2,2,2-trifluoroethyl)-[1,2,4]triazolo[4,3-a]pyridin-3-yl)quinolin-8-yl)-3-methylbutan-1-ol dihydrochloride Step A: Preparation of (Z)-ethyl 3-(2-methylquinolin-8-yl)but-2-enoate A solution of 8-bromo-2-methylquinoline (2.00 g, 9.01 mmol), (E)-ethyl but-2-enoate (3.36 mL, 27.0 mmol), N-cyclohexyl-N-methylcyclohexanamine (5.79 mL, 27.0 mmol), and Pd(PtBu$_3$)$_2$ (0.23 g, 0.45 mmol) in dioxane (10 mL) was stirred at reflux for 20 hours. After cooling to ambient temperature, water (20 mL) and ethyl acetate (30 mL) were added. The organic layer was separated, washed with brine, dried (sodium sulfate), filtered and concentrated under reduced pressure. The residue was purified by C-18 reverse phase flash chromatography (Biotage SP4 unit, C-18 40M column, 0-100% CH$_3$CN/water gradient; 30 column volumes) to give (Z)-ethyl 3-(2-methylquinolin-8-yl)but-2-enoate (0.81 g, 35.2%) as a solid.

Step B: Preparation of ethyl 3-methyl-3-(2-methylquinolin-8-yl)butanoate

To a mixture of Cu(I)I (2.42 g, 12.7 mmol) in ether (5 mL) was added a solution of 1.6 M MeLi (15.9 ml, 25.4 mmol) in ether at 0° C. and the mixture was stirred at 0° C. for 10 minutes. The solvent was removed under reduced pressure and cold DCM (10 mL) was added. The solvent was removed under reduced pressure. Cold DCM (40 mL) was added and the mixture was cooled to −78° C. TMSCl (1.54 mL, 12.7 mmol) was added, followed by a solution of (Z)-ethyl 3-(2-methylquinolin-8-yl)but-2-enoate (0.81 g, 3.17 mmol) in DCM (10 mL). The reaction mixture was warmed to 0° C. and stirred at 0° C. for 1 hour. The reaction mixture was quenched with saturated ammonium chloride solution. The organic layers was separated, washed with brine, dried (sodium sulfate), filtered and concentrated under reduced pressure. The residue was purified by flash chromatography on silica gel (7:1 hexane/ethyl acetate) to give ethyl 3-methyl-3-(2-methylquinolin-8-yl)butanoate (0.66 g, 76.8%) as an oil.

Step C: Preparation of 3-methyl-3-(2-methylquinolin-8-yl)butan-1-ol

To a solution of ethyl 3-methyl-3-(2-methylquinolin-8-yl)butanoate (0.66 g, 2.43 mmol) in THF (3 mL) was added 1.0

N LAH (3.65 mL, 3.65 mmol) in THF at 0° C. and stirred at 0° C. for 3 hours. Sodium sulfate decahydrate (2.0 g) was added and stirred at ambient temperature for 30 minutes. The solid was removed by filtration and washed with ethyl acetate (30 mL). The filtrate was concentrated under reduced pressure to give 3-methyl-3-(2-methylquinolin-8-yl)butan-1-ol (0.56 g, 100%) as a solid.

Step D: Preparation of 3-(2-(6-((R)-1-((S)-3-aminopyrrolidin-1-yl)-2,2,2-trifluoroethyl)-[1,2,4]triazolo[4,3-a]pyridin-3-yl)quinolin-8-yl)-3-methylbutan-1-ol dihydrochloride Prepared as described in Example 114, Steps A-B, using 3-methyl-3-(2-methylquinolin-8-yl)butan-1-ol in place of (1-(2-methylquinolin-8-yl)cyclopropyl)methanol in Step A. LCMS APCI (+) m/z 499 (M+H).

Example 225

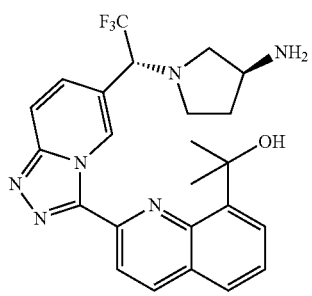 [SMILES: CC(C)(O)c1cccc2ccc(-c3nnc4ccc([C@@H](N5CC[C@H](N)C5)C(F)(F)F)cn34)nc12]

2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol Step A: Preparation of methyl 2-methylquinoline-8-carboxylate To a stirred solution of 2-methylquinoline-8-carboxylic acid (0.830 g, 4.43 mmol) in MeOH (20 mL) was added dropwise chlorotrimethylsilane (2.41 g, 22.2 mmol). The reaction mixture was heated at reflux overnight. After cooling, the reaction was concentrated under reduced pressure. The residue was dissolved in water and basified by dropwise addition of saturated aqueous $NaHCO_3$ solution. The mixture was extracted with EtOAc. The combined organic layers were washed with brine, dried and concentrated under reduced pressure. The residue was purified by flash chromatography on silica gel (3:1 hexane/EtOAc) to give methyl 2-methylquinoline-8-carboxylate (0.290 g, 33%).

Step B: Preparation of 2-(2-methylquinolin-8-yl)propan-2-ol

To a stirred solution of methyl 2-methylquinoline-8-carboxylate (0.290 g, 1.44 mmol) in THF (1 mL) was added dropwise a solution of MeMgBr in ether (3.0 M, 1.44 mL, 4.32 mmol) at −15° C. under nitrogen. The reaction mixture was stirred at −15° C. for 30 minutes and then quenched by the addition of saturated aqueous $NH_4Cl$ solution. The reaction mixture was extracted with EtOAc. The combined organic layers were washed with brine, dried and concentrated under reduced pressure. The residue was purified by flash chromatography on silica gel (1:1 hexanes/EtOAc) to give 2-(2-methylquinolin-8-yl)propan-2-ol (0.260 g, 90%).

Step C: Preparation of 8-(2-hydroxypropan-2-yl)quinoline-2-carbaldehyde

Prepared as described in Example 5, Step B, using 2-(2-methylquinolin-8-yl)propan-2-ol in place of 8-(cyclopropylmethoxy)-2-methylquinoline.

Step D: Preparation of tert-butyl (S)-1-((R)-2,2,2-trifluoro-1-(3-(8-(2-hydroxypropan-2-yl)quinolin-2-yl)-[1,2,4]triazolo[4,3-a]pyridin-6-yl)ethyl)pyrrolidin-3-ylcarbamate Prepared as described in Example 9B, Step F, using 8-(2-hydroxypropan-2-yl)quinoline-2-carbaldehyde in place of 8-methoxyquinoline-2-carbaldehyde.

Step E: Preparation of 2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol A mixture of tert-butyl (S)-1-((R)-2,2,2-trifluoro-1-(3-(8-(2-hydroxypropan-2-yl)quinolin-2-yl)-[1,2,4]triazolo[4,3-a]pyridin-6-yl)ethyl)pyrrolidin-3-ylcarbamate (56 mg, 0.098 mmol), DCM (1 mL) and 4N HCl in dioxane (0.3 mL) was stirred at ambient temperature for 3 hours. Removal of the solvents gave the crude product, which was purified by reverse phase preparative HPLC (5-95% acetonitrile/water) to give the product as a bis TFA salt. The combined fractions were basified by saturated aqueous $NaHCO_3$ solution and extracted with EtOAc. The organic layers were washed with brine, dried and concentrated under reduced pressure to give 2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol (14 mg, 30%). LCMS APCI (+) m/z 471 (M+H).

Example 226

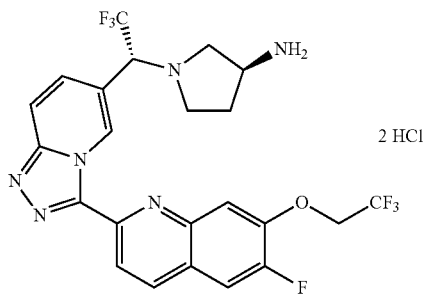 [SMILES: N[C@H]1CCN([C@H](c2ccc3nnc(-c4ccc5cc(F)c(OCC(F)(F)F)cc5n4)n3c2)C(F)(F)F)C1]

(S)-1-((R)-2,2,2-trifluoro-1-(3-(6-fluoro-7-(2,2,2-trifluoroethoxy)quinolin-2-yl)-[1,2,4]triazolo[4,3-a]pyridin-6-yl)ethyl)pyrrolidin-3-amine dihydrochloride Prepared according to the method of Example 119, Steps A-G, substituting 1,1,1-trifluoro-2-iodoethane for 2-iodopropane in Step C. FIA-MS APCI (+) m/z 529 (M+H).

Example 227

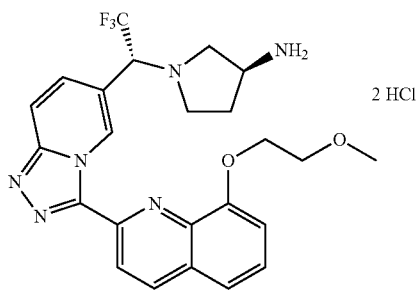 [SMILES: COCCOc1cccc2ccc(-c3nnc4ccc([C@@H](N5CC[C@H](N)C5)C(F)(F)F)cn34)nc12]

(S)-1-((R)-2,2,2-trifluoro-1-(3-(8-(2-methoxyethoxy)quinolin-2-yl)-[1,2,4]triazolo[4,3-a]pyridin-6-yl)ethyl)pyrrolidin-3-amine dihydrochloride Prepared according to the method of Example 148, substituting 2-methylquinolin-8-ol for 2-methylquinolin-7-ol. FIA-MS APCI (+) m/z 487 (M+H).

Example 228

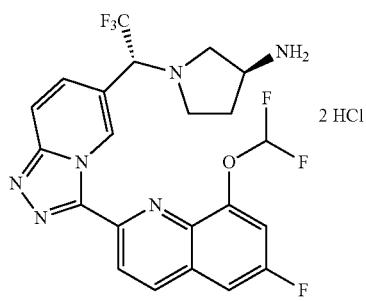 [SMILES: N[C@H]1CCN([C@H](c2ccc3nnc(-c4ccc5cc(F)cc(OC(F)F)c5n4)n3c2)C(F)(F)F)C1]

(S)-1-((R)-1-(3-(8-(difluoromethoxy)-6-fluoroquinolin-2-yl)-[1,2,4]triazolo[4,3-a]pyridin-6-yl)-2,2,2-trifluoroethyl)pyrrolidin-3-amine dihydrochloride Step A: Preparation of 8-(difluoromethoxy)-6-fluoro-2-methylquinoline To a mixture of 6-fluoro-2-methylquinolin-8-ol (0.15 g, 0.85 mmol) and potassium carbonate (4.2 g, 30 mmol) in acetonitrile (3.4 mL, 0.85 mmol) and water (3.4 mL, 0.85 mmol) was added 2-chloro-2,2-difluoroacetophenone (0.62 mL, 4.2 mmol). The vessel was sealed and the mixture was heated at 80° C. for 4 hours. The cooled reaction mixture was extracted with diethyl ether (2×30 mL), and the combined organic extracts were dried over magnesium sulfate, filtered and concentrated under reduced pressure at ambient temperature The resulting residue was purified by reverse phase chromatography on a C18 column (0-100% acetonitrile/water). Aqueous fractions containing the product were combined and extracted with diethyl ether (2×100 mL). The combined organic extracts were dried over magnesium sulfate, filtered and concentrated under reduced pressure at ambient temperature providing the title compound. Presence of water was noted and the material taken on as is assuming theoretical yield obtained (0.19 g, 100%).

Step B: Preparation of (S)-1-((R)-1-(3-(8-(difluoromethoxy)-6-fluoro quinolin-2-yl)-[1,2,4]triazolo[4,3-a]pyridin-6-yl)-2,2,2-trifluoroethyl)pyrrolidin-3-amine dihydrochloride Prepared according to the method of Example 140, substituting 8-(difluoromethoxy)-6-fluoro-2-methylquinoline for (R)-8-(1-methoxypropan-2-yloxy)-2-methylquinoline. FIA-MS APCI (+) m/z 497 (M+H).

Example 229

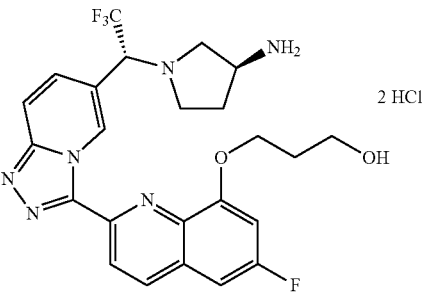 [SMILES: N[C@H]1CCN([C@H](c2ccc3nnc(-c4ccc5cc(F)cc(OCCCO)c5n4)n3c2)C(F)(F)F)C1]

3-(2-(6-((R)-1-((S)-3-aminopyrrolidin-1-yl)-2,2,2-trifluoroethyl)-[1,2,4]triazolo[4,3-a]pyridin-3-yl)-6-fluoro quinolin-8-yloxy)propan-1-ol dihydrochloride Step A: Preparation of tert-butyl (S)-1-((R)-1-(3-(8-(3-(tert-butyldimethylsilyloxy)propoxy)-6-fluoroquinolin-2-yl)-[1,2,4]triazolo[4,3-a]pyridin-6-yl)-2,2,2-trifluoroethyl)pyrrolidin-3-ylcarbamate Prepared according to the method of Example 148, substituting 6-fluoro-2-methylquinolin-8-ol for 2-methylquinolin-7-ol and (3-bromopropoxy)(tert-butyl)dimethylsilane for 1-bromo-2-methoxyethane.

Step B: Preparation of 3-(2-(6-((R)-1-((S)-3-aminopyrrolidin-1-yl)-2,2,2-trifluoroethyl)-[1,2,4]triazolo[4,3-a]pyridin-3-yl)-6-fluoro quinolin-8-yloxy)propan-1-ol dihydrochloride A solution of tert-butyl (S)-1-((R)-1-(3-(8-(3-(tert-butyldimethyl silyloxy)propoxy)-6-fluoroquinolin-2-yl)-[1,2,4]triazolo[4,3-a]pyridin-6-yl)-2,2,2-trifluoroethyl)pyrrolidin-3-ylcarbamate (0.18 g, 0.24 mmol) in dichloromethane (1 mL) and trifluoroacetic acid (2 mL) was stirred at ambient temperature for 30 minutes. The reaction mixture was concentrated under reduced pressure. The residue was purified by reverse phase chromatography on a C18 column (0-80% acetonitrile/water). The material isolated after purification was dissolved in methanol (0.5 mL) and added dropwise to hydrochloric acid (2M in diethyl ether; 5 mL). The resulting salt was collected by vacuum filtration to provide the title compound (0.12 g, 84%). FIA-MS APCI (+) m/z 505 (M+H).

Example 230

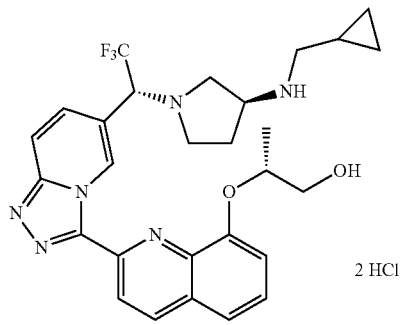 [SMILES: C[C@H](CO)Oc1cccc2ccc(-c3nnc4ccc([C@@H](N5CC[C@H](NCC6CC6)C5)C(F)(F)F)cn34)nc12]

2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol dihydrochloride To a stirred solution of (R)-2-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)propan-1-ol dihydro chloride (40 mg, 0.082 mmol) in MeOH (0.8 mL) was added DIEA (43 µL, 0.25 mmol). Cyclopropanecarbaldehyde (8.0 µL, 0.10 mmol) and trimethyl orthoformate (90 µL, 0.82 mmol) were added. The reaction was allowed to stir at ambient temperature overnight. NaBH₄ (6.2 mg, 0.16 mmol) was added. After stirring for 30 minutes, the reaction was quenched by the addition of a saturated aqueous NH₄Cl solution. The mixture was partitioned between DCM and water. The aqueous phase was extracted with DCM. The combined organic layers were washed with brine, dried and concentrated under reduced pressure. The residue was purified by reverse phase preparative HPLC (5-95% acetonitrile/water) to give the bis-TFA salt. The combined fractions were basified by saturated aqueous NaHCO₃ solution and extracted with EtOAc. The organic layers were washed with brine, dried and concentrated under reduced pressure to give the free base, which was treated with 4N HCl in dioxane to give 2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol dihydrochloride (39 mg, 88%) as a yellow solid. LCMS APCI (+) m/z 541 (M+H).

Example 231

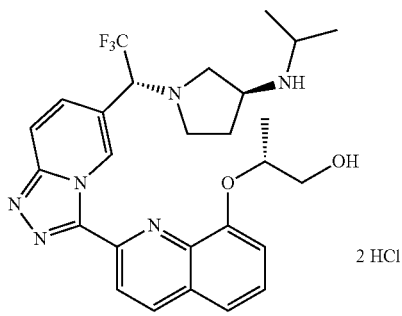 [SMILES: CC(C)N[C@H]1CCN([C@H](c2ccc3nnc(-c4ccc5cccc(O[C@H](C)CO)c5n4)n3c2)C(F)(F)F)C1]

2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol dihydrochloride To a stirred solution of (R)-2-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)propan-1-ol (Example 186; 36 mg, 0.074 mmol) in acetonitrile (1 mL) was added acetone (33 µL, 0.44 mmol). NaBH₃CN (9.3 mg, 0.15 mmol) was added followed by 1 drop of AcOH. The reaction was stirred at ambient temperature for 15 minutes and then quenched by the addition of saturated aqueous NaHCO₃ solution. The mixture was partitioned between DCM and water. The aqueous phase was extracted with DCM. The combined organic layers were washed with brine, dried and concentrated under reduced pressure. The residue was purified by reverse phase preparative HPLC (5-95% acetonitrile/water) to give the bis-TFA salt. The combined fractions were basified by saturated aqueous NaHCO₃ solution and extracted with EtOAc. The organic layers were washed with brine, dried and concentrated under reduced pressure to give the free base, which was treated with 4N HCl in dioxane to give 2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol dihydrochloride (26 mg, 67%) as a yellow solid. LCMS APCI (+) m/z 529 (M+H).

Example 232

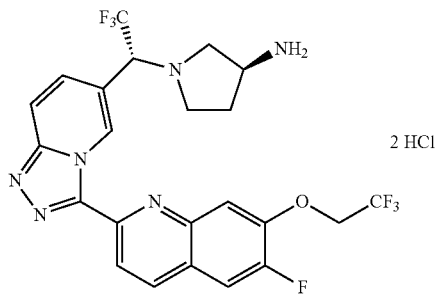 [SMILES: N[C@H]1CCN([C@H](c2ccc3nnc(-c4ccc5cc(F)c(OCC(F)(F)F)cc5n4)n3c2)C(F)(F)F)C1]

(S)-1-((R)-2,2,2-trifluoro-1-(3-(6-fluoro-8-(2,2,2-trifluoroethoxy)quinolin-2-yl)-[1,2,4]triazolo[4,3-a]pyridin-6-yl)ethyl)pyrrolidin-3-amine dihydrochloride Prepared according to the method of Example 226, substituting 6-fluoro-2-methylquinolin-8-ol for 6-fluoro-2-methylquinolin-7-ol. FIA-MS APCI (+) m/z 529 (M+H).

Example 233

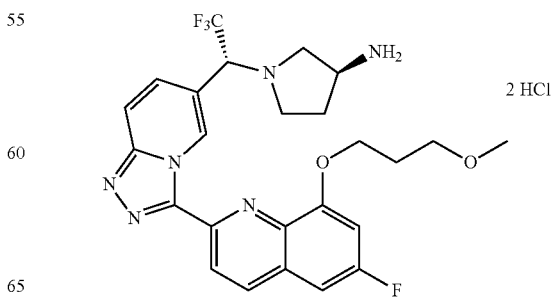

(S)-1-((R)-2,2,2-trifluoro-1-(3-(6-fluoro-8-(3-methoxypropoxy)quinolin-2-yl)-[1,2,4]triazolo[4,3-a]pyridin-6-yl)ethyl)pyrrolidin-3-amine dihydrochloride Step A: Preparation of 6-fluoro-8-(3-methoxypropoxy)-2-methylquinoline Triphenylphosphine (0.74 g, 2.8 mmol) was dissolved in tetrahydrofuran (0.94 mL, 1.1 mmol) and diisopropyl azodicarboxylate (0.35 mL, 1.8 mmol), 3-methoxypropan-1-ol (0.14 mL, 1.5 mmol) and 6-fluoro-2-methylquinolin-8-ol (0.20 g, 1.1 mmol) were added. The vessel was sealed and the mixture was stirred at 50° C. for 12 hours. The cooled reaction mixture was diluted with water (10 mL) and extracted with dichloromethane (2×20 mL). The combined organic extracts were dried over magnesium sulfate, filtered and concentrated under reduced pressure. The residue was purified by normal phase chromatography on silica gel (10-50% ethyl acetate/hexanes) to provide the title compound (0.22 g, 77%).

Step B: Preparation of 6-fluoro-8-(3-methoxypropoxy)quinoline-2-carbaldehyde

To a solution of 6-fluoro-8-(3-methoxypropoxy)-2-methylquinoline (0.22 g, 0.87 mmol) in dioxane (20 mL) and water (0.2 mL) was added selenium dioxide (0.12 g, 1.0 mmol) and the resultant mixture was heated at reflux for 5 hours. The cooled reaction mixture was filtered through a plug of Celite®, washing the solids with dichloromethane. The filtrate was concentrated under reduced pressure and the residue was purified by normal phase chromatography on silica gel (10-30% ethyl acetate/hexanes) to provide the title compound (0.20 g, 89%).

Step C: Preparation of tert-butyl (S)-1-((R)-2,2,2-trifluoro-1-(3-(6-fluoro-8-(3-methoxypropoxy)quinolin-2-yl)-[1,2,4]triazolo[4,3-a]pyridin-6-yl)ethyl)pyrrolidin-3-ylcarbamate A solution of tert-butyl (S)-1-((R)-2,2,2-trifluoro-1-(6-hydrazinylpyridin-3-yl)ethyl)pyrrolidin-3-ylcarbamate (0.15 g, 0.36 mmol) and 6-fluoro-8-(3-methoxypropoxy)quinoline-2-carbaldehyde (0.095 g, 0.36 mmol) in ethanol (1.8 mL, 0.36 mmol) was allowed to stir at ambient temperature for 12 hours. The solvent was removed under reduced pressure. The residue was dissolved in dichloromethane (1.8 mL) and iodosobenzene diacetate (0.13 g, 0.39 mmol) was added. The reaction mixture was stirred at ambient temperature for 1 hour. Ethyl acetate (20 mL) and saturated sodium bicarbonate (10 mL) were added. The organic layer was separated, washed with brine, dried over sodium sulfate, filtered and concentrated under reduced pressure. The residue was purified by reverse phase chromatography on a C18 column (0-100% acetonitrile/water) to give the title compound (0.12 g, 55%).

Step D: Preparation of (S)-1-((R)-2,2,2-trifluoro-1-(3-(6-fluoro-8-(3-methoxypropoxy)quinolin-2-yl)-[1,2,4]triazolo[4,3-a]pyridin-6-yl)ethyl)pyrrolidin-3-amine dihydrochloride To a solution of tert-butyl (S)-1-((R)-2,2,2-trifluoro-1-(3-(6-fluoro-8-(3-methoxypropoxy)quinolin-2-yl)-[1,2,4]triazolo[4,3-a]pyridin-6-yl)ethyl)pyrrolidin-3-ylcarbamate (0.12 g, 0.19 mmol) in dichloromethane (1 mL) was added hydrochloric acid (5-6M in 2-propanol; 6.5 mL, 0.19 mmol). The reaction mixture was stirred at ambient temperature for 30 minutes. The solvent was removed under reduced pressure, and the solid obtained was suspended in acetonitrile (3 mL) and stirred at ambient temperature for 5 minutes. The solid formed was collected by vacuum filtration to give the title compound (0.095 g, 80%). FIA-MS APCI (+) m/z 519 (M+H).

Example 234

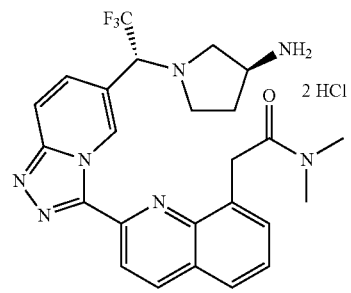 [SMILES: CN(C)C(=O)Cc1cccc2ccc(-c3nnc4ccc([C@@H](N5CC[C@H](N)C5)C(F)(F)F)cn34)nc12]

2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)-N,N-dimethylacetamide dihydrochloride Prepared as described in Example 30, using methyl 2-(2-methylquinolin-8-yl)acetate in place of methyl 2-methylquinoline-7-carboxylate in Step C, substituting tert-butyl (S)-1-((R)-2,2,2-trifluoro-1-(6-hydrazinylpyridin-3-yl)ethyl)pyrrolidin-3-ylcarbamate for tert-butyl (3S)-1-(2,2,2-trifluoro-1-(6-hydrazinylpyridin-3-yl)ethyl)pyrrolidin-3-ylcarbamate in Step D, and substituting dimethylamine for propan-2-amine in Step E. LCMS APCI (+) m/z 498 (M+H).

Example 235

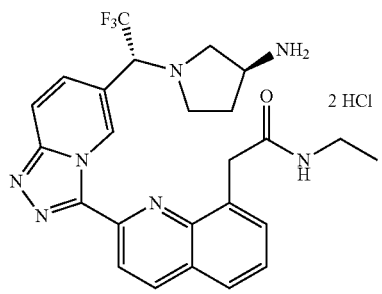 [SMILES: CCNC(=O)Cc1cccc2ccc(-c3nnc4ccc([C@@H](N5CC[C@H](N)C5)C(F)(F)F)cn34)nc12]

2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)-N-ethylacetamide dihydrochloride Prepared as described in Example 30, using methyl 2-(2-methylquinolin-8-yl)acetate in place of methyl 2-methylquinoline-7-carboxylate in Step C, substituting tert-butyl (S)-1-((R)-2,2,2-trifluoro-1-(6-hydrazinylpyridin-3-yl)ethyl)pyrrolidin-3-ylcarbamate for tert-butyl (3S)-1-(2,2,2-trifluoro-1-(6-hydrazinylpyridin-3-yl)ethyl)pyrrolidin-3-ylcarbamate in Step D, and substituting ethyl amine for propan-2-amine in Step E. LCMS APCI (+) m/z 498 (M+H).

Example 236

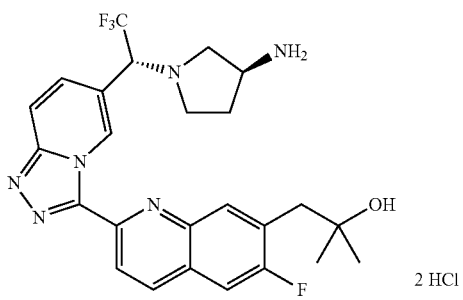 [SMILES: CC(C)(O)Cc1cc2nc(-c3nnc4ccc([C@@H](N5CC[C@H](N)C5)C(F)(F)F)cn34)ccc2cc1F]

2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol dihydrochloride

Step A: Preparation of 1-(6-fluoro-2-methylquinolin-7-yl)-2-methylpropan-2-ol To a stirred solution of methyl 2-(6-fluoro-2-methylquinolin-7-yl)acetate (0.650 g, 2.79 mmol) in toluene (14 mL) was added dropwise a solution of MeMgBr in ether (3.0 M, 2.79 mL, 8.36 mmol) at 0° C. under nitrogen. The reaction mixture was stirred at ambient temperature for 2 hours. The reaction was quenched by the addition of saturated aqueous NH$_4$Cl solution. The reaction mixture was extracted with EtOAc. The combined organic layers were washed with brine, dried and concentrated under reduced pressure. The residue was purified by flash chromatography on silica gel (1:2 hexanes/EtOAc) to give 1-(6-fluoro-2-methylquinolin-7-yl)-2-methylpropan-2-ol (0.202 g, 31%).

Step B: Preparation of 8-(2-hydroxypropan-2-yl)quinoline-2-carbaldehyde

Prepared as described in Example 5, Step B, using 1-(6-fluoro-2-methylquinolin-7-yl)-2-methylpropan-2-ol in place of 8-(cyclopropylmethoxy)-2-methylquinoline.

Step C: Preparation of 2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol dihydrochloride Prepared as described in Example 9B, Steps F-G, using 8-(2-hydroxypropan-2-yl)quinoline-2-carbaldehyde in place of 8-methoxyquinoline-2-carbaldehyde in Step F. LCMS APCI (+) m/z 503 (M+H).

Example 237

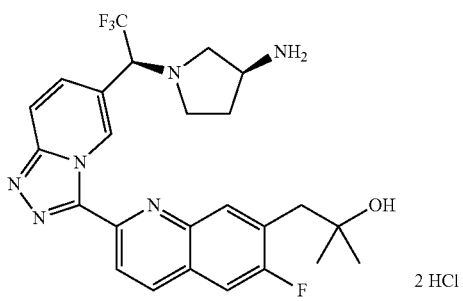 [SMILES: CC(C)(O)Cc1cc2nc(-c3nnc4ccc([C@H](N5CC[C@H](N)C5)C(F)(F)F)cn34)ccc2cc1F]

2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol dihydrochloride Prepared as described in Example 9B, Steps B-G, using dichloro{(R)-(+)-2,2'-bis[di(3,5-xylyl)-phosphino-1,1'-binaphthyl}[(2R)-(−)-1,1-bis(4-methoxyphenyl)-3-methyl-1,2-butanediamine in place of dichloro{(S)-(−)-2,2'-bis[di(3,5-xylyl)-phosphino-1,1'-binaphthyl}[(2S)-(+)-1,1-bis(4-methoxyphenyl)-3-methyl-1,2-butanediamine in Step B, and substituting 8-(2-hydroxypropan-2-yl)quinoline-2-carbaldehyde for 8-methoxyquinoline-2-carbaldehyde in Step F. LCMS APCI (+) m/z 503 (M+H).

Example 238

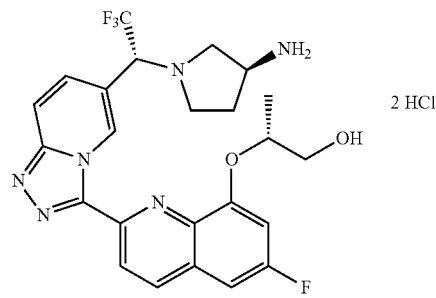 [SMILES: C[C@H](CO)Oc1cc(F)cc2ccc(-c3nnc4ccc([C@@H](N5CC[C@H](N)C5)C(F)(F)F)cn34)nc12]

(R)-2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-yloxy)propan-1-ol dihydrochloride

Step A: Preparation of tert-butyl (S)-1-((R)-1-(3-(8-((R)-1-(tert-butyldiphenyl silyloxy)propan-2-yloxy)-6-fluoroquinolin-2-yl)-[1,2,4]triazolo[4,3-a]pyridin-6-yl)-2,2,2-trifluoroethyl)pyrrolidin-3-ylcarbamate Prepared according to the method of Example 148, Steps A-C, substituting 6-fluoro-2-methylquinolin-8-ol for 2-methylquinolin-7-ol and (S)-1-(tert-butyldiphenylsilyloxy)propan-2-ol for 1-bromo-2-methoxyethane in Step A.

Step B: Preparation of (S)-1-((R)-1-(3-(8-((R)-1-(tert-butyldiphenyl silyloxy)propan-2-yloxy)-6-fluoroquinolin-2-yl)-[1,2,4]triazolo[4,3-a]pyridin-6-yl)-2,2,2-trifluoroethyl)pyrrolidin-3-amine A solution of tert-butyl (S)-1-((R)-1-(3-(8-(3-(tert-butyldimethylsilyloxy)propoxy)-6-fluoroquinolin-2-yl)-[1,2,4]triazolo[4,3-a]pyridin-6-yl)-2,2,2-trifluoroethyl)pyrrolidin-3-ylcarbamate (0.098 g, 0.12 mmol) in dichloromethane (1 mL) and trifluoroacetic acid (2 mL) was stirred at ambient temperature for 30 minutes. Reaction mixture concentrated under reduced pressure. The residue was purified by reverse phase chromatography on a C18 column (0-100% acetonitrile/water) to provide the title compound (0.045 g, 52%).

Step C: Preparation of (R)-2-(2-(6-((R)-1-((S)-3-aminopyrrolidin-1-yl)-2,2,2-trifluoroethyl)-[1,2,4]triazolo[4,3-a]pyridin-3-yl)-6-fluoro quinolin-8-yloxy)propan-1-ol dihydrochloride A solution of (S)-1-((R)-1-(3-(8-((R)-1-(tert-butyldiphenylsilyloxy)propan-2-yloxy)-6-fluoro quinolin-2-yl)-[1,2,4]triazolo[4,3-a]pyridin-6-yl)-2,2,2-trifluoroethyl)pyrrolidin-3-amine (0.045 g, 0.061 mmol) in tetrahydrofuran (0.5 mL) and tetrabutylammonium fluoride (1M in tetrahydrofuran; 0.18 mL) was stirred at ambient temperature for 90 minutes. The reaction mixture concentrated under reduced pressure. The residue was by reverse phase chromatography on a C18 column (0-100% acetonitrile/water). The material isolated after purification was dissolved in methanol (0.5 mL) and added dropwise to hydrochloric acid (2M in diethyl ether; 3 mL). The resulting salt was collected by vacuum filtration to provide the title compound (0.010 g, 30%). FIA-MS APCI (+) m/z 505 (M+H).

Example 239

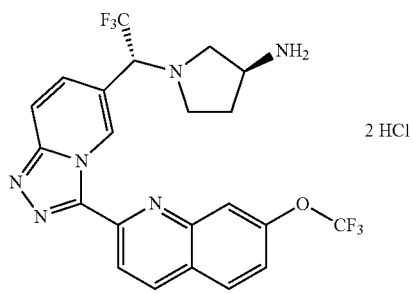 [SMILES: N[C@H]1CCN([C@H](c2ccc3nnc(-c4ccc5ccc(OC(F)(F)F)cc5n4)n3c2)C(F)(F)F)C1]

(S)-1-((R)-2,2,2-trifluoro-1-(3-(7-(trifluoromethoxy)quinolin-2-yl)-[1,2,4]triazolo[4,3-a]pyridin-6-yl)ethyl)pyrrolidin-3-amine dihydrochloride Prepared according to the method of Example 113, substituting 3-(trifluoromethoxy)aniline for 4-fluoro-3-methoxyaniline in Step A. FIA-MS APCI (+) m/z 497 (M+H).

Example 240

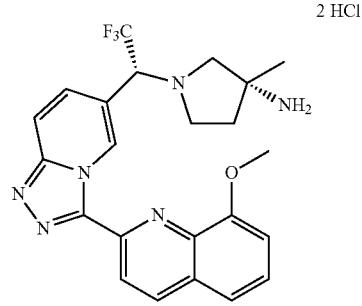 [SMILES: COc1cccc2ccc(-c3nnc4ccc([C@@H](N5CC[C@@](C)(N)C5)C(F)(F)F)cn34)nc12]

(R)-3-methyl-1-((R)-2,2,2-trifluoro-1-(3-(8-methoxyquinolin-2-yl)-[1,2,4]triazolo[4,3-a]pyridin-6-yl)ethyl)pyrrolidin-3-amine dihydrochloride Prepared as described in Example 9B, Steps F-G, using (R)-tert-butyl 3-methylpyrrolidin-3-ylcarbamate (from Preparation A) in place of (S)-tert-butyl pyrrolidin-3-ylcarbamate. MS APCI (+) m/z 457 (M+1) detected.

Example 241

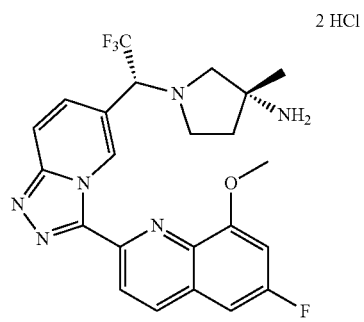 [SMILES: COc1cc(F)cc2ccc(-c3nnc4ccc([C@@H](N5CC[C@@](C)(N)C5)C(F)(F)F)cn34)nc12]

(R)-3-methyl-1-((R)-2,2,2-trifluoro-1-(3-(6-fluoro-8-methoxyquinolin-2-yl)-[1,2,4]triazolo[4,3-a]pyridin-6-yl)ethyl)pyrrolidin-3-amine dihydrochloride Prepared as described in Example 9B, Steps F-G, using (R)-tert-butyl 3-methylpyrrolidin-3-ylcarbamate (Preparation A) in place of (S)-tert-butyl pyrrolidin-3-ylcarbamate and using 6-fluoro-8-methoxyquinoline-2-carbaldehyde in place of 8-methoxyquinoline-2-carbaldehyde. MS APCI (+) m/z 475 (M+1) detected.

Example 242

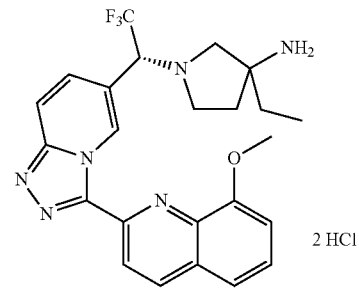 [SMILES: CCC1(N)CCN([C@H](c2ccc3nnc(-c4ccc5cccc(OC)c5n4)n3c2)C(F)(F)F)C1]

Diastereomer 1 of 3-ethyl-1-((R)-2,2,2-trifluoro-1-(3-(8-methoxyquinolin-2-yl)-[1,2,4]triazolo[4,3-a]pyridin-6-yl)ethyl)pyrrolidin-3-amine dihydrochloride Step A: Preparation of (+/−)benzyl 3-(tert-butoxycarbonylamino)-3-ethylpyrrolidine-1-carboxylate Prepared as described in International Publication No. WO 2009/140320A1, Example D, Steps A-D, using ethyl iodide in place of methyl iodide.

Step B: Separation of enantiomers benzyl 3-(tert-butoxycarbonylamino)-3-ethylpyrrolidine-1-carboxylate enantiomer 1 and benzyl 3-(tert-butoxycarbonylamino)-3-ethylpyrrolidine-1-carboxylate enantiomer 2

A racemic mixture of benzyl 3-(tert-butoxycarbonylamino)-3-ethylpyrrolidine-1-carboxylate (0.280 g, 0.8 mmol) was separated via preparative supercritical fluid chromatography under the following conditions: Column: IC 20 mm×250 mm; flow rate: 50 mL/min; mobile phase A: supercritical $CO_2$; mobile phase B: isopropyl alcohol; gradient: isocratic 10% isopropyl alcohol 90% supercritical $CO_2$; UV detection wavelength: 212 nm. Peak one: retention time: 4.34 minutes; recovery: Enantiomer 1 of benzyl 3-(tert-butoxycarbonylamino)-3-ethylpyrrolidine-1-carboxylate (0.120 g, 0.3 mmol). Peak two: retention time: 8.34 minutes; recovery: Enantiomer 2 of benzyl 3-(tert-butoxycarbonylamino)-3-ethylpyrrolidine-1-carboxylate (0.116 g, 0.3 mmol).

Step C: Preparation of Enantiomer 1 of tert-butyl 3-ethylpyrrolidin-3-ylcarbamate Prepared as described in International Application No. WO 2009/140320A1, Example D, Step E, using Enantiomer 1 of benzyl 3-(tert-butoxycarbonylamino)-3-ethylpyrrolidine-1-carboxylate in place of racemic benzyl 3-(tert-butoxycarbonylamino)-3-methylpyrrolidine-1-carboxylate.

Step D: Prepared as described in Example 9B, Steps F-G, using Enantiomer 1 of tert-butyl 3-ethylpyrrolidin-3-ylcarbamate in place of (S)-tert-butyl pyrrolidin-3-ylcarbamate in Step D. LCMS APCI (+) m/z 471 (M+H).

Example 243

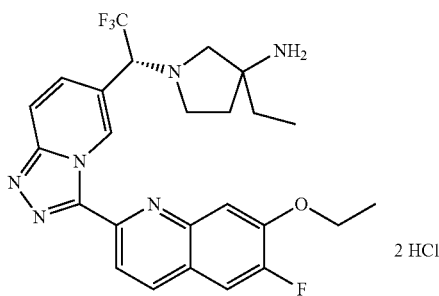 [SMILES: CCOc1cc2nc(-c3nnc4ccc([C@@H](N5CCC(N)(CC)C5)C(F)(F)F)cn34)ccc2cc1F]

Diastereomer 1 of 1-((R)-1-(3-(7-ethoxy-6-fluoro quinolin-2-yl)-[1,2,4]triazolo[4,3-a]pyridin-6-yl)-2,2,2-trifluoroethyl)-3-ethylpyrrolidin-3-amine dihydrochloride Prepared as described in Example 9, Steps D-G, using Enantiomer 1 of tert-butyl 3-ethylpyrrolidin-3-ylcarbamate (Example 242) in place of (S)-tert-butyl pyrrolidin-3-ylcarbamate in Step D, and substituting 7-ethoxy-6-fluoroquinoline-2-carbaldehyde for 8-methoxyquinoline-2-carbaldehyde in Step F. LCMS APCI (+) m/z 503 (M+H).

Example 244

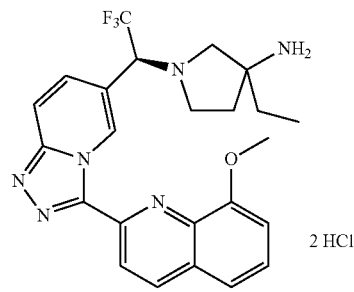 [SMILES: CCC1(N)CCN([C@@H](c2ccc3nnc(-c4ccc5cccc(OC)c5n4)n3c2)C(F)(F)F)C1]

Diastereomer 2 of 3-ethyl-1-((S)-2,2,2-trifluoro-1-(3-(8-methoxyquinolin-2-yl)-[1,2,4]triazolo[4,3-a]pyridin-6-yl)ethyl)pyrrolidin-3-amine dihydrochloride Step A: Preparation of (+/−)benzyl 3-(tert-butoxycarbonylamino)-3-ethylpyrrolidine-1-carboxylate Prepared as described in International Publication No. WO 2009/140320A1, Example D, Steps A-D, using ethyl iodide in place of methyl iodide.

Step B: Separation of enantiomers: benzyl 3-(tert-butoxycarbonylamino)-3-ethylpyrrolidine-1-carboxylate enantiomer 1 and benzyl 3-(tert-butoxycarbonylamino)-3-ethylpyrrolidine-1-carboxylate enantiomer 2

A racemic mixture of benzyl 3-(tert-butoxycarbonylamino)-3-ethylpyrrolidine-1-carboxylate (0.280 g, 0.8 mmol) was separated via preparative supercritical fluid chromatography under the following conditions: Column: IC 20 mm×250 mm; flow rate: 50 mL/min; mobile phase A: supercritical $CO_2$; mobile phase B: isopropyl alcohol; gradient: isocratic 10% isopropyl alcohol 90% supercritical $CO_2$; UV detection wavelength: 212 nm. Peak one: retention time: 4.34 minutes; recovery: Enantiomer 1 of benzyl 3-(tert-butoxycarbonylamino)-3-ethylpyrrolidine-1-carboxylate (0.120 g, 0.3 mmol). Peak two: retention time: 8.34 minutes; recovery: Enantiomer 2 of benzyl 3-(tert-butoxycarbonylamino)-3-ethylpyrrolidine-1-carboxylate (0.116 g, 0.3 mmol).

Step C: Preparation of Enantiomer 2 of tert-butyl 3-ethylpyrrolidin-3-ylcarbamate Prepared as described in International Application No. WO 2009/140320A1, Example D, Step E, using Enantiomer 2 of benzyl 3-(tert-butoxycarbonylamino)-3-ethylpyrrolidine-1-carboxylate in place of racemic benzyl 3-(tert-butoxycarbonylamino)-3-methylpyrrolidine-1-carboxylate.

Step D: Prepared as described in Example 9B, Steps B-G, using dichloro{(R)-(+)-2,2'-bis[di(3,5-xylyl)-phosphino-1,1'-binaphthyl}[(2R)-(−)-1,1-bis(4-methoxyphenyl)-3-methyl-1,2-butanediamine in place of dichloro{(S)-(−)-2,2'-bis[di(3,5-xylyl)-phosphino-1,1'-binaphthyl}[(2S)-(+)-1,1-bis(4-methoxyphenyl)-3-methyl-1,2-butanediamine in Step B, and substituting Enantiomer 2 of tert-butyl 3-ethylpyrrolidin- 3-ylcarbamate (Preparation J) for (S)-tert-butyl pyrrolidin-3-ylcarbamate in Step D. LCMS APCI (+) m/z 471 (M+H).

Example 245

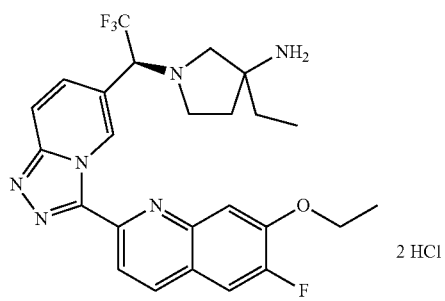 [SMILES: CCOc1cc2nc(-c3nnc4ccc([C@H](N5CCC(N)(CC)C5)C(F)(F)F)cn34)ccc2cc1F]

Diastereomer 2 of 1-((S)-1-(3-(7-ethoxy-6-fluoro-quinolin-2-yl)-[1,2,4]triazolo[4,3-a]pyridin-6-yl)-2,2,2-trifluoroethyl)-3-ethylpyrrolidin-3-amine dihydrochloride Prepared as described in Example 9B Steps B-G, using dichloro{(R)-(+)-2,2'-bis[di(3,5-xylyl)-phosphino-1,1'-binaphthyl}[(2R)-(−)-1,1-bis(4-methoxyphenyl)-3-methyl-1,2-butanediamine in place of dichloro{(S)-(−)-2,2'-bis[di(3,5-xylyl)-phosphino-1,1'-binaphthyl}[(2S)-(+)-1,1-bis(4-methoxyphenyl)-3-methyl-1,2-butanediamine in Step B, substituting Enantiomer 2 of tert-butyl 3-ethylpyrrolidin-3-ylcarbamate (Example 244) for (S)-tert-butyl pyrrolidin-3-ylcarbamate in Step D, and substituting 7-ethoxy-6-fluoro-quinoline-2-carbaldehyde for 8-methoxyquinoline-2-carbaldehyde in Step F. LCMS APCI (+) m/z 503 (M+H).

Example 246

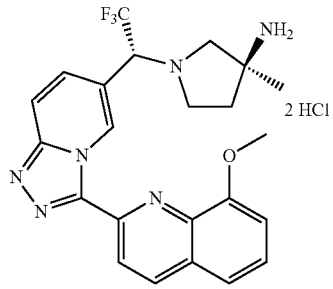 [SMILES: COc1cccc2ccc(-c3nnc4ccc([C@@H](N5CC[C@](C)(N)C5)C(F)(F)F)cn34)nc12]

(S)-3-methyl-1-((R)-2,2,2-trifluoro-1-(3-(8-methoxyquinolin-2-yl)-[1,2,4]triazolo[4,3-a]pyridin-6-yl)ethyl)pyrrolidin-3-amine dihydrochloride Prepared as described in Example 9B, Steps D-G, using (S)-tert-butyl 3-methylpyrrolidin-3-ylcarbamate (Preparation A) in place of (S)-tert-butyl pyrrolidin-3-ylcarbamate in Step D. LCMS APCI (+) m/z 457 (M+H).

Example 247

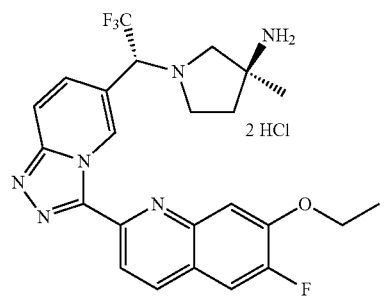 [SMILES: CCOc1cc2nc(-c3nnc4ccc([C@@H](N5CC[C@](C)(N)C5)C(F)(F)F)cn34)ccc2cc1F]

(S)-1-((R)-1-(3-(7-ethoxy-6-fluoro quinolin-2-yl)-[1,2,4]triazolo[4,3-a]pyridin-6-yl)-2,2,2-trifluoroethyl)-3-methylpyrrolidin-3-amine dihydrochloride Prepared as described in Example 9B, Steps D-G, using (S)-tert-butyl 3-methylpyrrolidin-3-ylcarbamate (Preparation A) in place of (S)-tert-butyl pyrrolidin-3-ylcarbamate in Step D, and substituting 7-ethoxy-6-fluoroquinoline-2-carbaldehyde for 8-methoxyquinoline-2-carbaldehyde in Step F. LCMS APCI (+) m/z 489 (M+H).

Example 248

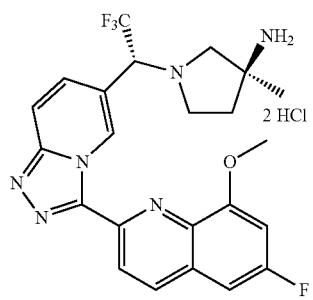 [SMILES: COc1cc(F)cc2ccc(-c3nnc4ccc([C@@H](N5CC[C@](C)(N)C5)C(F)(F)F)cn34)nc12]

(S)-3-methyl-1-((R)-2,2,2-trifluoro-1-(3-(6-fluoro-8-methoxyquinolin-2-yl)-[1,2,4]triazolo[4,3-a]pyridin-6-yl)ethyl)pyrrolidin-3-amine dihydrochloride Prepared as described in Example 9B, Steps D-G, using (S)-tert-butyl 3-methylpyrrolidin-3-ylcarbamate (Preparation A) in place of (S)-tert-butyl pyrrolidin-3-ylcarbamate in Step D, and substituting 6-fluoro-8-methoxyquinoline-2-carbaldehyde for 8-methoxyquinoline-2-carbaldehyde in Step F. LCMS APCI (+) m/z 475 (M+H).

Example 249

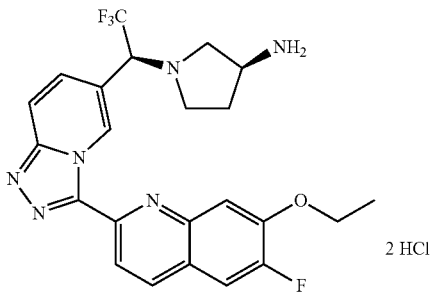 [SMILES: CCOc1cc2nc(-c3nnc4ccc([C@H](N5CC[C@H](N)C5)C(F)(F)F)cn34)ccc2cc1F]

(S)-1-((S)-1-(3-(7-ethoxy-6-fluoroquinolin-2-yl)-[1,2,4]triazolo[4,3-a]pyridin-6-yl)-2,2,2-trifluoroethyl)pyrrolidin-3-amine dihydrochloride Prepared as described in Example 9B, Steps A-G, using dichloro{(R)-(+)-2,2'-bis[di(3,5-xylyl)-phosphino-1,1'-binaphthyl}[(2R)-(−)-1,1-bis(4-methoxyphenyl)-3-methyl-1,2-butanediamine in place of dichloro{(S)-(−)-2,2'-bis[di(3,5-xylyl)-phosphino-1,1'-binaphthyl}[(2S)-(+)-1,1-bis(4-methoxyphenyl)-3-methyl-1,2-butanediamine in Step B, and substituting 7-ethoxy-6-fluoroquinoline-2-carbaldehyde for 8-methoxyquinoline-2-carbaldehyde in Step F. LCMS APCI (+) m/z 475 (M+H).

Example 250

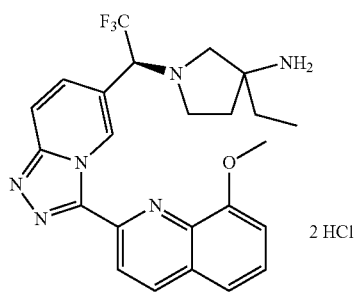 [SMILES: CCC1(N)CCN([C@@H](c2ccc3nnc(-c4ccc5cccc(OC)c5n4)n3c2)C(F)(F)F)C1]

Diastereomer 1 of 3-ethyl-1-((S)-2,2,2-trifluoro-1-(3-(8-methoxyquinolin-2-yl)-[1,2,4]triazolo[4,3-a]pyridin-6-yl)ethyl)pyrrolidin-3-amine dihydrochloride Prepared as described in Example 9B, Steps B-G, using dichloro{(R)-(+)-2,2'-bis[di(3,5-xylyl)-phosphino-1,1'-binaphthyl}[(2R)-(−)-1,1-bis(4-methoxyphenyl)-3-methyl-1,2-butanediamine in place of dichloro{(S)-(−)-2,2'-bis[di(3,5-xylyl)-phosphino-1,1'-binaphthyl}[(2S)-(+)-1,1-bis(4-methoxyphenyl)-3-methyl-1,2-butanediamine in Step B, and substituting Enantiomer 1 of tert-butyl 3-ethylpyrrolidin-3-ylcarbamate (from Preparation J) for (S)-tert-butyl pyrrolidin-3-ylcarbamate in Step D. LCMS APCI (+) m/z 471 (M+H).

Example 251

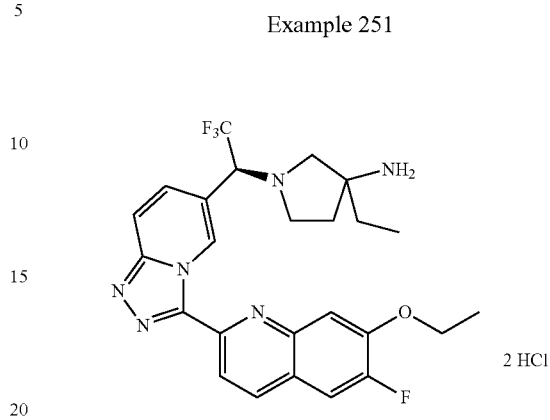

Diastereomer 1 of 1-((S)-1-(3-(7-ethoxy-6-fluoroquinolin-2-yl)-[1,2,4]triazolo[4,3-a]pyridin-6-yl)-2,2,2-trifluoroethyl)-3-ethylpyrrolidin-3-amine dihydrochloride Prepared as described in Example 9B Steps B-G, using dichloro{(R)-(+)-2,2'-bis[di(3,5-xylyl)-phosphino-1,1'-binaphthyl}[(2R)-(−)-1,1-bis(4-methoxyphenyl)-3-methyl-1,2-butanediamine in place of dichloro{(S)-(−)-2,2'-bis[di(3,5-xylyl)-phosphino-1,1'-binaphthyl}[(2S)-(+)-1,1-bis(4-methoxyphenyl)-3-methyl-1,2-butanediamine in Step B, substituting Enantiomer 1 of tert-butyl 3-ethylpyrrolidin-3-ylcarbamate (Preparation J) for (S)-tert-butyl pyrrolidin-3-ylcarbamate in Step D, and substituting 7-ethoxy-6-fluoroquinoline-2-carbaldehyde for 8-methoxyquinoline-2-carbaldehyde in Step F. LCMS APCI (+) m/z 503 (M+H).

Example 252

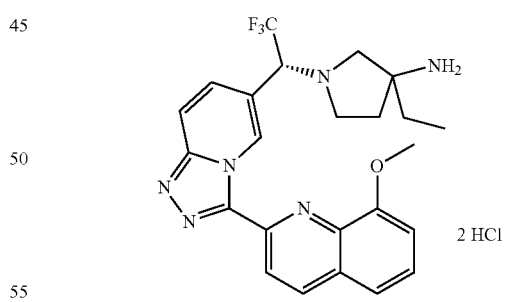

Diastereomer 2 of 3-ethyl-1-((R)-2,2,2-trifluoro-1-(3-(8-methoxyquinolin-2-yl)-[1,2,4]triazolo[4,3-a]pyridin-6-yl)ethyl)pyrrolidin-3-amine dihydrochloride Prepared as described in Example 9B, Steps D-G, using Enantiomer 2 of tert-butyl 3-ethylpyrrolidin-3-ylcarbamate (Preparation J) in place of (S)-tert-butyl pyrrolidin-3-ylcarbamate in Step D. LCMS APCI (+) m/z 471 (M+H).

Example 253

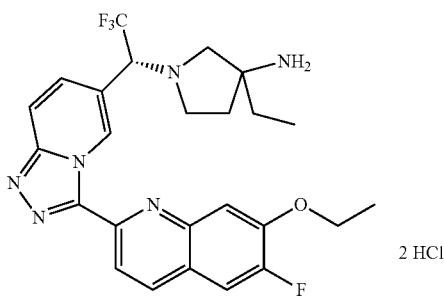 [SMILES: CCOc1cc2nc(-c3nnc4ccc([C@@H](N5CCC(N)(CC)C5)C(F)(F)F)cn34)ccc2cc1F]

Diastereomer 2 of 1-((R)-1-(3-(7-ethoxy-6-fluoro quinolin-2-yl)-[1,2,4]triazolo[4,3-a]pyridin-6-yl)-2, 2,2-trifluoroethyl)-3-ethylpyrrolidin-3-amine dihydrochloride Prepared as described in Example 9B, Steps D-G, using Enantiomer 2 of tert-butyl 3-ethylpyrrolidin-3-ylcarbamate (from Preparation J) in place of (S)-tert-butyl pyrrolidin-3-ylcarbamate in Step D, and substituting 7-ethoxy-6-fluoro-quinoline-2-carbaldehyde for 8-methoxyquinoline-2-carbaldehyde in Step F. LCMS APCI (+) m/z 503 (M+H).

Example 254

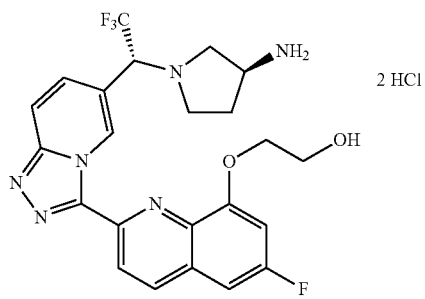 [SMILES: N[C@H]1CCN([C@H](c2ccc3nnc(-c4ccc5cc(F)cc(OCCO)c5n4)n3c2)C(F)(F)F)C1]

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-yloxy)ethanol dihydrochloride Prepared according to the method of Example 219 substituting 6-fluoro-2-methylquinolin-8-ol for 2-methylquinolin-8-ol in Step A. FIA-MS APCI (+) m/z 491 (M+H).

Example 255

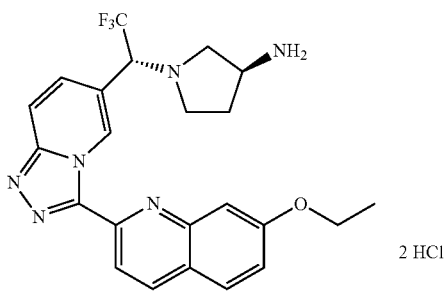 [SMILES: CCOc1ccc2ccc(-c3nnc4ccc([C@@H](N5CC[C@H](N)C5)C(F)(F)F)cn34)nc2c1]

(S)-1-((R)-1-(3-(7-ethoxyquinolin-2-yl)-[1,2,4]triazolo[4,3-a]pyridin-6-yl)-2,2,2-trifluoroethyl)pyrrolidin-3-amine dihydrochloride Step A: Preparation of 7-ethoxy-2-methylquinoline To a stirred mixture of 2-methylquinolin-7-ol (400 mg, 2.51 mmol), Cs$_2$CO$_3$ (2.46 g, 7.54 mmol) and NMP (12 mL) was added bromoethane (0.563 mL, 7.54 mmol). The reaction mixture was stirred at ambient temperature overnight. The reaction was partitioned between ether and water. The aqueous layer was extracted with ether. The combined organic layers were washed with water and brine, dried and concentrated under reduced pressure. The residue was purified by flash chromatography on silica gel (2:1 to 5:1 hexanes:EtOAc) to give 7-ethoxy-2-methylquinoline (416 mg, 88%).

Step B: Preparation of 7-ethoxyquinoline-2-carbaldehyde

Prepared as described in Example 5, Step B, using 7-ethoxy-2-methylquinoline in place of 8-(cyclopropylmethoxy)-2-methylquinoline.

Step C: Preparation of (S)-1-((R)-1-(3-(7-ethoxyquinolin-2-yl)-[1,2,4]triazolo[4,3-a]pyridin-6-yl)-2,2,2-trifluoroethyl)pyrrolidin-3-amine dihydrochloride Prepared as described in Example 9B, Steps F-G, using 7-ethoxyquinoline-2-carbaldehyde in place of 8-methoxyquinoline-2-carbaldehyde in Step F. LCMS APCI (+) m/z 457 (M+H).

Example 256

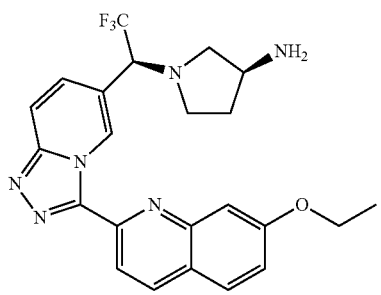

(S)-1-((S)-1-(3-(7-ethoxyquinolin-2-yl)-[1,2,4]triazolo[4,3-a]pyridin-6-yl)-2,2,2-trifluoroethyl)pyrrolidin-3-amine dihydrochloride Prepared as described in Example 9B, Steps B-G, using dichloro{(R)-(+)-2,2'-bis[di(3,5-xylyl)-phosphino-1,1'-binaphthyl][(2R)-(−)-1,1-bis(4-methoxyphenyl)-3-methyl-1, 2-butanediamine in place of dichloro{(S)-(−)-2,2'-bis[di(3,5-xylyl)-phosphino-1,1'-binaphthyl][(2S)-(+)-1,1-bis(4-methoxyphenyl)-3-methyl-1,2-butanediamine in Step B, and substituting 7-ethoxyquinoline-2-carbaldehyde for 8-methoxyquinoline-2-carbaldehyde in Step F. LCMS APCI (+) m/z 475 (M+H).

Example 257

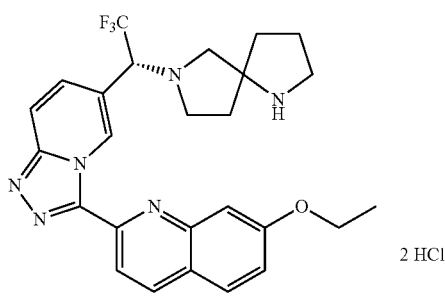 [SMILES: CCOc1ccc2ccc(-c3nnc4ccc([C@@H](N5CCC6(CCCN6)C5)C(F)(F)F)cn34)nc2c1]

2 HCl 7-ethoxy-2-(6-((1R)-2,2,2-trifluoro-1-(1,7-diazaspiro [4.4]nonan-7-yl)ethyl)-[1,2,4]triazolo[4,3-a]pyridin-3-yl)quinoline dihydrochloride Prepared as described in Example 9B, Steps B-G, using tert-butyl 1,7-diazaspiro[4.4]nonane-1-carboxylate in place of (S)-tert-butyl pyrrolidin-3-ylcarbamate in Step D, and substituting 7-ethoxyquinoline-2-carbaldehyde for 8-methoxyquinoline-2-carbaldehyde in Step F. LCMS APCI (+) m/z 497 (M+H).

Example 258

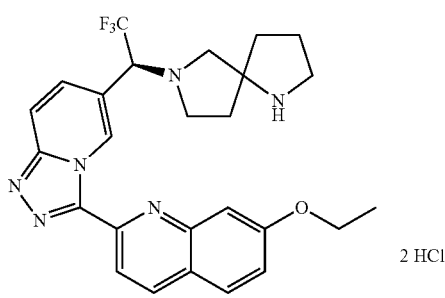 [SMILES: CCOc1ccc2ccc(-c3nnc4ccc([C@H](N5CCC6(CCCN6)C5)C(F)(F)F)cn34)nc2c1]

2 HCl 7-ethoxy-2-(6-((1S)-2,2,2-trifluoro-1-(1,7-diazaspiro [4.4]nonan-7-yl)ethyl)-[1,2,4]triazolo[4,3-a]pyridin-3-yl)quinoline dihydrochloride Prepared as described in Example 9B, Steps B-G, using dichloro{(R)-(+)-2,2'-bis[di(3,5-xylyl)-phosphino-1,1'-binaphthyl}[(2R)-(−)-1,1-bis(4-methoxyphenyl)-3-methyl-1,2-butanediamine in place of dichloro{(S)-(−)-2,2'-bis[di(3,5-xylyl)-phosphino-1,1'-binaphthyl}[(2S)-(+)-1,1-bis(4-methoxyphenyl)-3-methyl-1,2-butanediamine in Step B, substituting tert-butyl 1,7-diazaspiro[4.4]nonane-1-carboxylate for (S)-tert-butyl pyrrolidin-3-ylcarbamate in Step D, and substituting 7-ethoxyquinoline-2-carbaldehyde for 8-methoxyquinoline-2-carbaldehyde in Step F. LCMS APCI (+) m/z 497 (M+H).

Example 259

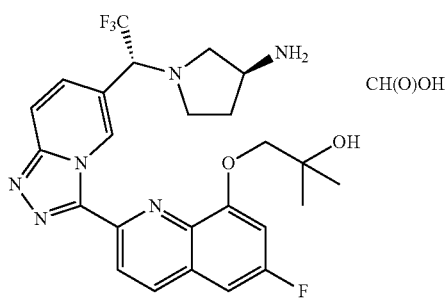

CH(O)OH 1-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-yloxy)-2-methylpropan-2-ol formate

Step A: Preparation of ethyl 2-(6-fluoro-2-methylquinolin-8-yloxy)acetate

Prepared according to the method of Example 219, Step A, substituting ethyl 2-bromoacetate for 2-bromoethyl acetate.

Step B: Preparation of 1-(6-fluoro-2-methylquinolin-8-yloxy)-2-methylpropan-2-ol To a solution of ethyl 2-(2-methylquinolin-8-yloxy)acetate (0.74 g, 3.0 mmol) in diethyl ether (15 mL, 3.0 mmol) was carefully added methylmagnesium bromide (3M in diethyl ether; 2.5 mL) by dropwise addition. The reaction mixture was allowed to stir at ambient temperature for 2 hours. The reaction mixture was poured into ammonium chloride (saturated aqueous; 50 mL) and extracted with dichloromethane (1×30 mL). The organic extract was dried over magnesium sulfate, filtered and concentrated under reduced pressure. The residue was purified by reverse phase chromatography on a C18 column (0-100% acetonitrile/water) providing the title compound (0.41 g, 60%).

Step C: Preparation of 1-(2-(6-((R)-1-((S)-3-aminopyrrolidin-1-yl)-2,2,2-trifluoroethyl)-[1,2,4]triazolo[4,3-a]pyridin-3-yl)-6-fluoro quinolin-8-yloxy)-2-methylpropan-2-ol formate Prepared according to the method of Example 140 substituting 1-(6-fluoro-2-methylquinolin-8-yloxy)-2-methylpropan-2-ol for (R)-8-(1-methoxypropan-2-yloxy)-2-methylquinoline. FIA-MS APCI (+) m/z 519 (M+H).

Example 260

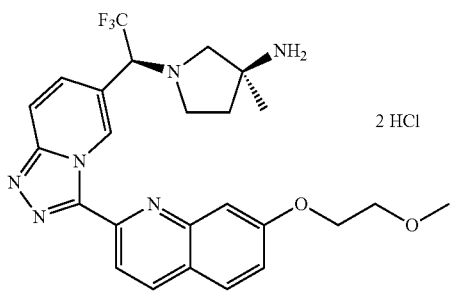 [SMILES: COCCOc1ccc2ccc(-c3nnc4ccc([C@H](N5CC[C@](C)(N)C5)C(F)(F)F)cn34)nc2c1]

(S)-3-methyl-1-((S)-2,2,2-trifluoro-1-(3-(7-(2-methoxyethoxy)quinolin-2-yl)-[1,2,4]triazolo[4,3-a]pyridin-6-yl)ethyl)pyrrolidin-3-amine dihydrochloride Step A: Preparation of 7-(2-methoxyethoxy)-2-methylquinoline To a stirred mixture of 2-methylquinolin-7-ol (300 mg, 1.88 mmol), $Cs_2CO_3$ (1.84 g, 5.65 mmol) and NMP (10 mL) was added 1-bromo-2-methoxyethane (0.786 g, 5.65 mmol). The reaction mixture was stirred at ambient temperature overnight. The reaction was partitioned between ether and water. The aqueous layer was extracted with ether. The combined organic layers were washed with water and brine, dried and concentrated under reduced pressure. The residue was purified by flash chromatography on silica gel (2:1 to 1:2 hexanes/EtOAc) to give 7-(2-methoxyethoxy)-2-methylquinoline (235 mg, 57%).

Step B: Preparation of 7-(2-methoxyethoxy)quinoline-2-carbaldehyde

To a solution of 7-(2-methoxyethoxy)-2-methylquinoline (235 mg, 1.08 mmol) in dioxane (3 mL) and water (0.03 mL) was added $SeO_2$ (132 mg, 1.19 mmol). The reaction mixture was heated at reflux for 2 hours. After cooling to ambient temperature, the solid was removed by filtration and washed with DCM. The filtrate was concentrated under reduced pressure and The residue was purified by flash chromatography on silica gel (4:1 hexanes/EtOAc) to give 7-(2-methoxyethoxy)quinoline-2-carbaldehyde (195 mg, 78%) as a white solid.

Step C: Preparation of tert-butyl (S)-3-methyl-1-((S)-2,2,2-trifluoro-1-(3-(7-(2-methoxyethoxy)quinolin-2-yl)-[1,2,4]triazolo[4,3-a]pyridin-6-yl)ethyl)pyrrolidin-3-ylcarbamate A mixture of tert-butyl (S)-3-methyl-1-((S)-2,2,2-trifluoro-1-(6-hydrazinylpyridin-3-yl)ethyl)pyrrolidin-3-ylcarbamate (53 mg, 0.14 mmol), 7-(2-methoxyethoxy)quinoline-2-carbaldehyde (30 mg, 0.13 mmol) and EtOH (1.4 mL) was stirred at ambient temperature overnight. The solvent was removed under reduced pressure. The residue was dissolved in DCM (1.4 mL) and iodosobenzene diacetate (54 mg, 0.17 mmol) was added. The reaction mixture was stirred at ambient temperature overnight and then loaded to a silica gel column eluting with 1:2 to 3:1 EtOAc/hexanes to give tert-butyl (S)-3-methyl-1-((S)-2,2,2-trifluoro-1-(3-(7-(2-methoxyethoxy)quinolin-2-yl)-[1,2,4]triazolo[4,3-a]pyridin-6-yl)ethyl)pyrrolidin-3-ylcarbamate (72 mg, 92%).

Step D: Preparation of (S)-3-methyl-1-((S)-2,2,2-trifluoro-1-(3-(7-(2-methoxyethoxy)quinolin-2-yl)-[1,2,4]triazolo[4,3-a]pyridin-6-yl)ethyl)pyrrolidin-3-amine dihydrochloride A mixture of tert-butyl (S)-3-methyl-1-((S)-2,2,2-trifluoro-1-(3-(7-(2-methoxyethoxy)quinolin-2-yl)-[1,2,4]triazolo[4,3-a]pyridin-6-yl)ethyl)pyrrolidin-3-ylcarbamate (72 mg, 0.12 mmol), DCM (1 mL) and 4N HCl in dioxane (0.3 mL) was stirred at ambient temperature overnight. Removal of the solvents under reduced pressure gave (S)-3-methyl-1-((S)-2,2,2-trifluoro-1-(3-(7-(2-methoxyethoxy)quinolin-2-yl)-[1,2,4]triazolo[4,3-a]pyridin-6-yl)ethyl)pyrrolidin-3-amine dihydrochloride (65 mg, 95%) as a yellow solid. LCMS APCI (+) m/z 501 (M+H). Specific rotation: $[\alpha]^{25}_D = -0.89°$ (c=0.97, MeOH).

Example 261

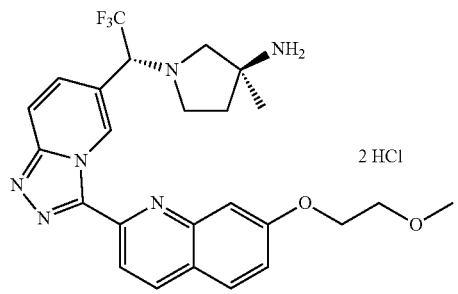 [SMILES: COCCOc1ccc2ccc(-c3nnc4ccc([C@@H](N5CC[C@](C)(N)C5)C(F)(F)F)cn34)nc2c1]

(S)-3-methyl-1-((R)-2,2,2-trifluoro-1-(3-(7-(2-methoxyethoxy)quinolin-2-yl)-[1,2,4]triazolo[4,3-a]pyridin-6-yl)ethyl)pyrrolidin-3-amine dihydrochloride Prepared as described in Example 9B, using (S)-tert-butyl 3-methylpyrrolidin-3-ylcarbamate in place of (S)-tert-butyl pyrrolidin-3-ylcarbamate in Step D, and substituting 7-(2-methoxyethoxy)quinoline-2-carbaldehyde for 8-methoxyquinoline-2-carbaldehyde in Step F. LCMS APCI (+) m/z 501 (M+H).

Example 262

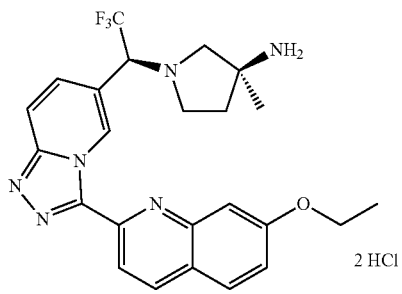 [SMILES: CCOc1ccc2ccc(-c3nnc4ccc([C@H](N5CC[C@](C)(N)C5)C(F)(F)F)cn34)nc2c1]

(S)-1-((S)-1-(3-(7-ethoxyquinolin-2-yl)-[1,2,4]tria-
zolo[4,3-a]pyridin-6-yl)-2,2,2-trifluoroethyl)-3-me-
thylpyrrolidin-3-amine dihydrochloride Prepared as described in Example 260, Steps C-D, using 7-ethoxyquinoline-2-carbaldehyde in place of 7-(2-methoxy-ethoxy)quinoline-2-carbaldehyde in Step C. LCMS APCI (+) m/z 471 (M+H).

Example 263

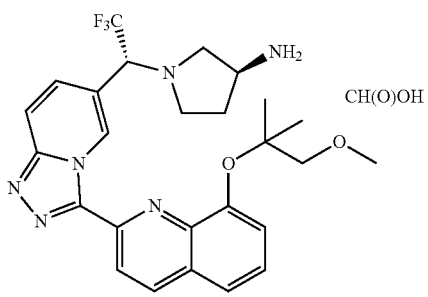

(S)-1-((R)-2,2,2-trifluoro-1-(3-(8-(1-methoxy-2-methylpropan-2-yloxy)quinolin-2-yl)-[1,2,4]triazolo[4,3-a]pyridin-6-yl)ethyl)pyrrolidin-3-amine formate Prepared according to the method of Example 192, substituting 1-methoxy-2-methylpropan-2-ol for (3-methyloxetan-3-yl)methanol. FIA-MS APCI (+) m/z 515 (M+H).

Example 264

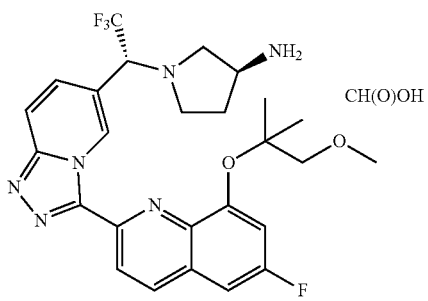

(S)-1-((R)-2,2,2-trifluoro-1-(3-(6-fluoro-8-(1-methoxy-2-methylpropan-2-yloxy)quinolin-2-yl)-[1,2,4]triazolo[4,3-a]pyridin-6-yl)ethyl)pyrrolidin-3-amine formate Prepared according to the method of Example 192, substituting 1-methoxy-2-methylpropan-2-ol for (3-methyloxetan-3-yl)methanol and 6-fluoro-2-methylquinolin-8-ol for 2-methylquinolin-8-ol. FIA-MS APCI (+) m/z 533 (M+H).

Example 265

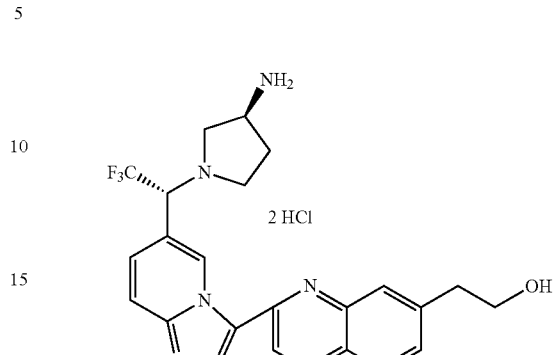

2-(2-(6-((R)-1-((S)-3-aminopyrrolidin-1-yl)-2,2,2-trifluoroethyl)-[1,2,4]triazolo[4,3-a]pyridin-3-yl)quinolin-7-yl)ethanol dihydrochloride Prepared as described in Example 114, using 2-(2-methylquinolin-7-yl)ethanol in place of (1-(2-methylquinolin-8-yl)cyclopropyl)methanol in Step A. LCMS APCI (+) m/z 457 (M+H).

Example 266

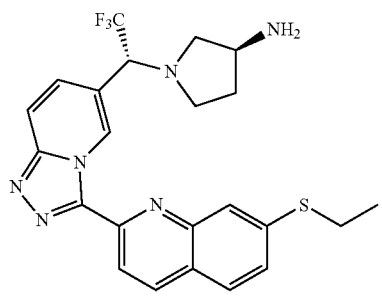 [SMILES: CCSc1ccc2ccc(-c3nnc4ccc([C@@H](N5CC[C@H](N)C5)C(F)(F)F)cn34)nc2c1]

(S)-1-((R)-1-(3-(7-(ethylthio)quinolin-2-yl)-[1,2,4]triazolo[4,3-a]pyridin-6-yl)-2,2,2-trifluoroethyl)pyrrolidin-3-amine hydrochloride Step A: Preparation of tert-butyl (S)-1-((R)-1-(3-(7-bromoquinolin-2-yl)-[1,2,4]triazolo[4,3-a]pyridin-6-yl)-2,2,2-trifluoroethyl)pyrrolidin-3-ylcarbamate Prepared as described in Example 2, Steps A-B, substituting tert-butyl (S)-1-((R)-2,2,2-trifluoro-1-(6-hydrazinylpyridin-3-yl)ethyl)pyrrolidin-3-ylcarbamate for tert-butyl (3S)-1-(2,2,2-trifluoro-1-(6-hydrazinylpyridin-3-yl)ethyl)pyrrolidin-3-ylcarbamate.

Step B: Preparation of tert-butyl (S)-1-((R)-1-(3-(7-(ethylthio)quinolin-2-yl)-[1,2,4]triazolo[4,3-a]pyridin-6-yl)-2,2,2-trifluoroethyl)pyrrolidin-3-ylcarbamate A mixture of $Pd_2$ $dba_3$-$CHCl_3$ (13.1 mg, 0.0127 mmol), (9,9-dimethyl-9H-xanthene-4,5-diyl)bis(diphenylphosphine) (14.7 mg, 0.0254 mmol), tert-butyl (S)-1-((R)-1-(3-(7-bromo quinolin-2-yl)-[1,2,4]triazolo[4,3-a]pyridin-6-yl)-2,2,2-trifluoroethyl)pyrrolidin-3-ylcarbamate (150 mg, 0.254 mmol), ethanethiol (31.5 mg, 0.507 mmol), DIEA (98.3 mg, 0.761 mmol) in dioxane was heated to 150° C. under microwave irradiation for 1 hour. After cooling, the reaction was concentrated under reduced pressure and purified by chromatography (SP4, 12M, eluting with a gradient of water/ACN 100:0 to 0:100, 30 column volumes) to yield tert-butyl (S)-1-((R)-1-(3-(7-(ethylthio)quinolin-2-yl)-[1,2,4]triazolo[4,3-a]pyridin-6-yl)-2,2,2-trifluoroethyl)pyrrolidin-3-ylcarbamate (95 mg, 65.4% yield) as an oil.

Step C: Preparation of (S)-1-((R)-1-(3-(7-(ethylthio)quinolin-2-yl)-[1,2,4]triazolo[4,3-a]pyridin-6-yl)-2,2,2-trifluoroethyl)pyrrolidin-3-amine hydrochloride tert-Butyl (S)-1-((R)-1-(3-(7-(ethylthio)quinolin-2-yl)-[1,2,4]triazolo[4,3-a]pyridin-6-yl)-2,2,2-trifluoroethyl)pyrrolidin-3-ylcarbamate (95 mg, 0.17 mmol) was stirred in TFA for 30 minutes. The reaction was concentrated to dryness, then diluted in 1 mL of methanol and added dropwise into 4N HCl in ether. The resulting precipitate was filtered and dried under vacuum to yield (S)-1-((R)-1-(3-(7-(ethylthio)quinolin-2-yl)-[1,2,4]triazolo[4,3-a]pyridin-6-yl)-2,2,2-trifluoroethyl)pyrrolidin-3-amine (56 mg, 71% yield) hydrochloride as a solid. LCMS APCI (+) m/z 473 (M).

Example 267

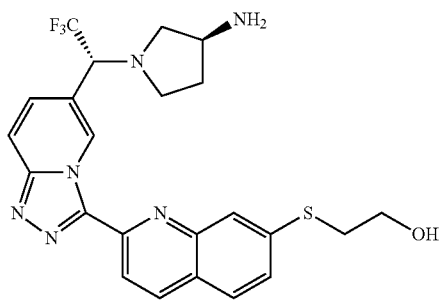 [SMILES: N[C@H]1CCN([C@H](c2ccc3nnc(-c4ccc5ccc(SCCO)cc5n4)n3c2)C(F)(F)F)C1]

2-(2-(6-((R)-1-((S)-3-aminopyrrolidin-1-yl)-2,2,2-trifluoroethyl)-[1,2,4]triazolo[4,3-a]pyridin-3-yl)quinolin-7-ylthio)ethanol hydrochloride Prepared as in Example 266, substituting ethanethiol in Step A with 2-mercaptoethanol. LCMS APCI (+) m/z 489 (M+H).

Example 268

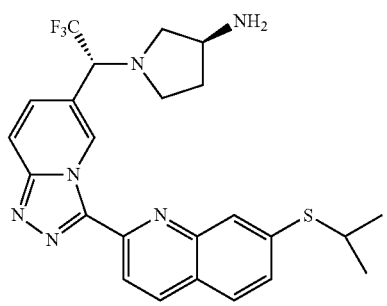 [SMILES: CC(C)Sc1ccc2ccc(-c3nnc4ccc([C@@H](N5CC[C@H](N)C5)C(F)(F)F)cn34)nc2c1]

(S)-1-((R)-2,2,2-trifluoro-1-(3-(7-(isopropylthio)quinolin-2-yl)-[1,2,4]triazolo[4,3-a]pyridin-6-yl)ethyl)pyrrolidin-3-amine hydrochloride Prepared as in Example 266, substituting ethanethiol in Step A with propane-2-thiol. LCMS APCI (+) m/z 487 (M+H).

Example 269

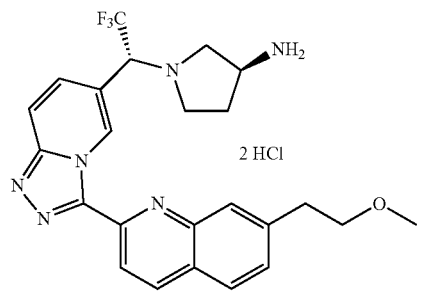 [SMILES: COCCc1ccc2ccc(-c3nnc4ccc([C@@H](N5CC[C@H](N)C5)C(F)(F)F)cn34)nc2c1]

(S)-1-((R)-2,2,2-trifluoro-1-(3-(7-(2-methoxyethyl)quinolin-2-yl)-[1,2,4]triazolo[4,3-a]pyridin-6-yl)ethyl)pyrrolidin-3-amine dihydrochloride Prepared as described in Example 153 using 3-bromoaniline in place of 3-bromo-4-fluoroaniline in Step A. LCMS APCI (+) m/z 471 (M+H).

Example 270

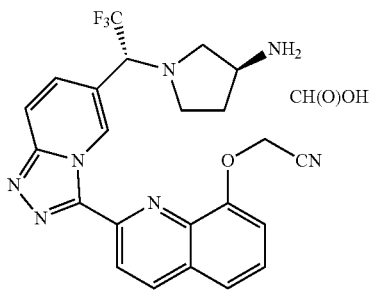

2-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)acetonitrile formate Step A: Preparation of tert-butyl (S)-1-((R)-1-(3-(8-(cyanomethoxy)quinolin-2-yl)-[1,2,4]triazolo[4,3-a]pyridin-6-yl)-2,2,2-trifluoroethyl)pyrrolidin-3-ylcarbamate Prepared according to the method of Example 219, Steps A-D, substituting 2-iodoacetonitrile for 2-bromoethyl acetate in Step A.

Step B: Preparation of 2-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)acetonitrile formate Prepared according to the method of Example 192, substituting tert-butyl (S)-1-((R)-1-(3-(8-(cyanomethoxy)quinolin-2-yl)-[1,2,4]triazolo[4,3-a]pyridin-6-yl)-2,2,2-trifluoroethyl)pyrrolidin-3-ylcarbamate for tert-butyl (S)-1-((R)-2,2,2-trifluoro-1-(3-(8-(3-methyloxetan-3-yl)methoxy)quinolin-2-yl)-[1,2,4]triazolo[4,3-a]pyridin-6-yl)ethyl)pyrrolidin-3-ylcarbamate in Step A. FIA-MS APCI (+) m/z 468 (M+H).

Example 271

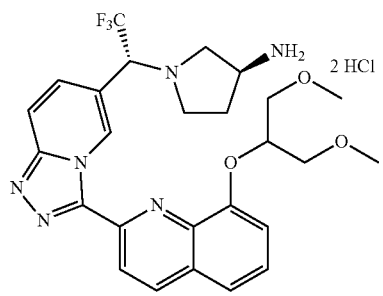 [SMILES: COCC(COC)Oc1cccc2ccc(-c3nnc4ccc([C@@H](N5CC[C@H](N)C5)C(F)(F)F)cn34)nc12]

((S)-1-((R)-1-(3-(8-(1,3-dimethoxypropan-2-yloxy)quinolin-2-yl)-[1,2,4]triazolo[4,3-a]pyridin-6-yl)-2,2,2-trifluoroethyl)pyrrolidin-3-amine dihydrochloride Step A: Preparation of 8-(1,3-dimethoxypropan-2-yloxy)-2-methylquinoline To a solution of 2-methylquinolin-8-ol (4.10 g, 25.76 mmol), PPh$_3$ (16.89 g, 64.39 mmol) and 1,3-dimethoxypropan-2-ol (4.02 g, 33.48 mmol) in THF (20 mL) was added DIAD (8.40 mL, 41.21 mmol) dropwise at ambient temperature. The reaction mixture was stirred at room temperature for two days. 4 N HCl (7.73 mL, 30.91 mmol in water), water (20 mL), and ethyl acetate (50 mL) were added. The aqueous layer was separated and washed with ethyl acetate. The aqueous layer was neutralized with ammonium hydroxide to about pH 9 and extracted with ethyl acetate (50 mL). The organic layer was separated, washed with brine, dried (sodium sulfate), filtered and concentrated under reduced pressure. The residue was purified by flash chromatography on silica gel (1:2 hexane/ethyl acetate) to give 8-(1,3-dimethoxypropan-2-yloxy)-2-methylquinoline (6.00 g, 89.15%) as an oil.

Step B: Preparation of (S)-1-((R)-1-(3-(8-(1,3-dimethoxypropan-2-yloxy)quinolin-2-yl)-[1,2,4]triazolo[4,3-a]pyridin-6-yl)-2,2,2-trifluoroethyl)pyrrolidin-3-amine dihydrochloride Prepared as described in Example 37, Steps A-C, using 8-(1,3-dimethoxypropan-2-yloxy)-2-methylquinoline in place of 8-ethyl-2-methylquinoline in Step B. LCMS APCI (+) m/z 531 (M+H).

Example 272

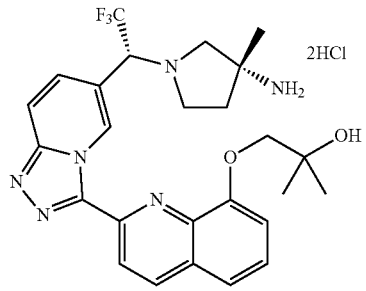 [SMILES: CC(C)(O)COc1cccc2ccc(-c3nnc4ccc([C@@H](N5CC[C@@](C)(N)C5)C(F)(F)F)cn34)nc12]

1-(2-(6-((R)-1-((R)-3-amino-3-methylpyrrolidin-1-yl)-2,2,2-trifluoroethyl)-[1,2,4]triazolo[4,3-a]pyridin-3-yl)quinolin-8-yloxy)-2-methylpropan-2-ol dihydrochloride Prepared as described in Example 9B, Steps A-G, using (R)-tert-butyl 3-methylpyrrolidin-3-ylcarbamate Preparation B) in place of (S)-tert-butyl pyrrolidin-3-ylcarbamate in Step D and using 8-(2-hydroxy-2-methylpropoxy)quinoline-2-carbaldehyde in place of 8-methoxyquinoline-2-carbaldehyde in Step F. MS APCI (+) m/z 515 (M+1) detected.

Example 273

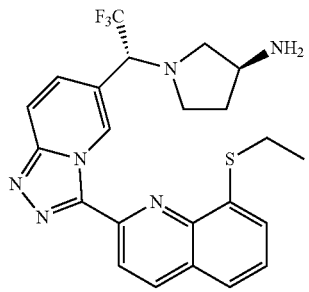 [SMILES: CCSc1cccc2ccc(-c3nnc4ccc([C@@H](N5CC[C@H](N)C5)C(F)(F)F)cn34)nc12]

(S)-1-((R)-1-(3-(8-(ethylthio)quinolin-2-yl)-[1,2,4]triazolo[4,3-a]pyridin-6-yl)-2,2,2-trifluoroethyl)pyrrolidin-3-amine hydrochloride Step A: Preparation of tert-butyl (S)-1-((R)-1-(3-(8-bromoquinolin-2-yl)-[1,2,4]triazolo[4,3-a]pyridin-6-yl)-2,2,2-trifluoroethyl)pyrrolidin-3-ylcarbamate Prepared as described in Example 9B, Steps A-G, using 8-bromoquinoline-2-carbaldehyde (WO 2010/022081) in place of 8-methoxyquinoline-2-carbaldehyde in Step F.

Step B: Preparation of tert-butyl (S)-1-((R)-1-(3-(8-(ethylthio)quinolin-2-yl)-[1,2,4]triazolo[4,3-a]pyridin-6-yl)-2,2,2-trifluoroethyl)pyrrolidin-3-ylcarbamate Pd$_2$dba$_3$.CHCl$_3$ (8.75 mg, 0.00845 mmol), (9,9-dimethyl-9H-xanthene-4,5-diyl)bis(diphenylphosphine) (9.78 mg, 0.0169 mmol), tert-butyl (S)-1-((R)-1-(3-(8-bromo quinolin-2-yl)-[1,2,4]triazolo[4,3-a]pyridin-6-yl)-2,2,2-trifluoroethyl)pyrrolidin-3-ylcarbamate (100 mg, 0.169 mmol), ethanethiol (31.5 mg, 0.507 mmol) and N-ethyl-N-isopropylpropan-2-amine (131 mg, 1.01 mmol) in dioxane were heated to 150° C. under microwave irradiation for 1 hour. After cooling, the reaction was concentrated under reduced pressure and purified by chromatography (SP4, 12M, eluting with a gradient of water/ACN 100:0 to 0:100, 30 column volumes) to yield tert-butyl (S)-1-((R)-1-(3-(8-(ethylthio)quinolin-2-yl)-[1,2,4]triazolo[4,3-a]pyridin-6-yl)-2,2,2-trifluoroethyl)pyrrolidin-3-ylcarbamate (60 mg, 62.0% yield)

Step C: Preparation of (S)-1-((R)-1-(3-(8-(ethylthio)quinolin-2-yl)-[1,2,4]triazolo[4,3-a]pyridin-6-yl)-2,2,2-trifluoroethyl)pyrrolidin-3-amine hydrochloride tert-butyl (S)-1-((R)-1-(3-(8-(ethylthio)quinolin-2-yl)-[1,2,4]triazolo[4,3-a]pyridin-6-yl)-2,2,2-trifluoroethyl)pyrrolidin-3-ylcarbamate (55 mg, 0.096 mmol) was stirred in TFA for 30 minutes. The reaction was concentrated to dryness, and the residue was diluted in 1 mL of methanol and added dropwise into 4N HCl in ether. The resulting precipitate was filtered and dried under vacuum to yield (S)-1-((R)-1-(3-(8-(ethylthio)quinolin-2-yl)-[1,2,4]triazolo[4,3-a]pyridin-6-yl)-2,2,2-trifluoroethyl)pyrrolidin-3-amine (16 mg, 35% yield) hydrochloride as a solid. LCMS APCI (+) m/z 473 (M+H).

Example 274

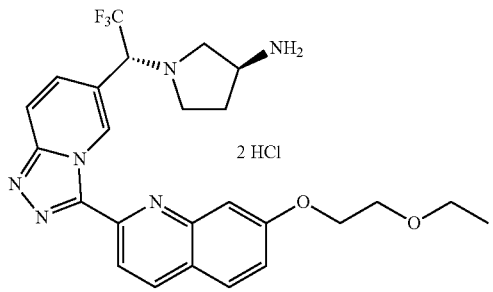 [SMILES: CCOCCOc1ccc2ccc(-c3nnc4ccc([C@@H](N5CC[C@H](N)C5)C(F)(F)F)cn34)nc2c1]

(S)-1-((R)-1-(3-(7-(2-ethoxyethoxy)quinolin-2-yl)-[1,2,4]triazolo[4,3-a]pyridin-6-yl)-2,2,2-trifluoroethyl)pyrrolidin-3-amine dihydrochloride Step A: Preparation of 7-(2-ethoxyethoxy)quinoline-2-carbaldehyde Prepared as described in Example 260, Step A to B, using 1-bromo-2-ethoxyethane in place of 1-bromo-2-methoxyethane in Step A.

Step B: Preparation of (S)-1-((R)-1-(3-(7-(2-ethoxyethoxy)quinolin-2-yl)-[1,2,4]triazolo[4,3-a]pyridin-6-yl)-2,2,2-trifluoroethyl)pyrrolidin-3-amine dihydrochloride Prepared as described in Example 9B, Steps F-G, using 7-(2-ethoxyethoxy)quinoline-2-carbaldehyde in place of 8-methoxyquinoline-2-carbaldehyde in Step F. LCMS APCI (+) m/z 501 (M+H).

Example 275

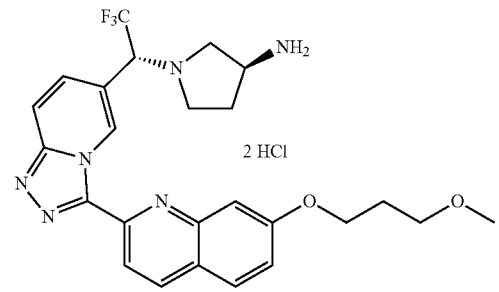

(S)-1-((R)-2,2,2-trifluoro-1-(3-(7-(3-methoxypropoxy)quinolin-2-yl)-[1,2,4]triazolo[4,3-a]pyridin-6-yl)ethyl)pyrrolidin-3-amine dihydrochloride Step A: Preparation of 7-(3-methoxypropoxy)quinoline-2-carbaldehyde Prepared as described in Example 260 Step A to B using 1-bromo-3-methoxypropane in place of 1-bromo-2-methoxyethane in Step A.

Step B: Preparation of S)-1-((R)-2,2,2-trifluoro-1-(3-(7-(3-methoxypropoxy)quinolin-2-yl)-[1,2,4]triazolo[4,3-a]pyridin-6-yl)ethyl)pyrrolidin-3-amine dihydrochloride Prepared as described in Example 9B, Steps F-G, using 7-(3-methoxypropoxy)quinoline-2-carbaldehyde in place of 8-methoxyquinoline-2-carbaldehyde in Step F. LCMS APCI (+) m/z 501 (M+H).

Example 276

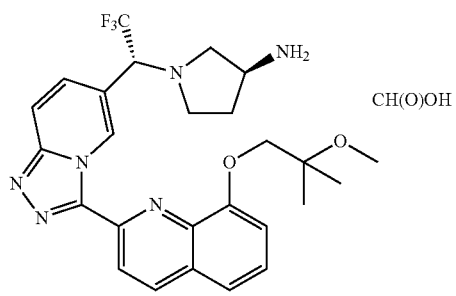

CH(O)OH (S)-1-((R)-2,2,2-trifluoro-1-(3-(8-(2-methoxy-2-methylpropoxy)quinolin-2-yl)-[1,2,4]triazolo[4,3-a]pyridin-6-yl)ethyl)pyrrolidin-3-amine formate

Step A: Preparation of 8-(2-methoxy-2-methylpropoxy)-2-methylquinoline

To a mixture of sodium hydride (60% in mineral oil; 0.013 g, 0.32 mmol) in anhydrous dimethylformamide (1.4 mL, 0.22 mmol) was added dropwise a solution of 2-methyl-1-(2-methylquinolin-8-yloxy)propan-2-ol (Example 259; 0.050 g, 0.22 mmol) in anhydrous dimethylformamide (1.4 mL, 0.22 mmol). The mixture was allowed to stir at ambient temperature for 30 minutes before by addition of iodomethane (0.054 mL, 0.86 mmol), and the resultant mixture allowed to stir at ambient temperature for 12 hours. The reaction mixture was poured into water (20 mL) and extracted with ethyl acetate (2×40 mL). The combined organic extracts were washed with brine, dried over sodium sulfate, filtered and concentrated under reduced pressure. The residue was purified by reverse phase chromatography on a C18 column (0-100% acetonitrile/water) providing the title compound (0.038 g, 73%).

Step B: Preparation of tert-butyl (S)-1-((R)-2,2,2-trifluoro-1-(3-(8-(2-methoxy-2-methylpropoxy)quinolin-2-yl)-[1,2,4]triazolo[4,3-a]pyridin-6-yl)ethyl)pyrrolidin-3-ylcarbamate Prepared according to the method of Example 140, Steps B-C, substituting 8-(2-methoxy-2-methylpropoxy)-2-methylquinoline for (R)-8-(1-methoxypropan-2-yloxy)-2-methylquinoline in Step B.

Step C: Preparation of (S)-1-((R)-2,2,2-trifluoro-1-(3-(8-(2-methoxy-2-methylpropoxy)quinolin-2-yl)-[1,2,4]triazolo[4,3-a]pyridin-6-yl)ethyl)pyrrolidin-3-amine formate Prepared according to the method of Example 192, Step B, substituting tert-butyl (S)-1-((R)-2,2,2-trifluoro-1-(3-(8-(2-methoxy-2-methylpropoxy)quinolin-2-yl)-[1,2,4]triazolo[4,3-a]pyridin-6-yl)ethyl)pyrrolidin-3-ylcarbamate for tert-Butyl (S)-1-((R)-2,2,2-trifluoro-1-(3-(8-((3-methyloxetan-3-yl)methoxy)quinolin-2-yl)-[1,2,4]triazolo[4,3-c]pyridin-6-yl)ethyl)pyrrolidin-3-ylcarbamate. FIA-MS APCI (+) m/z 515 (M+H).

Example 277

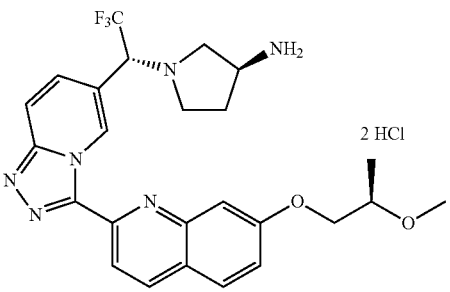 [SMILES: CO[C@H](C)COc1ccc2ccc(-c3nnc4ccc([C@@H](N5CC[C@H](N)C5)C(F)(F)F)cn34)nc2c1 ; "2 HCl"]

2 HCl (S)-1-((R)-2,2,2-trifluoro-1-(3-(7-((R)-2-methoxypropoxy)quinolin-2-yl)-[1,2,4]triazolo[4,3-a]pyridin-6-yl)ethyl)pyrrolidin-3-amine dihydrochloride

Step A: Preparation of (R)-1-(2-methylquinolin-7-yloxy)propan-2-ol

To a stirred mixture of 2-methylquinolin-7-ol (0.400 g, 2.51 mmol), $Cs_2CO_3$ (2.46 g, 7.54 mmol) and DMF (16 mL) was added (R)-2-methyloxirane (0.438 g, 7.54 mmol). The reaction mixture was heated at 80° C. for 2 hours. After cooling, the reaction mixture was partitioned between ether and water. The aqueous layer was extracted with ether. The combined organic layers were washed with water and brine, dried and concentrated under reduced pressure. The residue was purified by flash chromatography on silica gel (1% MeOH in EtOAc) to give (R)-1-(2-methylquinolin-7-yloxy)propan-2-ol (0.471 g, 86%).

Step B: Preparation of (R)-7-(2-methoxypropoxy)-2-methylquinoline

To a stirred suspension of NaH (60% dispersion in oil, 95 mg, 2.4 mmol) in DMF (8 mL) was added dropwise a solution of (R)-1-(2-methylquinolin-7-yloxy)propan-2-ol (344 mg, 1.58 mmol) in DMF (4 mL) at 0° C. under nitrogen. The reaction mixture was stirred at 0° C. for 30 minutes. MeI (0.198 mL, 3.17 mmol) was added dropwise. The reaction was stirred at ambient temperature overnight. The reaction mixture was partitioned between EtOAc and water. The aqueous layer was extracted with EtOAc. The combined organic layers were washed with water and brine, dried and concentrated under reduced pressure. The residue was purified by flash chromatography on silica gel (5:1 hexanes/EtOAc) to give (R)-7-(2-methoxypropoxy)-2-methylquinoline (185 mg, 51%).

Step C: Preparation of (R)-7-(2-methoxypropoxy)quinoline-2-carbaldehyde

Prepared as described in Example 5, Step B, using (R)-7-(2-methoxypropoxy)-2-methylquinoline in place of 8-(cyclopropylmethoxy)-2-methylquinoline.

Step D: Preparation of ((S)-1-((R)-2,2,2-trifluoro-1-(3-(7-((R)-2-methoxypropoxy)quinolin-2-yl)-[1,2,4]triazolo[4,3-a]pyridin-6-yl)ethyl)pyrrolidin-3-amine dihydrochloride Prepared as described in Example 9B, Steps F-G, using (R)-7-(2-methoxypropoxy)quinoline-2-carbaldehyde in place of 8-methoxyquinoline-2-carbaldehyde in Step F. LCMS APCI (+) m/z 501 (M+H).

Example 278

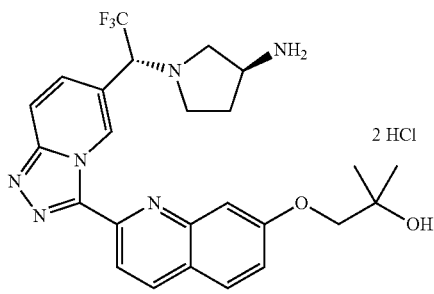 [SMILES: CC(C)(O)COc1ccc2ccc(-c3nnc4ccc([C@@H](N5CC[C@H](N)C5)C(F)(F)F)cn34)nc2c1 ; "2 HCl"]

1-(2-(6-((R)-1-((S)-3-aminopyrrolidin-1-yl)-2,2,2-trifluoroethyl)-[1,2,4]triazolo[4,3-a]pyridin-3-yl)quinolin-7-yloxy)-2-methylpropan-2-ol dihydrochloride Step A: Preparation of 2-methyl-1-(2-methylquinolin-7-yloxy)propan-2-ol Prepared as described in Example 277, Step A, using 2,2-dimethyloxirane in place of (R)-2-methyloxirane.

Step B: Preparation of 7-(2-hydroxy-2-methylpropoxy)quinoline-2-carbaldehyde

Prepared as described in Example 5, Step B, using 2-methyl-1-(2-methylquinolin-7-yloxy)propan-2-ol in place of 8-(cyclopropylmethoxy)-2-methylquinoline.

Step C: Preparation of 1-(2-(6-((R)-1-((S)-3-aminopyrrolidin-1-yl)-2,2,2-trifluoroethyl)-[1,2,4]triazolo[4,3-a]pyridin-3-yl)quinolin-7-yloxy)-2-methylpropan-2-ol dihydrochloride Prepared as described in Example 9B, Steps F-G, using 7-(2-hydroxy-2-methylpropoxy)quinoline-2-carbaldehyde in place of 8-methoxyquinoline-2-carbaldehyde in Step F. LCMS APCI (+) m/z 501 (M+H).

Example 279

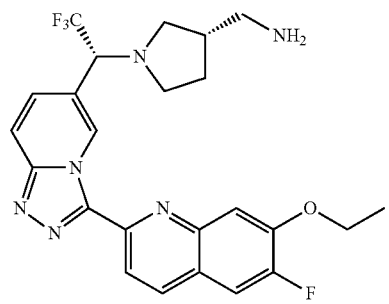 [SMILES: CCOc1cc2nc(-c3nnc4ccc([C@@H](N5CC[C@@H](CN)C5)C(F)(F)F)cn34)ccc2cc1F]

((S)-1-((R)-1-(3-(7-ethoxy-6-fluoroquinolin-2-yl)-[1,2,4]triazolo[4,3-a]pyridin-6-yl)-2,2,2-trifluoroethyl)pyrrolidin-3-yl)methanamine hydrochloride Prepared as in Example 133, replacing tert-butyl (S)-1-((R)-2,2,2-trifluoro-1-(6-hydrazinylpyridin-3-yl)ethyl)pyrrolidin-3-ylcarbamate in Step C with tert-butyl ((S)-1-((R)-2,2,2-trifluoro-1-(6-hydrazinylpyridin-3-yl)ethyl)pyrrolidin-3-yl)methylcarbamate. LCMS APCI (+) m/z 489 (M+H).

Example 280

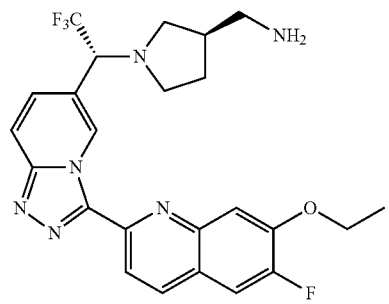 [SMILES: CCOc1cc2nc(-c3nnc4ccc([C@@H](N5CC[C@H](CN)C5)C(F)(F)F)cn34)ccc2cc1F]

((R)-1-((R)-1-(3-(7-ethoxy-6-fluoroquinolin-2-yl)-[1,2,4]triazolo[4,3-a]pyridin-6-yl)-2,2,2-trifluoroethyl)pyrrolidin-3-yl)methanamine hydrochloride Prepared as in Example 133, replacing tert-butyl (S)-1-((R)-2,2,2-trifluoro-1-(6-hydrazinylpyridin-3-yl)ethyl)pyrrolidin-3-ylcarbamate in Step C with tert-butyl ((R)-1-((R)-

2,2,2-trifluoro-1-(6-hydrazinylpyridin-3-yl)ethyl)pyrrolidin-3-yl)methylcarbamate. LCMS APCI (+) m/z 489 (M+H).

Example 281

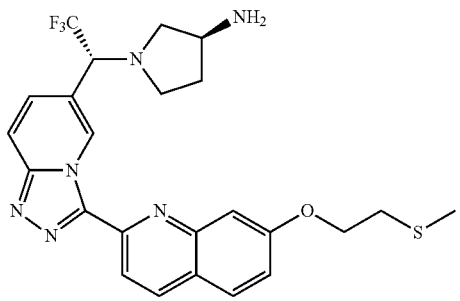 [SMILES: CSCCOc1ccc2ccc(-c3nnc4ccc([C@@H](N5CC[C@H](N)C5)C(F)(F)F)cn34)nc2c1]

(S)-1-((R)-2,2,2-trifluoro-1-(3-(7-(2-(methylthio)ethoxy)quinolin-2-yl)-[1,2,4]triazolo[4,3-a]pyridin-6-yl)ethyl)pyrrolidin-3-amine hydrochloride Prepared as in Example 275, substituting 1-bromo-3-methoxypropane in Step A with (2-chloroethyl)(methyl)sulfane. (LCMS APCI (+) m/z 489 (M+H). (LCMS APCI (+) m/z 489 (M+H).

Example 282

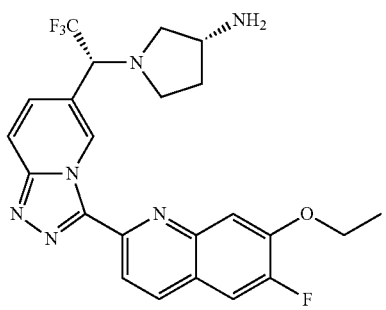 [SMILES: CCOc1cc2nc(-c3nnc4ccc([C@@H](N5CC[C@@H](N)C5)C(F)(F)F)cn34)ccc2cc1F]

(R)-1-((R)-1-(3-(7-ethoxy-6-fluoro quinolin-2-yl)-[1,2,4]triazolo[4,3-a]pyridin-6-yl)-2,2,2-trifluoroethyl)pyrrolidin-3-amine hydrochloride Prepared as in Example 133, replacing tert-butyl (S)-1-((R)-2,2,2-trifluoro-1-(6-hydrazinylpyridin-3-yl)ethyl)pyrrolidin-3-ylcarbamate in Step C with tert-butyl (R)-1-((R)-2, 2,2-trifluoro-1-(6-hydrazinylpyridin-3-yl)ethyl)pyrrolidin-3-ylcarbamate. (LCMS APCI (+) m/z 475 (M+H).

Example 283

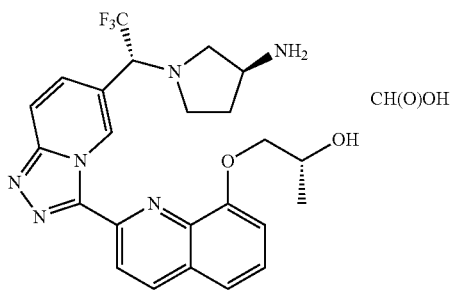

(R)-1-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)propan-2-ol formate Step A: Preparation of tert-butyl (S)-1-((R)-2,2,2-trifluoro-1-(3-(4-((R)-2-hydroxypropoxy)quinolin-2-yl)-[1,2,4]triazolo[4,3-a]pyridin-6-yl)ethyl)pyrrolidin-3-ylcarbamate Prepared according to the method of Example 187, substituting R-(+)-propylene oxide for S-(−)-propylene oxide.

Step B: Preparation of (S)-1-((R)-2,2,2-trifluoro-1-(3-(8-(2-methoxy-2-methylpropoxy)quinolin-2-yl)-[1,2,4]triazolo[4,3-a]pyridin-6-yl)ethyl)pyrrolidin-3-amine formate Prepared according to the method of Example 192, Step B, substituting tert-butyl (S)-1-((R)-2,2,2-trifluoro-1-(3-(4-((R)-2-hydroxypropoxy)quinolin-2-yl)-[1,2,4]triazolo[4,3-c]pyridin-6-yl)ethyl)pyrrolidin-3-ylcarbamate for tert-butyl (S)-1-((R)-2,2,2-trifluoro-1-(3-(8-((3-methyloxetan-3-yl)methoxy)quinolin-2-yl)-[1,2,4]triazolo[4,3-a]pyridin-6-yl)ethyl)pyrrolidin-3-ylcarbamate. FIA-MS APCI (+) m/z 487 (M+H).

Example 284

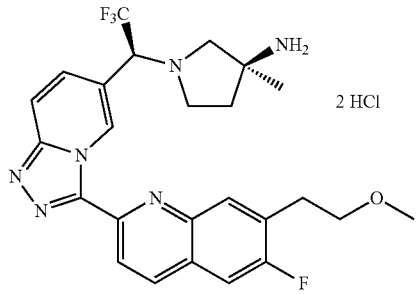 [SMILES: COCCc1cc2nc(-c3nnc4ccc([C@H](N5CC[C@](C)(N)C5)C(F)(F)F)cn34)ccc2cc1F ; "2 HCl"]

(S)-3-methyl-1-((S)-2,2,2-trifluoro-1-(3-(6-fluoro-7-(2-methoxyethyl)quinolin-2-yl)-[1,2,4]triazolo[4,3-a]pyridin-6-yl)ethyl)pyrrolidin-3-amine dihydrochloride Prepared as described in Example 9B, using dichloro{(R)-(+)-2,2'-bis[di(3,5-xylyl)-phosphino-1,1'-binaphthyl]}[(2R)-(−)-1,1-bis(4-methoxyphenyl)-3-methyl-1,2-butanediamine in place of dichloro{(S)-(−)-2,2'-bis[di(3,5-xylyl)-phosphino-1,1'-binaphthyl]}[(2S)-(+)-1,1-bis(4-methoxyphenyl)-3-methyl-1,2-butanediamine in Step B, substituting (S)-tert-butyl 3-methylpyrrolidin-3-ylcarbamate for (S)-tert-butyl pyrrolidin-3-ylcarbamate in Step D, and substituting 6-fluoro-7-(2-methoxyethyl)quinoline-2-carbaldehyde in place of 8-methoxyquinoline-2-carbaldehyde in Step F. LCMS APCI (+) m/z 503 (M+H).

Example 285

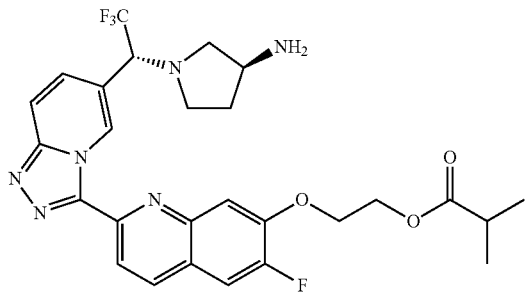 [SMILES: CC(C)C(=O)OCCOc1cc2nc(-c3nnc4ccc([C@@H](N5CC[C@H](N)C5)C(F)(F)F)cn34)ccc2cc1F]

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)ethyl isobutyrate Step A: Preparation of 7-(2-(tert-butyldimethylsilyloxy)ethoxy)-6-fluoro-2-methylquinoline To a stirred mixture of 2-methylquinolin-7-ol (1.54 g, 8.69 mmol), $Cs_2CO_3$ (8.50 g, 26.1 mmol) and NMP (43 mL) was added (2-bromoethoxy)(tert-butyl)dimethylsilane (6.24 g, 26.1 mmol). The reaction mixture was stirred at ambient temperature overnight. The reaction was partitioned between ether and water. The aqueous layer was extracted with ether. The combined organic layers were washed with water and brine, dried and concentrated under reduced pressure. The residue was purified by flash chromatography on silica gel (2:1 hexanes/EtOAc) to give 7-(2-(tert-butyldimethylsilyloxy)ethoxy)-6-fluoro-2-methylquinoline (2.75 g, 94%).

Step B: Preparation of 7-(2-(tert-butyldimethylsilyloxy)ethoxy)-6-fluoroquinoline-2-carbaldehyde To a solution of 7-(2-(tert-butyldimethylsilyloxy)ethoxy)-6-fluoro-2-methylquinoline (2.74 g, 8.17 mmol) in dioxane (24 mL) and water (0.24 mL) was added $SeO_2$ (0.997 g, 8.98 mmol). The reaction mixture was heated at reflux for 4 hours. After cooling to ambient temperature, the solid was removed by filtration and washed with DCM. The filtrate was concentrated under reduced pressure and The residue was purified by flash chromatography on silica gel (4:1 hexanes/EtOAc) to give 7-(2-(tert-butyldimethylsilyloxy)ethoxy)-6-fluoroquinoline-2-carbaldehyde (2.69 g, 94%).

Step C: Preparation of tert-butyl (S)-3-methyl-1-((S)-2,2,2-trifluoro-1-(3-(7-(2-methoxyethoxy)quinolin-2-yl)-[1,2,4]triazolo[4,3-a]pyridin-6-yl)ethyl)pyrrolidin-3-ylcarbamate A mixture of tert-butyl (S)-3-methyl-1-((S)-2,2,2-trifluoro-1-(6-hydrazinylpyridin-3-yl)ethyl)pyrrolidin-3-ylcarbamate (1.50 g, 4.01 mmol), 7-(2-(tert-butyldimethylsilyloxy)ethoxy)-6-fluoroquinoline-2-carbaldehyde (1.40 g, 4.01 mmol) and EtOH (30 mL) was stirred at ambient temperature overnight. The solvent was removed under reduced pressure. The residue was dissolved in DCM (30 mL) and iodobenzene diacetate (1.68 g, 5.21 mmol) was added. The reaction mixture was stirred at ambient temperature overnight. The mixture was partitioned between EtOAc and saturated aqueous $NaHCO_3$ solution. The aqueous layer was extracted with EtOAc. The combined organic layers were washed with brine, dried and concentrated under reduced pressure. The residue was purified by flash chromatography on silica gel (EtOAc) to give tert-butyl (S)-3-methyl-1-((S)-2,2,2-trifluoro-1-(3-(7-(2-methoxyethoxy)quinolin-2-yl)-[1,2,4]triazolo[4,3-a]pyridin-6-yl)ethyl)pyrrolidin-3-ylcarbamate (1.45 g, 51%).

Step D: Preparation of tert-butyl (S)-1-((R)-2,2,2-trifluoro-1-(3-(6-fluoro-7-(2-hydroxyethoxy)quinolin-2-yl)-[1,2,4]triazolo[4,3-a]pyridin-6-yl)ethyl)pyrrolidin-3-ylcarbamate To a stirred solution of tert-butyl (S)-3-methyl-1-((S)-2,2,2-trifluoro-1-(3-(7-(2-methoxyethoxy)quinolin-2-yl)-[1,2,4]triazolo[4,3-a]pyridin-6-yl)ethyl)pyrrolidin-3-ylcarbamate (1.37 g, 1.94 mmol) in THF (100 mL) was added tetrabutylammonium fluoride trihydrate (1.84 g, 5.83 mmol). The reaction mixture was stirred at ambient temperature for 2 hours. The mixture was partitioned between saturated aqueous $NH_4Cl$ solution and EtOAc. The aqueous layer was extracted with EtOAc. The combined organic layers were washed with water and brine, dried and concentrated under reduced pressure. The residue was purified by flash chromatography on silica gel (3% MeOH in EtOAc) to give tert-butyl (S)-1-((R)-2,2,2-trifluoro-1-(3-(6-fluoro-7-(2-hydroxyethoxy)quinolin-2-yl)-[1,2,4]triazolo[4,3-a]pyridin-6-yl)ethyl)pyrrolidin-3-ylcarbamate (1.01 g, 88%) as a white solid.

Step E: Preparation of 2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)-6-fluoroquinolin-7-yloxy)ethyl isobutyrate To a stirred solution of tert-butyl (S)-1-((R)-2,2,2-trifluoro-1-(3-(6-fluoro-7-(2-hydroxyethoxy)quinolin-2-yl)-[1,2,4]triazolo[4,3-a]pyridin-6-yl)ethyl)pyrrolidin-3-ylcarbamate (80 mg, 0.14 mmol) in DCM (1 mL) and $Et_3N$ (0.057 mL, 0.41 mmol) was added dropwise isobutyryl chloride (0.036 mL, 0.34 mmol) at 0° C. under nitrogen. The reaction mixture was warmed to ambient temperature and stirred overnight. The reaction mixture was diluted with DCM, washed with saturated aqueous $NaHCO_3$ solution and brine, dried and concentrated under reduced pressure. The residue was purified by reverse phase preparative HPLC (5-95% acetonitrile/water) to give 2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)-6-fluoroquinolin-7-yloxy)ethyl isobutyrate (75 mg, 84%).

Step F: Preparation of 2-(2-(6-((R)-1-((S)-3-aminopyrrolidin-1-yl)-2,2,2-trifluoroethyl)-[1,2,4]triazolo[4,3-a]pyridin-3-yl)-6-fluoro quinolin-7-yloxy)ethyl isobutyrate A mixture of 2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)-6-fluoro quinolin-7-yloxy)ethyl isobutyrate (75 mg, 0.11 mmol), DCM (1 mL) and 4N HCl in dioxane (0.3 mL) was stirred at ambient temperature for 3 hours. The solvents were removed under reduced pressure. The residue was purified by reverse phase preparative HPLC (5-95% acetonitrile/water) to give the product as the bis-TFA salt. The combined fractions were basified by saturated aqueous NaHCO₃ solution and extracted with EtOAc. The organic layers were washed with brine, dried and concentrated under reduced pressure to give 2-(2-(6-((R)-1-((S)-3-aminopyrrolidin-1-yl)-2,2,2-trifluoroethyl)-[1,2,4]triazolo[4,3-a]pyridin-3-yl)-6-fluoro quinolin-7-yloxy)ethyl isobutyrate (49 mg, 77%) as a white solid. LCMS APCI (+) m/z 561 (M+H).

Example 286

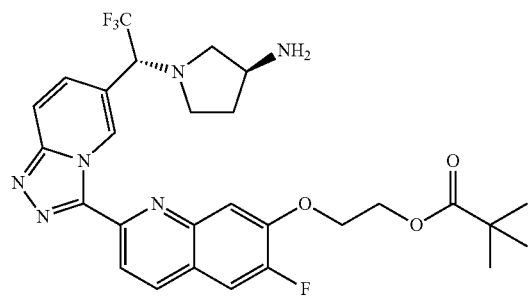 [SMILES: CC(C)(C)C(=O)OCCOc1cc2nc(-c3nnc4ccc([C@@H](N5CC[C@H](N)C5)C(F)(F)F)cn34)ccc2cc1F]

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)ethyl pivalate

Step A: Preparation of 2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)-6-fluoroquinolin-7-yloxy)ethyl isobutyrate To a stirred solution of tert-butyl (S)-1-((R)-2,2,2-trifluoro-1-(3-(6-fluoro-7-(2-hydroxyethoxy)quinolin-2-yl)-[1,2,4]triazolo[4,3-a]pyridin-6-yl)ethyl)pyrrolidin-3-ylcarbamate (Example 123, Step A; 100 mg, 0.169 mmol) and DMAP (21 mg, 0.17 mmol) in pyridine (1 mL) was added dropwise pivalic anhydride (0.063 mL, 0.34 mmol) at 0° C. under nitrogen. The reaction mixture was warmed to ambient temperature and heated at 60° C. for 3 hours. After cooling, the solvent was evaporated under reduced pressure. The residue was taken up in EtOAc, washed with saturated aqueous NaHCO₃ solution and brine, dried and concentrated under reduced pressure. The residue was purified by reverse phase preparative HPLC (5-95% acetonitrile/water) to give 2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)-6-fluoroquinolin-7-yloxy)ethyl isobutyrate (92 mg, 81%).

Step B: Preparation of 2-(2-(6-((R)-1-((S)-3-aminopyrrolidin-1-yl)-2,2,2-trifluoroethyl)-[1,2,4]triazolo[4,3-a]pyridin-3-yl)-6-fluoro quinolin-7-yloxy)ethyl pivalate A mixture of 2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)-6-fluoro quinolin-7-yloxy)ethyl isobutyrate (92 mg, 0.14 mmol), DCM (1 mL) and 4N HCl in dioxane (0.3 mL) was stirred at ambient temperature for 3 hours. The solvents were removed under reduced pressure. The residue was purified by reverse phase preparative HPLC (5-95% acetonitrile/water) to give the product as the bis-TFA salt. The combined fractions were basified by saturated aqueous NaHCO₃ solution and extracted with EtOAc. The organic layers were washed with brine, dried and concentrated under reduced pressure to give 2-(2-(6-((R)-1-((S)-3-aminopyrrolidin-1-yl)-2,2,2-trifluoroethyl)-[1,2,4]triazolo[4,3-a]pyridin-3-yl)-6-fluoro quinolin-7-yloxy)ethyl pivalate (66 mg, 84%) as a white solid. LCMS APCI (+) m/z 575 (M+H).

Example 287

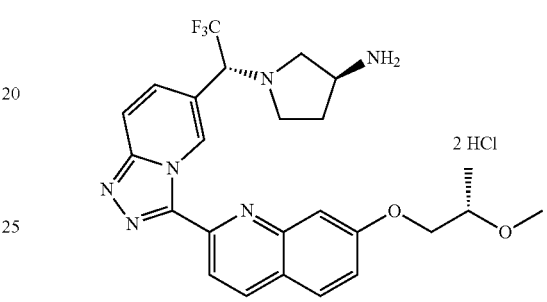

(S)-1-((R)-2,2,2-trifluoro-1-(3-(7-((S)-2-methoxypropoxy)quinolin-2-yl)-[1,2,4]triazolo[4,3-a]pyridin-6-yl)ethyl)pyrrolidin-3-amine dihydrochloride

Step A: Preparation of (S)-7-(2-methoxypropoxy)-2-methylquinoline

To a stirred solution of 2-methylquinolin-7-ol (1.00 g, 6.28 mmol), PPh₃ (4.12 g, 15.7 mmol) and (S)-2-methoxypropan-1-ol (0.679 g, 7.54 mmol) in THF (60 mL) was added dropwise diisopropyl azodicarboxylate (2.05 mL, 10.1 mmol) at 0° C. under nitrogen. The reaction mixture was stirred at ambient temperature overnight. The reaction was then heated at 50° C. for additional 2 hours. After cooling, to the reaction were added 4N HCl (3.1 mL), water (100 mL) and EtOAc (200 mL). The aqueous layer was separated and washed with EtOAc (100 mL). The aqueous was neutralized with ammonium hydroxide to about pH 9, extracted with EtOAc, washed with brine, dried and concentrated under reduced pressure. The residue was purified by flash chromatography on silica gel (1:1 hexane/EtOAc) to give (S)-7-(2-methoxypropoxy)-2-methylquinoline (0.738 g, 51%).

Step B: Preparation of (S)-7-(2-methoxypropoxy)quinoline-2-carbaldehyde

Prepared as described in Example 5, Step B, using (S)-7-(2-methoxypropoxy)-2-methylquinoline in place of 8-(cyclopropylmethoxy)-2-methylquinoline.

Step C: Preparation of (S)-1-((R)-2,2,2-trifluoro-1-(3-(7-((S)-2-methoxypropoxy)quinolin-2-yl)-[1,2,4]triazolo[4,3-a]pyridin-6-yl)ethyl)pyrrolidin-3-amine dihydrochloride Prepared as described in Example 9B, Steps F-G, using (S)-7-(2-methoxypropoxy)quinoline-2-carbaldehyde in place of 8-methoxyquinoline-2-carbaldehyde in Step F. LCMS APCI (+) m/z 501 (M+H).

Example 288

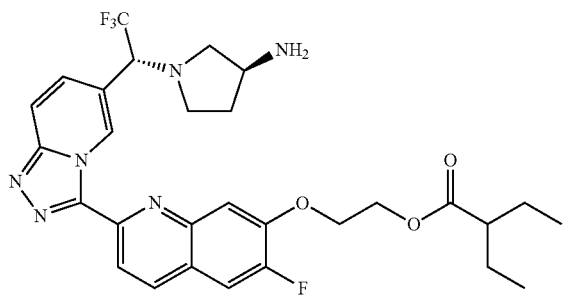 [SMILES: CCC(CC)C(=O)OCCOc1cc2nc(-c3nnc4ccc([C@@H](N5CC[C@H](N)C5)C(F)(F)F)cn34)ccc2cc1F]

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)ethyl 2-ethylbutanoate Prepared as described in Example 286 using 2-ethylbutanoyl chloride in place of pivalic anhydride in Step A. LCMS APCI (+) m/z 589 (M+H).

Example 289

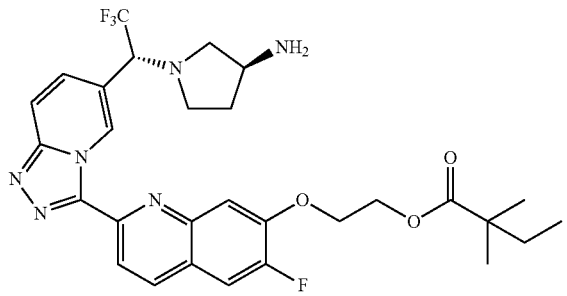 [SMILES: CCC(C)(C)C(=O)OCCOc1cc2nc(-c3nnc4ccc([C@@H](N5CC[C@H](N)C5)C(F)(F)F)cn34)ccc2cc1F]

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)ethyl 2,2-dimethylbutanoate Prepared as described in Example 286 using dimethylbutanoyl chloride in place of pivalic anhydride in Step A. LCMS APCI (+) m/z 589 (M+H).

Example 290

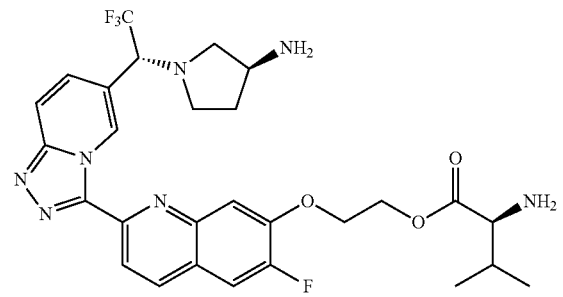 [SMILES: CC(C)[C@H](N)C(=O)OCCOc1cc2nc(-c3nnc4ccc([C@@H](N5CC[C@H](N)C5)C(F)(F)F)cn34)ccc2cc1F]

(S)-2-(2-(6-((R)-1-((S)-3-aminopyrrolidin-1-yl)-2,2,2-trifluoroethyl)-[1,2,4]triazolo[4,3-a]pyridin-3-yl)-6-fluoro quinolin-7-yloxy)ethyl 2-amino-3-methylbutanoate Step A: Preparation of (S)-2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)-6-fluoroquinolin-7-yloxy)ethyl 2-(tert-butoxycarbonylamino)-3-methylbutanoate To a stirred solution of tert-butyl (S)-1-((R)-2,2,2-trifluoro-1-(3-(6-fluoro-7-(2-hydroxyethoxy)quinolin-2-yl)-[1,2,4]triazolo[4,3-a]pyridin-6-yl)ethyl)pyrrolidin-3-ylcarbamate (Example 123, Step A; 100 mg, 0.169 mmol) and (S)-2-(tert-butoxycarbonylamino)-3-methylbutanoic acid (44.1 mg, 0.203 mmol) in DCM (2 mL) was added DMAP (41.4 mg, 0.339 mmol) and DCC (41.9 mg, 0.203 mmol) under nitrogen. The reaction mixture was stirred at ambient temperature for 4 hours and then poured into water. The mixture was extracted with DCM. The combined organic layers were washed with saturated aqueous NaHCO₃ solution and brine, dried, and concentrated under reduced pressure. The residue was purified by reverse phase preparative HPLC (5-95% acetonitrile/water) to give (S)-2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)-6-fluoro quinolin-7-yloxy)ethyl 2-(tert-butoxycarbonylamino)-3-methylbutanoate (110 mg, 82%).

Step B: Preparation of (S)-2-(2-(6-((R)-1-((S)-3-aminopyrrolidin-1-yl)-2,2,2-trifluoroethyl)-[1,2,4]triazolo[4,3-a]pyridin-3-yl)-6-fluoro quinolin-7-yloxy)ethyl 2-amino-3-methylbutanoate Prepared as described in Example 286, Step B, using (S)-2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)-6-fluoro quinolin-7-yloxy)ethyl 2-(tert-butoxycarbonylamino)-3-methylbutanoate in place of 2-(2-(6-((R)-1-((S)-3-(tert-butoxycarbonylamino)pyrrolidin-1-yl)-2,2,2-trifluoroethyl)-[1,2,4]triazolo[4,3-a]pyridin-3-yl)-6-fluoro quinolin-7-yloxy)ethyl isobutyrate in Step B. LCMS APCI (+) m/z 590 (M+H).

Example 291

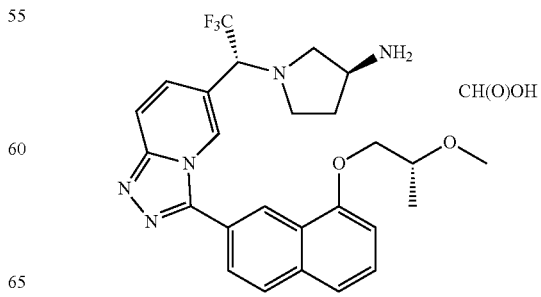

(S)-1-((R)-2,2,2-trifluoro-1-(3-(4-((R)-2-methoxypropoxy)quinolin-2-yl)-[1,2,4]triazolo[4,3-a]pyridin-6-yl)ethyl)pyrrolidin-3-amine formate Step A: Preparation of (R)-1-(2-methylquinolin-8-yloxy)propan-2-ol Prepared according to the method of Example 187, Step A, substituting R-(+)-propylene oxide for S-(−)-propylene oxide.

Step B: Preparation of (R)-8-(2-methoxypropoxy)-2-methylquinoline

Prepared according to the method of Example 276, Step A, substituting (R)-1-(2-methylquinolin-8-yloxy)propan-2-ol for 2-methyl-1-(2-methylquinolin-8-yloxy)propan-2-ol.

Step C: Preparation of tert-butyl (S)-1-((R)-2,2,2-trifluoro-1-(3-(4-((R)-2-methoxypropoxy)quinolin-2-yl)-[1,2,4]triazolo[4,3-a]pyridin-6-yl)ethyl)pyrrolidin-3-ylcarbamate Prepared according to the method of Example 140, Steps B-C, substituting (R)-8-(2-methoxypropoxy)-2-methylquinoline for (R)-8-(1-methoxypropan-2-yloxy)-2-methylquinoline in Step B.

Step D: Preparation of (S)-1-((R)-2,2,2-trifluoro-1-(3-(4-((R)-2-methoxypropoxy)quinolin-2-yl)-[1,2,4]triazolo[4,3-a]pyridin-6-yl)ethyl)pyrrolidin-3-amine formate Prepared according to the method of Example 192, Step B, substituting tert-butyl (S)-1-((R)-2,2,2-trifluoro-1-(3-(4-((R)-2-methoxypropoxy)quinolin-2-yl)-[1,2,4]triazolo[4,3-c]pyridin-6-yl)ethyl)pyrrolidin-3-ylcarbamate for tert-Butyl (S)-1-((R)-2,2,2-trifluoro-1-(3-(8-((3-methyloxetan-3-yl)methoxy)quinolin-2-yl)-[1,2,4]triazolo[4,3-a]pyridin-6-yl)ethyl)pyrrolidin-3-ylcarbamate. FIA-MS APCI (+) m/z 501 (M+H).

Example 292

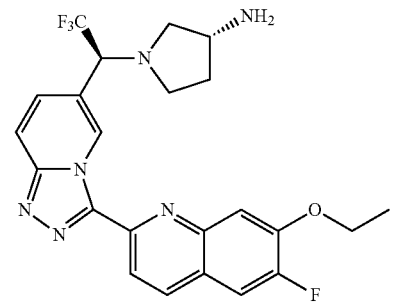 [SMILES: CCOc1cc2nc(-c3nnc4ccc([C@H](N5CC[C@@H](N)C5)C(F)(F)F)cn34)ccc2cc1F]

(R)-1-((S)-1-(3-(7-ethoxy-6-fluoro quinolin-2-yl)-[1,2,4]triazolo[4,3-a]pyridin-6-yl)-2,2,2-trifluoroethyl)pyrrolidin-3-amine hydrochloride Prepared as in Example 133 replacing tert-butyl (S)-1-((R)-2,2,2-trifluoro-1-(6-hydrazinylpyridin-3-yl)ethyl)pyrrolidin-3-ylcarbamate in step C with tert-butyl (R)-1-((S)-2,2,2-trifluoro-1-(6-hydrazinylpyridin-3-yl)ethyl)pyrrolidin-3-ylcarbamate. (LCMS APCI (+) m/z 475 (M+H).

Example 293

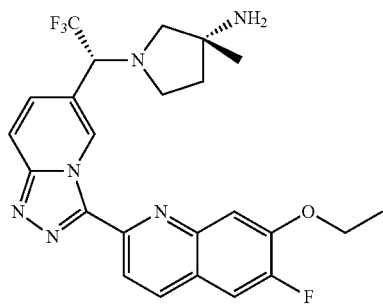 [SMILES: CCOc1cc2nc(-c3nnc4ccc([C@@H](N5CC[C@@](C)(N)C5)C(F)(F)F)cn34)ccc2cc1F]

(R)-1-((R)-1-(3-(7-ethoxy-6-fluoroquinolin-2-yl)-[1,2,4]triazolo[4,3-a]pyridin-6-yl)-2,2,2-trifluoroethyl)-3-methylpyrrolidin-3-amine hydrochloride Prepared as in Example 133 replacing tert-butyl (S)-1-((R)-2,2,2-trifluoro-1-(6-hydrazinylpyridin-3-yl)ethyl)pyrrolidin-3-ylcarbamate in step C with tert-butyl (R)-3-methyl-1-((R)-2,2,2-trifluoro-1-(6-hydrazinylpyridin-3-yl)ethyl)pyrrolidin-3-ylcarbamate. (LCMS APCI (+) m/z 489 (M+H).

Example 294

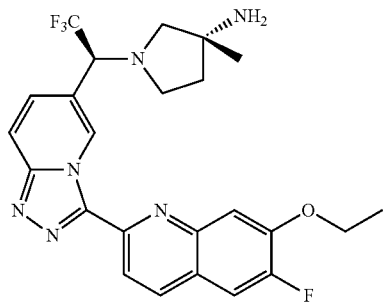 [SMILES: CCOc1cc2nc(-c3nnc4ccc([C@H](N5CC[C@@](C)(N)C5)C(F)(F)F)cn34)ccc2cc1F]

(R)-1-((S)-1-(3-(7-ethoxy-6-fluoroquinolin-2-yl)-[1,2,4]triazolo[4,3-a]pyridin-6-yl)-2,2,2-trifluoroethyl)-3-methylpyrrolidin-3-amine hydrochloride Prepared as in Example 133 replacing tert-butyl (S)-1-((R)-2,2,2-trifluoro-1-(6-hydrazinylpyridin-3-yl)ethyl)pyrrolidin-3-ylcarbamate in step C with tert-butyl (R)-3-methyl- 1-((S)-2,2,2-trifluoro-1-(6-hydrazinylpyridin-3-yl)ethyl)pyrrolidin-3-ylcarbamate. (LCMS APCI (+) m/z 489 (M+H).

Example 295

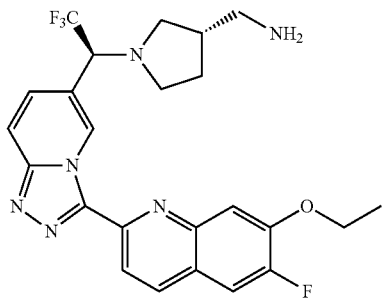 [SMILES: CCOc1cc2nc(-c3nnc4ccc([C@H](N5CC[C@@H](CN)C5)C(F)(F)F)cn34)ccc2cc1F]

((S)-1-((S)-1-(3-(7-ethoxy-6-fluoroquinolin-2-yl)-[1,2,4]triazolo[4,3-a]pyridin-6-yl)-2,2,2-trifluoroethyl)pyrrolidin-3-yl)methanamine hydrochloride Prepared as in Example 133 replacing tert-butyl (S)-1-((R)-2,2,2-trifluoro-1-(6-hydrazinylpyridin-3-yl)ethyl)pyrrolidin-3-ylcarbamate in step C with tert-butyl ((S)-1-((S)-2,2,2-trifluoro-1-(6-hydrazinylpyridin-3-yl)ethyl)pyrrolidin-3-yl)methylcarbamate (Prepared as described in Example 1, Steps A-F, using (R)-tert-butyl pyrrolidin-3-ylmethylcarbamate in place of (S)-tert-butyl pyrrolidin-3-ylcarbamate in Step C). (LCMS APCI (+) m/z 489 (M+H).

Example 296

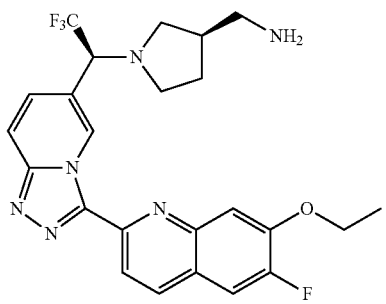 [SMILES: CCOc1cc2nc(-c3nnc4ccc([C@H](N5CC[C@H](CN)C5)C(F)(F)F)cn34)ccc2cc1F]

((R)-1-((S)-1-(3-(7-ethoxy-6-fluoroquinolin-2-yl)-[1,2,4]triazolo[4,3-a]pyridin-6-yl)-2,2,2-trifluoroethyl)pyrrolidin-3-yl)methanamine hydrochloride Prepared as in Example 133 replacing tert-butyl (S)-1-((R)-2,2,2-trifluoro-1-(6-hydrazinylpyridin-3-yl)ethyl)pyrrolidin-3-ylcarbamate in step C with tert-butyl ((R)-1-((S)-2,2,2-trifluoro-1-(6-hydrazinylpyridin-3-yl)ethyl)pyrrolidin-3-yl)methylcarbamate (Prepared as described in Example 1, Steps A-F, using (S)-tert-butyl pyrrolidin-3-ylmethylcarbamate in place of (S)-tert-butyl pyrrolidin-3-ylcarbamate in Step C. (LCMS APCI (+) m/z 489 (M+H).

Example 297

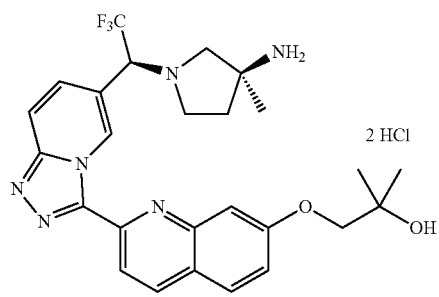 [SMILES: CC(C)(O)COc1ccc2ccc(-c3nnc4ccc([C@H](N5CC[C@](C)(N)C5)C(F)(F)F)cn34)nc2c1]

1-(2-(6-((S)-1-((S)-3-amino-3-methylpyrrolidin-1-yl)-2,2,2-trifluoroethyl)-[1,2,4]triazolo[4,3-a]pyridin-3-yl)quinolin-7-yloxy)-2-methylpropan-2-ol dihydrochloride Prepared as described in Example 260, Steps C-D, using 7-(2-hydroxy-2-methylpropoxy)quinoline-2-carbaldehyde in place of 7-(2-methoxyethoxy)quinoline-2-carbaldehyde in Step C. LCMS APCI (+) m/z 515 (M+H).

Example 298

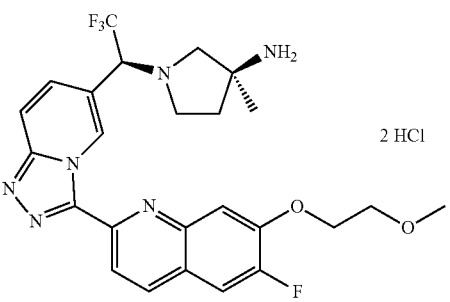 [SMILES: COCCOc1cc2nc(-c3nnc4ccc([C@H](N5CC[C@](C)(N)C5)C(F)(F)F)cn34)ccc2cc1F]

(S)-3-methyl-1-((S)-2,2,2-trifluoro-1-(3-(6-fluoro-7-(2-methoxyethoxy)quinolin-2-yl)-[1,2,4]triazolo[4,3-a]pyridin-6-yl)ethyl)pyrrolidin-3-amine dihydrochloride Prepared as described in Example 260, Steps C-D, using 6-fluoro-7-(2-methoxyethoxy)quinoline-2-carbaldehyde in place of 7-(2-methoxyethoxy)quinoline-2-carbaldehyde in Step C. LCMS APCI (+) m/z 519 (M+H).

Example 299

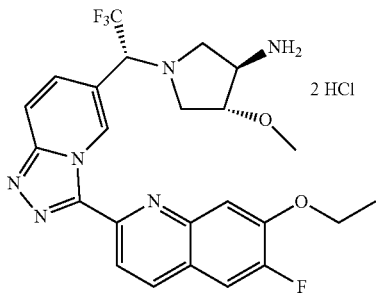 [SMILES: CCOc1cc2nc(-c3nnc4ccc([C@@H](N5C[C@@H](N)[C@H](OC)C5)C(F)(F)F)cn34)ccc2cc1F]

(3R,4R)-1-((R)-1-(3-(7-ethoxy-6-fluoro quinolin-2-yl)-[1,2,4]triazolo[4,3-a]pyridin-6-yl)-2,2,2-trifluoroethyl)-4-methoxypyrrolidin-3-amine dihydrochloride Step A: Preparation of (3R,4R)-tert-butyl 3-azido-4-methoxypyrrolidine-1-carboxylate To a solution of (3R,4R)-tert-butyl 3-azido-4-hydroxypyrrolidine-1-carboxylate (2.00 g, 8.76 mmol) and MeI (1.64 mL, 26.3 mmol) in DMF (20 mL) was added 60% NaH (0.701 g, 17.5 mmol) at 0° C. The mixture was warmed to ambient temperature and stirred at ambient temperature for 1 hour. Water (20 mL) and ether (40 mL) were added. The organic layer was separated, washed with brine, dried (sodium sulfate), filtered and concentrated under reduced pressure. The residue was purified by flash chromatography on silica gel (3:1 hexane/ethyl acetate) to give (3R,4R)-tert-butyl 3-azido-4-methoxypyrrolidine-1-carboxylate (2.04 g, 96.1%) as thick oil.

Step B: Preparation of (3R,4R)-tert-butyl 3-(benzyloxycarbonylamino)-4-methoxypyrrolidine-1-carboxylate A mixture of (3R,4R)-tert-butyl 3-azido-4-methoxypyrrolidine-1-carboxylate (2.04 g, 8.420 mmol) and PtO$_2$ (0.096 g, 0.42 mmol) in MeOH (100 mL) was charged with hydrogen (1 atmosphere) and stirred at ambient temperature for 2 days. Charcoal (2 g) was added to the solution and. The catalyst was removed by filtration and washed with MeOH (20 mL). The solvent was removed and dried to give (3R,4R)-tert-butyl 3-amino-4-methoxypyrrolidine-1-carboxylate. It was dissolved in dioxane (10 mL) and water (10 mL). Na$_2$CO$_3$ (1.34 g, 12.63 mmol) was added, followed by Cbz-Cl (1.87 mL, 12.63 mmol) at ambient temperature. The reaction mixture was stirred at ambient temperature for 3 hours. Ethyl acetate (50 ml) was added. The organic layer was separated, washed with brine, dried (sodium sulfate), filtered and concentrated under reduced pressure. The residue obtained was purified by flash chromatography on silica gel (1:1 hexane/ethyl acetate) to give (3R,4R)-tert-butyl 3-(benzyloxycarbonylamino)-4-methoxypyrrolidine-1-carboxylate (2.90 g, 98.3% yield) as oil.

Step C: Preparation of benzyl benzyl (3R,4R)-4-methoxypyrrolidin-3-ylcarbamate

To a solution of (3R,4R)-tert-butyl 3-(benzyloxycarbonylamino)-4-methoxypyrrolidine-1-carboxylate (2.90 g, 8.28 mmol) in DCM (20 mL) was added 4 N HCl (20.69 mL, 82.76 mmol) in dioxane. The reaction mixture was stirred at ambient temperature for 2 hours. The solvent was removed under reduced pressure. Saturated bicarbonate (20 mL) and DCM (50 mL) were added. The organic layer was separated, dried (sodium sulfate), filtered and concentrated under reduced pressure to give benzyl (3R,4R)-4-methoxypyrrolidin-3-ylcarbamate (2.0 g, 96.6%) as oil.

Step D: Preparation of benzyl tert-butyl (3R,4R)-1-((R)-1-(6-chloropyridin-3-yl)-2,2,2-trifluoroethyl)-4-methoxypyrrolidin-3-ylcarbamate Prepared as described in Example 145, Steps C-D, using tert-butyl (3R,4R)-4-methoxypyrrolidin-3-ylcarbamate in place of benzyl (3R,4R)-4-hydroxypyrrolidin-3-ylcarbamate in Step C.

Step E: Preparation of (3R,4R)-1-((R)-1-(3-(7-ethoxy-6-fluoro quinolin-2-yl)-[1,2,4]triazolo[4,3-a]pyridin-6-yl)-2,2,2-trifluoroethyl)-4-methoxypyrrolidin-3-amine dihydrochloride Prepared as described in Example 9B, Steps E-G, using tert-butyl (3R,4R)-1-((R)-1-(6-chloropyridin-3-yl)-2,2,2-trifluoroethyl)-4-methoxypyrrolidin-3-ylcarbamate in place of tert-butyl (S)-1-((R)-1-(6-chloropyridin-3-yl)-2,2,2-trifluoroethyl)pyrrolidin-3-ylcarbamate in Step E, and substituting 7-ethoxy-6-fluoroquinoline-2-carbaldehyde for 8-methoxyquinoline-2-carbaldehyde in Step F. LCMS APCI (+) m/z 505 (M+H).

Example 300

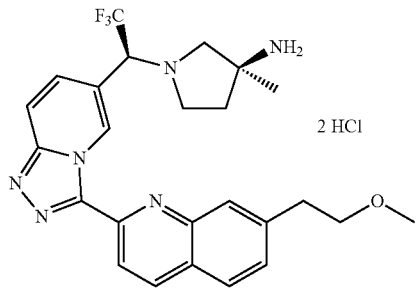 [SMILES: COCCc1ccc2ccc(-c3nnc4ccc([C@H](N5CC[C@](C)(N)C5)C(F)(F)F)cn34)nc2c1]

(S)-3-methyl-1-((S)-2,2,2-trifluoro-1-(3-(7-(2-methoxyethyl)quinolin-2-yl)-[1,2,4]triazolo[4,3-a]pyridin-6-yl)ethyl)pyrrolidin-3-amine dihydrochloride Prepared as described in Example 9B, using (R)-1-(6-chloropyridin-3-yl)-2,2,2-trifluoroethanol in place of (S)-1-(6-chloropyridin-3-yl)-2,2,2-trifluoroethanol in Step C, substituting (S)-tert-butyl 3-methylpyrrolidin-3-ylcarbamate for (S)-tert-butyl pyrrolidin-3-ylcarbamate in Step D, and substituting 7-(2-methoxyethyl)quinoline-2-carbaldehyde in place of 8-methoxyquinoline-2-carbaldehyde in Step F. LCMS APCI (+) m/z 485 (M+H).

Example 301

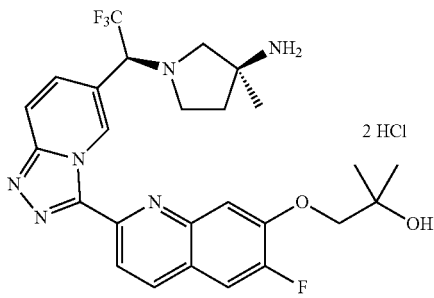 [SMILES: CC(C)(O)COc1cc2nc(-c3nnc4ccc([C@H](N5CC[C@](C)(N)C5)C(F)(F)F)cn34)ccc2cc1F]

1-(2-(6-((S)-1-((S)-3-amino-3-methylpyrrolidin-1-yl)-2,2,2-trifluoroethyl)-[1,2,4]triazolo[4,3-a]pyridin-3-yl)-6-fluoroquinolin-7-yloxy)-2-methylpropan-2-ol dihydrochloride Step A: Preparation of 1-(6-fluoro-2-methylquinolin-7-yloxy)-2-methylpropan-2-ol Prepared as described in Example 277, Step A, using 2,2-dimethyloxirane in place of (R)-2-methyloxirane, and substituting 6-fluoro-2-methylquinolin-7-ol for 2-methylquinolin-7-ol.

Step B: Preparation of 6-fluoro-7-(2-hydroxy-2-methylpropoxy)quinoline-2-carbaldehyde Prepared as described in Example 5, Step B, using 1-(6-fluoro-2-methylquinolin-7-yloxy)-2-methylpropan-2-ol in place of 8-(cyclopropylmethoxy)-2-methylquinoline.

Step C: Preparation of 1-(2-(6-((S)-1-((S)-3-amino-3-methylpyrrolidin-1-yl)-2,2,2-trifluoroethyl)-[1,2,4]triazolo[4,3-a]pyridin-3-yl)-6-fluoro quinolin-7-yloxy)-2-methylpropan-2-ol dihydrochloride Prepared as described in Example 260, Steps C-D, using 6-fluoro-7-(2-hydroxy-2-methylpropoxy)quinoline-2-carbaldehyde in place of 7-(2-methoxyethoxy)quinoline-2-carbaldehyde in Step C. LCMS APCI (+) m/z 533 (M+H).

Example 302

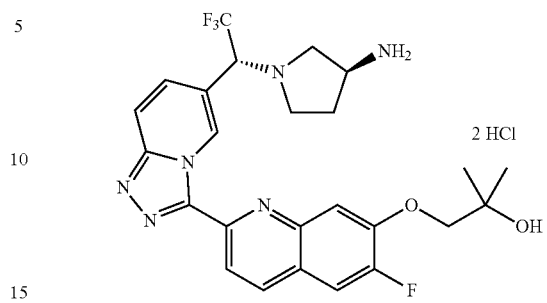

1-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)-2-methylpropan-2-ol dihydrochloride Prepared as described in Example 9B, Steps F-G, using 6-fluoro-7-(2-hydroxy-2-methylpropoxy)quinoline-2-carbaldehyde in place of 8-methoxyquinoline-2-carbaldehyde in Step F. LCMS APCI (+) m/z 519 (M+H).

Example 303

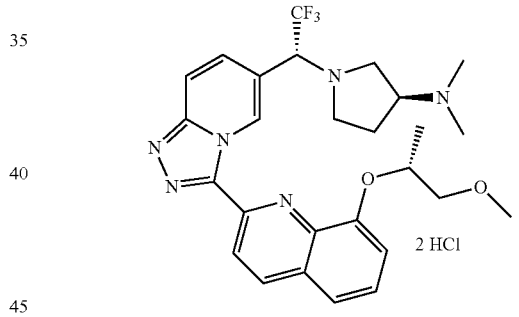

(S)—N,N-dimethyl-1-((R)-2,2,2-trifluoro-1-(3-(8-((R)-1-methoxypropan-2-yloxy)quinolin-2-yl)-[1,2,4]triazolo[4,3-a]pyridin-6-yl)ethyl)pyrrolidin-3-amine dihydrochloride To a stirred solution of (S)-1-((R)-2,2,2-trifluoro-1-(3-(8-((R)-1-methoxypropan-2-yloxy)quinolin-2-yl)-[1,2,4]triazolo[4,3-a]pyridin-6-yl)ethyl)pyrrolidin-3-amine (Example 140; 0.200 g, 0.400 mmol), formaldehyde (37 wt % in water, 0.565 mL, 7.59 mmol) and glacial acetic acid (0.041 mL, 0.719 mmol) in methanol (2 mL) cooled on an ice-water bath, was added slowly sodium cyanoborohydride (0.075 g, 1.20 mmol) and the mixture stirred for 2 hours. The mixture was neutralized with 1N NaOH solution and extracted with ethyl acetate. The combined organic extracts were washed with brine, dried (MgSO$_4$), filtered and concentrated under reduced pressure. The residue was purified by column chromatography (Biotage, 25M, 1% methanol/dichloromethane). The isolated product was stirred in 4N HCl in 1,4-dioxane for 45 minutes and concentrated under reduced pressure. The residue was stirred with acetonitrile and evaporated under reduced pressure until a solid was obtained. The solid stirred in acetonitrile, filtered and dried under vacuum to afford (S)—N,N-dimethyl-1-((R)-2,2,2-trifluoro-1-(3-(8-((R),-1-methoxypropan-2-yloxy)quinolin-2-yl)-[1,2,4]triazolo[4,3-a]pyridin-6-yl)ethyl)pyrrolidin-3-amine dihydrochloride. LCMS APCI (+) m/z 529 (M+H).

Example 304

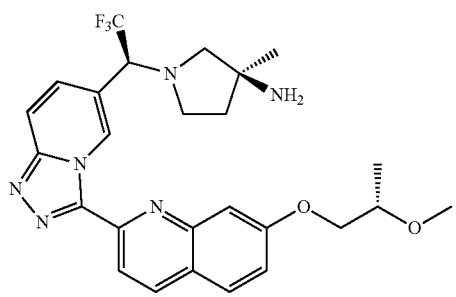 [SMILES: CO[C@@H](C)COc1ccc2ccc(-c3nnc4ccc([C@H](N5CC[C@](C)(N)C5)C(F)(F)F)cn34)nc2c1]

(S)-3-methyl-1-((S)-2,2,2-trifluoro-1-(3-(7-((S)-2-methoxypropoxy)quinolin-2-yl)-[1,2,4]triazolo[4,3-a]pyridin-6-yl)ethyl)pyrrolidin-3-amine Prepared as described in Example 9B, Steps D-G, using (S)-tert-butyl 3-methylpyrrolidin-3-ylcarbamate (Preparation B) in place of (S)-tert-butyl pyrrolidin-3-ylcarbamate in Step D and using (S)-7-(2-methoxypropoxy)quinoline-2-carbaldehyde (Example 287, Steps A-B) in place of 8-methoxyquinoline-2-carbaldehyde in Step F. MS APCI (+) m/z 515 (M+1) detected.

Example 305

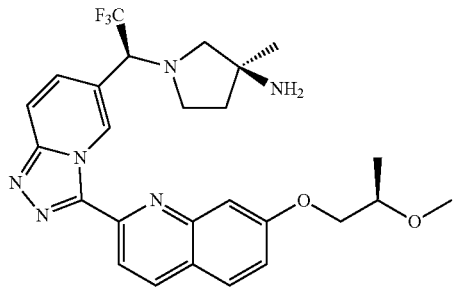 [SMILES: CO[C@H](C)COc1ccc2ccc(-c3nnc4ccc([C@H](N5CC[C@](C)(N)C5)C(F)(F)F)cn34)nc2c1]

(S)-3-methyl-1-((S)-2,2,2-trifluoro-1-(3-(7-((R)-2-methoxypropoxy)quinolin-2-yl)-[1,2,4]triazolo[4,3-a]pyridin-6-yl)ethyl)pyrrolidin-3-amine Prepared as described in Example 9B, Steps D-G, using (S)-tert-butyl 3-methylpyrrolidin-3-ylcarbamate (Preparation B) in place of (S)-tert-butyl pyrrolidin-3-ylcarbamate in Step D and using (R)-7-(2-methoxypropoxy)quinoline-2-carbaldehyde in place of 8-methoxyquinoline-2-carbaldehyde in Step F. MS APCI (+) m/z 515 (M+1) detected.

Example 306

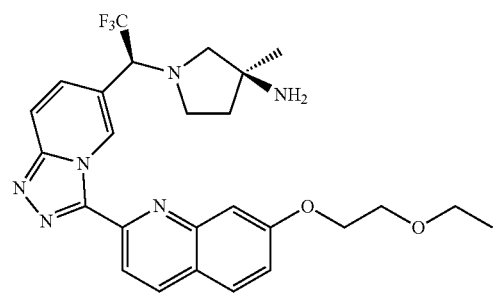 [SMILES: CCOCCOc1ccc2ccc(-c3nnc4ccc([C@H](N5CC[C@](C)(N)C5)C(F)(F)F)cn34)nc2c1]

(S)-1-((S)-1-(3-(7-(2-ethoxyethoxy)quinolin-2-yl)-[1,2,4]triazolo[4,3-a]pyridin-6-yl)-2,2,2-trifluoroethyl)-3-methylpyrrolidin-3-amine Prepared as described in Example 9B, Steps D-G, using (S)-tert-butyl 3-methylpyrrolidin-3-ylcarbamate (Preparation B) in place of (S)-tert-butyl pyrrolidin-3-ylcarbamate in Step D and using 7-(2-ethoxyethoxy)quinoline-2-carbaldehyde in place of 8-methoxyquinoline-2-carbaldehyde in Step F. MS APCI (+) m/z 515 (M+1) detected.

Example 307

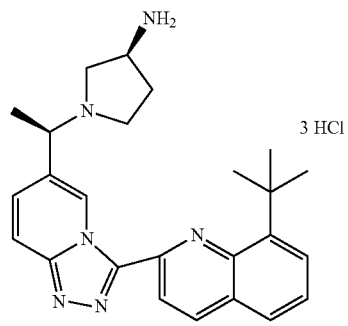 [SMILES: C[C@H](c1ccc2nnc(-c3ccc4cccc(C(C)(C)C)c4n3)n2c1)N1CC[C@H](N)C1]

(S)-1-((R)-1-(3-(8-tert-butylquinolin-2-yl)-[1,2,4]triazolo[4,3-a]pyridin-6-yl)ethyl)pyrrolidin-3-amine trihydrochloride Step A: Preparation of tert-butyl (S)-1-((R)-1-(3-(8-tert-butylquinolin-2-yl)-[1,2,4]triazolo[4,3-a]pyridin-6-yl)ethyl)pyrrolidin-3-ylcarbamate Enantiomerically pure tert-butyl (S)-1-((R)-1-(3-(8-tert-butylquinolin-2-yl)-[1,2,4]triazolo[4,3-a]pyridin-6-yl)ethyl)pyrrolidin-3-ylcarbamate was isolated from the racemate tert-butyl (3S)-1-(1-(3-(8-tert-butylquinolin-2-yl)-[1,2,4]triazolo[4,3-a]pyridin-6-yl)ethyl)pyrrolidin-3-ylcarbamate (prepared as in Example 307, Steps A-F) by chiral SFC (Supercritical Fluid Chromatography). Conditions for preparative chromatography: Chiralpak IC (Chiral Technologies) 20 mm×250 mm, 50% MeOH at 50 mL/min. Outlet pressure: 100 bar. Enantiomeric excess was determined by chiral HPLC (Chiralcel OD-H, 90% hexanes/10% (1:1 MeOH/EtOH) at 1.0 mL/min, >99% d.e. (R,S)-diastereomer).

Step B: Preparation of tert-butyl (S)-1-((R)-1-(3-(8-tert-butylquinolin-2-yl)-[1,2,4]triazolo[4,3-a]pyridin-6-yl)ethyl)pyrrolidin-3-ylcarbamate trihydrochloride To a solution of tert-butyl (S)-1-((R)-1-(3-(8-tert-butylquinolin-2-yl)-[1,2,4]triazolo[4,3-a]pyridin-6-yl)ethyl)pyrrolidin-3-ylcarbamate (0.197 g, 0.383 mmol) in DCM (1 mL) was added 4 N HCl (1.92 mL, 7.66 mmol) in IPA. The mixture was stirred at ambient temperature for 1 hour. The solvent was removed under reduced pressure and ether (5 mL) was added. The suspension was stirred at ambient temperature for 10 minutes and the solid formed was collected by filtration to give (S)-1-((R)-1-(3-(8-tert-butylquinolin-2-yl)-[1,2,4]triazolo[4,3-a]pyridin-6-yl)ethyl) pyrrolidin-3-amine (0.186 g, 92.8%) as solid. LCMS APCI (+) m/z 415 (M+H).

Example 308

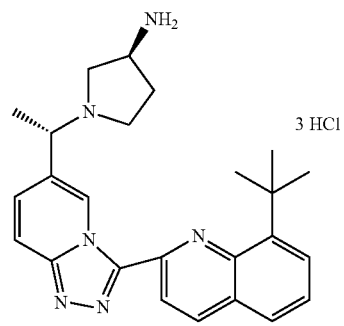 [SMILES: C[C@@H](c1ccc2nnc(-c3ccc4cccc(C(C)(C)C)c4n3)n2c1)N1CC[C@H](N)C1]

(S)-1-((S)-1-(3-(8-tert-butylquinolin-2-yl)-[1,2,4]triazolo[4,3-a]pyridin-6-yl)ethyl)pyrrolidin-3-amine trihydrochloride Step A: Preparation of tert-butyl (S)-1-((S)-1-(3-(8-tert-butylquinolin-2-yl)-[1,2,4]triazolo[4,3-a]pyridin-6-yl)ethyl)pyrrolidin-3-ylcarbamate Enantiomeric ally pure tert-butyl (S)-1-((S)-1-(3-(8-tert-butylquinolin-2-yl)-[1,2,4]triazolo[4,3-a]pyridin-6-yl)ethyl)pyrrolidin-3-ylcarbamate was isolated from the racemate tert-butyl (3S)-1-(1-(3-(8-tert-butylquinolin-2-yl)-[1,2,4]triazolo[4,3-a]pyridin-6-yl)ethyl)pyrrolidin-3-ylcarbamate (prepared as in Example 17, Steps A-F) by chiral SFC (Conditions for preparative chromatography: Chiralpak IC, Chiral Technologies 20 mm×250 mm, 50% MeOH at 50 mL/min. Outlet pressure: 100 bar). Enantiomeric excess was determined by chiral HPLC (Chiralcel OD-H, 90% hexanes/10% (1:1 MeOH/EtOH) at 1.0 mL/min, 99.2% d.e. (S,S)-diastereomer).

Step B: Preparation of tert-butyl (S)-1-((S)-1-(3-(8-tert-butylquinolin-2-yl)-[1,2,4]triazolo[4,3-a]pyridin-6-yl)ethyl)pyrrolidin-3-ylcarbamate trihydrochloride To a solution of tert-butyl (S)-1-((S)-1-(3-(8-tert-butylquinolin-2-yl)-[1,2,4]triazolo[4,3-a]pyridin-6-yl)ethyl)pyrrolidin-3-ylcarbamate (0.203 g, 0.39 mmol) in DCM (1 mL) was added 4 N HCl (1.97 mL, 7.89 mmol) in IPA. The mixture was stirred at ambient temperature for 1 hour. The solvent was removed under reduced pressure and ether (5 mL) was added. The suspension was stirred at ambient temperature for 10 minutes and the solid formed was collected by filtration to give (S)-1-((S)-1-(3-(8-tert-butylquinolin-2-yl)-[1,2,4]triazolo[4,3-a]pyridin-6-yl)ethyl) pyrrolidin-3-amine (0.204 g, 98.7%) as solid.

Example 309

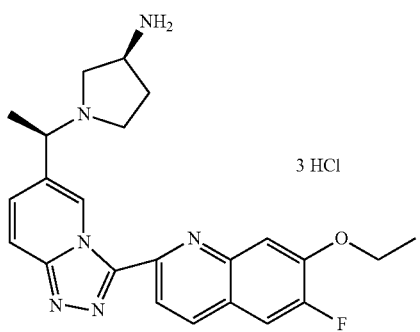 [SMILES: CCOc1cc2nc(-c3nnc4ccc([C@@H](C)N5CC[C@H](N)C5)cn34)ccc2cc1F]

(S)-1-((R)-1-(3-(7-ethoxy-6-fluoro quinolin-2-yl)-[1,2,4]triazolo[4,3-a]pyridin-6-yl)ethyl)pyrrolidin-3-amine trihydrochloride Step A: Preparation of 1-(6-fluoropyridin-3-yl)ethanone To a solution of 6-fluoronicotinonitrile (5.00 g, 41.0 mmol) in THF (50 mL) was added 1 N methylmagnesium bromide (16.4 mL, 49.1 mmol) in THF at 0° C. After addition, the mixture was warmed to ambient temperature and stirred at ambient temperature for 4 hours. Saturated sodium bicarbonate solution (50 mL) and ether (100 mL) were added. The organic layer was separated, washed with brine, dried (sodium sulfate), filtered and concentrated under reduced pressure. The residue was purified by flash chromatography on silica gel (5:1 hexane/ethyl acetate) to give 1-(6-fluoropyridin-3-yl)ethanone (0.85 g, 14.9%) as solid.

Step B: Preparation of tert-butyl (3S)-1-(1-(6-fluoropyridin-3-yl)ethyl)pyrrolidin-3-ylcarbamate To a solution of (S)-tert-butyl pyrrolidin-3-ylcarbamate (0.94 g, 5.04 mmol), 1-(6-fluoropyridin-3-yl)ethanone (0.35 g, 2.52 mmol) in THF (10 mL) was added tetraisopropoxytitanium (1.48 mL, 5.04 mmol) and the reaction mixture was stirred at ambient temperature for 18 hours. Ethanol (2 mL) and NaBH$_4$ (0.38 g, 10.1 mmol) were added and the mixture was stirred at ambient temperature for 2 hours. Water (10 mL), concentrated ammonium (2 mL) and ethyl acetate (20 mL) were added. The organic layer was separated, washed with brine, dried (sodium sulfate), filtered and concentrated under reduced pressure. The residue obtained was purified by flash chromatography on silica gel (1:1 hexane/ethyl acetate) to give tert-butyl (3S)-1-(1-(6-fluoropyridin-3-yl)ethyl)pyrrolidin-3-ylcarbamate (0.343 g, 44.0%) as solid.

Step C: Preparation of tert-butyl (3S)-1-(1-(3-(7-ethoxy-6-fluoro quinolin-2-yl)-[1,2,4]triazolo[4,3-a]pyridin-6-yl)ethyl)pyrrolidin-3-ylcarbamate Prepared as described in Example 1, Steps D-E, using tert-butyl (3S)-1-(1-(6-fluoropyridin-3-yl)ethyl)pyrrolidin- 3-ylcarbamate in place of tert-butyl (3S)-1-(1-(6-chloropyridin-3-yl)-2,2,2-trifluoroethyl)pyrrolidin-3-ylcarbamate in Step D and substituting 7-ethoxy-6-fluoroquinoline-2-carbaldehyde for 8-methoxyquinoline-2-carbaldehyde in Step E.

Step D: Preparation of (S)-1-((R)-1-(3-(7-ethoxy-6-fluoro quinolin-2-yl)-[1,2,4]triazolo[4,3-a]pyridin-6-yl)ethyl)pyrrolidin-3-amine trihydrochloride Prepared as described in Example 307 using tert-butyl (3S)-1-(1-(3-(7-ethoxy-6-fluoroquinolin-2-yl)-[1,2,4]triazolo[4,3-a]pyridin-6-yl)ethyl)pyrrolidin-3-ylcarbamate in place of tert-butyl (3S)-1-(1-(3-(8-tert-butylquinolin-2-yl)-[1,2,4]triazolo[4,3-a]pyridin-6-yl)ethyl)pyrrolidin-3-ylcarbamate in Step A. LCMS APCI (+) m/z 421 (M+H).

Example 310

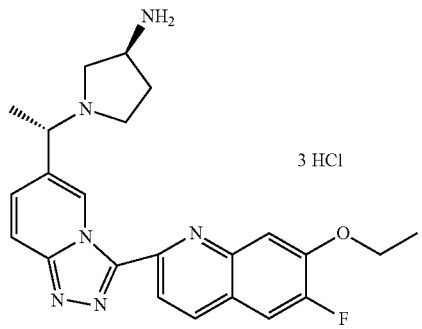 [SMILES: CCOc1cc2nc(-c3nnc4ccc([C@H](C)N5CC[C@H](N)C5)cn34)ccc2cc1F]

(S)-1-((S)-1-(3-(7-ethoxy-6-fluoroquinolin-2-yl)-[1,2,4]triazolo[4,3-a]pyridin-6-yl)ethyl)pyrrolidin-3-amine trihydrochloride Prepared as described in Example 308 using tert-butyl (3S)-1-(1-(3-(7-ethoxy-6-fluoroquinolin-2-yl)-[1,2,4]triazolo[4,3-a]pyridin-6-yl)ethyl)pyrrolidin-3-ylcarbamate in place of tert-butyl (3S)-1-(1-(3-(8-tert-butylquinolin-2-yl)-[1,2,4]triazolo[4,3-a]pyridin-6-yl)ethyl)pyrrolidin-3-ylcarbamate in Step A. LCMS APCI (+) m/z 421 (M+H).

Example 311

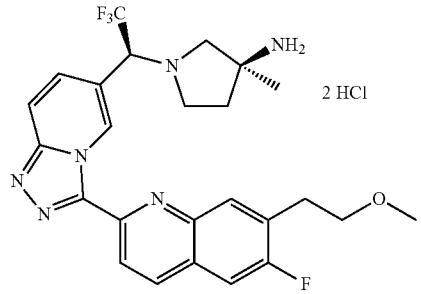 [SMILES: COCCc1cc2nc(-c3nnc4ccc([C@H](N5CC[C@](C)(N)C5)C(F)(F)F)cn34)ccc2cc1F]

(S)-3-methyl-1-((S)-2,2,2-trifluoro-1-(3-(6-fluoro-7-(2-methoxyethyl)quinolin-2-yl)-[1,2,4]triazolo[4,3-a]pyridin-6-yl)ethyl)pyrrolidin-3-amine Prepared as described in Example 9B, using (R)-1-(6-chloropyridin-3-yl)-2,2,2-trifluoroethanol in place of (S)-1-(6-chloropyridin-3-yl)-2,2,2-trifluoroethanol in Step C, substituting (S)-tert-butyl 3-methylpyrrolidin-3-ylcarbamate for (S)-tert-butyl pyrrolidin-3-ylcarbamate in Step D, and substituting 6-fluoro-7-(2-methoxyethyl)quinoline-2-carbaldehyde in place of 8-methoxyquinoline-2-carbaldehyde in Step F. LCMS APCI (+) m/z 485 (M+H).

Example 312

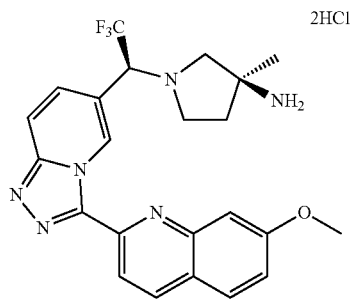 [SMILES: COc1ccc2ccc(-c3nnc4ccc([C@H](N5CC[C@](C)(N)C5)C(F)(F)F)cn34)nc2c1]

(S)-3-methyl-1-((S)-2,2,2-trifluoro-1-(3-(7-methoxyquinolin-2-yl)-[1,2,4]triazolo[4,3-a]pyridin-6-yl)ethyl)pyrrolidin-3-amine Prepared as described in Example 217, using (S)-tert-butyl 3-methylpyrrolidin-3-ylcarbamate (Preparation D) in place of (S)-tert-butyl pyrrolidin-3-ylcarbamate, and 7-methoxyquinoline-2-carbaldehyde in place of 7-methoxyquinoline-2-carbaldehyde. MS APCI (+) m/z 457 (M+1) detected.

Example 313

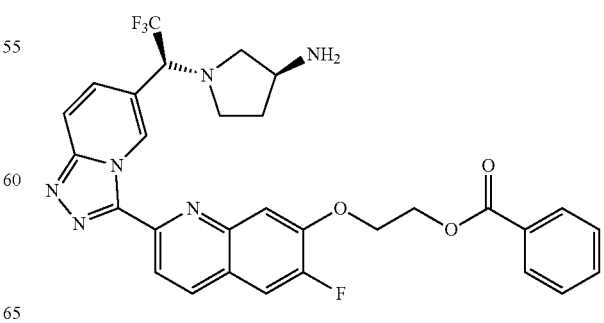

2-((2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yl)oxy)ethyl benzoate Prepared as described in Example 286 using benzoyl chloride in place of pivalic anhydride in Step A. LCMS APCI (+) m/z 595 (M+H).

Example 314

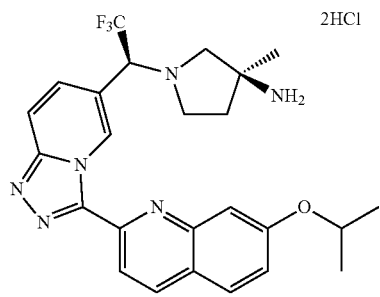 [SMILES: CC(C)Oc1ccc2ccc(-c3nnc4ccc([C@H](N5CC[C@](C)(N)C5)C(F)(F)F)cn34)nc2c1]

(S)-3-methyl-1-((S)-2,2,2-trifluoro-1-(3-(7-isopropoxyquinolin-2-yl)-[1,2,4]triazolo[4,3-a]pyridin-6-yl)ethyl)pyrrolidin-3-amine Prepared as described in Example 217, using (S)-tert-butyl 3-methylpyrrolidin-3-ylcarbamate (Preparation D) in place of (S)-tert-butyl pyrrolidin-3-ylcarbamate, and 7-isopropoxyquinoline-2-carbaldehyde in place of 7-methoxyquinoline-2-carbaldehyde. MS APCI (+) m/z 486 (M+1) detected.

Example 315

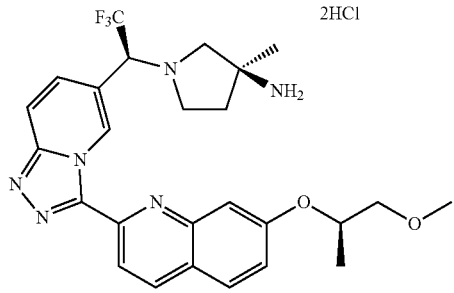 [SMILES: COC[C@@H](C)Oc1ccc2ccc(-c3nnc4ccc([C@H](N5CC[C@](C)(N)C5)C(F)(F)F)cn34)nc2c1]

(S)-3-methyl-1-((S)-2,2,2-trifluoro-1-(3-(7-(((R)-1-methoxypropan-2-yl)oxy)quinolin-2-yl)-[1,2,4]triazolo[4,3-a]pyridin-6-yl)ethyl)pyrrolidin-3-amine Prepared as described in Example 217, using (S)-tert-butyl 3-methylpyrrolidin-3-ylcarbamate (Preparation D) in place of (S)-tert-butyl pyrrolidin-3-ylcarbamate, and 7-(R)-1-(methoxypropan-2-yl)quinoline-2-carbaldehyde in place of 7-methoxyquinoline-2-carbaldehyde. MS APCI (+) m/z 515 (M+1) detected.

Example 316

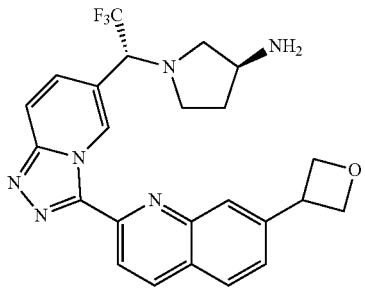 [SMILES: N[C@H]1CCN([C@H](c2ccc3nnc(-c4ccc5ccc(C6COC6)cc5n4)n3c2)C(F)(F)F)C1]

(S)-1-((R)-2,2,2-trifluoro-1-(3-(7-(oxetan-3-yl)quinolin-2-yl)-[1,2,4]triazolo[4,3-a]pyridin-6-yl)ethyl)pyrrolidin-3-amine Step A: Preparation of diethyl 2-(2-methylquinolin-7-yl)malonate A mixture of 7-bromo-2-methylquinoline (2.00 g, 9.01 mmol), Cu(I)I (0.172 g, 0.90 mmol), picolinic acid (0.222 g, 1.80 mmol), $Cs_2CO_3$ (8.80 g, 27.0 mmol) and diethyl malonate (2.73 mL, 18.0 mmol) in dioxane (25 mL) was stirred at 100° C. for hours. After cooling to ambient temperature, ethyl acetate (30 mL) and water (15 mL) were added. The organic layer was separated, washed with brine, dried (sodium sulfate), filtered and concentrated under reduced pressure. The residue obtained was purified by flash chromatography on silica gel (3:2 hexane/ethyl acetate) to give diethyl 2-(2-methylquinolin-7-yl)malonate (0.7 g, 2.32 mmol, 26% yield) as oil.

Step B: Preparation of 2-(2-methylquinolin-7-yl)propane-1,3-diol)

To a solution of 1.0 N LAH (15.3 mL, 15.3 mmol) in THF was added diethyl 2-(2-methylquinolin-7-yl)malonate (1.15 g, 3.82 mmol) in Ether (30 mL) slowly at 0° C. The reaction mixture was stirred at 0° C. for 2 hours. Sodium sulfate decahydrate (2.0 g) was added and stirred at ambient temperature for 30 minutes. The solid was removed by filtration and washed with ethyl acetate (50 mL). The filtrate was concentrated and the residue obtained was purified by C-18 reverse phase flash chromatography (Biotage SP4 unit, C-18 40M column, 0-70% $CH_3CN$/water gradient; 30 CV) to give 2-(2-methylquinolin-7-yl)propane-1,3-diol (0.34 g, 1.56 mmol, 41.0% yield) as a solid.

Step C: Preparation of 2-methyl-7-(oxetan-3-yl)quinoline

To a solution of 2-(2-methylquinolin-7-yl)propane-1,3-diol (0.100 g, 0.46 mmol) and $PPh_3$ (0.241 g, 0.921 mmol) in toluene (10 mL) was added zinc(II) dimethylcarbamodithioate (0.211 g, 0.690 mmol) and DEAD (0.145 ml, 0.921 mmol). The resulting mixture was stirred at ambient temperature for 30 hours. The solvent was removed under reduced pressure, and water (20 mL) and ethyl acetate (30 mL) were added. The organic layer was separated, washed with brine, dried (sodium sulfate), filtered and concentrated under reduced pressure. The residue obtained was purified by C-18 reverse phase flash chromatography (Biotage SP4 unit, C-18 25M column, 0-90% CH$_3$CN/water gradient; 25 CV)) to give 2-methyl-7-(oxetan-3-yl)quinoline (0.020 g, 0.100 mmol, 22% yield) as a solid.

Step D: Preparation of 7-(oxetan-3-yl)quinoline-2-carbaldehyde

2-Methyl-7-(oxetan-3-yl)quinoline (0.020 g, 0.100 mmol) was dissolved in dioxane (5 mL) and water (0.05 mL). The reaction was treated with SeO$_2$ (0.013 g, 0.120 mmol) and the mixture was heated to reflux for 2 hours. After cooling to ambient temperature, the solid was removed by filtration and washed with DCM. The filtrate was concentrated under reduced pressure to give 7-(oxetan-3-yl)quinoline-2-carbaldehyde (0.020 g, 0.0938 mmol, 93.4% yield) as a solid.

Step E: Preparation of tert-butyl (S)-1-((R)-2,2,2-trifluoro-1-(3-(7-(oxetan-3-yl)quinolin-2-yl)-[1,2,4]triazolo[4,3-a]pyridin-6-yl)ethyl)pyrrolidin-3-ylcarbamate Prepared as described in Example 9B, substituting 7-(oxetan-3-yl)quinoline-2-carbaldehyde in place of 8-methoxyquinoline-2-carbaldehyde in Step F.

Step F: Preparation of (S)-1-((R)-2,2,2-trifluoro-1-(3-(7-(oxetan-3-yl)quinolin-2-yl)-[1,2,4]triazolo[4,3-a]pyridin-6-yl)ethyl)pyrrolidin-3-amine A solution of tert-butyl (S)-1-((R)-2,2,2-trifluoro-1-(3-(7-(oxetan-3-yl)quinolin-2-yl)-[1,2,4]triazolo[4,3-a]pyridin-6-yl)ethyl)pyrrolidin-3-ylcarbamate (0.015 g, 0.026 mmol) in formic acid (0.51 ml, 13.2 mmol) was stirred at ambient temperature for 10 hours. The solvent was removed under reduced pressure to give (S)-1-((R)-2,2,2-trifluoro-1-(3-(7-(oxetan-3-yl)quinolin-2-yl)-[1,2,4]triazolo[4,3-a]pyridin-6-yl)ethyl)pyrrolidin-3-amine (0.012 g, 0.026 mmol, 97% yield) as a formic acid salt. LCMS APCI (+) m/z 469 (M+H).

Example 317

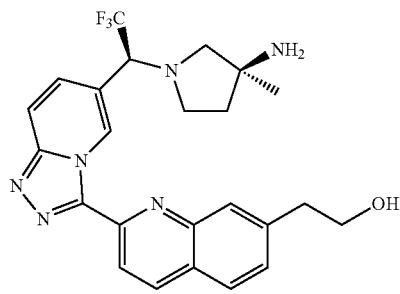 [SMILES: C[C@]1(N)CCN([C@@H](c2ccc3nnc(-c4ccc5ccc(CCO)cc5n4)n3c2)C(F)(F)F)C1]

2-(2-(6-((S)-1-((S)-3-amino-3-methylpyrrolidin-1-yl)-2,2,2-trifluoroethyl)-[1,2,4]triazolo[4,3-a]pyridin-3-yl)quinolin-7-yl)ethanol Step A: Preparation of methyl 2-(2-methylquinolin-7-yl)acetate 2-(3-aminophenyl)acetic acid (11.0 g, 72.8 mmol) was dissolved in 6 N HCl (200 mL) and heated to reflux. (E)-but-2-enal (11.9 mL, 146 mmol) was added dropwise over 10 minutes. The reaction was heated at reflux for 2 hours. After cooling to ambient temperature, the reaction mixture was basified with sodium hydroxide to pH~12 and ether (100 mL) was added. The aqueous layer was separated, acidified with saturated potassium hydrogen sulfate to pH~3-4, extracted with 3:1 CHCl$_3$:IPA (3×300 mL), dried (sodium sulfate) and concentrated to give a solid. The solid was dissolved in MeOH (200 mL). The residue was suspended in ethyl acetate (100 mL) and saturated sodium bicarbonate (50 mL). The organic layer was separated, washed with brine, dried (sodium sulfate) and concentrated. The residue obtained was purified by flash chromatography (5:1 DCM:ethyl acetate) to give methyl 2-(2-methylquinolin-7-yl)acetate as a solid.

Step B: Preparation of 2-(2-methylquinolin-7-yl)ethanol methyl 2-(2-methylquinolin-7-yl)acetate (5.78 g, 26.9 mmol) in THF (50 mL) was added 1M LAH (40.3 mL, 40.3 mmol) in THF at 0° C., followed by stirring at 0° C. for 3 hours. Sodium sulfate decahydrate (10.0 g) was added and stirred at ambient temperature for 30 minutes. The solid was removed by filtration and washed with ethyl acetate (100 mL). The filtrate was concentrated and the residue obtained was purified by flash chromatography (ethyl acetate) on silica gel to give 2-(2-methylquinolin-7-yl)ethanol (2.35 g, 12.6 mmol, 47% yield) as a solid.

Step C: Preparation of 7-(2-hydroxyethyl)quinoline-2-carbaldehyde 2-(2-methylquinolin-7-yl)ethanol (0.220 g, 1.17 mmol) was dissolved in dioxane (5 mL) and water (0.05 mL). The reaction was treated with SeO$_2$ (0.156 g, 1.41 mmol) and the mixture was heated to reflux for 2 hours. After cooling to ambient temperature, the solid was removed by filtration and washed with DCM. The filtrate was concentrated and the residue was purified by flash chromatography on silica gel (ethyl acetate/hexanes 5:1) to give 7-(2-hydroxyethyl)quinoline-2-carbaldehyde (0.21 g, 1.04 mmol, 89% yield) as a solid.

Step E: Preparation of tert-butyl (S)-1-((R)-2,2,2-trifluoro-1-(3-(7-(oxetan-3-yl)quinolin-2-yl)-[1,2,4]triazolo[4,3-a]pyridin-6-yl)ethyl)pyrrolidin-3-ylcarbamate Prepared as described in Example 9B, using (R)-1-(6-chloropyridin-3-yl)-2,2,2-trifluoroethanol in place of (S)-1-(6-chloropyridin-3-yl)-2,2,2-trifluoroethanol in Step C, substituting (S)-tert-butyl 3-methylpyrrolidin-3-ylcarbamate for (S)-tert-butyl pyrrolidin-3-ylcarbamate in Step D, and substituting 7-(2-hydroxyethyl)quinoline-2-carbaldehyde in place of 8-methoxyquinoline-2-carbaldehyde in Step F. LCMS APCI (+) m/z 471 (M+H).

Example 318

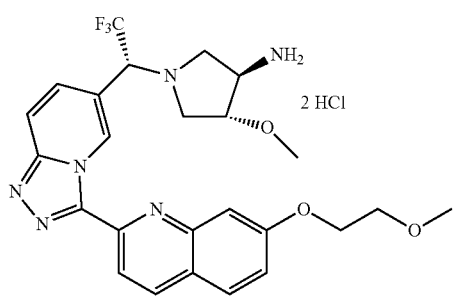 [SMILES: COCCOc1ccc2ccc(-c3nnc4ccc([C@@H](N5C[C@@H](N)[C@H](OC)C5)C(F)(F)F)cn34)nc2c1]

(3R,4R)-4-methoxy-1-((R)-2,2,2-trifluoro-1-(3-(7-(2-methoxyethoxy)quinolin-2-yl)-[1,2,4]triazolo[4,3-a]pyridin-6-yl)ethyl)pyrrolidin-3-amine Prepared as described in Example 299, substituting 7-methoxyethoxy-quinoline-2-carbaldehyde for 8-7-ethoxy-6-fluoroquinoline-2-carbaldehyde in Step F. LCMS APCI (+) m/z 517 (M+H).

Example 319

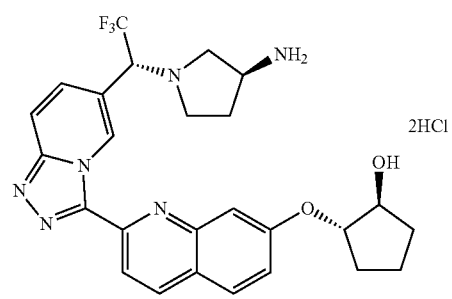 [SMILES: N[C@H]1CCN([C@H](c2ccc3nnc(-c4ccc5ccc(O[C@H]6CCC[C@@H]6O)cc5n4)n3c2)C(F)(F)F)C1]

Diastereomer 1 of trans-2-((2-(6-((R)-1-((S)-3-aminopyrrolidin-1-yl)-2,2,2-trifluoroethyl)-[1,2,4]triazolo[4,3-a]pyridin-3-yl)quinolin-7-yl)oxy)cyclopentanol di-hydrochloride Step A: Preparation of cis-(1S,2R)-2-(tert-butyldimethylsilyloxy)cyclopentanol To a stirred solution of cis-cyclopentane-1,2-diol (2.30 g, 22.5 mmol) and imidazole (3.07 g, 45.0 mmol) in DMF (80 mL) was added dropwise tert-butyldimethylsilyl chloride (3.39 g, 22.5 mmol) in DMF (30 mL) at 0° C. under nitrogen. The reaction mixture was stirred at ambient temperature overnight. The reaction was partitioned between ether and water. The aqueous layer was extracted with ether. The combined organic layers were washed with water and brine, dried and concentrated. The residue was purified by flash chromatography on silica gel (hexanes:EtOAc, 25:1) to give cis-(1S,2R)-2-(tert-butyldimethylsilyloxy)cyclopentanol (3.02 g, 62%).

Step B: Preparation of trans-7-((2-((tert-butyldimethylsilyl)oxy)cyclopentyl)oxy)-2-methylquinoline Prepared as described in Example 140, Step A, using cis-(1S,2R)-2-(tert-butyldimethylsilyloxy)cyclopentanol as a replacement for (S)-1-methoxypropan-2-ol, and substituting 2-methylquinolin-7-ol for 2-methylquinolin-8-ol.

Step C: Preparation of trans-2-((2-methylquinolin-7-yl)oxy)cyclopentanol

To a stirred solution of crude trans-7-((2-((tert-butyldimethylsilyl)oxy)cyclopentyl)oxy)-2-methylquinoline (3.0 g, 8.4 mmol) in THF (10 mL) was added 1.0 M TBAF in THF (17 mL, 17 mmol). After stirring at ambient temperature for 1 hour, saturated aqueous NH₄Cl was added to the reaction mixture. The mixture was extracted with EtOAc. The combined organic layers were washed with brine, dried and concentrated. The residue was purified by flash chromatography on silica gel (2% MeOH in EtOAc) to give trans-2-((2-methylquinolin-7-yl)oxy)cyclopentanol (0.065 g, 3% for two steps).

Step D: Preparation of trans-7-(2-hydroxycyclopentyl)oxy)quinoline-2-carbaldehyde Prepared as described in Example 5, Step B, using trans-2-((2-methylquinolin-7-yl)oxy)cyclopentanol in place of 8-(cyclopropylmethoxy)-2-methylquinoline.

Step E: Preparation of trans-tert-butyl ((3S)-1-((1R)-2,2,2-trifluoro-1-(3-(7-((2-hydroxycyclopentyl)oxy)quinolin-2-yl)-[1,2,4]triazolo[4,3-a]pyridin-6-yl)ethyl)pyrrolidin-3-yl)carbamate Prepared as described in Example 9 (Method B) Step F, using trans-7-((2-hydroxycyclopentyl)oxy)quinoline-2-carbaldehyde in place of 8-methoxyquinoline-2-carbaldehyde.

Step F: Preparation of diastereomer 1 of trans-tert-butyl ((3S)-1-((1R)-2,2,2-trifluoro-1-(3-(7-((2-hydroxycyclopentyl)oxy)quinolin-2-yl)-[1,2,4]triazolo[4,3-a]pyridin-6-yl)ethyl)pyrrolidin-3-yl)carbamate Diastereomer 1 of trans-tert-butyl ((3S)-1-((1R)-2,2,2-trifluoro-1-(3-(7-((2-hydroxycyclopentyl)oxy)quinolin-2-yl)-[1,2,4]triazolo[4,3-a]pyridin-6-yl)ethyl)pyrrolidin-3-yl)carbamate (26 mg, 99.64% purity) was separated from trans-tert-butyl 1-benzyl-3-(hydroxymethyl)pyrrolidin-3-ylcarbamate (68 mg) by chiral SFC. Conditions for analytical chromatography: Rt=9.915 min; Chiral Technologies CHIRALPAK® IC 4.6×150 mm, 70/30 heptane/EtOH at 0.8 mL/min. Conditions for preparative chromatography: Chiral Technologies CHIRALPAK® IB 21 mm×250 mm, 15% EtOH at 75 mL/min).

Step G: Preparation of diastereomer 1 of trans-2-((2-(6-((R)-1-((S)-3-aminopyrrolidin-1-yl)-2,2,2-trifluoroethyl)-[1,2,4]triazolo[4,3-a]pyridin-3-yl)quinolin-7-yl)oxy)cyclopentanol di-hydrochloride Prepared as described in Example 9 (Method B) Step G using diastereomer 1 of trans-tert-butyl ((3S)-1-((1R)-2,2,2-trifluoro-1-(3-(7-((2-hydroxycyclopentyl)oxy)quinolin-2-yl)-[1,2,4]triazolo[4,3-a]pyridin-6-yl)ethyl)pyrrolidin-3-yl)carbamate as a replacement for tert-butyl (S)-1-((R)-2,2,2- trifluoro-1-(3-(8-methoxyquinolin-2-yl)-[1,2,4]triazolo[4,3-a]pyridin-6-yl)ethyl)pyrrolidin-3-ylcarbamate. LCMS APCI (+) m/z 513 (M+H).

Example 320

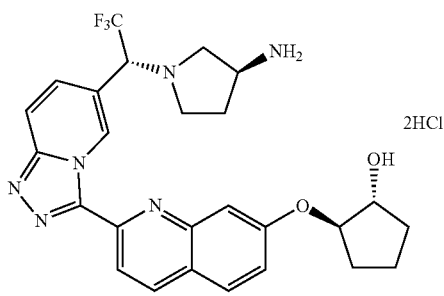 [SMILES: N[C@H]1CCN([C@H](c2ccc3nnc(-c4ccc5ccc(O[C@@H]6CCC[C@H]6O)cc5n4)n3c2)C(F)(F)F)C1]

Diastereomer 2 of trans-2-((2-(6-((R)-1-((S)-3-aminopyrrolidin-1-yl)-2,2,2-trifluoroethyl)-[1,2,4]triazolo[4,3-a]pyridin-3-yl)quinolin-7-yl)oxy)cyclopentanol di-hydrochloride Step A: Preparation of diastereomer 2 of trans-tert-butyl ((3S)-1-((1R)-2,2,2-trifluoro-1-(3-(7-((2-hydroxycyclopentyl)oxy)quinolin-2-yl)-[1,2,4]triazolo[4,3-a]pyridin-6-yl)ethyl)pyrrolidin-3-yl)carbamate The diastereomer 2 of trans-tert-butyl ((3S)-1-((1R)-2,2,2-trifluoro-1-(3-(7-((2-hydroxycyclopentyl)oxy)quinolin-2-yl)-[1,2,4]triazolo[4,3-a]pyridin-6-yl)ethyl)pyrrolidin-3-yl)carbamate (30 mg, 100% purity) was separated from trans-tert-butyl 1-benzyl-3-(hydroxymethyl)pyrrolidin-3-ylcarbamate (68 mg) by chiral SFC. Conditions for analytical chromatography: Rt=11.294 min; Chiral Technologies CHIRALPAK® IC 4.6×150 mm, 70/30 heptane/EtOH at 0.8 mL/min. Conditions for preparative chromatography: Chiral Technologies CHIRALPAK® IB 21 mm×250 mm, 15% EtOH at 75 mL/min).

Step B: Preparation of diastereomer 2 of trans-2-((2-(6-((R)-1-((S)-3-aminopyrrolidin-1-yl)-2,2,2-trifluoroethyl)-[1,2,4]triazolo[4,3-a]pyridin-3-yl)quinolin-7-yl)oxy)cyclopentanol di-hydrochloride Prepared as described in Example 9 (Method B) Step G using diastereomer 2 of trans-tert-butyl ((3S)-1-((1R)-2,2,2-trifluoro-1-(3-(7-((2-hydroxycyclopentyl)oxy)quinolin-2-yl)-[1,2,4]triazolo[4,3-a]pyridin-6-yl)ethyl)pyrrolidin-3-yl)carbamate as a replacement for tert-butyl (S)-1-((R)-2,2,2-trifluoro-1-(3-(8-methoxyquinolin-2-yl)-[1,2,4]triazolo[4,3-a]pyridin-6-yl)ethyl)pyrrolidin-3-ylcarbamate. LCMS APCI (+) m/z 513 (M+H).

Example 321

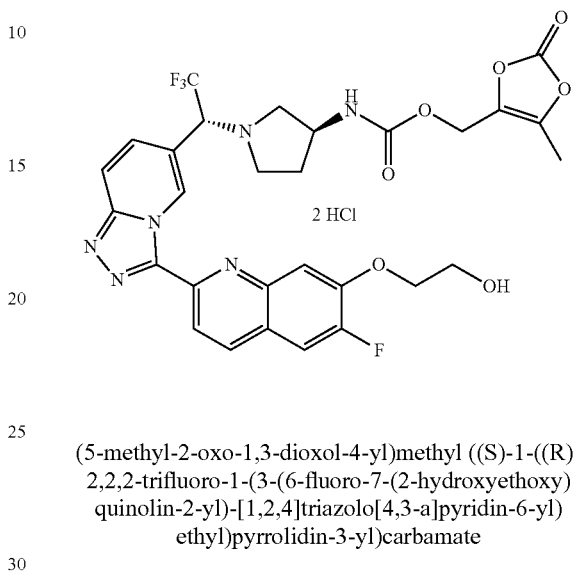

(5-methyl-2-oxo-1,3-dioxol-4-yl)methyl ((S)-1-((R)-2,2,2-trifluoro-1-(3-(6-fluoro-7-(2-hydroxyethoxy)quinolin-2-yl)-[1,2,4]triazolo[4,3-a]pyridin-6-yl)ethyl)pyrrolidin-3-yl)carbamate To a solution of 2-((2-(6-((R)-1-((S)-3-aminopyrrolidin-1-yl)-2,2,2-trifluoroethyl)-[1,2,4]triazolo[4,3-a]pyridin-3-yl)-6-fluoro quinolin-7-yl)oxy)ethanol (125 mg, 0.255 mmol) in DMF (1.5 mL) was added a solution of (5-methyl-2-oxo-1,3-dioxol-4-yl)methyl 4-nitrophenyl carbonate (prepared according to procedures described in J. Med. Chem. 1999, 42, 3994-4000, 71.2 mg, 0.255 mmol) in DMF (1 mL). The reaction mixture was stirred at ambient temperature for 30 minutes. The reaction was partitioned between EtOAc and water. The aqueous layer was extracted with EtOAc. The combined organic layers were washed with water and brine, dried and concentrated. The residue was purified by flash chromatography on silica gel (DCM:MeOH, 70:1 to 40:1) to give (5-methyl-2-oxo-1,3-dioxol-4-yl)methyl ((S)-1-((R)-2,2,2-trifluoro-1-(3-(6-fluoro-7-(2-hydroxyethoxy)quinolin-2-yl)-[1,2,4]triazolo[4,3-a]pyridin-6-yl)ethyl)pyrrolidin-3-yl)carbamate (131 mg, 80%). LCMS APCI (+) m/z 647 (M+H).

Example 322

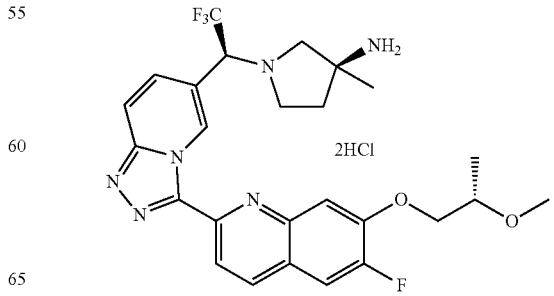

293

(S)-3-methyl-1-((S)-2,2,2-trifluoro-1-(3-(6-fluoro-7-((S)-2-methoxypropoxy)quinolin-2-yl)-[1,2,4]triazolo[4,3-a]pyridin-6-yl)ethyl)pyrrolidin-3-amine di-hydrochloride

Step A: Preparation of (S)-2-methoxypropyl 4-methylbenzenesulfonate

To a stirred solution of (S)-2-methoxypropan-1-ol (1.00 g, 11.1 mmol) in DCM (50 mL) was added Et$_3$N (2.33 mL, 16.6 mmol). A solution of toluene sulfonyl chloride (2.54 g, 13.3 mmol) in DCM (20 mL) was added dropwise at 0° C. under nitrogen. The reaction mixture was allowed to warm to ambient temperature and was stirred overnight. The reaction was diluted with DCM, washed with saturated aqueous NaHCO$_3$ and brine, dried and concentrated. The residue was purified by flash chromatography on silica gel (hexanes:EtOAc, 10:1 to 4:1) to give (S)-2-methoxypropyl 4-methylbenzenesulfonate (2.03 g, 75%).

Step B: Preparation of (S)-6-fluoro-7-(2-methoxypropoxy)-2-methylquinoline

To a stirred mixture of 6-fluoro-2-methylquinolin-7-ol (0.200 g, 1.13 mmol), Cs$_2$CO$_3$ (0.552 g, 1.69 mmol) and NMP (2.3 mL) was added (S)-2-methoxypropyl 4-methylbenzenesulfonate (0.303 g, 1.24 mmol). The reaction mixture was heated at 80° C. for 1 hour. After cooling, the reaction was partitioned between toluene and water. The aqueous layer was extracted with toluene. The combined organic layers were washed with water and brine, dried and concentrated to give the crude product, which was used in the next step without further purification.

Step C: Preparation of (S)-6-fluoro-7-(2-methoxypropoxy)quinoline-2-carbaldehyde To a solution of crude (S)-6-fluoro-7-(2-methoxypropoxy)-2-methylquinoline (0.281 g, 1.13 mmol) in dioxane (4 mL) and water (0.04 mL) was added SeO$_2$ (0.138 g, 1.24 mmol). The reaction mixture was heated at reflux for 3 hours. After cooling, the mixture was filtered through Celite®. The filtrate was concentrated. The residue was purified by flash chromatography on silica gel (hexanes:EtOAc, 4:1) to give (S)-6-fluoro-7-(2-methoxypropoxy)quinoline-2-carbaldehyde (0.251 g, 85% for two steps) as a solid.

Step D: Preparation of (S)-3-methyl-1-((S)-2,2,2-trifluoro-1-(3-(6-fluoro-7-((S)-2-methoxypropoxy)quinolin-2-yl)-[1,2,4]triazolo[4,3-a]pyridin-6-yl)ethyl)pyrrolidin-3-amine di-hydrochloride Prepared as described in Example 260 using (S)-6-fluoro-7-(2-methoxypropoxy)quinoline-2-carbaldehyde as a replacement for 7-(2-methoxyethoxy)quinoline-2-carbaldehyde in step B. LCMS APCI (+) m/z 533 (M+H).

294

Example 323

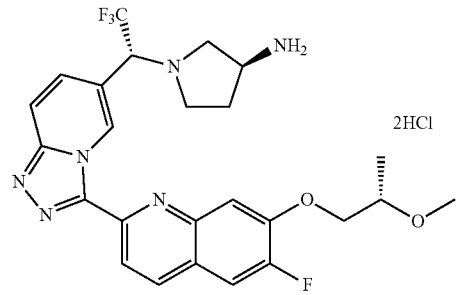 [SMILES: CO[C@@H](C)COc1cc2nc(-c3nnc4ccc([C@@H](N5CC[C@H](N)C5)C(F)(F)F)cn34)ccc2cc1F]

(S)-1-((R)-2,2,2-trifluoro-1-(3-(6-fluoro-7-((S)-2-methoxypropoxy)quinolin-2-yl)-[1,2,4]triazolo[4,3-a]pyridin-6-yl)ethyl)pyrrolidin-3-amine di-hydrochloride Prepared as described in Example 9 (Method B) using (S)-6-fluoro-7-(2-methoxypropoxy)quinoline-2-carbaldehyde as a replacement for 8-methoxyquinoline-2-carbaldehyde in Step F. LCMS APCI (+) m/z 519 (M+H).

Example 324

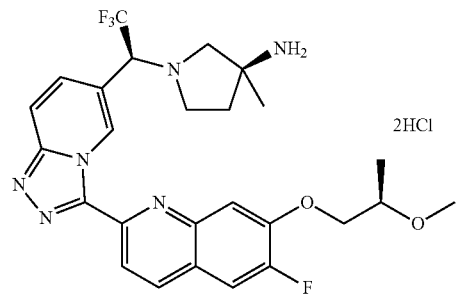 [SMILES: CO[C@H](C)COc1cc2nc(-c3nnc4ccc([C@H](N5CC[C@](C)(N)C5)C(F)(F)F)cn34)ccc2cc1F]

(S)-3-methyl-1-((S)-2,2,2-trifluoro-1-(3-(6-fluoro-7-((R)-2-methoxypropoxy)quinolin-2-yl)-[1,2,4]triazolo[4,3-a]pyridin-6-yl)ethyl)pyrrolidin-3-amine di-hydrochloride

Step A: Preparation of (R)-methyl 2-methoxypropanoate

To a stirred solution of (R)-methyl 2-hydroxypropanoate (5.00 g, 48.0 mmol) in ether (240 mL) was added Ag$_2$O (33.0 g, 144 mmol) and 4 Å molecular sieves (5 g). MeI (20.0 g, 144 mmol) were added to the mixture. The reaction was stirred at ambient temperature for 5 days. The mixture was filtered through Celite®. The filtrate was concentrated in a cold water bath under reduced pressure (300 mm Hg) to give (R)-methyl 2-methoxypropanoate as a colorless oil, which was used in the next step without further purification.

Step B: Preparation of (R)-2-methoxypropan-1-ol

To a stirred suspension of LiAlH$_4$ (1.5 g, 39 mmol) in ether (50 mL) was added dropwise a solution of crude (R)-methyl 2-methoxypropanoate (5.7 g, 48 mmol) in ether (20 ml) under nitrogen. The mixture was heated at reflux for 1 hour and then cooled to 0° C. The reaction was quenched by dropwise addition of water (1.5 mL), 15% NaOH aqueous solution (1.5 mL) and water (4.5 mL). The mixture was diluted with ether and stirred for 10 minutes. The mixture was filtered through Celite®. The filtrate was concentrated in a cold water bath under reduced pressure (300 mm Hg). The crude product was used in the next step without further purification.

Step C: Preparation of (R)-2-methoxypropyl 4-methylbenzenesulfonate

To a stirred solution of crude (R)-2-methoxypropan-1-ol (4.30 g, 47.7 mmol) in DCM (200 mL) was added Et$_3$N (10.0 mL, 71.6 mmol). A solution of toluene sulfonyl chloride (10.9 g, 57.3 mmol) in DCM (80 mL) was added dropwise at 0° C. under nitrogen. The reaction mixture was allowed to warm to ambient temperature and stirred overnight. The reaction was diluted with DCM, washed with saturated aqueous NaHCO$_3$ solution and brine, dried and concentrated. The residue was purified by flash chromatography on silica gel (hexanes:EtOAc, 10:1 to 4:1) to give (R)-2-methoxypropyl 4-methylbenzenesulfonate (6.43 g, 55% for three steps).

Step D: Preparation of (R)-6-fluoro-7-(2-methoxypropoxy)-2-methylquinoline

To a stirred mixture of 6-fluoro-2-methylquinolin-7-ol (0.200 g, 1.13 mmol), Cs$_2$CO$_3$ (0.552 g, 1.69 mmol) and NMP (2.3 mL) was added (R)-2-methoxypropyl 4-methylbenzenesulfonate (0.303 g, 1.24 mmol). The reaction mixture was heated at 80° C. for 1 hour. After cooling, the reaction was partitioned between toluene and water. The aqueous layer was extracted with toluene (2×). The combined organic layers were washed with water and brine, dried and concentrated. The residue was purified by flash chromatography on silica gel (hexanes:EtOAc, 1:1) to give (R)-6-fluoro-7-(2-methoxypropoxy)-2-methylquinoline (0.289 g, 103%).

Step E: Preparation of (R)-6-fluoro-7-(2-methoxypropoxy)quinoline-2-carbaldehyde To a solution of (R)-6-fluoro-7-(2-methoxypropoxy)-2-methylquinoline (0.281 g, 1.13 mmol) in dioxane (4 mL) and water (0.04 mL) was added SeO$_2$ (0.138 g, 1.24 mmol). The reaction mixture was heated at reflux for 3 hours. After cooling, the mixture was filtered through Celite®. The filtrate was concentrated. The residue was purified by flash chromatography on silica gel (hexanes:EtOAc, 4:1) to give (R)-6-fluoro-7-(2-methoxypropoxy)quinoline-2-carbaldehyde (0.219 g, 74%) as a solid.

Step F: Preparation of (S)-3-methyl-1-((S)-2,2,2-trifluoro-1-(3-(6-fluoro-7-((R)-2-methoxypropoxy)quinolin-2-yl)-[1,2,4]triazolo[4,3-a]pyridin-6-yl)ethyl)pyrrolidin-3-amine di-hydrochloride Prepared as described in Example 260 using (R)-6-fluoro-7-(2-methoxypropoxy)quinoline-2-carbaldehyde as a replacement for 7-(2-methoxyethoxy)quinoline-2-carbaldehyde in Step B. LCMS APCI (+) m/z 533 (M+H).

Example 325

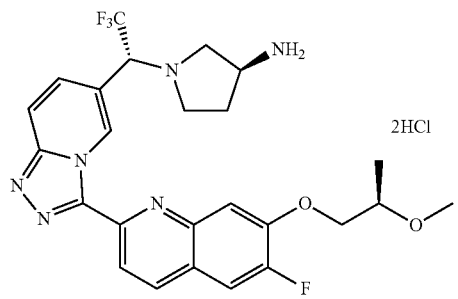 [SMILES: CO[C@H](C)COc1cc2nc(-c3nnc4ccc([C@@H](N5CC[C@H](N)C5)C(F)(F)F)cn34)ccc2cc1F]

(S)-1-((R)-2,2,2-trifluoro-1-(3-(6-fluoro-7-((R)-2-methoxypropoxy)quinolin-2-yl)-[1,2,4]triazolo[4,3-a]pyridin-6-yl)ethyl)pyrrolidin-3-amine di-hydrochloride Prepared as described in Example 9 (Method B) using (R)-6-fluoro-7-(2-methoxypropoxy)quinoline-2-carbaldehyde as a replacement for 8-methoxyquinoline-2-carbaldehyde in Step F. LCMS APCI (+) m/z 519 (M+H).

Example 326

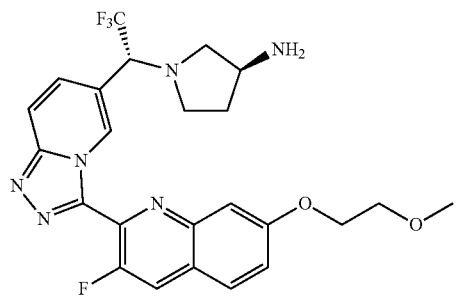 [SMILES: COCCOc1ccc2cc(F)c(-c3nnc4ccc([C@@H](N5CC[C@H](N)C5)C(F)(F)F)cn34)nc2c1]

(S)-1-((R)-2,2,2-trifluoro-1-(3-(3-fluoro-7-(2-methoxyethoxy)quinolin-2-yl)-[1,2,4]triazolo[4,3-a]pyridin-6-yl)ethyl)pyrrolidin-3-amine Step A: Preparation of (Z)-(1,2-dimethoxyvinyloxy)trimethylsilane LHMDS (301.9 mL, 317.0 mmol) was dissolved in 500 mL of THF, and cooled to −78° C. Methyl 2-methoxyacetate (28.5 ml, 288 mmol) was then added drop-wise, and the reaction mixture was allowed to stir for 30 minutes at −78° C. TMSCl (36.45 mL, 288.2 mmol) was added drop-wise, and the reaction was allowed to warm to ambient temperature. The mixture was then concentrated in vacuo (<20° C.), followed by purification on Celite® plug, and wash the Celite® was washed with petroleum ether. The crude residue was concentrated using a fit adapter (<20° C.), followed by application of a high vacuum with water bath cooling to remove TMS₂NH, affording (Z)-(1,2-dimethoxyvinyloxy)trimethylsilane (36 g, 70.87% yield) as a light yellow oil.

Step B: Preparation of (Z)-methyl 2-fluoro-3-methoxyacrylate (Z)-(1,2-Dimethoxyvinyloxy)trimethylsilane (6.00 g, 34.0 mmol) was dissolved in 200 mL of Hexanes and cooled to −78° C., followed by addition of KOtBu (7.64 g, 68.1 mmol). Dichlorofluoromethane (3.50 g, 34.0 mmol) was added over 3 minutes directly to the cooled solution. The reaction was then allowed to warm to ambient temperature over 2 hours. The reaction was then poured through Celite®, washed with Et₂O, and the combined organics concentrated in vacuo (20° C.). The crude material was then purified by flash column chromatography (10-20% ethyl acetate/Hexane) to afford (Z)-methyl 2-fluoro-3-methoxyacrylate (1.90 g, 41.6% yield) as a yellow oil. The (E) stereoisomer (360 mg) was also isolated.

Step C: Preparation of 3-fluoro-7-methoxyquinolin-2(1H)-one

To a solution of 3-methoxyaniline (1.718 mL, 15.29 mmol) in THF (12 mL) was added 2.5 N n-BuLi (5.965 mL, 14.91 mmol) in hexane at 0 C. The reaction mixture was stirred at 0 C for 5 minutes. (E)-methyl 3-fluoro-3-methoxyacrylate (1.00 g, 7.457 mmol) in THF (10 mL) was added. The mixture was stirred at 0° C. for one hour. 1 N HCl (20 mL) and ether (30 mL) were added. The organic layer was separated, washed with water, saturated sodium bicarbonate and brine, dried (sodium sulfate), filtered and concentrated under reduced pressure to give an oil. Sulfuric acid (70%; 8 mL) was added. The mixture was stirred at 56° C. (bath) for 2 hours. After cooling to ambient temperature, ice (20 g) and water (50 mL) were added. The mixture was stirred at ambient temperature for 10 minutes. The solid was collected by filtration and washed with water to give 3-fluoro-7-methoxyquinolin-2(1H)-one (1.40 g, 7.247 mmol, 97.19% yield) as a solid.

Step D: Preparation of 2-chloro-3-fluoro-7-methoxyquinoline

A mixture of 3-fluoro-7-methoxyquinolin-2(1H)-one (1.40 g, 7.25 mmol) and POCl₃ (13.3 ml, 145 mmol) was stirred at 110 C (bath) for 1 hour. The POCl₃ was removed under reduced pressure. Ethyl acetate (30 mL) and saturated sodium bicarbonate (30 mL) were added and stirred for 10 minutes. The organic layer was separated, washed with brine, dried (sodium sulfate), filtered and concentrated under reduced pressure. The crude residue was purified by flash chromatography on silica gel (10:1 hexane/ethyl acetate) to give 2-chloro-3-fluoro-7-methoxyquinoline (0.55 g, 2.60 mmol, 36% yield) as white solid.

Step E: Preparation of -fluoro-7-methoxy-2-methylquinoline

To a suspension of Cu(I)Br (1.49 g, 10.4 mmol) in THF (30 mL) was added 3M MeMgBr (6.93 ml, 20.8 mmol) in ether at −78° C. After stirring at −78° C. for 5 minutes, 2-chloro-3-fluoro-7-methoxyquinoline (0.55 g, 2.60 mmol) in THF (10 mL) was added. The reaction mixture was stirred at −78° C. for 1 hour, then allowed to warm to ambient temperature and stirred for 20 hours. Ammonium hydroxide (10 mL) was added slowly. The mixture was stirred at ambient temperature for 10 minutes, then passed through a pad of Celite® and washed with ether (50 mL). The filtrated was washed with brine (20 mL), dried (sodium sulfate), filtered and concentrated under reduced pressure. The crude residue was purified by flash chromatography 3:1 hexane/ethyl acetate to give 3-fluoro-7-methoxy-2-methylquinoline (0.255 g, 1.33 mmol, 51.3% yield) as a solid.

Step F: Preparation of 3-fluoro-2-methylquinolin-7-ol hydrobromide

To a solution of 3-fluoro-7-methoxy-2-methylquinoline (0.255 g, 1.33 mmol) in DCM (5 mL) was added BBr₃ (6.67 mL, 6.67 mmol) at 0° C. The mixture was stirred at 0° C. for 2 hours and at ambient temperature for 3 hours. Methanol (10 mL) was added slowly and the resulting mixture was stirred at ambient temperature for 1 hour. The solvent was removed under reduced pressure. The resulting solid was suspended in 1:1 ether/hexane and stirred at ambient temperature for 10 minutes. The solid was collected by filtration to give 3-fluoro-2-methylquinolin-7-ol hydrobromide (0.37 g, 1.43 mmol, 107% yield) as a solid.

Step G: Preparation of 3-fluoro-7-(2-methoxyethoxy)-2-methylquinoline

To a suspension of 3-fluoro-2-methylquinolin-7-ol hydrobromide (0.37 g, 1.43 mmol) and Cs₂CO₃ (1.08 g, 3.31 mmol) in NMP (6 mL) was added 1-bromo-2-methoxyethane (0.230 g, 1.66 mmol). The reaction mixture was stirred at ambient temperature for 24 hours. Water (10 mL) and toluene (20 mL) were added. The organic layer was separated, washed with brine, dried (sodium sulfate), filtered and concentrated under reduced pressure. The residue obtained was purified by flash chromatography on silica gel (2:1 hexane/ethyl acetate) to give 3-fluoro-7-(2-methoxyethoxy)-2-methylquinoline (0.234 g, 0.995 mmol, 90.1% yield).

Step H: Preparation of 3-fluoro-7-(2-methoxyethoxy)quinoline-2-carbaldehyde

A solution of 3-fluoro-7-(2-methoxyethoxy)-2-methylquinoline (0.234 g, 0.995 mmol) and SeO₂ (0.132 g, 1.19 mmol) in dioxane (10 mL) and water (0.1 mL) was stirred at 102° C. (bath) for 5 hours. The solid was removed by filtration. The filtrated was concentrated under reduced pressure. The residue obtained was purified by flash chromatography (1:1 hexane/ethyl acetate) to give 3-fluoro-7-(2-methoxyethoxy)quinoline-2-carbaldehyde (0.24 g, 0.963 mmol, 97% yield) as a solid.

Step I: Preparation of tert-butyl (3S)-1-((1R)-2,2,2-trifluoro-1-(3-(3-fluoro-7-(2-methoxyethoxy)quinolin-2-yl)-[1,2,4]triazolo[4,3-a]pyridin-6-yl)ethyl) pyrrolidin-3-ylcarbamate A mixture of tert-butyl (S)-1-((R)-2,2,2-trifluoro-1-(6-hydrazinylpyridin-3-yl)ethyl)pyrrolidin-3-ylcarbamate (0.080 g, 0.20 mmol) and 3-fluoro-7-(2-methoxyethoxy)quinoline-2-carbaldehyde (0.051 g, 0.20 mmol) in EtOH (10 mL) was stirred at ambient temperature for 3 hours. The solvent was removed. The residue obtained was dissolved in DCM (10 mL) and iodobenzene diacetate (0.078 g, 0.24 mmol) was added. The mixture was stirred at ambient temperature for 2 hours. The solvent was removed under reduced pressure. The residue obtained was purified by C-18 reverse phase flash chromatography (Biotage SP4 unit, C-18 25M column, 10-90% CH₃CN/water gradient; 25 CV)) to give tert-butyl (3S)-1-((1R)-2,2,2-trifluoro-1-(3-(3-fluoro-7-(2-methoxyethoxy)quinolin-2-yl)-[1,2,4]triazolo[4,3-a]pyridin-6-yl)ethyl)pyrrolidin-3-ylcarbamate (0.096 g, 0.159 mmol, 78% yield) as a solid.

Step J: Preparation of (3S)-1-((1R)-2,2,2-trifluoro-1-(3-(3-fluoro-7-(2-methoxyethoxy)quinolin-2-yl)-[1,2,4]triazolo[4,3-a]pyridin-6-yl)ethyl)pyrrolidin-3-amine To a solution of tert-butyl (3S)-1-((1R)-2,2,2-trifluoro-1-(3-(3-fluoro-7-(2-methoxyethoxy)quinolin-2-yl)-[1,2,4]triazolo[4,3-a]pyridin-6-yl)ethyl)pyrrolidin-3-ylcarbamate (0.096 g, 0.159 mmol) in DCM (0.5 mL) was added 5 N HCl (0.530 mL, 2.65 mmol) in IPA. The reaction mixture was stirred at ambient temperature for 2 hours. The solvent was removed under reduced pressure. The crude residue was suspended in ACN (5 mL) and stirred at ambient temperature for 10 minutes. The solid was collected by filtration to give (3S)-1-((1R)-2,2,2-trifluoro-1-(3-(3-fluoro-7-(2-methoxyethoxy)quinolin-2-yl)-[1,2,4]triazolo[4,3-a]pyridin-6-yl)ethyl)pyrrolidin-3-amine (0.078 g, 0.135 mmol, 85% yield) as a solid. LCMS APCI (+) m/z 505 (M+H).

Example 327

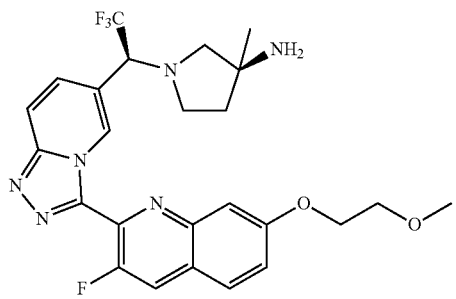 [SMILES: COCCOc1ccc2cc(F)c(-c3nnc4ccc([C@H](N5CC[C@](C)(N)C5)C(F)(F)F)cn34)nc2c1]

(S)-3-methyl-1-((R)-2,2,2-trifluoro-1-(3-(3-fluoro-7-(2-methoxyethoxy)quinolin-2-yl)-[1,2,4]triazolo[4,3-a]pyridin-6-yl)ethyl)pyrrolidin-3-amine Prepared as described in Example 327, substituting tert-butyl ((S)-3-methyl-1-((R)-2,2,2-trifluoro-1-(6-hydrazinylpyridin-3-yl)ethyl)pyrrolidin-3-yl)carbamate for 8-tert-butyl (S)-1-((R)-2,2,2-trifluoro-1-(6-hydrazinylpyridin-3-yl)ethyl)pyrrolidin-3-ylcarbamate in Step I. LCMS APCI (+) m/z 519 (M+H).

Example 328

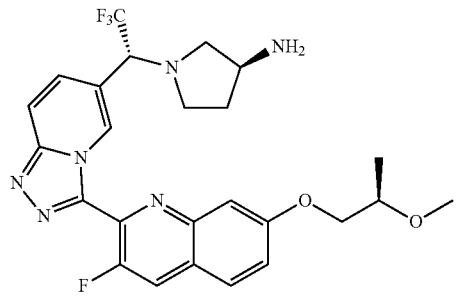 [SMILES: CO[C@H](C)COc1ccc2cc(F)c(-c3nnc4ccc([C@@H](N5CC[C@H](N)C5)C(F)(F)F)cn34)nc2c1]

(S)-1-((R)-2,2,2-trifluoro-1-(3-(3-fluoro-7-((R)-2-methoxypropoxy)quinolin-2-yl)-[1,2,4]triazolo[4,3-a]pyridin-6-yl)ethyl)pyrrolidin-3-amine Step A: Preparation of (R)-3-fluoro-7-(2-methoxypropoxy)-2-methylquinoline To a suspension of (R)-2-methoxypropyl 4-methylbenzenesulfonate (0.0530 g, 0.217 mmol) and $Cs_2CO_3$ (0.212 g, 0.651 mmol) in NMP (6 mL) was added (R)-2-methoxypropyl 4-methylbenzenesulfonate (0.053 g, 0.22 mmol). The reaction mixture was stirred at 100° C. for 2 hours. After cooling to the ambient temperature, water (10 mL) and toluene (20 mL) were added. The organic layer was separated, washed with brine, dried (sodium sulfate), filtered and concentrated under reduced pressure. The residue obtained was purified by flash chromatography on silica gel (3:1 hexane/ethyl acetate) to give (R)-3-fluoro-7-(2-methoxypropoxy)-2-methylquinoline (0.030 g, 0.120 mmol, 56% yield) as a solid.

Step B: Preparation of (R)-3-fluoro-7-(2-methoxypropoxy)quinoline-2-carbaldehyde A solution of (R)-3-fluoro-7-(2-methoxypropoxy)-2-methylquinoline (0.030 g, 0.120 mmol) and $SeO_2$ (0.0160 g, 0.144 mmol) in dioxane (10 mL) and water (0.1 mL) was stirred at 102° C. (bath) for 5 hours. The solid was removed by filtration. The mother liquor was concentrated under reduced pressure. The residue obtained was purified by flash chromatography 2.5:1 hexane/ethyl acetate to give (R)-3-fluoro-7-(2-methoxypropoxy)quinoline-2-carbaldehyde (0.024 g, 0.091 mmol, 76% yield) as a solid.

Step C: Preparation of (S)-1-((R)-2,2,2-trifluoro-1-(3-(3-fluoro-7-((R)-2-methoxypropoxy)quinolin-2-yl)-[1,2,4]triazolo[4,3-a]pyridin-6-yl)ethyl)pyrrolidin-3-amine Prepared as described in Example 327, substituting (R)-3-fluoro-7-(2-methoxypropoxy)quinoline-2-carbaldehyde for 3-fluoro-7-(2-methoxyethoxy)quinoline-2-carbaldehyde in Step I. LCMS APCI (+) m/z 519 (M+H).

What is claimed is:

1. A compound of general Formula I

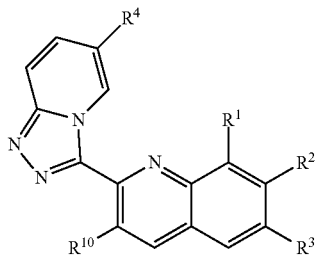

and stereoisomers, pharmaceutically acceptable salts and solvates thereof, wherein:

$R^1$ is H, halogen, CN, OH, (1-6C)alkyl, fluoro(1-6C)alkyl, difluoro(1-6C)alkyl, trifluoro(1-6C)alkyl, hydroxy(1-6C)alkyl, cyano(1-6C)alkyl, (1-3C alkoxy)(1-6C)alkyl (optionally substituted with hydroxy), di(1-3C alkoxy)(1-6C)alkyl, (1-6C)alkoxy, fluoro(1-6C)alkoxy, difluoro(1-6C)alkoxy, trifluoro(1-6C)alkoxy, hydroxy(2-6C)alkoxy, cyano(1-6C)alkoxy, (1-3C alkoxy)(2-6C)alkoxy, di(1-3C alkoxy)(2-6C)alkoxy, (3-6C cycloalkyl)methoxy, oxetanylmethoxy (optionally substituted with methyl), (1-6C alkyl)sulfanyl, —C(=O)NR$^a$R$^b$, —CH$_2$C(=O)NR$^c$R$^d$, or (3-6C)cycloalkyl optionally substituted with —CH$_2$OH or —CH$_2$O(1-4C alkyl);

R$^a$, R$^b$, R$^c$ and R$^d$ are independently selected from H and (1-4C)alkyl;

$R^2$ is H, halogen, CN, OH, (1-6C)alkyl, fluoro(1-6C)alkyl, difluoro(1-6C)alkyl, trifluoro(1-6C)alkyl, hydroxy(1-6C)alkyl, (1-3C alkoxy)(1-6C)alkyl, (1-6C)alkoxy (optionally substituted with (1-6C alkyl)C(=O)O—, amino(1-6C alkyl)C(=O)O—, or phenyl(C=O)O—), fluoro(1-6C)alkoxy, difluoro(1-6C)alkoxy, trifluoro(1-6C)alkoxy, hydroxy(2-6C)alkoxy, (1-3C alkoxy)(2-6C)alkoxy, (3-6C cycloalkyl)methoxy, (3-6C)cycloalkoxy (optionally substituted with OH), oxetanylmethoxy (optionally substituted with methyl), tetrahydropyranyloxy, (1-6C alkyl)sulfanyl, hydroxy(2-6C alkyl)sulfanyl, (1-3C alkylsulfanyl)(2-6C)alkoxy, —COOH, hetAr$^1$, —C(=O)NR$^e$R$^f$, —NR$^e$C(=O)R$^f$, oxetanyl, or cyclopropyl optionally substituted with —CH$_2$OH or —CH$_2$O(1-6C alkyl);

or $R^1$ and $R^2$ together with the atoms to which they are attached form a 5-6 membered heterocyclic ring having 1-2 ring heteroatoms independently selected from O and N, wherein said ring is optionally substituted with (1-4C)alkyl;

hetAr$^1$ is a 5-6 membered heteroaryl ring having one or two ring nitrogen atoms and optionally substituted with one or more groups selected from (1-6C)alkyl;

R$^e$ and R$^f$ are independently H, (1-6C)alkyl or cyclopropyl optionally substituted with (1-4C)alkyl;

$R^3$ is H, halogen or (1-6C)alkyl;

$R^4$ is

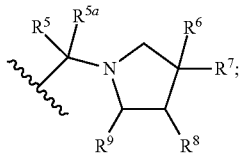

$R^5$ is CF$_3$, CH$_2$F, CHF$_2$, methyl or ethyl;

$R^{5a}$ is H or methyl;

or $R^5$ and $R^{5a}$ together with the atom to which they are attached form a cyclopropyl ring;

$R^6$ is H, NH$_2$, OH, (1-6C alkyl)NH—, fluoro(1-6C alkyl)NH—, hydroxy(1-6C alkyl)NH—, (3-6C cycloalkyl)CH$_2$NH—, (1-6C alkyl)C(=O)NH—, (1-6C alkyl)OC(=O)NH— (optionally substituted with 5-methyl-2-oxo-1,3-dioxol-4-yl) or amino(1-6C)alkyl-;

$R^7$ is H, (1-6C)alkyl, fluoro(1-6C)alkyl or hydroxy(1-6C)alkyl;

or $R^6$ and $R^7$ together with the atom to which they are attached form a 5-6 membered spirocyclic heterocycle having a ring nitrogen atom;

$R^8$ is H, halogen, OH, or (1-6C)alkoxy, or $R^6$ and $R^8$ together with the carbon atoms to which they are attached form a cyclopropyl ring optionally substituted with NH$_2$;

$R^9$ is H, or $R^6$ and $R^9$ together form a linking group having the formula —CH$_2$NH— which links the carbon atoms to which they are attached; and $R^{10}$ is H or halogen.

2. A compound according to claim 1, wherein:

$R^1$ is H, halogen, CN, OH, (1-6C)alkyl, fluoro(1-6C)alkyl, difluoro(1-6C)alkyl, trifluoro(1-6C)alkyl, hydroxy(1-6C)alkyl, cyano(1-6C)alkyl, (1-3C alkoxy)(1-6C)alkyl (optionally substituted with hydroxy), di(1-3C alkoxy)(1-6C)alkyl, (1-6C)alkoxy, fluoro(1-6C)alkoxy, difluoro(1-6C)alkoxy, trifluoro(1-6C)alkoxy, hydroxy(2-6C)alkoxy, cyano(1-6C)alkoxy, (1-3C alkoxy)(2-6C)alkoxy, di(1-3C alkoxy)(2-6C)alkoxy, (3-6C cycloalkyl)methoxy, oxetanylmethoxy (optionally substituted with methyl), (1-6C alkyl)sulfanyl, —C(=O)NR$^a$R$^b$, —CH$_2$C(=O)NR$^c$R$^d$, or (3-6C)cycloalkyl optionally substituted with —CH$_2$OH or —CH$_2$O(1-4C alkyl);

R$^a$, R$^b$, R$^c$ and R$^d$ are independently selected from H and (1-4C)alkyl;

$R^2$ is H, halogen, CN, OH, (1-6C)alkyl, fluoro(1-6C)alkyl, difluoro(1-6C)alkyl, trifluoro(1-6C)alkyl, hydroxy(1-6C)alkyl, (1-3C alkoxy)(1-6C)alkyl, (1-6C)alkoxy (optionally substituted with (1-6C alkyl)C(=O)O— or amino(1-6C alkyl)C(=O)O—), fluoro(1-6C)alkoxy, difluoro(1-6C)alkoxy, trifluoro(1-6C)alkoxy, hydroxy(2-6C)alkoxy, (1-3C alkoxy)(2-6C)alkoxy, (3-6C cycloalkyl)methoxy, oxetanylmethoxy (optionally substituted with methyl), tetrahydropyranyloxy, (1-6C alkyl)sulfanyl, hydroxy(2-6C alkyl)sulfanyl, (1-3C alkylsulfanyl)(2-6C)alkoxy, —COOH, hetAr$^1$, —C(=O)NR$^e$R$^f$, —NR$^e$C(=O)R$^f$, or cyclopropyl optionally substituted with —CH$_2$OH or —CH$_2$O(1-6C alkyl);

or $R^1$ and $R^2$ together with the atoms to which they are attached form a 5-6 membered heterocyclic ring having 1-2 ring heteroatoms independently selected from O and N, wherein said ring is optionally substituted with (1-4C)alkyl;

hetAr¹ is a 5-6 membered heteroaryl ring having one or two ring nitrogen atoms and optionally substituted with one or more groups selected from (1-6C)alkyl;

R$^e$ and R$^f$ are independently H, (1-6C)alkyl or cyclopropyl optionally substituted with (1-4C)alkyl;

R³ is H, halogen or (1-6C)alkyl;

R⁴ is

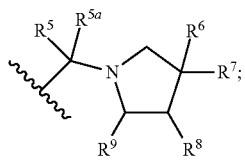

R⁵ is CF$_3$, CH$_2$F, CHF$_2$, methyl or ethyl;

R$^{5a}$ is H or methyl;

or R⁵ and R$^{5a}$ together with the atom to which they are attached form a cyclopropyl ring;

R⁶ is H, —NH$_2$, OH, (1-6C alkyl)NH—, fluoro(1-6C alkyl)NH—, hydroxy(1-6C alkyl)NH—, (3-6C cycloalkyl)CH$_2$NH—, (1-6C alkyl)C(=O)NH—, (1-6C alkyl)OC(=O)NH— or amino(1-6C)alkyl-;

R⁷ is H, (1-6C)alkyl, fluoro(1-6C)alkyl or hydroxy(1-6C) alkyl;

or R⁶ and R⁷ together with the atom to which they are attached form a 5-6 membered spirocyclic heterocycle having a ring nitrogen atom;

R⁸ is H, halogen, OH, or (1-6C)alkoxy, or

R⁶ and R⁸ together with the carbon atoms to which they are attached form a cyclopropyl ring optionally substituted with NH$_2$;

R⁹ is H, or

R⁶ and R⁹ together form a linking group having the formula —CH$_2$NH— which links the carbon atoms to which they are attached; and R¹⁰ is H.

3. A compound of claim 1, wherein R¹ is selected from H, (1-6C)alkyl, (3-6C)cycloalkyl optionally substituted with —CH$_2$OH or —CH$_2$O(1-4C alkyl), (1-6C)alkoxy, trifluoro (1-6C)alkoxy, hydroxy(2-6C)alkoxy, (1-3C alkoxy)(2-6C) alkoxy, and (3-6C)cycloalkylmethoxy.

4. A compound of claim 3, wherein R¹ is selected from H, methyl, ethyl, isopropyl, tert-butyl, cyclopropyl, methoxy, ethoxy, isopropoxy, trifluoromethoxy, 2-hydroxyethoxy, 2-hydroxypropoxy, 3-hydroxypropoxy, 2-methoxyethoxy, 3-methoxypropoxy, 2-methoxypropoxy, 3-methoxyprop-2-oxy, 2-ethoxyethoxy, 1,3-dimethoxypropan-2-yloxy and cyclopropylmethoxy.

5. A compound of claim 4, wherein R¹ is H.

6. A compound of claim 3, wherein R¹ (1-3C alkoxy)(2-6C)alkoxy.

7. A compound according to claim 1, wherein R² is selected from H, (1-3C alkoxy)(1-6C)alkyl, hydroxy(2-6C)alkoxy, and (1-6C)alkoxy which is optionally substituted with (1-6C alkyl)C(=O)O— or amino(1-6C alkyl)C(=O)O—.

8. A compound according to claim 7, wherein R² is selected from H, 2-methoxyethoxy, 3-methoxyprop-2-oxy, 2-methoxypropoxy, 2-ethyoxyethoxy, and 2-hydroxyethoxy.

9. A compound according to claim 8, wherein R² is H.

10. A compound according to claim 1, wherein R² is selected from halogen, CN, OH, (1-6C)alkyl, fluoro(1-6C)alkyl, difluoro(1-6C)alkyl, trifluoro(1-6C)alkyl, hydroxy(1-6C)alkyl, fluoro(1-6C)alkoxy, difluoro(1-6C)alkoxy, trifluoro(1-6C)alkoxy, (1-3C alkoxy)(2-6C)alkoxy, (3-6C cycloalkyl)methoxy, oxetanylmethoxy (optionally substituted with methyl), tetrahydropyranyloxy, (1-6C alkyl)sulfanyl, hydroxy(2-6C alkyl)sulfanyl, (1-3C alkylsulfanyl)(2-6C)alkoxy, —COOH, hetAr¹, —C(=O)NR$^e$R$^f$, —NR$^e$C(=O)R$^f$, and cyclopropyl optionally substituted with —CH$_2$OH or —CH$_2$O(1-6C alkyl).

11. A compound according to claim 1, wherein R³ is H.

12. A compound according to claim 1, wherein R³ is F.

13. A compound according to claim 1, wherein R⁵ is CF$_3$, CH$_2$F, CHF$_2$, methyl or ethyl and R$^{5a}$ is H.

14. A compound according to claim 13, wherein R⁵ is CF$_3$ and R$^{5a}$ is H.

15. A compound according to claim 1, wherein R⁶ is NH$_2$.

16. A compound according to claim 1, wherein R⁷ is H.

17. A compound according to claim 1, wherein R⁸ is H.

18. A compound according to claim 1, wherein R⁹ is H.

19. A compound according to claim 1, wherein R¹⁰ is H.

20. A compound of claim 1, selected from (3S)-1-(2,2,2-trifluoro-1-(3-(8-methoxyquinolin-2-yl)-[1,2,4]triazolo[4,3-a]pyridin-6-yl)ethyl)pyrrolidin-3-amine;

(3S)-1-(1-(3-(7-bromoquinolin-2-yl)-[1,2,4]triazolo[4,3-a]pyridin-6-yl)-2,2,2-trifluoroethyl)pyrrolidin-3-amine;

(3S)-1-(1-(3-(7-cyclopropylquinolin-2-yl)-[1,2,4]triazolo[4,3-a]pyridin-6-yl)-2,2,2-trifluoroethyl)pyrrolidin-3-amine;

(3S)-1-(2,2,2-trifluoro-1-(3-(7-(1-methyl-1H-pyrazol-4-yl)quinolin-2-yl)-[1,2,4]triazolo[4,3-a]pyridin-6-yl)ethyl)pyrrolidin-3-amine;

(3S)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-amine;

8-methoxy-2-(6-(2,2,2-trifluoro-1-(pyrrolidin-1-yl)ethyl)-[1,2,4]triazolo[4,3-a]pyridin-3-yl)quinolone;

(3S)-1-(2,2,2-trifluoro-1-(3-(8-methoxyquinolin-2-yl)-[1,2,4]triazolo[4,3-a]pyridin-6-yl)ethyl)pyrrolidin-3-ol;

(S)-1-((S)-2,2,2-trifluoro-1-(3-(8-methoxyquinolin-2-yl)-[1,2,4]triazolo[4,3-a]pyridin-6-yl)ethyl)pyrrolidin-3-amine;

(S)-1-((R)-2,2,2-trifluoro-1-(3-(8-methoxyquinolin-2-yl)-[1,2,4]triazolo[4,3-a]pyridin-6-yl)ethyl)pyrrolidin-3-amine (S)-1-((R)-2,2,2-trifluoro-1-(3-(8-methoxyquinolin-2-yl)-[1,2,4]triazolo[4,3-a]pyridin-6-yl)ethyl)pyrrolidin-3-amine;

(S)-1-((S)-1-(3-(8-(cyclopropylmethoxy)quinolin-2-yl)-[1,2,4]triazolo[4,3-a]pyridin-6-yl)-2,2,2-trifluoroethyl)pyrrolidin-3-amine;

(S)-1-((R)-1-(3-(8-(cyclopropylmethoxy)quinolin-2-yl)-[1,2,4]triazolo[4,3-a]pyridin-6-yl)-2,2,2-trifluoroethyl)pyrrolidin-3-amine;

(S)-1-((S)-1-(3-(7-cyclopropylquinolin-2-yl)-[1,2,4]triazolo[4,3-a]pyridin-6-yl)-2,2,2-trifluoroethyl)pyrrolidin-3-amine;

(S)-1-((R)-1-(3-(7-cyclopropylquinolin-2-yl)-[1,2,4]triazolo[4,3-a]pyridin-6-yl)-2,2,2-trifluoroethyl)pyrrolidin-3-amine;

(S)-1-((S)-2,2,2-trifluoro-1-(3-(7-(1-methyl-1H-pyrazol-4-yl)quinolin-2-yl)-[1,2,4]triazolo[4,3-a]pyridin-6-yl) ethyl)pyrrolidin-3-amine;

(S)-1-((R)-2,2,2-trifluoro-1-(3-(7-(1-methyl-1H-pyrazol-4-yl)quinolin-2-yl)-[1,2,4]triazolo[4,3-a]pyridin-6-yl) ethyl)pyrrolidin-3-amine;

(3R)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-amine;

(3S)-1-(1-(3-(8-tert-butylquinolin-2-yl)-[1,2,4]triazolo[4,3-a]pyridin-6-yl)ethyl)pyrrolidin-3-amine;

(3S)-1-(2,2,2-trifluoro-1-(3-(7-(pyridin-3-yl)quinolin-2-yl)-[1,2,4]triazolo[4,3-a]pyridin-6-yl)ethyl)pyrrolidin-3-amine;

(3S,4S)-1-(2,2,2-trifluoro-1-(3-(8-methoxyquinolin-2-yl)-[1,2,4]triazolo[4,3-a]pyridin-6-yl)ethyl)pyrrolidine-3,4-diol;

(3S)-1-(1-(3-(8-(Cyclopropylmethoxy)quinolin-2-yl)-[1,2,4]triazolo[4,3-a]pyridin-6-yl)-2,2,2-trifluoroethyl)-N-methylpyrrolidin-3-amine;

((3R)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-yl)methanamine;

(R)-1-((R)-1-(3-(8-(cyclopropylmethoxy)quinolin-2-yl)-[1,2,4]triazolo[4,3-a]pyridin-6-yl)-2,2,2-trifluoroethyl)pyrrolidin-3-amine;

(R)-1-((S)-1-(3-(8-(cyclopropylmethoxy)quinolin-2-yl)-[1,2,4]triazolo[4,3-a]pyridin-6-yl)-2,2,2-trifluoroethyl)pyrrolidin-3-amine;

((3S)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-yl)methanamine;

2-(6-(1-((1R,4R)-2,5-diazabicyclo[2.2.1]heptan-2-yl)-2,2,2-trifluoroethyl)-[1,2,4]triazolo[4,3-a]pyridin-3-yl)-8-(cyclopropylmethoxy)quinoline;

(1R,5S,6S)-3-(1-(3-(8-(cyclopropylmethoxy)quinolin-2-yl)-[1,2,4]triazolo[4,3-a]pyridin-6-yl)-2,2,2-trifluoroethyl)-3-azabicyclo[3.1.0]hexanesan-6-amine;

1-(1-(3-(8-(cyclopropylmethoxy)quinolin-2-yl)-[1,2,4]triazolo[4,3-a]pyridin-6-yl)-2,2,2-trifluoroethyl)-3-methylpyrrolidin-3-amine;

2-(6-(1-(3-amino-3-methylpyrrolidin-1-yl)-2,2,2-trifluoroethyl)-[1,2,4]triazolo[4,3-a]pyridin-3-yl)quinolin-8-ol;

(3S)-1-(2,2,2-trifluoro-1-(3-(7-(trifluoromethyl)quinolin-2-yl)-[1,2,4]triazolo[4,3-a]pyridin-6-yl)ethyl)pyrrolidin-3-amine;

2-(6-(1-((S)-3-aminopyrrolidin-1-yl)-2,2,2-trifluoroethyl)-[1,2,4]triazolo[4,3-a]pyridin-3-yl)-N-isopropylquinoline-7-carboxamide;

(S)-1-((R)-2,2,2-trifluoro-1-(3-(8-isopropoxyquinolin-2-yl)-[1,2,4]triazolo[4,3-a]pyridin-6-yl)ethyl)pyrrolidin-3-amine;

(3S)-1-(1-(3-(8-(cyclopropylmethoxy)quinolin-2-yl)-[1,2,4]triazolo[4,3-a]pyridin-6-yl)-2,2,2-trifluoroethyl)-N-isopropylpyrrolidin-3-amine;

(3S)-1-(1-(3-(8-((R)-1-methoxypropan-2-yloxy)quinolin-2-yl)-[1,2,4]triazolo[4,3-a]pyridin-6-yl)ethyl)pyrrolidin-3-amine;

2-(6-((R)-1-((S)-3-aminopyrrolidin-1-yl)-2,2,2-trifluoroethyl)-[1,2,4]triazolo[4,3-a]pyridin-3-yl)-N-isopropylquinoline-7-carboxamide;

2-(6-((R)-1-((S)-3-aminopyrrolidin-1-yl)-2,2,2-trifluoroethyl)-[1,2,4]triazolo[4,3-a]pyridin-3-yl)-N,N-dimethylquinoline-7-carboxamide;

(S)—N-methyl-1-((R)-2,2,2-trifluoro-1-(3-(8-isopropoxyquinolin-2-yl)-[1,2,4]triazolo[4,3-a]pyridin-6-yl)ethyl)pyrrolidin-3-amine;

(S)-1-((R)-1-(3-(8-ethylquinolin-2-yl)-[1,2,4]triazolo[4,3-a]pyridin-6-yl)-2,2,2-trifluoroethyl)pyrrolidin-3-amine;

2-(6-((R)-1-((S)-3-aminopyrrolidin-1-yl)-2,2,2-trifluoroethyl)-[1,2,4]triazolo[4,3-a]pyridin-3-yl)-N-ethylquinoline-7-carboxamide;

(S)-1-((R)-1-(3-(8-cyclopropylquinolin-2-yl)-[1,2,4]triazolo[4,3-a]pyridin-6-yl)-2,2,2-trifluoroethyl)pyrrolidin-3-amine;

(S)-1-((R)-2,2,2-trifluoro-1-(3-(8-(trifluoromethoxy)quinolin-2-yl)-[1,2,4]triazolo[4,3-a]pyridin-6-yl)ethyl)pyrrolidin-3-amine;

(S)-1-((R)-2,2,2-trifluoro-1-(3-(8-isopropylquinolin-2-yl)-[1,2,4]triazolo[4,3-a]pyridin-6-yl)ethyl)pyrrolidin-3-amine;

2-(6-((R)-1-((S)-3-aminopyrrolidin-1-yl)-2,2,2-trifluoroethyl)-[1,2,4]triazolo[4,3-a]pyridin-3-yl)-N-methylquinoline-7-carboxamide;

(S)-1-((R)-1-(3-(8-(cyclopropylmethoxy)quinolin-2-yl)-[1,2,4]triazolo pyridin-6-yl)-2,2,2-trifluoroethyl)-N-methylpyrrolidin-3-amine;

N-(2-(6-(1-((S)-3-aminopyrrolidin-1-yl)-2,2,2-trifluoroethyl)-[1,2,4]triazolo[4,3-a]pyridin-3-yl)quinolin-7-yl)isobutyramide;

(S)-1-((R)-1-(3-(8-tert-butylquinolin-2-yl)-[1,2,4]triazolo[4,3-a]pyridin-6-yl)-2,2,2-trifluoroethyl)pyrrolidin-3-amine;

2-(6-((R)-1-((S)-3-aminopyrrolidin-1-yl)-2,2,2-trifluoroethyl)-[1,2,4]triazolo[4,3-a]pyridin-3-yl)-N-tert-butylquinoline-7-carboxamide;

(R)-1-((R)-1-(3-(8-cyclopropylquinolin-2-yl)-[1,2,4]triazolo[4,3-a]pyridin-6-yl)-2,2,2-trifluoroethyl)pyrrolidin-3-amine;

2-(6-((S)-1-((S)-3-aminopyrrolidin-1-yl)-2,2,2-trifluoroethyl)-[1,2,4]triazolo[4,3-a]pyridin-3-yl)-N-isopropylquinoline-7-carboxamide;

2-(6-((R)-1-((R)-3-aminopyrrolidin-1-yl)-2,2,2-trifluoroethyl)-[1,2,4]triazolo[4,3-a]pyridin-3-yl)-N-isopropylquinoline-7-carboxamide;

N-((3S)-1-(1-(3-(8-(cyclopropylmethoxy)quinolin-2-yl)-[1,2,4]triazolo[4,3-a]pyridin-6-yl)-2,2,2-trifluoroethyl)pyrrolidin-3-yl)acetamide;

(S)-1-((S)-1-(3-(8-cyclopropylquinolin-2-yl)-[1,2,4]triazolo[4,3-a]pyridin-6-yl)-2,2,2-trifluoroethyl)pyrrolidin-3-amine;

2-(6-((S)-1-((R)-3-aminopyrrolidin-1-yl)-2,2,2-trifluoroethyl)-[1,2,4]triazolo[4,3-a]pyridin-3-yl)-N-isopropylquinoline-7-carboxamide;

2-(6-((R)-1-((S)-3-aminopyrrolidin-1-yl)-2,2,2-trifluoroethyl)-[1,2,4]triazolo[4,3-a]pyridin-3-yl)-N-(1-methylcyclopropyl)quinoline-7-carboxamide;

2-(6-((R)-1-((R)-3-aminopyrrolidin-1-yl)-2,2,2-trifluoroethyl)-[1,2,4]triazolo[4,3-a]pyridin-3-yl)-N-tert-butylquinoline-7-carboxamide;

2-(6-((R)-1-((R)-3-aminopyrrolidin-1-yl)-2,2,2-trifluoroethyl)-[1,2,4]triazolo[4,3-a]pyridin-3-yl)-N-(1-methylcyclopropyl)quinoline-7-carboxamide;

(R)-1-((S)-1-(3-(8-cyclopropylquinolin-2-yl)-[1,2,4]triazolo[4,3-a]pyridin-6-yl)-2,2,2-trifluoroethyl)pyrrolidin-3-amine;

N-isopropyl-2-(6-((R)-2,2,2-trifluoro-1-((S)-3-(methylamino)pyrrolidin-1-yl)ethyl)-[1,2,4]triazolo[4,3-a]pyridin-3-yl)quinoline-7-carboxamide;

N N-tert-butyl-2-(6-((R)-2,2,2-trifluoro-1-((S)-3-(methylamino)pyrrolidin-1-yl)ethyl)-[1,2,4]triazolo[4,3-a]pyridin-3-yl)quinoline-7-carboxamide;

2-(6-((R)-1-((R)-3-aminopyrrolidin-1-yl)-2,2,2-trifluoroethyl)-[1,2,4]triazolo[4,3-a]pyridin-3-yl)-N-tert-pentylquinoline-7-carboxamide;

(S)-1-((R)-1-(3-(8-cyclopropyl-7-fluoroquinolin-2-yl)-[1,2,4]triazolo[4,3-a]pyridin-6-yl)-2,2,2-trifluoroethyl)pyrrolidin-3-amine;

(R)-1-((R)-1-(3-(7-cyclopropylquinolin-2-yl)-[1,2,4]triazolo[4,3-a]pyridin-6-yl)-2,2,2-trifluoroethyl)pyrrolidin-3-amine;

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)-8-tert-butylquinoline;

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)-7-fluoroquinoline;

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)-7-chloroquinoline;

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)-8-cyclopropylquinoline;

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)-8-ethylquinoline;

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)-8-(cyclopropylmethoxy)quinoline;

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)-7-bromoquinoline;

(S)-1-((R)-1-(3-(7-cyclopropyl-8-methoxyquinolin-2-yl)-[1,2,4]triazolo[4,3-a]pyridin-6-yl)-2,2,2-trifluoroethyl)pyrrolidin-3-amine;

N-(2-(6-((R)-1-((S)-3-aminopyrrolidin-1-yl)-2,2,2-trifluoroethyl)-[1,2,4]triazolo[4,3-a]pyridin-3-yl)quinolin-7-yl)isobutyramide;

N-(2-(6-((R)-1-((S)-3-aminopyrrolidin-1-yl)-2,2,2-trifluoroethyl)-[1,2,4]triazolo[4,3-a]pyridin-3-yl)quinolin-7-yl)pivalamide;

(3R,4R)-1-((R)-2,2,2-trifluoro-1-(3-(8-isopropoxyquinolin-2-yl)-[1,2,4]triazolo[4,3-a]pyridin-6-yl)ethyl)pyrrolidine-3,4-diol;

(3R,4R)-1-((R)-1-(3-(8-ethylquinolin-2-yl)-[1,2,4]triazolo[4,3-a]pyridin-6-yl)-2,2,2-trifluoroethyl)pyrrolidine-3,4-diol;

(3R,4R)-1-((R)-1-(3-(8-tert-butylquinolin-2-yl)-[1,2,4]triazolo[4,3-a]pyridin-6-yl)-2,2,2-trifluoroethyl)pyrrolidine-3,4-diol;

2-(6-((R)-1-((S)-3-aminopyrrolidin-1-yl)-2,2,2-trifluoroethyl)-[1,2,4]triazolo[4,3-a]pyridin-3-yl)-8-isopropoxyquinoline-7-carbonitrile;

2-(6-((S)-1-((1S,4S)-2,5-diazabicyclo[2.2.1]heptan-2-yl)-2,2,2-trifluoroethyl)-[1,2,4]triazolo[4,3-a]pyridin-3-yl)-8-(cyclopropylmethoxy)quinoline;

2-(6-((S)-1-((1S,4S)-2,5-diazabicyclo[2.2.1]heptan-2-yl)-2,2,2-trifluoroethyl)-[1,2,4]triazolo[4,3-a]pyridin-3-yl)-7-cyclopropylquinoline;

(3R,4R)-1-((R)-1-(3-(8-cyclopropylquinolin-2-yl)-[1,2,4]triazolo[4,3-a]pyridin-6-yl)-2,2,2-trifluoroethyl)pyrrolidine-3,4-diol;

(S)-1-((R)-1-(3-(8-ethoxyquinolin-2-yl)-[1,2,4]triazolo[4,3-a]pyridin-6-yl)-2,2,2-trifluoroethyl)pyrrolidin-3-amine;

(S)—N-(2-fluoroethyl)-1-((R)-2,2,2-trifluoro-1-(3-(8-methoxyquinolin-2-yl)-[1,2,4]triazolo[4,3-a]pyridin-6-yl)ethyl)pyrrolidin-3-amine;

(S)—N-(2-fluoroethyl)-1-((R)-2,2,2-trifluoro-1-(3-(8-isopropoxyquinolin-2-yl)-[1,2,4]triazolo[4,3-a]pyridin-6-yl)ethyl)pyrrolidin-3-amine;

(3R,4R)-1-((S)-2,2,2-trifluoro-1-(3-(8-isopropoxyquinolin-2-yl)-[1,2,4]triazolo[4,3-a]pyridin-6-yl)ethyl)pyrrolidine-3,4-diol;

2-(6-((R)-1-((S)-3-aminopyrrolidin-1-yl)-2,2,2-trifluoroethyl)-[1,2,4]triazolo[4,3-a]pyridin-3-yl)-N-tert-butyl-8-cyclopropylquinoline-7-carboxamide;

2-(6-((R)-1-((S)-3-aminopyrrolidin-1-yl)-2,2,2-trifluoroethyl)-[1,2,4]triazolo[4,3-a]pyridin-3-yl)quinoline-7-carbonitrile;

2-(6-((S)-1-((R)-3-(tert-butoxycarbonylamino)pyrrolidin-1-yl)-2,2,2-trifluoroethyl)-[1,2,4]triazolo[4,3-a]pyridin-3-yl)quinoline-7-carboxylic acid;

(S)-1-((R)-2,2,2-trifluoro-1-(3-(6-fluoro-8-isopropoxyquinolin-2-yl)-[1,2,4]triazolo[4,3-a]pyridin-6-yl)ethyl)pyrrolidin-3-amine;

2-(6-((R)-1-((S)-3-aminopyrrolidin-1-yl)-2,2,2-trifluoroethyl)-[1,2,4]triazolo[4,3-a]pyridin-3-yl)-N-isopropylquinoline-8-carboxamide;

2-(6-((R)-1-((S)-3-aminopyrrolidin-1-yl)-2,2,2-trifluoroethyl)-[1,2,4]triazolo[4,3-a]pyridin-3-yl)quinoline-8-carbonitrile;

2-(6-((R)-1-((1S,4S)-2,5-diazabicyclo[2.2.1]heptan-2-yl)-2,2,2-trifluoroethyl)-[1,2,4]triazolo[4,3-a]pyridin-3-yl)quinoline-8-carbonitrile;

(R)-3-methyl-1-((S)-2,2,2-trifluoro-1-(3-(8-isopropoxyquinolin-2-yl)-[1,2,4]triazolo[4,3-a]pyridin-6-yl)ethyl)pyrrolidin-3-amine;

(R)-3-methyl-1-((R)-2,2,2-trifluoro-1-(3-(8-isopropoxyquinolin-2-yl)-[1,2,4]triazolo[4,3-a]pyridin-6-yl)ethyl)pyrrolidin-3-amine;

(S)-3-methyl-1-((S)-2,2,2-trifluoro-1-(3-(8-isopropoxyquinolin-2-yl)-[1,2,4]triazolo[4,3-a]pyridin-6-yl)ethyl)pyrrolidin-3-amine;

(S)-3-methyl-1-((R)-2,2,2-trifluoro-1-(3-(8-isopropoxyquinolin-2-yl)-[1,2,4]triazolo[4,3-a]pyridin-6-yl)ethyl)pyrrolidin-3-amine;

(R)-1-((S)-1-(3-(8-cyclopropylquinolin-2-yl)-[1,2,4]triazolo[4,3-a]pyridin-6-yl)-2,2,2-trifluoroethyl)-3-methylpyrrolidin-3-amine;

(R)-1-((R)-1-(3-(8-cyclopropylquinolin-2-yl)-[1,2,4]triazolo[4,3-a]pyridin-6-yl)-2,2,2-trifluoroethyl)-3-methylpyrrolidin-3-amine;

(S)-1-((S)-1-(3-(8-cyclopropylquinolin-2-yl)-[1,2,4]triazolo[4,3-a]pyridin-6-yl)-2,2,2-trifluoroethyl)-3-methylpyrrolidin-3-amine;

(S)-1-((R)-1-(3-(8-cyclopropylquinolin-2-yl)-[1,2,4]triazolo[4,3-a]pyridin-6-yl)-2,2,2-trifluoroethyl)-3-methylpyrrolidin-3-amine;

(S)-1-((R)-2,2,2-trifluoro-1-(3-(6-fluoro-8-(2-methoxyethoxy)quinolin-2-yl)-[1,2,4]triazolo[4,3-a]pyridin-6-yl)ethyl)pyrrolidin-3-amine;

2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)-2-methylpropanenitrile;

2-((S)-1-((R)-1-(3-(8-tert-butylquinolin-2-yl)-[1,2,4]triazolo[4,3-a]pyridin-6-yl)-2,2,2-trifluoroethyl)pyrrolidin-3-ylamino)ethanol;

2-((S)-1-((R)-2,2,2-trifluoro-1-(3-(8-isopropoxyquinolin-2-yl)-[1,2,4]triazolo[4,3-a]pyridin-6-yl)ethyl)pyrrolidin-3-ylamino)ethanol;

2-((S)-1-((R)-2,2,2-trifluoro-1-(3-(6-fluoro-8-isopropoxyquinolin-2-yl)-[1,2,4]triazolo[4,3-a]pyridin-6-yl)ethyl)pyrrolidin-3-ylamino)ethanol;

(R)-1-((S)-2,2,2-trifluoro-1-(3-(8-isopropoxyquinolin-2-yl)-[1,2,4]triazolo[4,3-a]pyridin-6-yl)ethyl)pyrrolidin-3-ol;

(R)-1-((S)-2,2,2-trifluoro-1-(3-(8-isopropoxyquinolin-2-yl)-[1,2,4]triazolo[4,3-a]pyridin-6-yl)ethyl)pyrrolidin-3-ol;

(S)-1-((R)-2,2,2-trifluoro-1-(3-(8-(1-methoxy-2-methylpropan-2-yl)quinolin-2-yl)-[1,2,4]triazolo[4,3-a]pyridin-6-yl)ethyl)pyrrolidin-3-amine;

N-(2-(6-((R)-2,2,2-trifluoro-1-((S)-3-hydroxypyrrolidin-1-yl)ethyl)-[1,2,4]triazolo[4,3-a]pyridin-3-yl)quinolin-7-yl)isobutyramide;

N-(2-(6-((R)-2,2,2-trifluoro-1-((S)-3-hydroxypyrrolidin-1-yl)ethyl)-[1,2,4]triazolo[4,3-a]pyridin-3-yl)quinolin-7-yl)pivalamide;

(S)-1-((R)-2,2,2-trifluoro-1-(3-(7-fluoro-8-(2-methoxyethoxy)quinolin-2-yl)-[1,2,4]triazolo[4,3-a]pyridin-6-yl)ethyl)pyrrolidin-3-amine;

(S)-1-((R)-2,2,2-trifluoro-1-(3-(7-fluoro-8-isopropoxyquinolin-2-yl)-[1,2,4]triazolo[4,3-a]pyridin-6-yl)ethyl)pyrrolidin-3-amine;

(S)-1-((R)-1-(3-(8-(1,3-dimethoxy-2-methylpropan-2-yl)quinolin-2-yl)-[1,2,4]triazolo[4,3-a]pyridin-6-yl)-2,2,2-trifluoroethyl)pyrrolidin-3-amine;

(S)-1-((R)-2,2,2-trifluoro-1-(3-(8-(2-methoxyethyl)quinolin-2-yl)-[1,2,4]triazolo[4,3-a]pyridin-6-yl)ethyl)pyrrolidin-3-amine;

(S)-1-((R)-2,2,2-trifluoro-1-(3-(8-(1-(methoxymethyl)cyclopropyl)quinolin-2-yl)-[1,2,4]triazolo[4,3-a]pyridin-6-yl)ethyl)pyrrolidin-3-amine;

(S)-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-amine;

(1-(2-(6-((R)-1-((S)-3-aminopyrrolidin-1-yl)-2,2,2-trifluoroethyl)-[1,2,4]triazolo[4,3-a]pyridin-3-yl)quinolin-8-yl)cyclopropyl)methanol;

(S)-1-((R)-2,2,2-trifluoro-1-(3-(6-fluoro-8-methoxyquinolin-2-yl)-[1,2,4]triazolo[4,3-a]pyridin-6-yl)ethyl)pyrrolidin-3-amine;

(S)-1-((R)-2,2,2-trifluoro-1-(3-(7-isopropoxy-8-methylquinolin-2-yl)-[1,2,4]triazolo[4,3-a]pyridin-6-yl)ethyl)pyrrolidin-3-amine;

(S)-1-((R)-2,2,2-trifluoro-1-(3-(7-(2-methoxyethoxy)-8-methylquinolin-2-yl)-[1,2,4]triazolo[4,3-a]pyridin-6-yl)ethyl)pyrrolidin-3-amine;

(3S)-1-((1R)-2,2,2-trifluoro-1-(3-(8-(1-methoxypropan-2-yloxy)quinolin-2-yl)-[1,2,4]triazolo[4,3-a]pyridin-6-yl)ethyl)pyrrolidin-3-amine;

(S)-1-((R)-2,2,2-trifluoro-1-(3-(6-fluoro-7-isopropoxyquinolin-2-yl)-[1,2,4]triazolo[4,3-a]pyridin-6-yl)ethyl)pyrrolidin-3-amine;

(S)-1-((R)-2,2,2-trifluoro-1-(3-(6-fluoro-7-(2-methoxyethoxy)quinolin-2-yl)-[1,2,4]triazolo[4,3-a]pyridin-6-yl)ethyl)pyrrolidin-3-amine;

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-yl)-2-methylpropan-1-ol;

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)ethyl acetate;

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)ethanol;

(S)-1-((R)-2,2,2-trifluoro-1-(3-(7-methoxy-8-methylquinolin-2-yl)-[1,2,4]triazolo[4,3-a]pyridin-6-yl)ethyl)pyrrolidin-3-amine;

(1-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-yl)cyclopropyl)methanol;

(S)-1-((R)-2,2,2-trifluoro-1-(3-(6-fluoro-8-(1-(hydroxymethyl)cyclopropyl)quinolin-2-yl)-[1,2,4]triazolo[4,3-a]pyridin-6-yl)ethyl)pyrrolidin-3-ol;

(S)-1-((R)-2,2,2-trifluoro-1-(3-(8-methoxy-6-methylquinolin-2-yl)-[1,2,4]triazolo[4,3-a]pyridin-6-yl)ethyl)pyrrolidin-3-amine;

(S)-1-((R)-2,2,2-trifluoro-1-O-(8-isopropoxy-6-methylquinolin-2-yl)-[1,2,4]triazolo[4,3-a]pyridin-6-yl)ethyl)pyrrolidin-3-amine;

(3S,4R)-4-amino-1-((R)-2,2,2-trifluoro-1-(3-(8-isopropoxyquinolin-2-yl)-[1,2,4]triazolo[4,3-a]pyridin-6-yl)ethyl)pyrrolidin-3-ol;

(3S,4R)-4-amino-1-((R)-1-(3-(8-tert-butylquinolin-2-yl)-[1,2,4]triazolo[4,3-a]pyridin-6-yl)-2,2,2-trifluoroethyl)pyrrolidin-3-ol;

(3S,4R)-4-amino-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-ol;

(3S,4R)-4-amino-1-((R)-2,2,2-trifluoro-1-(3-(6-fluoro-8-isopropoxyquinolin-2-yl)-[1,2,4]triazolo[4,3-a]pyridin-6-yl)ethyl)pyrrolidin-3-ol;

(S)-1-((R)-1-(3-(7-ethoxy-6-fluoroquinolin-2-yl)-[1,2,4]triazolo[4,3-a]pyridin-6-yl)-2,2,2-trifluoroethyl)pyrrolidin-3-amine;

(S)-1-((R)-1-(3-(7-(cyclopropylmethoxy)-6-fluoroquinolin-2-yl)-[1,2,4]triazolo[4,3-a]pyridin-6-yl)-2,2,2-trifluoroethyl)pyrrolidin-3-amine;

(S)-1-((S)-2,2,2-trifluoro-1-(3-(6-fluoro-8-isopropoxyquinolin-2-yl)-[1,2,4]triazolo[4,3-a]pyridin-6-yl)ethyl)pyrrolidin-3-amine;

(S)-1-((S)-2,2,2-trifluoro-1-(3-(6-fluoro-7-methoxyquinolin-2-yl)-[1,2,4]triazolo[4,3-a]pyridin-6-yl)ethyl)pyrrolidin-3-amine;

(3S,4R)-4-amino-1-((R)-2,2,2-trifluoro-1-(3-(8-methoxyquinolin-2-yl)-[1,2,4]triazolo[4,3-a]pyridin-6-yl)ethyl)pyrrolidin-3-ol;

(S)-1-((R)-2,2,2-trifluoro-1-(3-(7-methoxy-6-methylquinolin-2-yl)-[1,2,4]triazolo[4,3-a]pyridin-6-yl)ethyl)pyrrolidin-3-amine;

(S)-1-((R)-2,2,2-trifluoro-1-(3-(7-methoxyquinolin-2-yl)-[1,2,4]triazolo[4,3-a]pyridin-6-yl)ethyl)pyrrolidin-3-amine;

(S)-1-((R)-2,2,2-trifluoro-1-(3-(8-((R)-1-methoxypropan-2-yloxy)quinolin-2-yl)-[1,2,4]triazolo[4,3-a]pyridin-6-yl)ethyl)pyrrolidin-3-amine;

(S)-1-((R)-2,2,2-trifluoro-1-(3-(8-((S)-1-methoxypropan-2-yloxy)quinolin-2-yl)-[1,2,4]triazolo[4,3-a]pyridin-6-yl)ethyl)pyrrolidin-3-amine;

(S)-1-((R)-2,2,2-trifluoro-1-(3-(7-isopropoxyquinolin-2-yl)-[1,2,4]triazolo[4,3-a]pyridin-6-yl)ethyl)pyrrolidin-3-amine;

(S)-1-((R)-1-(3-(8-cyclopropyl-7-methoxyquinolin-2-yl)-[1,2,4]triazolo[4,3-a]pyridin-6-yl)-2,2,2-trifluoroethyl)pyrrolidin-3-amine;

(3S)-1-((1R)-2,2,2-trifluoro-1-(3-(8-methyl-8,9-dihydrofuro[2,3-h]quinolin-2-yl)-[1,2,4]triazolo[4,3-a]pyridin-6-yl)ethyl)pyrrolidin-3-amine;

(3R,4R)-4-amino-1-((R)-1-(3-(8-tert-butylquinolin-2-yl)-[1,2,4]triazolo[4,3-a]pyridin-6-yl)-2,2,2-trifluoroethyl)pyrrolidin-3-ol;

(3S,4R)-4-amino-1-((R)-2,2,2-trifluoro-1-(3-(8-isopropoxyquinolin-2-yl)-[1,2,4]triazolo[4,3-a]pyridin-6-yl)ethyl)pyrrolidin-3-ol;

(3S,4R)-4-amino-1-((R)-2,2,2-trifluoro-1-(3-(6-fluoro-8-isopropoxyquinolin-2-yl)-[1,2,4]triazolo[4,3-a]pyridin-6-yl)ethyl)pyrrolidin-3-ol;

(S)-1-((R)-2,2,2-trifluoro-1-(3-(7-(2-methoxyethoxy) quinolin-2-yl)-[1,2,4]triazolo[4,3-a]pyridin-6-yl)ethyl) pyrrolidin-3-amine;

(S)-1-((R)-2,2,2-trifluoro-1-(3-(7-((R)-1-methoxypropan-2-yloxy)quinolin-2-yl)-[1,2,4]triazolo[4,3-a]pyridin-6-yl)ethyl)pyrrolidin-3-amine;

(S)-1-((R)-2,2,2-trifluoro-1-(3-(7-((S)-1-methoxypropan-2-yloxy)quinolin-2-yl)-[1,2,4]triazolo[4,3-a]pyridin-6-yl)ethyl)pyrrolidin-3-amine;

(S)-1-((R)-1-(3-(8-cyclopropyl-7-isopropoxyquinolin-2-yl)-[1,2,4]triazolo[4,3-a]pyridin-6-yl)-2,2,2-trifluoroethyl)pyrrolidin-3-amine;

(S)-1-((R)-1-(3-(8-cyclopropyl-7-(2-methoxyethoxy) quinolin-2-yl)-[1,2,4]triazolo[4,3-a]pyridin-6-yl)-2,2,2-trifluoroethyl)pyrrolidin-3-amine;

(S)-1-((R)-2,2,2-trifluoro-1-(3-(6-fluoro-7-(2-methoxyethyl)quinolin-2-yl)-[1,2,4]triazolo[4,3-a]pyridin-6-yl)ethyl)pyrrolidin-3-amine;

(S)-3-(fluoromethyl)-1-((R)-2,2,2-trifluoro-1-(3-(8-isopropoxyquinolin-2-yl)-[1,2,4]triazolo[4,3-a]pyridine-6-yl)ethyl)pyrrolidine-3-amine;

(R)-3-(fluoromethyl)-1-((R)-2,2,2-trifluoro-1-(3-(8-isopropoxyquinolin-2-yl)-[1,2,4]triazolo[4,3-a]pyridine-6-yl)ethyl)pyrrolidine-3-amine;

(S)-1-((R)-2,2,2-trifluoro-1-(3-(6-fluoro-7-(tetrahydro-2H-pyran-4-yloxy)quinolin-2-yl)-[1,2,4]triazolo[4,3-a]pyridin-6-yl)ethyl)pyrrolidin-3-amine;

2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-ol;

(S)-1-((R)-1-(3-(8-(cyclopropylmethoxy)-6-fluoroquinolin-2-yl)-[1,2,4]triazolo[4,3-a]pyridin-6-yl)-2,2,2-trifluoroethyl)pyrrolidin-3-amine;

(S)-1-((R)-2,2,2-trifluoro-1-(3-(6-fluoro-8-((R)-1-methoxypropan-2-yloxy)quinolin-2-yl)-[1,2,4]triazolo[4,3-a]pyridin-6-yl)ethyl)pyrrolidin-3-amine;

(S)-1-((R)-2,2,2-trifluoro-1-(3-(6-fluoro-7-((R)-1-methoxypropan-2-yloxy)quinolin-2-yl)-[1,2,4]triazolo[4,3-a]pyridin-6-yl)ethyl)pyrrolidin-3-amine;

(S)-1-((R)-2,2,2-trifluoro-1-(3-(8-(trifluoromethyl)quinolin-2-yl)-[1,2,4]triazolo[4,3-a]pyridin-6-yl)ethyl)pyrrolidin-3-amine;

(3R)-4-fluoro-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-amine;

2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-ol;

(1-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yl)cyclopropyl)methanol;

(S)-1-((R)-2,2,2-trifluoro-1-(3-(6-fluoro-7-(1-(methoxymethyl)cyclopropyl)quinolin-2-yl)-[1,2,4]triazolo[4,3-a]pyridin-6-yl)ethyl)pyrrolidin-3-amine;

(S)-1-((R)-2,2,2-trifluoro-1-(3-(8-fluoro-7-(2-methoxyethyl)quinolin-2-yl)-[1,2,4]triazolo[4,3-a]pyridin-6-yl)ethyl)pyrrolidin-3-amine;

(S)-1-((R)-2,2,2-trifluoro-1-(3-(8-fluoro-7-methoxyquinolin-2-yl)-[1,2,4]triazolo[4,3-a]pyridin-6-yl)ethyl)pyrrolidin-3-amine;

(S)-1-((R)-2,2,2-trifluoro-1-(3-(8-fluoroquinolin-2-yl)-[1,2,4]triazolo[4,3-a]pyridin-6-yl)ethyl)pyrrolidin-3-amine;

(S)-3-(fluoromethyl)-1-((R)-2,2,2-trifluoro-1-(3-(8-methoxyquinolin-2-yl)-[1,2,4]triazolo[4,3-a]pyridin-6-yl)ethyl)pyrrolidin-3-amine;

(R)3-(fluoromethyl)-1-((R)-2,2,2-trifluoro-1-(3-(8-methoxyquinolin-2-yl)-[1,2,4]triazolo[4,3-a]pyridin-6-yl)ethyl)pyrrolidin-3-amine;

(S)-1-((R)-2,2,2-trifluoro-1-(3-(8-fluoro-7-(1-methyl-1H-pyrazol-4-yl)quinolin-2-yl)-[1,2,4]triazolo[4,3-a]pyridin-6-yl)ethyl)pyrrolidin-3-amine;

(S)-1-((R)-1-(3-(7-cyclopropyl-8-fluoroquinolin-2-yl)-[1,2,4]triazolo[4,3-a]pyridin-6-yl)-2,2,2-trifluoroethyl)pyrrolidin-3-amine;

(S)-1-((R)-2,2,2-trifluoro-1-(3-(6-fluoro-7-(1-methyl-1H-pyrazol-4-yl)quinolin-2-yl)-[1,2,4]triazolo[4,3-a]pyridin-6-yl)ethyl)pyrrolidin-3-amine;

(S)-1-((R)-1-(3-(8-chloro-7-(2-methoxyethoxy)quinolin-2-yl)-[1,2,4]triazolo[4,3-a]pyridin-6-yl)-2,2,2-trifluoroethyl)pyrrolidin-3-amine;

(S)-1-((R)-1-(3-(8-chloro-7-methoxyquinolin-2-yl)-[1,2,4]triazolo[4,3-a]pyridin-6-yl)-2,2,2-trifluoroethyl)pyrrolidin-3-amine;

(S)-1-((R)-1-(3-(7-cyclopropyl-6-fluoroquinolin-2-yl)-[1,2,4]triazolo[4,3-a]pyridin-6-yl)-2,2,2-trifluoroethyl)pyrrolidin-3-amine;

(S)-1-((R)-1-(3-(8-cyclopropyl-6-fluoroquinolin-2-yl)-[1,2,4]triazolo[4,3-a]pyridin-6-yl)-2,2,2-trifluoroethyl)pyrrolidin-3-amine;

(S)-1-((R)-1-(3-(6,8-difluoro-7-methoxyquinolin-2-yl)-[1,2,4]triazolo[4,3-a]pyridin-6-yl)-2,2,2-trifluoroethyl)pyrrolidin-3-amine;

(S)-1-((R)-2,2,2-trifluoro-1-(3-(8-fluoro-7-(2-methoxyethoxy)quinolin-2-yl)-[1,2,4]triazolo[4,3-a]pyridin-6-yl)ethyl)pyrrolidin-3-amine;

(S)-1-((R)-2,2,2-trifluoro-1-(3-(8-fluoro-7-((R)-1-methoxypropan-2-yloxy)quinolin-2-yl)-[1,2,4]triazolo[4,3-a]pyridin-6-yl)ethyl)pyrrolidin-3-amine;

(3S,4R)-4-amino-1-((R)-1-(3-(8-cyclopropyl-6-fluoroquinolin-2-yl)-[1,2,4]triazolo[4,3-a]pyridin-6-yl)-2,2,2-trifluoroethyl)pyrrolidin-3-ol;

(S)-1-((R)-2,2,2-trifluoro-1-(3-(8-chloroquinolin-2-yl)-[1,2,4]triazolo[4,3-a]pyridin-6-yl)ethyl)pyrrolidin-3-amine;

(S)-1-((R)-2,2,2-trifluoro-1-(3-(8-methylquinolin-2-yl)-[1,2,4]triazolo[4,3-a]pyridin-6-yl)ethyl)pyrrolidin-3-amine;

(S)-1-((R)-2,2,2-trifluoro-1-(3-(6-fluoro-8-methylquinolin-2-yl)-[1,2,4]triazolo[4,3-a]pyridin-6-yl)ethyl)pyrrolidin-3-amine;

(S)-1-((R)-2,2,2-trifluoro-1-(3-(8-(methoxymethyl)quinolin-2-yl)-[1,2,4]triazolo[4,3-a]pyridin-6-yl)ethyl)pyrrolidin-3-amine;

(R)-2-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)propan-1-ol;

(S)-1-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)propan-2-ol;

((R)-3-amino-1-((R)-2,2,2-trifluoro-1-(3-(8-isopropoxyquinolin-2-yl)-[1,2,4]triazolo[4,3-a]pyridin-6-yl)ethyl)pyrrolidin-3-yl)methanol;

((R)-3-amino-1-((R)-1-(3-(8-tert-butylquinolin-2-yl)-[1,2,4]triazolo[4,3-a]pyridin-6-yl)-2,2,2-trifluoroethyl)pyrrolidin-3-yl)methanol;

(S)-1-((R)-2,2,2-trifluoro-1-(3-(8-methyl-7-(1-methyl-1H-pyrazol-4-yl)quinolin-2-yl)-[1,2,4]triazolo[4,3-a]pyridin-6-yl)ethyl)pyrrolidin-3-amine;

(S)-1-((R)-2,2,2-trifluoro-1-(3-(8-((3-methyloxetan-3-yl)methoxy)quinolin-2-yl)-[1,2,4]triazolo[4,3-a]pyridin-6-yl)ethyl)pyrrolidin-3-amine;

Diastereomer 1 of 3-methyl-1-((R)-2,2,2-trifluoro-1-(3-(8-methoxyquinolin-2-yl)-[1,2,4]triazolo[4,3-a]pyridin-6-yl)ethyl)pyrrolidin-3-ol;
Diastereomer 2 of 3-methyl-1-((R)-2,2,2-trifluoro-1-(3-(8-methoxyquinolin-2-yl)-[1,2,4]triazolo[4,3-a]pyridin-6-yl)ethyl)pyrrolidin-3-ol;
Diastereomer 1 of 1-((R)-1-(3-(8-tert-butylquinolin-2-yl)-[1,2,4]triazolo[4,3-a]pyridin-6-yl)-2,2,2-trifluoroethyl)-3-methylpyrrolidin-3-ol;
Diastereomer 2 of 1-((R)-1-(3-(8-tert-butylquinolin-2-yl)-[1,2,4]triazolo[4,3-a]pyridin-6-yl)-2,2,2-trifluoroethyl)-3-methylpyrrolidin-3-ol;
(3-amino-1-((R)-2,2,2-trifluoro-1-(3-(8-isopropoxyquinolin-2-yl)-[1,2,4]triazolo[4,3-a]pyridin-6-yl)ethyl)pyrrolidin-3-yl)methanol;
(S)-1-((R)-2,2,2-trifluoro-1-(3-(7-((3-methyloxetan-3-yl)methoxy)quinolin-2-yl)-[1,2,4]triazolo[4,3-a]pyridin-6-yl)ethyl)pyrrolidin-3-amine;
3-methyl-1-((S)-2,2,2-trifluoro-1-(3-(8-isopropoxyquinolin-2-yl)-[1,2,4]triazolo[4,3-a]pyridin-6-yl)ethyl)pyrrolidin-3-ol Diastereomer 1;
3-methyl-1-((S)-2,2,2-trifluoro-1-(3-(7-(1-methyl-1H-pyrazol-4-yl)quinolin-2-yl)-[1,2,4]triazolo[4,3-a]pyridin-6-yl)ethyl)pyrrolidin-3-ol Diastereomer 1;
Diastereomer 2 of 3-methyl-1-((S)-2,2,2-trifluoro-1-(3-(7-(1-methyl-1H-pyrazol-4-yl)quinolin-2-yl)-[1,2,4]triazolo[4,3-a]pyridin-6-yl)ethyl)pyrrolidin-3-ol;
Diastereomer 1 of 3-methyl-1-((S)-2,2,2-trifluoro-1-(3-(6-fluoro-8-isopropoxyquinolin-2-yl)-[1,2,4]triazolo[4,3-a]pyridin-6-yl)ethyl)pyrrolidin-3-ol;
Diastereomer 2 of 3-methyl-1-((S)-2,2,2-trifluoro-1-(3-(6-fluoro-8-isopropoxyquinolin-2-yl)-[1,2,4]triazolo[4,3-a]pyridin-6-yl)ethyl)pyrrolidin-3-ol;
(3S)-1-((1R)-1-(3-(7-(1,3-dimethyl-1H-pyrazol-5-yl)-6-fluoroquinolin-2-yl)-[1,2,4]triazolo[4,3-a]pyridin-6-yl)-2,2,2-trifluoroethyl)pyrrolidin-3-amine;
(3S)-1-((1R)-1-(3-(7-(1,3-dimethyl-1H-pyrazol-4-yl)-6-fluoroquinolin-2-yl)-[1,2,4]triazolo[4,3-a]pyridin-6-yl)-2,2,2-trifluoroethyl)pyrrolidin-3-amine;
(3S)-1-((1R)-1-(3-(7-(1,5-dimethyl-1H-pyrazol-4-yl)-6-fluoroquinolin-2-yl)-[1,2,4]triazolo[4,3-a]pyridin-6-yl)-2,2,2-trifluoroethyl)pyrrolidin-3-amine;
3-methyl-1-((S)-2,2,2-trifluoro-1-(3-(8-isopropoxyquinolin-2-yl)-[1,2,4]triazolo[4,3-a]pyridin-6-yl)ethyl)pyrrolidin-3-ol Diastereomer 2;
2-(6-((R)-1-((S)-3-aminopyrrolidin-1-yl)-2,2,2-trifluoroethyl)-[1,2,4]triazolo[4,3-a]pyridin-3-yl)quinolin-8-ol;
2-(6-((R)-1-((S)-3-aminopyrrolidin-1-yl)-2,2,2-trifluoroethyl)-[1,2,4]triazolo[4,3-a]pyridin-3-yl)-N-isopropyl-8-methylquinoline-7-carboxamide;
(3R,4S)-4-fluoro-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-amine;
(3R,4R)-4-fluoro-1-((R)-2,2,2-trifluoro-1-(3-(6-fluoro-7-methoxyquinolin-2-yl)-[1,2,4]triazolo[4,3-a]pyridin-6-yl)ethyl)pyrrolidin-3-amine;
(S)-1-((R)-2,2,2-trifluoro-1-(3-(8-((S)-2-methoxypropoxy)quinolin-2-yl)-[1,2,4]triazolo[4,3-a]pyridin-6-yl)ethyl)pyrrolidin-3-amine;
(3S)-1-((1R)-1-(3-(7-(1,3-dimethyl-1H-pyrazol-5-yl)-8-methylquinolin-2-yl)-[1,2,4]triazolo[4,3-a]pyridin-6-yl)-2,2,2-trifluoroethyl)pyrrolidin-3-amine;
(3S)-1-((1R)-1-(3-(7-(1,5-dimethyl-1H-pyrazol-4-yl)-8-methylquinolin-2-yl)-[1,2,4]triazolo[4,3-a]pyridin-6-yl)-2,2,2-trifluoroethyl)pyrrolidin-3-amine;
(S)-1-((R)-1-(3-(7-(difluoromethoxy)-6-fluoroquinolin-2-yl)-[1,2,4]triazolo[4,3-a]pyridin-6-yl)-2,2,2-trifluoroethyl)pyrrolidin-3-amine;
(S)-3-methyl-1-((S)-2,2,2-trifluoro-1-(3-(6-fluoro-8-isopropoxyquinolin-2-yl)-[1,2,4]triazolo[4,3-a]pyridin-6-yl)ethyl)pyrrolidin-3-amine;
(S)-3-methyl-1-((S)-2,2,2-trifluoro-1-(3-(6-fluoro-8-methoxyquinolin-2-yl)-[1,2,4]triazolo[4,3-a]pyridin-6-yl)ethyl)pyrrolidin-3-amine;
2-(2-(6-((R)-1-((S)-3-aminopyrrolidin-1-yl)-2,2,2-trifluoroethyl)-[1,2,4]triazolo[4,3-a]pyridin-3-yl)quinolin-8-yloxy)ethanol;
(S)-1-((S)-1-(3-(7-ethoxy-6-fluoroquinolin-2-yl)-[1,2,4]triazolo[4,3-a]pyridin-6-yl)-2,2,2-trifluoroethyl)-3-methylpyrrolidin-3-amine;
(S)-3-methyl-1-((S)-2,2,2-trifluoro-1-(3-(6-fluoro-8-((R)-1-methoxypropan-2-yloxy)quinolin-2-yl)-[1,2,4]triazolo[4,3-a]pyridin-6-yl)ethyl)pyrrolidin-3-amine;
(S)-3-methyl-1-((S)-2,2,2-trifluoro-1-(3-(7-(1-methyl-1H-pyrazol-4-yl)quinolin-2-yl)-[1,2,4]triazolo[4,3-a]pyridin-6-yl)ethyl)pyrrolidin-3-amine;
(S)-1-((S)-1-(3-(7-cyclopropylquinolin-2-yl)-[1,2,4]triazolo[4,3-a]pyridin-6-yl)-2,2,2-trifluoroethyl)-3-methylpyrrolidin-3-amine;
3-(2-(6-((R)-1-((S)-3-aminopyrrolidin-1-yl)-2,2,2-trifluoroethyl)-[1,2,4]triazolo[4,3-a]pyridin-3-yl)quinolin-8-yl)-3-methylbutan-1-ol;
2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol;
(S)-1-((R)-2,2,2-trifluoro-1-(3-(6-fluoro-7-(2,2,2-trifluoroethoxy)quinolin-2-yl)-[1,2,4]triazolo[4,3-a]pyridin-6-yl)ethyl)pyrrolidin-3-amine;
(S)-1-((R)-2,2,2-trifluoro-1-(3-(8-(2-methoxyethoxy)quinolin-2-yl)-[1,2,4]triazolo[4,3-a]pyridin-6-yl)ethyl)pyrrolidin-3-amine;
(S)-1-((R)-1-(3-(8-(difluoromethoxy)-6-fluoroquinolin-2-yl)-[1,2,4]triazolo[4,3-a]pyridin-6-yl)-2,2,2-trifluoroethyl)pyrrolidin-3-amine;
3-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-yloxy)propan-1-ol;
2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol;
2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol;
(S)-1-((R)-2,2,2-trifluoro-1-(3-(6-fluoro-8-(2,2,2-trifluoroethoxy)quinolin-2-yl)-[1,2,4]triazolo[4,3-a]pyridin-6-yl)ethyl)pyrrolidin-3-amine;
(S)-1-((R)-2,2,2-trifluoro-1-(3-(6-fluoro-8-(3-methoxypropoxy)quinolin-2-yl)-[1,2,4]triazolo[4,3-a]pyridin-6-yl)ethyl)pyrrolidin-3-amine;
2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)-N,N-dimethylacetamide;
2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)-N-ethylacetamide;
2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol;
2-(2-(6-((R)-1-((S)-3-aminopyrrolidin-1-yl)-2,2,2-trifluoroethyl)-[1,2,4]triazolo[4,3-a]pyridin-3-yl)quinolin-8-yl)propan-2-ol;

(R)-2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-yloxy)propan-1-ol;

(S)-1-((R)-2,2,2-trifluoro-1-(3-(7-(trifluoromethoxy)quinolin-2-yl)-[1,2,4]triazolo[4,3-a]pyridin-6-yl)ethyl)pyrrolidin-3-amine;

(R)-3-methyl-1-((R)-2,2,2-trifluoro-1-(3-(8-methoxyquinolin-2-yl)-[1,2,4]triazolo[4,3-a]pyridin-6-yl)ethyl)pyrrolidin-3-amine;

(R)-3-methyl-1-((R)-2,2,2-trifluoro-1-(3-(6-fluoro-8-methoxyquinolin-2-yl)-[1,2,4]triazolo[4,3-a]pyridin-6-yl)ethyl)pyrrolidin-3-amine;

Diastereomer 1 of 3-ethyl-1-((R)-2,2,2-trifluoro-1-(3-(8-methoxyquinolin-2-yl)-[1,2,4]triazolo pyridin-6-yl)ethyl)pyrrolidin-3-amine;

Diastereomer 1 of 1-((R)-1-(3-(7-ethoxy-6-fluoroquinolin-2-yl)-[1,2,4]triazolo[4,3-a]pyridin-6-yl)-2,2,2-trifluoroethyl)-3-ethylpyrrolidin-3-amine;

Diastereomer 2 of 3-ethyl-1-((S)-2,2,2-trifluoro-1-(3-(8-methoxyquinolin-2-yl)-[1,2,4]triazolo[4,3-a]pyridin-6-yl)ethyl)pyrrolidin-3-amine;

Diastereomer 2 of 1-((S)-1-(3-(7-ethoxy-6-fluoroquinolin-2-yl)-[1,2,4]triazolo[4,3-a]pyridin-6-yl)-2,2,2-trifluoroethyl)-3-ethylpyrrolidin-3-amine;

(S)-3-methyl-1-((R)-2,2,2-trifluoro-1-(3-(8-methoxyquinolin-2-yl)-[1,2,4]triazolo[4,3-a]pyridin-6-yl)ethyl)pyrrolidin-3-amine;

S)-1-((R)-1-(3-(7-ethoxy-6-fluoroquinolin-2-yl)-[1,2,4]triazolo[4,3-a]pyridin-6-yl)-2,2,2-trifluoroethyl)-3-methylpyrrolidin-3-amine;

(S)-3-methyl-1-((R)-2,2,2-trifluoro-1-(3-(6-fluoro-8-methoxyquinolin-2-yl)-[1,2,4]triazolo[4,3-a]pyridin-6-yl)ethyl)pyrrolidin-3-amine;

(S)-1-((S)-1-(3-(7-ethoxy-6-fluoroquinolin-2-yl)-[1,2,4]triazolo[4,3-a]pyridin-6-yl)-2,2,2-trifluoroethyl)pyrrolidin-3-amine;

Diastereomer 1 of 3-ethyl-1-((S)-2,2,2-trifluoro-1-(3-(8-methoxyquinolin-2-yl)-[1,2,4]triazolo[4,3-a]pyridin-6-yl)ethyl)pyrrolidin-3-amine;

Diastereomer 1 of 1-((S)-1-(3-(7-ethoxy-6-fluoroquinolin-2-yl)-[1,2,4]triazolo[4,3-a]pyridin-6-yl)-2,2,2-trifluoroethyl)-3-ethylpyrrolidin-3-amine;

Diastereomer 2 of 3-ethyl-1-((R)-2,2,2-trifluoro-1-(3-(8-methoxyquinolin-2-yl)-[1,2,4]triazolo[4,3-a]pyridin-6-yl)ethyl)pyrrolidin-3-amine;

Diastereomer 2 of 1-((R)-1-(3-(7-ethoxy-6-fluoroquinolin-2-yl)-[1,2,4]triazolo[4,3-a]pyridin-6-yl)-2,2,2-trifluoroethyl)-3-ethylpyrrolidin-3-amine;

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-yloxy)ethanol;

(S)-1-((R)-1-(3-(7-ethoxyquinolin-2-yl)-[1,2,4]triazolo[4,3-a]pyridin-6-yl)-2,2,2-trifluoroethyl)pyrrolidin-3-amine;

(S)-1-((S)-1-(3-(7-ethoxyquinolin-2-yl)-[1,2,4]triazolo[4,3-a]pyridin-6-yl)-2,2,2-trifluoroethyl)pyrrolidin-3-amine;

7-ethoxy-2-(6-((1R)-2,2,2-trifluoro-1-(1,7-diazaspiro[4.4]nonan-7-yl)ethyl)-[1,2,4]triazolo[4,3-a]pyridin-3-yl)quinoline;

7-ethoxy-2-(6-((1S)-2,2,2-trifluoro-1-(1,7-diazaspiro[4.4]nonan-7-yl)ethyl)-[1,2,4]-triazolo[4,3-a]pyridin-3-yl)quinoline;

1-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-8-yloxy)-2-methylpropan-2-ol;

(S)-3-methyl-1-((S)-2,2,2-trifluoro-1-(3-(7-(2-methoxyethoxy)quinolin-2-yl)-[1,2,4]triazolo[4,3-a]pyridin-6-yl)ethyl)pyrrolidin-3-amine;

(S)-3-methyl-1-((S)-2,2,2-trifluoro-1-(3-(7-(2-methoxyethoxy)quinolin-2-yl)-[1,2,4]triazolo[4,3-a]pyridin-6-yl)ethyl)pyrrolidin-3-amine;

(S)-1-((S)-1-(3-(7-ethoxyquinolin-2-yl)-[1,2,4]triazolo[4,3-a]pyridin-6-yl)-2,2,2-trifluoroethyl)-3-methylpyrrolidin-3-amine;

(S)-1-((R)-2,2,2-trifluoro-1-(3-(8-(1-methoxy-2-methylpropan-2-yloxy)quinolin-2-yl)-[1,2,4]triazolo[4,3-a]pyridin-6-yl)ethyl)pyrrolidin-3-amine (S)-1-((R)-2,2,2-trifluoro-1-(3-(6-fluoro-8-(1-methoxy-2-methylpropan-2-yloxy)quinolin-2-yl)-[1,2,4]triazolo[4,3-a]pyridin-6-yl)ethyl)pyrrolidin-3-amine;

2-(2-(6-((R)-1-((S)-3-aminopyrrolidin-1-yl)-2,2,2-trifluoroethyl)-[1,2,4]triazolo[4,3-a]pyridin-3-yl)quinolin-7-yl)ethanol (S)-1-((R)-1-(3-(7-(ethylthio)quinolin-2-yl)-[1,2,4]triazolo[4,3-a]pyridin-6-yl)-2,2,2-trifluoroethyl)pyrrolidin-3-amine;

2-(2-(6-((R)-1-((S)-3-aminopyrrolidin-1-yl)-2,2,2-trifluoroethyl)-[1,2,4]triazolo[4,3-a]pyridin-3-yl)quinolin-7-ylthio)ethanol;

(S)-1-((R)-2,2,2-trifluoro-1-(3-(7-(isopropylthio)quinolin-2-yl)-[1,2,4]triazolo[4,3-a]pyridin-6-yl)ethyl)pyrrolidin-3-amine;

(S)-1-((R)-2,2,2-trifluoro-1-(3-(7-(2-methoxyethyl)quinolin-2-yl)-[1,2,4]triazolo[4,3-a]pyridin-6-yl)ethyl)pyrrolidin-3-amine;

2-(2-(6-((R)-1-((R)-3-amino-3-methylpyrrolidin-1-yl)-2,2,2-trifluoroethyl)-[1,2,4]triazolo[4,3-a]pyridin-3-yl)quinolin-8-yloxy)acetonitrile;

((S)-1-((R)-1-(3-(8-(1,3-dimethoxypropan-2-yloxy)quinolin-2-yl)-[1,2,4]triazolo[4,3-a]pyridin-6-yl)-2,2,2-trifluoroethyl)pyrrolidin-3-amine;

1-(2-(6-((R)-1-((R)-3-amino-3-methylpyrrolidin-1-yl)-2,2,2-trifluoroethyl)-[1,2,4]triazolo[4,3-a]pyridin-3-yl)quinolin-8-yloxy)-2-methylpropan-2-ol;

(S)-1-((R)-1-(3-(8-(ethylthio)quinolin-2-yl)-[1,2,4]triazolo[4,3-a]pyridin-6-yl)-2,2,2-trifluoroethyl)pyrrolidin-3-amine;

(S)-1-((R)-1-(3-(7-(2-ethoxyethoxy)quinolin-2-yl)-[1,2,4]triazolo[4,3-a]pyridin-6-yl)-2,2,2-trifluoroethyl)pyrrolidin-3-amine;

(S)-1-((R)-2,2,2-trifluoro-1-(3-(7-(3-methoxypropoxy)quinolin-2-yl)-[1,2,4]triazolo[4,3-a]pyridin-6-yl)ethyl)pyrrolidin-3-amine;

(S)-1-((R)-2,2,2-trifluoro-1-(3-(8-(2-methoxy-2-methylpropoxy)quinolin-2-yl)-[1,2,4]triazolo[4,3-a]pyridin-6-yl)ethyl)pyrrolidin-3-amine;

(S)-1-((R)-2,2,2-trifluoro-1-(3-(7-((R)-2-methoxypropoxy)quinolin-2-yl)-[1,2,4]triazolo pyridin-6-yl)ethyl)pyrrolidin-3-amine;

1-(2-(6-((R)-1-((S)-3-aminopyrrolidin-1-yl)-2,2,2-trifluoroethyl)-[1,2,4]triazolo[4,3-a]pyridin-3-yl)quinolin-7-yloxy)-2-methylpropan-2-ol;

((S)-1-((R)-1-(3-(7-ethoxy-6-fluoroquinolin-2-yl)-[1,2,4]triazolo[4,3-a]pyridin-6-yl)-2,2,2-trifluoroethyl)pyrrolidin-3-yl)methanamine;

((R)-1-((R)-1-(3-(7-ethoxy-6-fluoroquinolin-2-yl)-[1,2,4]triazolo[4,3-a]pyridin-6-yl)-2,2,2-trifluoroethyl)pyrrolidin-3-yl)methanamine;

(S)-1-((R)-2,2,2-trifluoro-1-(3-(7-(2-(methylthio)ethoxy)quinolin-2-yl)-[1,2,4]triazolo[4,3-a]pyridin-6-yl)ethyl)pyrrolidin-3-amine;

(R)-1-((R)-1-(3-(7-ethoxy-6-fluoroquinolin-2-yl)-[1,2,4]
triazolo[4,3-a]pyridin-6-yl)-2,2,2-trifluoroethyl)pyrrolidin-3-amine;

(R)-1-(2-(6-((R)-1-((S)-3-aminopyrrolidin-1-yl)-2,2,2-trifluoroethyl)-[1,2,4]triazolo[4,3-a]pyridin-3-yl)
quinolin-8-yloxy)propan-2-ol;

(S)-3-methyl-1-((S)-2,2,2-trifluoro-1-(3-(6-fluoro-7-(2-methoxyethyl)quinolin-2-yl)-[1,2,4]triazolo[4,3-a]pyridin-6-yl)ethyl)pyrrolidin-3-amine;

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)ethyl isobutyrate;

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)ethyl pivalate;

(S)-1-((R)-2,2,2-trifluoro-1-(3-(7-((S)-2-methoxypropoxy)quinolin-2-yl)-[1,2,4]triazolo[4,3-a]pyridin-6-yl)ethyl)pyrrolidin-3-amine;

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)ethyl 2-ethylbutanoate;

2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)ethyl 2,2-dimethylbutanoate;

(S)-2-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)ethyl 2-amino-3-methylbutanoate;

(S)-1-((R)-2,2,2-trifluoro-1-(3-(8-((R)-2-methoxypropoxy)quinolin-2-yl)-[1,2,4]triazolo[4,3-a]pyridin-6-yl)ethyl)pyrrolidin-3-amine;

(R)-1-((S)-1-(3-(7-ethoxy-6-fluoroquinolin-2-yl)-[1,2,4]triazolo[4,3-a]pyridin-6-yl)-2,2,2-trifluoroethyl)pyrrolidin-3-amine;

(R)-1-((S)-1-(3-(7-ethoxy-6-fluoroquinolin-2-yl)-[1,2,4]triazolo[4,3-a]pyridin-6-yl)-2,2,2-trifluoroethyl)-3-methylpyrrolidin-3-amine;

((S)-1-((S)-1-(3-(7-ethoxy-6-fluoroquinolin-2-yl)-[1,2,4]triazolo[4,3-a]pyridin-6-yl)-2,2,2-trifluoroethyl)pyrrolidin-3-yl)methanamine;

((R)-1-((S)-1-(3-(7-ethoxy-6-fluoroquinolin-2-yl)-[1,2,4]triazolo[4,3-a]pyridin-6-yl)-2,2,2-trifluoroethyl)pyrrolidin-3-yl)methanamine;

1-(2-(6-((S)-1-((S)-3-amino-3-methylpyrrolidin-1-yl)-2,2,2-trifluoroethyl)-[1,2,4]triazolo[4,3-a]pyridin-3-yl)quinolin-7-yloxy)-2-methylpropan-2-ol;

(S)-3-methyl-1-((S)-2,2,2-trifluoro-1-(3-(6-fluoro-7-(2-methoxyethoxy)quinolin-2-yl)-[1,2,4]triazolo[4,3-a]pyridin-6-yl)ethyl)pyrrolidin-3-amine;

(3R,4R)-1-((R)-1-(3-(7-ethoxy-6-fluoroquinolin-2-yl)-[1,2,4]triazolo[4,3-a]pyridin-6-yl)-2,2,2-trifluoroethyl)-4-methoxypyrrolidin-3-amine;

(S)-3-methyl-1-((S)-2,2,2-trifluoro-1-(3-(7-(2-methoxyethyl)quinolin-2-yl)-[1,2,4]triazolo[4,3-a]pyridin-6-yl)ethyl)pyrrolidin-3-amine;

1-(2-(6-((S)-1-((S)-3-amino-3-methylpyrrolidin-1-yl)-2,2,2-trifluoroethyl)-[1,2,4]triazolo[4,3-a]pyridin-3-yl)-6-fluoroquinolin-7-yloxy)-2-methylpropan-2-ol;

1-(2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yloxy)-2-methylpropan-2-ol;

(S)—N,N-dimethyl-1-((R)-2,2,2-trifluoro-1-(3-(8-((R)-1-methoxypropan-2-yloxy)quinolin-2-yl)-[1,2,4]triazolo[4,3-a]pyridin-6-yl)ethyl)pyrrolidin-3-amine;

(S)-3-methyl-1-((S)-2,2,2-trifluoro-1-(3-(7-((S)-2-methoxypropoxy)quinolin-2-yl)-[1,2,4]-triazolo[4,3-a]pyridin-6-yl)ethyl)pyrrolidin-3-amine;

(S)-3-methyl-1-((S)-2,2,2-trifluoro-1-(3-(7-((R)-2-methoxypropoxy)quinolin-2-yl)-[1,2,4]triazolo[4,3-a]pyridin-6-yl)ethyl)pyrrolidin-3-amine;

(S)-1-((S)-1-(3-(7-(2-ethoxyethoxy)quinolin-2-yl)-[1,2,4]triazolo[4,3-a]pyridin-6-yl)-2,2,2-trifluoroethyl)-3-methylpyrrolidin-3-amine;

(S)-1-((R)-1-(3-(8-tert-butylquinolin-2-yl)-[1,2,4]triazolo[4,3-a]pyridin-6-yl)ethyl)pyrrolidin-3-amine;

(S)-1-((S)-1-(3-(8-tert-butylquinolin-2-yl)-[1,2,4]triazolo[4,3-a]pyridin-6-yl)ethyl)pyrrolidin-3-amine;

(S)-1-((R)-1-(3-(7-ethoxy-6-fluoroquinolin-2-yl)-[1,2,4]triazolo[4,3-a]pyridin-6-yl)ethyl)pyrrolidin-3-amine;

(S)-1-((S)-1-(3-(7-ethoxy-6-fluoroquinolin-2-yl)-[1,2,4]triazolo[4,3-a]pyridin-6-yl)ethyl)pyrrolidin-3-amine;

(S)-3-methyl-1-((S)-2,2,2-trifluoro-1-(3-(6-fluoro-7-(2-methoxyethyl)quinolin-2-yl)-[1,2,4]triazolo[4,3-a]pyridin-6-yl)ethyl)pyrrolidin-3-amine;

(S)-3-methyl-1-((S)-2,2,2-trifluoro-1-(3-(7-methoxyquinolin-2-yl)-[1,2,4]triazolo[4,3-a]pyridin-6-yl)ethyl)pyrrolidin-3-amine;

2-((2-(6-((R)-1-((S)-3-aminopyrrolidin-1-yl)-2,2,2-trifluoroethyl)-[1,2,4]triazolo[4,3-a]pyridin-3-yl)-6-fluoroquinolin-7-yl)oxy)ethyl benzoate;

(S)-3-methyl-1-((S)-2,2,2-trifluoro-1-[3-(7-isopropoxyquinolin-2-yl)-[1,2,4]triazolo[4,3-a]pyridin-6-yl)ethyl]pyrrolidin-3-amine;

(S)-3-methyl-1-((S)-2,2,2-trifluoro-1-(3-(7-(((R)-1-methoxypropan-2-yl)oxy)quinolin-2-yl)-[1,2,4]triazolo[4,3-a]pyridin-6-yl)ethyl)pyrrolidin-3-amine;

(S)-1-((R)-2,2,2-trifluoro-1-(3-(7-(oxetan-3-yl)quinolin-2-yl)-[1,2,4]triazolo[4,3-a]pyridin-6-yl)ethyl)pyrrolidin-3-amine;

2-(2-(6-((S)-1-((S)-3-amino-3-methylpyrrolidin-1-yl)-2,2,2-trifluoroethyl)-[1,2,4]triazolo[4,3-a]pyridin-3-yl)quinolin-7-yl)ethanol;

(3S,4R)-4-methoxy-1-((R)-2,2,2-trifluoro-1-(3-(7-(2-methoxyethoxy)quinolin-2-yl)-[1,2,4]triazolo[4,3-a]pyridin-6-yl)ethyl)pyrrolidin-3-amine;

Diastereomer 1 of trans-2-((2-(6-((R)-1-((S)-3-aminopyrrolidin-1-yl)-2,2,2-trifluoroethyl)-[1,2,4]triazolo[4,3-a]pyridin-3-yl)quinolin-7-yl)oxy)cyclopentanol di-hydrochloride;

Diastereomer 2 of trans-2-((2-(6-((R)-1-((S)-3-aminopyrrolidin-1-yl)-2,2,2-trifluoroethyl)-[1,2,4]triazolo[4,3-a]pyridin-3-yl)quinolin-7-yl)oxy)cyclopentanol di-hydrochloride;

(5-methyl-2-oxo-1,3-dioxol-4-yl)methyl ((S)-1-((R)-2,2,2-trifluoro-1-(3-(6-fluoro-7-(2-hydroxyethoxy)quinolin-2-yl)-[1,2,4]triazolo[4,3-a]pyridin-6-yl)ethyl)pyrrolidin-3-yl)carbamate;

(S)-3-methyl-1-((S)-2,2,2-trifluoro-1-(3-(6-fluoro-7-((S)-2-methoxypropoxy)quinolin-2-yl)-[1,2,4]triazolo[4,3-a]pyridin-6-yl)ethyl)pyrrolidin-3-amine;

(S)-1-((R)-2,2,2-trifluoro-1-(3-(6-fluoro-7-((S)-2-methoxypropoxy)quinolin-2-yl)-[1,2,4]triazolo[4,3-a]pyridin-6-yl)ethyl)pyrrolidin-3-amine;

(S)-3-methyl-1-((S)-2,2,2-trifluoro-1-(3-(6-fluoro-7-((R)-2-methoxypropoxy)quinolin-2-yl)-[1,2,4]triazolo[4,3-a]pyridin-6-yl)ethyl)pyrrolidin-3-amine;

(S)-1-((R)-2,2,2-trifluoro-1-(3-(6-fluoro-7-((R)-2-methoxypropoxy)quinolin-2-yl)-[1,2,4]triazolo[4,3-a]pyridin-6-yl)ethyl)pyrrolidin-3-amine;

(S)-1-((R)-2,2,2-trifluoro-1-(3-(3-fluoro-7-(2-methoxyethoxy)quinolin-2-yl)-[1,2,4]triazolo[4,3-a]pyridin-6-yl)ethyl)pyrrolidin-3-amine (S)-3-methyl-1-((R)-2,2,2-trifluoro-1-(3-(3-fluoro-7-(2-methoxyethoxy)quinolin-2-yl)-[1,2,4]triazolo[4,3-a]pyridin-6-yl)ethyl)pyrrolidin-3-amine;

(S)-1-((R)-2,2,2-trifluoro-1-(3-(3-fluoro-7-((R)-2-methoxypropoxy)quinolin-2-yl)-[1,2,4]triazolo[4,3-a]pyridin-6-yl)ethyl)pyrrolidin-3-amine; and pharmaceutically acceptable salts thereof.

21. A composition comprising a compound according to claim 1 or a pharmaceutically acceptable salt thereof, and a pharmaceutically acceptable diluent or carrier.

22. A method of treating a PIM-1 and/or PIM-2 and/or PIM-3 kinase-mediated condition in a mammal, wherein the condition is cancer, which comprises administering to said mammal a therapeutically effective amount of a compound of Formula I as defined in claim 1, or a pharmaceutically acceptable salt thereof.

23. A process for the preparation a compound of claim 1, which comprises:

(a) reacting a corresponding compound of formula II or a protected derivative thereof

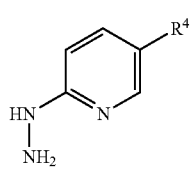

where R⁴ is as defined for Formula I, with a corresponding compound having the formula III or a protected derivative thereof

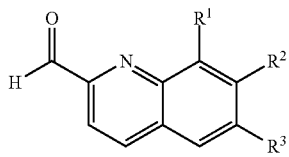

where R¹, R² and R³ are as defined for Formula I, in the presence of an organo hypervalent iodine reagent; or (b) for a compound of Formula I where R² is hetAr¹ or a cyclopropyl ring optionally substituted with —CH₂OH or —CH₂O(1-6C alkyl), reacting a corresponding compound having the formula IV or a protected derivative thereof:

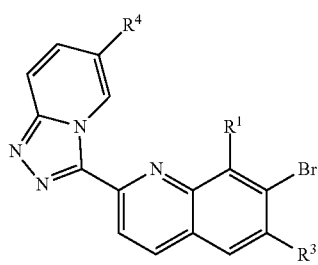

where R¹, R³ and R⁴ are as defined for Formula I, with a reagent having the formula

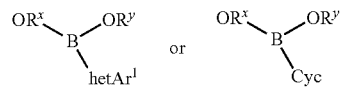

respectively, where hetAr¹ is as defined for Formula I, Cyc is cyclopropyl optionally substituted with —CH₂OH or —CH₂O(1-6C alkyl), and $R^x$ and $R^y$ are H or (1-6C)alkyl, or $R^x$ and $R^y$ together with the atoms to which they are connected form a 5-6 membered ring optionally substituted with 1-4 substituents selected from (1-3C alkyl), wherein said reaction takes place in the presence of a palladium catalyst and optionally in the presence of a base and a ligand; or (c) for a compound of Formula I where R² is —NR$^e$C(=O)R$^f$, reacting a corresponding compound having the formula IV or a protected derivative thereof:

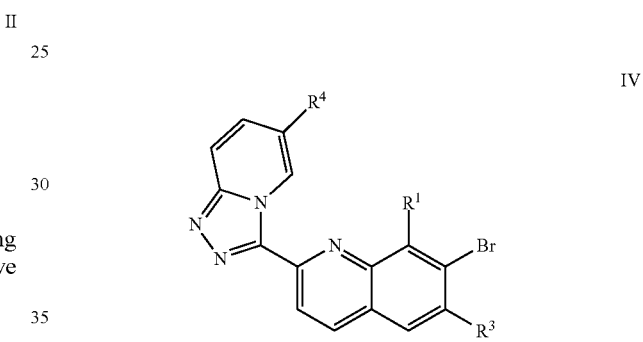

where R¹, R³ and R⁴ are as defined for Formula I, with a reagent having the formula HNR$^e$C(=O)R$^f$ in the presence of a base and a metal catalyst; or (d) for a compound of Formula I where R² is (1-6C alkyl)sulfanyl or hydroxy(2-6C alkyl)sulfanyl, reacting a corresponding compound having the formula IV or a protected derivative thereof:

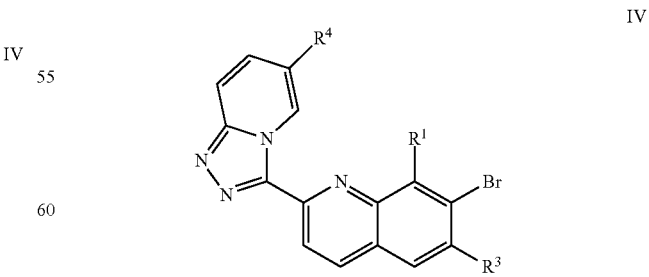

where R¹, R², R³ and R⁴ are as defined for Formula I, with a reagent having the formula HS(1-6C alkyl) or HS(1-6C alkyl)OH, respectively, in the presence of a base; or (e) for a compound of Formula I where $R^2$ is —C(=O)NR$^e$R$^f$, coupling a corresponding compound having the formula V or a protected derivative thereof:

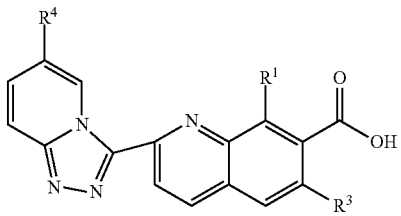

V where $R^1$, $R^3$ and $R^4$ are as defined for Formula I, with a reagent having the formula HNR$^e$R$^f$, where R$^e$ and R$^f$ are as defined for Formula I, in the presence of a base and a coupling reagent; or (f) for a compound of Formula I where $R^1$ is —CH$_2$C(=O)NR$^c$R$^d$, coupling a corresponding compound having the formula VI or a protected derivative thereof

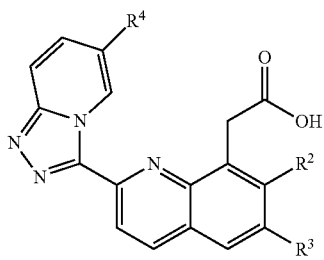

VI where $R^2$, $R^3$ and $R^4$ are as defined for Formula I, with a reagent having the formula HNR$^c$R$^d$, where R$^c$ and R$^d$ are as defined for Formula I, in the presence of a base and a coupling reagent; or (g) for a compound of Formula I where $R^2$ is (1-6C)alkoxy substituted with (1-6C alkyl)C(=O)O—, coupling a corresponding compound having the formula VII or a protected derivative thereof

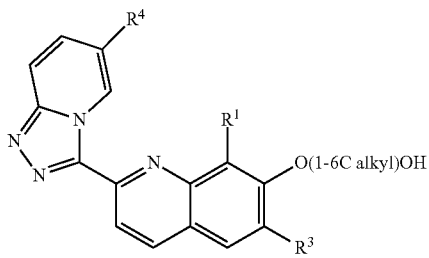

VII where $R^1$, $R^3$ and $R^4$ are as defined for Formula I, with a (1-6C)alkyl acid anhydride or a (1-6C)alkyl acid chloride in the presence of a base; or (h) for a compound of Formula I where $R^2$ is (1-6C)alkoxy substituted with amino(1-6C alkyl)C(=O)O—, coupling a corresponding compound having the formula VII or a protected derivative thereof

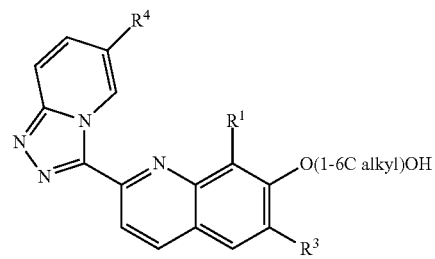

VII where $R^1$, $R^3$ and $R^4$ are as defined for Formula I, with a compound having the formula P$^1$NH(1-6C alkyl)C(=O)OH where P$^1$ is H or an amine protecting group, in the presence of a base and a coupling reagent; or (i) for a compound of Formula I where $R^4$ is a moiety having the structure

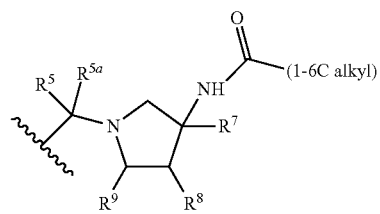

where $R^5$, $R^{5a}$, and $R^7$ are as defined for Formula I, $R^8$ is H, halogen, OH, or (1-6C)alkoxy, and $R^9$ is H, reacting a corresponding compound having the formula VIII

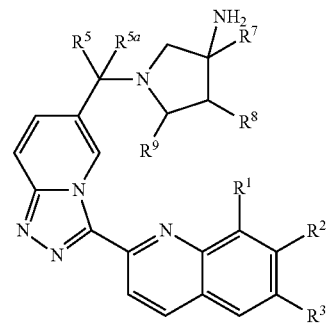

VIII where $R^1$, $R^2$, $R^3$, $R^5$, $R^{5a}$, and $R^7$ are as defined for Formula I, $R^8$ is H, halogen, OH, or (1-6C)alkoxy, and $R^9$ is H, with a (1-6C)alkylcarboxylic acid anhydride or a (1-6C)alkylcarboxylic acid chloride in the presence of a base; or (j) for a compound of Formula I where $R^4$ is a moiety having the structure

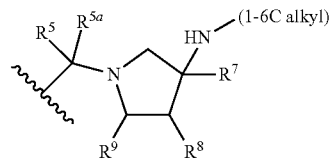

where $R^5$, $R^{5a}$, and $R^7$ are as defined for Formula I, $R^8$ is H, halogen, OH, or (1-6C)alkoxy, and $R^9$ is H, reacting a corresponding compound having the formula VIII

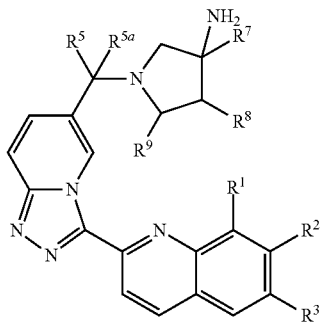

VIII where $R^1$, $R^2$, $R^3$, $R^5$, $R^{5a}$ and $R^7$ are as defined for Formula I, $R^8$ is H, halogen, OH, or (1-6C)alkoxy, and $R^9$ is H, with a (1-6C)aldehyde or a protected (1-6C)aldehyde in the presence of a catalyst and a base followed by treatment with a reducing agent; or (k) for a compound of Formula I where $R^4$ is a moiety having the structure

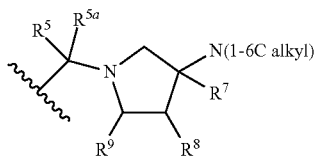

where $R^5$, $R^{5a}$, and $R^7$ are as defined for Formula I, $R^8$ is H, halogen, OH, or (1-6C)alkoxy, and $R^9$ is H, reacting a corresponding compound having the formula VIII

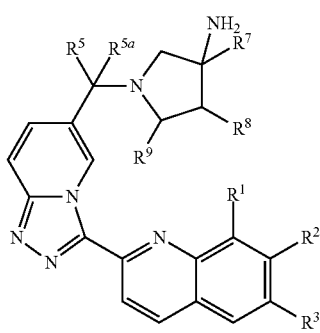

VIII where $R^1$, $R^2$, $R^3$, $R^5$, $R^{5a}$, and $R^7$ are as defined for Formula I, $R^8$ is H, halogen, OH, or (1-6C)alkoxy, and $R^9$ is H, in the presence of a reagent having the formula HC(=O)(1-5C alkyl) and a reducing agent; or (l) for a compound of Formula I where $R^4$ is a moiety having the structure

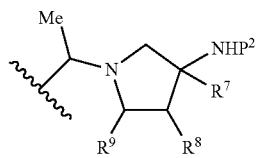

where $R^7$ is as defined for Formula I, $R^8$ is H, halogen, OH, or (1-6C)alkoxy, $R^9$ is H, and $P^2$ is H or an amine protecting group, reacting a corresponding compound having the formula IX

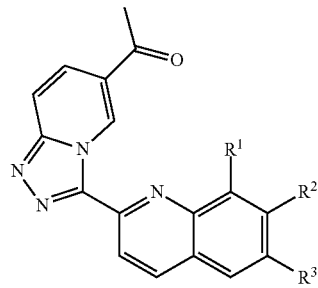

IX where $R^1$, $R^2$, and $R^3$ are as defined for Formula I, in the presence of a Lewis acid, followed by treatment with a reducing agent; and
removing any protecting group or groups and, if desired, forming a salt.

24. A compound having the formula II-A

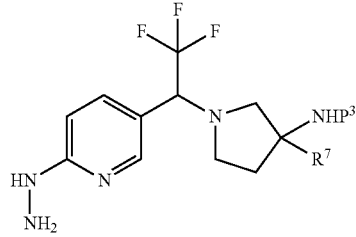

II-A including enantiomers and diastereomers thereof, where $P^3$ is H or an amine protecting group and $R^7$ is H, (1-6C)alkyl, fluoro(1-6C)alkyl or hydroxy(1-6C)alkyl.

25. A compound of claim 24, wherein $R^7$ is H or (1-6C) alkyl.

26. A compound of claim 25, wherein $R^7$ is H or methyl.

* * * * *